United States Patent
Graf

(10) Patent No.: US 11,918,611 B2
(45) Date of Patent: Mar. 5, 2024

(54) PROBIOTIC BACTERIAL STRAINS PRODUCING ANTIMICROBIAL PROTEINS AND COMPOSITIONS COMPRISING THESE FOR USE IN THE TREATMENT OF DIARRHEAL AND OTHER MICROBIAL DISEASES

(71) Applicant: CRIGASSENI AG, Beckenried (CH)

(72) Inventor: Federico Graf, Beckenried (CH)

(73) Assignee: CRIGASSENI AG, Beckenried (CH)

( * ) Notice: Subject to any disclaimer, the term of this patent is extended or adjusted under 35 U.S.C. 154(b) by 0 days.

(21) Appl. No.: 17/052,139

(22) PCT Filed: May 2, 2019

(86) PCT No.: PCT/EP2019/061259
§ 371 (c)(1),
(2) Date: Oct. 30, 2020

(87) PCT Pub. No.: WO2019/211382
PCT Pub. Date: Nov. 7, 2019

(65) Prior Publication Data
US 2021/0077543 A1 Mar. 18, 2021

(30) Foreign Application Priority Data
May 3, 2018 (EP) ..................... 18170567

(51) Int. Cl.
| | |
|---|---|
| *A61K 39/02* | (2006.01) |
| *A61K 35/741* | (2015.01) |
| *A61P 31/04* | (2006.01) |
| *C12N 9/14* | (2006.01) |
| *A61K 47/02* | (2006.01) |
| *A61K 47/18* | (2017.01) |
| *A61K 47/26* | (2006.01) |

(52) U.S. Cl.
CPC ............ *A61K 35/741* (2013.01); *A61P 31/04* (2018.01); *C12N 9/14* (2013.01); *A61K 47/02* (2013.01); *A61K 47/183* (2013.01); *A61K 47/26* (2013.01)

(58) Field of Classification Search
None
See application file for complete search history.

(56) References Cited

U.S. PATENT DOCUMENTS 10,980,845 B2 * 4/2021 Berry ................... A61K 31/715
2014/0106435 A1    4/2014 Kwack, III et al.

FOREIGN PATENT DOCUMENTS

| WO | WO 2012/080789 A1 | 6/2012 |
| WO | WO 2015/155244 A1 | 10/2015 |
| WO | 2016172476 A1 | 10/2016 |

OTHER PUBLICATIONS

Yang et al (Front. Cell. Infect. Microbiol., Jul. 18, 2017).*
Claes et al (PlosOne. Feb. 2012 | vol. 7 | Issue 2 | e31588, pp. 1-8).*
Biller et al al (J. Pediatr. Gastroenterol. Nutr. 1995. 221: 224-1226).*
Segers et al (Microbial Cell Factories vol. 13 (7). 2014; pp. 1-16).*
Segarra-Newnhamm (Ann Pharmacother Jul. 2007;41(7):1212-21).*
https://en.wikipedia.org/wiki/Lacticaseibacillus_rhamnosus. Jan. 29, 2023.*
Viswesaran, et al., "ACMD, A Hololog of the Magor Autolysin ACMA of Lactoccus Lacits, Binds to the Cell Wall and Contributes to the Cell Separation and Autolysisi", PLOS One, vol. 8, No. 8, Aug. 8, 2013.
Buist, et al., "Molecular Cloihng and Nucleotide Sequence of the Gene Encoding the Major Peptidoglycan Hydrolase O Flactoccos Lactis, A Muramidase Needed for Cell Separation", Journal of Bacteriology, vol. 177, No. 6, Mar. 1, 1995.
International Search Report and Written Opinion dated Oct. 23, 2019, for PCT/EP2019/061259.
Pedicord, VA., et al, Exploiting a host-commensal interaction to promote intestinal barrier function and enteric pathogen tolerance, Sci Immunol, Sep. 2016, 1(3); pp. 1-29.

* cited by examiner

*Primary Examiner* — Jennifer E Graser
(74) *Attorney, Agent, or Firm* — Bryan D. Zerhusen; Nicholas R. Herrel; CANTOR COLBURN LLP

(57) ABSTRACT

The present invention is directed to a bacterial, preferably probiotic bacterial peptidoglycan hydrolase (PGH), a peptidoglycan hydrolase (PGH)-comprising bacterial, preferably probiotic bacterial strain or a peptidoglycan hydrolase (PGH)-comprising composition for use in the therapeutic or prophylactic treatment of a bacterial infection, preferably for the treatment of a bacterial infection resulting in diarrhea. Further aspects of the present invention relate to corresponding methods for preparing a medicament and to a corresponding method of treatment.

22 Claims, 10 Drawing Sheets

Figure 1:
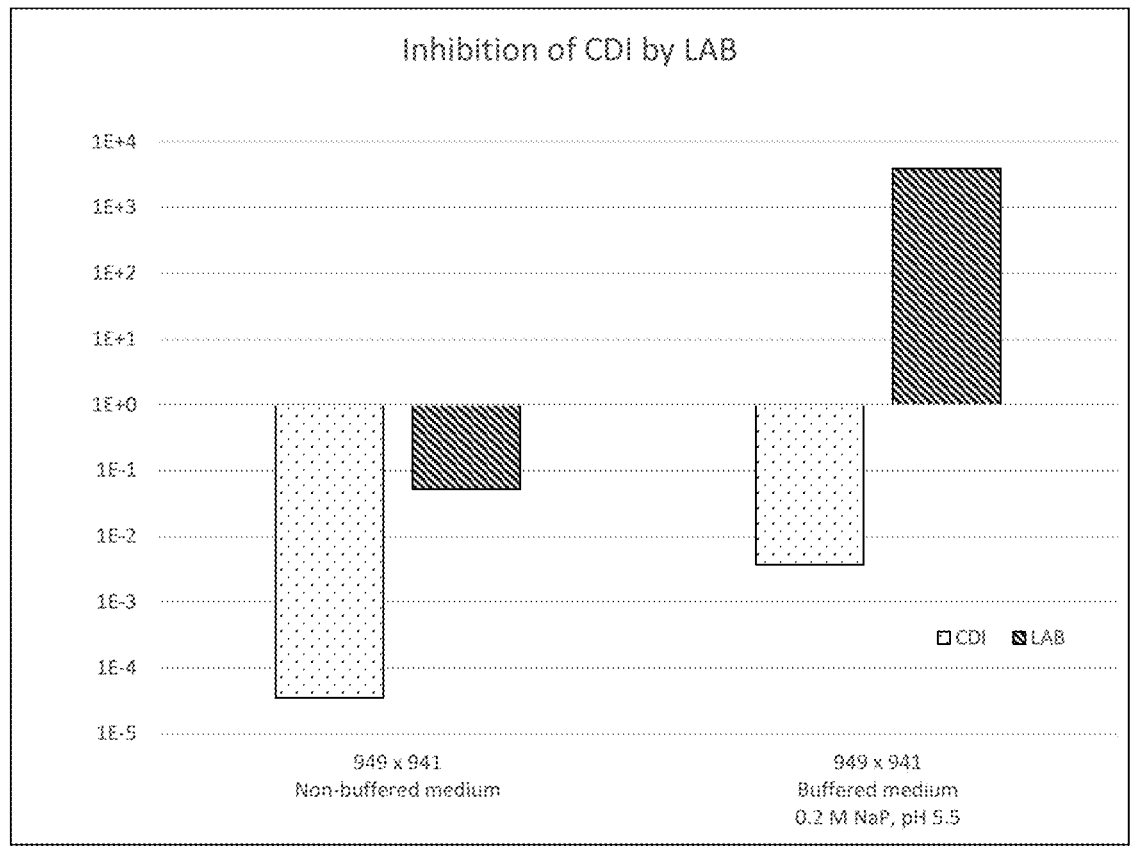

Specification includes a Sequence Listing.

SEQUENCE LISTING

```
<160> NUMBER OF SEQ ID NOS: 163

<210> SEQ ID NO 1
<211> LENGTH: 1677
<212> TYPE: DNA
<213> ORGANISM: Lactobacillus gasseri CCOS 960
```

<400> SEQUENCE: 1

```
atgcttgctc aagcagcggt cgaatcagct tggggtcaat caggtttggc acaatcgcct    60
aataataact tattcggtat taagggctct tacaatgggc aatcagtaaa tatgaatact   120
ggtgagtacg gcagcaatgg ttattacact actaacgctg gatttagaaa gtatccatca   180
tatactgaat catttgaaga taatggctct ttattacgta accaaatggg taactattac   240
tctggtacgt gggtagaaaa ttcaaagaac tacgctcaag caactcaaaa tggtttacaa   300
ggcaagtatg caacagcgcc aaactatgct cagacactta atagtgttat tgcagctaat   360
ggatttgata agtacgatcc cgttacccaa gttgttaacg aaaatcgtac agtcgcacaa   420
accacaccaa ttatgagtgc cccagttgat gctagcgttg gtactcaagt tggtactgca   480
agaactggtc aaaacgtaaa tgttactaag tacatcactt ataacaatgg tgttaagcgt   540
gcatatattg gtactggctg gattaacgca cttgcattta gtccaattac tactaataca   600
actactaagc aaaatactgc cgctaatact aataatcaag caagtcaagc agttaagacg   660
ccagtcgcac aaactcaaca agttaagagt caagcacctg cagctccagt aaaagctgca   720
actgtaaaaag taagagtgc cgctgaagtt aaaactccag ttcaaactac cactttaaac   780
gttaaaactg aaaataaagc agcacaacct gtaaagcaat tagctgtttc attagctgtt   840
gcacctaaga aggttgaagt taagaagaac gttgtgaaag ctgaaccagc taagacaact   900
ccagtaaaaa ctgaaactac taaaactgaa acaaagaag ttaagactgc aactccagta   960
gttaaaacta ctgatacagt taaaaagtt gaaactccag cagttaaacc agttgaatct  1020
gtaaagaagg aatcaactcc agttgttaag actactccag ttactgtaac taaagaagct  1080
gcaaagacca ccgaagctcc agtagttaaa cctaagaagg ttgaagttaa ggaaattaag  1140
actactccag taactactag tgctaaaact gttgtaaagc ctgttcaaag ttaccaaagt  1200
gcagtaacta ctgctgcaaa caataactat ggtactcaat ggattagtac taatactgct  1260
cctaaggctg catctactgt tttaattaag gttactaaga ctgttgatgt tttatcagca  1320
ccagatggtc aaaaattaga ccaacaagtt gaagctggct cagaatttgt tgttgttgct  1380
tctaagtact acaatggcaa cttatattac gaaattagta atggtaaatg gattatggca  1440
aaatatacta ctcaagaagc acaaattact gcaaaatctg gtgtattaac tattaattct  1500
aagccagact atggtgtacc agtatggcgt gttccaggtc aagatcaaat tgctggtaag  1560
ttcttgaaag acggctcaag ctggagatac ttccgtgtag caaacgttca aggacaaact  1620
tggtatgacc ttggcggaaa tcaatgggta tctgccaagt ctgtactagt tcgttaa     1677
```

<210> SEQ ID NO 2
<211> LENGTH: 627
<212> TYPE: DNA
<213> ORGANISM: Lactobacillus gasseri CCOS 960

<400> SEQUENCE: 2

```
atgccgcgta gacgccgtca aaaaaatatt caatatgtaa ttgcaagagc ctttgctatt    60
tgctttactt tggtagtaat tttatcaggc ttttttgtact ggcgtcacga ggtcgcggtt   120
aatgaacaat taaggcaagc gcagttagaa aaggaacgcg ctcttcaaag taaagaaagg   180
tttattaaag tagtagctcc aattgctcaa agagcagata agccttatgg tttatttcca   240
agtgttacca ttgcgcaagc atgcttagaa agtaattttg gtcaaagtga gctttcaaaa   300
aaatattata atttgttcgg tgtcaagggga accgatccta atactagccg agagctgacg   360
acttcggaat ttgttaatga tcactgggaa actgtaactg gtcgttttca aatttataat   420
```

```
tcttatgaag aatctattca ggcacatacg cggttatttg tgaatggaac tagctggaat      480
aaagatcaat atcagcatgt tttagctgca aaagattatg caagtcaagc gcaagcttta      540
gagacggatg gttatgcgac tgatccaggt tatgctaaaa agctaattga tttaattaaa      600
gagttcaatt taacgcaata tgattaa                                          627
```

<210> SEQ ID NO 3
<211> LENGTH: 1542
<212> TYPE: DNA
<213> ORGANISM: Lactobacillus gasseri CCOS 960

<400> SEQUENCE: 3

```
atggttatta cactactaac gctggattta gagaagtatc catcatatac tgaatcattt       60
gaagataatg gctctttatt acgtaaccaa atgggtaact attactctgg tacgtgggta      120
gaaaattcaa agaactacgc tcaagcaact caaaatggtt tacaaggcaa gtatgcaaca      180
gcgccaaact atgctcagac acttaatagt gttattgcag ctaatggatt tgataagtac      240
gatcccgtta cccaagttgt taacgaaaat cgtacagtcg cacaaccac accaattatg       300 agtgccccag ttgatgctag cgttggtact caagttggta ctgcaagaac tggtcaaaac      360
gtaaatgtta ctaagtacat cacttataac aatggtgtta agcgtgcata tattggtact      420
ggctggatta acgcacttgc atttagtcca attactacta atacaactac taagcaaaat      480
actgccgcta atactaataa tcaagcaagt caagcagtta gacgccagt cgcacaaact       540 caacaagtta agagtcaagc acctgcagct ccagtaaaag ctgcaactgt aaaagtaaag      600
agtgccgctg aagttaaaac tccagttcaa actaccactt taaacgttaa aactgaaaat      660
aaagcagcac aacctgtaaa gcaattagct gtttcattag ctgttgcacc taagaaggtt      720
gaagttaaga gaacgttgt gaaagctgaa ccagctaaga caactccagt aaaaactgaa       780
actactaaaa ctgaaaacaa agaagttaag actgcaactc cagtagttaa aactactgat      840
acagttaaaa aagttgaaac tccagcagtt aaaccagttg aatctgtaaa gaaggaatca      900
actccagttg ttaagactac tccagttact gtaactaaag aagctgcaaa gaccaccgaa      960
gctccagtag ttaaacctaa gaaggttgaa gttaaggaaa ttaagactac tccagtaact     1020
actagtgcta aaactgttgt aaagcctgtt caaagttacc aaagtgcagt aactactgct     1080
gcaaacaata actatggtac tcaatggatt agtactaata ctgctcctaa ggctgcatct     1140
actgttttaa ttaaggttac taagactgtt gatgttttat cagcaccaga tggtcaaaaa     1200
ttagaccaac aagttgaagc tggctcagaa tttgttgttg ttgcttctaa gtactacaat     1260
ggcaacttat attacgaaat tagtaatggt aaatggatta tggcaaaata tactactcaa     1320
gaagcacaaa ttactgcaaa atctggtgta ttaactatta attctaagcc agactatggt     1380
gtaccagtat ggcgtgttcc aggtcaagat caaattgctg gtaagttctt gaaagacggc     1440
tcaagctgga gatacttccg tgtagcaaac gttcaaggac aaacttggta tgaccttggc     1500
ggaaatcaat gggtatctgc caagtctgta ctagttcgtt aa                        1542
```

<210> SEQ ID NO 4
<211> LENGTH: 315
<212> TYPE: DNA
<213> ORGANISM: Lactobacillus gasseri CCOS 960

<400> SEQUENCE: 4

```
atgaaaaaaa gaacattcac tggtattgct accgcggcac ttatcacaac tgccggtata       60
tcagttacca acaaccttaa accagaaaat ccattaaaaa ctggtgaagg tactgttcaa      120
```

```
gctgcaacat atcaacaaga attttaaac aaagctattc cagctgctac aactgcatca    180
tctaagtatg gtacttatac ttcagttatg cttgctcaag cagcggtcga atcagcttgg    240
gtcaatcagg tttggcacaa tcgcctaata ataacttatt cggtattaag ggctcttaca    300
atgggcaatc agtaa                                                     315
```

<210> SEQ ID NO 5
<211> LENGTH: 2319
<212> TYPE: DNA
<213> ORGANISM: Lactobacillus plantarum CCOS 893

<400> SEQUENCE: 5

```
ttgctaagta ccgctttgct gccgatgttg agtggtaaag ctgatacggc aagtacaaat     60
caaaaaccgg cagctgcgac taagggaaac agcgctgctt cagctgcaag ccaacaagtg    120
accttaagtg ctggcagtca gacggaaacg acagcggccg gtgcgactga ccaatcagtt    180
gccagtgacg gtgccaagac tgacgatcaa gctgaatcga ccagcacgac gacggctact    240
accagtgcga caagtcgtgt cacagtgcgg gcagccagtc aagtcgctaa agctgacagt    300
acagaactgc aaagtcagtc ctccgccagt gaagctgcca aggataacgc ggctgctagt    360
gctacggcgg actccacaac tagtgctgtt gatcaacttg ataaaacggc caaagctagt    420
gcagccacga gccaagccag tcacagtacg actaatgaga cggctaaagc cagcgcggcc    480
gcaagtcagg atagtcatgt cactacggac caatccagcg tgactgtgac gagtgaagta    540
gccaaatcag ccgcatcgtc agccgcacct aagcaagcga ctgagcaggc ggtagccgcg    600
aaaatctcac caaagattga gacggctgtg gcggctgatg cggtccagtc atcagcgatg    660
atggcacggt ccacgcgggc aatgactagt caggaaatct tcctgagtca gattaaagcg    720
ggggcaatct ctggttggaa caagtatcaa gtcttgccat cagtcacggc cgcacaggca    780
attctggaaa gtggttgggg acaatcacaa cttgcaactc agggaaacaa cttattcggt    840
atcaagggaa gttatcatgg gcaatcaatc tacttcccaa cccaggaatg gaatggctca    900
caatacatta cgattcaaga cgcttttcgg aagtacccga attggtcagc tagtgttgaa    960
gatcatggcg cctttttggt tgtcaatccg cgttacagca atttaattgg ggttaccgat   1020
tatcggcgcg ttgccagtct cttgcaacaa gacggctacg caaccgcgcc aacgtacgcg   1080
agttcgctga tcagcatcat tgaatataac aagctcacg agtgggatca agaagcgctc   1140
agtggtcagg caagtggcgg aaatgataat aaccaagttc agcctgatca agacgtcacc   1200
ccaaccagtg gtacacataa gtttactaag acaacgacaa ttcacaatgc gccggacgcc   1260
acgagtgccg tagtgggtac ttacaacgct ggtgaaacag tcaattacaa tggtaagtta   1320
acggtcggta atgcaacttg gttacgctat cagtcctatt ctggcgtatc acggtatgtg   1380
atgattagtc aaacaacaac taatgataat aataaccagg cgacagttac gccagctagt   1440
gggtcgtata agtttaccgc aaagaccaac attcgatcag ctgcaagcaa aacggctcaa   1500
gtggtcggca cttataatgc tggtgagacg gtttactata tggcaagat taccacgggt   1560 gggacaactt ggttacggta tttatcctat tcaggcgctc agcattacgt ggctatgagt   1620
ggtgatgagg ttggttctgt ggctaaaccg gacgtggttg caaccagtgg gtcgtatcgt   1680
ttcacgaaaa cgacagcaat caagagttca cctgcaacta gtgcgacaac ggttgggtct   1740
tataatgctg gcgatacggt ctattacaat ggtaaggtga cgacaaatgg tcagacttgg   1800
ttacgttaca tgtcttactc aggtgcccag cattatgtgc aaattagtgg tgagagtacg   1860
tcgaccaatg ttgataaacc gcaagtaacg cctcaaagtg gtagttatcg ctttacgcaa   1920
```

| | |
|---|---:|
| acaacggcga ttaagaatac accggccgga aatgccccaa gtgtcggtac ctatagtgct | 1980 |
| ggtgatacag tctactacaa cgctaaggta acggctaacg ccagacttg gttacggtat | 2040 |
| ttgtcttatt cgggcgccca acattacgta gcgattagtg gtaatgccgc taccggaaat | 2100 |
| acgacgtcta agccggtaac aaacagtcaa ggggcgttcc gcttcgtaac gacgactaat | 2160 |
| attcgtacgg cgccaagtac gcgcgcaagc gttgtcggtg aatataaccc aggtgaaacg | 2220 |
| gtttattaca atgggacggt tcaagctgag ggttacacgt ggctccgata tctgagtcgc | 2280 |
| tccggtgcaa cgcactatgt tgctaagctt gaaggctag | 2319 |

```
<210> SEQ ID NO 6
<211> LENGTH: 639
<212> TYPE: DNA
<213> ORGANISM: Lactobacillus plantarum CCOS 893

<400> SEQUENCE: 6
```

| | |
|---|---:|
| atggcgggta agcggcgaaa atcgcgccgg aagcaacgga caaagacaca attatttgtg | 60 |
| aagaagggcc gccttcagtg ggtcaatatc ttattagtgt tggcggcgat ggtggggatg | 120 |
| gtttggtata ttcagcataa ttgggcggtt aagtcgcggg ttacggcgac agcacctaca | 180 |
| acaacgcatg cggcatttat taaaaagcta gtaccagctg cgcaacagct tgatcagcaa | 240 |
| taccacgtgc tggctagtat cacgctaagt caggcgatt tggaatcgga ttggggacaa | 300 |
| agtaccaatg cgacagagaa taataattta tttggggtta gtccacgtc gggacggctc | 360 |
| atgacgacgc aggagtatta tgacggggcc tatcatacgg tcaaacggcg cttcgccgtt | 420 |
| tatgatagct ggcacgcttc gctggtcgat catgccaaga aattggcgta cggaacgact | 480 |
| tgggattctc agcactacgc tgcggtgatt aaggcaactg attatcagac agctgcgcaa | 540 |
| gcattgcaga cggctggata tgcgactgat ccaagttatg cacaaaaatt aattaatatt | 600 |
| attcaaaaat atgacttaca acggtatgat agaaagtaa | 639 |

```
<210> SEQ ID NO 7
<211> LENGTH: 1266
<212> TYPE: DNA
<213> ORGANISM: Lactobacillus plantarum CCOS 893

<400> SEQUENCE: 7
```

| | |
|---|---:|
| atgagcagtg ttttaggaat tacattagca aagcctgtac aagggaaagc tgatcaaaca | 60 |
| tcaagtccta gtaccactaa agttaaagcc gcaacttcag gtgctacctc agaagtatca | 120 |
| tcaattagta caattacggc taacagtgct actaacgtgt cttcagcaac ccatcaattt | 180 |
| tcaacagcaa ctactactag ccagcaggcc agttcagcca ctagtaatat ttccacaact | 240 |
| acagcaagca aacaaatatc taaatccact actggtaagc taaattcaaa tgagacagca | 300 |
| actacaagta atagcgcggc tacctccgta gacagtacgg caccatatat accagcaaaa | 360 |
| tccaatgtca gtttcaccga caacatcaag tcaactattg caaatactcc gacaacggta | 420 |
| gcagcaccag ctattcctag tcatagcacg caatttattg atgattcagc ccctatcaca | 480 |
| tccccgacac ccgttacaac taattctatc catgttcgac catttacagt acatagttca | 540 |
| ttttcgttta aaccaggtca attttacgc ttcacacttc ctaatgttgc tttacttcgc | 600 |
| gatgacgttg aacaaggtgt tccaaattac gtaaaaaact ttttcattgc aattaaacct | 660 |
| ggtgcaatga ttgggtggtc acaatatcat attctaccat ccatttctgg agcacaagca | 720 |
| ttactcgaaa gtggttgggg aaaatccaca ttatcagttc aaggtcataa tttatttgga | 780 |
| atcaaaggct catatcatgg tcattctatt gaaatgccaa caacagaata tttaaatggc | 840 |

| gaagacgtaa cgattgaggc tacctttcga aaatacccag actgggcaac tagtattgtt | 900 |
| gatcatggcg cattccttaa tcaaaattct cgttaccgta atttgcttgg agtaaaaaat | 960 |
| tattcgaccg ttgcatggga tttgcaaaac gatggctacg caacggcacc taactatgcc | 1020 |
| acttcattaa ttaatgccat tcaagattac gatctgcagg aatgggatca agaagccttt | 1080 |
| acgggcaata ctggttcgac aactacaacc accggtaacc acaggtccgg cacttatacc | 1140 |
| tttattcaga attcgaatat ccggacagaa ccatccttat ctgcacctat cattggtgtt | 1200 |
| tattatcctg gggacgtggt taattacaca ggtcagatta aagccgaagg atatacttgg | 1260 |
| ttataa | 1266 |

<210> SEQ ID NO 8
<211> LENGTH: 777
<212> TYPE: DNA
<213> ORGANISM: Lactobacillus plantarum CCOS 893

<400> SEQUENCE: 8

| atggtcgttc cagttgatat ttggaaccaa cgtggcgatg cttctgacca agttaccttta | 60 |
| aaatggccgg ataatcgtaa acctaaagcg gcatttacgg ttaaccgcac cctggcagct | 120 |
| cccggtaaca cgatcaagtt tacaaatgcc tcatccaaaa acgcaaccag ctataaatgg | 180 |
| gaatttgacg gtgccacaaa gacgaccagc accgccaaaa accccacggt cacttaccgt | 240 |
| aaggctggca cttataacgt cacattaacc gctaaaaata aggatggcca acggcacgtt | 300 |
| acaatgaaaa agctcattac gattacaccg aaagctcaag gcgctttaac cttactatcc | 360 |
| aagaacgcca agaccagtgc ctccggatac acgaatagta gtgaagcacc taaaatggcg | 420 |
| gtggatggga aactcgatac taaatggtgt gcaaccggta aggcaccgca taccttgagg | 480 |
| ctggatttag gccgtcaaac gactgtgagt gcggttaaat tagcgcatgc caaagctggt | 540 |
| ggcgaaggtg ctgatatgaa cacccgcgct tggaccattc aggtcagcac tgatggcaaa | 600 |
| cgctacacgg acgttgcccg gacctacaat aacacgcaag ccactagtct caatactttc | 660 |
| gcggctactt cggcgcgcta cgtccggtta gtagtcgata aaccaaccca agttgctgac | 720 |
| accgccgttc ggatttacga aatggacgtg ctaggattga cgcaaacact caaataa | 777 |

<210> SEQ ID NO 9
<211> LENGTH: 285
<212> TYPE: DNA
<213> ORGANISM: Lactobacillus plantarum CCOS 893

<400> SEQUENCE: 9

| atgcgtaagg acaccgctag cacaatcaaa ctctacacca cggacctaga cgtcactgcc | 60 |
| gatacccagg ttagtttaac cgctaaggca tctggtaaat ctacagctaa actagtggtg | 120 |
| accttaaagg acggccgcac taagaccatc gcgggtgacc ggacactcag caagcactgg | 180 |
| acgaccgtta gctatgacgt tagtcagtta acaaaaaaac aatcaaaggc cttagcctca | 240 |
| aaatcagtgc cgccgagact gatgctagct acagcgttca attag | 285 |

<210> SEQ ID NO 10
<211> LENGTH: 1227
<212> TYPE: DNA
<213> ORGANISM: Lactobacillus crispatus CCOS 961

<400> SEQUENCE: 10

| atgaagaaga gacttttgac cagttttgct gctgccgcaa tgcttacttc tgtagctgtg | 60 |
| ccagcagtaa atactacgat gatgaatcaa gcctcaagcc aacgagtttc tgccgctacc | 120 |

```
gctgatcaaa ctgcattttt aaacaaggct gccaagcagg cagttaaagc agctaaaaaa      180
tatggaactt tgccatcagt gatgattgcc caggcaataa ctgagtcagg ctggggaaag      240
tcaggattag ccgtgaatgc taataacctt tttgggatga aggctgatga ttcttggaca      300
ggtgagactt atactgccaa gactagagaa gaagataaaa acggtaagag ctactatatt      360
actgctaagt ttagaaaata cccatctttt gaacaatcat ttgaagataa tgggagtaag      420
ttgagaaatg gtgtttcttg ggatccgttg cgttataagg cacttggat tgaaaatgca       480 tcaacttatg cagctgcaac caaggctttg accggtacgt atgctacaga ctctaagtat      540
gataaggcat taaatagtca tattactagt tctaatttga ctaagtatga tccagtaacc      600
gttaatacta ctagaactta tactgctggc aaggatagtt caacttataa ttggccaact      660
gctccatctg ttgccagtgt tattggctct gttaaagctg gtgaaaaagt agtagttacc      720
aagactatta cttcccatga tggttcaagc agaatgtata ttgatggtcg cggttgggtt      780
aatggctcag ttttggacaa gagcagttcc gcaactaagg aaccagtaac tcaggcacct      840
aagaatgtgc cagctgtttc taagaacttg atgcataatg cctatgttta tgaccaaaat      900
ggtaagaagc taagggcaa gatgtacaag accagtgatg aaaacggtgg taagtggatc       960
aatacttatg gtaccaagac catcaagggt aagacctact accgtgtcgg tgaaaatgaa     1020
tacattgcag ctggtaatat tgatggtagc ctcagattct tgaagaagaa tgcttatgtt     1080
tacaatcaat atggcaatcg cgataacaat ttgaagcaca gaagaatag ccaaattgct      1140 acttacggca gtgctataac tatcaatggt aagaaatact ataaggtagg tattcgtcaa     1200
tacgttaaga aatcgaactt catgtaa                                          1227

<210> SEQ ID NO 11
<211> LENGTH: 648
<212> TYPE: DNA
<213> ORGANISM: Lactobacillus crispatus CCOS 961

<400> SEQUENCE: 11
atggcaagaa aacgtaaatc aagagtacca aaaagtgtca aaaccgttgt gcgtgtattc       60
gtaattctat ttattctgat ggttgctttt gtcggcttta gatattatag gcgttacgcg      120
attcaatcag agcagattca acaagcacag ctgcaaaaag aacaggaagc agcaaaacta      180
ttaaaacaga aaaagacttt atcaaaaaaa attggtccga ttgcgcgcga agtggacaag      240
tcgtatgact tattgccaag catcacgatt gctcaagcct gcctagaaag taattatgga      300
caaagtgatt tgtcgcaaaa atacaacaat cttttttggtg ttaaaggatc caacccgaac      360
acttcggcag tgatgacaac taaggaatat gtaaagaata agtgggttac cgtgaaggcg      420
cgtttccaaa tatatgactc atatgaggct tctattcggg ctcacgctag attattccag      480
aatgggacaa cgtggaacca cgatcagtat aagcatgttc tagcatccaa agattataag      540
acacaagcta agccttggt taccgacggc tatgcgactg atccggacta tgccgataag       600
ctgattaatt tgattgaaca gtttgatctt gaaaatatg ataagtaa                    648

<210> SEQ ID NO 12
<211> LENGTH: 315
<212> TYPE: DNA
<213> ORGANISM: Lactobacillus gasseri CCOS 960

<400> SEQUENCE: 12
atgaaaaatg aattaaaaca agtgttgaat gactttatct cacttgctaa gactcattat       60
gatagaaaag gcaacgaata cttattagaa caacttgaag ttgctttaga taagttagaa      120
```

```
cataatgttc aagatgaagt agatgaagcc cgtgcaactt atcaaaatat aaatactatt    180
tgtcttacta accatcttca cttggaaaca gatgaagaag cattacttga aaagattaaa    240
gaattttcaa tgagtaaagg ctggcttggt ggcttaaaca gttggaatac aactaatact    300
tggcctggaa gataa                                                    315
```

<210> SEQ ID NO 13
<211> LENGTH: 141
<212> TYPE: DNA
<213> ORGANISM: Lactobacillus gasseri CCOS 960

<400> SEQUENCE: 13

```
gtggggaatg ctgtaatagg agctgctacg ggagctactc gcggagtaag ttggtgcaga     60
ggattcggac catggggaat gactgcctgt ggcttaggag gtgctgcaat tggaggatat    120
ctgggatata agagtaatta a                                             141
```

<210> SEQ ID NO 14
<211> LENGTH: 228
<212> TYPE: DNA
<213> ORGANISM: Lactobacillus gasseri CCOS 960

<400> SEQUENCE: 14

```
atgaaaaatt ttaatacatt atcatttgaa acattggcta acatagttgg tgggagaaat     60 aatttgggctg ctaatatagg tggagtaggt ggagcgacag tcgctggatg ggctcttgga    120
aatgcagttt gcggtcctgc ttgtggcttt gttggagcac actatgttcc aatagcatgg    180
gctggcgtaa cggcagctac tggtggattc ggaaagataa gaaagtag                228
```

<210> SEQ ID NO 15
<211> LENGTH: 996
<212> TYPE: DNA
<213> ORGANISM: Lactobacillus gasseri CCOS 960

<400> SEQUENCE: 15

```
atgattggaa agaaactca aatacgttta gtaaataaat tagaaaatat acaccacgtt     60
gttgttcaag cttcagcact cgatggaagt aatgtatttg tcctacaatt acttcataga    120
cagagcgatg ttattgttta tcaaactcca aatgatagcg aaactgtgac ctttaatgag    180
gatcatccaa ttttatactt gaaaggaccc aattcagctg gtacagcggg tggacatact    240
caaacttggg tacaaagtgg agaagacaat aaatggttcg ttggaactaa acctaaaaag    300
catggtaata cttattggac aacgcaaatt gcgcgagtaa cagttcctgg ctatcaaact    360
caaattttta ccagtaatac ggagttgcca agactttctt atcttaatcg cgcaggttca    420
ggctatggcg atggaagtgt agcttatcct ggcaaagatt tagttagagt agaagcagct    480
gtttcaccga ataaacaata tttcttaatt gcaagtattg acatcaatca cacaggtcat    540
tttgctatct ataatcttga tgaagttaat aaaaaactag atcaagcaga gaaaaagct    600 gaagatgtta atattcagag cttgaattgt ttaggtgcat taatatccc atatttaat    660 gatcaaaaga ttatttcgat tcaaggctat ggaattgatg ataataagga catttatatt    720
tccagtcagc ccagcccgca tacaacgttc ttaggatttc caaacaagg caaaccacgt    780 gaaattgtta aaattccctg gggaatatcc gatctaagta aatggtcagt ggtaaattta    840
gacaacagtt taaaattaga tgcactaaac ttttgcactg aatttgaagg aattcaagta    900
actggtgatt gtctttactt aaccgttgcc tatcaccaac gaaacagtga tttgactact    960
ttgatgaatc gaatatatca ggttgaaaaa ttttag                              996
```

<210> SEQ ID NO 16
<211> LENGTH: 1461
<212> TYPE: DNA
<213> ORGANISM: Lactobacillus crispatus CCOS 961

<400> SEQUENCE: 16

| | | | | | |
|---|---|---|---|---|---|
| atgataacag | gtattaagcg | gttaagacag | acaaaaagat | gggctggatt | agccgctttt | 60 |
| ttattaggaa | ttttagctgt | tttatcagtt | atatatttta | ttgtaatttt | aattgcagca | 120 |
| atgggagctg | ctacagatga | tgaatgtgat | acaggaggaa | acaaggagg | agtagtagaa | 180 |
| ggacgaatta | gtgtcattga | atcacctaag | tatggacaga | ccgctatgat | gcatatagcg | 240 |
| gatgctgtgc | atgagaaaac | tgggattagt | gctagattac | tttttgctca | atgggacag | 300 |
| gaaacaggta | atggtgatag | ttcagttgct | aaacatgatc | ataactttgg | tggtatgact | 360 |
| tattcagaag | gaagcactat | cggtaccaaa | ggtgaaagcc | gtggtagtga | aggtggtaat | 420 |
| tacgttcact | acaagaactt | aagtgatttt | gcgaccgagt | gggctgtgac | ggttcagaat | 480 |
| ggttttaaaa | agctggatt | aggaaaagat | gctacagttg | ctcaatatgc | tcatgcaatg | 540 |
| aaaaaagcag | gatactatac | cgcagctgaa | agtgattacc | aagcaggtat | ggaagctcaa | 600 |
| gctaaaaaat | atgatgcctt | gaaaggcaat | aaatcactag | ctaaaggtga | tgggtctagt | 660 |
| ggctcagata | attcagctga | ggaagattgt | aagccaataa | gcggcaaatg | ggggtggcca | 720 |
| ttcaagtcaa | ttcctaaaaa | aggaccaggt | aatacaatct | caggtgagca | attatttggt | 780 |
| aagtcatcta | caagaacagg | tggctttcat | gatggtgttg | actttggtac | tgttccatat | 840 |
| ggtggacaag | atattttggc | aattcatggt | ggaaccgtta | agaaaattgc | atttcaagga | 900 |
| catactcaag | atggtctagg | aatgtacgtt | tgggtagaag | gctccgacgg | ttggaatgtc | 960 |
| atttatcagg | aattcggctt | tgatgaagca | gatttgaaat | acgtcaaggt | agaggtaggc | 1020 |
| gacaaagttt | cagtaggaga | taaaataggt | cacttagcaa | gtaatgcaca | tggtattact | 1080 |
| cacgttcaca | ttggtgcaac | tgaaaaagat | tttgctaccg | cagagctctc | tgcgtacaaa | 1140 |
| gatgatggta | cttggaaaga | cccaattaaa | ttaattaaag | atggtttgaa | caatgatgca | 1200 |
| gaatctgaag | aagatgatgg | cttatcaaaa | actgaatctg | aagcacgtga | ctggattgtt | 1260 |
| cagagagaat | ctggaggtag | atgggacgca | gttaacccag | ctaacccaag | tgtttatgga | 1320 |
| cgttatcaat | aaagagaga | atatcttaat | ggtgattaca | gtcataagaa | tcaaacaagg | 1380 |
| gtagcaaata | aatatgtaaa | aggcagatat | ggttcatggc | gtaatgcaca | aaaattctgg | 1440 |
| atgaaacata | cctggtatta | a | | | | 1461 |

<210> SEQ ID NO 17
<211> LENGTH: 981
<212> TYPE: DNA
<213> ORGANISM: Lactobacillus crispatus CCOS 961

<400> SEQUENCE: 17

| | | | | | |
|---|---|---|---|---|---|
| atggttaaaa | gtattacacc | tcatttgttt | tatcgcttga | tgggatgca | ccatgttgta | 60 |
| gcccaagttg | gtgtagtaaa | tggtgatcat | gttttgcct | tgcaacttct | tcacagtgca | 120 |
| catgatgtgt | tggtttatag | aaaacatgaa | ggtttaacta | agaacatcga | ttatactgat | 180 |
| ccacacttag | taatgatggg | ctttggccac | acgcaaacct | gggtagcagc | taatgacaag | 240 |
| gatgaatatt | tcgtaggtgc | taaaccaaat | tcaggcaact | ggactactca | aattgcacga | 300 |
| gtaaagtacc | caagactttt | accagaaaga | tatacttcaa | atacacaact | tccacgtttg | 360 |
| tcacacttga | atcacgtaac | cgacgttcct | tatgatggtc | atgatcactt | gcacagagta | 420 |

-continued

```
gaagcttcag tttcaccaaa tggcaagtac ttcatgattg cttcaatttg ggatgatggt    480
tcaggtcact ttggtttgtt tgacttaaat gaagtaaacc aaaagttgaa tgaaaatggc    540
actaagaaca cgccaattac tgatttgcat tgccttagtg cttttcacat tgataacttt    600
gatcatccaa gcgtggcacc aagtgaagaa gctccacaaa tgattgattc tgttcagggc    660
tacgccattg atgatgacaa gaatatttat atttctaacc aattgtcacc aagattgat    720 catgcgaatg tgaagttac tacttggtca cgtaagatcg ttaagtttcc atggggtgaa    780
actaatccag agaactggca agtagcaatg attgatggta ttgatttgcc tgatcgctac    840
agtgaagtag aaagtattca tgttcaggcg ccagatgaca tttatctaac tgtggcttac    900
caccaaaaat atgtcaaaga tggcgagttt aagttaagaa ctttggagaa tcaaattttc    960
cacattagtg atttaggcta a                                              981
```

<210> SEQ ID NO 18
<211> LENGTH: 936
<212> TYPE: DNA
<213> ORGANISM: Lactobacillus crispatus CCOS 961

<400> SEQUENCE: 18

```
atgttagatg caacaaatat tagaatttta gatagattcg atatgaatac aggttacaga     60
gctgtagttc aaaaaggtaa tgtaggatca aagtatgttt atggtttaca gttaagaaat    120
aaccagacag aaacacatgt attgcgtggc ttccgtggca acgtgacaac ccctgtgctt    180
actttagtag gtgcagcagc tggacacacc caaacttggg aatattcagg tagatctggt    240
aaatggttcg ttggtactaa aaacaagaat aaatgggctt ctcaaattgc tcgagcagat    300
attagataca aatcatatgc ttcatcaaat actgaattcc cacgtttagc atacttgaac    360
cgcgcaggta atcctgaaga tcaatgctct ggtgatgaaa tggaacgcgc tgaagtagca    420
gtttcaccag attatagtat gcttttaatt gctactattg agaataatgg aacaggccac    480
ttttcaattt atgacctaaa tgtcattaat aatgcattag atgaggctgg aaataatggt    540
ttcgtaaata tgggaaatta tcaatgtgaa actagttta cagtatatgg tttgtatgga    600
tctgttttaa actctgtaca aggttatgat cttgataatt ctggtaatat ttatattact    660
agtcaaaaat caccaagttt aagtaatggt tcatggtcat actatcacaa ggaaattgta    720
aaaattccgt tttatgcacg taatgatcaa tctcaatggg aaaatgtaaa cttaagtgca    780
tttggtggat tagatatttc aggtgaacat agtgaagttg aaagtatcca aattattgat    840
gaaaatcacg ttacttaac tgttgcatac catgctaatg ttaacggtaa aaataaaact    900
gtttcaaata aggtttatga attagcttgg gactaa                              936
```

<210> SEQ ID NO 19
<211> LENGTH: 252
<212> TYPE: DNA
<213> ORGANISM: Lactobacillus crispatus CCOS 961

<400> SEQUENCE: 19

```
atgaacaaat ttgaaacttt aacttatgaa gaactgtcag ctgttttcgg tggtaacggt     60
ggtaaagcaa gacgccgtag aaaaatcaca aattgtgcta aagctattgg aatgggagcg    120
ttgaaggatg gactaaaaata tggcattgca ggcactgcat ttggtactcc aattggtaca    180
gtaggtggag ctatatttgg tgctaatgtg ggtattatta gcggatcagt ttcttgtgta    240
tcacatttgt aa                                                        252
```

<210> SEQ ID NO 20
<211> LENGTH: 198
<212> TYPE: DNA
<213> ORGANISM: Lactobacillus crispatus CCOS 961

<400> SEQUENCE: 20

| | | |
|---|---|---|
| atgaagaatt ttaaggtagt aaataatatt gagctaaata gagttgttgg tggtaaaatt | 60 |
| attcgattaa ctccatatat gttgtataat actaagacac ataaaactat cccagattac | 120 |
| ggtgcaattt ggggtaaagc gggtcaaacc gtagccaatg gatggttaca atatggacca | 180 |
| tggggcagta gaggttaa | 198 |

<210> SEQ ID NO 21
<211> LENGTH: 219
<212> TYPE: DNA
<213> ORGANISM: Lactobacillus crispatus CCOS 961

<400> SEQUENCE: 21

| | | |
|---|---|---|
| atggtaaagt ttcaagaact aaaagaaaat caattaagtc aagttttagg cggtacacat | 60 |
| cacaagcgcg gaggcggaaa gtaccattac tatggtaatg gtgtatattg caaccgatat | 120 |
| tattgtcatg ataatttagc acaaatgtgg gatagcgttg gtcgtattat gtatactgga | 180 |
| tggcagaagg atggaccatt tgcgcatcct ttggtgtaa | 219 |

<210> SEQ ID NO 22
<211> LENGTH: 675
<212> TYPE: DNA
<213> ORGANISM: Lactobacillus crispatus CCOS 961

<400> SEQUENCE: 22

| | | |
|---|---|---|
| atgaaaaaaa ctgaaagtaa gtttgcactt ttagctgctt taattgctat tttagctttt | 60 |
| gcctctattc ccttatggca aaacaatctg aatagtttac gaccacaaac tcacacggtt | 120 |
| aagaaaaaga agactgctaa aaagaaaaaa gtcgttcatc ttacttgggg ttacccttt | 180 |
| aagaagctct atgaaaagaa atcaaatttt aaatctggac aaaagtttgg tgaaactgac | 240 |
| gtcattcgtc gagtctatcc tagcaagagt tattttcatg atggctatga cttcggattt | 300 |
| agtgaagttg acattcttc cgtatatgct gtgcatgcag gaactgtcca tcgtgttaaa | 360 |
| tacgccccag gtttaggact ttatatttgg attatttccg atgatggcta tgttgaagtt | 420 |
| taccaggaag gcttcctcag tattactgat atttatgtta aaaaaggtca aaaagtcaag | 480 |
| ttgggacaaa aaattggtaa actgaccggc tctcacattc atttaggagt tactaagaca | 540 |
| gataaagatt acattgataa aaagcatgac aatacgccat gcaaatacta ttggaaagat | 600 |
| aatggcactt ggttaaatcc aatgaaaatc attgaagata tctaagggc agcaggtaaa | 660 |
| gatccagtcc aataa | 675 |

<210> SEQ ID NO 23
<211> LENGTH: 624
<212> TYPE: DNA
<213> ORGANISM: Lactobacillus crispatus CCOS 961

<400> SEQUENCE: 23

| | | |
|---|---|---|
| atgaaatttc gtaaattaat aatttctttg ttaggtactg cattattaac ttcaagcgtt | 60 |
| ggtttatcaa ccaccactgc ttctgctgat acgcttgatg actcacaaaa tacaactgaa | 120 |
| gttcaaccca agaacctcaa gtgggcttat ccgtttaaag ccaacaagaa aaatggtgtt | 180 |
| cgtccaatgt ataatgcaca aacttttggc ataactaact atatgcgttc tactcacca | 240 |

```
ccttcctact ttcatgatgg ttgggatttt ggttttttcag aagttgggca ttctaacgta    300
tatgcaattc atcaaggtac tgttaaaaag gttgcttatg caacggcct tggctggttc      360 atctgggtta ttagtcctga taattacgtt gaagtttacc aagaagggtt taataagaaa    420
aaagacattt atgttaagac tggtcaaaag attaaattag atcaaaagat cggtaagcta    480
actggctcac acttacacct tggcgttact caaacaaata aagattacat aaacaaatat    540
ggttttccat gtaagaattg gaacgttaac aacggaactt ggctcaatcc aatcgaggtt    600
atcaaaagca acttaaagaa atag                                           624

<210> SEQ ID NO 24
<211> LENGTH: 1293
<212> TYPE: DNA
<213> ORGANISM: Bifidobacterium bifidum CCOS 571

<400> SEQUENCE: 24
atgaggatgc agcagatcaa acacggcggc aggaggccgc gccccagttc agccccacc     60 atcatcgcgg ccatgctctg cgtggtggcc cttgtggcgg caggcacggc atggtggatg   120 ctgcgcccc agcaaaaaga cacgctcgaa catctcgcgc agccacagtc ctcctcttcg    180
acgctgaacc gcgacaaggc ccccacaccg aaaccgcaga atctcagga gcggcagaag    240 gcagccggtg actccccgc ggccaaggcg agccgcgcca tcgccacgat gagtctcgat    300
gaacgggccg gcagctcat catggcaccg atgttcgcag cggcaatcc ggccgatctc     360 agcgccctca tcagcacacg ccatgtcggt tccgtggtgc tcatcggcaa ctggaacaac    420
ggcacagccg cagccaagac cgccgctgac gcgctgcaaa gctatgctcc gagcggcaac    480
cagctgatcg tctccaccga tcaggaaggc ggccaggtgc agcatctcaa gggcagtgga    540
ttcgacacga tgccgtccgc ggtggcgcag ggccagatga gcgctgacac gctgcgctcc    600
tccgcaaaga cctggggcgg ccagctcaag caagccggca tcaacgtcga cctggccccg    660
gtattgggga cggtgcaggt caagcgttcc tcgaacgctc cgattggcgc gctgaaccgc    720
gatttcggtt tggattccaa cggaaacgcg cagcacggca tcgcgttcgt cgaaggcatg    780
cgcgacgcgg gcgtcggcgc gaccgtcaag cactaccccg gtttgggcgc ggtgaccggc    840
aataccgatt tcacgaccga aggcatcctc gacaccacga ccacgcttga tggcgaggag    900
ataggcgcgt tcaacaccac gatcaagcag gcgaagccgg ctatggtgat gatgtcgctg    960
gcgacctacc agcgcatcga ctcgtcggcg cccgccgcgt tctccagcaa gatcatcgac   1020
ggcacgctgc gcggcagcgt cggctatgac ggcgtggtga tctcagactc cctttcggcc   1080
gcggcggtca gcggcatagc gaccaaggac ctgggcgtgc gtctggtgga cgccggcggc   1140
gatttggcgt gcataggcga tacgtcatat gtgacgccga ttcttgacgg tatcatcgcc   1200
cgtgcgcagt ccgacccggc cttcgcgaag aaggtgacgg cctccgcaac gcgcgtaatg   1260
accctgaaat accagatggg actggcgaag tga                                1293

<210> SEQ ID NO 25
<211> LENGTH: 5808
<212> TYPE: DNA
<213> ORGANISM: Bifidobacterium bifidum CCOS 571

<400> SEQUENCE: 25
atggcagttc gcagacttgg tggccgcatc gtggctttcg ccgccacagt ggccttgtca    60
ataccgttag ggttgttaac aaattcagcg tgggcggtcg aggacgccac ccgatccgac   120
tccaccacgc agatgagctc cacgccggag gtggtctact ccagcgccgt ggattccaag   180
```

-continued

```
cagaatcgca cctcggattt cgacgccaac tggaagttca tgctgtccga ttccgtgcag    240
gcgcaggatc cggcgttcga cgattcggcc tggcagcagg tcgacctgcc gcatgactac    300
agcatcacgc agaagtactc gcagagtaat gaggccgaaa gcgcatacct tcccggcggc    360
accggctggt accgcaagtc cttcaccatc gaccgggacc tcgccggcaa gcgcatcgcc    420
atcaacttcg acggcgtgta catgaacgcc accgtctggt tcaacggcgt caagctcggc    480
acccatccgt acggctactc gccgttctcc ttcgacctga ccggcaacgc caagttcggt    540
ggggagaaca ccatcgtcgt caaggtcgag aacaggctgc cgtccagccg ctggtactcc    600
ggctccggca tctaccgcga cgtcaccctc accgtcaccg acggcgtgca cgtcggcaat    660
aacggcgtgg ccatcaagac cccgagcctc gccacccaaa acggcggcaa cgtgacgatg    720
aacctcacca ccaaggtcgc caacgacacc aaggccgcgg cgaacatcac cctcaagcag    780
accgtgttcc ccaagggagg caagaccgac gccgccatcg gcaccgtcac caccgcatcc    840
aagtccatcg cggccggtgc cagcgcggac gtgacctcca cgatcaccgc cgcctcgccc    900
aagctgtgga gcatcaagaa cccgaacctg tacaccgtgc gcaccgaagt gctcaacggc    960
ggcaaggtgc tcgacactta cgacaccgaa tacggcttcc gctggaccgg cttcgatgcg   1020
accagcggtt tctcgctcaa cggcgagaaa gtcaagctca agggcgtctc aatgcatcat   1080
gaccagggat cgctcggtgc ggtcgccaac cgccgcgcca tcgagcgcca ggtcgagatt   1140
ctccagaaga tgggcgtcaa ctcgatccgc accacgcaca accccgcagc caaggcgctg   1200
attgacgtct gcaacgagaa gggcgtcctc gtggtcgaag aggtcttcga catgtggaac   1260
cggtcgaaga acggcaacac cgaggattac ggcaagtggt tcggccaggc catcgccggt   1320
gacaacgccg tcctgggtgg cgacaaggac gagacctggg ccaagttcga cctgaccagc   1380
accatcaacc gtgacaggaa cgccccgtcc gtcatcatgt ggtcgctcgg caacgagatg   1440
atggaaggca tcagcggcag cgtctcgggc ttccggcta cctccgccaa gctggtcgca   1500
tggacgaagg ccgcggacag caccgcccg atgacctacg cgacaacaa gatcaaggcc   1560 aactggaacg agtcgaacac catgggcgac aacctgaccg ccaacggcgg cgtggtcggc   1620
accaactact ccgacggcgc gaactacgac aagatccgca cgacccaccc ctcatgggcc   1680
atctacggtt ccgagacggc gtccgccatc aacagccgag gcatctacaa ccgcaccacc   1740
ggcggcgccc agtcaagcga caagcagctg accagctatg acaattccgc agtcggctgg   1800
ggtgccgtcg ccagctccgc ctggtacgac gtggtccagc gcgatttcgt cgccggcaca   1860
tacgtgtgga ccggcttcga ctatctcggc gaacccaccc cgtggaacgg caccggctcc   1920
ggcgccgtgg gctcctggcc gtcgccgaag aactcgtact tcggcatcgt cgacaccgca   1980
ggattcccga aggacaccta ttacttctat cagagccagt ggaacgacga cgtgcacacg   2040
ctgcacatcc tccccgcatg gaacgagaac gtcgtcgcca gggctccgg caacaacgtg   2100 ccggtcgtcg tctacaccga cgcggccaag gtcaagctgt acttcacacc gaagggcagc   2160
accgaaaagc gactgatcgg agagaagtcc ttcaccaaga agaccaccgc ggccggatac   2220
acctatcagg tctacgaggg cgccgacaag gactccaccg cccacaagaa catgtacctg   2280
acctggaacg tgccgtgggc cgagggcacc atctccgccg aagcatacga cgagaacaac   2340
aggctgatcc ccgaggggtc caccgagggc aacgcgtcgg tgaccaccac cggcaaggcc   2400
gcgaagctta agccgatgc cgaccgcaag acgatcaccg cggacggcaa ggacctgtcg   2460
tacatcgagg tcgacgtgac cgacgccaac ggccatatcg tccccgatgc cgccaaccgc   2520
gtcaccttcg acgtcaaggg cgccggcaaa ctggtcggcg tcgacaacgg cagctcgccg   2580
```

```
gatcacgact cctatcaggc cgacaaccgc aaggcgttca gcggcaaggt gctcgccatc    2640
gtccagtcca ccaaggaggc gggcgagatc accgtcaccg ccaaggccga cggtctgcaa    2700
tcatccacag tgaagatcgc caccaccgcc gtccccggca ccagcaccga aagacggtc    2760 cgcagcttct actactcgcg caactactac gtcaagaccg gcaacaagcc gattttgccg    2820
agtgatgtcg aggtgcgcta ctccgacggc acgtcggacc gtcagaacgt cacatgggac    2880
gcagtcagcg acgaccagat cgccaaggcc ggttcgttca gcgtggccgg cacggtcgcc    2940
gggcagaaga tctccgtgcg cgtgacgatg atcgacgaga tcggtgcgct gctcaactat    3000
tcggccagca caccggtcgg cacgcccgcc gtgctgcctg gctcgcgtcc ggccgtgctg    3060
cccgacggca ccgtgaccag cgcgaacttc gccgtcgact ggaccaagcc cgctgacacc    3120
gtgtacaaca cggccggcac cgtcaaggtc cccggcaccg ccaccgtctt cggcaaggag    3180
ttcaaggtca ccgcgacgat ccgcgtgcag cggtcgcagg tcaccatcgg cagcagcgtc    3240
tccggcaatg cgctgcgcct gactcagaac atccccgccg acaagcagtc cgacacgctg    3300
gacgccatca aggacggctc cacgaccgtc gacgccaata ccggcggcgg cgcgaacccg    3360
tcagcatgga ccaactgggc gtactcgaag gccggccaca acaccgccga gatcaccttc    3420
gagtacgcga ccgagcagca gctcggccag attgtcatgt acttcttccg cgacagcaac    3480
gcggtgaggt tccccgacgc cggcaagacg aagatccaga tctccgcgga cggcaagaac    3540
tggacggatc tcgctgccac ggagaccatc gcggcccagg agtcgtccga ccgagtcaag    3600
ccgtacacct atgacttcgc tccggtggga gccacgttcg tcaaggtcac ggtcaccaac    3660
gccgacacca caacccccag cggcgtggtc tgcgccggcc tgaccgagat cgagctgaag    3720
accgcgacca gcaagttcgt cacgaacacg tccgccgcgc tctcgtcgct gacggtgaac    3780
ggcacgaagg tctccgactc cgtgctcgcc gccggctcct acaacacgcc cgcgatcatc    3840
gcggacgtca agccgagggc gaaggcaac gccagcgtca ccgtgctgcc cgcgcacgac    3900
aacgtgatcc gcgtgatcac cgagtccgag gaccacgtca cgcgcaagac cttcactatc    3960
aacctgggca cggagcagga attccccgca gactccgatg aacgcgacta cccggccgcc    4020
gacatgacgg tcaccgcggg tagcgaacag acgtccggca ccgcgaccga aggcccgaag    4080
aaattcgcgg tcgacggcaa caccagcacg tactggcatt ccaactggac gcccaccacc    4140
gtgaacgacc tgtggatcgc cttcgagctc cagaaaccca ccaagctcga cgcgctgcgc    4200
tacctgccgc gccccgcggg cagcaagaac ggctccgtca ccgaatacaa ggttcaggtc    4260
agcgatgacg gcaccaactg gaccgacgcg ggctccggca catggaccac cgattacggc    4320
tggaagctcg ccgagttcaa tcagccggtg accaccaagc acgtgcggct caaggccgtc    4380
cacacctatg cggattccgg caacgacaag ttcatgtccg cctccgaaat ccgcctgcgc    4440
aaggccgtcg acaccaccga catcagcggc gcgaccgtga ccgtgccgc caagctgacc    4500 gtcgaccggg tggacgccga ccatcccgcc accttcgcca cgaaggacgt gacggtgacg    4560
ttgggcgacg ccacgctgcg ctacggcgtg gactacctgc tcgactacgc gggcaacacc    4620
gccgtcggca aggccacggt gaccgtgcgc ggcatcgaca agtactccgg caccgtcgcc    4680
aagacgttca ccatcgaact gaagaacgcc ccggcgccgg aaccgacgct gacctcggtg    4740
agcgtcaaga ccaagccttc caagctgacc tacgtggtcg gcgacgcgtt cgacccggca    4800
ggactggtgc tgcagctcaa ctatgacgac gacagcaccg gcaccgtgac ctggaacacg    4860
cagacggccg gcgacttcac gttcaagcct gcgctcgacg cgaagctcaa ggtcaccgac    4920
aagaccgtca ccgtcaccta ccagggcaag tccgcggtca tcgacatcac cgtctcgcag    4980
```

```
cccgccccga ccgtcagcaa gacggatctg gacaaggcca tcaaggcgat cgaggccaag    5040
aacccggatt catccaagta cacggccgac tcgtggaaga ccttcgcgga cgccatggcg    5100
catgccaagg ccgtcatcgc ggatgattcc gccacccagc aggacatcga taacgcgctc    5160
aaggcgctga ccgacgccta cgccgggctg accgagaaga cgcccgaacc cgcccccgtc    5220
agcaagtccg agctggacaa gaagatcaag gcgatcgagg ccgagaagct ggacgggtcg    5280
aagtacacgg ccgagtcgtg gaaggcgttc gagaccgccc tggcgcatgc caaggccgtc    5340
atcgccagcg attccgccac ccagcaggat gtggacgcgg cccttggcgc cctgacctcc    5400
gctcgtgacg gactgaccga gaagggcgag gtcaagcccg acccgaagcc tgaaccgggc    5460
accgtcgaca aggcggcgct ggataaggcg gtcaagaagg tcgaggccga aagctggac    5520 gggtcgaagt acacgccga ctcgtggaag gcgttcgaga ccgccctggc gcatgccaag    5580
gccgtcatcg gcaacgccaa ctccacgcag ttcgacatcg acaacgcgct gtcgatgctc    5640
aacgacgccc gcgccgcgct caaggagaag cccggccgca tcatcgccat catcgatggc    5700
agcgcactga gcaagaccgg cgcatccgtc gccgtcatcg cctccgtcgc ggccgcgatg    5760
ctggcggtcg gtgccggcgt catggcgttg cgccgcaagc gctcctga              5808

<210> SEQ ID NO 26
<211> LENGTH: 465
<212> TYPE: DNA
<213> ORGANISM: Bifidobacterium bifidum CCOS 571

<400> SEQUENCE: 26
atgcattcgc gaccgatgtt cccgattccg gagacgcagg tcggcgacgg ctgggtcggc      60
gacgtcgact acacgaagca ggccacgaag caggacagca atttcctcgt cgactgggtg     120
cgcgtgtacc aatccgaggg gcagccggtg acgcgtttcg acgacctgga cggcgccgag     180
agcggcgcgt accggagcgc ccccgcctca cggaccgagg ggctgaccgc agtgagcaac     240
ggcgacgccg cctggcggaa caagaacaac ttctactacg gcgacagcc gcggtatgag     300 accagccgtt cccatgccgt gccctgatg cagggccgat cgccctgcg cttgcggggc     360 ccacaaacac tctgccgaat ccggacgaat gcttttaccc gcagcgagcg acccgttgca     420
ggcaaggttg tgccgccgaa tcggcgaaat cgcgcggcgc cgtga                    465

<210> SEQ ID NO 27
<211> LENGTH: 558
<212> TYPE: DNA
<213> ORGANISM: Bifidobacterium bifidum CCOS 571

<400> SEQUENCE: 27
atgatttcgg cgagccgaga gatacactcc atcaacctgt accgcaatgg gtatgagaac      60
gcgctgaaca cgttcaagcg catcaaggtc gaagtgtcct ccaacgagga cttctccgac     120
gcgaacgtgc tgttcggcac cgccgacgtc gaggaaaccg ccgcgaccaa gctcgccgcg     180
cagaccatca acctgaccac gcccgtcacc gcgcggtacg tgcgcatctg gcagaagggc     240
cattgcatcc agaacacgaa ctcctcatgg aagggatacg gcaacggcgt gggcttgcgc     300
gaaatcgagg tcatcgccaa gctcaaggac ggcgagaccc tgccggacgc gcaggagacg     360
cgcaacatcg cgctcggcaa gttgccgtat gtgtacggcc tcgacccgac caacatcgcg     420
gcgatcagcg acggcaagca ggacgacaac tacgccgtgc acaacagcac cggcgagcgg     480
tggctgcagt tcgaatacaa gaaccgctac cgtatccacg agggctcaag ccgggcacct     540
atccgctggt ccgcatag                                                  558
```

```
<210> SEQ ID NO 28
<211> LENGTH: 327
<212> TYPE: DNA
<213> ORGANISM: Bifidobacterium bifidum CCOS 571

<400> SEQUENCE: 28
atgagacaat tattccgccg tatcacgacc atatccgcca catgcgcgtt ggccgtttcg    60
gttgcagccg cagtcgcggt ggccgccgaa cccaccacag gcaacatact taccggcaaa   120
ctgcccacga ccaacagcac gcatctgatc ggcgacggcg acaccggatt cggcccgacc   180
gacagcaaca tcaccaaaat catcgccgga gaagagaacg gcagcgcgga aaacaacgga   240
tacgccagct gggacgacgt atacctgcaa tatgatttcg gcgagccgag agatacactc   300
catcaacctg taccgcaatg ggtatga                                       327

<210> SEQ ID NO 29
<211> LENGTH: 5796
<212> TYPE: DNA
<213> ORGANISM: Bifidobacterium bifidum CCOS 571

<400> SEQUENCE: 29
atgagaaaac gagtggtttc agtggcccctt gcggttgcgc tcgctgtcgc cccactgggg    60
gtggtcagca cagcgtccgc cgcgccgctt tctgcaagtg atttgcaaac tctcgcgctc   120
cgttcagcgg ctagctccaa tgacgcgaac gccaacgatg tcgccaccgt cgcggacgat   180
gctgccgtga acggctggac gattgaccgc aacaccgcca aaggcggcga aattcttgca   240
gccggcactg gcgattatgc gggatggact catttcaagt ccacctccgc caacggcaat   300
gccaccagca gcagtggcta tccggctgtc gccattagcg gcaagacgat tgacctgact   360
cgggctggag agttctccat caaggtcaag tccccgcagg ctggttccgc gaaccgtttc   420
ggcttctacc tcggctacaa ggatccgggc aacgccctgt tcctgggcta tgacaagggg   480
ggctggttct ggcagaagta tgtcggaggc aatggcgatt ggtacaacgg cacacgtgtc   540
gctgcccctg ccgcgaacgc tgaaatcacc gtcaacgtct cctggactgc cgccaaggtt   600
gccacgctga ctattgacgg acagaaggcg ttcgatgtgg attactcctc gatgaccgcg   660
ctgaccgaca agctcgccat gaaggccggc tcttactccg gcaccagcga agtcactgat   720
gtctacttca aaaacttcac cgtgggtgaa gtcgccaagc acaacgtgac cggcaaggtc   780
gtcgacgcca gcggcgccgc catcgccggc gccgaagtcg tcaccggcaa gaactccgcc   840
accaccgcgg cggacggcac cttcaccctc accggcctcg ccgccggcga ctacacgctg   900
accgtgtccg ccgaaggcta cgatgacgcc accaagaccg tcaccgtcgc cgatggcaat   960
gcctcagtcg gcaacatcac gctgaacaag tcggccgaag tcgctactga cacgctctcc  1020
accgccgcca tggacgtgcg cgtgaagaag aacttcccgt ccgtgtacga ctacacgatg  1080
aagaagctcg acggcaagat catgtacggc cagccgaagg acgtgcgcgt catcaccatt  1140
aacggcaccg acgtgacgct gaaggactcc gacgtgacct tcaagaaggt cagcgcgacc  1200
gaggcccagt acacgctgaa cgtcaagagc ggcgacaaga tcaacgcggt cgtcaccgtg  1260
cagatcaagg tcgtcgacaa tacgctcaag ctcaacgtca ccaagatcgt gaacaaggcg  1320
gatgacgcca agaccgaggc cgaggagaac ccggtccaga cgattgcgtt cccgaaccag  1380
agcctcatct ccgtgcgctc cggtcaggac ggcgcccagt tcaccggcgc ccgcatgtcg  1440
tccgacactg ccaggcccgg tgacaccaac ttcgacatca ccgccgacac cacggtcagc  1500
aatgcgaacg actacaccta cggcttcgtc tcgggcaatg gcctgagcgc cggcctgtgg  1560
```

```
tccaactccg agcacgacgg caccaccgtc ggcaacaccg tcgccggcgg tgcgaggaac    1620
acccgcgtgc tcacctccac ccagaaggtc ggcaaggcca cctccttcgg tctgggcact    1680
gcaccgtggt actaccaccg cgtcgtgacc gacacgaaga agaacaccta caccgtcgaa    1740
gagaccgaca tgccgaagat ggccgtcgcc atcgccggcg acgagaacga ggacggcacg    1800
gtcaactggg aagatggcgc gatcgcatac cgcgacatca tgaacaaccc atacaagtcc    1860
gaggaagtgc ccgagctggt cgcatggcgc atcgccatga acttcggctc ccaggcgcag    1920
aacccgttcc tgaccacgct tgacaacgtc aagaaggtcg ccctcaacac cgacggcctc    1980
ggccagtccg tgctgctcaa gggctacggc aacgaaggcc acgactccgg ccatccggac    2040
tacggcgaca tcaacacccg cgccggcggc gccgcggaca tgaacaccct gatggagaag    2100
ggcaccaagt acggcgcccg cttcggcgtg cacgtcaacg cgtccgaaat gtacccggaa    2160
gccaaggcct tcagcgagga catggtgcgt cgcaactcca gtggcggcct gagctacggc    2220
tggaactggc tggatcaggg catcggcatc gacggcatct acgatctcgc ctccggcatg    2280
cgcaagtccc gcttcgctga cctcaagagc aaggtcggcg acaacatgga cttcatctac    2340
ctcgacgtgt ggggcaacaa cacctccggc gccgaggact cgtgggaaac ccgcaagatg    2400
agccaaatga tcaaccagaa cggctggcgt atgaccaccg aatggggcgc cggcaacgag    2460
tatgacgcaa ccttccagca ctgggccgcc gaccttacct acggtggttc cgccatgaag    2520
ggcgagaatt ctcaggtcat gcgcttcctg cgcaaccacc agaaggacag ctgggtcggc    2580
gactacccgt cgtacggcca ggccgcgaac gccccgctgc tcggcggcta cagcatgaag    2640
gacttcgaag gctggcaggg acgcaacgac tacgccgcgt acatcaggaa cctgtacacg    2700
cacgacgtgt ccaccaagtt catccagcac ttcaaggtcg tccgctgggt caacagcccg    2760
ctcgacgcca cctccgtgaa ggatgcctcc gtcaacaacg gcaacgagca gatcacgctg    2820
aaggacgacc acggcaacgt cgtcgtcctg tcccgtggct ccaacgacac caacaacacc    2880
gcgtaccgca accgcaccat cacgctcaac ggcatcaccg tggcgtccgg cgcggtctcc    2940
ccgggcaaca gcaacaccgt caagggcact gagtcctacc tgctgccgtg gctgtgggac    3000
gtgaacaccg gcaagctcgt caagtcctcc gatgagaagc tgtaccactg gaatacccag    3060
ggcggcacca ccgagtggac cctgccgaag gattggcaga acctcgcctc cgtcaaggtg    3120
taccagctca ccgaccaggg caagaccaac gagaagaccg tcgccgtctc cggcggcaag    3180
atctcgctga ccgccgaggc cgagacccca tacgtcgtga ccaagggctc cgagaagcag    3240
atctccgtca gtggagcga aggcatgcac gtcgtggacg ccggcttcaa cggcggccag    3300
aacaccctca aggacaactg gccgtctcc ggcaccggca aggccgaggt cgaaggcacc    3360
aacaacgcca tgctgcgcct gaccggtgac gtgaaggtct cccagaagct caccgacctg    3420
accgcgggca agcgttacgc gatctacgtg ggcgtggaca accgcaccaa ctccccggcc    3480
aagatcaccg tgaccaacgg caccaaggtc ctcgccacca cgagaccgg caagtcgatc    3540
gccaagaact acatcaaggc gtacggccac aacacgtact cgaacactga aggcggcagc    3600
agctacttcc agaacatgta cgtgtggttc gtggctccgg aaagcggcga cgtcaaggtg    3660
acgctctcgc actccggcgc atgcgacaac accgaccatg tgtacttcga tgacgtgcgc    3720
gtgcttgaga acggttacaa gggcctgacg ctcaacgctg acggcaccct gaagacgctc    3780
accaacgact tcgaggacaa tgcccagggc atctggccgt tcgtggtctc cggctccgaa    3840
ggcgtcgagg acaaccgtat ccacctgtcc gagctgcatg acccgttcac gcaggccggc    3900
tgggatgtca agaagatgga cgacgtgctc gacggcaagt ggtccgtcaa ggccaacggc    3960
```

-continued

```
ctgatccaga agggcacgct gatctaccag acgatcccgc agaacgtcaa gctggaaccg    4020
ggcgagacct acaaggtgtc gttcaagtac cagtccggct ccgacgacat ctacgccatc    4080
gccaccggtg acggcgagta caacgccagc accgtcaagc tcaccaacct gaagaaggcc    4140
ctgggcgagg acggcacggc cgagttcgag atcaccggtt ccatcaccgg cgacagctgg    4200
ttcggcatct actcgacctc caccgctccc gacctgcaga acacgtccga ttccgccgcc    4260
aacttcggtg gctacaagga cttcgtcctc gatgacctga aggtcgagca cgtggcatcc    4320
gccgagcaca ccaaggccga cgccgaggcg aagctcaagg aagtcaagga cacctacgac    4380
ggcaagagcg gcgactactc cgccgaagtc tggaccacgt acgtgaacac ggtggccgag    4440
atcgaggcgc tcatcgccaa ggataagccc gactacacca ccgcctacaa caaggctgtg    4500
gcgctggccg agtacatgaa gaacgcaccg ggcgacgact cgaacgatgc gtacgacgtg    4560
gcgaccgacg cctacaccgt cgaggcgggc agccagcagg cactgtcggg cggcaatgag    4620
ggcccggcaa gcctcgccca ggacggcaat gccggcactc actggcacac ctcctggagc    4680
gccaacgcag tgtccgccgg taccgcctgg tatcagttca acctgaacga gccgacgacc    4740
atcgacggtc tgcgttacat ggcccgcagt ggcggcgcga acgcgaacgg caagatcaag    4800
aagtacaaga ttacgctgac gctgtccgac ggcaccacca aggacgtcgt caccaatggc    4860
acgttcacca cgaccagcgg tgtctggcag aaggtcaagt tcgacgcggt caagaacgtc    4920
accaaggtgc gcatcaccgc tctcgaaacc gcgggacagt ccgcgggcga ggtgaacacg    4980
tacgcctccg ctgccgagct gcgtgtcacc acggttcgcg acgtgccgag caccgaggtc    5040
aaggtcaaca agtgcgatct gcagaacctg tacgatgacg cttccgccct gaccgaggcc    5100
acctacaccg ccgacacctg gaaggtgctc gtcgccaagc gcgacgccgc caagaaggtg    5160
ctggacgacg agaacgccac cgcgcacgac gtggctctcg cctaccagaa cctgaaggat    5220
gccatcgccg ccctggaaga gcgcgtggac acctccaagc tcgccggcct ggtcgccgat    5280
gccgagaagc tcaaggaatc cgcgtacacc aaggattcgt gggccgcgtt caagaaggct    5340
ctggatgccg ccaaggccgt cctgaacaat gcgaacgcca ccaaggctga cgtcgatgcc    5400
gcgtacaacg cgctgaacgc cgcgatgaag gccctgaagc ccgcctcctc caagccgact    5460
ccgaacccgg agacgaccga caagagcaag ttgcaggcca ccatcgatca ggccaaggcc    5520
ctggatctga gcggttacac gaagaagtcc gcccaggccg tgcgtgacgc cctcgccaag    5580
gcccagagcg tcctcgccga tgacaacgcc acccaggctg acatcgacgc cgcgcagaag    5640
gccctcgctg acgcgatcgc cgcactggag aaggccgatg ccaacggcaa cgccatctcc    5700
aagacgggtg cgaacgtcgc cgtcatcggc atggccggca tgatgctggt cgccgccgct    5760
ggcgcggtgt tcatcgcccg caagcgcgcc gagtga                              5796
```

<210> SEQ ID NO 30
<211> LENGTH: 2604
<212> TYPE: DNA
<213> ORGANISM: Bifidobacterium bifidum CCOS 571

<400> SEQUENCE: 30

```
atggtttcgc cacatcatct tttgaagatt gcgactgcgc tgtctgcggt tgcgttgacg      60
gcttccgttg cggttacgcc ggcttacgca ttgcaggata ttgcgattga ggatgctgtt     120
gcacagagcg gtcccgttac tgcagataat ggcgttgttg tgcagtctga cgatcagtct     180
gacgatcaga cgggcgacca gcagtcgcaa gacggcatgc tgacaatcc gaatgcgaaa      240
cttccggata ccgtcagtga cgagatttcc gacgatgcca ccgtggtttc ggaagacctg     300
```

```
gccgttaccc ccgaaggtga ggtcaagaat attgaaaccg gcgaaaccgt gaccgatgcg    360
acactggtcg gtacgcagga tcagcagccg gatccgctcg ccaaaaccaa cggcgaatcc    420
ttcattccgg taagtgcgga agatgtcaaa aatgctgtag ccgacgcgaa cgtacagctc    480
tccaaattcg aaggcaatga atacggcgcg cactggggca cttacaacaa tacgaaagcc    540
ttcttcgact accagaacaa cctgttcgtg cagcaagcca aaggcgtgat cgacgtttcc    600
gaatggcaag cgacatcga ctgggccaaa gcgaaagccg acggcgtgga aggcgtgatc    660
atccgcctcg gctacggttg gggcaacaat gctgacagga aagcacaacg taacatttcc    720
gaatgcaagc gacttggtat cccgttcggc atctactggt attcctacgc ggacactccg    780
tcgattgcca aagaagaagg tgccggcgtg gtcgccaaac tcaagcgatt cggtgtgcgc    840
gcgagcgact ggcgtaccc cgtgtactac gacctggaaa agtggacgtg gaaggggcat    900
cagccgccca ccgatccgaa cgtgtacagc gatatcgtca acaattggta cggcgcgctg    960
cagtccgccg gatacaagaa cctgggcgtc tactcgtaca ccagctacct gcaaggcccg   1020
ctgaaacatg ccgacattta cgccaaaacc acgtgggtgg cgcagtacgg cgctcgcatg   1080
ggattcgact cgttcccgac caacagtcgc ggatggcaat acaccagctc cggcaaagtg   1140
ggcggcatca ggggcaatgt ggatatgaat gcgtttggga ataaggagta tgtgaatggc   1200
gggagtagta atgatttaca agcggccatt gatgtacgca aaatgactgc agttaccatt   1260
ccgaatggca attattacat caatgttcgt tccaaagtcg cgtccagtgt tgatgttcct   1320
ggtggaagtg ctgcggattc caccgccatt cagttgtatt ccggcaacag ttccaaggct   1380
cagcagttca cttttactag gcagtctgat gggagctacg agatcgtcaa tgtgaattcc   1440
ggcaaggctt tggacgtgcg taatggtgtt gctgagaata cgctgtagt gcaacagtat   1500 tctcgaaata attcccaggc tcagcgatgg tttattcgtg attccggagc gggatcttat   1560
ttgcagtccg ctctcggtaa ttgggttctg gatttgagtg gcggaaatac tgcgaatggt   1620
gctgcgattc ggctgtatgc gccaaatggc actgcttcac agctgtttgt tgtttcgtca   1680
agcgatgcca gtatagctac tggagtgtcg atgattatca cttcggttgc gaataaaaaa   1740
cttgtcacga atgtgacggg tgcgtcaacg gcgaacgggg cgcgagtcca gcttgattca   1800
agtaataata cgaacgccca gaaatatcga tttgaatcaa tcggcaacgg aacttacaag   1860
attatcaatg ctaattcagg caaggtgctg gatgtggctg gcggatccac tgctgatgga   1920
gcggcattgc agcaatatac gagtaacaat actgttgctc agcagtggac agtgcggaat   1980
tacggcagcg gcaggattgc gctggtgtcg gtgaacgcca acaaagctgt cgatattcca   2040
ggtggcaatg ccgtgcagca ggctcagctg cagctttatt cgccgaatgg cactgttgct   2100
cagcagtggt tggtcgcaaa ggcgccgttg acgttgcgcg aacgtttgaa cgaaaccgca   2160
gccaagcata ggcaggatct gccggatggc acctacacgt tcggatcgaa gcttaatacg   2220
tccatgaaga tggatgtaag cggcgcttcc cgttcaaatt atggaaacgt gcagatctgg   2280
gcgggtaatg gaaccaatgc tcagaagtgg aaagtgacgc atgattccaa cggatacgtg   2340
accttgacca gtgtgaactc cggcaaagtg ttggatgtga atggcggcgt atctgccaac   2400
ggaaccaacg tgcaacagta cgattccaat ggaacatacg ctcagaagtg gatagcagtc   2460
aaaaactccg atggctcata cacgttccag tcggcgctcg cggaaaacaa agttcttgat   2520 gtttcggggtg cttctacctc gaatggtgcc aatgtgcaac tgtataccgc aaatggcacg   2580
aatgctcaaa agtgggtgaa atag                                          2604
```

```
<210> SEQ ID NO 31
<211> LENGTH: 2337
<212> TYPE: DNA
<213> ORGANISM: Bifidobacterium bifidum CCOS 571

<400> SEQUENCE: 31
atgtcattcg atctcattcc ggaaccgcaa tccgtgacat tgaaagggga tgccgccgat      60
tcggatgatg ccggagctcc ggtacccgtc gcgttgccgc tcgtaggccg catctcggaa     120
gatcgcgaca tcgatgacat cgccggcgtt ttcccgaccc agcttgccga tgatatcgaa     180
gcggcgacgg gcctgcgctg gacatcgcc agcgatgtca tggtggccgg actgccgcg      240 ccaaatgccg cgattgcgca cccggttccg ccacacgctt catgctggaa gtcgttcatc     300
acactgagac tcgaccccc atccctggag ccgcaggaat accgctgac catcgcacgc     360 tccggcatag acgtcgtcgg cggcgatacg gaaggcgtgc gcaacggcgt gcagacccttt    420 cgccagatca tccgtcagtg cgcgccggcg ctgcctcgac tcgtcatcgc ggacaaaccg     480
gcgtacaagg tccgcggcta ctatctcgac gccacgcgcg gccgcgtccc cacgctcgac     540
tggctgaaaa catgggccga ccggctgtgc ctgtacaagt acaaccagct tcagctatac     600
atcgagcaca cgttcatgtt cgacgatctg agcgagactt ggcgcggcac cagcccgctc     660
aagcccgccg acatcatcgc gttcgacgaa tactgcgcgc ggctcggcat cgagctggtg     720
ccgtcggtct cgactttcgg acaccagtac atggcgatgc gcacgcgcga gctgcgccat     780
ctcggcgagt ttcccgagga cgccgaccgt cggtacggtt tcgtggagcg cagcgtcac    840 cacacgctca acatcaccga accggagtcc ctcgcgttct cgttcaagct gatcgatgct     900
tacatgcagc tgttccgcac acgcaagttc aacatctgcg gcgatgagac gttcgacttg     960
ggtcgcggcc gttccaagcc cgaagccgaa cgccgcggcg tggccgcgat gtacgccgac    1020
ttcgtatcgc agctgtgccg tcacttgtct gagcgcggcc gcgatccgat gttctggggc    1080
gacatcgctg tggagatgcc gcagatcctc ggcctgttgc cggataacgt cacgctgctc    1140
aactggctgt acgcgccggg catcggcgaa gacaaggtac gcctcgtcgc gcaggccggg    1200
gccccgcagt acgtgtgctc ggcggtgtgg tgctggaatg cgctgctgcc gcgcctcgac    1260
gactcgtgga caacatctc ccgactcgcg cgctacggcg tgaagtacgg tgcggtcggg     1320
tacctggtga ccgactgggg tgattacggg catgtcaacg acccgcgcat ggcggtttcc    1380
ggcatgatat tcggcgcgca gtgcgcgtgg aatccgatgg ctcatatcca gggtgaggcc    1440
gggtgcggcg acgcgaaga aggctctgct gccggttatg ccgatgccgc cgccgatgtc    1500
gtccgcgaga acaaggccgc cgcggacggg gattccccgg cgccgctccc gtcgagctcg    1560
gaaagcgacg attaccggg tggcgcggcc gacgcgattg cggcgcgcc ggccggcggc     1620 gatgggtcgt gtgccgagat gtgccgtcgc gtggccgagg tcgaatacgg cgaccgttcg    1680
ggcggcatag tcgaggcact gcgagatgcc gcctgtcgtg tggcgttcgg ctgggatgac    1740
atggtctggt actgcgagct ggatgaaggc gacgacggg tgaatcgcga tgccgcatcg    1800
gcgatgcatc tcggcgtgca tgggttcagc ggggaatacg ggcgggagtg ggaggcccga    1860
ctgctgggca gtgccgatct tgatgaggct cggcgcacga tgctgcaagg gctgtcgccg    1920
catatcgtcc gcgcggccga ggcgaacgag gcgctgctgt gcgacgccat gcgactcggc    1980
gccgccgccg gtcgcgcatc gcgtttgggt gcggctcggc gtgatgtgcc ggcgatgctg    2040
gccgccatcg aggggcagcg ctggttcaac ttggtcggct tgtgccttgc gcggcggcat    2100
gacgtcatca cggtcgatgc cggcgatatc gcccgcgcgt cggccggatt gatcgaaccg    2160
```

```
gacgcaggct cttccgcagg gccggaagcc gtgcaggatg tctcgattcg agtggcacgt    2220
ggtctggagc gctggttcga gacctactgc gacttgtggc gttctgtcag cgcggaatcg    2280
gaattggccc gcatcgcctc catcgtgtgg cgctgtgccg acgccctgcg ttcataa       2337

<210> SEQ ID NO 32
<211> LENGTH: 915
<212> TYPE: DNA
<213> ORGANISM: Bifidobacterium bifidum CCOS 571

<400> SEQUENCE: 32
atggctgata gattcggagc tttctgcct cacgacacct cgggcgacgt tgcccagctg      60
cacggcatcg gtctgcaaaa attcggcgac acctggtatg catatggcga gaacaaggta    120
aacggcaatt tgttccaggg cgtgtgctgt tatacaacca ccgatttcat cgcatggcgc    180
agccacggca tcgtacttga tgtgcaagaa gacggctccg ccctcgccgc tgaccgtatc    240
ggcgagcggc cgaaggtgct gcattgcccc gccaccggca aatatgtcat gtatattcat    300
gccgaaacgc ccgactacgg atacgcgcac atcgcgtcg ccgtgccga cgccccaacc      360 ggcccgttcg cattccagac caccatcacg tggcgtggct acctgagccg tgacatcggc    420
gtcttccagg acgaggacgg cagcggctac atcatgagcg aggaccgcga ccatggcacg    480
cacatttacc gtctcgccga cgactacctc accatcgtcg aggacgtcgc ctgtgagcgt    540
gccaccgact acccatacgg cctggaatcg ccgaccatca tcaagaagga cggcctgtac    600
tactggttcg gctcgcaact gaccagctgg gacaccaacg acaacaagta ctccaccgcc    660
accgacctgc acgcccgtg gagcgagtgg aagctgttcg cgccggaggg tgcgaagacc     720
tacgattcgc aggtcgatat cgtggtgccg ctggacgacg acccgtacaa cagcgagcac    780
ttcctgttca tcggcgaccg ctggcaggag catgacctcg gcaactcgcc gatcgtacag    840
atgccgattt ccatcgccga cggcgtggcg tcgctgacgt ggagcgacac ctacgagggc    900
accacccacc gctga                                                     915

<210> SEQ ID NO 33
<211> LENGTH: 1905
<212> TYPE: DNA
<213> ORGANISM: Bifidobacterium bifidum CCOS 571

<400> SEQUENCE: 33
atgatgcaat tcaccatgtc cggaaccatg ctgcgcttcg atgagacgac gctgcggttc      60
tcattcagcc gcgacggtgc gacctggagc ggctgcgacg gcatagagcc gcagctgacg    120
cgcgaggatc gttcattctc gttcgccggc gccgctaccg tcacgcatga gcggatcgag    180
accggcaccg gagtcggcgt gcgcagcgtg ttcgccgggt tcgcgggtgc ggattacgct    240
tttgagacgt atatctggat cgagcggtcg agcggcgacg tgctatgcga atgggtgcca    300
ctgcgcgagt gtggggccga gccgcgcatc gacaggggtgc tttggcctgc gccgctgtcc    360
ttcgaccatg cggacgcgca tgacgtgacg ctcatcaccc acgagcaggg cgtgatgata    420
ccgaataact ggcctaccga ggtcggcact gatgcggtct ccttcggcgg gcggttcgag    480
actgcgggcg ggtacatgcc ctggttcgcg cagttgcgca gcgacgggca tgcgtacatc    540
gccatctgcg agacgccatg gaacgcagga tatgacatcg accatccggc cggcggaccg    600
tacacgcacg tcggaatgtg gttcgagcca agtctcggcc gcatggatta ccgtcgtgtc    660
gtgcgatatc gtctcctcga ccacgccgac catacgccg tctgcaagac gtaccgcgct    720
tacgtcaacg aacgcggccg gctgcgcacg ctggcggaga aggcggcgcg caacccgtcg    780
```

```
gtgcgtgacc tgctcggccg ttcatgggtg catgtcggca tcaagacgaa ggttcagccg      840
gactcgtcgt tctatgatcc cgcgcagccc ggcaagaatg attcgctcgt cacgttcgcg      900
cagcgcgaac ggcagatgcg cacgctgcac gaaatgggtg ccgggcggct gtacctgcat      960
ctggacggct gggcgcagcc cggctacgac aacggccatc ccgactatct gcccgcatgc     1020
cgcgaggccg gcggctggaa gggcatgaaa tcgctggtcg acgcctgtca tgagcaggga     1080
gacctgttcg gcacgcatga ccaataccgc gactattact tcgccgcgcg cacgttcgac     1140
ccgcgcaatg cgatccgact ggcggacggc acgatgcccg agcacgcgat gtgggccggc     1200
gggcgccaaa cgtacctgtg cgccgagctt gcgccggatt acgtgcgccg caacttcagt     1260
gagatcgcca cgcacggcat cgcgctggac tgcgcgtatc tggacgtgtt cacctgcaat     1320
gaaggcgacg aatgctcgca tcccgagcac cgcatgaccc gccgcggatg ctacgagcgc     1380
cgcgccgaat gcttcgaata cctgctggcg cacggcattc tcacctcgtc cgaggaggtg     1440
tccgactggg cggtgccgag cctggtgttc tgccattacg cgccgtacga cttccagatg     1500
cgctcccccg acgcgcctcg gcacggcatc ccggtgccgt tgtacaacct cgtctaccat     1560
gactgcgtga tccagccgtg gatgatggat cgggtggccg gtggcgacga ctacatgctg     1620
tacgcgctgc tcaacggcgg tgcgccgtac ctgatccgtg acgccgcata tgccggcatg     1680
gacggtgata tgaatgccgc actgcgcgcc cgtaccgaga tgacatcga gcggtgtgcg     1740 gtcgtggccg gctgcaccg cgcgtcggc atgcaggagc tcgtgcggca tgaccttgtc     1800
ggcggcgacc cgctggtgca gcgctcggtc ttcgccgacg caccgccgt gacgtgtgat     1860 ttccacgcgc agacgtatga ggtagcagcg aacggttctc attaa                     1905

<210> SEQ ID NO 34
<211> LENGTH: 3417
<212> TYPE: DNA
<213> ORGANISM: Bifidobacterium bifidum CCOS 571

<400> SEQUENCE: 34
atgcgagcga atggtaattc cacgcatgag attctaggca aaatcgtgac ggccatcgcg       60
tcgatcgcca tgaccgcggc gttcgcggtt ccggccatgg cggccagcga cagcgacacg      120
gcggccgact ccggcacgac ccaacagtcg ggccagtaca agatctaccc ccagccgcag      180
aacaccgagt atggcgacgg cagtctgatt ctgcgcgaca aggcgaacac cgtcgtggaa      240
ccgggaatcg attccgccac caaggcccgt ctgaacgagg ccctgaagct caagggcatc      300
gagaccaccg cggccgacgc cgtgcccgaa accgcgtacc agctcaacgt gctggtcggc      360
atcaacggat ccaacggcgt ggtcgacaag tacgccaagc agctgatcgc cgacggcacc      420
ctgaaggtgg acgacagcac gttctccaag aacgactcct atgtgcttgc cgtccgtcag      480
ggcaacgcga agacgcccga cacgatcctc gtgctcggcc gcgacaccga ttccgcgttc      540
tacggcctga ctaccctgta ccagatcttc agcagctgc cggccgcgc cgtcagcaac      600 ctgaccttca gcgactgggc cgacgtcaag tcccgcggct tcatcgaggg ctattacggc      660
agcccgtgga gcaccaagga ccgcgtgaac ctgatgacct ggggcggcta ctacaagatg      720
aacacctacg tgtacgcccc caaggacgat ccgctgcacc gcaacaactg gcgcggcctg      780
tacaccgaag accagatcga gaacgagatc aagccgcagg ccgaggccgg caacaagtcg      840
aaggtgcgtt tcgtttacgc gctcgcgccc ttccataacg acggcgaggc tagggggcaag      900 cacttccgct tcgacaccga ggagcactac cagaaggacc tcaaggaact caaggccaag      960
tacatgcaga ccattgacgc cggcgtacgc cagatcgcac tgctcgccga cgactccacc     1020
```

```
gactggggtg cgcagtacgg caacgacaac acctacgtgc gcgtgctgaa ggacctgacc    1080
gactggatcc acgagctgca gcaggagaag aacgacgacg gcaccgcgaa gtacgagggc    1140
ctcaaggaca cgatcctcta ctgcccggcc ctgtacagct acaccggagc cggtgacgcc    1200
tggtacaagg acatcccatc caacgtgcag atcgtcatga ccggcggccg caccttcggc    1260
gtggccagca aggacttcgc cgacacgttc accaagaaca ccggtcgcgc cccgttcatg    1320
tggatcaact ggccgtgctc cgacatgaac cgcaacaccg cctaccagta cctggtcatg    1380
ggaggccaga acaacttcct caagcccggc gccacatacg gcacctacga cggcatcatg    1440
ctcaacccga tgcagcagtc cgagccgagc aagcagggca tcttcatggc cgccgactac    1500
agctggaacc tgtggcagag cgaaaaggac ggacaacagt cctgggagga ctccttcagc    1560
tacatcgacc acaactcgcc gatcgcgtcc aagggctccc gtggcctgcg tgacctcgcc    1620
atgaacatgc gcatcctcaa cgacggcggc atcgacggcg ctcacaagga tgccgagtat    1680
gacgccgtca acaagtggtg gatcaacaat gagtccgtcg actacaccgg caagctcgac    1740
gtcaagggcg tcctgaccga actcaagggc aagctggacg gcggcaccgc caccgcggcc    1800
gacttcagcc aggcgctcac cgtctacacc acgctgcagc gcgccgcgaa gaactaccgc    1860
gcgaaccccg gcgacaagaa catgtttgac cagatcgaac cgtggatcag ctactgggac    1920
gacctgaccg cctccgccat cgactacatc accgccgcca gcaggcgct cgcgggtgac    1980 accgagaccc gaaggcgac ctacgcaacc gcgaaggcc ctttcgccaa gtccgacacg    2040
catacgatcg ccgattacta ccagcgcaac aagcccgccc gtggcggcct ggtcatcgtg    2100
cgcccgaccg tgcaggcgct cgattccttc gtcaaggcca agaccagcgg cagcgtcacc    2160
ccgacgccct ccgacgccac ggtcagcacg aacggcgtgg gtgccgcggc atggcatgag    2220
aacgtcgatc cgaaggccgt catcgacggt gacgacagca cgttcttctg gatgcagtcc    2280
gccggctgcg actgtgtcaa ggccaacgcc gccctcaccg tcacctacgc cgaggcccgc    2340
aaggccaagg agttccgctt catccaggcg gaaaaggggcg gtgacacgat cgtcaacggc    2400
aagatcgaat accaggatgc agatggcaac tggaccaaga tcggcgacgt gaacggcaac    2460
cagaagcaga tcttcacgct ggactccgcc gcgaccgtca aggccgtgcg catcaccaac    2520
ttggcccaga cctccaagtg gtggaaggtg tacgacctgt ccgccaccaa gatcgacgaa    2580
cccggtacgg tgaccaagga cgcgctgaac gccaaggtcg ccgaagccga aaggtcgac    2640 tccgccgact ggaccaagtc gagccgcgag gctctcgccg acgcgattgc cgccgccaag    2700
gccgtcgctg ccgaccagga cgccacgcag gccaaggtcg acgccgccgt cgccgcgctc    2760
gaatcggcga tgaagggtgt cgaacggtac acggcgaaga ccgccgacca gctgaaggcc    2820
gagcacgtct ccaacgacga tgccacctac accgaggcga gctacaacaa gtaccagtcc    2880
gcgtacgacg acttcgccgc cgcgctggcc aacgccgacg atctggcgaa ggccgacggc    2940
gaggcgctgg aagcggccta caccgccgcg aagtccgcgt tgcgctacga ccagtccgca    3000
cgcgactacg cgcagctcgc gctgaacgac gccgagcctt acgtgggcaa ggcctccgag    3060
tacaccaagg acagctatgc caagttcacc gtcgcgtatg aggccctgag caagcagctg    3120
aaggccgacc cgaacggcga gggcgatccc gccacctaca ccgcgctgcg cgctgcactc    3180
gacaaggcca tcaagggcct ggtcaagagc gacggcaccg agctggagcg gcctggcgag    3240
aagcccggcg agaagcccgg cgagaacaag cccggcgaga gccgggtgt caacaagccc    3300 ggcgccgacg gcagctgtc caacacgggc gccgacgtct cggtctcat cgccgcgatg    3360 acgatgttgg ccgcggtggg cgtgacgatg gccggcctgc gcaagcggat cggctga      3417
```

<210> SEQ ID NO 35
<211> LENGTH: 5268
<212> TYPE: DNA
<213> ORGANISM: Bifidobacterium bifidum CCOS 571

<400> SEQUENCE: 35

| | | | | | |
|---|---|---|---|---|---|
| atgaaccgaa | gaatatctat | gtggttgcgc | ggtcgtggct | ctccatggag | acctgccgcc | 60 |
| gccgtgatcg | ccacggtatc | catgatgctg | gcgacggtca | tgggccccca | tttcgcgggg | 120 |
| atgcgggcgc | aggccgtcga | gcccgtgcag | accaccacca | tctcgcacac | caagatcgcc | 180 |
| ggcgacggca | actacttcac | gttcgccgac | aacgcctggg | atccgggcaa | cgacgtgcat | 240 |
| acgtggtcca | aggcgccatc | cgacagcctc | ccggcggagg | acatctggta | tacggtccga | 300 |
| ttcttcggca | gcgcaatcga | cgtctatgca | ggcaagaaca | ggcccatggg | caaggtgaaa | 360 |
| tactatattg | acggagcgga | aaaaggcacg | tacagcctgt | acaacgcctc | caacatcaac | 420 |
| gagacgaaaa | tcgcgtcgtt | caccggactt | gacgaaggtg | agcacgtgtt | caaggcggtg | 480 |
| gccacaggcg | agcgggacac | gaattccacg | aacgcgctga | tcgactgcgc | caaggtcgtc | 540 |
| gtgacccatc | agccgtacgt | ggtcaccggc | gtcacactcg | acacgacctc | gatgacgctg | 600 |
| ggcgttggcg | acagcaagcg | gatctcgtat | acggtggcgc | ccgattacgc | gaccatcgat | 660 |
| gacatgacct | acacgagcgg | cgacacgagt | gtcgccacag | tcggcgcaga | tggcacggtc | 720 |
| accgcggtcg | cgccgggagc | caccgccatc | accgtggcct | cgactgcggc | cggcatcagc | 780 |
| aagatcgtcg | acgtcaccgt | cgccaggatg | gcaccgaacc | tgaccggcgg | catcgtggac | 840 |
| cccgatacgc | aatacacgca | gaagcggttc | gacgaggtga | aggccctcac | gacgaacaac | 900 |
| cgggcgctga | agcatggaa | gaacgacaag | gtcaacagcg | agatctcgct | cgccgcggtc | 960 |
| ggcaccaccg | tctcgaacct | gacggtcacc | gcaaacgacc | tgacgtcgca | gggcggcgac | 1020 |
| gtcatcgcca | aaagcaacgt | cacggccacg | ttcatcaagt | ccaccaaggc | atacaacggc | 1080 |
| agctatctcg | gctacggaga | cccgaaccgc | gaggtgcccg | ccgccaccga | gaccaaccgc | 1140 |
| tccgaaagca | acgacatcct | ctaccaaagc | ggcccgatca | cggtgaaggc | caatcaggtg | 1200 |
| cagaacatct | gggtatcgtt | cgccataccg | aaggacgcca | aggccggcac | ctacaccacc | 1260 |
| acgctgaccc | ccaccgcaga | cgggatggaa | acgccgctca | cattcaccta | caccatcgag | 1320 |
| gtgaaggccg | ctacgctgcc | cgatccggca | gagtatgaga | agaacttcga | cgtggaactg | 1380 |
| tggcagtacc | cgtattcctc | cgcggaatac | tacggcgtca | ccccgttctc | ggacgagcac | 1440 |
| ctgcagatcc | tcagatcaag | catggaactg | tacaagtcca | tcggcggcca | cgccatcaca | 1500 |
| accaccatca | cgaggacgc | atggtccggc | cagacctaca | gcgccaacgc | catccactac | 1560 |
| ccgtcgatgt | tgaagtggac | caagagcggg | ggcgggttca | cctacgactt | caccgacttc | 1620 |
| gacaagtggg | tgacgttcaa | caagggactc | ggcatcggcg | acaagatcgt | gatatacagc | 1680 |
| atcgcgccct | ggcacggcaa | cttcacgtac | tgggagaacg | ggacgatgaa | gtccgagaaa | 1740 |
| tacacggtcg | gatccgagcg | ctggaggagc | gtgtggaccg | acttcctgcg | caagctcatc | 1800 |
| gagcatctga | tggacaaggg | ctggttcgac | gagtcgtaca | tcggcatcga | cgagcgcggc | 1860 |
| ttcagcgccg | acgcgttcga | cctgatcgac | tcgatacgga | atatccacga | cgtgccgttg | 1920 |
| aagaccgccg | gcgcgatgga | cggcttcgtc | aacaagttcg | acctggcgct | gcgcgtcacc | 1980 |
| gacctgaacg | tcggcgacac | cgccgcggcg | gccatcccca | ccgacttcac | ccggctgatc | 2040 |
| gaggcgcgtg | aggcaaaggg | ccttcgcacc | acgctgtact | cctgcaccga | gcatgagccc | 2100 |
| ggcaacttct | cgctgtccgc | cccggtcgaa | agctactggt | cggtggtcaa | cgcggggcgag | 2160 |

```
cagaccagcg gcttcctgcg ctgggcgtac gacgcatggg tggccgaccc gctcaacgac    2220
gccacgcaca acgccttcga gcccggcgac ccgttcctga tttatccgag cgagaagagc    2280
ggagacaagg tgtccaagtc gtccgtgcgc ctggagcgca tcgccgaggg cgtgcgcgac    2340
gtgaacaaga tcaggctcat ggtcaccgag atcccctcgc tgcaggccga tgccgacgcg    2400
atgtacgcga agatcagaac gacggtgacg acctcgcact cgtatctgac cgccgcgcag    2460
gtcacgcagc ttgccaatga gatgagcgga ttcaagggtg acctcgacac gctcaccgac    2520
aagtacatat ccctcaaggc gcaaggcaca agcacggtgg aatccgttgc catcgacggc    2580
ggcgaccagg agatcatgct gggcacggcg aagcagctga ccgcgacact caagccggcg    2640
aacctgctga acgcgtccgt gacatggcgc tcgtccaaga ccggcgtcgc cacggtatcc    2700
gccaagggcg tggtgaccgc cgccggcgtg ggctccacca cgatcaccgc cacgtccaag    2760
gccgacccga cgaaatcggc gagcatcacc ctcaccgtga cgccacaggt cgtggcgcag    2820
gggctgcact actactcgtt cgacgactcg aacgccaacg actcctgggg cacccgcaac    2880
ggcaccgccg acgccacggc gcaatacgtt gacggcaagt ccggcaaggc gctcaaggtc    2940
acggacggca aaggcgtgac cctggccggc ggcaacgaca tcgcgaagac ggatccgtgg    3000
acgatcggct actgggtgcg ttccgacgcc gaactcaccg gccgctcggc cgtgatgacg    3060
agcgcggacg gcaagtactc ggccgacctc aagatggacg ccgaccgcga atctggcttc    3120
cgtgtcggca ccgccagcgg cgacgtgctc accttccggt acgacttcca gccgggcacg    3180
tggtattaca tcgcgtggac tcaggacaag gcagccggac tgaccatgta cgtcaacggc    3240
acgaagatcg gcgtgacgaa cacgtggacg aagatgcacg atgtcgtcgc cccgatcgac    3300
gtgatcggcg gccccggctt cactggcctg atcgacgagg tgaagatcta caagcgcgtg    3360
ctctccgaca ccgagatcgc ggccggcatg ctgctgcccg gtctcaacct cgccgagcat    3420
gagaccgata tgtacatcgg cgggacgtac accatcgtcg ccaacctgca gggcggcgac    3480
ggcgatggta cagtcacgtt cgagtcgagc gaccccgacca tcgccaaggt cgacgcctcc    3540
ggcaccgtta ccggagtgtc ccgcggaacg gcggtcatta ccgtccgggg aggtggattc    3600
accgacatgg tgaccgtcaa cgtgagccgc gaactcacca tcaagaacac gctgccgcag    3660
tacaagctcg accagacgaa ggtcacggac gtgcacaagt cactcgacac gtccaaccag    3720
tacttcggcc agcccgacat gatccgcacg aagagcggcc gtctgatcac ctcgttcccg    3780
caagggcacg gcaagggacc gttgatcatg aagatcagcg acgacgacgg cgccacctgg    3840
acgcgcaaga ccgacatccc cgcgtcgtgg gccggttcgc aggagacgcc gaccctgtac    3900
gtgctcaacc tggccgacgg caccgaacgc atcatgatga tcaccgcctg cccgggctgg    3960
ggtaccgact ccgccggcaa caggtacgga tggaacacat cgtattccga cgacaacggt    4020
gagacctgga ccgaataccg gcactggcag tccaaccgca cgtacgacaa cgccaacaac    4080
gacgccatcg tcgccatggc gagtctcgtg cagctcaagg actccgacgg caacgacatc    4140
cagaaatgga tgggcgtcta ccacaactac gcgtacgtca atttcaggac gtacctcacc    4200
ttcgacgaga acggcgacga gcagtggagc gaatcggagc cgtatcttgc gcaatggcgc    4260
agcatcgaaa gcgcatacca gatgtgcgag atcggcatgt tccgttctcc cgacggcaag    4320
cggatcatcg gtctggcgcg cagccagtcg cacaacaacc cggcgacact gatctactcc    4380
gatgatgagg gtgagacgtg gagcaagccg atggatctgc ccggctcgct ggcgggcgaa    4440
cggcacaaga ttgcctacga tccgatttcc ggccgtctgc tggtcacgtt ccgcgagatc    4500
aactacgatc tcaacggcaa caaccggttc gacggcggca acgactggaa cgccggcgac    4560
```

-continued

```
tgggtggcct gggtcggtac ctacgaccag ctcattaacc aggaggacgg cgaataccgc      4620
atcctgctgg ccgaggactg gacgagcaac gcgaagtcgg gcgacaccgg ctacgcgggc      4680
gtagcggtgc tcgacgacgg tacgttcatc atggacacgt acggtcactg ggacaaggaa      4740
ttctcgcaga actggcccgg cggcgtcacc accgaccgct gctatatcaa gcaggcgaag      4800
ttcaagctcg gcgaggtcga atacgcgaac ggtctcatcg accgcagcgg actgaaggcg      4860
gcaatcaagc gggcagaggc gctgaatgcg gccgactaca cggctgactc gtgggcgaag      4920
atggatgccg cagtgaaggc cgcgaaggcc ggagacgccg acgattccct gcaacaggcg      4980
caggttgacg cgctcgccgc cgccatcgat gcgccatcg acgggttgaa ggccaaggat      5040
gacggtgaca agcccggacc gggtgatggt ggcaagcccg gcgcgggtga cggcaagcct      5100
gacgacggcg gcaagcccga tcccggcaag ccgggcaagg gcgacgagac caagcccgat      5160
accggcaaga agggcgggct gagcgccacc ggtgccggca tcgttccgat cgccgccgcg      5220
gccctgacgc tcatggccgg tgcggcgctc gcactggcca agcgctga               5268
```

<210> SEQ ID NO 36
<211> LENGTH: 4884
<212> TYPE: DNA
<213> ORGANISM: Bifidobacterium bifidum CCOS 571

<400> SEQUENCE: 36

```
atgcgattga ggagagtgaa agcggccata ggcagtgtcc tggcagccgt gacactactg        60
agtatgtcgc tgaccggcgt cacggcggcg caagccagcg atgacaatct tgcactgaat       120
cagaccgtaa cggccagttc atatgaagtg gcgacgactg cgcccgagaa ggccgtggac       180
ggcgatctcg gcacacgctg gggcaccgcg cagaacaagg ccgcaaacga atggatcgag       240
gtcggcttgg gcgcaccaa gaccgtcaag cagatcaaca tcgatttcga gcgcaaagat       300
gccgatcaga acatcaccag ttttaaagtc gagctgaagc agggcgacac ctataccaag       360
gtgtatcaga aggacacccg cgccaagcaa caggagatca tcctgcttga ccaggcacag       420
caggcgtccg ccgtgaaggt gaccgtactg tccgccgacg gcggcaccat gaactgggtc       480
aacgtgggca tcaacgagat ttccgtgtac tccgcaccca aggagaccgt gctcgacacg       540
gccgacacga accacatgct cggcgccacc atgaccgcct ccagcaacga gacggcgacg       600 ctcaccccg caaggcgat cgaccagaac cgcaccggcc gcaacaaccg ttgggccagc       660
ggctacgaga ccccgagcaa catctggctg aaggcggaat cccgcggct caccgcggtc       720 aaggacatcc gcatctattt cttcgagcgt gacgtgaatc cgaagcctac caatgtccag       780
agcttcgacc tgtcctacac cgactccgaa ggcaccgagc acacgctcaa gtccggctac       840
gcgatgacgg cctccgggac cggttatgtc gctgacgtcg tcatccagct cgatcaggcc       900
gtcaacgccc gctcgctcaa gctgtcgaac ttcgcgatca aaagctccga atacaacaac       960
gtgagcgtcg ccgaatggga ggcgtattcg aacgatcagg ccgagccggg cgccacgctc      1020
gacagcgtgg tctccgacct cgaatccaac cacctgacca tcgagaccga caccgacacg      1080
ctggctctgc ccactgtgcc cgacggctac accgtcaagt tcaacggcgc cgactacgag      1140
cagctcatcg ccgccgacgg caccgtcaac caccccgctgg tcgacaagac cgtgcaggtc      1200
gcctacgtcg tcaccgacac cgccaccggc aacaccaaga cgacctccga catcccctac      1260
gtcgtcaaag gcaccaacca gcagcaggaa ggcaacaacg ccaagccgac catcatcccc      1320
gaaatcgccg aatggcattc gaccagtgcc gccaagctgg cggcctccgc cgtgacgaag      1380
gtcgtctacg acgatgattc gctcaaggcc gtggtcgacg agttcgtcgc cgactacaag      1440
```

```
gacttcaccg gcatcaagct gaccgccaag aagggcgccg ccgaagccgg tgcgttcaac    1500
ttcgtcaaga ccgactccac ggccgcgatc gcgcagctcg gcgacgaagg ctacacgatg    1560
gacatccggg ccgaccgcgt ggtcgccaag tcgtccagcg tgaccggcaa catgtacgcg    1620
atgcagacga tcctgcagat gaccaagcag gacgccagcg gcttcgtgat cggttcgatg    1680
cgcgactacc cgcgcttcac cacccgcgga ctcctgctcg acgtggcccg caagcccgtc    1740
tcgctggaga tgatgcgcga gatcacccgc acgatgcgct actacaagat gaacgacttc    1800
caggcgcatc tgtccgacaa ctacatcttc ctggagaact acggcaaggg cgacaacgag    1860
gacgaggcgt tcaaggccta tgacgcgttc cgtctcgaat ccagcctgac caacgacaag    1920
ggcgaatcgc ccacggccga ggactactcc atctccaaga agacgttcaa gcagttcatc    1980
caggacgagc gcgccctcgg catgaacgtc gtgccggaga tcgacgtgcc cgcgcacgcc    2040
aactccttca cgaagatctg gcccgagctc atggtgaagg acgggtctc cccgatcaac     2100 agcaaccgac cgctcatcga ccacctcgac gtgtccaagc ccgagaccat cgccaagatc    2160
aaggagatct tcgacgacta caccaagggc gacgacccga cgttcgacag cgacacgacc    2220
gtgcacatcg gtgccgacga gttcctctac aactacacgg cataccgtaa gttcatcaac    2280
gagatcgtcc cctacatcaa ggacacgaac accgtgcgca tgtggggcgg cctgacttgg    2340
atcaacgacc acaagacgga gatcaccaag gacgcgatcg agaacgtcga gatgaacctg    2400
tggtccaagg actgggccga cggcctccag atgtacaaca tgggctacaa gctgatcaac    2460
acgatcgacg actacggcta catggtgccc aacggcagct acggacgtgc caacgcgtac    2520
ggcgacctgc tgaacatcag ccgcgtcttc gacagcttcg agcccaacaa gatccgcagc    2580
agcggcggct accaggccgt gccctccggc gacgaccaga tgctcggcgc gcgttcgcg     2640 atctggagcg acaacatcga caagagcgca tcgggtctga ccgaatccga cctgtactgg    2700
cgcttcttcg acgcgatgcc gttctacgcc gagaagacct gggccgccac cggcaaggag    2760
aagggcaccg ccgcgaaact cacggcgctg ccgccaagc agggaaccgg ccctcgcacc     2820
aacccgtact accaggccac ttcgaagaac agcgtctacg agagctacga cttcaacgac    2880
gggctcgccg acgccagcgg caacggccgc gacctgacca tcggcgacgg cagcaaggcc    2940
gccgtcaagg accagtcgct caagctcgcc ggcggctcca gctatgccac atccaagctc    3000
gacaagctcg gcaacggcaa cgagctgacg ttcgacgtga cgctccagca ggctgccaag    3060
cccggagaca tcctcttcga ggccgacgct ccgtacggca cgcatgacat ccgcgtcatg    3120
gagaacggca agctcggctt cacgcgagag ctgtacaact actacttcga ttacgagctg    3180
ccggtcggca agacggtcac cgtgaccatc aaggtggacc agcagaccac gaagctgtat    3240
gttgacggcg aattcgtgag cgacgcgacc ggcaagtaca tcgacaaggg catcgagaag    3300
aagaccggca tcaccgccgc gaccttcgca ctgccgctgc agcgtatcgg ctcgaagacc    3360
tctgcgatca acgcgtcat cgacaacgtc atcgtcaaga agtccgaggc cgagacagac     3420
cagtacaaca agtcctgctg gaccggcacg accaattccg agacccaata caacgacacg    3480
gaaggtctgc tgcggtacgc gttcgacaac aacccgagca ccatctggca ttccaactgg    3540
aagggcgcca cggacaagct gaccggttcg aactcgttct acgccgagat cgacatgtgc    3600
cagaagtaca cgatcaacca gttctccttc acgccgcgta ccagccagga cagcggacag    3660
gtgaccaagg ccgatctgta cgtcaaggcc aacgcgaacg acgagtggaa gcaggtcgcc    3720
acggatcagg tgttcgaggc cagccgcgcc aagaagacct tcatgttcga cgagcaggaa    3780
gtgcggtacg tcaagttcgt ggccaagtcc tcgaacgatg gctgggtcgc ggtctccgag    3840
```

```
ttcggcgtgg cgaacaagcc gtcctccacc gtgcgcgtat cgtcgcggc cgatccggcc      3900 gaaggcggta cggtgagcgt agccgccgag ggcgaaaccg gcaccgatac ggccgtggac      3960
gtcgcatccg gtgcctcggt gaccgccaag gcggtcacgg cggatggcta caggttcagc      4020
ggctggttca cgacgccag tgagacggcg gtttccaccg atgccacgta cacgttcgca       4080
gccgacggca acacggctct gaccgcgaag ttcaccaagg actccacgcc ggatcccggc      4140
ccgaagccga ccatcagctc gatcgccgtc accaagccga ccgtcaccga ttacaaggtc      4200
ggcgacacgt tcgacgccac tggactggcg gtcaccgcca caatgtcgga cggcagcacg      4260
aagaccctga cggccggcga gtacacgctc tcagccacgc aggacggtgc gcgcgtcgcg      4320
cttgacaagg cgttcgccaa ggccggaaag gtcacggtca cggtcaccgc caacggcaag      4380
accgccacct tcgacgtgac cgtgacggcc aaggatcccg atccggaacc cgcgacgctc      4440
aagtccatca aggtcacgtc caagccggac aaggccacgt acaccgtgga tgagacgttc      4500
gccaagaccg tctcgcggt gacgggcacc tggtccgacg gcaagacggc gctgctgaag       4560
gacggcgaat acaagctgtc cgcggtcgac gccgacggca agaccgtcga cttgaccaag      4620
ccgttcacgg ccgcgggcga cgtcaccgtc acagtgacct ccggcaagct caccgactcc      4680
ttcacgatca ccgtcaaggc aaagaccgtg accccgactc ctggcgacaa caagccgggc      4740
gagaacaagc ccggtgccga caagccgaag ccgaacacgc ctgacgaggt cgccaagacc      4800
ggtgcttcgg tcacgcgcgt cgtcttcagc gccctgttgc tgttgtccgc aggctacctg      4860
ctggtgcgta agcgcaggat ctga                                              4884
```

<210> SEQ ID NO 37
<211> LENGTH: 5883
<212> TYPE: DNA
<213> ORGANISM: Bifidobacterium bifidum CCOS 571

<400> SEQUENCE: 37

```
atgcgcagca aggcattagg aggcctgctt gccgcggctc tgtcgttgag cccggcagtg        60
gccatcggcg tgcagacggc gtacgcggca ggcggcgata cggcggcgac cgaatacacg       120
ctgtacccca agccgcattc gatccgttat gacagcggac agtacattct tcgcgacatc       180
aacgtcatct atgacgatga catcgatgaa gccacccagg accgactgga cgaagtggcg       240
gcgctcaaga acctgaacgt caccgaatcc gacgccgcag tcagcggcaa gaccaacgtc       300
tatgtgggcg tgaacggttc cgatggcaag gccgagactg ccatcgaaag caagtacagc       360
ccggattccg ccatcttcga caagaccgac tcatacttcc tcaagtccga caacggcacg       420
atctccgtgc tcggcaaaga caccgacgcc agcttctacg gcctgaccac cctgtaccag       480
gtgctcggcc agatcgatag cctgacgatc cgcaacttca ccgtcaccga ctacgccgac       540
gtggtcagcc gcggtttcat cgaaggctac tacggcaacc cgtggagcac tcaggaccgc       600
atcaacctga tgaagtgggg cggctactac aagctcaact cgtacttcta cgcccccaag       660
gacgatccga agcacaactc gcagtggcgt acgctgtaca cgcaggacga gctcgacacc       720
aagatcaagc cgctcgccga tgccggcaac gcctccaaga cgcgtttcgt gttcgctctg       780
cacccgttca tgaacaacgc gattcggttc aactccgagg cgaactatca ggccgatctg       840
aaggtgctgc aggacaagtt cgcgcagacc atcgggtcg gcgtacgcca gatcgccatc       900
ctggccgatg acgcggcgaa cgtgggtggt aacaattaca ccaagctgct caccgatatg       960
gtcgcgtggc tcaaggaaat gaagaagacc tacccggacc tcaagaccac gctgccgttc      1020
gtcacgcagg aatacatggg caacggcatg agctacttcg ccaacttccc caaggaagtg      1080
```

-continued

| | |
|---|---|
| cagatcgtca tgaccggcgg acgcgtctgg ggcgaggtct cgcagaactt caccgacacg | 1140 |
| ttcacctcga acgtcggccg cggcccctac atgtggatca actggccgtg ctccgacaac | 1200 |
| tcgaagagcc acctgatcat gggcggctac gacacgttcc tgcatccggg cgtcgacccg | 1260 |
| tcgaagatcc agggcatcgt gctcaacccg atgcagcagt ccgagccgag caaggtcggc | 1320 |
| atcttcggca acgccaccta ctcgtggaac atctggcgga gcaagagcga ggccgaccag | 1380 |
| gcatggcagg attcgttctc gttcgtcgac acaactccg ctgtgccgac cgccgcgtcg | 1440 |
| aacgcgctgc gtgagctgtc caagcacacc atcaaccaga acatggattc gcgcgtcacc | 1500 |
| gcgctgcagg agtccgtgga cctggctccc gcactgaccg ccgccaaggc gaagctggct | 1560 |
| gacggcacca tcaccgccca cgacctgacc gacatcaagg ccgcgttcgt cacgctgcag | 1620 |
| aaggcagcca agacctaccg cgccaagggc gatgcgaaga tgctcggcga catcggcaag | 1680 |
| gactacaccg ggcaggacgc caacgagcag atcgccccgt ggatcgactg ctgggatgac | 1740 |
| accaccaagg ccgcgctcgc ctacatcgcg ggtatcgagg ccgcgctgaa cggcgacacg | 1800 |
| tcctcgacgc tcaaggagta ctccgacgcg cagtccgcgt tcgccgcgtc caagaagcac | 1860 |
| ggcttctact acgtgaacca caccgagtac gccgaagtcg gcgtgcagca catcgtgccg | 1920 |
| ttcatcaagg cgatggactc ctacctgtcc aacaaggtgc agcaggaggc cgacccgaac | 1980 |
| gtcgtgacca agacgtacat cagcgacgtg ttcaccacgc cgacctccgg ctcgatcgaa | 2040 |
| gacatcttcg acggcaaaga cagcacggtc acggtgttcc agaacccgaa ctacctgcac | 2100 |
| aagggcaact acgtcggcgt gaagttcagc aaggccacca cgctcaagag catccgcttc | 2160 |
| gcgttcaacg gcggcaagaa ccacttctac cactccaagc tgcagaccac cacggacggc | 2220 |
| gagaactgga ccgacgtgcc ggatgcgacg ttcgagcgcc cgaagggctc cgaggagccg | 2280 |
| atcaaagtca ccggtctgaa catcaccggc gtcaccggcg tgcgactgat cgccaccgcc | 2340 |
| gacaacggcg atgacctgtg gctcggcatc aagggcatcg acgtcaacaa ggtcgagaag | 2400 |
| gagactctcg ctccgtacac ggcgactggc gtgcagctgg agaacctcaa cgccacctac | 2460 |
| agcagcacca aggagcagat gatcgacggc aacccgtcca cgatcaccta cctcaaggac | 2520 |
| ccgaacggcg acaagatcgc ggccggcgcg ccgtgatcg tcgatctggg ctccagcaag | 2580 |
| ccgatcggcg aggtcacgat taccggtcat gcctccagcc ccgacgaccg tccgagccag | 2640 |
| ggcgtcgtcg aggtcagcga tgacaaggcc acctggacca gcttggtga cctgagagac | 2700 |
| gacgtcacct ccacggtgag cggcaacgtg accgggcgct acgtacgcat ccgcaacacc | 2760 |
| gccgccaaga acgtgtggtg gcgcgtggcc gagatcaccg tgaccccgcc cgagaccgcc | 2820 |
| gatccgctca agtcggtgta cacgaacaag acgcagcacg ggtacaccgc cacgctgggc | 2880 |
| gccaatacgg cggagctgtt cgacaaatcg cacacgatgc ttgacggcgg ccagtacgcc | 2940 |
| ggactcgatc tgctggcgat ccgtgatctg accgacgtcg agctgaacac cggtaacgca | 3000 |
| aaccccagcc tgcagatctc cgacaacgga ctcgtctgga ccactgtcga gccgggcaac | 3060 |
| ctcacgggca agaccgcccg ctacgtgcgc gtgatcaatg gcaccgacgg agcggccttc | 3120 |
| tcggtcaaca agctcaaggt cggctttttcc acggtcggca agttcggcaa gctggtctca | 3180 |
| tccgacatcc agaagcgcaa cgattgggga accgacaccc gcgaaagcgg caacgcgttc | 3240 |
| gacggcgata tgaccacggt catcaagttc gccggccagc cgcgacaggg caacaccgcg | 3300 |
| gtgttcgatc tcggtcagcc gatcgacatc acctcgctgc gcatctacac gcaggacacg | 3360 |
| cagtacgact acatccgcga caccaaggtg cagatgtccg tcgatggcaa gacctgggtt | 3420 |
| gacgcgttcg agattggcga cggcgtgtcc gacaccgaca ccacgaccgc gttcggcgac | 3480 |

```
ataagcgaca cgaacaagaa gaccgattcc aactacccga acgtcttcta ctacggcaag    3540
gacgacatcg ccaacggcac cggcatgcgc tacctgcgtc tgctgaccac cgccgactac    3600
ccgcagcgtg cactcgcgtt caacgagttc atggtgaatc agggcgccta cgtctccacc    3660
gaggcgaacg cggcgttctc cgccaccaag gtcgaggagc gcggccacgc gccgagcaac    3720
atgatcgacg gcgacctgac caccacgtac aagccgagtg cggccaatgg ctccctcacc    3780
tacaagatcg atgacccgag cgacatcaag tcgttccgca tcgtgcagtc gggtgccgcc    3840
agcggtgcga ccgtcaccgg tacggtgtac gacgcggcga ccggaaccac tgccggtgtg    3900
acggctcgtg cagccgcccg ctccgcctcc gaggtgacgt tcggaacgct ggaacaggcg    3960
atcaacgagt tcaaggtgcc ggacggcaag cagctgctca gcgtcaagat cgcgtggggt    4020
aacgccatcc ccgagatctc cgagttcatc acgctcgact cggccgacac cgacgccgac    4080
atcaccacgg ccaaggcggc gctcaaggag aagatcgacg cgaccgtcga cacttccgcc    4140
tggaccgcga acgccaagac cgcgtatgac gaggccaagg ccaccgccca ggctgtgtac    4200
ggcagcccgc tggtcggcaa ggcttcgatc gacgccgcag ccagcgccgt gcaaagcgcc    4260
atcgacgccg cgcagaccaa ggccgacgcc gccgcggtcg ccgcgctgcg caagctcgtg    4320
gacgcagccg tcaccaacga cggccacttc tacacgacag tgacgttcac cgcgtacacc    4380
gacgcgctcg acgaggtcaa ggaagcgctg aaggacacga acaacctgtc cacagcagac    4440
gccgcaagcc tcaagaaggc cgtcgatgac gctctcgccg cgctgaagga ctccacctac    4500
cagcgtgagc tcgcgacgat cgccgtcgac agcttcgcca cgatcgacga ggccgactac    4560
accacgaact cctacgcggc tttcaaggcc gctaaggagg cgctcgacac cctgatcgcc    4620
gccgacggca ccaagccggc cacgttcaag accaagaccc ccgagtacac caccgccaag    4680
accgcgctgg tgaacgtcgc cgccctcaag gcccagatcg cgcacgagag caactacgtg    4740
gaggcgaact acaccgccga ctcgtggaag gcgtactccg acgcgctcaa ggccgcaaag    4800
gcggagctgg tcaacggcac caccgattcg gtggccgccg cgctgaccgc gctgaccact    4860
gccgagaacg cgctggtgcg caccacgacg ccgcccgaca ccaccgtgct cgacgagacc    4920
atcgccgaca tggaaaaggt taacggcagc gagtacacca ccgacagcta caaggccctg    4980
accgacgcca tcgccaaggc gaagagcgac aaggccaagg gggatgccgg cctcaaccag    5040
cagaacatcg acgccatgaa ggcggcgaag gaggccctgg tctccaccgt cgaactcaag    5100
gcgaaggtcg ccgaagccgg caaggttgac tcgtccaagt acaccacggc cagctacgag    5160
gcgctctcca agctgctcgc cgcgaaggac gacaccacct ccgacccggt cgtcaagggt    5220
ctcgacacgc tgtacaagtc cggcaccgtc aaggagctcg ccgagcgcgt cgccgccatc    5280
gacgccgcgg tcgccaagct ggatgcccgc gccaccggtg tcaaggacta cgtggacggc    5340
atcaagctca aggacaacga caagggctac tacaccgacg ccagctacaa ggcctactcc    5400
gacgcctaca aggcgctgaa gaagctggcc gcgccggtg aaggcgaagt cgggattgcc    5460
gagttcaccg aagccaagga ggcgttcgaa gccgccgagg ccaagcttgc ctacaagtcc    5520
gcggactacg gcaagatcga tgacctgctc gccaaggtcc cctcggacct gagcggctac    5580
accgccgact cggtggcgaa gttcgaggcg gccaagaagg ccgtgaagcg cggactgacc    5640
atcgaccagc agagcaaggt cgacgcgatg gccgacgcgc tcgaagccgc catcaagggc    5700
ctgactctca gtcgcaggc acccggtggc aacaagggcg acggaaccca gagcggcact    5760
cataagggtg acgacatctc caagaccggc gccgacgtgc aggtgttcgc gatcatcatc    5820
```

```
gcgctcgcca cgtgcgctgg cctgggcgcc gtggcctacg cccgtcgccg ccgcgaggcg    5880
tga                                                                  5883

<210> SEQ ID NO 38
<211> LENGTH: 5772
<212> TYPE: DNA
<213> ORGANISM: Bifidobacterium bifidum CCOS 571

<400> SEQUENCE: 38
atggcgacac tcatgtgcgg cctgatcaca tccggacgtc tcgcgcgcgc cgtggaaccg      60
gcgatcgccg cgtcacggc gagcggtgcc gccgccgacg ccatgctgc ggccgccgca      120 gtcgacggcg atccggcgac ctactggcag tcacccgcag actcgtcgat gcaggactac     180
cgccgcttcc tcgacttcga cctgcacggc acatacagca tctcgcagat cgacatcacc     240
aacctcgccg gctcgtacta ccactacgag gtctatctgt ccaaggacgg cgccgattac     300
ggcaaggtgg cctacaagag cgatgacgcc cccgcgaccg tgccgccga cacgcatccc      360 atcgatgcca ccgaagccgc atacgcgcgc atcagcgtca gctacaactc cgccgcccag     420
caggtcaacc tcgccgaagt cgcttttcca ggcaccaagg tctccgacga gcaggccagc     480
cccaaggcca tctccgtcac cgacttcgac tcaagctcgt ggggccggga gtgggcccgc     540
gtagagaccg acgccgacta tgccgccgag aagaccgtca ccgaggtcag aaacctcgtc     600
ggccgcgtga tcgcgagcg gtgggtcgac aagttcgact ccagctgcg cggcaaggcc      660 gacggcaagg acgtgttcga aatctcagac gccggcgacg accggatctc catccgcggc     720
aacaacggcg tctcgctcgc atccggcctc aattattatc tgcgccactg gtgcaaggtc     780
gactacaacc cgctgttcgg ctcccagctg tccatgccgg agagcctgcc tgcagtcggc     840
cggaaaatcc tcaaatacac gaactacgag taccggtacg cgctcaactt ctgcacctac     900
tcgtacacga tggcgttctg gaactgggat gattacgagc cgttcctcga ctgggcggcg     960
atgaacggcg tgaacctcat gctcgacatc gtcggacagg aggaggtgct gcgcgagacg    1020
ctcacccaat acggctacag cgacgacgag gtgcgcgaat acctgtccgg gccgggatac    1080
tacgcatggt tctacatgca gaacctgtac tcggtcggag gccccctgcc cgccgcatgg    1140
ttcgagcagc gcgtcgagct cggccgcagg atccacgacc gcatgcaggc gtacggcatc    1200
acgccggtca tccagggctt cggcggtcag gtgccggtcg acttccagga gaagaacccg    1260
acgtcggtgg ccgcgtcgtc cggcacatgg tccggtttcg accgccgta catgatcaag    1320 acgtatctga ccgacgccga caaggcggcc ggcaaggagg actacttcca gaaggtcggc    1380
gacacgttct acaaagctca ggagaacgtg ttcggcaagg tgtcgaacta ctacgcggtc    1440
gatccgttcc atgagggcgg cacgattcca gacggcttcg acatcgtcga catctaccgc    1500
accgtgcagc gcaagatgct cgaccatgac ccggcggccg tgtgggtgat gcagcagtgg    1560
cagtggggca tcgacgagac gaagctctcc gggctcgcgg acaagggtca ggcgcttgtg    1620
ctcgacctgc agagcgacct gcgctcgcag gccagcccga tggagaacca gggcgtgccg    1680
tgggtgtgga acatgttgca caacttcggc ggacgcatgg gccttgacgg agtgccggag    1740
gtgatctccc aggacatcac gaaagcctac aactccagcg gttacatgcg cggcatcggc    1800
atcacgcccg aagccatcga caattcgccg atcgtctacg agctgctgtt cgacatgacc    1860
tgggagcagg atccggtcga ctatcgctcc tggacgcagg agtatgccga gcgccggtac    1920
ggcggaaccg acgggacgat cgagaaggcg tgggacatcc tgcttgacac cgcctacaag    1980
cacacggacg gcgaatacta tcagggtgcg ggcgaatcca tcatcaacgc ccgcccgtcc    2040
```

```
gacaacacca tcggctcggc gtccacgtgg ggccacagcg acatagatta cgacaagcgg    2100
cagttcgaga aggccgcggc cctgttcgag caggcgtatg actcgtacaa ggactcggcc    2160
ggcttccgct acgattacgt cgacgtgatg cggcaggtgc tggccaacag cttccaggaa    2220
taccagccgc tcgccgggca ggcgtacaag tcgggcgatc tggagacgtt ccggacactg    2280
tcgtcccgga tgctggacat catcaaggcg caggacaagc tgctttccag ctcggacgac    2340
ttcctcgtgg gcgcatggat cgacgacgcc cgcacgatgc tcgacggcgc ggacgattgg    2400
accgccgacc tgttcgagct caacgcgcgt gcgctcgtca ccacgtgggg tctgaacaag    2460
aacggctcgc tcatcgacta ttccaaccgc cagtgggccg ggctgaccgg cgactactac    2520
tatcggcggt ggaagacgta cgtggacaac cggctgaaca aactggagca cggcaccgac    2580
ttcaccgacc cggactggtt cgactacggc tggcagtggg cgaaccgcaa agcgacgag    2640 gacgggtatg gtttcgcgac cgaagccgcg gatgacgtcg accagaaagc gctcggcaag    2700
atcatcctcg accagtattc ggtcaccgcg atggacgacg tcaccgacgg tggcaccgcg    2760
gtcgaacgca cgaacctggc gctgggacat gacgtgaccg acgaggacac cggcaccgtc    2820
gtccctgacg tgaccgacgg caacaccgac accggctgga cgcagacggg caagaccgac    2880
gccacgctgg tggtcgacct cgacggcacg tattcgatca ccggcgccgg catcaccctg    2940
cagcagatcg cggccgactt cccgctgcgc tacgagatcg atgtctggaa cggctcggga    3000
tgggtcgaga taggccgcag cgaagccgat gccgtcagct ccaagaacga ggtcgccgcc    3060
gacatactcg gctccaaggt gcgttggaag ttgcattcga cgaacgggcg ggacctgacc    3120
ggcatctacg agctgtccgt ctggggagcc gcgcagccgc agcccgagta cacgaatctg    3180
gcgcttggcg gcgccgcaag cgccggcccc agcgagcggc ccgcgtcgaa cggcaacgac    3240
ggcgacgacg gtacgctgtg ggtcggcaac gggtcagacc cgaactggta tcggatcgac    3300
ctggcgtcgg cgcagcgtgt ggaccgcgtg cggctcgtgt tcgagacggc cggccgcctg    3360
ttccagttca gggtcgtcgc ggggctcgct gacggtaccg agcggacact gatcgacgag    3420
acgcagaacc agggcgccct cgatcaggtg tatgcggcga atcttggcga ggaggtcgaa    3480
cacgtcaccg tggagttcac ggggtcggtc ggcggcaccg catggccggc gctcgccgaa    3540
ctcgaactgc tgcaggaggc cggcgacacc atcgaaggcg tgaacatcgc cacctcggcc    3600
gccatcacgt cgtcgcccac caaggacgcg cccgagaacg ccggcgcgct ggtgacggc    3660 aaggcgaccg catgggtgtc ccgcgacggc gccacgccgg catggttcca gctcgactac    3720
gccaaggccc gtgaggtcga cagcatacgg ctcaagttcg aggaaggcca gcccgaccgc    3780
agcatgcagt tcacgttgaa ggtgatcgac gcgaacggcg acgaacatac ggtcgccgaa    3840
cgaaccgaag ccgacctgag caaacagcag ggcatcgtga tggacgtgcc ggtcggcatg    3900
agcatcacac gcatccgcat ggacatcgcc gacgcccgca tccctccag cggctcgccc    3960 gcatggccgc tggtgtccga gatcgaggtc tacgcgacgc ccggcaacgt ggctcgcgac    4020
gccaagacga cggcctcgga cggctcgacg ctcacggccg ccgacctcgc caagctgacg    4080
gacggagacc gcgacagcgc ggccaccttg acggccacgg ccgacaagac cctgacattc    4140
acgctcgcga aggccgcgga catcaacatg ctcggcctgc tggcctccgg taacagcgag    4200
ccggtgcggt tcaaggccga ataccgcgtg gtgccgcagg acggcggcgg tgcgggcgat    4260
ggtgcagccg accagtggaa gacgctgacc gactattccg gcaatgcgca gatgaagccg    4320
gagatcgtgg cccgccttgc acggcccgtc tacaccgacg cggtacgcat caccgtgctc    4380
aacgagaacc ccgtcgccat caacgagttg tacctgtatc aggcggatgc aggggcgtct    4440
```

```
ctggaaagct acctctcgtc cgtcgagacc gtgctcggca agctcaccgt cggcgaatac    4500
gccggcaacg tcacccgggc ggcgaagacc aagctcgaag tcgtgctgga gcgggcgcgg    4560
gcggcgctgg acgccggact gacctcgcgc gaggccggcc ggtggacgac aaccgtcgaa    4620
gacgcggtgt ccgagttcta ccgcaccggc tacgtgtcgc tcgaccgcaa cgcgctgtat    4680
gtggcgatcg atgacgccgc ggcgctgatc gcgtctctgg acgcgcatgg cctgcccgcg    4740
tcgtcggccg cattggccga ggcgagggca agcgccaagc aggtctccga cgcctacggc    4800
acggtgacgc aacaggatct cgatgacgcc gcggctgcgt tgcggcggtc ggccgacacg    4860
gcgctcgcgc agcttgacgc gcaggagcgc tatcaggtcg tgctggatgc ggcggtcaag    4920
acgctggagg acgcgcagac ggcgggcagc gtcggcgaat acgaggggca gcatccgcaa    4980
agcgccgcgg acgctctgcg ccaggccatc gacgacgcca aggccgcaca cggtgcagcc    5040
gccggagacg ccgataaggt ggacgccgcg gcggacgcgc tgcgccaggc gacgaccgcg    5100
ttcaacgagt caatcgtgca catcgatgcg gccgcgttgg atgcggcgaa gcgggcggcg    5160
accggtctgg tcgaatcgca gtacgacagg gctgcgtggg cgacgatgcg tgaggctctt    5220
gcggccgccg agacaccgat catggcgcac atctcccagg ccgacgtgga caccttgcg    5280 gcacggctga atgatgccat cgccgcgctg tccgacgcgc gtctggaccg tggcccgctg    5340
tctgacgcca tcgcgtcggc tcaggctctc aaggaaggcg attacactgc cgaatcgtgg    5400
aaggcgttcg ccgaggcgtt ggccgccgcg caggaggagt gcggacggcg atccaccacg    5460
cagggcgatc tggacaaggc cgtaaaggcc ctgactcagg ctcgcgacgg gctggagcgc    5520
aagcagcccg gcggcggtga ggaaccagga ggtggcgagg atcccgagca gcctggcagc    5580
ggcgggcaga ccgagcgtcc cggtggcgtc aagcccggcg ccggcggcaa cgccgatacc    5640
tccaaacctg gcacggcggg cacgaaaacc ctctcgaaga cgggcgccca gacgctgctg    5700
ctcgcagtga cggcgtgcat catgcttgcc gcgggattct ccatcacgac ggcgcgctcc    5760
cgtcgccggt ga                                                        5772

<210> SEQ ID NO 39
<211> LENGTH: 3339
<212> TYPE: DNA
<213> ORGANISM: Bifidobacterium bifidum CCOS 571

<400> SEQUENCE: 39
atggagaaaa gctccaatag acgtttcggt gtgcgtaccg ttgcggccat tgtagccggc      60
ctgatggtcg gtggcatgtg caccgcgatg acggccagcg ccgccgacga tagtgcagcc     120
gggtacagtg ccacggctcc cgtgaatctc acccgcccgg ccaccgtccc gagcatggac     180
ggctggaccg acggcaccgg cgcatggacg ctgggtgaag caccgcgt cgtgtcgagc       240 gatgcactgg ccgcgcgtgc gcagagcctg gcatccgagc tgaccaagtt caccgacgtg     300
gacatcaagg ccgcgaccgg ttcagcgacg ggcaaagaca tctcgctcac gttggatgca     360
tcgaagaagg ccgaactggg tgatgaggga ttcaagctgt ccatcggctc gaagggcctt     420
gaggtcatcg gcgcgaccga catcggcgtg ttctacggca cccgttccgt ctcgcagatg     480
cttcgccagg ccagctgac cctgcccgcc ggcacggtcg ccacgaagcc gaagtacaag     540
gagcgcggcg ctacgctgtg cgcctgccag atcaacatct ccactgactg gatcgaccgt     600
ttcctgtcgg acatggccga cctgcgcctc aactacgtgc tgctggagat gaagctcaag     660
ccggaagagg acaacaccaa gaaggccgcc acatggtcgt actacacgcg cgacgacgtc     720
aagaagttcg tcaagaaggc gaataactac ggcatcgacg tgattccgga gattaactcc     780
```

```
ccgggccaca tgaacgtctg gctggagaac tacccggagt accagcttgc cgacaactca    840
ggccggaagg atcccaacaa gctcgacatc tccaacccgg aggccgtgaa gttctacaag    900
acgctgattg acgaatacga cggcgtattc accacgaaat actggcacat gggcgccgac    960
gagtacatga tcggcaccag cttcgacaac tacagcaagt tgaagacgtt cgccgaaaag   1020
cagtacggag ccggcgcgac accgaatgat gcgttcaccg gcttcatcaa tgacatagat   1080
aaatacgtca aggccaaggg caagcagctg cgcatctgga cgacggcat cgtcaacacc    1140
aagaacgtct ccctgaacaa ggacatcgtc atcgaatact ggtatggtgc cggccgcaag   1200
ccgcaggagc tcgtccagga cggatacacg ttgatgaacg cgacccaggc cctgtactgg   1260
tcccgttcgg cgcaagtgta caaggtcaac gccgcaagac tgtacaacaa caactggaac   1320
gtcggaacct tgacggcgg acgacagatc gacaagaact acgacaaact gaccggtgcg    1380
aaggtgtcca tctggcccga cagctcgatc taccagaccg agaacgaggt cgagaaggag   1440
atcttcgacg gcatgcgctt catctcacag atgacctggt ccgattcccg cccgtgggcg   1500
acgtggaacg atatgaaggc ggacatcgac aagatcggct acccgctgga catccgcgaa   1560
tacgactaca ccccggtcga tgccggcatc tacgacatcc cccagttgaa gtcgatctcc   1620
aaaggtccgt gggagctcat caccacgcct gacggctact accagatgaa ggatacagtg   1680
tccggaaagt gtcttgcgct cttcaccgga agcaagcatc tcgatgtcgt cacccaggtc   1740
ggcgcgacgc cggaactgcg caactgcgcc gacgtgtccg tcggtcagga tcagcgcgac   1800
accgccaatg agcgtaacac gcagaagtgg cagatccgcg ccgacaagga tggcaagtac   1860
accatctccc cggcgctgac gcagcagcgt ctcgccatcg ccaccggcaa cgagcagaac   1920
atcgatctgg agacccatcg tcccgccgct ggcaccgtcg ctcagttccc ggctgacctg   1980
gtcagcgaca cgcgctgtt cacgctcacc ggccacatgg gcatgtccgc caccgtggac    2040
tccaagaccg tgaacccggc ctccccgtcc aagatcaccg tcaaggtgag ggccgcatcc   2100
aacgcgaaca ccggtgacgt caccgtcacc ccggtcgtgc cggaaggctg ggagatcaag   2160
cccggaagcg tcagcctcaa gtcgattccg gccggcaagg ccgccatcgc ctacttcaac   2220
gtggtcaaca ccactgggac gggcgacgcc accgtgcagt tcaagctcac caacaccaag   2280
accggtgaag agctcggcac caccagcgtg gcgctgaccg gcagcctgac caaggacgtg   2340
gaagcaagcg actacgcggc gagctctcag gagaccaccg gcgagcatgc tcccgtgggc   2400
aacgccttcg acaagaacgc aaacacgttc tggcacagca agtactccaa ccccagcgcc   2460
aatcttccgc actggctggc gttcaaggcg tcgcccggcg agggcaacaa gattgcggcc   2520
atcacccacc tgtaccgtca ggacaagctg aacggcccgg ccaagaacgt cgcagtgtac   2580
gtggtggcgg ccagcgacgc caacagcgtt gccgatgtca ccaactgggg tgaacccgtc   2640
gccacggctg agttcccgta caccaaggaa ctgcagacca tcgcgctgcc gaataccatt   2700
ccgtccggtg acgtgtacgt caagttccag atcaacgacg catggggcct caccgaaacc   2760
agcgcaggcg tcacctgggc ggctgtcgcc gagctggctg cgacgccaa ggccactccg    2820
gtcgagctca ccgagcccga gcagccgaag acaacccccg aggtgacgga gactccggag   2880
gctacgggtg tgaccgttc tggcgatggt gttgccaatg cgcgctgtc gctgaagaag    2940
ggcaccaccg cgcagctgac cgcgaaggtc gcgccggatg acgcggacca ggcggtgacg   3000
tgggcctcca gcgatgacaa ggtcgtgacg gtcgacaaga ccggcaaggt gaccgccgtc   3060
gcgaagggcg tggcgaaggt gaccgcgacc acggcgaacg gcaagtccgc ctctgtgacc   3120
gtcaccgtca ccgaggactc tgaggtgccc ggcccgactg gcccgaccga gccgaccaaa   3180
```

| | |
|---|---:|
| ccgggtacgg agaagccgac cacgaagccg accacgaagc cgaacgacgg caagctcagc | 3240 |
| gccaccggcg ccgacacggc ggtgctcgcc accatcgcgg ctctgttcgc gctggccggc | 3300 |
| ggtgcggtcg tcgcggttcg tcgccgcagc gtccgctga | 3339 |

<210> SEQ ID NO 40
<211> LENGTH: 2022
<212> TYPE: DNA
<213> ORGANISM: Bifidobacterium breve CCOS 586

<400> SEQUENCE: 40

| | |
|---|---:|
| atgaacggtc aaacatctct gcaaggatgg accatcatcc ccatgccgca aaccatgcag | 60 |
| cataaagcga acatcgcatt gctgccaatg tgcggacgaa tcaacgaagc gcgcgcagtc | 120 |
| ggtgacgatc ggcacatact tgccgtgcag ctcatcgacg acatccgcgc agccaccgga | 180 |
| ttggaatggg atatcgccac cggcgaccgc tggccgggat tcatcaccct gacgaccttt | 240 |
| gacgaccccc atgcacaccc gtccggtgca tatacgctcg atgtcacccc ggacggcgtg | 300 |
| accgtagcgg gagcggattt cgaggtgtgt cgtaacggcg tgcagacttt gcgtcagctc | 360 |
| atccgccaat gcggcgccgc cctgccctgc ctgcacatcg aggaccgacc cgccttcgaa | 420 |
| acgcgcggct actacctcga cgtcacccgc gggcgcgtcc ccaccctcga ctggctcaaa | 480 |
| cactgggccg acaagctctg cctgtacaaa tacaaccagc tccagctcta catcgaacac | 540 |
| accttcgcgt tcgactcgat gagcgagacc tggcgcggtt ccagcccgct caccccgcgc | 600 |
| gacatcctcg aattcgacga ctactgcgcc gaacgcggca tcgagctggt cccgtcggtc | 660 |
| tccacgttcg dacacctcta catggcccctg cgcacgcaat ccctgcgcga cctcggcgag | 720 |
| ttccccgaaa ccgccgacga gccgttcgga ttcatcgacc gcatgcacca ccacacattg | 780 |
| aacatcagcg acgaccgcgc cttcgacctg tcatgccggc ttatcgacga ctacctgcag | 840 |
| ctgttccgct ccgacaaatt caacatctgc gccgacgaga ccttcgacct cggcaagggc | 900 |
| cggtccaagc ccctcgccga ccgcatcggc gtcgcggcca tgtacgccga ctacgtcacc | 960 |
| cgcctgtgcc gccacctcga agcccggggc aggcggccga tgatgtgggg cgacatcgcc | 1020 |
| ctcgaacacc ccgagatcct cgaccggctc cccgaaaccg tcaccctgct caactggcag | 1080 |
| tacgaccctc aggtcacgga cgagaagatc cgcaccgtcg ccgaatccgg tgccaagcag | 1140 |
| atcgtatgcc cggccgtatg gtgctggaac gcgctcctgc cgcgcatcga cgacgcctgg | 1200 |
| aacaacatca cccgcatggc ccgctacggc gcgcaatacc atgcgcaagg catgctcatc | 1260 |
| accgactggg gcgacttcgg ccacgtcaac gacccgcgca tggccatccc cggcatgatc | 1320 |
| atcggcgcac aggaatcatg gaacccggga cgaatcccgg atgaggccga catgctccgc | 1380 |
| cgcatctccc gactcgaata ccacgacgcc agcggcgaac tgcttgatat ccttgctcgc | 1440 |
| gcaagccatg cggccagttt cgaatggaac cacctgatca cttggctgga acttgatgac | 1500 |
| ggacaaggcg gagtcaacac cggggtcctg caaaccatcc cgggactgct gccggaaaac | 1560 |
| gaacgaccgg acgatgtgat ccgttccctc cagaacgaaa gcaagacacc gtcacttgcg | 1620 |
| gaatcccgac gaatgctgct ccgctatctg aaacaccgca tcacgctcgg cgaaaccgca | 1680 |
| gatcaccttc tgcaggccag taccogtcga atctccgcga tcaccgcgac cgcaggaccg | 1740 |
| cggaacgcag gaaacgccgc tgcattccgc atagccgtcg aggggcagcg actgctgaac | 1800 |
| cgggttggcc tccgacttgc gtccgagacc gggatcactg acactttgca gccgaacacc | 1860 |
| acgtctcaac atgacgatga ggcgaacctt gctgaagcat tggagatctg gatggaggcg | 1920 |

| | |
|---|---|
| tatgcgacgc aatggagcac ggtcagccga gactccgaac tccgtcggct gcaagatacg | 1980 |
| gtgtggaagt taacggacca tctgcgcttc caatccgtct ga | 2022 |

<210> SEQ ID NO 41
<211> LENGTH: 525
<212> TYPE: DNA
<213> ORGANISM: Bifidobacterium breve CCOS 586

<400> SEQUENCE: 41

| | |
|---|---|
| atgaaatatc ccgacatccc gaacgtcacc aaggaatatc tggacgaagt gcggcccgcc | 60 |
| atcaacgccg gcggatcatg ctcggccacg gccggagcca ccatcggcgc ccttagcccg | 120 |
| cccttggtcg tcgatggcac cagcatcgac atcgacgcca gcggcgtgcc cgtggcctcg | 180 |
| atcaactcat acagcgtggg ccaatgcacc tggtgggccg ccgcccgacg gcaacagatc | 240 |
| ggcaaaccgg tggaccccta catgggccac ggctacatgt gggcggccag cgccgagaaa | 300 |
| cacggatacc ccaccggcgg cacaatccaa ctgggcgacg tgatgagctt cgagcgagga | 360 |
| gtgctgggag ccagcggcga atacgggcac gtcgccatcc tcgaggaaat ccacgaggac | 420 |
| ggttccatcc tcatcagcga gtccggcgtc gaccaacgcc gcgcctggac acgcctgctg | 480 |
| acacgcgagc aggccgagaa ccccggcatc acctacatcc actag | 525 |

<210> SEQ ID NO 42
<211> LENGTH: 1851
<212> TYPE: DNA
<213> ORGANISM: Bifidobacterium breve CCOS 586

<400> SEQUENCE: 42

| | |
|---|---|
| atgagattgt catcaggtga tcacgctggg cgtgcttctg ctcggactcg acacaggaaa | 60 |
| tggctgcggt ctggcttggc agcggtgctg tcgatggcca cgctggcggc attggccgca | 120 |
| ccggcaagcg ccaccgacac catgccgtgg ggaggccagt atgccgatac cagccatccg | 180 |
| gagcagtctg cggagccaa ccagccatat cagcatggct ataccggtct ggatattctg | 240 |
| aactggaacc cggacgcgga taaggactcg gaatacctgc gctcccgtgt accgttgcag | 300 |
| acccgcatcg ccgccaacgc cgcgacgcag aaagacccga acctgccggc cgatacggag | 360 |
| atgttcaacc ttgctggcga ctacggcaac gcgttcttcg agtcgttcca cgacaacagc | 420 |
| gtgttctcgc agtacctgtt caactactgg cagtacacgg attattacgg tacctggcat | 480 |
| ggtcagccga ctgcgaacgt gccaaagagc ctctacgacg agaaggccca gtctgactgg | 540 |
| actcagaaat ggtttgagtt cggtacgttg aatctgccga atgccgcata ccaatgtc | 600 |
| gcgcacaaga atggcgcgaa gtcgattgcg acgatcttct attctggcaa cgaccgagga | 660 |
| gaacagacct ataaggacct gcttcaaggc aagcgtgccg acggcaccta tccggtggct | 720 |
| gacaagctgg tggagattgc caagtactat ggttttgatg gttacttcgt taaccaggaa | 780 |
| tccagtgtga attctgctga tgtgccggcc taccaagact tcatgaagca gatcatcgat | 840 |
| cagggcattt atatccagtg gtacgactcc gccacatacc cgaatggcgg cgtcagctat | 900 |
| caaaacatgt tcaacgatgc caattcgccg tgggtgcagg atccgaacaa gggtaaaatc | 960 |
| tctgattcga tcttcctgaa ctactggttc agcggcaaca tgctacaaga ttcagctgat | 1020 |
| cacgccaaga gccttggcat tgatccgaag tacgcggtat tcgcgggtat cgaggccgga | 1080 |
| cagaagaaat ttggtagcat cgccagcaac gcgaattata tgaatgtcaa ccttgacgct | 1140 |
| gacggcaagc cctatgtgag ccttgcggca cttggcaccg atttcgtctc ccacgagttg | 1200 |
| ggtgacgaca agaaggtcta cccgaagtat cagaaccagg tattcgaccg cgaacgccgt | 1260 |

-continued

| | |
|---|---|
| ctgtggactg gttcgtccac cggtgagaag ggcacgacgg atatatctga tccgtatatt | 1320 |
| gatgatggta cgagcagcga tagctggaag ggtttcgctt cgcagatcgc cgagcgctcc | 1380 |
| gtcatcgacg gtccggtctt ctccacatcg ttcaacaccg gtcatggtct cgaatggcga | 1440 |
| gacaacggcg aacagaccag caaccagcag tggggcaata tcaacctcca agacattctg | 1500 |
| ccgacatggc agtggtggat tgatgccgat tccgacccgc tgcaagccga cttcgactat | 1560 |
| ggcaagaaat atgaagcggc accacgcttt aactacacca aggtcggcgg ctacgaaggc | 1620 |
| ggcgattcgc tggtgttgag cggcaagctg tccagcgaca acaccgtccg tctctacaag | 1680 |
| accgacttga gcgtcgctgc cggctccaag gtcgaactga cctacaacaa gctcaacagc | 1740 |
| gacgattcca agctgcaact cggcctcatt ttcgccgacg acaccaagac tatagtgccg | 1800 |
| gtggacatgg agacggtggg gcaagcaacg gctggaagac cgcaactgta g | 1851 |

<210> SEQ ID NO 43
<211> LENGTH: 1884
<212> TYPE: DNA
<213> ORGANISM: Bifidobacterium breve CCOS 586

<400> SEQUENCE: 43

| | |
|---|---|
| atggaattca ccgtatccgg cactaccgtg cgattcgatg aacgaacgat gcagttcgct | 60 |
| tttacgcgcg acggtgccga atggaatacc tgcgctgatt tcaagccgac cctgcaatgc | 120 |
| acgcaaggca ccttcgcgtt cgccgatgcc acttccatca cccacgaaca acgcgaaacc | 180 |
| ggcacgggaa ccggcattcg cagcatcttc accggctttg gcacagcgc atactccttt | 240 |
| gaaacctatg tatgggtgga gcgcgcctcc ggcgatgtgc tcttcgaatg gattccgctc | 300 |
| aatgagcaag ggctgaccgt caccggtgtg acgtggcctg cggcaatcgc cttcgaccgt | 360 |
| gacgactccc acgacgtgac gcttattacc cacgaacagg gcgtgatgat tcccaacaca | 420 |
| tggcctaccg ccgtgagcac caaagatatc accttcgacg gccgcttcga acggctggc | 480 |
| ggttacatgc cgtggttcgc gcagctccgc gcagacggac acgggtatat cgccatctgc | 540 |
| gaaactccat ggaatgccgg ttacggcatc gaccatccca gcaatggccc gtacacccat | 600 |
| atcaatactt ggtttgagcc aagcctcggc acaatgaatt atcgccgcgt ggtacgctac | 660 |
| cagttcctcg accacgccga tcatacggcg gtgtgcaagg cctatcgttc gtacgtcaac | 720 |
| gaacgaggtc gcctgcgtac gctcgccgaa aaggcggcgc gcaatccctc cgtgcgcgac | 780 |
| ctgattggtc gttcatgggt gcacgtcggc atcaaaacca aagtgcagcc cgactcgttc | 840 |
| tactatgaca aggaccaccc cgaaaagaac gattcattgg tcaccttgc gcagcgcgaa | 900 |
| aagcaaatgc gaacattgca cagcatgggt gcaggccgac tgtacatgca cttggatggt | 960 |
| tgggcacagc ccggatacga caacgcacac cccgactatt gccggcttg tcaggaggca | 1020 |
| ggcggctggg aaggcatgaa gtcgctggtc gacgcctgcc atgagcaagg cgatattttc | 1080 |
| ggcacgcatg accagtaccg cgattactac ttcaccgcgc aaaccttga tgccaacaat | 1140 |
| gcgattcggc tggcagacgg tacgatgccc gaacacgcac gctgggcggg cggccaccag | 1200 |
| acctacctgt gcgccgagct cgcaccggac tacgtacgcc gcaatttcac ccagattgcc | 1260 |
| gcgcatggca tcaagctcga ctgtgcatac ttggatgttt tcacctgcaa cgaaggcgac | 1320 |
| gaatgctcga accccgaaca ccgcatgacc cgccgcgaat gctttgaccg ccgcaccgaa | 1380 |
| tgcttcgaat atctgctctc gcacggcatc ctctcctcgt ccgaagaggt atcggactgg | 1440 |
| gcagtgccaa gctgatatt ctgccattac gcgccatacg acttccagat gcgctcaccc | 1500 |
| aacgagccgc gccaaggtgt gccggtgccg ctgtataacc tcgtctacca tgattgcgtt | 1560 |

```
atcgaaccat ggatgatgga gcgtgtggtg aacggcgacg attacatgct gtacgccttg    1620
ctgaacggcg gagctccata cctgattcgc gatgccgcat acatcggcgt tgacggcgac    1680
atggacgacg aacagcgcgc tcgcacggaa aacgacatcg aacgctgcca tacggtcgct    1740
gcattccatg agcgggtcgg catgcaggaa ctggttcgtc acgagttcgt ggatgatgat    1800
ccgctggtgc agcgttcggt attcgtggac ggcactgcgg tcacttgcga cttccatacg    1860
caaacctatc gcatcaccga ttga                                            1884

<210> SEQ ID NO 44
<211> LENGTH: 714
<212> TYPE: DNA
<213> ORGANISM: Bifidobacterium breve CCOS 586

<400> SEQUENCE: 44
atgtcgaccg atcagttacg tcaatcggcc agcgtatggg gctcacagct ggcagccgcc      60
ggcattaacg tcgatcttgc acccgtgctg ggcacggtag tggcgaatcg ggccgccaac     120
gcccccattg gtgcgctcta tcgcgatttc ggactggacg cggcaggcaa cgcggctcag     180
ggcacggcgt ttgtgcaggg catggccgat gccggagtcc aatccgccat caaacattat     240
ccgggattgg gcgcggtaac cggcaacacg gatttcaccg ccgacggcat cctggatacg     300
accaccacct ggatggcac ggaaatcaag gcgtttgaca ccaccatcga ccaggccgac      360
cctgccatgt gatgatggc attggccacc tatcaggcca ttgaccccaa tgatcccgcg     420
gtgttttcct caatcatcat tgacgggcat cttcgcggcg atctgggata tgacggcgta     480
gtgatttcgg attcgatgtc ggcagcgcc gtgagcgcct acgacaccac tcaattggga     540
gtcaaactcg tggaagccgg cggcgatttg gcctgcatcg gatacaccaa ctatgtcgcg     600
ccgattctgg atggattgtc tacgcgagcg gcatcggatc ccgccttcgc caatgaggtc     660
actcagtcgg cgattcgtgt gatgacgttg aaaatcaaga tgggattggc ctaa           714

<210> SEQ ID NO 45
<211> LENGTH: 402
<212> TYPE: DNA
<213> ORGANISM: Bifidobacterium breve CCOS 586

<400> SEQUENCE: 45
gtgtcgatcg gcgaggacac ggccggtgtg cggttgtgcg gcgaagttcg cggcggcggt      60
ctgttcctgt atcctctggg agaagggcag attcgcaaaa tctccgacgt gccgccacc     120 accgataccg cgttgttcga caaggatat gaaggatccg caagctaccg catcccgtct      180
ttggtgacta cgccctccgg tgtgacgatt gccggtgccg accaacgtgt ggtcatctcc     240
aacgatgccc caatgagatc catttcgttg tccgccgctc cttggatagc ggacagacgt     300
ggctgccgct gcaaaccgtc atcgcctttc ccggtgatgg gctggatggc gcgagcgtca     360
tcgactcatg catcgtctgt gatcgtgaga caggccgtgt ga                        402

<210> SEQ ID NO 46
<211> LENGTH: 1302
<212> TYPE: DNA
<213> ORGANISM: Bifidobacterium breve CCOS 586

<400> SEQUENCE: 46
atgtccacct ttccacagct ggccacccat ccgggcatga cccggccgc ggtcatccaa       60 ggcgaccgtt ggcgcatcgg catcatcacc gaatcgctcg tccgcctcga atggcaggac     120
aacggcaagt tcgaagacca cgccacccaa atgatcgtca atcgcgattg gttgtcggat     180
```

```
gacgcgaacg gtgcggatgg cgcgaaccgt gcggacggca cttcaaaccc gccgaagttc      240
acgaagaccg agcgcgacgg gctgctcatc atcgatacgc cggcgctgcg cctcacctac      300
gacatgcagc cgttcagtaa ggaaggtctg agcatcgtcg tcaaaggcgt ggcgaattcc      360
cagatgaata cgtggcacta cggcgaagcc caggacggca acctgcgcgg caccgcgcgt      420
acgctggacg cggtcgacgg tgagatcgaa ctggggctcg gcgtgatctc ccgcgacggc      480
tgggccgtgc tcgacgattc cgcatcaaac gtgatcgtcg aaggcgccga agccgccacc      540
gtcaagggcg aggccaaccc attcggtatg tgggtcattc gcgcgagca ccccggcaag      600 gatctgtatg tcttcggata cggccatcgg tacatcgaag ccgtgcagga cttctacaag      660
ctcaccggcc cgacgccgct gctgccgcgc ttcgcgctcg gcaactggtg gagccgctac      720
caccggtaca cggaagccga gtatctggag cttgtcgatc gcttcgagca ggaaggcctg      780
ccgttcacca cggccgtcat cgacatggac tggcatctgg tcgacaatgt cgacccgaag      840
tatggatccg gatggaccgg ctacacgtgg aaccgtgaat tcttccccga ccccgagcga      900
ttccagcgca ttctgcacga gcatggactg cgcacgacgc tcaacgtcca cccgcgcgac      960
ggcgttcgag catttgaaga cggctatgcc aaagtcgccg aacacatggg cattgacccg      1020
gcgggcggcc agccggtcga gttcgatctg accagtccgc gattcatgga agcgtacttc      1080
gacctgcacc atgggctcga aaccctgggc accgatttct ggtggctgga ctggcagcag      1140
ggcggcgtga cccgccagaa gggtcttgac ccgctgtgga tgctgaacca catgcattat      1200
ctcgactccg ccgtgacggg cgctggccgc tcacgttctc gcgatatgcc ggcccgggct      1260
cgcaccgtta tccggtcggg ttctccggcg acacagtcgt ga                        1302

<210> SEQ ID NO 47
<211> LENGTH: 1017
<212> TYPE: DNA
<213> ORGANISM: Bifidobacterium breve CCOS 586

<400> SEQUENCE: 47
gtgattgatg tttctgcctg gcagggcaat atcaactggc aggccgtgaa aaactcaggc      60
gtggaaggcg caatcattcg cattggctac gggtgggaca cgggtttga caagcaggca      120 cttcgcaata tcagcgagtg caggcgtttg ggtattccgt ttggcatata cctctattcg      180
tacgcttatg acgccaatac cggtgctgct gagggatcca gtttagtgaa cctgctgcag      240
aaagccggtg tgagctcaag cgatttgggc tatccggtgt attacgactt agagaggtgg      300
acctggacgg gtcatgaggt gcccaacgac cctgggacgt atgacggcat tgtcaatgct      360
tggtatggca ggttgcaatc cgctggatac aacaatcttg ctgtgtattc atacacttct      420
tatctgaata ctgcgctcaa tagtggcaat atccactcta agacccgttg ggttgcgcag      480
tatggttcct cgatgggcta tacggcattc cccaccaacg accgtggctg gcagtacacc      540
agcaggggca gcgtgagcgg cattagcggc accgtggatt tgaatgcgtt tggtaatcaa      600
actgccacgt cctcggctcc tagcgttcct gtctaccgtg tctacaatcc caacagcgga      660
ttgcaccatt acacgatgaa ttacaacgaa gtcataatgc tggttggtaa ggggtggcga      720
tacgagaaaa ccgcctttag agcgggccaa tccggcatac ctgtctaccg tgtctacaat      780
ccgaatgacg gaaaccatct gttcacgatg aatagttacg agcgagacaa tctggctcgt      840
ttggggtggc acgatgaagg cgtgtcttgg tacgtgcctt ccggcggatc cattaacgta      900
taccgtttgt ataacccgaa caatggtgag catgttttca ccacggaata tggcgagtat      960
gtgcttgttg gcagggctgg atggcatcag gaaggcgttg cctggacatc tctgtga       1017
```

<210> SEQ ID NO 48
<211> LENGTH: 375
<212> TYPE: DNA
<213> ORGANISM: Bifidobacterium longum CCOS 974

<400> SEQUENCE: 48

```
gtggggattc cagttcgatc cggcgggtat cagctcatcg gagccaagaa gaccttcatc    60
gacgagatga accaatggat gaaaaccgaa tccaacaagc cgttcctgtt caccgaatac   120
ggtgcggaca ccgatgccgg tgtgcacaag ctgccgagcg tgcaatggag tgaagagtac   180
caatgtgagt acctcgccat gcagcacgaa gtgttcgaca tgttcgaggc agtagtgggc   240
gagcaggtat ggaacctctg cgacttccaa accggtgaag catcatgcg cgtcgacggc    300
aataagaagc gtcttcactc gcgaccgtca gcccaaagcc gccgcctatg tactcaagga   360
gcgttgggag actaa                                                    375
```

<210> SEQ ID NO 49
<211> LENGTH: 1203
<212> TYPE: DNA
<213> ORGANISM: Bifidobacterium longum CCOS 974

<400> SEQUENCE: 49

```
gtggcgacaa tatgtgcttt ggcagtggtg ttggccggcg tggcagccta cggatggcat    60
gtcggatggt tcgccaaatc cacatcaaac ggcaacacca ccactcccca gacctcccag   120
acaagtgcgt taccacgcgc cgacgttcct tccccgaaga agaacgaacc ggccgcacaa   180
gcccaacgtg cggtatccgc catgacactt gaggaacgtg tgggacagtt agtgatggtg   240
ccgttgcttg ccggttccga tccctcctcg ttggcttcaa caatcgccga tgagcacatt   300
ggctcggcca ttctcattgg caattggaat accggcgtcg atacggtcaa gaccgcgacc   360
gcgcaactcc aaggatatgc gccggccggc aatcgtctca tcatcgccac cgatcaggag   420
ggtggtcagg tgcagcatct gactggtacc ggtttcgaca caatgcccag tgccgttgag   480
cagggcacaa tgtccgctga cgcattgcgt caatcggcag gcacgtgggg ttcgcaatta   540
gctgctgctg gcataaatgt cgatttggca ccggtgctcg gcacggtggt gggcgatcgt   600
gcctcaaata ctccgattgg cgcgctggat cgtgatttcg gattggatgc ggccggcaac   660
gccgaacatg gcatcgccgt tattgaaggt ttgcgagacg ctcaggtcgg cgcggcggtc   720
aaacattatc ctgggttggg cgcggtaagc ggcaataccg acttcaccac cgaaggcatt   780
ctggatacga ccaccacgtt ggacgggggcc gaggcaggtg cctttgacca ggcgatcacc   840
aagaccgatc ccgcaatggc gatgatgtcg ttggccacgt atcaatccat cgacccgaat   900
aatccggcgg tgttttcttc tacgattatc gacggtcata ttcgcaacgc cctgaagtac   960
acgggcgtgg tgatttcgga ttcgatgtct gccgaagcgt taagcagcta cgatgtaagc  1020
caattgggag taaagcttgt cgaggcgggc ggcgacatgt cctgcatcgg tcagacggat  1080
tacgtaaagc caattgtgga cggcctcaac gaacgggcga agtccgatcc ggctttcgct  1140
tcgaaggtga cggcggcggc gactcgcgta atggcattga aaatcaagat gggactggcc  1200
tga                                                                1203
```

<210> SEQ ID NO 50
<211> LENGTH: 1896
<212> TYPE: DNA
<213> ORGANISM: Bifidobacterium longum CCOS 974

<400> SEQUENCE: 50

```
atggaattca ccgtatccgg cactaccgtg cgattcgatg aacgaacaat gcagttcgct      60
tttacgcgcg acggtgccga atggaatacc tgcgctgatt tcaagccgac cctgcaatgc     120
gcgcaaggca ccttcgcgtt cgcggatgcc acttccatca cccatgagca gcgtgaaacc     180
ggcacgggaa ccggcattcg cagcatcttc accggctttg gcacagcgc atactccttt      240
gaaacctatg tatgggtgga gcgtgcctca ggcgatgtgc tcttcgaatg gattccgctc     300
aatgagcaag gcctgaacat caccaatgtg acgtggcccg cagccatgga cttcgattgc     360
gccgacgacc atgacacgac actcatcacc catgagcaag gtgtgatgat ccccaacaca     420
tggcctaccg ccgtgagcac caaagacatc gccttcgacg ccgcttcga acggctggc      480
ggttacatgc cgtggttcgc gcagctccgc gcagacggac acgggtatat cgccatctgc     540
gaaactccat ggaatgccgg ttacggcatc gaccatccca gcaatggccc gtacacccat     600
atcaatactt ggtttgagcc aagcctcggc acaatgaatt atcgccgcgt ggtacgctac     660
cagttcctcg accacgccga tcacacgcg gtgtgcaagg cctatcgttc gtacgtcaac      720
gaacgaggtc gcctgcgtac gctcgccgaa aaggcggcgc gcaatccctc cgtgcgtgac     780
ctgattggtc gctcgtgggt gcacatcggc atcaaaacca agtgcagcc cgactcgtac      840
tactacgata aggaccaccc cgagaaaaac gagtcgctgg tcaccttcgc acagcgcgaa     900
aagcaaatgc gaacactgca cggcatgggt gcaggccgac tgtacatgca cttggatggt     960
tgggcacagc ccggatacga caacgcacac cccgactatc tgccggcctg tcaggaggca    1020
ggcggctggg aaggcatgaa gtcgctggtc gacgcctgcc atgagcaagg cgatattttc    1080
ggcacgcatg accagtaccg cgattactac ttcaccgcgc aaacctttga tgccaacaat    1140
gcgattcggc tggcagacgg tacgatgccc gaacacgcac gctgggcggg cggccgccag    1200
acctacctgt gcgccgagct cgcaccggac tacgtgcgcc gcaatttcac ccagattgcc    1260
gcgcatggca tcaaactcga ctgtgcatac ttggatgtct tcacctgcaa cgaaggcgac    1320
gaatgctcga accccgaaca ccgcatgacc cgccgcgaat gctttgaccg ccgcgccgag    1380
tgcttcgaat atctgctctc gcacggcatc ctctcctcgt ccgaagaggt atcggactgg    1440
gcagtgccaa gcctgatatt ctgccattac gcgccatacg acttccagat gcgctcaccc    1500
aacgagccgc gccaaggtgt gccggtgccg ctgtataacc tcgtctacca tgattgcgtt    1560
atcgagccgt ggatgatgga gcgtgtggtg gacggcgacg attacatgct gtacgccttg    1620
ctcaacggcg gagctccata cctgattcgc gatgccgcat acatcggcgt tgacggcgac    1680
atggacgacg aacagcgcgc tcgcacggaa aacgacatcg aacgctgcca tacggtcgct    1740
gcattccatg agcgggtcgg catgcaggaa ctggttcgtc acgagttcgt ggatgatgat    1800
ccgctggtgc agcgttcggt attcgcggac ggcactgcgg tcacttgcga cttccatacg    1860
caaacctatc gcatcaccga ctgcccgcat cactga                              1896
```

<210> SEQ ID NO 51
<211> LENGTH: 948
<212> TYPE: DNA
<213> ORGANISM: Bifidobacterium longum CCOS 974

<400> SEQUENCE: 51

```
gtgggaatcc tcaacaaagg caagccgaaa cacggacacc tgcaccggcg cgtgggcatg      60
acgctgaccg cgcttgccgt cgcggtctcc atggcgttcg ccccggcggc gatgccgac      120
atgcagggcg tggacatgag caactggcag tgcggcgcgg acgtgtacaa catgcaggcc     180
```

```
gatttcatcg tggtcggcac cacatggggc accgggcaag tcaacaacaa ctgcttggtg      240
tccggcgtca acacggacgc caaccgcatg atcgcccagg cacaagcatc cggcaagaaa      300
ttcggtttgt atcactacgc gatgggaggc aacccggagg cggaagccca attcttctat      360
cgcaacacgt cgaactattg gcgtcacggc atcgtggcgt tggattggga gatggacgac      420
aaccccgcat ggggcgattg ggattgggta cgccgattca cggcggagtg tgaacggctc      480
tcgggcggcg tcaagccgct gctctacacc ggccccgtgg ccggcaccat ccccggcgac      540
atccgcgcca actacggttt gtggatcgcg cagtacgcga acatgagccc gaccggctac      600
caggccaacc cgtggatgct gggcgcgtac ggcgaggcca tgcgacagta cagcggtacc      660
ggcgtggtca acacgtggag tcccatcgac ctcaacatct tccgtggcga aggctggcag      720
tggatctgta cgccaacccc accggctcca cagccccggc cccggcaacg cccgcgcccg      780
tgcagccgag cactcccacg ccaacaccaa acacgggtgg catcagccac gtcatgcaat      840
ggggagaaac catctgggga ctcgccgtcg cctatgatgc ttggcccctg tccgcgtggc      900
atacgccgag cggtgacatc aaccgctact acgtgggcga cgtcgtaa               948
```

<210> SEQ ID NO 52
<211> LENGTH: 2136
<212> TYPE: DNA
<213> ORGANISM: Bifidobacterium longum CCOS 974

<400> SEQUENCE: 52

```
gtgcccacat tcgaatataa ggctgatgcc gcaacgccgt gtctcaccct gattcccgct       60
ccggtgacat tggaatacac gcatggcacg gctatgatcg ggtccttggt gacgatcgag      120
aaacgaattc ccgaatatgc cgtcaccgaa gatgccgatg agacctggga aacgctgcca      180
atcgagcagc tgtccagcga actcgagcgt tactgcggcg tcgccgtccg tacgcgccga      240
gtactcacag ccacagatga agccgacgcc ggtgccaatg ccgccgaaaa agcgcgagat      300
gcgggcgtgg gtgcgggtgc gggcgcgggt gcgccggcag cgatgaacgg caccgtcata      360
ttgctgtgtg tggatgcgcg attggcgcat gacgaataca cgctggatgt gttcgcctca      420
gataccatcg ccgtgcgtgg tggcagcgaa agcggattgc ggtacggcat gcagacactg      480
cggcagatga tcaggcaaac ctcgcggacc ttgccctgcc tgcatatcca agacaagcct      540
gcgttcgcgg tgcgcgccta cagtcttgac gtgacgcgcg ggcgtgtgcc gacgatggcg      600
ttcctcacct ggttcatcga ccagctggcg ttgtataagt acaaccaatt ccagctgtac      660
gtggaacatg ccttcgcttt cggcgagctc agcgaagcgt ggcgcggcac tgacccgctc      720
acggccgacg acatcatgtt cctggacgaa tactgcgcac accacggcat cgaactggtg      780
ccgtccttgg ccactttcgg gcacatgtat atgaacctgc gcaccgtga acatcgtgga      840 ctgggagagt tccccgaaga cgccgaccgt ccgttcagtt tcatcgaacg aatggaacac      900
cacacactga acgcagccaa ccccaagtcg cacgatttcg cctcgcgcct aatcgaggaa      960
tacgcgccgc tgttccgctc gcggtccttc aatattggtg gcgatgagac tttcgacttg     1020
ggccgtggcc ggtccgtaca ggactcgccg ggcgccagtc gcgatgagct gtatgccgat     1080
ttcgtcaaag acctatgcag cacgcttgcc catcgtggtc tacaaccgat gctgtgggcg     1140
gatatcgcgc tcgagaatcc gcacaccatg gacttgctgc ccggcgacat cacgatgctc     1200
aactggatgt atgagccgga tatcgacgaa agcaagatcc agaccatcgc atcacaaggc     1260
cgccgccaat tcgtgtgccc tgccgtgcgt gcgtggagcc ggttcttccc cgactatgac     1320
ggtgcctggc tgaacacgta ccgcatggcg gtggctgggc tcaaatatgg tgcggaaggc     1380
```

| | |
|---|---|
| atggtggtca ccgattgggg tgactatggg catgtcaatg atccgcggtt gagcgtgccg | 1440 |
| ggactgtgct acggtgcgca aaacgcgtgg aacccggttg caattgacgc atgcgaaatg | 1500 |
| aaccatcgga tttctaatct ggcgtatggc gacgaatccg gttggcttat ggattcactc | 1560 |
| gctcgcatcg actccgatgg agtgtcgttc ccctgggacc tcgccgtgca agtgctggaa | 1620 |
| ctggaatacg gttccggcac cggcatgctg aatacggatg tggcatcgta tgtggaacgg | 1680 |
| tcgtgcgggg gagagctcat gtttgaccgt gcgctgggat gcgccgacgc gcgccgccga | 1740 |
| ttgctcctgc ggaaccatgc ccgtctcgaa cgacgccggg attgcgaccg ggcgttgatt | 1800 |
| gattgcggca gtgcggttgt cgcggtgctc gatggcttgg cacgaggagg attgaacccg | 1860 |
| gagctgctgt gggtgatgct ggatgggcag cggttgttca atagactggg tgaggaactg | 1920 |
| ctggtattgg ctggcggcga ggacgcctgt gacaccaagg atgtgaccgg ccgtgcgctg | 1980 |
| gatgcctcgc gccgcgcccg tcttgccgcc gatttggagt tgtggttcga acggtaccgt | 2040 |
| gtgcagtggc tgtccatcgg ccgttacgcc gaattggcgc gtatcgccca tgtggtgtgg | 2100 |
| tcgtttgcgg acatattgcg tagggggagcg ctatag | 2136 |

<210> SEQ ID NO 53
<211> LENGTH: 1905
<212> TYPE: DNA
<213> ORGANISM: Bifidobacterium longum CCOS 974

<400> SEQUENCE: 53

| | |
|---|---|
| atggtggaaa agaagcggct cgacggctcg gatgcgaagg gcgcgacggg tgcggcgcgt | 60 |
| gcgacgggca tgctgcgtgc gttgcgtgcg cgtgcggcgg cgtccggtgc ggggcgcggc | 120 |
| gtgaccgcgg cggtgacgtc cgtcgcggcg gtggcgatgt gggcgcgggt gtgcgtcact | 180 |
| ccggccagtg cgctcgcgga tgtgaacgcc gacgcggacg cgtccggcgt ccggtccgcg | 240 |
| gcctccgcga ccgcctcgga cggaacctca tccgacgcgc gctcgcaggc gcggtccgcg | 300 |
| acttccgcga cgcgtccggt cgcgaacggt gtgacggtcg ccgatgagac ggctgccgac | 360 |
| gcgatgccgg acaatccgga tgccgagctg ccggacaagg tgtccgccga gatctccgat | 420 |
| gacgcgatgg tggtgtccga gcaatatgcg gctacgccgg aaggcgagtt gaaggacatc | 480 |
| gagacgggcg agacggtcac cgatccgaag atcgtgggca cggagagcaa gcagcccgat | 540 |
| ccgttggcga gacggatgg cgagtcgttc attccggtga gtgccgcgga tgtgaaggag | 600 |
| aaggtcgctg cgaacggcgg tgacgtgaac gcggtctcct cgaagacgcg cgcggccaac | 660 |
| gcgtcggtga agctcgccgc gttgcagaac aacgagtacg gtgcgcactg gggcacgtac | 720 |
| aacggtacgc aggcgttctt cgacgcgcgc aacaacctgt tcgcccagca ggcgaagggc | 780 |
| gtgatcgacg tgtccgcatg gcagaacacg atcgactggc aggcggtgaa gaacgcgggc | 840 |
| gtcgagggcg cgatcatccg tctgagctac ggctgggca atggcttcga cgtgcaggcg | 900 |
| aagcgcaaca tcagcgaatg caagcgtctc ggcatcccgt tcggcgtgta cgtcttctcg | 960 |
| tatgcggaaa gtgcggccga cggcgcatcc gagggtgcgg acgtggtgaa cctgctgcgc | 1020 |
| caggcaggcg tgaatccggg cgacctgagt tacccggtgt tctacgatct ggagaactgg | 1080 |
| acgtacacgg ggcacaagag cccaacgagt ccgagcgtgt acgacggtat ggtgaactcc | 1140 |
| tggtacggca aactgcaggc ggccggttac aacaatctga gcgtctactc gtacacgagc | 1200 |
| tacctgaaca gcgcgctcaa cagctccaac atccacggca agaccgttg ggtcgcccag | 1260 |
| tatgctcca ccatgcagta caccgcgttc cccacgaacg accgcggctg gcagtacacg | 1320 |
| agcggcggct ccatcaacgg catttccggt cgcgtggata tgaatgcgtt cggcaactat | 1380 |

```
caattcactc cgcggttca gataacttgg gtttatcgct ctgaagatat tgctgtcgga   1440
gcatcggttg attacccttc atcggatatt gattacaaat ggcaatcgta taatttatcc   1500
agcaaacgtt ggaaaaccat caccgattgg acaggtgcca attgggcggg ttgggtggac   1560
cagttaggag actattggct acacgtggaa gcacgtgact ctcggactcg caagattatc   1620
ggatcgcaga caatcgcttt caggtatgca cccggtacaa cgcgtgtggc ggcaacatat   1680 gcggatggc agaacaatca tgtgttgctg ggggaaagtt caaataatgc ggctgcccat   1740
tatgagatta aaatctatga tgttagacgc agcaaatggg tgcaaggttt caagggaccg   1800
tgggcgattt ggaagcccaa aaagggtata tattggactc attatgaggt atatacctct   1860
gatgggagac tcgcggacac taagacttat gcgttcggtg tctaa           1905

<210> SEQ ID NO 54
<211> LENGTH: 174
<212> TYPE: DNA
<213> ORGANISM: Lactococcus lactis CCOS 949

<400> SEQUENCE: 54
atgagtacaa aagattttaa cttggatttg gtatctgttt cgaagaaaga ttcaggtgca    60
tcaccacgca ttacaagtat ttcgctatgt acacccggtt gtaaaacagg agctctgatg   120
ggttgtaaca tgaaaacagc aacttgtcat tgtagtattc acgtaagcaa ataa         174

<210> SEQ ID NO 55
<211> LENGTH: 2982
<212> TYPE: DNA
<213> ORGANISM: Lactococcus lactis CCOS 949

<400> SEQUENCE: 55
atgataaaaa gttcatttaa agctcaaccg tttttagtaa gaaatacaat tttatctcca    60
aacgataaac ggagttttac tgaatatact caagtcattg agactgtaag taaaaataaa   120 gttttttttgg aacagttact actagctaat cctaaactct atgatgttat gcagaaatat   180
aatgctggtc tgttaaagaa gaaaagggtt aaaaaattat ttgaatctat ttacaagtat   240
tataagagaa gttatttacg atcaactcca tttggattat ttagtgaaac ttcaattggt   300
gttttttcga aaagttcaca gtacaagtta atgggaaaga ctacaaaggg tataagattg   360
gatactcagt ggttgattcg cctagttcat aaaatggaag tagatttctc aaaaaagtta   420
tcatttacta gaaataatgc aaattataag tttggagatc gagttttca agtttatacc    480 ataaatagta gtgagcttga agaagtaaat attaaatata cgaatgttta tcaaattatt   540
tctgaatttt gtgagaatga ctatcaaaaa tatgaagata tttgtgaaac tgtaacgctt   600
tgctatggag acgaatatag agaactatcg gaacaatatc ttggcagtct gatagttaat   660
cattatttga tctctaattt acaaaaagat ttgttgtcag attttcttg gaacactttt   720 ttgactaaag ttgaagcaat agatgaagat aaaaaatata taattcctct gaaaaaagtt   780
caaaagttta ttcaagaata ctcagaaata gaaattggtg aaggtattga gaaactgaaa   840
gaaatatatc aggaaatgtc acaaattctt gagaatgata attatattca aattgattta   900
attagtgata gtgaaataaa ttttgatgtt aaacaaaagc aacaattaga catttagct    960 gagttttag gaaatacgac aaaatctgta agaagaacat atttggatga ctataaggat   1020
aaatttatcg aaaatatgg tgtagatcaa gaagtacaaa taacagaatt atttgattct   1080
acatttggca taggagctcc atataattat aatcatcctc gaaatgactt ttatgagtcc   1140
gaaccgagta ctctatacta ttcagaagag gagagagaaa agtacctcag catgtatgta   1200
```

-continued

| | |
|---|---|
| gaagccgtta aaaatcataa tgtaattaat cttgacgact tagagtctca ttatcaaaaa | 1260 |
| atggacttag aaaagaaaag tgaacttcaa gggttagaat tattttttgaa tttggcaaag | 1320 |
| gagtatgaaa aagatatttt tattttaggg gatatcgttg gaaataataa tttgggaggg | 1380 |
| gcatcaggta gattttctgc actctctccg gagttaacaa gttatcatag aacgatagta | 1440 |
| gattctgtcg aaagagaaaa tgagaataaa gaaattacat cgtgtgaaat agtatttctt | 1500 |
| ccagaaaata tcagacatgc taacgttatg catacatcaa ttatgaggag gaaagtactt | 1560 |
| ccattttta caagtacaag tcacaatgaa gttctgttaa ctaatatcta tattggaata | 1620 |
| gacgaaaaag aaaaatttta tgcacgagac atttcaactc aagaggtatt gaaattctac | 1680 |
| attacaagca tgtacaataa aacgttattc agtaatgagc taagatttct ttacgaaatt | 1740 |
| tcattagatg acaagtttgg taatttacct tgggaactta tttacagaga ctttgattat | 1800 |
| attccacgtt tagtatttga cgaaatagta atatctcctg ctaaatggaa aatttgggga | 1860 |
| agggatgtaa atagtaagat gacaataaga gaacttattc aaagcaaaga aattcccaaa | 1920 |
| gagttttata ttgtcaatgg agataataaa gtttatttat cacaggaaaa cccattggat | 1980 |
| atggaaattt tagagtcggc gataaagaag agctcaaaaa gaaagatttt tatagagcta | 2040 |
| caagaatatt ttgaagatga aaatatcata ataaaggag aaaaggggag agttgccgat | 2100 |
| gttgtagtgc ctttattag aacgagagca ttaggtaatg aagggagagc atttataaga | 2160 |
| gagaaaagag tttcggttga acggcgtgaa aaattgccct taacgagtg ctttatcta | 2220 |
| aagttgtaca tttctataaa tcgtcaaaat gaatttttac tgtcgtatct tccagatatt | 2280 |
| cagaaaatag tagcaaacct gggtggaaat ctattcttcc taagatatac tgatcctaaa | 2340 |
| ccacatatta gattgcgtat aaaatgttca gatttatttt tagcttacgg atctattctt | 2400 |
| gaaatcttaa aaaggagtcg gaaaaatagg ataatgtcaa cttttgatat ttctatttat | 2460 |
| gatcaagaag tagaaagata tggtggattt gatactttag agttatccga agcaatattt | 2520 |
| tgtgccgatt ctaaaattat tcctaatttg cttacattga taaaagatac taataatgat | 2580 |
| tggaaagtcg atgatgtatc aatcttggtg aattatttat atctgaaatg cttctttgag | 2640 |
| aatgataaca aaaggattct taattttttg aatttagtta gtcctaaaaa ggttaaagaa | 2700 |
| aatgtcaatg aaaagattga acattatctt aagcttctga agttaataa tctaggtgac | 2760 |
| caaattttt atgacaagaa ttttaaagaa ttaaagcatg ccataaaaaa tttatttta | 2820 |
| aaaatgatag ctcaagattt tgaacttcag aaagtttatt caattattga cagtatcatt | 2880 |
| catgtccata ataaccgact aattggtatt gaacgagata aagagaaatt aatttattac | 2940 |
| acacttcaaa ggttgtttgt ttcggaagaa tacatgaaat ga | 2982 |

<210> SEQ ID NO 56
<211> LENGTH: 1801
<212> TYPE: DNA
<213> ORGANISM: Lactococcus lactis CCOS 949

<400> SEQUENCE: 56

| | |
|---|---|
| atggatgaag tgaaagaatt cacatcaaaa caatttttta atactttact tactcttcca | 60 |
| agcaccttga agttaatttt tcagttggaa aaacgttatg caatttattt aattgtgcta | 120 |
| aatgctatca cagcttttgt tccgttggct agtcttttta tttatcaaga tttaataaac | 180 |
| tctgtgctag gttcagggag acatcttatc aatattatta tcatctattt tattgttcaa | 240 |
| gtgataacaa cagttctggg acagctggaa agttatgtta gtggaaaatt tgatatgcga | 300 |
| ctttcttaca gtatcaatat gcgcctcatg aggactacct catctcttga attaagtgat | 360 |

| | |
|---|---|
| tatgagcagg ctgatatgta taatatcata gaaaaagtta ctcaagacag cacttacaag | 420 |
| ccttttcagc tatttaatgc tatcattgtt gtgctttcat cgtttatctc attgttatct | 480 |
| agtctatttt ttattggaac atggaacatt ggggtagcaa ttttactcct tattgttcca | 540 |
| gtattatctt tggtactttt tctcagagtg ggacaattag agttttttaat ccagtggcag | 600 |
| agagcaagtt ctgaaagaga aacatggtat attgtatatt tattgactca tgattttca | 660 |
| tttaaagaaa tcaagttaaa taatattagc aattacttca ttcataaatt tggaaaatta | 720 |
| aagaaaggat ttatcaacca agatttagct attgctcgta agaagacata tttcaatatt | 780 |
| tttcttgatt tcattttgaa tttgataaat attcttacga tatttgctat gatcctttcg | 840 |
| gtaagagcag gaaaacttct tataggtaat ttggtaagtc tcatacaagc tatttctaaa | 900 |
| atcaatactt attctcaaac aatgattcaa aatatttaca tcatttataa tactagtttg | 960 |
| tttatggaac aactttttga gtttttaaag agagaaagtg tagttcacaa aaaaatagaa | 1020 |
| gatactgaaa tatgcaatca acatatagga actgttaaag taattaattt atcatatgtt | 1080 |
| taccctaatt cgaatgcctt tgcactaaag aatatcaatt tatcctttga aaaggagaa | 1140 |
| ttaactgcta ttgtaggaaa aaatggttca gggaaaagta cactagtaaa gataatttca | 1200 |
| ggattatatc aaccaactat gggaataatc caatacgaca aaatgagaag tagtttgatg | 1260 |
| cctgaggagt tttatcagaa aaacatatcg gtgctgttcc aagattttgt gaagtatgag | 1320 |
| ttaacgataa gagagaatat aggattgagt gatttgtctt ctcaatggga agatgagaaa | 1380 |
| attattaaag tactagataa tttaggactc gatttttga aaactaataa tcaatatgta | 1440 |
| cttgatacgc agtaggaaa ttggtttcaa gaagggcatc aacttcagg aggtcagtgg | 1500 |
| caaaaaattg cattagcaag gacattcttt aagaaagctt caatttatat tttagatgaa | 1560 |
| ccaagtgctg cactcgatcc tgtagctgaa aagaaaatat ttgattattt tgttgctctt | 1620 |
| tcggaaaata atatttcaat tttcattttct catagtttga atgctgccag aaaagcaaat | 1680 |
| aaaatcgtgg ttatgaaaga tggacaggtc gaagatgttg gaagtcatga tgtccttctg | 1740 |
| agaagatgtc aatactatca agaactttat tattcagagc aatatgagga taatgatgaa | 1800 |
| t | 1801 |

<210> SEQ ID NO 57
<211> LENGTH: 1113
<212> TYPE: DNA
<213> ORGANISM: Lactococcus lactis CCOS 949

<400> SEQUENCE: 57

| | |
|---|---|
| atgttagcgg agttaaaaaa taaagataac tcaaagatat atcagaaaaa gatagacaat | 60 |
| tatattgaat atattgttag caaactttca acatatgggc ttttaacagg atcactttat | 120 |
| tcgggagcag ctggcattgc attaagtatc ctacatttac gagaagatga cgaaaaatat | 180 |
| aagaatcttc ttgatagcct aaatagatat atcgaatatt tcgtcagaga aaaaattgaa | 240 |
| ggatttaatt tggaaaacat tactcctcct gattatgacg tgattgaagg tttatctggg | 300 |
| atactttcct atctattatt aatcaacgac gagcaatatg atgatttgaa aatactcatt | 360 |
| atcaattttt tatcaaatct gactaaagaa aacaaaggac taatatcgct ttacatcaaa | 420 |
| tcggagaatc agatgtctca atcagaaagt gagatgtatc cactaggctg tttgaatatg | 480 |
| ggattagcac atggacttgc tggagtgggc tgtatcttag cttatgccca cataaaagga | 540 |
| tatagtaatg aagcctcgtt gtcagctttg caaaaaatta ttttttattta tgaaaagttt | 600 |
| gaacttgaaa ggaaaaaaca gtttctatgg aaagatggac ttgtagcaga tgaattaaaa | 660 |

```
aaagagaaag taattaggga agcaagtttc attagagatg catggtgcta tggaggtcca      720
ggtattagtc tgctatactt atacggagga ttagcactgg ataatgacta ttttgtagat      780
aaagcagaaa aatattaga gtcagctatg caaaggaaac ttggtattga ttcatatatg       840
atttgccatg gctattctgg tttaatgaaa atttgttctt tatttaagcg gctattaaat      900 acaaaaagt ttgattcata catggaagaa tttaatgtta atagtgagca aattcttgaa       960
gaatacggag atgaaagtgg cacgggtttt cttgaaggaa taagtggctg tatactggta     1020
ttatcgaaat ttgaatattc aatcaatttt acttattgga gacaagcact gttacttttt     1080
gacgattttt tgaaaggagg gaagaggaaa tga                                  1113
```

<210> SEQ ID NO 58
<211> LENGTH: 738
<212> TYPE: DNA
<213> ORGANISM: Lactococcus lactis CCOS 949

<400> SEQUENCE: 58

```
atgagaagat atttaatact tattgtggcc ttaatagggaa taacaggttt atcagggtgt       60
tatcaaacaa gtcataaaaa ggtgaggttt gacgaaggaa gttatactaa ttttatttat      120
gataataaat cgtatttcgt aactgataag gagattcctc aggagaacgt taacaattcc      180
aaagtaaaat tttataagct gttgattgtt gacatgaaaa gtgagaaact tttatcaagt      240
agcaacaaaa atagtgtgac tttggtctta ataatatttt atgaggcttc tgacaagtcg      300
ctatgtatgg gtattaacga cagatactat aagatacttc cagaaagtga taaggggggcg     360 gtcaaagctt tgagattaca aaactttgat gtgacaagcg atatttctga tgataatttt      420
gttattgata aaaatgattc acgaaaaatt gactatatgg gaaatattta cagtatatcg      480
gacaccaccg tatctgatga agaattggga gaatatcagg atgttttagc tgaagtacgt      540
gtgtttgatt cagttagtgg caaaagtatc ccgaggtctg aatgggggag aattgataag      600
gatggttcaa attccaaaca gagtaggacg gaatgggatt atggcgaaat ccattctatt      660
agaggaaaat ctcttactga agcatttgcc gttgagataa atgatgattt taagcttgca      720
acgaaggtag gaaactag                                                    738
```

<210> SEQ ID NO 59
<211> LENGTH: 2049
<212> TYPE: DNA
<213> ORGANISM: Lactococcus lactis CCOS 949

<400> SEQUENCE: 59

```
gtgaaaaaaa tactaggttt cctttttatc gtttgttcgt tgggtttatc agcaactgtg       60
catggggaga caacaaattc acaacagtta ctctcaaata atattaatac ggaattaatt      120
aatcataatt ctaatgcaat tttatcttca acagagggat caacgactga ttcgattaat      180
ctaggggcgc agtcacctgc agtaaaaatcg acaacaagga ctgaattgga tgtaactggt      240
gctgctaaaa cttttattaca gacatcagct gttcaaaaag aaatgaaagt ttcgttgcaa      300
gaaactcaag ttagttctga attcagtaag agagatagcg ttacaaataa agaagcagtt      360
ccagtatcta aggatgagct acttgagcaa agtgaagtag tcgtttcaac atcatcgatt      420
caaaaaaata aatcctcga taataagaag aatagagcta acttcgttac ttcctctccg       480
cttattaagg aaaaaccatc aaattctaaa gatgcatctg gtgtaattga taattctgct      540
tctcctctat cttatcgtaa agctaaggaa gtggtatctc ttagcaaacc tttaaaaaat      600
caaaaagtag aggcacaacc tctattgata agtaattctt ctgaaaagaa agcaagtgtt      660
```

| | |
|---|---:|
| tatacaaatt cacatgattt ttgggattat cagtgggata tgaaatatgt gacaaataat | 720 |
| ggagaaagct atgcgctcta ccagccctca agaaaattt ctgttggaat tattgattca | 780 |
| ggaatcatgg aagaacatcc tgatttgtca aatagtttag gaaattattt taaaaatctt | 840 |
| gttcctaagg gagggtttga taatgaagaa cctgatgaaa ctggaaatcc aagtgatatt | 900 |
| gtcgacaaaa tgggacacgg gacggaagtc gcaggtcaga ttacagcaaa tggtaatatt | 960 |
| ttaggagtag caccagggat tactgtaaat atatacagag tatttggtga aaatctttcg | 1020 |
| aaatcggaat gggtagctag agcaataaga agagctgcgg atgatgggaa caaggtcatc | 1080 |
| aatataagtg ctggacagta tcttatgatt tcaggatcgt atgatgatgg aacaaatgat | 1140 |
| tatcaagagt atcttaatta aagtcagca ataaattatg caacagcaaa aggaagtatt | 1200 |
| gttgtcgcag ctcttggtaa tgatagttta aacatacaag ataaccaaac aatgataaac | 1260 |
| tttcttaagc gtttcagaag tataaaggtt cctggaaaag ttgtagatgc accgagtgta | 1320 |
| tttgaggatg taatagccgt aggtggaata gatggttatg gtaatatttc tgattttagt | 1380 |
| aatatttgag cggatgcaat ttatgctcct gctggcacaa cggccaattt taaaaaatat | 1440 |
| gggcaagata aatttgtcag tcagggttat tatttgaaag attggctttt tacaactact | 1500 |
| aatactggct ggtaccaata tgtttatggc aactcatttg ctactcctaa agtatctggg | 1560 |
| gcactggcat tagtagttga taaatatgga ataaagaatc ctaaccaact aaaaaggttt | 1620 |
| cttctaatga attctccaga agttaatggg aatagagtat tgaatattgt tgatttattg | 1680 |
| aatgggaaaa ataaagcttt tagcttagat acagataaag gtcaggatga tgctattaac | 1740 |
| cataaatcga tggagaatct taaagagtct agggatacaa tgaaacagga acaagataaa | 1800 |
| gaaattcaaa gaaatacaaa taacaatttt tctatcaaaa atgattttca taacatttca | 1860 |
| aaagaagtaa tttcagttga ttataatatt aatcaaaaaa tggctaataa tcgaaattcg | 1920 |
| agaggtgctg tttctgtacg aagtcaagaa attttacctg ttactggaga tggagaagat | 1980 |
| tttttaccgg ctttaggtat agtgtgtatc tcaatccttg gtatattgaa agaaagact | 2040 |
| aaaaattga | 2049 |

<210> SEQ ID NO 60
<211> LENGTH: 687
<212> TYPE: DNA
<213> ORGANISM: Lactococcus lactis CCOS 949

<400> SEQUENCE: 60

| | |
|---|---:|
| gtgtataaaa ttttaatagt tgatgatgat caggaaattt taaaattaat gaagacagca | 60 |
| ttagaaatga gaaactatga agttgcgacg catcaaaaca tttcacttcc cttggatatt | 120 |
| actgattttc agggatttga tttgattttg ttagatatca tgatgtcaaa tattgaaggg | 180 |
| acagaaattt gtaaaaggat tcgcagagaa atatcaactc caattatctt tgttagtgcg | 240 |
| aaagatacag aagaggatat tataaacggc ttaggtattg gtggggatga ctatattact | 300 |
| aagccttta gccttaaaca gttggttgca aaagtggaag caaatataaa gcgagaggaa | 360 |
| cgcaataaac atgcagttca tgttttttca gagattcgta gagatttagg accaattaca | 420 |
| tttatttag aagaaggcg agtctgtgtc aatggtcaaa caattccact gacttgtcgt | 480 |
| gaatacgata ttcttgaatt actatcacaa cgaacttcta agtttatac gagagaggat | 540 |
| attatgatg acgtatatga tgaatattct aatgcacttt ttcggtcaat ctcggaatat | 600 |
| atttatcaga ttaggagtaa gtttgcacca tacgatatta atccgataaa aacggttcgg | 660 |
| ggacttgggt atcagtggca tgggtaa | 687 |

```
<210> SEQ ID NO 61
<211> LENGTH: 1345
<212> TYPE: DNA
<213> ORGANISM: Lactococcus lactis CCOS 949

<400> SEQUENCE: 61
atgggtaaaa aatattcaat gcgtcgacgg atatggcaag ctgtcattga aattatcata      60
ggtacttgtc tacttatcct gttgttactg ggcttgactt tctttctacg acaaattgga     120
caaatcagtg gttcagaaac tattcgttta tctttagatt cagataattt aactatttct     180
gatatcgaac gtgatatgaa acactaccca tatgattata ttattttga caatgataca      240 agtaaaattt tgggaggaca ttatgtcaag tcggatgtac ctagttttgt agcttcaaaa     300
cagtcttcac ataatattac agaaggagaa attacttata cttattcaag caataagcat     360
ttttcagttg ttttaagaca aaacagtatg cctgaattta caaatcatac gcttcgttca     420
atttcttata atcaatttac ttacctttc ttttttcttg gtgaaataat actcattatt      480
ttttctgtct atcatctcat tagagaattt tctaagaatt ttcaagccgt tcaaaagatt     540
gcattgaaga tgggggaaat aactactttt cctgaacaag aggaatcaaa aattattgaa     600
tttgatcagg ttctgaataa cttatattcg aaaagtaagg agttagcttt ccttattgaa     660
gcggagcgtc atgaaaaaca tgatttatcc ttccaggttg ctgcactttc acatgatgtt     720
aagcaccctt taacagtatt aaaaggaaat attgaactgc tagagatgac tgaagtaaat     780
gaacaacaag ctgattttat tgagtcaatg aaaaatagtt tgactgtttt tgacaagtat     840
tttaacacaa tgattagtta tacaaaactt ttgaatgatg aaaatgatta caaagcgata     900
atctccctgg aggattttt gatagattta tcagttgagt tggaagagtt gtcaacaact      960
tatcaagtgg attatcagct agttaaaaaa acagatttaa ccacttttta cggaaataca    1020
ttagctttaa gtcgagcact tatcaatatc tttgttaatg cctgtcagta tgctaaagag    1080
ggtgaaaaaa tagtcagttt gagtatttat gatgatgaaa aatatctcta ttttgaaatc    1140
tggaataatg gtcatccttt ttctgaacaa gcaaaaaaaa atgctggaaa actattttc    1200 acagaagata ctggacgtag tgggaaacac tatgggattg gactatcttt tgctcaaggt    1260
gtagctttaa aacatcaagg aaacttaatt ctcagtaatc ctcaaaaagg tggggcagaa    1320
gttatcctaa aaataaaaaa gtaat                                          1345

<210> SEQ ID NO 62
<211> LENGTH: 678
<212> TYPE: DNA
<213> ORGANISM: Lactococcus lactis CCOS 949

<400> SEQUENCE: 62
atgcaggtaa aaattcaaaa tctttctaaa acatataaag aaaagcaggt gctacaagat      60
atcagttttg atattaaatc tggaacagtc tgtggtttat taggagttaa cggtgcagga     120
aaatcaactt tgatgaaaat tttgtttggt ttaatttctg cagatactgg aaaaattttt     180
tttgatggac aagaaaagac aaataatcaa cttggagcct aatcgaggc tccagcaata     240 tatatgaatt tatctgcttt cgataatctt aaaactaagg ctttgctttt tggaatttca     300
gataagagaa ttcatgaaac tctagaagtg attggtttgg cagaaacagg aagaaaaga     360 gcaggaaaat tctctttagg gatgaaacaa cgtttgggaa ttggtatggc tattcttaca     420 gaaccctcaat ttttaattct tgatgaacct actaatggtt tggatcctga tggtattgcg    480
gagttgttaa acttaatctt aaaacttaaa gctaaaggtg tgacaatctt gatttctagt    540
```

-continued

| catcagttgc acgaaataag taaagtagct agtcaaatta ttattttgaa caaaggtaag | 600 |
| attcgttata atcatgcgaa caataaagaa gacgacattg aacagttatt ctttaagatt | 660 |
| gtgcatggag gaatgtga | 678 |

<210> SEQ ID NO 63
<211> LENGTH: 729
<212> TYPE: DNA
<213> ORGANISM: Lactococcus lactis CCOS 949

<400> SEQUENCE: 63

| atgaaaagaa taatagcatc agaagcaata aaattaaaaa aatcaggaac tcttagattg | 60 |
| gtattaatta tcccttttgt gactctattt atagcatttc ttatgggtgg aatacagatt | 120 |
| tttagtgttt tttcaattta ttggtgggaa actggttttt tattccttt gatgagtttg | 180 |
| cttttctttt atgatataaa atcagaggag caagctggaa attttcaaaa tgtgaaatgg | 240 |
| aaaaagctga gttggaaaat tcatttggcc aaaatgttgt tgatttggct aagaggtata | 300 |
| ctagcgagca tagtcttgat tattttgctt tatttggttg cttttgtgtt tcaaggtatt | 360 |
| gtagtggtgg attttatgaa agtaagtgtg gcattgattg ctatattact agcagcttct | 420 |
| tggaatttac cctttatata cttgattttc aagtggatta atacttacgt attgttagct | 480 |
| gcgaataccct tgatttgttt aattgttgcc ccttttgttg cacaaactcc agtatggttc | 540 |
| ttgctaccat acacttatca ctataaagtt acagaaagtt tgttaaatat caaaccatca | 600 |
| ggagatttgt taacagggaa gataaatttc agtatttggg aagttttatt accatttgga | 660 |
| ctttccatag ttgtaacgat aggagtttcg tatttactta aaggagtgat agaacatgat | 720 |
| aagaagtga | 729 |

<210> SEQ ID NO 64
<211> LENGTH: 645
<212> TYPE: DNA
<213> ORGANISM: Lactococcus lactis CCOS 949

<400> SEQUENCE: 64

| atgataagaa gtgaatgtct caaattaaaa aatagcttag ggttttattt agttttctc | 60 |
| tttactttat tagagctttt aacggttcct atttatttag cttttggaag aagtcatgtt | 120 |
| tcaatgactg atttatcgct catgattttt ttgttttttc cgttactggt tacaattttg | 180 |
| tctattctaa tctttgaaca ggagagtctg gccaatcgtt tccaagaaat aaatgtaaat | 240 |
| aaaaaaagta gcagaatttg gttatcaaag ctaatagtag tggatttcct tttgttcttt | 300 |
| ccatcagcaa tgatctggat aattacggga gtttcacagg cagtagggca acaaggaatg | 360 |
| atgatcgcaa cagctagctg gttgatggca atttttctta atcattttca tcttttattg | 420 |
| acctttataa tcaatcgagg agggagcatg attatcgcga ttattgaaat attactcatt | 480 |
| attttttgcca gtaataaagt tttattagca gcttattggt gtcccattgc tttacctgtt | 540 |
| aattttatga taactgggcg gtgtgctat ctgatagctg ccgtagggtg gattgtttta | 600 |
| tccacaataa ttcttgtagc attatctaaa aaaaagatta gataa | 645 |

<210> SEQ ID NO 65
<211> LENGTH: 1320
<212> TYPE: DNA
<213> ORGANISM: Lactococcus lactis CCOS 949

<400> SEQUENCE: 65

```
atgccagttt ctcgtattaa agttaaaaat agacatttaa aaaagaaagc caaaaaacca    60
ctggctttt ataaaccagc gaccaaattt gctggcgctg ttctcattgc aggaactttg    120
acgaccactc atgagctttt gctccaacaa acaagcccaa tggttcaggc tgcaaccaat    180
tccacagaag cttttattga agtattgct gcatcagcaa aaccagttgc cgatagtaat    240
ggtctttatc cttcagttat gattgctcaa gctattttgg aaagtaactg gggttcaagc    300
caactttctc gtgcccccta ttataattta ttcggtattc aaggaactta tcaaggaaaa    360
agcgttgttt ttaaaactca agaatatctc aatggtaaat gggtcacaaa agatatgcca    420
tttagggttt atccttcctt taatcaaagt ttccaagaca atgcttatgt tttaaaaact    480
acaaactttg gaaatggtcc ttattatgct aaagcttggc gagcaaacgc ggcaaccctat   540
caagctgcaa ccgcagcctt aacaggaaaa tatgcaactg accctaatta tggtgcttcc    600
ctgaatcgaa ttatttctca atataatttg actcgttttg acggtgcttc ttctgctggt    660
acttctaatt ccggtggttc aacagctaca ataccaata ataattcaaa tacaagctca    720
accacttata cagttaaatc tggcgataca ctttggggaa tttcgcaaaa atatggaatt    780
agtgttgctc aaattcaaag cgcaaacaat cttaaaagta cagtcatcta tattgggcaa    840
aagcttgtat tgacaacttc aagttcttcg tctaatacaa atagttcaac ttcttcagga    900
aattctgccg gaactacaac gcctactact tcggtcactc ctgccaaacc agcttcacag    960
acgacgatta aggttaaatc tggtgatacg ctttggggac tctctgtcaa atataaaacg   1020
acgattgctc aactcaagag ttggaatcat ttgaattctg atacaatttt cattggacaa   1080
aacttgattg tttcacaatc tgccggttct tcaagttctt caacaggttc aagctcagcc   1140
tctacgagtt caacttctaa ctcttctgca gcttcaaata cctctatcca taaggttgtt   1200
aaaggagata cgctttgggg actttcacaa aaatctggta gcccaattgc ttcaattaag   1260
gcttggaatc atttatcaag tgataccatt ttaattggtc aatatcttcg tattaaataa   1320
```

<210> SEQ ID NO 66
<211> LENGTH: 1044
<212> TYPE: DNA
<213> ORGANISM: Lactococcus lactis CCOS 949

<400> SEQUENCE: 66

```
atgaaaaagg tgattaaacg gaaggttata ttatttagcc ttccttttt attgctttta    60
ttgccaattc tagcttttctt tgctctattt gtaggttcaa gtgatttatc ttcagataca    120
gatattaata ccaatacacc acagcaacaa actgccaaag tgatttggga tagagttcta    180
aaagaaggtg gaacgaaaga aggggcagct gctttacttg gtaataatca agcagaaagt    240
gaacttcaac cttcaattat tcaatctaat gcaacctata tgaagcaaa agcaatggat    300
accactttag gcggttatgc tttcggtttg gctcaatggg atagtggcag agagtaaaac    360
ttgctaaaact atgcgaaaag tcagaaaaaa tcttggacag atactaatct tcaagttgag    420
ttcatgtttg agcaagacgg tacagattca acgttactta acaattaat caaaggaact    480
aatgttaagc aaacgactga agatattatg cgaaagtggg aacgtgcagg ggcggttgat    540
agccttccaa aacgtcaagg ttttgcggaa tattggtaca cgttcatgac gactggtggt    600
gatagtggaa ctggtggtgg ttcaggaatt actccagata taccttcagg ttggacttta    660
gataaaccaa ttaatacaag tggttatctt gcgacaagtt atgagtataa acaatgtacg    720
tggtttacat ggaatcgagc ccaagatttc ggtattactt ttggaatgta tatgggaaat    780
```

| | |
|---|---|
| ggtgctgatt ggcaacatca agcaggatat actgtaacga ctactccaac acttcatagt | 840 |
| gcggttagct ttagtggagg tcaaacagta ggcggtcaat ggactgctga cccacaatac | 900 |
| ggtcacgtgg cctttgtgga aggaatacat tcagacggtt cagtcttgat tcacagtca | 960 |
| ggaactggtt ttagtacagt ttatactttc caagtattaa caaaagcaca agctagtcaa | 1020 |
| ttacattatg tgataggaaa ataa | 1044 |

<210> SEQ ID NO 67
<211> LENGTH: 894
<212> TYPE: DNA
<213> ORGANISM: Lactococcus lactis CCOS 949

<400> SEQUENCE: 67

| | |
|---|---|
| atgcagtata aaaaaaaga aaacaaggtt ttggtaattt ttgtactggt cgtaatttt | 60 |
| attttgtgtg gatgcatata tgtcttacta gtcagatata cccatactga taaaataacg | 120 |
| acgatcagtt ataagcagcc aactaaaaca tcggcttcta acggttatgt agagcaaaaa | 180 |
| ggtgaagaag ctgctgtggg tagtataaca cttgtagatg atgctggtgt accagaatgg | 240 |
| gttaaagttc cctcaaaggt aaatctagat aaatttactg atttatctac gaataatatc | 300 |
| actatttatc gaattaacaa tccggaagtc ttaaaaacag ttaccaatcg tacagatcaa | 360 |
| cggatgaaaa tgtcagaagt tatagctaag tatcctaatg ctttgattat gaatgcttcc | 420 |
| gcttttgata tgcagacagg acaagtagct ggatttcaaa ttaataatgg gaagttgatt | 480 |
| caagactgga gtccaggtac aacgactcaa tatgcttttg ttattaacaa agatggttcg | 540 |
| tgcaaaattt atgattcaag tacacctgct ttaactatta ttaaaaatgg agggcaacaa | 600 |
| gcctatgatt ttggtactgc gattatccgt gatggtaaaa ttcaaccaag tgatggctca | 660 |
| gtagattgga agattcatat tttattgcg aatgataaag ataataatct ctatgctatt | 720 |
| ttgagtgata caaatgcagg ttatgataat ataatgaaat cagtatcaaa tttgaagctc | 780 |
| caaaatatgt tattacttga tagtggcggc tcaagtcaac tatctgtcaa tggtaaaacg | 840 |
| attgttgcta gtcaagatga tcgagccgta ccggattata ttgtgatgaa ataa | 894 |

<210> SEQ ID NO 68
<211> LENGTH: 1500
<212> TYPE: DNA
<213> ORGANISM: Lactococcus lactis CCOS 949

<400> SEQUENCE: 68

| | |
|---|---|
| ttgactaata atgataaaac taagcgctta aaaaaggaaa aatttattgc gggaacagcg | 60 |
| ctgattttag gaatgacgac ttttggcgtg gctggccatg ctgatggagt aactgttgga | 120 |
| agtagttcag atgcatcatc aagcacaggt agctcaagtt catcatcagg tacagggggt | 180 |
| tcaagttcat catcaagtac aggtagctca agctcatcat caaattcaaa tgcttcaagt | 240 |
| tcatcgtcaa gtacaggtaa ttcaagttca tcatcaaaac caagtacttc aggttcgaca | 300 |
| tcaaaaccaa gtaatccaag ttcatcaaca aataataatt caactagtaa ttcctctaca | 360 |
| acaactcaag caccatcaac ttcagtttct accatagctc cttcagcatc aacttctaca | 420 |
| gttgcaccct ctaattattc acaggataat gcctactatc aaacatcaac tgcagcacaa | 480 |
| attcctaatt cttcagcaga ttcagctcct tctatttacg ctggccctgt tttgaaaaca | 540 |
| attgaagcag ctaagtcaat tgataaaatt gatacttcta gtacagaagc ctttattaaa | 600 |
| agtattgcag accgcgtgag aatttttagct ggtaagaata atttgtatgc atcaattatc | 660 |
| ttggcacagg cgattttaga atctggttct ggtcaaagta atatgagtca gcagtatttt | 720 |

| | | | | | |
|---|---|---|---|---|---|
| aatatttca | atattacagg | tgcttattta | ggaaaatcaa | tttcatttaa gacggaagaa | 780 |
| ttttcgggaa | ataatcctta | ttatattgaa | caaagtttta | gagtttatag taattatgac | 840 |
| caagccttgg | atgattatat | taatttaatg | attaaaggga | caacttggaa ctcagaaatt | 900 |
| tatgctggcg | catggaagtc | acatgctaag | acttaccaag | aggcggctca agcattgcaa | 960 |
| ggaattttg | ctactgaccc | agcatatgca | caaaaattaa | ttgaaattat tcaagaatat | 1020 |
| aaattagatg | cttatgataa | tgttgatagt | acaacacaag | ttgtagatag taaaaattcct | 1080 |
| gaaagtccat | tggcggcatc | aaaattagat | aattcagctt | atccagaata taatggggta | 1140 |
| gaatatccag | gtgctgatag | ttatgctttt | ggtaattgta | cacagtatgt ttataaccgt | 1200 |
| atcattcaat | taggtgggct | cgttggaaca | catatgggaa | atggtggaga atggggaatt | 1260 |
| aatgcccaag | ctcaaggtta | tttcacaaca | actgttccaa | ctgagggtta tgctgttagc | 1320 |
| ttcccaccag | gagtagctgg | ttcaagttca | gaatatggtc | acgtagcttt tgttgaaaag | 1380 |
| gtttattcag | ataactctat | tctcgtttca | gagatgaatg | ttaaaggtaa taatattgtc | 1440 |
| agcgaacgcc | atatttctgc | tggtgtagct | gctttggcaa | cttatattca acctaaataa | 1500 |

<210> SEQ ID NO 69
<211> LENGTH: 780
<212> TYPE: DNA
<213> ORGANISM: Lactococcus lactis CCOS 949

<400> SEQUENCE: 69

| | | | | | |
|---|---|---|---|---|---|
| atgtcaagta | ttgaaaatat | gattgcttgg | atgcaagcac | gaaagggtaa ggtaacttac | 60 |
| tcaatgacct | tgcgaatggg | tcctagaagt | tatgactgca | gctcgtcagt attctttgca | 120 |
| atgattgctg | gaggttttct | gtcagaaggt | tcaatgggta | atactgaaac cttgtttgga | 180 |
| atgtcaggaa | cgaagctgaa | agaaatcagt | cgtggagagg | tccatcgtgg cgatatcttc | 240 |
| atctcaggca | ctccaggagg | ttcggctggt | tcagatgggc | atactggtat tttcctaagc | 300 |
| aatggctcat | tcattcactg | ctcttatact | cacaatggaa | ttgcggttga tacgaatgat | 360 |
| gcatacatga | gtactcgctt | gccacatcac | ttttatcgga | ttgttggttc aggttcagca | 420 |
| aatactgaca | gcaagcctca | aatggttaca | ttaaatgttg | atggacagtt tggaaatgcg | 480 |
| actgctaaac | gattgcaaga | atactttgat | acagctggta | agatggagt aatcagtcac | 540 |
| cagtacaaac | aaacctttaa | tcaaaatatc | tatgctgcgc | agtttgattc atcactgact | 600 |
| ggttcaaacg | tggttaaagc | attgcaaaga | ttcttaggca | ttggccaaga cggcttgttt | 660 |
| ggccaaggta | caattaaagc | actacaaaaa | catcttggaa | cgacgcaaga cggaactatc | 720 |
| agcccagttt | ctgattctgt | tagagaattg | caacggcgat | tgaatgcgaa taaattataa | 780 |

<210> SEQ ID NO 70
<211> LENGTH: 816
<212> TYPE: DNA
<213> ORGANISM: Lactococcus lactis CCOS 949

<400> SEQUENCE: 70

| | | | | | |
|---|---|---|---|---|---|
| atgaaaccta | aaatgagacg | taaacttaaa | aaaatgggag | cttttatctt tacagcatcc | 60 |
| atgattgcaa | tgatcgcctt | acttggttta | gtacgaattc | gaccggtaga acctcctaaa | 120 |
| aaagcagcaa | ctgaaaaaat | tgttgtaaat | catatttgg | atgagaaggt tttggatttg | 180 |
| aataaaccag | ttgttgacct | ttcggggttgg | caacgtccag | aagatattga ttacaacacc | 240 |
| ttaagtcagc | atgtgattgg | tgcggttatt | cgtgtcaatg | gttcttatgg tcatgctgat | 300 |
| aattcagcaa | gcaaggatgg | agaagatact | gcctataaac | agcacattaa agctttccaa | 360 |

```
gagcggggaa tcccgactgc ggtttatgct tttgtgactg gagaaaacac ttctgaaatg    420
aggaagcaag caagagactt ttatcgtcga gcaagccctt ataagccgac ctattattgg    480
cttgatgtcg aggtaaccaa tatgaaaaat atgaaccaag ggattgaggc ttttcgctct    540
gagttggaga acaaggagc taaaaacatt ggtatttatg cccaagactg gttcttgcga    600
gataatcaaa taaaagttga taaatttaaa gcgatttgga ttgctgccta tggacgaaat    660
acaggttatt gggatgcttc accagaaacg actttaagtt ataaaatgca acaatttact    720
gaccaaggaa ctttaccagg ttactcggga aatgttgatt tgaatatggt taataaccaa    780
accaactata atgaattgtt taaaaatcaa aaataa                             816
```

<210> SEQ ID NO 71
<211> LENGTH: 2613
<212> TYPE: DNA
<213> ORGANISM: Lactococcus lactis CCOS 949

<400> SEQUENCE: 71

```
atggataaaa gaagcaaaga aaactttaaa gcttcgctca atgtccagaa acgtgtctct     60
gatggaattg atgcgaatgc ctttagaaaa cctcgacaag ccacgcaatt aagtaaacag    120
gcgtttaaag aagggaaaaa aacactcaaa attcgccgaa aaaactatcg aaaattaaaa    180
gctggttcag gtttacaagt tgtcgcagcc aaaaagaaag ttcttgaagc aaaagcagat    240
aaaaccgttt ctaaagcggt ttttaaaaat gcaaagaaat ctgatccaac acgagcagct    300
aatcaagcga aaggctatgc caagaatcaa gccaagcaaa cagcagtcaa ccacttagtg    360
ttatcgcctc ttgaaaaaga tgatacttta agagaaggtt cagacctcta tagaaagact    420
caacgtacca aaagtgggtt aaaactttct aaggatgttg tcacttcttc cgctaaagct    480
tcggttaatc tttcaaacca tacttacggt ttagccaatc gaagtgttaa tattgttcga    540
ggccgtgggt ttgtcagaac tccttctgaa ttggggttca gaaggcaagc cgcaaaaaga    600
atgcggaact ttcaaaataa gctgagtgcc gcaagaaagg caaaaaaggc ggagcaagga    660
ttttctttga ttcggtcaat cttaaaaggc caacaaaccc tgagtcgtgc gtttacttta    720
atcgtgacct ccaaagggtt actcgtcgtt cttgctgtta tgtttatatt gtgtctcttg    780
ggaatcctta acatggcctc ctctgttcca acaaagcaag atgactttca actgacaaag    840
tcttggacat atttcacaaa acttgatgca gacaattcag agaacggaaa ctctttttat    900
acgcctttgg atgatgtgat gttttatatg aatgatcaat ttgaagatta aatttacaa    960 gatcaagtgc ctgtaggttc aaatggcgca gcacttccta atcaaaatta tgaacaatat   1020
cttacaggcc tttggtcagc cttaaatggc tcttctcctg attataagct aacaacaatg   1080
gaggctttgg agacggataa gcgttctaaa tattatcttt ctcctgatga ttattcagat   1140
tttaaagaac gtgttaatga agtcggttat gatagccttg atggtcaact tcagtttcct   1200
tatcaaacag agagtttggt tatcaatcgt agatatggct acgaacggaa tggagataaa   1260
actgaactcc acgcaagcat tgatgttagt tcagccccag ggcaagattt aacttcacca   1320
atgcacggaa ttgttaattc tgtgactgac cctaatacat tggtcatttc tgaagctgaa   1380
aatgcacggt tgacaattgt tgggattaat agcggacggt ttattggtgg tgaaacagta   1440
gatgctggaa cacttcttgg caaggccaca aagtcaagtc ttaatatgac ctatgaaaaa   1500
tataatgaag atgataaaaa atgggaaaaa gttaatccag cattttattt tcctaaagtg   1560
acctatactc agtttacctc tttagcttca gatagctttg atccaggaaa agtgttttct   1620
gaacgtgcgg aggccgttta taatttctta accaaacttg gctataaaaa agaaggaatt   1680
```

```
tgcgctatct taggttcttt tactgaagaa tctcaaatca atcctaagcg agctgaagga    1740
gattatttat ctccaccagt tggtgcttct ggtaattctt gggatgatcc ggcttggtta    1800
gctatgggtg ggttggatat ttacggaaaa tatccaaata ttcttcatag agggttgggg    1860
ttaggtcaat ggacagatac atctgatggt tctgaaagac acactttact tttaaattat    1920
gccaaagcaa aaataaaaa atggtacgac ttagaccttc agcttgattt tatgctcaat    1980
ggagatactc cagggaatca aaccatgttt aaaaataccg ctagtaatgc cgtctcttct    2040
tcaattccag aactgaccaa ctacttcttg acttactggg aaggaaatcc aggtgacaag    2100
attcaggcac gtgtacaagc cgcccaaaat tggttcactt acttctcaaa taacggtggc    2160
tccgatgcgg atatgagcgc ttcatcaaaa gaactctttg agaaatataa agacaaaatt    2220
aaacctctcc cttctaataa agaaacacaa caagggcaag gatggcctgg gaatggctat    2280
gaacctggga attgtacttg gtatgtcttt aatcgtcaag ctcaaattgg tcataatatt    2340
aatggctata tgggtaatgg tggccaatgg ggttataact atactaaaac tccaggagct    2400
acaattgatt ctaaaccaca agtgggagat gcggtaagtt tctctccagg tgttgcaggg    2460
tctagttcag aatatgggca cgtggctcaa gttgaagttg tcaatccaga tggtacattt    2520
ttagtttctg aaatgaacac tttaggcctt tattcaatgg gctatcgaat gtttaaacca    2580
ggagcaggaa tgacatttgt tcattttaaa taa                                 2613

<210> SEQ ID NO 72
<211> LENGTH: 978
<212> TYPE: DNA
<213> ORGANISM: Lactococcus lactis CCOS 949

<400> SEQUENCE: 72
atggaaaaag gattattagt cgatattgga cgaaaatatt ggtcaatagc agagttaaaa      60
agattagttc ttttacttca agagcataag ctgacacatt tacaacttca tctcaatgaa     120
aatgaaggat ttgcgctaaa ttttactgac agccctgtca gtaaaaaata ttcagaaaat     180
atgctcaaag aattgaaaga atttgcaaaa acacacgaaa tcactttgat tcctgatttt     240
gatagtccag gtcacatggg ctccttatta gagcaaaatc ctgaatttgc actacctgac     300
agcaatcaac aagcggtaga tgttactaat ccagcagtca ttgattggat tatgggaata     360
attgataaga tagtcgatat ttttcccagat tcagatactt ttcatatcgg ggctgatgaa     420
tttattgatt tcggcaaat tgaaaaatat ccttatttag tggagaaaac tcgggaaaaa     480
tatggaaata aggcaagtgg tttagagttt tattatgact atgttaatca attgaccgag     540
catttgcaga aaaaggaaa acaagttcgt atttggaatg atggatttt acgaaaagac     600 cttcagtcat tggttccttt gaataaaaat gtggaggttt gttattggac aaactgggac     660
aaagggatgg cagaagtcaa agaatggtta actaagggtt ataccttaat aaatttttgt     720
gataatgacc tttattatgt tttaggtgaa gaagcaggct attcttatcc aacggctgaa     780
aaactggaaa gggaaggaaa aattcaaaaa ttttctggtc agcaatattt aaatcaagaa     840
gagatgaaag ctgtcagagg aacttacttt tcgatttggg ctgacaatgc tgcagctaag     900
tctgtcagtg aaattttaga cgatcttagc aaggtacttc cggtatttat gaaaatttat     960
ggaggaaatg atgaataa                                                   978

<210> SEQ ID NO 73
<211> LENGTH: 1641
<212> TYPE: DNA
<213> ORGANISM: Lactococcus lactis CCOS 949
```

<400> SEQUENCE: 73

```
atgaaaaaat cgaaaaaatt ttttattaga atatgccttt ctacaggaat tttggcatct    60
gcaactttac tgacagcttg ttttggaact ccagcaaaac atgtgaaagc taattataaa   120
gtgacagcag aagcaattcc agattaccaa agtaagaatg ctcccatttc atcttattgg   180
atgcctgata aatttctaga atggtcagcg aaaatgaca aagatttagt ttacaatcaa   240
tcccgagtgc cacttaccaa agaatttct cctgataaac taagtccatc caatcaaaat   300
cagaacaaaa agacaaaaat tgtcgccttg tcgatgatga actcacaaac ttctggaaat   360
ccttcgcggg gcacgacaaa atttgagagc tatactttg attattggca atatattgac    420
acactggttt attggggtgg ctcatctggt gaaggaataa ttgtaactcc gtcagcagat   480
gttattgatg aagcacacag caatggtgtt ccggtacttg aacaattttt cttgccgcct   540
aaagaatacg gtggaaaagt agattgggtc aaaacaatgc tcaaaaaaga tgagcaagga   600
caatatccat ttgccagtca aatggttaag gttgccaaga cttatggatt tgagggttgg   660
tttatcaatg aagaaaccca agggctaaat gctgacgatg cagctaacat gaaagccttg   720
attcaacagg tgaaaaaaga agattctagt cttcaaatca tgtggtatga tgccatgact   780
aaagatggaa aagtggattg gcaaaatcag ttaaatgacc aaaatgcgac atttgtacaa   840
gataaagcag cagacgcgat gtttttaaat ttctggtgga ctcaaaataa tttggccgac   900
caaaaattac ttgaaaaatc gaatctctat gctaaaaatc acaatattga cccttataat   960
atttatgccg aatagatgt gcaagcgaaa gacgtccaaa ctccagttaa atggaacctt  1020
ttagaaaaag gaaatcaagc cactcaaaca tcaattggac tctatgcagc aagcgctacc  1080
tacactaacg caagtaattg ggatgatttt caaaatcgtg aatcagcatt ctgggtcaat  1140
caaaaagcag accctcgtca agttgatcac tctgttaatg aatcatggac aggactttcc  1200
aaatatgttc tggaaaaatc agcaataagc ggtaatgaat ttaatactaa ttttaattta  1260
ggaaatggtt ataactattt taagctggt caaaaaatct cagaaatgga ttggaacgac  1320
cgcagtttag caggtatttt accatcttac cgctggatta ttgacaacga aggaaaaaat  1380
aaaataagtc caagcttcga ctttgcaaat gcttataacg gtggaaattc actgaaatt t  1440
atggctgaac atttagatgc aggcaaaagc tcaaacatca cattgtttgc tagtgatttg  1500
aaaattgcta tgggagcaaa attctctgtt agtatgcgct cagaccaagc gcttaaagtt  1560
tctgcaatct tagaactagc aaatggtcaa aaagttagca ttgcaggaga taaaagcctg  1620
actgagaatt ggtcaaaata a                                             1641
```

<210> SEQ ID NO 74
<211> LENGTH: 630
<212> TYPE: DNA
<213> ORGANISM: Lactococcus lactis CCOS 949

<400> SEQUENCE: 74

```
atgaaatata aaactcgacg aagaaaacca atcgacgtc aatccttgtt aaaacagctc     60
atctttattt tcctagttat tttaggaatc ttagtctata ataaaatttt taataaccaa   120
gcacaaaagc cgtctgaagc acaacttcaa gaaattaatg aacataaatt catcaaagaa   180
attgctccac tcgctcaaaa atcacaaaaa gaaagtcaag tactagcttc tatcaccatt   240
gctcaggcct gtcttgagtc taattttggc aaaagcgaac ttgcaagtaa atatcataac   300
ctttttggtg tcaagcatc tgatgatgtg ccaaggtttt cgcttgctac gcaagaatat    360
gaaaatggtc agtgggtcac tgtccaaggt gttttccgtg tttatccaaa ttttgctgat   420
```

```
tcagtttcgg cacacaccca gctttctctt tacggaacaa catggaattc taaacaatat    480
gcttcagttc ttagtgcaac tgattataaa actgctgcta aagccgttca aaattctggc    540
tatgcaacag accccactta tgctgacaaa cttatcaata tgattgaaac ttatcattta    600
aatcaatatg ataaaagttc aagtatttaa                                     630
```

<210> SEQ ID NO 75
<211> LENGTH: 780
<212> TYPE: DNA
<213> ORGANISM: Lactococcus lactis CCOS 949

<400> SEQUENCE: 75

```
atgtcaagta ttgaaaatat gattgcttgg atgcaagcac gaaagggtaa ggtaacttac     60
tcaatgacct tgcgaatggg tcctagaagt tatgactgca gctcgtcagt attctttgca    120
atgattgctg gaggttttct gtcagaaggt tcaatgggta atactgaaac cttgtttgga    180
atgtcaggaa cgaagctgaa agaaatcagt cgtggagagg tccagcgtgg cgatatcttc    240
atctcaggca ctccaggagg ttcagctggt tcggacggac acgggtat tttcttaagt     300 aacggttcat tcattcactg ttcttacact cacaatggaa ttgcggttga tacgaatgat    360
gcatatatga gtactcgctt accacatcac ttttatcgaa ttgttggttc aggttctgga    420
aatactgaca ataaacctca atggttaca ttaaatgttg atggccagtt tggtaatgcg    480
actgctaaac gattacaaga atactttgat acggctggta agacggagt aatcagtcac    540 cagtacaaac aaacccttaa tcaaaatatt tatgctgcac agtttgattc atcactgaca    600
ggctcaaaag tggtcaaagc attgcaaaga ttcttaggca ttggccaaga cggcttgttt    660
gggcaagcta cgattaaagc cttacagaaa caccttggaa caacgcaaga cggaactatc    720
agcccagttt ctgattctgt tagagaatta caaagacgat tgaatgcgaa taaattataa    780
```

<210> SEQ ID NO 76
<211> LENGTH: 780
<212> TYPE: DNA
<213> ORGANISM: Lactococcus lactis CCOS 949

<400> SEQUENCE: 76

```
atgtcaagta ttgaaaatat gattgcttgg atgcaagcac gaaaaggtaa agttacctat     60
tcaatgactt cacgaatggg tccaaaaagt tatgattgta gttcatcagt tttctttgca    120
atgattgctg gaggttttct gtcagaaggt tcaatgggta atactgaaac cttgtttgga    180
atgtcaggaa caaagctgaa agaaatcagt cgaggagaag tccagcgtgg cgatatcttc    240
atttcaggta ctccaggagg ttcagctggt tcggacggac acgggtat tttcttaagt     300 aacggttcat tcattcactg ttcttacact cacaatggaa ttgcggttga tacgaatgat    360
gcatatatga gtactcgctt accacaccac ttttatcgaa tcgttggttc tggttcagga    420
aagactgaca gtaaacctca atgattaca ttgaatgttg acggtcaatt tggtaatgcg    480
acagctaaac gattgcaaga atactttgat acggctggta agacggagt aatcagtcac    540 cagtataaac aaacccttaa ccaaaatatt tatgctgcac agtttgattc atcactgaca    600
ggctcaaacg tggtaaaagc attgcaaaga ttcctaggaa ttggccaaga cggattattt    660
ggtcaaggaa ctatcaaagc tttacagaag catcttggaa caacgcaaga cggaactatc    720
agcccagtat ctgattctgt gagagaatta caacggagat aaatgcgaa taaattataa    780
```

<210> SEQ ID NO 77
<211> LENGTH: 1212
<212> TYPE: DNA
<213> ORGANISM: Lactococcus lactis CCOS 949

<400> SEQUENCE: 77

| | | | | | |
|---|---|---|---|---|---|
| atgactaagc | gcttaaagaa | aaaagcaaaa | ccagttgttt | ttctagctct | tgttcttggt | 60 |
| tgtgcattaa | ttttatcagg | agttcttggt | ttggcgggac | atttaaacga | acaagaatcg | 120 |
| tctaaaacaa | aaaagaaaag | tcaattgtca | gaaactaaaa | ggagttcaac | ttccccaaaa | 180 |
| aatatggata | aaaatattga | gcagatgact | ttgaacaaaa | agttggtca | gttatttatg | 240 |
| acaggaatgc | cagcaaataa | ctataatcag | gcaacttttg | atgcgattga | aaagtatcaa | 300 |
| gtaggtagta | ttattttgac | tggtcgctct | aatctcagtg | tcccagaaat | gaaagatatt | 360 |
| actgacaaac | tacaaggctt | agaaccggct | aatcgcaaac | tcttgatatc | ctgtgaccaa | 420 |
| gagggaggaa | atgttcaagt | tctccaaggt | cagggttttt | cacagattcc | tgatggatta | 480 |
| actcaaggaa | gttggacagc | tgataaatta | caaaaggaat | cacaaacttg | ggaagtgaa | 540 |
| ctttacgcag | ctggagtgaa | ttttgactta | gcaccagttg | ctgaccaagt | tttatctgcc | 600 |
| gactttgctc | cacaaaatgc | tccaattggc | tattggagtc | gccaatatgc | ttatgataaa | 660 |
| gcaagtatca | taagccatgc | tcaagcattt | acggaaggca | tgaaagcagc | caaggttttg | 720 |
| acaactgcta | acatttttcc | agggcttgga | gcggtgacag | gcaatacaga | tatcagtgca | 780 |
| ggtgttagag | atgaccaaac | gaattccaat | agcgaatctg | ttcaaatttt | caagagattta | 840 |
| atctcttctg | ggacaccttc | gattatgacc | gcaaccgcta | tttatgataa | aattgacccct | 900 |
| aatcttcccg | gtgctttttc | atccaaaatg | gttgatggtt | tactacggaa | acaattaggc | 960 |
| tttgatggtt | tggttattac | agatgattta | tcaaatgctg | tccaagtaca | atcatggacg | 1020 |
| cctggtcaaa | gggcagtttt | agcattgtca | gcaggaaatg | accttgtttt | agcaaatgag | 1080 |
| cctacacaaa | ttccagaaat | gatctcagaa | gttttgcaaa | aggtaaaagc | agacccagac | 1140 |
| tttgctaaaa | aaatcagtca | atcagccaca | agagtgatta | agtaaaaga | agaaatgaaa | 1200 |
| cttgtagaat | ag | | | | | 1212 |

<210> SEQ ID NO 78
<211> LENGTH: 939
<212> TYPE: DNA
<213> ORGANISM: Lactococcus lactis CCOS 949

<400> SEQUENCE: 78

| | | | | | |
|---|---|---|---|---|---|
| atgattgccc | aagggatttt | agaatcaagt | ggtggacaaa | gtgccttagc | aagcaattat | 60 |
| aataatattt | ttggagttaa | atacacttct | ggtacacctg | tttatctacc | aacacaagag | 120 |
| tatttgaatg | gaacaatgac | aaatgttgtt | gaacccttcc | aagcttatag | ctcagtttat | 180 |
| gacgcatgtg | ttgcccaagc | taaaatgtta | cgtgcttcat | catattattc | tggggcttgg | 240 |
| cgtgaaaata | caagttctta | cttagatgcg | acagcttggc | ttgaaggacg | ttatgccacg | 300 |
| gatccaactt | atgcttctaa | attgaatagc | gtgatttctg | aacttggttt | aagtgtttat | 360 |
| gaccaaggag | gagaaatatc | aggaggaact | gctgttacaa | ctagttcatc | agcctcaaca | 420 |
| aattcagctg | gcacatacaa | agtacaagag | ggtgattcat | tatcagcaat | cgctgctcaa | 480 |
| tatggtacaa | ctgttgatgc | acttgtgtca | gcaaatagtt | tagaaaatgc | gaacgatatt | 540 |
| catgtaggag | aagtttttgca | agttgctggt | gctagcacaa | ctacaacaag | taccaataca | 600 |
| acttccaatg | tatcgtcaag | ttctactttat | accgtcaaat | caggagatag | tttatattcg | 660 |

```
attgcggaac aatatggaat gactgtttca tcactgatgt cagccaatgg aatttatgat    720
gttaattcaa tgcttcaagt aggacaagta ttgcaagtaa ctgtaagtac tagtgcaaca    780
acttcaaaca caacgacttc aaacagttat acaattcaaa atggtgacag catttattca    840
attgccacag caaatggtat gacagctgac caattagcag ccctcaatgg atttggaatt    900
aatgacatga ttcatccagg acaaacaatt agaatctaa                           939
```

<210> SEQ ID NO 79
<211> LENGTH: 1041
<212> TYPE: DNA
<213> ORGANISM: Lactococcus lactis CCOS 949

<400> SEQUENCE: 79

```
atggaaaaag caattaagcg gaaggttata ttagttagcc ttccttttt gttgctttta     60 ttgccaatat tagctttctt ttcattattt gttggttcaa attcttcttc agatacagat   120
attaatacta atacaccaca gcaacaaact gccaaagtga tttgggatag agttctaaaa   180
gaaggtggaa cgaaagaagg ggcggctgct ttacttggta ataatcaagc agaaagtgaa   240
cttcaacctt caattattca atctaatgca acttataatg aagcaaaagc aatggatacc   300
actttaggcg ttatgctttt cggcttggct caatgggata gtggcaggcg agtaaacttg   360
ctaaactatg cgaaaagtca gaaaaaatct tggacagata ctaatcttca agttgagttc   420
atgtttgagc aagacggtac agattcaacg ttacttaaac aattagtcaa aggaactaat   480
gttaagcaaa cgactgaaga tattatgcga agtgggaaac gtgcaggggc ggttgatagc   540
cttccaaaac gtcaaggttt tgcggaatat tggtacacgt tcatgacgac tggtggtgat   600
agtggaactg gtggtggttc aggaattact ccagatatac cttctggttg gactttagat   660
aaaccaatta tacaagtgg ttatcttgcg acaagttatg agtataaaca atgtacatgg   720
ttcacatgga atcgagccaa agatttcggt atcacttttg gaatgtatat gggaaatggt   780
gctgattggc aacatcaagc aggatatact gtaacgacaa ctccgacact ccatagtgcg   840
gttagcttta gcggtggtca aacagtaggc ggtcaatgga acgcagaccc tgtttacggt   900
cacgtggctt ttgtggaagg aatacactct gacggttcag tcttaatttc acagtcagga   960
actggtttta gtgcggttta ctttccaa gtgctgacaa aagcacaagc cagtcaatta   1020
cattacgtga taggaaaata a                                             1041
```

<210> SEQ ID NO 80
<211> LENGTH: 2154
<212> TYPE: DNA
<213> ORGANISM: Lactococcus lactis CCOS 949

<400> SEQUENCE: 80

```
atgaagataa acaaaattga tacccgtcat ggtactgcta atcaatccac tttttcacat     60
gggaattgcc ttccttacac tggttttcct tggggaatga attattttc cccttcaacc    120 ggtgctgctc gtggagcttg gtggtttcat ccagaagacc gtacctttga aggctaccga    180
atcactcacc aacccagtcc ttggatggga gatttctcac atttgacaat gacgcctgtt    240
gcaggtcctt tgcctgaaac ttccttgtgg cacacagtga gttcataccg tccagaagaa    300
tcaactttta atccaacgca actcaaaatt actcaattac gttatcagat tacatctcag    360
ttaattccat caatgtatgg tggaattcta tcaatgaatt atcaaaattt aagccttaaa    420
gataatggct tgatgcttca tctccccggt tcttatgaac ttcaacaact tgacgattac    480
agcttagagc tttcaattat taattttgcg ggttgtgaag atgaaaattt tactttctat    540
```

```
ctcaaattta ctgctgacca accttttgtt ttaagtggaa atttatctga tgaagattct     600
tctgttcgct tagatttcaa agcagccaag caggttcaaa tacattttgc tacctctttt     660
atttccaagg aacaagccgc tcttaatctg gagcgtgaac aagataattc agcagaaaca     720
tatttggaaa atgctgaatc agcttggaat aaccttttt cacgtatcga aattgagcat      780
cataatcaac aagaagtttc cactttctat cacaatcttt atcgctcatt tctctttcca     840
caaacttttt atgaatttga ccaagagcat caaaaaatcc attacgatac aagctctaaa     900
actgtcaaga aaggcccgct ctatacaaac aatggcttct gggatacttt ccgaacagtc     960
tatccgcttt atagtctaat agccgttgac gagtacggtg atatgctcga aggtttccta    1020
aattcttatc gtgcgactgg ttttcttcca aaatggcttt ctcctgatga acgtggtcta    1080
atgcccggta ccttgataga cgctgtcatt gctgatgctg caagcaaaaa cattcgtcct    1140
gatttgatgc ccgagttttt ggaagcaatg aaaaaaggag ccacaagtca atctgaaaac    1200
tctaattacg gccgtcgtgg cacaaaagat tatctaaaac ttggttatgt tccgctcact    1260
caccatgaat cagttaatca cactttagat tacgcatttt ctgattattg tatttctcaa    1320
gtggcgaaac aaaccggtga caagaaaatt tcagacttct atgcccatca agcaaaagac    1380
tatcaaaata ttttgattc tgaaactggt tttatgcgag caaagatgc tgacggaaat       1440
ttcagagctg acttttaga tattcgttgg ggtcgtgatt atgcagaagg ttctgcttgg      1500
cagacttctt ggtcagttct tcatgatttt gctggattga ttaaactaca tggctcaaga    1560
gaaaattttg aaaacaaact catcgagctt tgcaaccaac gaccaaattt caatgttgaa    1620
ggatatggtt ttgaaattca cgaaatgagt gaaatggctg ctatcgaatt tggacaagtg    1680
gctatctcaa atcaaccaag tttccattac ccataccttt ttagctacat tggtaaacct    1740
tggatggcta cgccttaat caaaaattta ctgacagaaa catttaatga tagtccgaag    1800
ggctatcctg gtgacgaaga taatggaaca atggcagctt ggtatatttt ttcaagttta    1860
ggattctatc cagtcacagc tgcttctaat caatatgtat taggaattcc actctgggac    1920
aaagctagaa tcaaccttc ctctggtcag caacttacta ttcttgcaga accaaatgct    1980
ccgcaacaag ttttcgtcaa ccaaatcaca tttactgaca aaaagtcaa tgatactttt     2040
atcaagcacg aagaattgat aaaaggcgga accctaaaat ttgatttagg aatcgtacca    2100
aatccactta atatacgaa cgaacaactt ccttattcac tgacagaaaa ttaa            2154
```

<210> SEQ ID NO 81
<211> LENGTH: 1155
<212> TYPE: DNA
<213> ORGANISM: Lactococcus lactis CCOS 949

<400> SEQUENCE: 81

```
ttggtcaaaa taagttttga tgttaagaaa tttgaaggtc aaacaatcaa aaaaatcggt      60
ttaagcataa atctgatca agcaatggat tttaaagcca ttaatctagg agaaatgact    120
ttgaccaatg gtcaaaaagt cgctccaatc gcactttcgg atgcaaaagt aactgatgaa    180
gcttttgaag aagaaggaac agtaggcggt tttagacttt cttggaaatc agatgcaaat    240
aaaaataatt tttctactta tgaaatctat cagttgaatg atgatggaag taagaatttt    300
ttaggagcaa gcaatatcaa tgccttcttt gttaatgcct aaaacgcgg caaaaatatc    360
aattcaacaa aatttgaaat tgtcccaatt aataaggctg gagaatctgg acattcagtt    420
acgacctctg tgaatggcc agataattca ttagctaaag cggcatttgt agcagataaa    480
accctagtta caattggtga aaaagtaact ttaatgaatc aatctaatct agcttccgtc    540
```

-continued

```
aaatataaat gggatattga tggtgcaagt cccgctactt ctacagaaaa gaatcctcaa      600
gtaagttttg ataaagcagg gagttattcc gtcaaattaa cggtcatcaa tgaaaaagga      660
caagaagatt cagtcactca aactgaactg attactgtaa ttgatcaacc agtagaatta      720
acaaattttg cattaaatca atccgttcaa gtagacagtt tcactaatga atctgaatca      780
ggaccaaaag cagttgatgg aaaattaaat accaaatggt gtgccgttgg cccaggtaaa      840
cacaatatta caattgacat tggaaaatca gaaaaaatca atcaagtcct gattgaccat      900
gcgcaaaaag gaggagaatc gcctgacatg aatacttctg attacaccat tgagatttca      960
aaggataatc aaaattggac agaagttgtc aacgttaaga aaaatataatt gggagaaacc     1020 aaagattctt tcaaacagac agaagcgcgt tacgttagaa tcacagccac taaaccaaca     1080
caaggagcag ataccgctgt tcgtttatat gaaatacaag tattaggaca aaaaaaagct     1140
gacaaagggc tgtaa                                                      1155
```

<210> SEQ ID NO 82
<211> LENGTH: 57
<212> TYPE: PRT
<213> ORGANISM: Lactococcus lactis CCOS 949

<400> SEQUENCE: 82

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55
```

<210> SEQ ID NO 83
<211> LENGTH: 1191
<212> TYPE: DNA
<213> ORGANISM: Lactococcus lactis CCOS 949

<400> SEQUENCE: 83

```
tagtacttgt acactccccc agtcatcggt ctttacctta ggaagcgccc tccttgcggt       60
taggcaacct acttcgggta ctcccaactc ccgtggtgtg acgggcggtg tgtacaaggc      120
ccgggaacgt attaccgcg gcgtgctgat ccgcgattac tagcgattcc gacttcatgt      180
aggcgagttg cagcctacaa tccgaactga gaatggtttt aagagattag ctaaacatca      240
ctgtctcgcg actcgttgta ccatccattg tagcacgtgt gtagcccagg tcataagggg      300
catgatgatt tgacgtcatc cccaccttcc tccggtttat caccggcagt ctcgttagag      360
tgcccaactt aatgatggca actaacaata ggggttgcgc tcgttgcggg acttaaccca      420
acatctcacg acacgagctg acgacaacca tgcaccacct gtatcccgtg tcccgaagga      480
acttcctatc tctaggaata gcacgagtat gtcaagacct ggtaaggttc ttcgcgttgc      540
ttcgaattaa accacatgct ccaccgcttg tgcgggcccc cgtcaattcc tttgagtttc      600
aaccttgcgg tcgtactccc caggcggagt gcttattgcg ttagctgcga tacagagaac      660
ttatagctcc ctacatctag cactcatcgt ttacggcgtg gactaccagg gtatctaatc      720
ctgtttgctc cccacgcttt cgagcctcag tgtcagttac aggccagaga gccgctttcg      780
ccaccggtgt tcctccatat atctacgcat ttcaccgcta cacatggaat tccactctcc      840
tctcctgcac tcaagtctac cagtttccaa tgcatacaat ggttgagcca ctgccttttta      900
```

-continued

| | |
|---|---|
| caccagactt aataaaccac ctgcgctcgc tttacgccca ataaatccgg acaacgctcg | 960 |
| ggacctacgt attaccgcgg ctgctggcac gtagttagcc gtccctttct gggtagttac | 1020 |
| cgtcacttga tgagctttcc actctcacca acgttcttct ctaccaacag agttttacga | 1080 |
| tccgaaaacc ttcttcactc acgcggcgtt gctcggtcag actttcgtcc attgccgaag | 1140 |
| attccctact gctgcctccc gtaagaattt gggccgtgtc tcagtcccaa t | 1191 |

<210> SEQ ID NO 84
<211> LENGTH: 1710
<212> TYPE: DNA
<213> ORGANISM: Lactobacillus jensenii CCOS 962

<400> SEQUENCE: 84

| | |
|---|---|
| atgactaaac aaactttgca agctgaagct aatggtcgta atggtaagat taagtttgat | 60 |
| attaatattg ataataacga aataaaagat ataaaggtta ccaaatctag tgaaacacca | 120 |
| gcaatattta atcaggtttt tgataaatta aaaaattcca ttatagagga gcaatcattt | 180 |
| gatgtagacg ctgtatcggg cgctacaatt atgacaagtg ctttacttga ttctggaaaa | 240 |
| aaggctttga atcaggcagg agttacacca gtagctaaag agagcgataa aacacatcgg | 300 |
| gaagtaaacc tagatgtaga tgttgccgtc attggctcag gtgccgcagg attgattgca | 360 |
| gcttgccgag ctctttcaat gggaaaaaat gtagtagttc ttgaaaagaa tggttattta | 420 |
| ggtggagcta caatattaaa tggttcaaat gtagtagcta caggttctaa cttggctcag | 480 |
| caattatttg gtactgaggc acaagaagat agtagtaaac ggcttttttgc tgatattact | 540 |
| cgtgaatgcc gaggtacaaa ttatcctgaa ttatcaaaag ttttggttga aaatattggt | 600 |
| aaagctgttg atttttattaa agagtttgcg ggtttgactt atcaaaaagc agaaacacaa | 660 |
| acaattgagc attcagttaa tcggcaagtg aaatgccaa gtgaaagctc atatgaatta | 720 |
| attaaaaaga tagcagctgc cttttgaagaa aagggtggca agattttact tgatgctcgt | 780 |
| gttgaaaaaa tcaattctga aaatggtgta cctattagtc tagttgctga aggaaagcac | 840 |
| caaactacaa acgttaagtt caaatcactt attttagctg ccggtggttg gggtgccaaa | 900 |
| gactttaaag aaaagcgaac ttcgattcct tattatggtc caatgacttc aactggagat | 960 |
| tatttcttct ttaacaaggg attaaatttg gctagtcgta atttagattg gtataaagtt | 1020 |
| tatccacatg ggttagaagt tgaacctgga attgctaaac ttacaactta ttcaacaaaa | 1080 |
| gaagcaagtg atatgggggc aattttttatt aatcgggctg gtaatagaat tgtaaatgaa | 1140 |
| tcagatccat acactcattt tagagatgca attgctgctc aaaaagatca gatagctttt | 1200 |
| gttcttatgg atcaaagaat ttggaacaga ttttatgaat taatgcttaa atatggtttt | 1260 |
| actgctgatg aaattagtca ttattttgca cttgatggca aacaaagccc aattttagta | 1320 |
| aaaggcactc ttgaaaccgt agctaataaa gctggtatta attttgaaaa tttacagcat | 1380 |
| actttatcta attatcaaaa ttatgccaaa aatggcaaag atcctgagtt cggacgtgaa | 1440 |
| gcaaaattta tgcatgaata ttcaggtgat acttactacg ttattgaaca aaaacttcgc | 1500 |
| ttctgtacaa ctttaggtgg gtatgaaact aatagccaaa tgcaattatt aaataatgat | 1560 |
| atgaagccag tggctaatta ttatgcagct ggtgaagtaa ttggtggtgc caatggtcat | 1620 |
| gactctatgc caagtatgat gaattcatgg agttatgctt caggcttttt agctggaact | 1680 |
| aatgccagcg acaattgtaa taatcgataa | 1710 |

<210> SEQ ID NO 85
<211> LENGTH: 2154
<212> TYPE: DNA
<213> ORGANISM: Lactobacillus jensenii CCOS 962

<400> SEQUENCE: 85

| | | | | | |
|---|---|---|---|---|---|
| atgaaaacta | aaaaaatcac | tggcgttgct | accgcagctt | tactagcctc | cgttgctgtg | 60 |
| ccagttacca | acaatttagc | taatattcag | acttcctata | ctgctaaagc | agtcactggt | 120 |
| caacagcaag | cattttaaa | tacagctata | cctaatgctg | aagcagcttc | tgctaggtat | 180 |
| ggaacgtata | cttccgtcat | gcttgcacaa | tcaatacttg | aatctggttg | gggcgcttca | 240 |
| cttctcgcca | cacaggctaa | taacctattt | ggtatgaaag | gttcatataa | tggacaaact | 300 |
| tattatacta | atacttcaga | atgggcctct | ggaacaggtt | attacaatat | aaatgctggt | 360 |
| tttagaaaat | atccttcttg | gcagcatctc | tttgaagata | tggttacaa | attaagaaca | 420 |
| ggtactaccg | ataatccaag | tcgttataga | atggcttgga | ttgaaaatgc | tgcaaactat | 480 |
| caagtggcta | cacagggctt | gaaagatggg | ggttatgcta | cttcaccaac | ttatcctcaa | 540 |
| tcgttaaata | gagtaatttc | ttcttacggt | cttaatcaat | acgatccgtc | tgtagatacc | 600 |
| acaactaaaa | caatgagagt | tttatcaaat | ggaacagttt | attccggtcc | agccgattct | 660 |
| agtgtagtta | gtgcaactgg | taatattact | gctggtcaag | tggttactgt | tgataaaaca | 720 |
| gttacttata | aaaatggact | aagttatatg | catattagca | atggttggat | taatggttca | 780 |
| ttgttaaccg | gaagttcaac | tcaagctacc | acaacagaaa | aagcaggaac | aacaaccgat | 840 |
| gcaggtaatg | cagcaattaa | ggtagtatac | acgagtgcaa | ttgcagaatg | gaaaaatcca | 900 |
| ggtagtggag | tagtaggcta | cttacaaaag | ggaacgaccc | aaacagtagt | tggaaaaatc | 960 |
| caagtaaatg | gagcatggtg | gtataagcta | tcatcaggta | attgggtacc | aggggaatat | 1020 |
| gtatatgtca | caggtgcatc | aagaatacca | acaattgata | caatgtagt | aaatcaaaat | 1080 |
| acaaaagtaa | aaataaaata | tatatcaggc | tatagcatag | cagtatggtc | aaatccagca | 1140 |
| ataggaacaa | caggccaata | tttaaaagac | ggaacagaag | tacaaacgat | tggatatact | 1200 |
| acagctaatg | gcaagaaatg | gtataaatta | gcgaataata | cgtggatacc | agcagaatat | 1260 |
| actgaagtag | taagttcatc | aacagtggta | acgaatatta | ctaatgaaag | taatacagta | 1320 |
| gcgataaaatt | atccgcacta | cagtatagct | gtatggagtg | aaccaggtag | aaactcaaca | 1380 |
| ggaaagtact | tatcagatgg | gacaaaagtc | caaacagtag | ttataccac | agtaaatggt | 1440 |
| aagaaatggt | ataagctagc | agataatacg | tggataccgg | cagagtatac | taaagtagta | 1500 |
| agttcatcaa | cagtagtaac | gaatattact | aatgaaagta | atacagtagc | gataaattat | 1560 |
| ccgcactaca | gcatagctgt | atggggtgaa | ccagtaaaa | actcaacagg | aaagtactta | 1620 |
| tcagatggaa | caaaagtcca | aacagtaggt | tataccacag | taaatggcaa | gaaatggtat | 1680 |
| aagctagcag | ataatacgtg | gataccagca | gaatatacga | aagcagtaag | ttcaacggat | 1740 |
| actactagcg | gaaataatac | agtaacagta | aattatccag | gctatagcat | agtagtatgg | 1800 |
| agtgaaccag | gcagaaactc | aacaggaaag | tacatatcgg | atggaacaag | tgtaaaatat | 1860 |
| tacgcaaccg | caaattataa | tggtcaaaca | tggtataaga | taggtgaaaa | ccaatgggta | 1920 |
| ccaggtcaat | atgtaaaagt | aaatgcatca | ataatagtg | aagcgtgac | agtaaaatac | 1980 |
| atatccggat | atggtatagc | aatatggtca | aatccaggca | gaattcaac | aggaaagtat | 2040 |
| ctggagaatg | gcacaacagt | aaaatatttt | gagacccaaa | attacaatgg | ccaaacatgg | 2100 |
| tataaaatag | gtgaaaacca | atgggtacca | gcacaatatg | ttagtgtaaa | ttaa | 2154 |

<210> SEQ ID NO 86
<211> LENGTH: 2328
<212> TYPE: DNA
<213> ORGANISM: Lactobacillus jensenii CCOS 962

<400> SEQUENCE: 86

| | | | | | |
|---|---|---|---|---|---|
| atggcagaga | ataatcatcg | ttcagcaagt | aatactgcac | ctaagaattc | tcgaatggcc | 60 |
| aacttgcatc | atgatagtgg | tcaacccaag | agacgcctct | ggctacaaat | tcttaagtgg | 120 |
| ttttcaattg | gtattttgct | gatactcgtt | tctggcgtcg | gtttatttgc | ttattacgcc | 180 |
| aaagacgctc | catcaattag | tcaagatcaa | ctacaaagtg | gtggttcaag | tagtttctat | 240 |
| actagtgatg | gtaaattcct | tctttcatta | ggttcagaaa | aaagaactta | tgttaagaat | 300 |
| tctgatattc | ctcaaacttt | gaaagatgca | gtagtatctg | tagaagataa | agatttttat | 360 |
| caagaaaatt | tagggattga | cccaatcaga | attgttggtt | caatcgtctc | aaatgccaag | 420 |
| tcaagtggta | ttgcagctgg | tggttcaagt | atcacccagc | aattagttaa | gttaactgtt | 480 |
| ttctctaccg | ctgcttcgca | aagaactcta | aagagaaagg | ctcaagaagc | ttggctggca | 540 |
| attagagttg | agcatgacta | caccaaaaat | caaattttgg | aatactacat | taataaggtt | 600 |
| tacatgaact | atggtgtata | tggcatggga | acagctgccg | attactacta | cggcaagtca | 660 |
| ctaaaagatc | ttgacttagc | acaaacggca | ttaattgctg | ggatgcctaa | tgccccagtt | 720 |
| gcttatgatc | cttatactta | cccaaaggca | gctaaatatc | gtcgtgatat | tgttttaaat | 780 |
| gcaatgtatg | ctaatggtaa | gatcagtaag | gctcaattaa | aggcagccaa | ggctgaatca | 840 |
| attacacaag | gccttaaaac | ccaacaaaat | agttcagaat | cttcaattag | aaggattgat | 900 |
| gatccttata | ttaaggaagc | aatttcagaa | gttaaatcca | agggttatga | tccttataat | 960 |
| gataacttaa | agattacttt | gaacatcgat | caagatgctc | aaaacaaact | ttatgaactt | 1020 |
| gcaaatggtt | caagtattcc | atttttcatca | agtaaaatgc | aagttggtgc | aaccatcatt | 1080 |
| aatccaagca | acggtcacgt | tgtagcaata | attggtggac | gtaatttacc | atctgttcaa | 1140 |
| ttgggacttg | accgggcagt | acaaactggc | cgctcaactg | gttcatctat | taaaccagtt | 1200 |
| ttagattatg | cacccgcaat | tgaatatttg | aactggtcaa | cagcacacta | ccttgaagat | 1260 |
| actaaatatg | tatatccctgg | tacaagcatc | cagctttatg | actgggataa | caaatatatg | 1320 |
| ggtaaaatga | cgatgcgcta | tgcccttgaa | caatcaagaa | atgttccagc | tgttaaaacc | 1380 |
| ttagctaaag | taggtatgaa | gaaagcttca | ctatttgcta | aaaagatgaa | catttcagtt | 1440 |
| ggttcaaatc | aaggtctttc | agtagccatc | ggtgcaaatg | cttcttccct | tcaaatggct | 1500 |
| ggtgcatatg | ccgcctttgc | aaatgaaggt | gtttactaca | agccacaatt | tgtatctcaa | 1560 |
| attgaaacag | ctgacggtgt | ggttcactcc | tactcagcaa | ctggaacacg | agttatgaag | 1620 |
| aaatcaactg | cctacatgat | tactgatatg | cttaaaggtg | ttctaactga | aggttctggt | 1680 |
| actaatgcga | gaactggtct | ttatgaagct | ggtaaaactg | gtactgttaa | atattctgat | 1740 |
| gatgaattag | taaatatatcc | ttcatacgca | aacactccaa | agatgcatg | gttcgttggt | 1800 |
| tatactaaga | atattcaat | tgggatttgg | accggttatg | acaatttaag | cgatggtaca | 1860 |
| attagtggtc | aaggccaata | tgcttcccaa | tatctttata | gtatatgat | gaagtactta | 1920 |
| atgagtgata | aggaaaacag | caattggact | aagccaagca | atgttgttag | aaaacgaatt | 1980 |
| gttaaaggtt | ctgacccact | tgaagttact | tcctcaaaga | aaattcaac | ctctgagttg | 2040 |
| ttcctacgtg | gtcacacacc | agatggctca | acgaggatt | ctgatgaaag | ttcttcatca | 2100 |
| tcaaattctt | caagttcttc | taaagataac | gaagtagtaa | ctaataagag | cagcagttct | 2160 |

```
tcaagttctt catctagtga aggacatgaa gatggctcaa cttctaactc aagtagtagt    2220
caatcaagca gtggtggcag tcctaacaac aatcaaggaa caactactaa taatcaaacg    2280
aataacaaca ataatactgg ccaaaacaat ggcggcggta ataattaa                 2328

<210> SEQ ID NO 87
<211> LENGTH: 6270
<212> TYPE: DNA
<213> ORGANISM: Lactobacillus jensenii CCOS 962

<400> SEQUENCE: 87
atgttttcaa aaataatat gaaaatgcgc atgcaaaagg ttgctgataa agagcaacaa      60
cattttgctt tgcgtaaatt aaatgttggg ttggtatccg ttttaatggg tactacatta    120
tttttcgtgg gacaaacatc aatagctaag gctgatacac tagaatctac taagactagt    180
gtcactgaaa ttagttctag ctctaattct aatcaagaaa agttagaaca agctaaggct    240
gtaagttctc aagagcaaac tacaagtact gaagaaaatg tagattcagc ttcatcaagt    300
caatcaaaaa gtgaaaacaa ttctagctct agtgcgaagt cagaagtaag tactcaagat    360
agaactgata gcaatgacaa tgctactact aatcaagtag atactacgca agtatctact    420
acttcattga aagctgttca atcttctaat caagctgcta acttattagc tgaaagcaaa    480
gttgaagatt caacaacagc taatgttagt gatttcgatt catttaactc agctttgatg    540
aatcaaaata ttactactat taacattaat agtgactttt caagtggtaa ctatggtaca    600
aatgttgaac accgtagagt tgttcctcgt actttagtaa ttaatggtaa tggtcataca    660
gttgaccttg gttcaattgg ttacttcatg aatccaggtg gtaatcaagc agctgattgg    720
acagtagaaa atggtacttt ctattctaag agtgctgttg gtccatttgc tcttactggt    780
gatcacggta ctgataaggc ttggcaggca accaatggtg cagtacaccg tatgacttac    840
aaggatatga cagtttatgc tggtggtggt gcttatgctg caaatgctga aattgattta    900
gaaggtacta acaatttaaa cgctaccgct tcatatcaat ctaagttctc aaatggtact    960
gtttatactg aaactggtgg taacagatca ggtgttgaag gtcaatggat tattattaag   1020
gataatgcta atgtgactgt taacactgat cacggtcaag ctatttcaac tgaatactct   1080
gatggaaatc acagaattga agttggtgaa atgccacttt aaatggtaa ctatttatat   1140 accacttacg gtactcctta tggtggtggt aagatagctg ttcttctcaaa cggtgcaaat   1200 ggtggtactg taatcttcca taagggttct aagtcacact ttactatgcc aaatcaaaat   1260
gtaactggct ttggtggtaa tggttttagt aactatggta ctggttctgt tctttactta   1320
ggtgcagcta atactactat tgaaaaaggt gcagaagtta caattgataa ccctaaagaa   1380
gctaataacg ataacagtat cttcattcgt tcagacggaa cacaattaaa tatctttggt   1440
aacttaatta tcaatgatgg tgcgcgtgac tatactattc gtgccgataa ccgtgtaagc   1500
atcaatgtgg gtcaaagtat tgcagatgat gattacagta atgataatgg taaattaatt   1560
attaatcgta acggtgactt ctacttgaat aacgatggtg tgctctctc aatgtgggga   1620 ccaattacca ttaatgttaa ttcaggagct gctttagaag tttactcaac tggaattaat   1680
aatgtatctg gttctggtgc aaatcctgct ttaatgagag ttggtggaag cagtaaatta   1740
aacgtttata acgtggtac tttcatttta agtgatagta gtaatggtaa agttagtcta   1800
gttgatgatt acaatgcaaa tggtaacttc aacttcgaca atactgcaaa agttattttt   1860
gatatttcaa acaacaataa ccaaaatagt agaattttg ctttaaatgg tactgtatat   1920
gcaactcatg acaaggtaag agctatgctc acaccaagtt ctaatattgc tgatatgggt   1980
```

```
accctttaaga cggttcaatt taatactagt ggtcaaggcg gtgtgactgg ggatgcatta   2040
cactctgagt atcaaaacca agcctacaat aacattgttg cgattagaga tgcgattaga   2100
actggtcaat tacgttacct tgaattctca actcgttcag taaataatgc aagtattact   2160
ggtgaaggac atggctttac tgataatggt gcacaaatta agggttcagt agttgatgaa   2220
tcaactaaca ctggtgcggt agccgttgcc tacgacaaag ataataataa agttggttca   2280
ggtaatgttg atgaccaagg taactttaca attaacttag ataagccgct tcttaacaaa   2340
gaagaagtta agttagaat tgaaacccct cgtggtgcta gtggttttgt ttcaactacc    2400
gctcctttag gtccaactgc taagagtcca attactgttg ctaaagatga taatttagca   2460
ggtcaagatg ctagccaata catcaccaat aaagatgaaa ttgcaaacat taagccaggt   2520
actactgact atgaaccaac ctttaagagt gcagcttgga agagtgttga tactaatacc   2580
aagaagggta ttattactgt aacttatgca gataacacta ctactgactt agacgtagac   2640
ttaaatgtag tagacaagat tactgatgct gacaagttca ctccagaagg tggaacaatt   2700
aaagttgata atggtcataa attagatggt aatgatgctt atgaagcaat caagaaccac   2760
gatgatttac cagcagataa agcaggctac aactggggttg tagatgaaaa tcatccagcc   2820
gttgatacta ctaagcctgg tgatcaaact ggctatgttc aagtaactta caatgatggc   2880
agtaaatcag atttagttcc tgttactgtt catgtaattg ctgataatga aaaatacact   2940
gctattggta agactcaaaa cctccaaaaa ggccaaagtg caaatcctca agactttatc   3000
gctaataaag atggagaagt tagccaagat ggcaagacct atactaagtt gcctgatggt   3060
actaaatatg aatgggtaga tggaggaatt gatacttcta ctattggtcc aaaacaagct   3120
caagttaagg taacttatcc agatggaacc actcaaattg ttccagtaaa ggctaacgta   3180
tattctgatg ctaacttatc aactgttgtt ggtaaggata ttaatgccgg atacaaagaa   3240
gacttgacta accgtgcaat tgatgcaatt gataaggata agtcaactaa ccttccaact   3300
gatccatcag cttatacttg ggtaaatggc gcacctgata catcaaagac aggtgatatt   3360
ccagcgactg taaaggtaac gtatccagat ggttcataca atactgttga tgtaactgtt   3420
catgttacta gtgatgctga aaagtattca ccagttccag agaccatttc tgttccaaag   3480
ggtactgact tatcaggtcg agcaaaagat ggtattgcta atgctgataa agatgctaat   3540
ggtaaggaaa agttaccaga tggtacaaaa tatgaatggg acggcggagt tccaaatact   3600
tcagtaacta ataataagta tggtcatgta aaggtaacgt atccagatgg tagttctaca   3660
gtagttgaag taccttttaaa tattaccgat aataataagt cagatgctga aaagcataat   3720
ccacaagcta atatccttca tgcaacattg aatcaagatc ttagttcaaa tgattgggct   3780
aaaaaaggca ttttaaatgc tgatgagcaa gatggagcaa catttagatg gagaaagggt   3840
tatgttcctg atacttctaa agaaggccaa gtttggggta ttgttgtagt aagctatcca   3900
gattcatcaa ttaatgaagt tcgagttcca gttatcgtcc aaagtgatgc aagtaaatac   3960
ggtattgaaa ctcaagaaat caatgttcat gaaggaaccg atattagttc agatgaatgg   4020
gctagaaaag gtattttgaa tgccgatcaa gctggaaaac agaatgaaca attaccagat   4080
ggaactagct acacttgggc aaatggtaat gttccagata ctacaaagcc aaataagaag   4140
acaggttatg taactgtaac tttcccagat aatagtagca gaactgttcc agtaatcgtt   4200
aatgtaattg gtgatggtag aagtgatgct gaaaagtatc aacttaaggc tcatgatatt   4260
tggacttata taaacgatac tcctgttgca gaaaaggcag tttcaaatct tgacgaacta   4320
aaagatgtta gttcaattac ttgggcaact acaccagatg tttctaaggt tggtaacgtt   4380
```

```
ccagcgattg tagttgtaac ttataaagat ggtacttcta atgctgctcc tattaacatt    4440
gaggttaagg gattagcaaa tgattataag cctgaaggta caactattta tgcaggttta    4500
aatgaagata taactaacag agctgcagat ggtattgcta ataaagatca aatgccagta    4560
gcaaataaac cagaaggtac tgttcacaca acttattcat ggaaggataa tataattcct    4620
gatactacta aacctggtac caagtatgga attgtagaag ttaacttccc agatggttca    4680
actaaggatg ttccagttga agttaaggta actagtctag catctgatta ccaaaataag    4740
attgatacta agcaaattat tgctaagtac aagggtaata tacctcaagc ctctgacggt    4800
attgctaaca agatcaagc aactaaagaa ggagacaaag acttcccaag tttagctgat    4860
gtgttagctc ctaatggtat tcaatggaag aagaactttg aacccgattt gagtaagcca    4920
ggcttaacaa gtggtgaagc aattcttacc tttaaggatg gttcaactgc cgaagttaca    4980
attccggtat tagttcaaac tgatgctgat cgcaatactc cagaaactca gactattaag    5040
acacttcctg acaaacagt aaatcctgaa gatggtgtaa ttaatttaca taagcctggt    5100
gaaaataacc cacaattgcc agatggaacg aaggtaactt tgataatca atcagatgtt    5160 gatgacttta ctaagcatgg aatgccaggt tctgataaga gcttcgatgc tactgtaact    5220
tatccagatg gaacaactga caagattaag ttgccggtac acattacagc tgataatgaa    5280
gttaatactc caattactca aggtattatt acacctaagg atagtgtgcc agatgccaat    5340
aaaggtattg ctaacttaaa gaaggctact accaaagaag gtaaaactta tcctgcattg    5400
ccagagaaca ccacggttga atgggttaac cctggtcaaa tgaagactga gcttgaaaat    5460
gcaaagggtg gtacaaccaa gaattacgat gctgtagtaa tttatccaga taaatcaact    5520
gaaattgttt caattccagt aactgttgct actgatgcag atacttataa agtagtaaca    5580
caaccaatcg atttgaagga tagaaactta cctgacaacg ctgatgatgg aattactaac    5640
cttcataaac cagcagactt taagactcca caattgccag atggtacaca tgcagaatgg    5700
caagataagg atgctgctca agaagtagtt aagaacttga agccaggtga aactgtaaaa    5760
cttccagcta ctgttgtctt cccagatggt tccaagaagg gtgaaggcat tgatgtaagt    5820
gttcacttac atggtcaatc tgatgattat aatattgaaa cacaaccagt aaatactgat    5880
aaagatggta attttacctga aaatgctgac tctggtatta agaacttagg aaagttacct    5940
gaaggaactc acgcaagctg gggtgatggt gcccaagata ttgccaagaa tttgaagcta    6000
ggtgaaacta aggatgtacc agcaacagtt gtcttcccag atggctcaaa gaaggaaatt    6060
acaattccag ttcatagaga aggtcaatct gatggttatg atgttgaacc acaactagta    6120
aatactgata aaatggaca actacctaat gcaaaggaag gtattaagaa cttagccgat    6180
ttaccagaag gaacaaatca acctgggcag atagagctca agataaaatt aataagacta    6240
agcctggtac agatacaact gctcaagtag                                     6270
```

<210> SEQ ID NO 88
<211> LENGTH: 645
<212> TYPE: DNA
<213> ORGANISM: Lactobacillus jensenii CCOS 962

<400> SEQUENCE: 88

```
atggcacgtt caggatctcg agtaaaaaaa acaaccctaa ctttagttaa agtctttgga      60
gtattactta tcttagtagt ggcgtttgtt tgctttcggt attaccgtag acaagcaatc     120
aataatgaat taattagaca agaacaacta gcaagagaac aggctgcagc taaggaatta     180
aagataaaaa cagatttcat aaaaaaaata gggccaattg ctcaaaaagc tgatcaaggc     240
```

```
tttgctcttt tgccaagtat tacaattgcc caagcttgtt tagaaagtaa ctatggccaa      300
agtgaactat ctcaaaagta taataattta tttggcgtaa aaagtaatga tcccaatact      360
tcaaaatttt tatctactaa agaatatgtt aatggcaaat ggattacagt aaaagctagt      420
ttccaaattt atgattcata tgaatcttca attcaagctc atgctagatt atttcaaaat      480
ggtactactt ggaacaaaga tcaatatcaa catgttttag cagcaaaaga ttataaaacc      540
caggctaaag cactagttac agatggttat gcaacagatc ctgattatgc ttccaagtta      600
attaacttaa ttgaacaatt taatttaaat aaatatgaca attaa                     645
```

<210> SEQ ID NO 89
<211> LENGTH: 558
<212> TYPE: PRT
<213> ORGANISM: Lactobacillus gasseri CCOS 960

<400> SEQUENCE: 89

```
Met Leu Ala Gln Ala Ala Val Glu Ser Ala Trp Gly Gln Ser Gly Leu
1               5                   10                  15

Ala Gln Ser Pro Asn Asn Asn Leu Phe Gly Ile Lys Gly Ser Tyr Asn
            20                  25                  30

Gly Gln Ser Val Asn Met Asn Thr Gly Glu Tyr Gly Ser Asn Gly Tyr
        35                  40                  45

Tyr Thr Thr Asn Ala Gly Phe Arg Lys Tyr Pro Ser Tyr Thr Glu Ser
    50                  55                  60

Phe Glu Asp Asn Gly Ser Leu Leu Arg Asn Gln Met Gly Asn Tyr Tyr
65                  70                  75                  80

Ser Gly Thr Trp Val Glu Asn Ser Lys Asn Tyr Ala Gln Ala Thr Gln
                85                  90                  95

Asn Gly Leu Gln Gly Lys Tyr Ala Thr Ala Pro Asn Tyr Ala Gln Thr
            100                 105                 110

Leu Asn Ser Val Ile Ala Ala Asn Gly Phe Asp Lys Tyr Asp Pro Val
        115                 120                 125

Thr Gln Val Val Asn Glu Asn Arg Thr Val Ala Gln Thr Thr Pro Ile
    130                 135                 140

Met Ser Ala Pro Val Asp Ala Ser Val Gly Thr Gln Val Gly Thr Ala
145                 150                 155                 160

Arg Thr Gly Gln Asn Val Asn Val Thr Lys Tyr Ile Thr Tyr Asn Asn
                165                 170                 175

Gly Val Lys Arg Ala Tyr Ile Gly Thr Gly Trp Ile Asn Ala Leu Ala
            180                 185                 190

Phe Ser Pro Ile Thr Thr Asn Thr Thr Thr Lys Gln Asn Thr Ala Ala
        195                 200                 205

Asn Thr Asn Asn Gln Ala Ser Gln Ala Val Lys Thr Pro Val Ala Gln
    210                 215                 220

Thr Gln Gln Val Lys Ser Gln Ala Pro Ala Pro Val Lys Ala Ala
225                 230                 235                 240

Thr Val Lys Val Lys Ser Ala Ala Glu Val Lys Thr Pro Val Gln Thr
                245                 250                 255

Thr Thr Leu Asn Val Lys Thr Glu Asn Lys Ala Ala Gln Pro Val Lys
            260                 265                 270

Gln Leu Ala Val Ser Leu Ala Val Ala Pro Lys Lys Val Glu Val Lys
        275                 280                 285

Lys Asn Val Val Lys Ala Glu Pro Ala Lys Thr Thr Pro Val Lys Thr
    290                 295                 300
```

```
Glu Thr Thr Lys Thr Glu Asn Lys Glu Val Lys Ala Thr Pro Val
305                 310                 315                 320

Val Lys Thr Thr Asp Thr Val Lys Lys Val Glu Thr Pro Ala Val Lys
                325                 330                 335

Pro Val Glu Ser Val Lys Lys Glu Ser Thr Pro Val Val Lys Thr Thr
            340                 345                 350

Pro Val Thr Val Thr Lys Glu Ala Ala Lys Thr Thr Glu Ala Pro Val
        355                 360                 365

Val Lys Pro Lys Val Glu Val Lys Glu Ile Lys Thr Thr Pro Val
    370                 375                 380

Thr Thr Ser Ala Lys Thr Val Val Lys Pro Val Gln Ser Tyr Gln Ser
385                 390                 395                 400

Ala Val Thr Thr Ala Ala Asn Asn Asn Tyr Gly Thr Gln Trp Ile Ser
                405                 410                 415

Thr Asn Thr Ala Pro Lys Ala Ala Ser Thr Val Leu Ile Lys Val Thr
                420                 425                 430

Lys Thr Val Asp Val Leu Ser Ala Pro Asp Gly Gln Lys Leu Asp Gln
            435                 440                 445

Gln Val Glu Ala Gly Ser Glu Phe Val Val Ala Ser Lys Tyr Tyr
    450                 455                 460

Asn Gly Asn Leu Tyr Tyr Glu Ile Ser Asn Gly Lys Trp Ile Met Ala
465                 470                 475                 480

Lys Tyr Thr Thr Gln Glu Ala Gln Ile Thr Ala Lys Ser Gly Val Leu
                485                 490                 495

Thr Ile Asn Ser Lys Pro Asp Tyr Gly Val Pro Val Trp Arg Val Pro
            500                 505                 510

Gly Gln Asp Gln Ile Ala Gly Lys Phe Leu Lys Asp Gly Ser Ser Trp
        515                 520                 525

Arg Tyr Phe Arg Val Ala Asn Val Gln Gly Gln Thr Trp Tyr Asp Leu
    530                 535                 540

Gly Gly Asn Gln Trp Val Ser Ala Lys Ser Val Leu Val Arg
545                 550                 555

<210> SEQ ID NO 90
<211> LENGTH: 208
<212> TYPE: PRT
<213> ORGANISM: Lactobacillus gasseri CCOS 960

<400> SEQUENCE: 90

Met Pro Arg Arg Arg Gln Lys Asn Ile Gln Tyr Val Ile Ala Arg
1               5                   10                  15

Ala Phe Ala Ile Cys Phe Thr Leu Val Val Ile Leu Ser Gly Phe Leu
                20                  25                  30

Tyr Trp Arg His Glu Val Ala Val Asn Glu Gln Leu Arg Gln Ala Gln
            35                  40                  45

Leu Glu Lys Glu Arg Ala Leu Gln Ser Lys Glu Arg Phe Ile Lys Val
        50                  55                  60

Val Ala Pro Ile Ala Gln Arg Ala Asp Lys Pro Tyr Gly Leu Phe Pro
65                  70                  75                  80

Ser Val Thr Ile Ala Gln Ala Cys Leu Glu Ser Asn Phe Gly Gln Ser
                85                  90                  95

Glu Leu Ser Lys Lys Tyr Tyr Asn Leu Phe Gly Val Lys Gly Thr Asp
            100                 105                 110

Pro Asn Thr Ser Arg Glu Leu Thr Thr Ser Glu Phe Val Asn Asp His
        115                 120                 125
```

Trp Glu Thr Val Thr Gly Arg Phe Gln Ile Tyr Asn Ser Tyr Glu Glu
    130                 135                 140

Ser Ile Gln Ala His Thr Arg Leu Phe Val Asn Gly Thr Ser Trp Asn
145                 150                 155                 160

Lys Asp Gln Tyr Gln His Val Leu Ala Ala Lys Asp Tyr Ala Ser Gln
                165                 170                 175

Ala Gln Ala Leu Glu Thr Asp Gly Tyr Ala Thr Asp Pro Gly Tyr Ala
            180                 185                 190

Lys Lys Leu Ile Asp Leu Ile Lys Glu Phe Asn Leu Thr Gln Tyr Asp
                195                 200                 205

<210> SEQ ID NO 91
<211> LENGTH: 513
<212> TYPE: PRT
<213> ORGANISM: Lactobacillus gasseri CCOS 960

<400> SEQUENCE: 91

Met Val Ile Thr Leu Leu Thr Leu Asp Leu Glu Lys Tyr Pro Ser Tyr
1               5                   10                  15

Thr Glu Ser Phe Glu Asp Asn Gly Ser Leu Leu Arg Asn Gln Met Gly
            20                  25                  30

Asn Tyr Tyr Ser Gly Thr Trp Val Glu Asn Ser Lys Asn Tyr Ala Gln
        35                  40                  45

Ala Thr Gln Asn Gly Leu Gln Gly Lys Tyr Ala Thr Ala Pro Asn Tyr
50                  55                  60

Ala Gln Thr Leu Asn Ser Val Ile Ala Ala Asn Gly Phe Asp Lys Tyr
65                  70                  75                  80

Asp Pro Val Thr Gln Val Val Asn Glu Asn Arg Thr Val Ala Gln Thr
                85                  90                  95

Thr Pro Ile Met Ser Ala Pro Val Asp Ala Ser Val Gly Thr Gln Val
            100                 105                 110

Gly Thr Ala Arg Thr Gly Gln Asn Val Asn Val Thr Lys Tyr Ile Thr
        115                 120                 125

Tyr Asn Asn Gly Val Lys Arg Ala Tyr Ile Gly Thr Gly Trp Ile Asn
130                 135                 140

Ala Leu Ala Phe Ser Pro Ile Thr Thr Asn Thr Thr Thr Lys Gln Asn
145                 150                 155                 160

Thr Ala Ala Asn Thr Asn Asn Gln Ala Ser Gln Ala Val Lys Thr Pro
                165                 170                 175

Val Ala Gln Thr Gln Gln Val Lys Ser Gln Ala Pro Ala Ala Pro Val
            180                 185                 190

Lys Ala Ala Thr Val Lys Val Lys Ser Ala Ala Glu Val Lys Thr Pro
        195                 200                 205

Val Gln Thr Thr Thr Leu Asn Val Lys Thr Glu Asn Lys Ala Ala Gln
210                 215                 220

Pro Val Lys Gln Leu Ala Val Ser Leu Ala Val Ala Pro Lys Lys Val
225                 230                 235                 240

Glu Val Lys Lys Asn Val Val Lys Ala Glu Pro Ala Lys Thr Thr Pro
                245                 250                 255

Val Lys Thr Glu Thr Thr Lys Thr Glu Asn Lys Glu Val Lys Thr Ala
            260                 265                 270

Thr Pro Val Val Lys Thr Thr Asp Thr Val Lys Val Glu Thr Pro
        275                 280                 285

Ala Val Lys Pro Val Glu Ser Val Lys Lys Glu Ser Thr Pro Val Val
290                 295                 300

```
Lys Thr Thr Pro Val Thr Val Thr Lys Glu Ala Ala Lys Thr Thr Glu
305                 310                 315                 320

Ala Pro Val Val Lys Pro Lys Val Glu Val Lys Glu Ile Lys Thr
                325                 330                 335

Thr Pro Val Thr Thr Ser Ala Lys Thr Val Val Lys Pro Val Gln Ser
                340                 345                 350

Tyr Gln Ser Ala Val Thr Ala Ala Asn Asn Asn Tyr Gly Thr Gln
            355                 360                 365

Trp Ile Ser Thr Asn Thr Ala Pro Lys Ala Ala Ser Thr Val Leu Ile
            370                 375                 380

Lys Val Thr Lys Thr Val Asp Val Leu Ser Ala Pro Asp Gly Gln Lys
385                 390                 395                 400

Leu Asp Gln Gln Val Glu Ala Gly Ser Glu Phe Val Val Ala Ser
                405                 410                 415

Lys Tyr Tyr Asn Gly Asn Leu Tyr Tyr Glu Ile Ser Asn Gly Lys Trp
                420                 425                 430

Ile Met Ala Lys Tyr Thr Thr Gln Glu Ala Gln Ile Thr Ala Lys Ser
    435                 440                 445

Gly Val Leu Thr Ile Asn Ser Lys Pro Asp Tyr Gly Val Pro Val Trp
        450                 455                 460

Arg Val Pro Gly Gln Asp Gln Ile Ala Gly Lys Phe Leu Lys Asp Gly
465                 470                 475                 480

Ser Ser Trp Arg Tyr Phe Arg Val Ala Asn Val Gln Gly Gln Thr Trp
                485                 490                 495

Tyr Asp Leu Gly Gly Asn Gln Trp Val Ser Ala Lys Ser Val Leu Val
            500                 505                 510

Arg

<210> SEQ ID NO 92
<211> LENGTH: 104
<212> TYPE: PRT
<213> ORGANISM: Lactobacillus gasseri CCOS 960

<400> SEQUENCE: 92

Met Lys Lys Arg Thr Phe Thr Gly Ile Ala Thr Ala Ala Leu Ile Thr
1               5                   10                  15

Thr Ala Gly Ile Ser Val Thr Asn Asn Leu Lys Pro Glu Asn Pro Leu
                20                  25                  30

Lys Thr Gly Glu Gly Thr Val Gln Ala Ala Thr Tyr Gln Gln Glu Phe
            35                  40                  45

Leu Asn Lys Ala Ile Pro Ala Ala Thr Thr Ala Ser Ser Lys Tyr Gly
    50                  55                  60

Thr Tyr Thr Ser Val Met Leu Gln Ala Ala Val Glu Ser Ala Trp
65                  70                  75                  80

Val Asn Gln Val Trp His Asn Arg Leu Ile Ile Thr Tyr Ser Val Leu
                85                  90                  95

Arg Ala Leu Thr Met Gly Asn Gln
            100

<210> SEQ ID NO 93
<211> LENGTH: 772
<212> TYPE: PRT
<213> ORGANISM: Lactobacillus plantarum CCOS 893
```

```
<400> SEQUENCE: 93

Met Leu Ser Thr Ala Leu Leu Pro Met Leu Ser Gly Lys Ala Asp Thr
1               5                   10                  15

Ala Ser Thr Asn Gln Lys Pro Ala Ala Thr Lys Gly Asn Ser Ala
            20                  25                  30

Ala Ser Ala Ala Ser Gln Gln Val Thr Leu Ser Ala Gly Ser Gln Thr
        35                  40                  45

Glu Thr Thr Ala Ala Gly Ala Thr Asp Gln Ser Val Ala Ser Asp Gly
    50                  55                  60

Ala Lys Thr Asp Asp Gln Ala Glu Ser Thr Ser Thr Thr Ala Thr
65                  70                  75                  80

Thr Ser Ala Thr Ser Arg Val Thr Val Arg Ala Ala Ser Gln Val Ala
                85                  90                  95

Lys Ala Asp Ser Thr Glu Leu Gln Ser Gln Ser Ala Ser Glu Ala
            100                 105                 110

Ala Lys Asp Asn Ala Ala Ser Ala Thr Ala Asp Ser Thr Thr Ser
        115                 120                 125

Ala Val Asp Gln Leu Asp Lys Thr Ala Lys Ser Ala Ala Thr Ser
    130                 135                 140

Gln Ala Ser His Ser Thr Thr Asn Glu Thr Ala Lys Ala Ser Ala Ala
145                 150                 155                 160

Ala Ser Gln Asp Ser His Val Thr Thr Asp Gln Ser Ser Val Thr Val
                165                 170                 175

Thr Ser Glu Val Ala Lys Ser Ala Ala Ser Ala Ala Pro Lys Gln
            180                 185                 190

Ala Thr Glu Gln Ala Val Ala Ala Lys Ile Ser Pro Lys Ile Glu Thr
        195                 200                 205

Ala Val Ala Ala Asp Ala Val Gln Ser Ser Ala Met Met Ala Arg Ser
    210                 215                 220

Thr Arg Ala Met Thr Ser Gln Glu Ile Phe Leu Ser Gln Ile Lys Ala
225                 230                 235                 240

Gly Ala Ile Ser Gly Trp Asn Lys Tyr Gln Val Leu Pro Ser Val Thr
                245                 250                 255

Ala Ala Gln Ala Ile Leu Glu Ser Gly Trp Gly Ser Gln Leu Ala
            260                 265                 270

Thr Gln Gly Asn Asn Leu Phe Gly Ile Lys Gly Ser Tyr His Gly Gln
        275                 280                 285

Ser Ile Tyr Phe Pro Thr Gln Glu Trp Asn Gly Ser Gln Tyr Ile Thr
    290                 295                 300

Ile Gln Asp Ala Phe Arg Lys Tyr Pro Asn Trp Ser Ala Ser Val Glu
305                 310                 315                 320

Asp His Gly Ala Phe Leu Val Val Asn Pro Arg Tyr Ser Asn Leu Ile
                325                 330                 335

Gly Val Thr Asp Tyr Arg Arg Val Ala Ser Leu Leu Gln Gln Asp Gly
            340                 345                 350

Tyr Ala Thr Ala Pro Thr Tyr Ala Ser Ser Leu Ile Ser Ile Ile Glu
        355                 360                 365

Tyr Asn Lys Leu His Glu Trp Asp Gln Glu Ala Leu Ser Gly Gln Ala
    370                 375                 380

Ser Gly Gly Asn Asp Asn Asn Gln Val Gln Pro Asp Gln Asp Val Thr
385                 390                 395                 400

Pro Thr Ser Gly Thr His Lys Phe Thr Lys Thr Thr Ile His Asn
                405                 410                 415
```

Ala Pro Asp Ala Thr Ser Ala Val Val Gly Thr Tyr Asn Ala Gly Glu
            420                 425                 430

Thr Val Asn Tyr Asn Gly Lys Leu Thr Val Gly Asn Ala Thr Trp Leu
            435                 440                 445

Arg Tyr Gln Ser Tyr Ser Gly Val Ser Arg Tyr Val Met Ile Ser Gln
    450                 455                 460

Thr Thr Thr Asn Asp Asn Asn Asn Gln Ala Thr Val Thr Pro Ala Ser
465                 470                 475                 480

Gly Ser Tyr Lys Phe Thr Ala Lys Thr Asn Ile Arg Ser Ala Ala Ser
                485                 490                 495

Lys Thr Ala Gln Val Val Gly Thr Tyr Asn Ala Gly Glu Thr Val Tyr
            500                 505                 510

Tyr Asn Gly Lys Ile Thr Thr Gly Gly Thr Thr Trp Leu Arg Tyr Leu
            515                 520                 525

Ser Tyr Ser Gly Ala Gln His Tyr Val Ala Met Ser Gly Asp Glu Val
    530                 535                 540

Gly Ser Val Ala Lys Pro Asp Val Val Ala Thr Ser Gly Ser Tyr Arg
545                 550                 555                 560

Phe Thr Lys Thr Thr Ala Ile Lys Ser Ser Pro Ala Thr Ser Ala Thr
                565                 570                 575

Thr Val Gly Ser Tyr Asn Ala Gly Asp Thr Val Tyr Tyr Asn Gly Lys
            580                 585                 590

Val Thr Thr Asn Gly Gln Thr Trp Leu Arg Tyr Met Ser Tyr Ser Gly
            595                 600                 605

Ala Gln His Tyr Val Gln Ile Ser Gly Glu Ser Thr Ser Thr Asn Val
    610                 615                 620

Asp Lys Pro Gln Val Thr Pro Gln Ser Gly Ser Tyr Arg Phe Thr Gln
625                 630                 635                 640

Thr Thr Ala Ile Lys Asn Thr Pro Ala Gly Asn Ala Pro Ser Val Gly
                645                 650                 655

Thr Tyr Ser Ala Gly Asp Thr Val Tyr Tyr Asn Ala Lys Val Thr Ala
            660                 665                 670

Asn Gly Gln Thr Trp Leu Arg Tyr Leu Ser Tyr Ser Gly Ala Gln His
            675                 680                 685

Tyr Val Ala Ile Ser Gly Asn Ala Ala Thr Gly Asn Thr Thr Ser Lys
    690                 695                 700

Pro Val Thr Asn Ser Gln Gly Ala Phe Arg Phe Val Thr Thr Thr Asn
705                 710                 715                 720

Ile Arg Thr Ala Pro Ser Thr Arg Ala Ser Val Val Gly Glu Tyr Asn
                725                 730                 735

Pro Gly Glu Thr Val Tyr Tyr Asn Gly Thr Val Gln Ala Glu Gly Tyr
            740                 745                 750

Thr Trp Leu Arg Tyr Leu Ser Arg Ser Gly Ala Thr His Tyr Val Ala
    755                 760                 765

Lys Leu Glu Gly
    770

<210> SEQ ID NO 94
<211> LENGTH: 212
<212> TYPE: PRT
<213> ORGANISM: Lactobacillus plantarum CCOS 893

<400> SEQUENCE: 94

Met Ala Gly Lys Arg Arg Lys Ser Arg Arg Lys Gln Arg Thr Lys Thr
1               5                   10                  15

Gln Leu Phe Val Lys Lys Gly Arg Leu Gln Trp Val Asn Ile Leu Leu
                20                  25                  30

Val Leu Ala Ala Met Val Gly Met Val Trp Tyr Ile Gln His Asn Trp
            35                  40                  45

Ala Val Lys Ser Arg Val Thr Ala Thr Ala Pro Thr Thr Thr His Ala
        50                  55                  60

Ala Phe Ile Lys Lys Leu Val Pro Ala Ala Gln Gln Leu Asp Gln Gln
65                  70                  75                  80

Tyr His Val Leu Ala Ser Ile Thr Leu Ser Gln Ala Ile Leu Glu Ser
                85                  90                  95

Asp Trp Gly Gln Ser Thr Asn Ala Thr Glu Asn Asn Asn Leu Phe Gly
            100                 105                 110

Val Lys Ser Thr Ser Gly Arg Leu Met Thr Thr Gln Glu Tyr Tyr Asp
        115                 120                 125

Gly Ala Tyr His Thr Val Lys Arg Arg Phe Ala Val Tyr Asp Ser Trp
    130                 135                 140

His Ala Ser Leu Val Asp His Ala Lys Lys Leu Ala Tyr Gly Thr Thr
145                 150                 155                 160

Trp Asp Ser Gln His Tyr Ala Ala Val Ile Lys Ala Thr Asp Tyr Gln
                165                 170                 175

Thr Ala Ala Gln Ala Leu Gln Thr Ala Gly Tyr Ala Thr Asp Pro Ser
            180                 185                 190

Tyr Ala Gln Lys Leu Ile Asn Ile Gln Lys Tyr Asp Leu Gln Arg
        195                 200                 205

Tyr Asp Arg Lys
    210

<210> SEQ ID NO 95
<211> LENGTH: 421
<212> TYPE: PRT
<213> ORGANISM: Lactobacillus plantarum CCOS 893

<400> SEQUENCE: 95

Met Ser Ser Val Leu Gly Ile Thr Leu Ala Lys Pro Val Gln Gly Lys
1               5                   10                  15

Ala Asp Gln Thr Ser Ser Pro Ser Thr Thr Lys Val Lys Ala Ala Thr
                20                  25                  30

Ser Gly Ala Thr Ser Glu Val Ser Ser Ile Ser Thr Ile Thr Ala Asn
            35                  40                  45

Ser Ala Thr Asn Val Ser Ser Ala Thr His Gln Phe Ser Thr Ala Thr
        50                  55                  60

Thr Thr Ser Gln Gln Ala Ser Ser Ala Thr Ser Asn Ile Ser Thr Thr
65                  70                  75                  80

Thr Ala Ser Lys Gln Ile Ser Lys Ser Thr Thr Gly Lys Leu Asn Ser
                85                  90                  95

Asn Glu Thr Ala Thr Thr Ser Asn Ser Ala Ala Thr Ser Val Asp Ser
            100                 105                 110

Thr Ala Pro Tyr Ile Pro Ala Lys Ser Asn Val Ser Phe Thr Asp Asn
        115                 120                 125

Ile Lys Ser Thr Ile Ala Asn Thr Pro Thr Thr Val Ala Ala Pro Ala
    130                 135                 140

Ile Pro Ser His Ser Thr Gln Phe Ile Asp Asp Ser Ala Pro Ile Thr
145                 150                 155                 160

Ser Pro Thr Pro Val Thr Thr Asn Ser Ile His Val Arg Pro Phe Thr
                165                 170                 175

Val His Ser Ser Phe Ser Phe Lys Pro Gly Gln Phe Leu Arg Phe Thr
                180                 185                 190

Leu Pro Asn Val Ala Leu Leu Arg Asp Asp Val Glu Gln Gly Val Pro
            195                 200                 205

Asn Tyr Val Lys Asn Phe Phe Ile Ala Ile Lys Pro Gly Ala Met Ile
        210                 215                 220

Gly Trp Ser Gln Tyr His Ile Leu Pro Ser Ile Ser Gly Ala Gln Ala
225                 230                 235                 240

Leu Leu Glu Ser Gly Trp Gly Lys Ser Thr Leu Ser Val Gln Gly His
                245                 250                 255

Asn Leu Phe Gly Ile Lys Gly Ser Tyr His Gly His Ser Ile Glu Met
            260                 265                 270

Pro Thr Thr Glu Tyr Leu Asn Gly Glu Asp Val Thr Ile Glu Ala Thr
        275                 280                 285

Phe Arg Lys Tyr Pro Asp Trp Ala Thr Ser Ile Val Asp His Gly Ala
            290                 295                 300

Phe Leu Asn Gln Asn Ser Arg Tyr Arg Asn Leu Leu Gly Val Lys Asn
305                 310                 315                 320

Tyr Ser Thr Val Ala Trp Asp Leu Gln Asn Asp Gly Tyr Ala Thr Ala
                325                 330                 335

Pro Asn Tyr Ala Thr Ser Leu Ile Asn Ala Ile Gln Asp Tyr Asp Leu
            340                 345                 350

Gln Glu Trp Asp Gln Glu Ala Phe Thr Gly Asn Thr Gly Ser Thr Thr
        355                 360                 365

Thr Thr Thr Gly Asn His Arg Ser Gly Thr Tyr Thr Phe Ile Gln Asn
370                 375                 380

Ser Asn Ile Arg Thr Glu Pro Ser Leu Ser Ala Pro Ile Ile Gly Val
385                 390                 395                 400

Tyr Tyr Pro Gly Asp Val Asn Tyr Thr Gly Gln Ile Lys Ala Glu
                405                 410                 415

Gly Tyr Thr Trp Leu
            420

<210> SEQ ID NO 96
<211> LENGTH: 258
<212> TYPE: PRT
<213> ORGANISM: Lactobacillus plantarum CCOS 893

<400> SEQUENCE: 96

Met Val Val Pro Val Asp Ile Trp Asn Gln Arg Gly Asp Ala Ser Asp
1               5                   10                  15

Gln Val Thr Leu Lys Trp Pro Asp Asn Arg Lys Pro Lys Ala Ala Phe
            20                  25                  30

Thr Val Asn Arg Thr Leu Ala Ala Pro Gly Asn Thr Ile Lys Phe Thr
        35                  40                  45

Asn Ala Ser Ser Lys Asn Ala Thr Ser Tyr Lys Trp Glu Phe Asp Gly
    50                  55                  60

Ala Thr Lys Thr Thr Ser Thr Ala Lys Asn Pro Val Thr Tyr Tyr Arg
65                  70                  75                  80

Lys Ala Gly Thr Tyr Asn Val Thr Leu Thr Ala Lys Asn Lys Asp Gly
                85                  90                  95

Gln Arg His Val Thr Met Lys Lys Leu Ile Thr Ile Thr Pro Lys Ala
            100                 105                 110

Gln Gly Ala Leu Thr Leu Leu Ser Lys Asn Ala Lys Thr Ser Ala Ser
        115                 120                 125

```
Gly Tyr Thr Asn Ser Ser Glu Ala Pro Lys Met Ala Val Asp Gly Lys
            130                 135                 140

Leu Asp Thr Lys Trp Cys Ala Thr Gly Lys Ala Pro His Thr Leu Arg
145                 150                 155                 160

Leu Asp Leu Gly Arg Gln Thr Thr Val Ser Ala Val Lys Leu Ala His
                165                 170                 175

Ala Lys Ala Gly Gly Glu Gly Ala Asp Met Asn Thr Arg Ala Trp Thr
            180                 185                 190

Ile Gln Val Ser Thr Asp Gly Lys Arg Tyr Thr Asp Val Ala Arg Thr
                195                 200                 205

Tyr Asn Asn Thr Gln Ala Thr Ser Leu Asn Thr Phe Ala Ala Thr Ser
210                 215                 220

Ala Arg Tyr Val Arg Leu Val Val Asp Lys Pro Thr Gln Val Ala Asp
225                 230                 235                 240

Thr Ala Val Arg Ile Tyr Glu Met Asp Val Leu Gly Leu Thr Gln Thr
                245                 250                 255

Leu Lys

<210> SEQ ID NO 97
<211> LENGTH: 94
<212> TYPE: PRT
<213> ORGANISM: Lactobacillus plantarum CCOS 893

<400> SEQUENCE: 97

Met Arg Lys Asp Thr Ala Ser Thr Ile Lys Leu Tyr Thr Thr Asp Leu
1               5                   10                  15

Asp Val Thr Ala Asp Thr Gln Val Ser Leu Thr Ala Lys Ala Ser Gly
            20                  25                  30

Lys Ser Thr Ala Lys Leu Val Val Thr Leu Lys Asp Gly Arg Thr Lys
        35                  40                  45

Thr Ile Ala Gly Asp Arg Thr Leu Ser Lys His Trp Thr Thr Val Ser
    50                  55                  60

Tyr Asp Val Ser Gln Leu Thr Lys Lys Gln Ser Lys Ala Leu Ala Ser
65                  70                  75                  80

Lys Ser Val Pro Pro Arg Leu Met Leu Ala Thr Ala Phe Asn
                85                  90

<210> SEQ ID NO 98
<211> LENGTH: 408
<212> TYPE: PRT
<213> ORGANISM: Lactobacillus crispatus CCOS 961

<400> SEQUENCE: 98

Met Lys Lys Arg Leu Leu Thr Ser Phe Ala Ala Ala Ala Met Leu Thr
1               5                   10                  15

Ser Val Ala Val Pro Ala Val Asn Thr Thr Met Met Asn Gln Ala Ser
            20                  25                  30

Ser Gln Arg Val Ser Ala Ala Thr Ala Asp Gln Thr Ala Phe Leu Asn
        35                  40                  45

Lys Ala Ala Lys Gln Ala Val Lys Ala Ala Lys Lys Tyr Gly Thr Leu
    50                  55                  60

Pro Ser Val Met Ile Ala Gln Ala Ile Thr Glu Ser Gly Trp Gly Lys
65                  70                  75                  80

Ser Gly Leu Ala Val Asn Ala Asn Asn Leu Phe Gly Met Lys Ala Asp
                85                  90                  95
```

Asp Ser Trp Thr Gly Glu Thr Tyr Thr Ala Lys Thr Arg Glu Asp
            100                 105                 110

Lys Asn Gly Lys Ser Tyr Tyr Ile Thr Ala Lys Phe Arg Lys Tyr Pro
        115                 120                 125

Ser Phe Glu Gln Ser Phe Glu Asp Asn Gly Ser Lys Leu Arg Asn Gly
    130                 135                 140

Val Ser Trp Asp Pro Leu Arg Tyr Lys Gly Thr Trp Ile Glu Asn Ala
145                 150                 155                 160

Ser Thr Tyr Ala Ala Thr Lys Ala Leu Thr Gly Thr Tyr Ala Thr
                165                 170                 175

Asp Ser Lys Tyr Asp Lys Ala Leu Asn Ser His Ile Thr Ser Ser Asn
            180                 185                 190

Leu Thr Lys Tyr Asp Pro Val Thr Val Asn Thr Thr Arg Thr Tyr Thr
        195                 200                 205

Ala Gly Lys Asp Ser Ser Thr Tyr Asn Trp Pro Thr Ala Pro Ser Val
    210                 215                 220

Ala Ser Val Ile Gly Ser Val Lys Ala Gly Glu Lys Val Val Val Thr
225                 230                 235                 240

Lys Thr Ile Thr Phe His Asp Gly Ser Ser Arg Met Tyr Ile Asp Gly
                245                 250                 255

Arg Gly Trp Val Asn Gly Ser Val Leu Asp Lys Ser Ser Ala Thr
            260                 265                 270

Lys Glu Pro Val Thr Gln Ala Pro Lys Asn Val Pro Ala Val Ser Lys
        275                 280                 285

Asn Leu Met His Asn Ala Tyr Val Tyr Asp Gln Asn Gly Lys Lys Leu
    290                 295                 300

Lys Gly Lys Met Tyr Lys Thr Ser Asp Glu Asn Gly Gly Lys Trp Ile
305                 310                 315                 320

Asn Thr Tyr Gly Thr Lys Thr Ile Lys Gly Lys Thr Tyr Tyr Arg Val
                325                 330                 335

Gly Glu Asn Glu Tyr Ile Ala Ala Gly Asn Ile Asp Gly Ser Leu Arg
            340                 345                 350

Phe Leu Lys Lys Asn Ala Tyr Val Tyr Asn Gln Tyr Gly Asn Arg Asp
        355                 360                 365

Asn Asn Leu Lys His Lys Lys Asn Ser Gln Ile Ala Thr Tyr Gly Ser
    370                 375                 380

Ala Ile Thr Ile Asn Gly Lys Lys Tyr Tyr Lys Val Gly Ile Arg Gln
385                 390                 395                 400

Tyr Val Lys Lys Ser Asn Phe Met
                405

<210> SEQ ID NO 99
<211> LENGTH: 215
<212> TYPE: PRT
<213> ORGANISM: Lactobacillus crispatus CCOS 961

<400> SEQUENCE: 99

Met Ala Arg Lys Arg Lys Ser Arg Val Pro Lys Ser Val Lys Thr Val
1               5                   10                  15

Val Arg Val Phe Val Ile Leu Phe Ile Leu Met Val Ala Phe Val Gly
            20                  25                  30

Phe Arg Tyr Tyr Arg Arg Tyr Ala Ile Gln Ser Glu Gln Ile Gln Gln
        35                  40                  45

Ala Gln Leu Gln Lys Glu Gln Glu Ala Ala Lys Leu Leu Lys Gln Lys
    50                  55                  60

```
Lys Asp Phe Ile Lys Lys Ile Gly Pro Ile Ala Arg Glu Val Asp Lys
 65                  70                  75                  80

Ser Tyr Asp Leu Leu Pro Ser Ile Thr Ile Ala Gln Ala Cys Leu Glu
                 85                  90                  95

Ser Asn Tyr Gly Gln Ser Asp Leu Ser Gln Lys Tyr Asn Asn Leu Phe
            100                 105                 110

Gly Val Lys Gly Ser Asn Pro Asn Thr Ser Ala Val Met Thr Thr Lys
            115                 120                 125

Glu Tyr Val Lys Asn Lys Trp Val Thr Val Lys Ala Arg Phe Gln Ile
        130                 135                 140

Tyr Asp Ser Tyr Glu Ala Ser Ile Arg Ala His Ala Arg Leu Phe Gln
145                 150                 155                 160

Asn Gly Thr Thr Trp Asn His Asp Gln Tyr Lys His Val Leu Ala Ser
                165                 170                 175

Lys Asp Tyr Lys Thr Gln Ala Lys Ala Leu Val Thr Asp Gly Tyr Ala
            180                 185                 190

Thr Asp Pro Asp Tyr Ala Asp Lys Leu Ile Asn Leu Ile Glu Gln Phe
            195                 200                 205

Asp Leu Glu Lys Tyr Asp Lys
        210                 215

<210> SEQ ID NO 100
<211> LENGTH: 430
<212> TYPE: PRT
<213> ORGANISM: Bifidobacterium bifidum CCOS 571

<400> SEQUENCE: 100

Met Arg Met Gln Gln Ile Lys His Gly Gly Arg Arg Pro Arg Pro Ser
1               5                   10                  15

Ser Ala Pro Thr Ile Ile Ala Ala Met Leu Cys Val Val Ala Leu Val
                20                  25                  30

Ala Ala Gly Thr Ala Trp Trp Met Leu Arg Pro Gln Gln Lys Asp Thr
            35                  40                  45

Leu Glu His Leu Ala Gln Pro Gln Ser Ser Ser Thr Leu Asn Arg
 50                  55                  60

Asp Lys Ala Pro Thr Pro Lys Pro Gln Lys Ser Gln Glu Arg Gln Lys
 65                  70                  75                  80

Ala Ala Gly Asp Ser Pro Ala Ala Lys Ala Ser Arg Ala Ile Ala Thr
                 85                  90                  95

Met Ser Leu Asp Glu Arg Ala Gly Gln Leu Ile Met Ala Pro Met Phe
            100                 105                 110

Ala Gly Gly Asn Pro Ala Asp Leu Ser Ala Leu Ile Ser Thr Arg His
            115                 120                 125

Val Gly Ser Val Val Leu Ile Gly Asn Trp Asn Asn Gly Thr Ala Ala
        130                 135                 140

Ala Lys Thr Ala Ala Asp Ala Leu Gln Ser Tyr Ala Pro Ser Gly Asn
145                 150                 155                 160

Gln Leu Ile Val Ser Thr Asp Gln Glu Gly Gly Val Gln His Leu
                165                 170                 175

Lys Gly Ser Gly Phe Asp Thr Met Pro Ser Ala Val Ala Gln Gly Gln
            180                 185                 190

Met Ser Ala Asp Thr Leu Arg Ser Ser Ala Lys Thr Trp Gly Gly Gln
        195                 200                 205

Leu Lys Gln Ala Gly Ile Asn Val Asp Leu Ala Pro Val Leu Gly Thr
        210                 215                 220
```

Val Gln Val Lys Arg Ser Ser Asn Ala Pro Ile Gly Ala Leu Asn Arg
225                 230                 235                 240

Asp Phe Gly Leu Asp Ser Asn Gly Asn Ala Gln His Gly Ile Ala Phe
            245                 250                 255

Val Glu Gly Met Arg Asp Ala Gly Val Gly Ala Thr Val Lys His Tyr
        260                 265                 270

Pro Gly Leu Gly Ala Val Thr Gly Asn Thr Asp Phe Thr Thr Glu Gly
    275                 280                 285

Ile Leu Asp Thr Thr Thr Leu Asp Gly Glu Glu Ile Gly Ala Phe
290                 295                 300

Asn Thr Thr Ile Lys Gln Ala Lys Pro Ala Met Val Met Met Ser Leu
305                 310                 315                 320

Ala Thr Tyr Gln Arg Ile Asp Ser Ser Ala Pro Ala Ala Phe Ser Ser
                325                 330                 335

Lys Ile Ile Asp Gly Thr Leu Arg Gly Ser Val Gly Tyr Asp Gly Val
            340                 345                 350

Val Ile Ser Asp Ser Leu Ser Ala Ala Ala Val Ser Gly Ile Ala Thr
        355                 360                 365

Lys Asp Leu Gly Val Arg Leu Val Asp Ala Gly Gly Asp Leu Ala Cys
    370                 375                 380

Ile Gly Asp Thr Ser Tyr Val Thr Pro Ile Leu Asp Gly Ile Ile Ala
385                 390                 395                 400

Arg Ala Gln Ser Asp Pro Ala Phe Ala Lys Lys Val Thr Ala Ser Ala
                405                 410                 415

Thr Arg Val Met Thr Leu Lys Tyr Gln Met Gly Leu Ala Lys
            420                 425                 430

<210> SEQ ID NO 101
<211> LENGTH: 1935
<212> TYPE: PRT
<213> ORGANISM: Bifidobacterium bifidum CCOS 571

<400> SEQUENCE: 101

Met Ala Val Arg Arg Leu Gly Gly Arg Ile Val Ala Phe Ala Ala Thr
1               5                   10                  15

Val Ala Leu Ser Ile Pro Leu Gly Leu Leu Thr Asn Ser Ala Trp Ala
            20                  25                  30

Val Glu Asp Ala Thr Arg Ser Asp Ser Thr Gln Met Ser Ser Thr
        35                  40                  45

Pro Glu Val Val Tyr Ser Ser Ala Val Asp Ser Lys Gln Asn Arg Thr
    50                  55                  60

Ser Asp Phe Asp Ala Asn Trp Lys Phe Met Leu Ser Asp Ser Val Gln
65                  70                  75                  80

Ala Gln Asp Pro Ala Phe Asp Ser Ala Trp Gln Gln Val Asp Leu
                85                  90                  95

Pro His Asp Tyr Ser Ile Thr Gln Lys Tyr Ser Gln Ser Asn Glu Ala
            100                 105                 110

Glu Ser Ala Tyr Leu Pro Gly Gly Thr Gly Trp Tyr Arg Lys Ser Phe
        115                 120                 125

Thr Ile Asp Arg Asp Leu Ala Gly Lys Arg Ile Ala Ile Asn Phe Asp
    130                 135                 140

Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                165                 170                 175

```
Ala Lys Phe Gly Gly Glu Asn Thr Ile Val Lys Val Glu Asn Arg
            180                 185                 190

Leu Pro Ser Ser Arg Trp Tyr Ser Gly Ser Gly Ile Tyr Arg Asp Val
        195                 200                 205

Thr Leu Thr Val Thr Asp Gly Val His Val Gly Asn Asn Gly Val Ala
    210                 215                 220

Ile Lys Thr Pro Ser Leu Ala Thr Gln Asn Gly Gly Asn Val Thr Met
225                 230                 235                 240

Asn Leu Thr Thr Lys Val Ala Asn Asp Thr Lys Ala Ala Ala Asn Ile
                245                 250                 255

Thr Leu Lys Gln Thr Val Phe Pro Lys Gly Gly Lys Thr Asp Ala Ala
            260                 265                 270

Ile Gly Thr Val Thr Thr Ala Ser Lys Ser Ile Ala Ala Gly Ala Ser
        275                 280                 285

Ala Asp Val Thr Ser Thr Ile Thr Ala Ala Ser Pro Lys Leu Trp Ser
    290                 295                 300

Ile Lys Asn Pro Asn Leu Tyr Thr Val Arg Thr Glu Val Leu Asn Gly
305                 310                 315                 320

Gly Lys Val Leu Asp Thr Tyr Asp Thr Glu Tyr Gly Phe Arg Trp Thr
                325                 330                 335

Gly Phe Asp Ala Thr Ser Gly Phe Ser Leu Asn Gly Glu Lys Val Lys
            340                 345                 350

Leu Lys Gly Val Ser Met His His Asp Gln Gly Ser Leu Gly Ala Val
        355                 360                 365

Ala Asn Arg Arg Ala Ile Glu Arg Gln Val Glu Ile Leu Gln Lys Met
    370                 375                 380

Gly Val Asn Ser Ile Arg Thr Thr His Asn Pro Ala Ala Lys Ala Leu
385                 390                 395                 400

Ile Asp Val Cys Asn Glu Lys Gly Val Leu Val Val Glu Glu Val Phe
                405                 410                 415

Asp Met Trp Asn Arg Ser Lys Asn Gly Asn Thr Glu Asp Tyr Gly Lys
            420                 425                 430

Trp Phe Gly Gln Ala Ile Ala Gly Asp Asn Ala Val Leu Gly Gly Asp
        435                 440                 445

Lys Asp Glu Thr Trp Ala Lys Phe Asp Leu Thr Ser Thr Ile Asn Arg
    450                 455                 460

Asp Arg Asn Ala Pro Ser Val Ile Met Trp Ser Leu Gly Asn Glu Met
465                 470                 475                 480

Met Glu Gly Ile Ser Gly Ser Val Ser Gly Phe Pro Ala Thr Ser Ala
                485                 490                 495

Lys Leu Val Ala Trp Thr Lys Ala Ala Asp Ser Thr Arg Pro Met Thr
            500                 505                 510

Tyr Gly Asp Asn Lys Ile Lys Ala Asn Trp Asn Glu Ser Asn Thr Met
        515                 520                 525

Gly Asp Asn Leu Thr Ala Asn Gly Val Val Gly Thr Asn Tyr Ser
    530                 535                 540

Asp Gly Ala Asn Tyr Asp Lys Ile Arg Thr Thr His Pro Ser Trp Ala
545                 550                 555                 560

Ile Tyr Gly Ser Glu Thr Ala Ser Ala Ile Asn Ser Arg Gly Ile Tyr
                565                 570                 575

Asn Arg Thr Thr Gly Gly Ala Gln Ser Ser Asp Lys Gln Leu Thr Ser
            580                 585                 590
```

```
Tyr Asp Asn Ser Ala Val Gly Trp Gly Ala Val Ala Ser Ala Trp
            595                 600                 605

Tyr Asp Val Val Gln Arg Asp Phe Val Ala Gly Thr Tyr Val Trp Thr
610                 615                 620

Gly Phe Asp Tyr Leu Gly Glu Pro Thr Pro Trp Asn Gly Thr Gly Ser
625                 630                 635                 640

Gly Ala Val Gly Ser Trp Pro Ser Pro Lys Asn Ser Tyr Phe Gly Ile
                645                 650                 655

Val Asp Thr Ala Gly Phe Pro Lys Asp Thr Tyr Tyr Phe Gln Ser
                660                 665                 670

Gln Trp Asn Asp Asp Val His Thr Leu His Ile Leu Pro Ala Trp Asn
            675                 680                 685

Glu Asn Val Val Ala Lys Gly Ser Gly Asn Asn Val Pro Val Val Val
        690                 695                 700

Tyr Thr Asp Ala Ala Lys Val Lys Leu Tyr Phe Thr Pro Lys Gly Ser
705                 710                 715                 720

Thr Glu Lys Arg Leu Ile Gly Glu Lys Ser Phe Thr Lys Thr Thr
                725                 730                 735

Ala Ala Gly Tyr Thr Tyr Gln Val Tyr Glu Gly Ala Asp Lys Asp Ser
            740                 745                 750

Thr Ala His Lys Asn Met Tyr Leu Thr Trp Asn Val Pro Trp Ala Glu
        755                 760                 765

Gly Thr Ile Ser Ala Glu Ala Tyr Asp Glu Asn Asn Arg Leu Ile Pro
        770                 775                 780

Glu Gly Ser Thr Glu Gly Asn Ala Ser Val Thr Thr Gly Lys Ala
785                 790                 795                 800

Ala Lys Leu Lys Ala Asp Ala Asp Arg Lys Thr Ile Thr Ala Asp Gly
                805                 810                 815

Lys Asp Leu Ser Tyr Ile Glu Val Asp Val Thr Asp Ala Asn Gly His
                820                 825                 830

Ile Val Pro Asp Ala Ala Asn Arg Val Thr Phe Asp Val Lys Gly Ala
            835                 840                 845

Gly Lys Leu Val Gly Val Asp Asn Gly Ser Ser Pro Asp His Asp Ser
        850                 855                 860

Tyr Gln Ala Asp Asn Arg Lys Ala Phe Ser Gly Lys Val Leu Ala Ile
865                 870                 875                 880

Val Gln Ser Thr Lys Glu Ala Gly Glu Ile Thr Val Thr Ala Lys Ala
                885                 890                 895

Asp Gly Leu Gln Ser Ser Thr Val Lys Ile Ala Thr Thr Ala Val Pro
            900                 905                 910

Gly Thr Ser Thr Glu Lys Thr Val Arg Ser Phe Tyr Tyr Ser Arg Asn
        915                 920                 925

Tyr Tyr Val Lys Thr Gly Asn Lys Pro Ile Leu Pro Ser Asp Val Glu
    930                 935                 940

Val Arg Tyr Ser Asp Gly Thr Ser Asp Arg Gln Asn Val Thr Trp Asp
945                 950                 955                 960

Ala Val Ser Asp Asp Gln Ile Ala Lys Ala Gly Ser Phe Ser Val Ala
                965                 970                 975

Gly Thr Val Ala Gly Gln Lys Ile Ser Val Arg Val Thr Met Ile Asp
            980                 985                 990

Glu Ile Gly Ala Leu Leu Asn Tyr  Ser Ala Ser Thr Pro  Val Gly Thr
        995                 1000                1005
```

```
Pro Ala Val Leu Pro Gly Ser Arg Pro Ala Val Leu Pro Asp Gly
1010                1015                1020

Thr Val Thr Ser Ala Asn Phe Ala Val Asp Trp Thr Lys Pro Ala
1025                1030                1035

Asp Thr Val Tyr Asn Thr Ala Gly Thr Val Lys Val Pro Gly Thr
1040                1045                1050

Ala Thr Val Phe Gly Lys Glu Phe Lys Val Thr Ala Thr Ile Arg
1055                1060                1065

Val Gln Arg Ser Gln Val Thr Ile Gly Ser Ser Val Ser Gly Asn
1070                1075                1080

Ala Leu Arg Leu Thr Gln Asn Ile Pro Ala Asp Lys Gln Ser Asp
1085                1090                1095

Thr Leu Asp Ala Ile Lys Asp Gly Ser Thr Thr Val Asp Ala Asn
1100                1105                1110

Thr Gly Gly Gly Ala Asn Pro Ser Ala Trp Thr Asn Trp Ala Tyr
1115                1120                1125

Ser Lys Ala Gly His Asn Thr Ala Glu Ile Thr Phe Glu Tyr Ala
1130                1135                1140

Thr Glu Gln Gln Leu Gly Gln Ile Val Met Tyr Phe Phe Arg Asp
1145                1150                1155

Ser Asn Ala Val Arg Phe Pro Asp Ala Gly Lys Thr Lys Ile Gln
1160                1165                1170

Ile Ser Ala Asp Gly Lys Asn Trp Thr Asp Leu Ala Ala Thr Glu
1175                1180                1185

Thr Ile Ala Ala Gln Glu Ser Ser Asp Arg Val Lys Pro Tyr Thr
1190                1195                1200

Tyr Asp Phe Ala Pro Val Gly Ala Thr Phe Val Lys Val Thr Val
1205                1210                1215

Thr Asn Ala Asp Thr Thr Thr Pro Ser Gly Val Val Cys Ala Gly
1220                1225                1230

Leu Thr Glu Ile Glu Leu Lys Thr Ala Thr Ser Lys Phe Val Thr
1235                1240                1245

Asn Thr Ser Ala Ala Leu Ser Ser Leu Thr Val Asn Gly Thr Lys
1250                1255                1260

Val Ser Asp Ser Val Leu Ala Ala Gly Ser Tyr Asn Thr Pro Ala
1265                1270                1275

Ile Ile Ala Asp Val Lys Ala Glu Gly Glu Gly Asn Ala Ser Val
1280                1285                1290

Thr Val Leu Pro Ala His Asp Asn Val Ile Arg Val Ile Thr Glu
1295                1300                1305

Ser Glu Asp His Val Thr Arg Lys Thr Phe Thr Ile Asn Leu Gly
1310                1315                1320

Thr Glu Gln Glu Phe Pro Ala Asp Ser Asp Glu Arg Asp Tyr Pro
1325                1330                1335

Ala Ala Asp Met Thr Val Thr Ala Gly Ser Glu Gln Thr Ser Gly
1340                1345                1350

Thr Ala Thr Glu Gly Pro Lys Lys Phe Ala Val Asp Gly Asn Thr
1355                1360                1365

Ser Thr Tyr Trp His Ser Asn Trp Thr Pro Thr Thr Val Asn Asp
1370                1375                1380

Leu Trp Ile Ala Phe Glu Leu Gln Lys Pro Thr Lys Leu Asp Ala
1385                1390                1395
```

```
Leu Arg Tyr Leu Pro Arg Pro Ala Gly Ser Lys Asn Gly Ser Val
1400            1405                1410

Thr Glu Tyr Lys Val Gln Val Ser Asp Asp Gly Thr Asn Trp Thr
1415            1420                1425

Asp Ala Gly Ser Gly Thr Trp Thr Thr Asp Tyr Gly Trp Lys Leu
1430            1435                1440

Ala Glu Phe Asn Gln Pro Val Thr Thr Lys His Val Arg Leu Lys
1445            1450                1455

Ala Val His Thr Tyr Ala Asp Ser Gly Asn Asp Lys Phe Met Ser
1460            1465                1470

Ala Ser Glu Ile Arg Leu Arg Lys Ala Val Asp Thr Thr Asp Ile
1475            1480                1485

Ser Gly Ala Thr Val Thr Val Pro Ala Lys Leu Thr Val Asp Arg
1490            1495                1500

Val Asp Ala Asp His Pro Ala Thr Phe Ala Thr Lys Asp Val Thr
1505            1510                1515

Val Thr Leu Gly Asp Ala Thr Leu Arg Tyr Gly Val Asp Tyr Leu
1520            1525                1530

Leu Asp Tyr Ala Gly Asn Thr Ala Val Gly Lys Ala Thr Val Thr
1535            1540                1545

Val Arg Gly Ile Asp Lys Tyr Ser Gly Thr Val Ala Lys Thr Phe
1550            1555                1560

Thr Ile Glu Leu Lys Asn Ala Pro Ala Pro Glu Pro Thr Leu Thr
1565            1570                1575

Ser Val Ser Val Lys Thr Lys Pro Ser Lys Leu Thr Tyr Val Val
1580            1585                1590

Gly Asp Ala Phe Asp Pro Ala Gly Leu Val Leu Gln Leu Asn Tyr
1595            1600                1605

Asp Asp Asp Ser Thr Gly Thr Val Thr Trp Asn Thr Gln Thr Ala
1610            1615                1620

Gly Asp Phe Thr Phe Lys Pro Ala Leu Asp Ala Lys Leu Lys Val
1625            1630                1635

Thr Asp Lys Thr Val Thr Val Thr Tyr Gln Gly Lys Ser Ala Val
1640            1645                1650

Ile Asp Ile Thr Val Ser Gln Pro Ala Pro Thr Val Ser Lys Thr
1655            1660                1665

Asp Leu Asp Lys Ala Ile Lys Ala Ile Glu Ala Lys Asn Pro Asp
1670            1675                1680

Ser Ser Lys Tyr Thr Ala Asp Ser Trp Lys Thr Phe Ala Asp Ala
1685            1690                1695

Met Ala His Ala Lys Ala Val Ile Ala Asp Asp Ser Ala Thr Gln
1700            1705                1710

Gln Asp Ile Asp Asn Ala Leu Lys Ala Leu Thr Asp Ala Tyr Ala
1715            1720                1725

Gly Leu Thr Glu Lys Thr Pro Glu Pro Ala Pro Val Ser Lys Ser
1730            1735                1740

Glu Leu Asp Lys Lys Ile Lys Ala Ile Glu Ala Glu Lys Leu Asp
1745            1750                1755

Gly Ser Lys Tyr Thr Ala Glu Ser Trp Lys Ala Phe Glu Thr Ala
1760            1765                1770

Leu Ala His Ala Lys Ala Val Ile Ala Ser Asp Ser Ala Thr Gln
1775            1780                1785
```

```
Gln Asp Val Asp Ala Ala Leu Gly Ala Leu Thr Ser Ala Arg Asp
    1790            1795                1800

Gly Leu Thr Glu Lys Gly Glu Val Lys Pro Asp Pro Lys Pro Glu
    1805            1810                1815

Pro Gly Thr Val Asp Lys Ala Ala Leu Asp Lys Ala Val Lys Lys
    1820            1825                1830

Val Glu Ala Glu Lys Leu Asp Gly Ser Lys Tyr Thr Ala Asp Ser
    1835            1840                1845

Trp Lys Ala Phe Glu Thr Ala Leu Ala His Ala Lys Ala Val Ile
    1850            1855                1860

Gly Asn Ala Asn Ser Thr Gln Phe Asp Ile Asp Asn Ala Leu Ser
    1865            1870                1875

Met Leu Asn Asp Ala Arg Ala Ala Leu Lys Glu Lys Pro Gly Arg
    1880            1885                1890

Ile Ile Ala Ile Ile Asp Gly Ser Ala Leu Ser Lys Thr Gly Ala
    1895            1900                1905

Ser Val Ala Val Ile Ala Ser Val Ala Ala Ala Met Leu Ala Val
    1910            1915                1920

Gly Ala Gly Val Met Ala Leu Arg Arg Lys Arg Ser
    1925            1930                1935

<210> SEQ ID NO 102
<211> LENGTH: 154
<212> TYPE: PRT
<213> ORGANISM: Bifidobacterium bifidum CCOS 571

<400> SEQUENCE: 102

Met His Ser Arg Pro Met Phe Pro Ile Pro Glu Thr Gln Val Gly Asp
1               5                   10                  15

Gly Trp Val Gly Asp Val Asp Tyr Thr Lys Gln Ala Thr Lys Gln Asp
                20                  25                  30

Ser Asn Phe Leu Val Asp Trp Val Arg Val Tyr Gln Ser Glu Gly Gln
            35                  40                  45

Pro Val Thr Arg Phe Asp Leu Asp Gly Ala Glu Ser Gly Ala Tyr
        50                  55                  60

Arg Ser Ala Pro Ala Ser Arg Thr Glu Gly Leu Thr Ala Val Ser Asn
65                  70                  75                  80

Gly Asp Ala Ala Trp Arg Asn Lys Asn Asn Phe Tyr Tyr Gly Gly Gln
                85                  90                  95

Pro Arg Tyr Glu Thr Ser Arg Ser His Ala Val Pro Leu Met Gln Gly
                100                 105                 110

Arg Phe Ala Leu Arg Leu Arg Gly Pro Gln Thr Leu Cys Arg Ile Arg
            115                 120                 125

Thr Asn Ala Phe Thr Arg Ser Glu Arg Pro Val Ala Gly Lys Val Val
        130                 135                 140

Pro Pro Asn Arg Arg Asn Arg Ala Ala Pro
145                 150

<210> SEQ ID NO 103
<211> LENGTH: 185
<212> TYPE: PRT
<213> ORGANISM: Bifidobacterium bifidum CCOS 571

<400> SEQUENCE: 103

Met Ile Ser Ala Ser Arg Glu Ile His Ser Ile Asn Leu Tyr Arg Asn
1               5                   10                  15
```

```
Gly Tyr Glu Asn Ala Leu Asn Thr Phe Lys Arg Ile Lys Val Glu Val
             20                  25                  30

Ser Ser Asn Glu Asp Phe Ser Asp Ala Asn Val Leu Phe Gly Thr Ala
         35                  40                  45

Asp Val Glu Glu Thr Ala Ala Thr Lys Leu Ala Ala Gln Thr Ile Asn
     50                  55                  60

Leu Thr Thr Pro Val Thr Ala Arg Tyr Val Arg Ile Trp Gln Lys Gly
65                  70                  75                  80

His Cys Ile Gln Asn Thr Asn Ser Ser Trp Lys Gly Tyr Gly Asn Gly
                 85                  90                  95

Val Gly Leu Arg Glu Ile Glu Val Ile Ala Lys Leu Lys Asp Gly Glu
            100                 105                 110

Thr Leu Pro Asp Ala Gln Glu Thr Arg Asn Ile Ala Leu Gly Lys Leu
        115                 120                 125

Pro Tyr Val Tyr Gly Leu Asp Pro Thr Asn Ile Ala Ala Ile Ser Asp
    130                 135                 140

Gly Lys Gln Asp Asp Asn Tyr Ala Val His Asn Ser Thr Gly Glu Arg
145                 150                 155                 160

Trp Leu Gln Phe Glu Tyr Lys Asn Arg Tyr Arg Ile His Glu Gly Ser
                165                 170                 175

Ser Arg Ala Pro Ile Arg Trp Ser Ala
            180                 185

<210> SEQ ID NO 104
<211> LENGTH: 108
<212> TYPE: PRT
<213> ORGANISM: Bifidobacterium bifidum CCOS 571

<400> SEQUENCE: 104

Met Arg Gln Leu Phe Arg Arg Ile Thr Thr Ile Ser Ala Thr Cys Ala
1               5                  10                  15

Leu Ala Val Ser Val Ala Ala Ala Val Ala Val Ala Ala Glu Pro Thr
             20                  25                  30

Thr Gly Asn Ile Leu Thr Gly Lys Leu Pro Thr Thr Asn Ser Thr His
         35                  40                  45

Leu Ile Gly Asp Gly Asp Thr Gly Phe Gly Pro Thr Asp Ser Asn Ile
    50                  55                  60

Thr Lys Ile Ile Ala Gly Glu Glu Asn Gly Ser Ala Glu Asn Asn Gly
65                  70                  75                  80

Tyr Ala Ser Trp Asp Asp Val Tyr Leu Gln Tyr Asp Phe Gly Glu Pro
                 85                  90                  95

Arg Asp Thr Leu His Gln Pro Val Pro Gln Trp Val
            100                 105

<210> SEQ ID NO 105
<211> LENGTH: 1931
<212> TYPE: PRT
<213> ORGANISM: Bifidobacterium bifidum CCOS 571

<400> SEQUENCE: 105

Met Arg Lys Arg Val Val Ser Val Ala Leu Val Ala Leu Ala Val
1               5                  10                  15

Ala Pro Leu Gly Val Val Ser Thr Ala Ser Ala Ala Pro Leu Ser Ala
             20                  25                  30

Ser Asp Leu Gln Thr Leu Ala Leu Arg Ser Ala Ala Ser Ser Asn Asp
         35                  40                  45
```

```
Ala Asn Ala Asn Asp Val Ala Thr Val Ala Asp Asp Ala Ala Val Asn
 50                  55                  60

Gly Trp Thr Ile Asp Arg Asn Thr Ala Lys Gly Gly Glu Ile Leu Ala
 65                  70                  75                  80

Ala Gly Thr Gly Asp Tyr Ala Gly Trp Thr His Phe Lys Ser Thr Ser
                 85                  90                  95

Ala Asn Gly Asn Ala Thr Ser Ser Gly Tyr Pro Ala Val Ala Ile
                100                 105                 110

Ser Gly Lys Thr Ile Asp Leu Thr Arg Ala Gly Glu Phe Ser Ile Lys
                115                 120                 125

Val Lys Ser Pro Gln Ala Gly Ser Ala Asn Arg Phe Gly Phe Tyr Leu
130                 135                 140

Gly Tyr Lys Asp Pro Gly Asn Ala Leu Phe Leu Gly Tyr Asp Lys Gly
145                 150                 155                 160

Gly Trp Phe Trp Gln Lys Tyr Val Gly Gly Asn Gly Asp Trp Tyr Asn
                165                 170                 175

Gly Thr Arg Val Ala Ala Pro Ala Ala Asn Ala Glu Ile Thr Val Asn
                180                 185                 190

Val Ser Trp Thr Ala Ala Lys Val Ala Thr Leu Thr Ile Asp Gly Gln
                195                 200                 205

Lys Ala Phe Asp Val Asp Tyr Ser Ser Met Thr Ala Leu Thr Asp Lys
210                 215                 220

Leu Ala Met Lys Ala Gly Ser Tyr Ser Gly Thr Ser Glu Val Thr Asp
225                 230                 235                 240

Val Tyr Phe Lys Asn Phe Thr Val Gly Glu Val Ala Lys His Asn Val
                245                 250                 255

Thr Gly Lys Val Val Asp Ala Ser Gly Ala Ala Ile Ala Gly Ala Glu
                260                 265                 270

Val Val Thr Gly Lys Asn Ser Ala Thr Thr Ala Ala Asp Gly Thr Phe
                275                 280                 285

Thr Leu Thr Gly Leu Ala Ala Gly Asp Tyr Thr Leu Thr Val Ser Ala
                290                 295                 300

Glu Gly Tyr Asp Asp Ala Thr Lys Thr Val Thr Val Ala Asp Gly Asn
305                 310                 315                 320

Ala Ser Val Gly Asn Ile Thr Leu Asn Lys Ser Ala Glu Val Ala Thr
                325                 330                 335

Glu Thr Leu Ser Thr Ala Ala Met Asp Val Arg Val Lys Lys Asn Phe
                340                 345                 350

Pro Ser Val Tyr Asp Tyr Thr Met Lys Lys Leu Asp Gly Lys Ile Met
                355                 360                 365

Tyr Gly Gln Pro Lys Asp Val Arg Val Ile Thr Ile Asn Gly Thr Asp
370                 375                 380

Val Thr Leu Lys Asp Ser Asp Val Thr Phe Lys Lys Val Ser Ala Thr
385                 390                 395                 400

Glu Ala Gln Tyr Thr Leu Asn Val Lys Ser Gly Asp Lys Ile Asn Ala
                405                 410                 415

Val Val Thr Val Gln Ile Lys Val Asp Asn Thr Leu Lys Leu Asn
                420                 425                 430

Val Thr Lys Ile Val Asn Lys Ala Asp Asp Ala Lys Thr Glu Ala Glu
                435                 440                 445

Glu Asn Pro Val Gln Thr Ile Ala Phe Pro Asn Gln Ser Leu Ile Ser
450                 455                 460
```

```
Val Arg Ser Gly Gln Asp Gly Ala Gln Phe Thr Gly Ala Arg Met Ser
465                 470                 475                 480

Ser Asp Thr Ala Arg Pro Gly Asp Thr Asn Phe Asp Ile Thr Ala Asp
                485                 490                 495

Thr Thr Val Ser Asn Ala Asn Asp Tyr Thr Tyr Gly Phe Val Ser Gly
            500                 505                 510

Asn Gly Leu Ser Ala Gly Leu Trp Ser Asn Ser Glu His Asp Gly Thr
            515                 520                 525

Thr Val Gly Asn Thr Val Ala Gly Gly Ala Arg Asn Thr Arg Val Leu
        530                 535                 540

Thr Ser Thr Gln Lys Val Gly Lys Ala Thr Ser Phe Gly Leu Gly Thr
545                 550                 555                 560

Ala Pro Trp Tyr Tyr His Arg Val Val Thr Asp Thr Lys Lys Asn Thr
                565                 570                 575

Tyr Thr Val Glu Glu Thr Asp Met Pro Lys Met Ala Val Ala Ile Ala
            580                 585                 590

Gly Asp Glu Asn Glu Asp Gly Thr Val Asn Trp Glu Asp Gly Ala Ile
        595                 600                 605

Ala Tyr Arg Asp Ile Met Asn Asn Pro Tyr Lys Ser Glu Glu Val Pro
        610                 615                 620

Glu Leu Val Ala Trp Arg Ile Ala Met Asn Phe Gly Ser Gln Ala Gln
625                 630                 635                 640

Asn Pro Phe Leu Thr Thr Leu Asp Asn Val Lys Lys Val Ala Leu Asn
                645                 650                 655

Thr Asp Gly Leu Gly Gln Ser Val Leu Leu Lys Gly Tyr Gly Asn Glu
            660                 665                 670

Gly His Asp Ser Gly His Pro Asp Tyr Gly Asp Ile Asn Thr Arg Ala
            675                 680                 685

Gly Gly Ala Ala Asp Met Asn Thr Leu Met Glu Lys Gly Thr Lys Tyr
        690                 695                 700

Gly Ala Arg Phe Gly Val His Val Asn Ala Ser Glu Met Tyr Pro Glu
705                 710                 715                 720

Ala Lys Ala Phe Ser Glu Asp Met Val Arg Arg Asn Ser Ser Gly Gly
                725                 730                 735

Leu Ser Tyr Gly Trp Asn Trp Leu Asp Gln Gly Ile Gly Ile Asp Gly
            740                 745                 750

Ile Tyr Asp Leu Ala Ser Gly Met Arg Lys Ser Arg Phe Ala Asp Leu
        755                 760                 765

Lys Ser Lys Val Gly Asp Asn Met Asp Phe Ile Tyr Leu Asp Val Trp
770                 775                 780

Gly Asn Asn Thr Ser Gly Ala Glu Asp Ser Trp Glu Thr Arg Lys Met
785                 790                 795                 800

Ser Gln Met Ile Asn Gln Asn Gly Trp Arg Met Thr Thr Glu Trp Gly
                805                 810                 815

Ala Gly Asn Glu Tyr Asp Ala Thr Phe Gln His Trp Ala Ala Asp Leu
            820                 825                 830

Thr Tyr Gly Gly Ser Ala Met Lys Gly Glu Asn Ser Gln Val Met Arg
        835                 840                 845

Phe Leu Arg Asn His Gln Lys Asp Ser Trp Val Gly Asp Tyr Pro Ser
850                 855                 860

Tyr Gly Gln Ala Ala Asn Ala Pro Leu Leu Gly Gly Tyr Ser Met Lys
865                 870                 875                 880
```

Asp Phe Glu Gly Trp Gln Gly Arg Asn Asp Tyr Ala Ala Tyr Ile Arg
                885                 890                 895

Asn Leu Tyr Thr His Asp Val Ser Thr Lys Phe Ile Gln His Phe Lys
            900                 905                 910

Val Val Arg Trp Val Asn Ser Pro Leu Asp Ala Thr Ser Val Lys Asp
            915                 920                 925

Ala Ser Val Asn Asn Gly Asn Glu Gln Ile Thr Leu Lys Asp Asp His
            930                 935                 940

Gly Asn Val Val Val Leu Ser Arg Gly Ser Asn Asp Thr Asn Asn Thr
945                 950                 955                 960

Ala Tyr Arg Asn Arg Thr Ile Thr Leu Asn Gly Ile Thr Val Ala Ser
            965                 970                 975

Gly Ala Val Ser Pro Gly Asn Ser Asn Thr Val Lys Gly Thr Glu Ser
            980                 985                 990

Tyr Leu Leu Pro Trp Leu Trp Asp Val Asn Thr Gly Lys Leu Val Lys
            995                 1000                1005

Ser Ser Asp Glu Lys Leu Tyr His Trp Asn Thr Gln Gly Gly Thr
        1010                1015                1020

Thr Glu Trp Thr Leu Pro Lys Asp Trp Gln Asn Leu Ala Ser Val
        1025                1030                1035

Lys Val Tyr Gln Leu Thr Asp Gln Gly Lys Thr Asn Glu Lys Thr
        1040                1045                1050

Val Ala Val Ser Gly Gly Lys Ile Ser Leu Thr Ala Glu Ala Glu
        1055                1060                1065

Thr Pro Tyr Val Val Thr Lys Gly Ser Glu Lys Gln Ile Ser Val
        1070                1075                1080

Lys Trp Ser Glu Gly Met His Val Val Asp Ala Gly Phe Asn Gly
        1085                1090                1095

Gly Gln Asn Thr Leu Lys Asp Asn Trp Ala Val Ser Gly Thr Gly
        1100                1105                1110

Lys Ala Glu Val Glu Gly Thr Asn Asn Ala Met Leu Arg Leu Thr
        1115                1120                1125

Gly Asp Val Lys Val Ser Gln Lys Leu Thr Asp Leu Thr Ala Gly
        1130                1135                1140

Lys Arg Tyr Ala Ile Tyr Val Gly Val Asp Asn Arg Thr Asn Ser
        1145                1150                1155

Pro Ala Lys Ile Thr Val Thr Asn Gly Thr Lys Val Leu Ala Thr
        1160                1165                1170

Asn Glu Thr Gly Lys Ser Ile Ala Lys Asn Tyr Ile Lys Ala Tyr
        1175                1180                1185

Gly His Asn Thr Tyr Ser Asn Thr Glu Gly Gly Ser Ser Tyr Phe
        1190                1195                1200

Gln Asn Met Tyr Val Trp Phe Val Ala Pro Glu Ser Gly Asp Val
        1205                1210                1215

Lys Val Thr Leu Ser His Ser Gly Ala Cys Asp Asn Thr Asp His
        1220                1225                1230

Val Tyr Phe Asp Asp Val Arg Val Leu Glu Asn Gly Tyr Lys Gly
        1235                1240                1245

Leu Thr Leu Asn Ala Asp Gly Thr Leu Lys Thr Leu Thr Asn Asp
        1250                1255                1260

Phe Glu Asp Asn Ala Gln Gly Ile Trp Pro Phe Val Val Ser Gly
        1265                1270                1275

```
Ser Glu Gly Val Glu Asp Asn Arg Ile His Leu Ser Glu Leu His
    1280            1285                1290
Asp Pro Phe Thr Gln Ala Gly Trp Asp Val Lys Lys Met Asp Asp
    1295            1300                1305
Val Leu Asp Gly Lys Trp Ser Val Lys Ala Asn Gly Leu Ile Gln
    1310            1315                1320
Lys Gly Thr Leu Ile Tyr Gln Thr Ile Pro Gln Asn Val Lys Leu
    1325            1330                1335
Glu Pro Gly Glu Thr Tyr Lys Val Ser Phe Lys Tyr Gln Ser Gly
    1340            1345                1350
Ser Asp Asp Ile Tyr Ala Ile Ala Thr Gly Asp Gly Glu Tyr Asn
    1355            1360                1365
Ala Ser Thr Val Lys Leu Thr Asn Leu Lys Lys Ala Leu Gly Glu
    1370            1375                1380
Asp Gly Thr Ala Glu Phe Glu Ile Thr Gly Ser Ile Thr Gly Asp
    1385            1390                1395
Ser Trp Phe Gly Ile Tyr Ser Thr Ser Thr Ala Pro Asp Leu Gln
    1400            1405                1410
Asn Thr Ser Asp Ser Ala Ala Asn Phe Gly Gly Tyr Lys Asp Phe
    1415            1420                1425
Val Leu Asp Asp Leu Lys Val Glu His Val Ala Ser Ala Glu His
    1430            1435                1440
Thr Lys Ala Asp Ala Glu Ala Lys Leu Lys Glu Val Lys Asp Thr
    1445            1450                1455
Tyr Asp Gly Lys Ser Gly Asp Tyr Ser Ala Glu Val Trp Thr Thr
    1460            1465                1470
Tyr Val Asn Thr Val Ala Glu Ile Glu Ala Leu Ile Ala Lys Asp
    1475            1480                1485
Lys Pro Asp Tyr Thr Thr Ala Tyr Asn Lys Ala Val Ala Leu Ala
    1490            1495                1500
Glu Tyr Met Lys Asn Ala Pro Gly Asp Asp Ser Asn Asp Ala Tyr
    1505            1510                1515
Asp Val Ala Thr Asp Ala Tyr Thr Val Glu Ala Gly Ser Gln Gln
    1520            1525                1530
Ala Leu Ser Gly Gly Asn Glu Gly Pro Ala Ser Leu Ala Gln Asp
    1535            1540                1545
Gly Asn Ala Gly Thr His Trp His Thr Ser Trp Ser Ala Asn Ala
    1550            1555                1560
Val Ser Ala Gly Thr Ala Trp Tyr Gln Phe Asn Leu Asn Glu Pro
    1565            1570                1575
Thr Thr Ile Asp Gly Leu Arg Tyr Met Ala Arg Ser Gly Gly Ala
    1580            1585                1590
Asn Ala Asn Gly Lys Ile Lys Lys Tyr Lys Ile Thr Leu Thr Leu
    1595            1600                1605
Ser Asp Gly Thr Thr Lys Asp Val Val Thr Asn Gly Thr Phe Thr
    1610            1615                1620
Thr Thr Ser Gly Val Trp Gln Lys Val Lys Phe Asp Ala Val Lys
    1625            1630                1635
Asn Val Thr Lys Val Arg Ile Thr Ala Leu Glu Thr Ala Gly Gln
    1640            1645                1650
Ser Ala Gly Glu Val Asn Thr Tyr Ala Ser Ala Ala Glu Leu Arg
    1655            1660                1665
```

-continued

Val Thr Thr Val Arg Asp Val Pro Ser Thr Glu Val Lys Val Asn
1670                1675                1680

Lys Cys Asp Leu Gln Asn Leu Tyr Asp Asp Ala Ser Ala Leu Thr
    1685                1690                1695

Glu Ala Thr Tyr Thr Ala Asp Thr Trp Lys Val Leu Val Ala Lys
1700                1705                1710

Arg Asp Ala Ala Lys Lys Val Leu Asp Asp Glu Asn Ala Thr Ala
    1715                1720                1725

His Asp Val Ala Leu Ala Tyr Gln Asn Leu Lys Asp Ala Ile Ala
1730                1735                1740

Ala Leu Glu Glu Arg Val Asp Thr Ser Lys Leu Ala Gly Leu Val
    1745                1750                1755

Ala Asp Ala Glu Lys Leu Lys Glu Ser Ala Tyr Thr Lys Asp Ser
1760                1765                1770

Trp Ala Ala Phe Lys Lys Ala Leu Asp Ala Ala Lys Ala Val Leu
    1775                1780                1785

Asn Asn Ala Asn Ala Thr Lys Ala Asp Val Asp Ala Ala Tyr Asn
1790                1795                1800

Ala Leu Asn Ala Ala Met Lys Ala Leu Lys Pro Ala Ser Ser Lys
    1805                1810                1815

Pro Thr Pro Asn Pro Glu Thr Thr Asp Lys Ser Lys Leu Gln Ala
1820                1825                1830

Thr Ile Asp Gln Ala Lys Ala Leu Asp Leu Ser Gly Tyr Thr Lys
    1835                1840                1845

Lys Ser Ala Gln Ala Val Arg Asp Ala Leu Ala Lys Ala Gln Ser
1850                1855                1860

Val Leu Ala Asp Asp Asn Ala Thr Gln Ala Asp Ile Asp Ala Ala
    1865                1870                1875

Gln Lys Ala Leu Ala Asp Ala Ile Ala Ala Leu Glu Lys Ala Asp
1880                1885                1890

Ala Asn Gly Asn Ala Ile Ser Lys Thr Gly Ala Asn Val Ala Val
    1895                1900                1905

Ile Gly Met Ala Gly Met Met Leu Val Ala Ala Gly Ala Val
1910                1915                1920

Phe Ile Ala Arg Lys Arg Ala Glu
    1925                1930

<210> SEQ ID NO 106
<211> LENGTH: 867
<212> TYPE: PRT
<213> ORGANISM: Bifidobacterium bifidum CCOS 571

<400> SEQUENCE: 106

Met Val Ser Pro His His Leu Leu Lys Ile Ala Thr Ala Leu Ser Ala
1               5                   10                  15

Val Ala Leu Thr Ala Ser Val Ala Val Thr Pro Ala Tyr Ala Leu Gln
            20                  25                  30

Asp Ile Ala Ile Glu Asp Ala Val Ala Gln Ser Gly Pro Val Thr Ala
        35                  40                  45

Asp Asn Gly Val Val Val Gln Ser Asp Gln Ser Asp Asp Gln Thr
    50                  55                  60

Gly Asp Gln Gln Ser Gln Asp Gly Met Pro Asp Asn Pro Asn Ala Lys
65                  70                  75                  80

Leu Pro Asp Thr Val Ser Asp Glu Ile Ser Asp Asp Ala Thr Val Val
                85                  90                  95

Ser Glu Asp Leu Ala Val Thr Pro Glu Gly Val Lys Asn Ile Glu
            100                 105                 110

Thr Gly Glu Thr Val Thr Asp Ala Thr Leu Val Gly Thr Gln Asp Gln
            115                 120                 125

Gln Pro Asp Pro Leu Ala Lys Thr Asn Gly Ser Phe Ile Pro Val
130                 135                 140

Ser Ala Glu Asp Val Lys Asn Ala Val Ala Asp Ala Asn Val Gln Leu
145                 150                 155                 160

Ser Lys Phe Glu Gly Asn Glu Tyr Gly Ala His Trp Gly Thr Tyr Asn
                165                 170                 175

Asn Thr Lys Ala Phe Phe Asp Tyr Gln Asn Asn Leu Phe Val Gln Gln
            180                 185                 190

Ala Lys Gly Val Ile Asp Val Ser Glu Trp Gln Gly Asp Ile Asp Trp
            195                 200                 205

Ala Lys Ala Lys Ala Asp Gly Val Glu Gly Val Ile Ile Arg Leu Gly
            210                 215                 220

Tyr Gly Trp Gly Asn Asn Ala Asp Arg Lys Ala Gln Arg Asn Ile Ser
225                 230                 235                 240

Glu Cys Lys Arg Leu Gly Ile Pro Phe Gly Ile Tyr Trp Tyr Ser Tyr
                245                 250                 255

Ala Asp Thr Pro Ser Ile Ala Lys Glu Glu Gly Ala Gly Val Val Ala
            260                 265                 270

Lys Leu Lys Arg Phe Gly Val Arg Ala Ser Asp Leu Ala Tyr Pro Val
            275                 280                 285

Tyr Tyr Asp Leu Glu Lys Trp Thr Trp Lys Gly His Gln Pro Pro Thr
290                 295                 300

Asp Pro Asn Val Tyr Ser Asp Ile Val Asn Asn Trp Tyr Gly Ala Leu
305                 310                 315                 320

Gln Ser Ala Gly Tyr Lys Asn Leu Gly Val Tyr Ser Tyr Thr Ser Tyr
                325                 330                 335

Leu Gln Gly Pro Leu Lys His Ala Asp Ile Tyr Ala Lys Thr Thr Trp
            340                 345                 350

Val Ala Gln Tyr Gly Ala Arg Met Gly Phe Asp Ser Phe Pro Thr Asn
            355                 360                 365

Ser Arg Gly Trp Gln Tyr Thr Ser Ser Gly Lys Val Gly Gly Ile Arg
370                 375                 380

Gly Asn Val Asp Met Asn Ala Phe Gly Asn Lys Glu Tyr Val Asn Gly
385                 390                 395                 400

Gly Ser Ser Asn Asp Leu Gln Ala Ala Ile Asp Val Arg Lys Met Thr
                405                 410                 415

Ala Val Thr Ile Pro Asn Gly Asn Tyr Tyr Ile Asn Val Arg Ser Lys
            420                 425                 430

Val Ala Ser Ser Val Asp Val Pro Gly Gly Ser Ala Ala Asp Ser Thr
            435                 440                 445

Ala Ile Gln Leu Tyr Ser Gly Asn Ser Ser Lys Ala Gln Gln Phe Thr
450                 455                 460

Phe Thr Arg Gln Ser Asp Gly Ser Tyr Glu Ile Val Asn Val Asn Ser
465                 470                 475                 480

Gly Lys Ala Leu Asp Val Arg Asn Gly Val Ala Glu Asn Asn Ala Val
                485                 490                 495

Val Gln Gln Tyr Ser Arg Asn Asn Ser Gln Ala Gln Arg Trp Phe Ile
            500                 505                 510

Arg Asp Ser Gly Ala Gly Ser Tyr Leu Gln Ser Ala Leu Gly Asn Trp
            515                 520                 525

Val Leu Asp Leu Ser Gly Asn Thr Ala Asn Gly Ala Ala Ile Arg
530                 535                 540

Leu Tyr Ala Pro Asn Gly Thr Ala Ser Gln Leu Phe Val Val Ser Ser
545                 550                 555                 560

Ser Asp Ala Ser Ile Ala Thr Gly Val Ser Met Ile Thr Ser Val
                565                 570                 575

Ala Asn Lys Lys Leu Val Thr Asp Val Thr Gly Ala Ser Thr Ala Asn
            580                 585                 590

Gly Ala Arg Val Gln Leu Asp Ser Ser Asn Thr Asn Ala Gln Lys
            595                 600                 605

Tyr Arg Phe Glu Ser Ile Gly Asn Gly Thr Tyr Lys Ile Ile Asn Ala
            610                 615                 620

Asn Ser Gly Lys Val Leu Asp Val Ala Gly Gly Ser Thr Ala Asp Gly
625                 630                 635                 640

Ala Ala Leu Gln Gln Tyr Thr Ser Asn Asn Thr Val Ala Gln Gln Trp
            645                 650                 655

Thr Val Arg Asn Tyr Gly Ser Gly Arg Ile Ala Leu Val Ser Val Asn
            660                 665                 670

Ala Asn Lys Ala Val Asp Ile Pro Gly Gly Asn Ala Val Gln Gln Ala
            675                 680                 685

Gln Leu Gln Leu Tyr Ser Pro Asn Gly Thr Val Ala Gln Gln Trp Leu
            690                 695                 700

Val Ala Lys Ala Pro Leu Thr Leu Arg Glu Arg Leu Asn Glu Thr Ala
705                 710                 715                 720

Ala Lys His Arg Gln Asp Leu Pro Asp Gly Thr Tyr Thr Phe Gly Ser
                725                 730                 735

Lys Leu Asn Thr Ser Met Lys Met Asp Val Ser Gly Ala Ser Arg Ser
            740                 745                 750

Asn Tyr Gly Asn Val Gln Ile Trp Ala Gly Asn Gly Thr Asn Ala Gln
            755                 760                 765

Lys Trp Lys Val Thr His Asp Ser Asn Gly Tyr Val Thr Leu Thr Ser
770                 775                 780

Val Asn Ser Gly Lys Val Leu Asp Val Asn Gly Val Ser Ala Asn
785                 790                 795                 800

Gly Thr Asn Val Gln Gln Tyr Asp Ser Asn Gly Thr Tyr Ala Gln Lys
            805                 810                 815

Trp Ile Ala Val Lys Asn Ser Asp Gly Ser Tyr Thr Phe Gln Ser Ala
            820                 825                 830

Leu Ala Glu Asn Lys Val Leu Asp Val Ser Gly Ala Ser Thr Ser Asn
            835                 840                 845

Gly Ala Asn Val Gln Leu Tyr Thr Ala Asn Gly Thr Asn Ala Gln Lys
            850                 855                 860

Trp Val Lys
865

<210> SEQ ID NO 107
<211> LENGTH: 778
<212> TYPE: PRT
<213> ORGANISM: Bifidobacterium bifidum CCOS 571

<400> SEQUENCE: 107

Met Ser Phe Asp Leu Ile Pro Glu Pro Gln Ser Val Thr Leu Lys Gly
1               5                   10                  15

```
Asp Ala Ala Asp Ser Asp Ala Gly Ala Pro Val Pro Val Ala Leu
            20                  25                  30

Pro Leu Val Gly Arg Ile Ser Glu Asp Arg Asp Ile Asp Ile Ala
            35                  40                  45

Gly Val Phe Pro Thr Gln Leu Ala Asp Ile Glu Ala Ala Thr Gly
50                  55                  60

Leu Arg Trp Asp Ile Ala Ser Asp Val Met Val Ala Gly Leu Pro Ala
65                  70                  75                  80

Pro Asn Ala Ala Ile Ala His Pro Val Pro His Ala Ser Cys Trp
                85                  90                  95

Lys Ser Phe Ile Thr Leu Arg Leu Asp Pro Pro Ser Leu Glu Pro Gln
                100                 105                 110

Glu Tyr Arg Leu Thr Ile Ala Arg Ser Gly Ile Asp Val Val Gly Gly
                115                 120                 125

Asp Thr Glu Gly Val Arg Asn Gly Val Gln Thr Leu Arg Gln Ile Ile
        130                 135                 140

Arg Gln Cys Ala Pro Ala Leu Pro Arg Leu Val Ile Ala Asp Lys Pro
145                 150                 155                 160

Ala Tyr Lys Val Arg Gly Tyr Tyr Leu Asp Ala Thr Gly Arg Val
                165                 170                 175

Pro Thr Leu Asp Trp Leu Lys Thr Trp Ala Asp Arg Leu Cys Leu Tyr
                180                 185                 190

Lys Tyr Asn Gln Leu Gln Leu Tyr Ile Glu His Thr Phe Met Phe Asp
                195                 200                 205

Asp Leu Ser Glu Thr Trp Arg Gly Thr Ser Pro Leu Lys Pro Ala Asp
        210                 215                 220

Ile Ile Ala Phe Asp Glu Tyr Cys Ala Arg Leu Gly Ile Glu Leu Val
225                 230                 235                 240

Pro Ser Val Ser Thr Phe Gly His Gln Tyr Met Ala Met Arg Thr Arg
                245                 250                 255

Glu Leu Arg His Leu Gly Glu Phe Pro Glu Asp Ala Asp Arg Arg Tyr
                260                 265                 270

Gly Phe Val Glu Arg Gln Arg His His Thr Leu Asn Ile Thr Glu Pro
                275                 280                 285

Glu Ser Leu Ala Phe Ser Phe Lys Leu Ile Asp Ala Tyr Met Gln Leu
        290                 295                 300

Phe Arg Thr Arg Lys Phe Asn Ile Cys Gly Asp Glu Thr Phe Asp Leu
305                 310                 315                 320

Gly Arg Gly Arg Ser Lys Pro Glu Ala Glu Arg Gly Val Ala Ala
                325                 330                 335

Met Tyr Ala Asp Phe Val Ser Gln Leu Cys Arg His Leu Ser Glu Arg
                340                 345                 350

Gly Arg Asp Pro Met Phe Trp Gly Asp Ile Ala Val Glu Met Pro Gln
        355                 360                 365

Ile Leu Gly Leu Leu Pro Asp Asn Val Thr Leu Leu Asn Trp Leu Tyr
        370                 375                 380

Ala Pro Gly Ile Gly Glu Asp Lys Val Arg Leu Val Ala Gln Ala Gly
385                 390                 395                 400

Ala Pro Gln Tyr Val Cys Ser Ala Val Trp Cys Trp Asn Ala Leu Leu
                405                 410                 415

Pro Arg Leu Asp Asp Ser Trp Asn Asn Ile Ser Arg Leu Ala Arg Tyr
                420                 425                 430
```

```
Gly Val Lys Tyr Gly Ala Val Gly Tyr Leu Val Thr Asp Trp Gly Asp
            435                 440                 445

Tyr Gly His Val Asn Asp Pro Arg Met Ala Val Ser Gly Met Ile Phe
        450                 455                 460

Gly Ala Gln Cys Ala Trp Asn Pro Met Ala His Ile Gln Gly Glu Ala
465                 470                 475                 480

Gly Cys Gly Asp Gly Glu Gly Ser Ala Ala Gly Tyr Ala Asp Ala
                485                 490                 495

Ala Ala Asp Val Val Arg Glu Asn Lys Ala Ala Asp Gly Asp Ser
            500                 505                 510

Pro Ala Pro Leu Pro Ser Ser Glu Ser Asp Asp Tyr Thr Gly Gly
            515                 520                 525

Ala Ala Asp Ala Ile Ala Gly Ala Pro Ala Gly Gly Asp Gly Ser Cys
            530                 535                 540

Ala Glu Met Cys Arg Arg Val Ala Glu Val Glu Tyr Gly Asp Arg Ser
545                 550                 555                 560

Gly Gly Ile Val Glu Ala Leu Arg Asp Ala Ala Cys Arg Val Ala Phe
                565                 570                 575

Gly Trp Asp Asp Met Val Trp Tyr Cys Glu Leu Asp Glu Gly Asp Gly
            580                 585                 590

Arg Met Asn Arg Asp Ala Ala Ser Ala Met His Leu Gly Val His Gly
                595                 600                 605

Phe Ser Gly Glu Tyr Gly Arg Glu Trp Glu Ala Arg Leu Leu Gly Ser
            610                 615                 620

Ala Asp Leu Asp Glu Ala Arg Arg Thr Met Leu Gln Gly Leu Ser Pro
625                 630                 635                 640

His Ile Val Arg Ala Ala Glu Ala Asn Glu Ala Leu Leu Cys Asp Ala
                645                 650                 655

Met Arg Leu Gly Ala Ala Ala Gly Arg Ala Ser Arg Leu Gly Ala Ala
            660                 665                 670

Arg Arg Asp Val Pro Ala Met Leu Ala Ala Ile Glu Gly Gln Arg Trp
            675                 680                 685

Phe Asn Leu Val Gly Leu Cys Leu Ala Arg Arg His Asp Val Ile Thr
690                 695                 700

Val Asp Ala Gly Asp Ile Ala Arg Ala Ser Ala Gly Leu Ile Glu Pro
705                 710                 715                 720

Asp Ala Gly Ser Ser Ala Gly Pro Glu Ala Val Gln Asp Val Ser Ile
                725                 730                 735

Arg Val Ala Arg Gly Leu Glu Arg Trp Phe Glu Thr Tyr Cys Asp Leu
            740                 745                 750

Trp Arg Ser Val Ser Ala Glu Ser Glu Leu Ala Arg Ile Ala Ser Ile
            755                 760                 765

Val Trp Arg Cys Ala Asp Ala Leu Arg Ser
770                 775

<210> SEQ ID NO 108
<211> LENGTH: 304
<212> TYPE: PRT
<213> ORGANISM: Bifidobacterium bifidum CCOS 571

<400> SEQUENCE: 108

Met Ala Asp Arg Phe Gly Ala Phe Leu Pro His Asp Thr Ser Gly Asp
1               5                   10                  15

Val Ala Gln Leu His Gly Ile Gly Leu Gln Lys Phe Gly Asp Thr Trp
            20                  25                  30
```

Tyr Ala Tyr Gly Glu Asn Lys Val Asn Gly Asn Leu Phe Gln Gly Val
                35                  40                  45

Cys Cys Tyr Thr Thr Thr Asp Phe Ile Ala Trp Arg Ser His Gly Ile
    50                  55                  60

Val Leu Asp Val Gln Glu Asp Gly Ser Ala Leu Ala Ala Asp Arg Ile
65                  70                  75                  80

Gly Glu Arg Pro Lys Val Leu His Cys Pro Ala Thr Gly Lys Tyr Val
                85                  90                  95

Met Tyr Ile His Ala Glu Thr Pro Asp Tyr Gly Tyr Ala His Ile Gly
                100                 105                 110

Val Ala Val Ala Asp Ala Pro Thr Gly Pro Phe Ala Phe Gln Thr Thr
                115                 120                 125

Ile Thr Trp Arg Gly Tyr Leu Ser Arg Asp Ile Gly Val Phe Gln Asp
                130                 135                 140

Glu Asp Gly Ser Gly Tyr Ile Met Ser Glu Asp Arg Asp His Gly Thr
145                 150                 155                 160

His Ile Tyr Arg Leu Ala Asp Asp Tyr Leu Thr Ile Val Glu Asp Val
                165                 170                 175

Ala Cys Glu Arg Ala Thr Asp Tyr Pro Tyr Gly Leu Glu Ser Pro Thr
                180                 185                 190

Ile Ile Lys Lys Asp Gly Leu Tyr Tyr Trp Phe Gly Ser Gln Leu Thr
                195                 200                 205

Ser Trp Asp Thr Asn Asp Asn Lys Tyr Ser Thr Ala Thr Asp Leu His
                210                 215                 220

Gly Pro Trp Ser Glu Trp Lys Leu Phe Ala Pro Glu Gly Ala Lys Thr
225                 230                 235                 240

Tyr Asp Ser Gln Val Asp Ile Val Val Pro Leu Asp Asp Pro Tyr
                245                 250                 255

Asn Ser Glu His Phe Leu Phe Ile Gly Asp Arg Trp Gln His Asp
                260                 265                 270

Leu Gly Asn Ser Pro Ile Val Gln Met Pro Ile Ser Ile Ala Asp Gly
                275                 280                 285

Val Ala Ser Leu Thr Trp Ser Asp Thr Tyr Gly Thr Thr His Arg
                290                 295                 300

<210> SEQ ID NO 109
<211> LENGTH: 634
<212> TYPE: PRT
<213> ORGANISM: Bifidobacterium bifidum CCOS 571

<400> SEQUENCE: 109

Met Met Gln Phe Thr Met Ser Gly Thr Met Leu Arg Phe Asp Glu Thr
1               5                   10                  15

Thr Leu Arg Phe Ser Phe Ser Arg Asp Gly Ala Thr Trp Ser Gly Cys
                20                  25                  30

Asp Gly Ile Glu Pro Gln Leu Thr Arg Glu Asp Arg Ser Phe Ser Phe
                35                  40                  45

Ala Gly Ala Ala Thr Val Thr His Glu Arg Ile Glu Thr Gly Thr Gly
    50                  55                  60

Val Gly Val Arg Ser Val Phe Ala Gly Phe Gly Ala Asp Tyr Ala
65                  70                  75                  80

Phe Glu Thr Tyr Ile Trp Ile Glu Arg Ser Ser Gly Asp Val Leu Cys
                85                  90                  95

Glu Trp Val Pro Leu Arg Glu Cys Gly Ala Glu Pro Arg Ile Asp Arg

```
            100                 105                 110
Val Leu Trp Pro Ala Pro Leu Ser Phe Asp His Ala Asp Ala His Asp
            115                 120                 125

Val Thr Leu Ile Thr His Glu Gln Gly Val Met Ile Pro Asn Asn Trp
            130                 135                 140

Pro Thr Glu Val Gly Thr Asp Ala Val Ser Phe Gly Gly Arg Phe Glu
145                 150                 155                 160

Thr Ala Gly Gly Tyr Met Pro Trp Phe Ala Gln Leu Arg Ser Asp Gly
                165                 170                 175

His Ala Tyr Ile Ala Ile Cys Glu Thr Pro Trp Asn Ala Gly Tyr Asp
                180                 185                 190

Ile Asp His Pro Ala Gly Gly Pro Tyr Thr His Val Gly Met Trp Phe
            195                 200                 205

Glu Pro Ser Leu Gly Arg Met Asp Tyr Arg Arg Val Val Arg Tyr Arg
            210                 215                 220

Leu Leu Asp His Ala Asp His Thr Ala Val Cys Lys Thr Tyr Arg Ala
225                 230                 235                 240

Tyr Val Asn Glu Arg Gly Arg Leu Arg Thr Leu Ala Glu Lys Ala Ala
                245                 250                 255

Arg Asn Pro Ser Val Arg Asp Leu Leu Gly Arg Ser Trp Val His Val
            260                 265                 270

Gly Ile Lys Thr Lys Val Gln Pro Asp Ser Ser Phe Tyr Asp Pro Ala
            275                 280                 285

Gln Pro Gly Lys Asn Asp Ser Leu Val Thr Phe Ala Gln Arg Glu Arg
            290                 295                 300

Gln Met Arg Thr Leu His Glu Met Gly Ala Gly Arg Leu Tyr Leu His
305                 310                 315                 320

Leu Asp Gly Trp Ala Gln Pro Gly Tyr Asp Asn Gly His Pro Asp Tyr
                325                 330                 335

Leu Pro Ala Cys Arg Glu Ala Gly Gly Trp Lys Gly Met Lys Ser Leu
            340                 345                 350

Val Asp Ala Cys His Glu Gln Gly Asp Leu Phe Gly Thr His Asp Gln
            355                 360                 365

Tyr Arg Asp Tyr Tyr Phe Ala Ala Arg Thr Phe Asp Pro Arg Asn Ala
            370                 375                 380

Ile Arg Leu Ala Asp Gly Thr Met Pro Glu His Ala Met Trp Ala Gly
385                 390                 395                 400

Gly Arg Gln Thr Tyr Leu Cys Ala Glu Leu Ala Pro Asp Tyr Val Arg
                405                 410                 415

Arg Asn Phe Ser Glu Ile Ala Thr His Gly Ile Ala Leu Asp Cys Ala
            420                 425                 430

Tyr Leu Asp Val Phe Thr Cys Asn Glu Gly Asp Glu Cys Ser His Pro
            435                 440                 445

Glu His Arg Met Thr Arg Arg Gly Cys Tyr Glu Arg Arg Ala Glu Cys
            450                 455                 460

Phe Glu Tyr Leu Leu Ala His Gly Ile Leu Thr Ser Ser Glu Glu Val
465                 470                 475                 480

Ser Asp Trp Ala Val Pro Ser Leu Val Phe Cys His Tyr Ala Pro Tyr
                485                 490                 495

Asp Phe Gln Met Arg Ser Pro Asp Ala Pro Arg His Gly Ile Pro Val
            500                 505                 510

Pro Leu Tyr Asn Leu Val Tyr His Asp Cys Val Ile Gln Pro Trp Met
            515                 520                 525
```

```
Met Asp Arg Val Ala Gly Gly Asp Asp Tyr Met Leu Tyr Ala Leu Leu
        530                 535                 540
Asn Gly Gly Ala Pro Tyr Leu Ile Arg Asp Ala Ala Tyr Ala Gly Met
545                 550                 555                 560
Asp Gly Asp Met Asn Ala Ala Leu Arg Ala Arg Thr Glu Asn Asp Ile
                565                 570                 575
Glu Arg Cys Ala Val Ala Gly Leu His Arg Arg Val Gly Met Gln
            580                 585                 590
Glu Leu Val Arg His Asp Leu Val Gly Gly Asp Pro Leu Val Gln Arg
            595                 600                 605
Ser Val Phe Ala Asp Gly Thr Ala Val Thr Cys Asp Phe His Ala Gln
            610                 615                 620
Thr Tyr Glu Val Ala Ala Asn Gly Ser His
625                 630

<210> SEQ ID NO 110
<211> LENGTH: 1138
<212> TYPE: PRT
<213> ORGANISM: Bifidobacterium bifidum CCOS 571

<400> SEQUENCE: 110

Met Arg Ala Asn Gly Asn Ser Thr His Glu Ile Leu Gly Lys Ile Val
1               5                   10                  15
Thr Ala Ile Ala Ser Ile Ala Met Thr Ala Ala Phe Ala Val Pro Ala
                20                  25                  30
Met Ala Ala Ser Asp Ser Asp Thr Ala Ala Asp Ser Gly Thr Thr Gln
            35                  40                  45
Gln Ser Gly Gln Tyr Lys Ile Tyr Pro Gln Pro Gln Asn Thr Glu Tyr
    50                  55                  60
Gly Asp Gly Ser Leu Ile Leu Arg Asp Lys Ala Asn Thr Val Val Glu
65                  70                  75                  80
Pro Gly Ile Asp Ser Ala Thr Lys Ala Arg Leu Asn Glu Ala Leu Lys
                85                  90                  95
Leu Lys Gly Ile Glu Thr Thr Ala Ala Asp Ala Val Pro Glu Thr Ala
                100                 105                 110
Tyr Gln Leu Asn Val Leu Val Gly Ile Asn Gly Ser Asn Gly Val Val
            115                 120                 125
Asp Lys Tyr Ala Lys Gln Leu Ile Ala Asp Gly Thr Leu Lys Val Asp
    130                 135                 140
Asp Ser Thr Phe Ser Lys Asn Asp Ser Tyr Val Leu Ala Val Arg Gln
145                 150                 155                 160
Gly Asn Ala Lys Thr Pro Asp Thr Ile Leu Val Leu Gly Arg Asp Thr
                165                 170                 175
Asp Ser Ala Phe Tyr Gly Leu Thr Thr Leu Tyr Gln Ile Phe Gln Gln
                180                 185                 190
Leu Pro Gly Arg Ala Val Ser Asn Leu Thr Phe Ser Asp Trp Ala Asp
            195                 200                 205
Val Lys Ser Arg Gly Phe Ile Glu Gly Tyr Gly Ser Pro Trp Ser
    210                 215                 220
Thr Lys Asp Arg Val Asn Leu Met Thr Trp Gly Gly Tyr Tyr Lys Met
225                 230                 235                 240
Asn Thr Tyr Val Tyr Ala Pro Lys Asp Pro Leu His Arg Asn Asn
                245                 250                 255
Trp Arg Gly Leu Tyr Thr Glu Asp Gln Ile Glu Asn Glu Ile Lys Pro
            260                 265                 270
```

```
Gln Ala Glu Ala Gly Asn Lys Ser Lys Val Arg Phe Val Tyr Ala Leu
            275                 280                 285

Ala Pro Phe His Asn Asp Gly Glu Ala Arg Gly Lys His Phe Arg Phe
            290                 295                 300

Asp Thr Glu Glu His Tyr Gln Lys Asp Leu Lys Glu Leu Lys Ala Lys
305                 310                 315                 320

Tyr Met Gln Thr Ile Asp Ala Gly Val Arg Gln Ile Ala Leu Leu Ala
                325                 330                 335

Asp Asp Ser Thr Asp Trp Gly Ala Gln Tyr Gly Asn Asp Asn Thr Tyr
            340                 345                 350

Val Arg Val Leu Lys Asp Leu Thr Asp Trp Ile His Glu Leu Gln Gln
            355                 360                 365

Glu Lys Asn Asp Asp Gly Thr Ala Lys Tyr Glu Gly Leu Lys Asp Thr
            370                 375                 380

Ile Leu Tyr Cys Pro Ala Leu Tyr Ser Tyr Thr Gly Ala Gly Asp Ala
385                 390                 395                 400

Trp Tyr Lys Asp Ile Pro Ser Asn Val Gln Ile Val Met Thr Gly Gly
                405                 410                 415

Arg Thr Phe Gly Val Ala Ser Lys Asp Phe Ala Asp Thr Phe Thr Lys
            420                 425                 430

Asn Thr Gly Arg Ala Pro Phe Met Trp Ile Asn Trp Pro Cys Ser Asp
            435                 440                 445

Met Asn Arg Asn Thr Ala Tyr Gln Tyr Leu Val Met Gly Gly Gln Asn
            450                 455                 460
```

```
Asn Phe Leu Lys Pro Gly Ala Thr Tyr Gly Thr Tyr Asp Gly Ile Met
465                 470                 475                 480

Leu Asn Pro Met Gln Gln Ser Glu Pro Ser Lys Gln Gly Ile Phe Met
            485                 490                 495

Ala Ala Asp Tyr Ser Trp Asn Leu Trp Gln Ser Glu Lys Asp Gly Gln
        500                 505                 510

Gln Ser Trp Glu Asp Ser Phe Ser Tyr Ile Asp His Asn Ser Pro Ile
    515                 520                 525

Ala Ser Lys Gly Ser Arg Gly Leu Arg Asp Leu Ala Met Asn Met Arg
530                 535                 540

Ile Leu Asn Asp Gly Gly Ile Asp Gly Ala His Lys Asp Ala Glu Tyr
545                 550                 555                 560

Asp Ala Val Asn Lys Trp Trp Ile Asn Asn Glu Ser Val Asp Tyr Thr
            565                 570                 575

Gly Lys Leu Asp Val Lys Gly Val Leu Thr Glu Leu Lys Gly Lys Leu
            580                 585                 590

Asp Gly Gly Thr Ala Thr Ala Ala Asp Phe Ser Gln Ala Leu Thr Val
        595                 600                 605

Tyr Thr Thr Leu Gln Arg Ala Ala Lys Asn Tyr Arg Ala Asn Pro Gly
    610                 615                 620

Asp Lys Asn Met Phe Asp Gln Ile Glu Pro Trp Ile Ser Tyr Trp Asp
625                 630                 635                 640

Asp Leu Thr Ala Ser Ala Ile Asp Tyr Ile Thr Ala Ala Lys Gln Ala
            645                 650                 655

Leu Ala Gly Asp Thr Glu Thr Ala Lys Ala Thr Tyr Ala Thr Ala Lys
            660                 665                 670

Ala Ala Phe Ala Lys Ser Asp Thr His Thr Ile Ala Asp Tyr Tyr Gln
        675                 680                 685

Arg Asn Lys Pro Ala Arg Gly Gly Leu Val Ile Val Arg Pro Thr Val
    690                 695                 700

Gln Ala Leu Asp Ser Phe Val Lys Ala Lys Thr Ser Gly Ser Val Thr
705                 710                 715                 720

Pro Thr Pro Ser Asp Ala Thr Val Ser Thr Asn Gly Val Gly Ala Ala
            725                 730                 735

Ala Trp His Glu Asn Val Asp Pro Lys Ala Val Ile Asp Gly Asp Asp
            740                 745                 750

Ser Thr Phe Phe Trp Met Gln Ser Ala Gly Cys Asp Cys Val Lys Ala
        755                 760                 765

Asn Ala Ala Leu Thr Val Thr Tyr Ala Glu Ala Arg Lys Ala Lys Glu
    770                 775                 780

Phe Arg Phe Ile Gln Ala Glu Lys Gly Gly Asp Thr Ile Val Asn Gly
785                 790                 795                 800

Lys Ile Glu Tyr Gln Asp Ala Asp Gly Asn Trp Thr Lys Ile Gly Asp
            805                 810                 815

Val Asn Gly Asn Gln Lys Gln Ile Phe Thr Leu Asp Ser Ala Ala Thr
            820                 825                 830

Val Lys Ala Val Arg Ile Thr Asn Leu Ala Gln Thr Ser Lys Trp Trp
        835                 840                 845

Lys Val Tyr Asp Leu Ser Ala Thr Lys Ile Asp Glu Pro Gly Thr Val
    850                 855                 860

Thr Lys Asp Ala Leu Asn Ala Lys Val Ala Glu Ala Lys Val Asp
865                 870                 875                 880

Ser Ala Asp Trp Thr Lys Ser Ser Arg Glu Ala Leu Ala Asp Ala Ile
```

```
                885                 890                 895
Ala Ala Ala Lys Ala Val Ala Ala Asp Gln Asp Ala Thr Gln Ala Lys
            900                 905                 910

Val Asp Ala Ala Val Ala Ala Leu Glu Ser Ala Met Lys Gly Val Glu
            915                 920                 925

Arg Tyr Thr Ala Lys Thr Ala Asp Gln Leu Lys Ala Glu His Val Ser
            930                 935                 940

Asn Asp Asp Ala Thr Tyr Thr Glu Ala Ser Tyr Asn Lys Tyr Gln Ser
945                 950                 955                 960

Ala Tyr Asp Asp Phe Ala Ala Leu Ala Asn Ala Asp Asp Leu Ala
            965                 970                 975

Lys Ala Asp Gly Glu Ala Leu Glu Ala Ala Tyr Thr Ala Ala Lys Ser
            980                 985                 990

Ala Leu Arg Tyr Asp Gln Ser Ala Arg Asp Tyr Ala Gln Leu Ala Leu
            995                1000                1005

Asn Asp Ala Glu Pro Tyr Val Gly Lys Ala Ser Glu Tyr Thr Lys
    1010                1015                1020

Asp Ser Tyr Ala Lys Phe Thr Val Ala Tyr Glu Ala Leu Ser Lys
    1025                1030                1035

Gln Leu Lys Ala Asp Pro Asn Gly Glu Gly Asp Pro Ala Thr Tyr
    1040                1045                1050

Thr Ala Leu Arg Ala Ala Leu Asp Lys Ala Ile Lys Gly Leu Val
    1055                1060                1065

Lys Ser Asp Gly Thr Glu Leu Glu Arg Pro Gly Glu Lys Pro Gly
    1070                1075                1080

Glu Lys Pro Gly Glu Asn Lys Pro Gly Glu Lys Pro Gly Val Asn
    1085                1090                1095

Lys Pro Gly Ala Asp Gly Lys Leu Ser Asn Thr Gly Ala Asp Val
    1100                1105                1110

Phe Gly Leu Ile Ala Ala Met Thr Met Leu Ala Ala Val Gly Val
    1115                1120                1125

Thr Met Ala Gly Leu Arg Lys Arg Ile Gly
    1130                1135

<210> SEQ ID NO 111
<211> LENGTH: 1755
<212> TYPE: PRT
<213> ORGANISM: Bifidobacterium bifidum CCOS 571

<400> SEQUENCE: 111

Met Asn Arg Arg Ile Ser Met Trp Leu Arg Gly Arg Gly Ser Pro Trp
1               5                   10                  15

Arg Pro Ala Ala Ala Val Ile Ala Thr Val Ser Met Met Leu Ala Thr
            20                  25                  30

Val Met Gly Pro His Phe Ala Gly Met Arg Ala Gln Ala Val Glu Pro
        35                  40                  45

Val Gln Thr Thr Thr Ile Ser His Thr Lys Ile Ala Gly Asp Gly Asn
    50                  55                  60

Tyr Phe Thr Phe Ala Asp Asn Ala Trp Asp Pro Gly Asn Asp Val His
65                  70                  75                  80

Thr Trp Ser Lys Ala Pro Ser Asp Ser Leu Pro Ala Glu Asp Ile Trp
                85                  90                  95

Tyr Thr Val Arg Phe Phe Gly Ser Ala Ile Asp Val Tyr Ala Gly Lys
            100                 105                 110
```

```
Asn Arg Pro Met Gly Lys Val Lys Tyr Tyr Ile Asp Gly Ala Glu Lys
            115                 120                 125

Gly Thr Tyr Ser Leu Tyr Asn Ala Ser Asn Ile Asn Glu Thr Lys Ile
130                 135                 140

Ala Ser Phe Thr Gly Leu Asp Glu Gly Glu His Val Phe Lys Ala Val
145                 150                 155                 160

Ala Thr Gly Glu Arg Asp Thr Asn Ser Thr Asn Ala Leu Ile Asp Cys
                165                 170                 175

Ala Lys Val Val Thr His Gln Pro Tyr Val Val Thr Gly Val Thr
            180                 185                 190

Leu Asp Thr Thr Ser Met Thr Leu Gly Val Gly Asp Ser Lys Arg Ile
            195                 200                 205

Ser Tyr Thr Val Ala Pro Asp Tyr Ala Thr Ile Asp Asp Met Thr Tyr
        210                 215                 220

Thr Ser Gly Asp Thr Ser Val Ala Thr Val Gly Ala Asp Gly Thr Val
225                 230                 235                 240

Thr Ala Val Ala Pro Gly Ala Thr Ala Ile Thr Val Ala Ser Thr Ala
                245                 250                 255

Ala Gly Ile Ser Lys Ile Val Asp Val Thr Val Ala Arg Met Ala Pro
                260                 265                 270

Asn Leu Thr Gly Gly Ile Val Asp Pro Asp Thr Gln Tyr Thr Gln Lys
            275                 280                 285

Arg Phe Asp Glu Val Lys Ala Leu Thr Thr Asn Asn Arg Ala Leu Lys
    290                 295                 300

Ala Trp Lys Asn Asp Lys Val Asn Ser Glu Ile Ser Leu Ala Ala Val
305                 310                 315                 320

Gly Thr Thr Val Ser Asn Leu Thr Val Thr Ala Asn Asp Leu Thr Ser
                325                 330                 335

Gln Gly Gly Asp Val Ile Ala Lys Ser Asn Val Thr Ala Thr Phe Ile
                340                 345                 350

Lys Ser Thr Lys Ala Tyr Asn Gly Ser Tyr Leu Gly Tyr Gly Asp Pro
            355                 360                 365

Asn Arg Glu Val Pro Ala Ala Thr Glu Thr Asn Arg Ser Glu Ser Asn
    370                 375                 380

Asp Ile Leu Tyr Gln Ser Gly Pro Ile Thr Val Lys Ala Asn Gln Val
385                 390                 395                 400

Gln Asn Ile Trp Val Ser Phe Ala Ile Pro Lys Asp Ala Lys Ala Gly
                405                 410                 415

Thr Tyr Thr Thr Thr Leu Thr Ala Thr Ala Asp Gly Met Glu Thr Pro
                420                 425                 430

Leu Thr Phe Thr Tyr Thr Ile Glu Val Lys Ala Ala Thr Leu Pro Asp
            435                 440                 445

Pro Ala Glu Tyr Glu Lys Asn Phe Asp Val Glu Leu Trp Gln Tyr Pro
    450                 455                 460

Tyr Ser Ser Ala Glu Tyr Tyr Gly Val Thr Pro Phe Ser Asp Glu His
465                 470                 475                 480

Leu Gln Ile Leu Arg Ser Ser Met Glu Leu Tyr Lys Ser Ile Gly Gly
                485                 490                 495

His Ala Ile Thr Thr Ile Asn Glu Asp Ala Trp Ser Gly Gln Thr
            500                 505                 510

Tyr Ser Ala Asn Ala Ile His Tyr Pro Ser Met Val Lys Trp Thr Lys
            515                 520                 525

Ser Gly Gly Gly Phe Thr Tyr Asp Phe Thr Asp Phe Asp Lys Trp Val
```

```
            530                 535                 540
Thr Phe Asn Lys Gly Leu Gly Ile Gly Asp Lys Ile Val Ile Tyr Ser
545                 550                 555                 560

Ile Ala Pro Trp His Gly Asn Phe Thr Tyr Trp Glu Asn Gly Thr Met
                565                 570                 575

Lys Ser Glu Lys Tyr Thr Val Gly Ser Glu Arg Trp Arg Ser Val Trp
                580                 585                 590

Thr Asp Phe Leu Arg Lys Leu Ile Glu His Leu Met Asp Lys Gly Trp
                595                 600                 605

Phe Asp Glu Ser Tyr Ile Gly Ile Asp Glu Arg Gly Phe Ser Ala Asp
            610                 615                 620

Ala Phe Asp Leu Ile Asp Ser Ile Arg Asn Ile His Asp Val Pro Leu
625                 630                 635                 640

Lys Thr Ala Gly Ala Met Asp Gly Phe Val Asn Lys Phe Asp Leu Ala
                645                 650                 655

Leu Arg Val Thr Asp Leu Asn Val Gly Asp Thr Ala Ala Ala Ala His
                660                 665                 670

Pro Thr Asp Phe Thr Arg Leu Ile Glu Ala Arg Glu Ala Lys Gly Leu
                675                 680                 685

Arg Thr Thr Leu Tyr Ser Cys Thr Glu His Glu Pro Gly Asn Phe Ser
690                 695                 700

Leu Ser Ala Pro Val Glu Ser Tyr Trp Ser Val Val Asn Ala Gly Glu
705                 710                 715                 720

Gln Thr Ser Gly Phe Leu Arg Trp Ala Tyr Asp Ala Trp Val Ala Asp
                725                 730                 735

Pro Leu Asn Asp Ala Thr His Asn Ala Phe Glu Pro Gly Asp Pro Phe
                740                 745                 750

Leu Ile Tyr Pro Ser Glu Lys Ser Gly Asp Lys Val Ser Lys Ser Ser
                755                 760                 765

Val Arg Leu Glu Arg Ile Ala Glu Gly Val Arg Asp Val Asn Lys Ile
                770                 775                 780

Arg Leu Met Val Thr Glu Ile Pro Ser Leu Gln Ala Asp Ala Asp Ala
785                 790                 795                 800

Met Tyr Ala Lys Ile Arg Thr Thr Val Thr Thr Ser His Ser Tyr Leu
                805                 810                 815

Thr Ala Ala Gln Val Thr Gln Leu Ala Asn Glu Met Ser Gly Phe Lys
                820                 825                 830

Gly Asp Leu Asp Thr Leu Thr Asp Lys Tyr Ile Ser Leu Lys Ala Gln
                835                 840                 845

Gly Thr Ser Thr Val Glu Ser Val Ala Ile Asp Gly Asp Gln Glu
850                 855                 860

Ile Met Leu Gly Thr Ala Lys Gln Leu Thr Ala Thr Leu Lys Pro Ala
865                 870                 875                 880

Asn Leu Leu Asn Ala Ser Val Thr Trp Arg Ser Ser Lys Thr Gly Val
                885                 890                 895

Ala Thr Val Ser Ala Lys Gly Val Val Thr Ala Ala Gly Val Gly Ser
                900                 905                 910

Thr Thr Ile Thr Ala Thr Ser Lys Ala Asp Pro Thr Lys Ser Ala Ser
                915                 920                 925

Ile Thr Leu Thr Val Thr Pro Gln Val Val Ala Gln Gly Leu His Tyr
                930                 935                 940

Tyr Ser Phe Asp Asp Ser Asn Ala Asn Asp Ser Trp Gly Thr Arg Asn
945                 950                 955                 960
```

-continued

Gly Thr Ala Asp Ala Thr Ala Gln Tyr Val Asp Gly Lys Ser Gly Lys
            965                 970                 975
Ala Leu Lys Val Thr Asp Gly Lys Gly Val Thr Leu Ala Gly Gly Asn
            980                 985                 990
Asp Ile Ala Lys Thr Asp Pro Trp Thr Ile Gly Tyr Trp Val Arg Ser
            995                 1000                1005
Asp Ala Glu Leu Thr Gly Arg Ser Ala Val Met Thr Ser Ala Asp
        1010                1015                1020
Gly Lys Tyr Ser Ala Asp Leu Lys Met Asp Ala Asp Arg Glu Ser
        1025                1030                1035
Gly Phe Arg Val Gly Thr Ala Ser Gly Asp Val Leu Thr Phe Arg
        1040                1045                1050
Tyr Asp Phe Gln Pro Gly Thr Trp Tyr Tyr Ile Ala Trp Thr Gln
        1055                1060                1065
Asp Lys Ala Ala Gly Leu Thr Met Tyr Val Asn Gly Thr Lys Ile
        1070                1075                1080
Gly Val Thr Asn Thr Trp Thr Lys Met His Asp Val Val Ala Pro
        1085                1090                1095
Ile Asp Val Ile Gly Gly Pro Gly Phe Thr Gly Leu Ile Asp Glu
        1100                1105                1110
Val Lys Ile Tyr Lys Arg Val Leu Ser Asp Thr Glu Ile Ala Ala
        1115                1120                1125
Gly Met Leu Leu Pro Gly Leu Asn Leu Ala Glu His Glu Thr Asp
        1130                1135                1140
Met Tyr Ile Gly Gly Thr Tyr Thr Ile Val Ala Asn Leu Gln Gly
        1145                1150                1155
Gly Asp Gly Asp Gly Thr Val Thr Phe Glu Ser Ser Asp Pro Thr
        1160                1165                1170
Ile Ala Lys Val Asp Ala Ser Gly Thr Val Thr Gly Val Ser Arg
        1175                1180                1185
Gly Thr Ala Val Ile Thr Val Arg Gly Gly Gly Phe Thr Asp Met
        1190                1195                1200
Val Thr Val Asn Val Ser Arg Glu Leu Thr Ile Lys Asn Thr Leu
        1205                1210                1215
Pro Gln Tyr Lys Leu Asp Gln Thr Lys Val Thr Asp Val His Lys
        1220                1225                1230
Ser Leu Asp Thr Ser Asn Gln Tyr Phe Gly Gln Pro Asp Met Ile
        1235                1240                1245
Arg Thr Lys Ser Gly Arg Leu Ile Thr Ser Phe Pro Gln Gly His
        1250                1255                1260
Gly Lys Gly Pro Leu Ile Met Lys Ile Ser Asp Asp Gly Ala
        1265                1270                1275
Thr Trp Thr Arg Lys Thr Asp Ile Pro Ala Ser Trp Ala Gly Ser
        1280                1285                1290
Gln Glu Thr Pro Thr Leu Tyr Val Leu Asn Leu Ala Asp Gly Thr
        1295                1300                1305
Glu Arg Ile Met Met Ile Thr Ala Cys Pro Gly Trp Gly Thr Asp
        1310                1315                1320
Ser Ala Gly Asn Arg Tyr Gly Trp Asn Thr Ser Tyr Ser Asp Asp
        1325                1330                1335
Asn Gly Glu Thr Trp Thr Glu Tyr Arg His Trp Gln Ser Asn Arg
        1340                1345                1350

```
Thr Tyr Asp Asn Ala Asn Asn Asp Ala Ile Val Ala Met Ala Ser
    1355                1360                1365

Leu Val Gln Leu Lys Asp Ser Asp Gly Asn Asp Ile Gln Lys Trp
    1370                1375                1380

Met Gly Val Tyr His Asn Tyr Ala Tyr Val Asn Phe Arg Thr Tyr
    1385                1390                1395

Leu Thr Phe Asp Glu Asn Gly Asp Glu Gln Trp Ser Glu Ser Glu
    1400                1405                1410

Pro Tyr Leu Ala Gln Trp Arg Ser Ile Glu Ser Ala Tyr Gln Met
    1415                1420                1425

Cys Glu Ile Gly Met Phe Arg Ser Pro Asp Gly Lys Arg Ile Ile
    1430                1435                1440

Gly Leu Ala Arg Ser Gln Ser His Asn Asn Pro Ala Thr Leu Ile
    1445                1450                1455

Tyr Ser Asp Asp Glu Gly Glu Thr Trp Ser Lys Pro Met Asp Leu
    1460                1465                1470

Pro Gly Ser Leu Ala Gly Glu Arg His Lys Ile Ala Tyr Asp Pro
    1475                1480                1485

Ile Ser Gly Arg Leu Leu Val Thr Phe Arg Glu Ile Asn Tyr Asp
    1490                1495                1500

Leu Asn Gly Asn Asn Arg Phe Asp Gly Gly Asn Asp Trp Asn Ala
    1505                1510                1515

Gly Asp Trp Val Ala Trp Val Gly Thr Tyr Asp Gln Leu Ile Asn
    1520                1525                1530

Gln Glu Asp Gly Glu Tyr Arg Ile Leu Leu Ala Glu Asp Trp Thr
    1535                1540                1545

Ser Asn Ala Lys Ser Gly Asp Thr Gly Tyr Ala Gly Val Ala Val
    1550                1555                1560

Leu Asp Asp Gly Thr Phe Ile Met Asp Thr Tyr Gly His Trp Asp
    1565                1570                1575

Lys Glu Phe Ser Gln Asn Trp Pro Gly Gly Val Thr Thr Asp Arg
    1580                1585                1590

Cys Tyr Ile Lys Gln Ala Lys Phe Lys Leu Gly Glu Val Glu Tyr
    1595                1600                1605

Ala Asn Gly Leu Ile Asp Arg Ser Gly Leu Lys Ala Ala Ile Lys
    1610                1615                1620

Arg Ala Glu Ala Leu Asn Ala Ala Asp Tyr Thr Ala Asp Ser Trp
    1625                1630                1635

Ala Lys Met Asp Ala Ala Val Lys Ala Lys Ala Gly Asp Ala
    1640                1645                1650

Asp Asp Ser Leu Gln Gln Ala Gln Val Asp Ala Leu Ala Ala Ala
    1655                1660                1665

Ile Asp Ala Ala Ile Asp Gly Leu Lys Ala Lys Asp Asp Gly Asp
    1670                1675                1680

Lys Pro Gly Pro Gly Asp Gly Lys Pro Gly Ala Gly Asp Gly
    1685                1690                1695

Lys Pro Asp Asp Gly Gly Lys Pro Asp Pro Gly Lys Pro Gly Lys
    1700                1705                1710

Gly Asp Glu Thr Lys Pro Asp Thr Gly Lys Lys Gly Gly Leu Ser
    1715                1720                1725

Ala Thr Gly Ala Gly Ile Val Pro Ile Ala Ala Ala Leu Thr
    1730                1735                1740

Leu Met Ala Gly Ala Ala Leu Ala Leu Ala Lys Arg
```

<210> SEQ ID NO 112
<211> LENGTH: 1627
<212> TYPE: PRT
<213> ORGANISM: Bifidobacterium bifidum CCOS 571

<400> SEQUENCE: 112

| | | | | | | | | | | | | | | |
|---|---|---|---|---|---|---|---|---|---|---|---|---|---|---|
| Met | Arg | Leu | Arg | Arg | Val | Lys | Ala | Ala | Ile | Gly | Ser | Val | Leu | Ala | Ala |
| 1 | | | | 5 | | | | | 10 | | | | | 15 | |
| Val | Thr | Leu | Leu | Ser | Met | Ser | Leu | Thr | Gly | Val | Thr | Ala | Ala | Gln | Ala |
| | | | 20 | | | | | 25 | | | | | 30 | | |
| Ser | Asp | Asp | Asn | Leu | Ala | Leu | Asn | Gln | Thr | Val | Thr | Ala | Ser | Ser | Tyr |
| | | | 35 | | | | | 40 | | | | | 45 | | |
| Glu | Val | Ala | Thr | Thr | Ala | Pro | Glu | Lys | Ala | Val | Asp | Gly | Asp | Leu | Gly |
| | | | 50 | | | | | 55 | | | | | 60 | | |
| Thr | Arg | Trp | Gly | Thr | Ala | Gln | Asn | Lys | Ala | Ala | Asn | Glu | Trp | Ile | Glu |
| 65 | | | | | 70 | | | | | 75 | | | | | 80 |
| Val | Gly | Leu | Gly | Gly | Thr | Lys | Thr | Val | Lys | Gln | Ile | Asn | Ile | Asp | Phe |
| | | | | 85 | | | | | 90 | | | | | 95 | |
| Glu | Arg | Lys | Asp | Ala | Asp | Gln | Asn | Ile | Thr | Ser | Phe | Lys | Val | Glu | Leu |
| | | | 100 | | | | | 105 | | | | | 110 | | |
| Lys | Gln | Gly | Asp | Thr | Tyr | Thr | Lys | Val | Tyr | Gln | Lys | Asp | Thr | Arg | Ala |
| | | | 115 | | | | | 120 | | | | | 125 | | |
| Lys | Gln | Gln | Glu | Ile | Ile | Leu | Leu | Asp | Gln | Ala | Gln | Gln | Ala | Ser | Ala |
| | | | 130 | | | | | 135 | | | | | 140 | | |
| Val | Lys | Val | Thr | Val | Leu | Ser | Ala | Asp | Gly | Gly | Thr | Met | Asn | Trp | Val |
| 145 | | | | | 150 | | | | | 155 | | | | | 160 |
| Asn | Val | Gly | Ile | Asn | Glu | Ile | Ser | Val | Tyr | Ser | Ala | Pro | Lys | Glu | Thr |
| | | | | 165 | | | | | 170 | | | | | 175 | |
| Val | Leu | Asp | Thr | Ala | Asp | Thr | Asn | His | Met | Leu | Gly | Ala | Thr | Met | Thr |
| | | | 180 | | | | | 185 | | | | | 190 | | |
| Ala | Ser | Ser | Asn | Glu | Thr | Ala | Thr | Leu | Thr | Pro | Asp | Lys | Ala | Ile | Asp |
| | | | 195 | | | | | 200 | | | | | 205 | | |
| Gln | Asn | Arg | Thr | Gly | Arg | Asn | Asn | Arg | Trp | Ala | Ser | Gly | Tyr | Glu | Thr |
| | | | 210 | | | | | 215 | | | | | 220 | | |
| Pro | Ser | Asn | Ile | Trp | Leu | Lys | Ala | Glu | Phe | Pro | Arg | Leu | Thr | Ala | Val |
| 225 | | | | | 230 | | | | | 235 | | | | | 240 |
| Lys | Asp | Ile | Arg | Ile | Tyr | Phe | Phe | Glu | Arg | Asp | Val | Asn | Pro | Lys | Pro |
| | | | | 245 | | | | | 250 | | | | | 255 | |
| Thr | Asn | Val | Gln | Ser | Phe | Asp | Leu | Ser | Tyr | Thr | Asp | Ser | Glu | Gly | Thr |
| | | | 260 | | | | | 265 | | | | | 270 | | |
| Glu | His | Thr | Leu | Lys | Ser | Gly | Tyr | Ala | Met | Thr | Ala | Ser | Gly | Thr | Gly |
| | | | 275 | | | | | 280 | | | | | 285 | | |
| Tyr | Val | Ala | Asp | Val | Val | Ile | Gln | Leu | Asp | Gln | Ala | Val | Asn | Ala | Arg |
| | | | 290 | | | | | 295 | | | | | 300 | | |
| Ser | Leu | Lys | Leu | Ser | Asn | Phe | Ala | Ile | Lys | Ser | Ser | Glu | Tyr | Asn | Asn |
| 305 | | | | | 310 | | | | | 315 | | | | | 320 |
| Val | Ser | Val | Ala | Glu | Trp | Glu | Ala | Tyr | Ser | Asn | Asp | Gln | Ala | Glu | Pro |
| | | | | 325 | | | | | 330 | | | | | 335 | |
| Gly | Ala | Thr | Leu | Asp | Ser | Val | Val | Ser | Asp | Leu | Glu | Ser | Asn | His | Leu |
| | | | 340 | | | | | 345 | | | | | 350 | | |
| Thr | Ile | Glu | Thr | Asp | Thr | Asp | Thr | Leu | Ala | Leu | Pro | Thr | Val | Pro | Asp |
| | | | 355 | | | | | 360 | | | | | 365 | | |

Gly Tyr Thr Val Lys Phe Asn Gly Ala Asp Tyr Glu Gln Leu Ile Ala
    370                 375                 380

Ala Asp Gly Thr Val Asn His Pro Leu Val Asp Lys Thr Val Gln Val
385                 390                 395                 400

Ala Tyr Val Val Thr Asp Thr Ala Thr Gly Asn Thr Lys Thr Thr Ser
                    405                 410                 415

Asp Ile Pro Tyr Val Val Lys Gly Thr Asn Gln Gln Gln Glu Gly Asn
                420                 425                 430

Asn Ala Lys Pro Thr Ile Ile Pro Glu Ile Ala Glu Trp His Ser Thr
            435                 440                 445

Ser Ala Ala Lys Leu Ala Ala Ser Ala Val Thr Lys Val Val Tyr Asp
450                 455                 460

Asp Asp Ser Leu Lys Ala Val Val Asp Glu Phe Val Ala Asp Tyr Lys
465                 470                 475                 480

Asp Phe Thr Gly Ile Lys Leu Thr Ala Lys Lys Gly Ala Ala Glu Ala
                    485                 490                 495

Gly Ala Phe Asn Phe Val Lys Thr Asp Ser Thr Ala Ala Ile Ala Gln
                500                 505                 510

Leu Gly Asp Glu Gly Tyr Thr Met Asp Ile Arg Ala Asp Arg Val Val
            515                 520                 525

Ala Lys Ser Ser Ser Val Thr Gly Asn Met Tyr Ala Met Gln Thr Ile
530                 535                 540

Leu Gln Met Thr Lys Gln Asp Ala Ser Gly Phe Val Ile Gly Ser Met
545                 550                 555                 560

Arg Asp Tyr Pro Arg Phe Thr Thr Arg Gly Leu Leu Leu Asp Val Ala
                    565                 570                 575

Arg Lys Pro Val Ser Leu Glu Met Met Arg Glu Ile Thr Arg Thr Met
                580                 585                 590

Arg Tyr Tyr Lys Met Asn Asp Phe Gln Ala His Leu Ser Asp Asn Tyr
            595                 600                 605

Ile Phe Leu Glu Asn Tyr Gly Lys Gly Asp Asn Glu Asp Glu Ala Phe
    610                 615                 620

Lys Ala Tyr Asp Ala Phe Arg Leu Glu Ser Ser Leu Thr Asn Asp Lys
625                 630                 635                 640

Gly Glu Ser Pro Thr Ala Glu Asp Tyr Ser Ile Ser Lys Lys Thr Phe
                    645                 650                 655

Lys Gln Phe Ile Gln Asp Glu Arg Ala Leu Gly Met Asn Val Val Pro
                660                 665                 670

Glu Ile Asp Val Pro Ala His Ala Asn Ser Phe Thr Lys Ile Trp Pro
            675                 680                 685

Glu Leu Met Val Lys Gly Arg Val Ser Pro Ile Asn Ser Asn Arg Pro
    690                 695                 700

Leu Ile Asp His Leu Asp Val Ser Lys Pro Glu Thr Ile Ala Lys Ile
705                 710                 715                 720

Lys Glu Ile Phe Asp Asp Tyr Thr Lys Gly Asp Asp Pro Thr Phe Asp
                    725                 730                 735

Ser Asp Thr Thr Val His Ile Gly Ala Asp Glu Phe Leu Tyr Asn Tyr
                740                 745                 750

Thr Ala Tyr Arg Lys Phe Ile Asn Glu Ile Val Pro Tyr Ile Lys Asp
            755                 760                 765

Thr Asn Thr Val Arg Met Trp Gly Gly Leu Thr Trp Ile Asn Asp His
    770                 775                 780

```
Lys Thr Glu Ile Thr Lys Asp Ala Ile Glu Asn Val Glu Met Asn Leu
785                 790                 795                 800

Trp Ser Lys Asp Trp Ala Asp Gly Leu Gln Met Tyr Asn Met Gly Tyr
            805                 810                 815

Lys Leu Ile Asn Thr Ile Asp Asp Tyr Gly Tyr Met Val Pro Asn Gly
        820                 825                 830

Ser Tyr Gly Arg Ala Asn Ala Tyr Gly Asp Leu Leu Asn Ile Ser Arg
    835                 840                 845

Val Phe Asp Ser Phe Glu Pro Asn Lys Ile Arg Ser Ser Gly Gly Tyr
850                 855                 860

Gln Ala Val Pro Ser Gly Asp Asp Gln Met Leu Gly Ala Ala Phe Ala
865                 870                 875                 880

Ile Trp Ser Asp Asn Ile Asp Lys Ser Ala Ser Gly Leu Thr Glu Ser
            885                 890                 895

Asp Leu Tyr Trp Arg Phe Phe Asp Ala Met Pro Phe Tyr Ala Glu Lys
        900                 905                 910

Thr Trp Ala Ala Thr Gly Lys Glu Lys Gly Thr Ala Ala Lys Leu Thr
    915                 920                 925

Ala Leu Ala Ala Lys Gln Gly Thr Gly Pro Arg Thr Asn Pro Tyr Tyr
930                 935                 940

Gln Ala Thr Ser Lys Asn Ser Val Tyr Glu Ser Tyr Asp Phe Asn Asp
945                 950                 955                 960

Gly Leu Ala Asp Ala Ser Gly Asn Gly Arg Asp Leu Thr Ile Gly Asp
            965                 970                 975

Gly Ser Lys Ala Ala Val Lys Asp Gln Ser Leu Lys Leu Ala Gly Gly
        980                 985                 990

Ser Ser Tyr Ala Thr Ser Lys Leu Asp Lys Leu Gly Asn Gly Asn Glu
    995                 1000                1005

Leu Thr Phe Asp Val Thr Leu Gln Gln Ala Ala Lys Pro Gly Asp
    1010                1015                1020

Ile Leu Phe Glu Ala Asp Ala Pro Tyr Gly Thr His Asp Ile Arg
    1025                1030                1035

Val Met Glu Asn Gly Lys Leu Gly Phe Thr Arg Glu Leu Tyr Asn
    1040                1045                1050

Tyr Tyr Phe Asp Tyr Glu Leu Pro Val Gly Lys Thr Val Thr Val
    1055                1060                1065

Thr Ile Lys Val Asp Gln Gln Thr Thr Lys Leu Tyr Val Asp Gly
    1070                1075                1080

Glu Phe Val Ser Asp Ala Thr Gly Lys Tyr Ile Asp Lys Gly Ile
    1085                1090                1095

Glu Lys Lys Thr Gly Ile Thr Ala Ala Thr Phe Ala Leu Pro Leu
    1100                1105                1110

Gln Arg Ile Gly Ser Lys Thr Ser Ala Ile Asn Gly Val Ile Asp
    1115                1120                1125

Asn Val Ile Val Lys Lys Ser Glu Ala Glu Thr Asp Gln Tyr Asn
    1130                1135                1140

Lys Ser Cys Trp Thr Gly Thr Thr Asn Ser Glu Thr Gln Tyr Asn
    1145                1150                1155

Asp Thr Glu Gly Leu Leu Arg Tyr Ala Phe Asp Asn Asn Pro Ser
    1160                1165                1170

Thr Ile Trp His Ser Asn Trp Lys Gly Ala Thr Asp Lys Leu Thr
    1175                1180                1185
```

```
Gly Ser Asn Ser Phe Tyr Ala Glu Ile Asp Met Cys Gln Lys Tyr
1190                1195                1200

Thr Ile Asn Gln Phe Ser Phe Thr Pro Arg Thr Ser Gln Asp Ser
1205                1210                1215

Gly Gln Val Thr Lys Ala Asp Leu Tyr Val Lys Ala Asn Ala Asn
1220                1225                1230

Asp Glu Trp Lys Gln Val Ala Thr Asp Gln Val Phe Glu Ala Ser
1235                1240                1245

Arg Ala Lys Lys Thr Phe Met Phe Asp Glu Gln Glu Val Arg Tyr
1250                1255                1260

Val Lys Phe Val Ala Lys Ser Ser Asn Asp Gly Trp Val Ala Val
1265                1270                1275

Ser Glu Phe Gly Val Ala Asn Lys Pro Ser Ser Thr Val Arg Val
1280                1285                1290

Phe Val Ala Ala Asp Pro Ala Glu Gly Gly Thr Val Ser Val Ala
1295                1300                1305

Ala Glu Gly Glu Thr Gly Thr Asp Thr Ala Val Asp Val Ala Ser
1310                1315                1320

Gly Ala Ser Val Thr Ala Lys Ala Val Thr Ala Asp Gly Tyr Arg
1325                1330                1335

Phe Ser Gly Trp Phe Thr Thr Ala Ser Glu Thr Ala Val Ser Thr
1340                1345                1350

Asp Ala Thr Tyr Thr Phe Ala Ala Asp Gly Asn Thr Ala Leu Thr
1355                1360                1365

Ala Lys Phe Thr Lys Asp Ser Thr Pro Asp Pro Gly Pro Lys Pro
1370                1375                1380

Thr Ile Ser Ser Ile Ala Val Thr Lys Pro Thr Val Thr Asp Tyr
1385                1390                1395

Lys Val Gly Asp Thr Phe Asp Ala Thr Gly Leu Ala Val Thr Ala
1400                1405                1410

Thr Met Ser Asp Gly Ser Thr Lys Thr Leu Thr Ala Gly Glu Tyr
1415                1420                1425

Thr Leu Ser Ala Thr Gln Asp Gly Ala Ala Val Ala Leu Asp Lys
1430                1435                1440

Ala Phe Ala Lys Ala Gly Lys Val Thr Val Thr Val Thr Ala Asn
1445                1450                1455

Gly Lys Thr Ala Thr Phe Asp Val Thr Val Thr Ala Lys Asp Pro
1460                1465                1470

Asp Pro Glu Pro Ala Thr Leu Lys Ser Ile Lys Val Thr Ser Lys
1475                1480                1485

Pro Asp Lys Ala Thr Tyr Thr Val Asp Glu Thr Phe Ala Lys Thr
1490                1495                1500

Gly Leu Ala Val Thr Gly Thr Trp Ser Asp Gly Lys Thr Ala Leu
1505                1510                1515

Leu Lys Asp Gly Glu Tyr Lys Leu Ser Ala Val Asp Ala Asp Gly
1520                1525                1530

Lys Thr Val Asp Leu Thr Lys Pro Phe Thr Ala Ala Gly Asp Val
1535                1540                1545

Thr Val Thr Val Thr Ser Gly Lys Leu Thr Asp Ser Phe Thr Ile
1550                1555                1560

Thr Val Lys Ala Lys Thr Val Thr Pro Thr Pro Gly Asp Asn Lys
1565                1570                1575
```

-continued

```
Pro Gly Glu Asn Lys Pro Gly Ala Asp Lys Pro Lys Pro Asn Thr
    1580                1585                1590

Pro Asp Glu Val Ala Lys Thr Gly Ala Ser Val Thr Ala Val Val
    1595                1600                1605

Phe Ser Ala Leu Leu Leu Leu Ser Ala Gly Tyr Leu Leu Val Arg
    1610                1615                1620

Lys Arg Arg Ile
    1625

<210> SEQ ID NO 113
<211> LENGTH: 1960
<212> TYPE: PRT
<213> ORGANISM: Bifidobacterium bifidum CCOS 571

<400> SEQUENCE: 113

Met Arg Ser Lys Ala Leu Gly Gly Leu Ala Ala Ala Leu Ser Leu
1               5                   10                  15

Ser Pro Ala Val Ala Ile Gly Val Gln Thr Ala Tyr Ala Ala Gly
                20                  25                  30

Asp Thr Ala Ala Thr Glu Tyr Thr Leu Tyr Pro Lys Pro His Ser Ile
            35                  40                  45

Arg Tyr Asp Ser Gly Gln Tyr Ile Leu Arg Asp Ile Asn Val Ile Tyr
    50                  55                  60

Asp Asp Asp Ile Asp Glu Ala Thr Gln Asp Arg Leu Asp Glu Val Ala
65                  70                  75                  80

Ala Leu Lys Asn Leu Asn Val Thr Glu Ser Asp Ala Ala Val Ser Gly
                85                  90                  95

Lys Thr Asn Val Tyr Val Gly Val Asn Gly Ser Asp Gly Lys Ala Glu
                100                 105                 110

Thr Ala Ile Glu Ser Lys Tyr Ser Pro Asp Ser Ala Ile Phe Asp Lys
                115                 120                 125

Thr Asp Ser Tyr Phe Leu Lys Ser Asp Asn Gly Thr Ile Ser Val Leu
            130                 135                 140

Gly Lys Asp Thr Asp Ala Ser Phe Tyr Gly Leu Thr Thr Leu Tyr Gln
145                 150                 155                 160

Val Leu Gly Gln Ile Asp Ser Leu Thr Ile Arg Asn Phe Thr Val Thr
                165                 170                 175

Asp Tyr Ala Asp Val Val Ser Arg Gly Phe Ile Glu Tyr Tyr Gly
                180                 185                 190

Asn Pro Trp Ser Thr Gln Asp Arg Ile Asn Leu Met Lys Trp Gly Gly
                195                 200                 205

Tyr Tyr Lys Leu Asn Ser Tyr Phe Tyr Ala Pro Lys Asp Asp Pro Lys
    210                 215                 220

His Asn Ser Gln Trp Arg Thr Leu Tyr Thr Gln Asp Glu Leu Asp Thr
225                 230                 235                 240

Lys Ile Lys Pro Leu Ala Asp Ala Gly Asn Ala Ser Lys Thr Arg Phe
                245                 250                 255

Val Phe Ala Leu His Pro Phe Met Asn Asn Ala Ile Arg Phe Asn Ser
                260                 265                 270

Glu Ala Asn Tyr Gln Ala Asp Leu Lys Val Leu Gln Asp Lys Phe Ala
            275                 280                 285

Gln Thr Ile Gly Val Gly Val Arg Gln Ile Ala Ile Leu Ala Asp Asp
    290                 295                 300

Ala Ala Asn Val Gly Gly Asn Asn Tyr Thr Lys Leu Leu Thr Asp Met
305                 310                 315                 320
```

-continued

Val Ala Trp Leu Lys Glu Met Lys Lys Thr Tyr Pro Asp Leu Lys Thr
                325                 330                 335

Thr Leu Pro Phe Val Thr Gln Glu Tyr Met Gly Asn Gly Met Ser Tyr
            340                 345                 350

Phe Ala Asn Phe Pro Lys Glu Val Gln Ile Val Met Thr Gly Gly Arg
        355                 360                 365

Val Trp Gly Glu Val Ser Gln Asn Phe Thr Asp Thr Phe Thr Ser Asn
    370                 375                 380

Val Gly Arg Gly Pro Tyr Met Trp Ile Asn Trp Pro Cys Ser Asp Asn
385                 390                 395                 400

Ser Lys Ser His Leu Ile Met Gly Gly Tyr Asp Thr Phe Leu His Pro
                405                 410                 415

Gly Val Asp Pro Ser Lys Ile Gln Gly Ile Val Leu Asn Pro Met Gln
            420                 425                 430

Gln Ser Glu Pro Ser Lys Val Gly Ile Phe Gly Asn Ala Thr Tyr Ser
        435                 440                 445

Trp Asn Ile Trp Arg Ser Lys Ser Glu Ala Asp Gln Ala Trp Gln Asp
    450                 455                 460

Ser Phe Ser Phe Val Asp His Asn Ser Ala Val Pro Thr Ala Ala Ser
465                 470                 475                 480

Asn Ala Leu Arg Glu Leu Ser Lys His Thr Ile Asn Gln Asn Met Asp
                485                 490                 495

Ser Arg Val Thr Ala Leu Gln Glu Ser Val Asp Leu Ala Pro Ala Leu
            500                 505                 510

Thr Ala Ala Lys Ala Lys Leu Ala Asp Gly Thr Ile Thr Ala His Asp
        515                 520                 525

Leu Thr Asp Ile Lys Ala Ala Phe Val Thr Leu Gln Lys Ala Ala Lys
    530                 535                 540

Thr Tyr Arg Ala Lys Gly Asp Ala Lys Met Leu Gly Asp Ile Gly Lys
545                 550                 555                 560

Asp Tyr Thr Gly Gln Asp Ala Asn Glu Gln Ile Ala Pro Trp Ile Asp
                565                 570                 575

Cys Trp Asp Asp Thr Thr Lys Ala Ala Leu Ala Tyr Ile Ala Gly Ile
            580                 585                 590

Glu Ala Ala Leu Asn Gly Asp Thr Ser Ser Thr Leu Lys Glu Tyr Ser
        595                 600                 605

Asp Ala Gln Ser Ala Phe Ala Ala Ser Lys Lys His Gly Phe Tyr Tyr
    610                 615                 620

Val Asn His Thr Glu Tyr Ala Glu Val Gly Val Gln His Ile Val Pro
625                 630                 635                 640

Phe Ile Lys Ala Met Asp Ser Tyr Leu Ser Asn Lys Val Gln Gln Glu
                645                 650                 655

Ala Asp Pro Asn Val Val Thr Lys Thr Tyr Ile Ser Asp Val Phe Thr
            660                 665                 670

Thr Pro Thr Ser Gly Ser Ile Glu Asp Ile Phe Asp Gly Lys Asp Ser
        675                 680                 685

Thr Val Thr Val Phe Gln Asn Pro Asn Tyr Leu His Lys Gly Asn Tyr
    690                 695                 700

Val Gly Val Lys Phe Ser Lys Ala Thr Thr Leu Lys Ser Ile Arg Phe
705                 710                 715                 720

Ala Phe Asn Gly Gly Lys Asn His Phe Tyr His Ser Lys Leu Gln Thr
                725                 730                 735

-continued

```
Thr Thr Asp Gly Glu Asn Trp Thr Asp Val Pro Asp Ala Thr Phe Glu
            740                 745                 750
Arg Pro Lys Gly Ser Glu Glu Pro Ile Lys Val Thr Gly Leu Asn Ile
        755                 760                 765
Thr Gly Val Thr Gly Val Arg Leu Ile Ala Thr Ala Asp Asn Gly Asp
    770                 775                 780
Asp Leu Trp Leu Gly Ile Lys Gly Ile Asp Val Asn Lys Val Glu Lys
785                 790                 795                 800
Glu Thr Leu Ala Pro Tyr Thr Ala Thr Gly Val Gln Leu Glu Asn Leu
                805                 810                 815
Asn Ala Thr Tyr Ser Ser Thr Lys Glu Gln Met Ile Asp Gly Asn Pro
            820                 825                 830
Ser Thr Ile Thr Tyr Leu Lys Asp Pro Asn Gly Asp Lys Ile Ala Ala
        835                 840                 845
Gly Ala Ala Val Ile Val Asp Leu Gly Ser Ser Lys Pro Ile Gly Glu
    850                 855                 860
Val Thr Ile Thr Gly His Ala Ser Ser Pro Asp Asp Arg Pro Ser Gln
865                 870                 875                 880
Gly Val Val Glu Val Ser Asp Asp Lys Ala Thr Trp Thr Lys Leu Gly
                885                 890                 895
Asp Leu Arg Asp Asp Val Thr Ser Thr Val Ser Gly Asn Val Thr Gly
            900                 905                 910
Arg Tyr Val Arg Ile Arg Asn Thr Ala Ala Lys Asn Val Trp Trp Arg
        915                 920                 925
Val Ala Glu Ile Thr Val Thr Pro Pro Glu Thr Ala Asp Pro Leu Lys
    930                 935                 940
Ser Val Tyr Thr Asn Lys Thr Gln His Gly Tyr Thr Ala Thr Leu Gly
945                 950                 955                 960
Ala Asn Thr Ala Glu Leu Phe Asp Lys Ser His Thr Met Leu Asp Gly
                965                 970                 975
Gly Gln Tyr Ala Gly Leu Asp Leu Leu Ala Ile Arg Asp Leu Thr Asp
            980                 985                 990
Val Glu Leu Asn Thr Gly Asn Ala Asn Pro Ser Leu Gln Ile Ser Asp
        995                 1000                1005
Asn Gly Leu Val Trp Thr Thr Val Glu Pro Gly Asn Leu Thr Gly
    1010                1015                1020
Lys Thr Ala Arg Tyr Val Arg Val Ile Asn Gly Thr Asp Gly Ala
    1025                1030                1035
Ala Phe Ser Val Asn Lys Leu Lys Val Gly Phe Ser Thr Val Gly
    1040                1045                1050
Lys Phe Gly Lys Leu Val Ser Ser Asp Ile Gln Lys Arg Asn Asp
    1055                1060                1065
Trp Gly Thr Asp Thr Arg Glu Ser Gly Asn Ala Phe Asp Gly Asp
    1070                1075                1080
Met Thr Thr Val Ile Lys Phe Ala Gly Gln Pro Arg Gln Gly Asn
    1085                1090                1095
Thr Ala Val Phe Asp Leu Gly Gln Pro Ile Asp Ile Thr Ser Leu
    1100                1105                1110
Arg Ile Tyr Thr Gln Asp Thr Gln Tyr Asp Tyr Ile Arg Asp Thr
    1115                1120                1125
Lys Val Gln Met Ser Val Asp Gly Lys Thr Trp Val Asp Ala Phe
    1130                1135                1140
```

Glu Ile Gly Asp Gly Val Ser Asp Thr Asp Thr Thr Ala Phe
1145                1150                1155

Gly Asp Ile Ser Asp Thr Asn Lys Lys Thr Asp Ser Asn Tyr Pro
1160                1165                1170

Asn Val Phe Tyr Tyr Gly Lys Asp Asp Ile Ala Asn Gly Thr Gly
1175                1180                1185

Met Arg Tyr Leu Arg Leu Leu Thr Thr Ala Asp Tyr Pro Gln Arg
1190                1195                1200

Ala Leu Ala Phe Asn Glu Phe Met Val Asn Gln Gly Ala Tyr Val
1205                1210                1215

Ser Thr Glu Ala Asn Ala Ala Phe Ser Ala Thr Lys Val Glu Glu
1220                1225                1230

Arg Gly His Ala Pro Ser Asn Met Ile Asp Gly Asp Leu Thr Thr
1235                1240                1245

Thr Tyr Lys Pro Ser Ala Ala Asn Gly Ser Leu Thr Tyr Lys Ile
1250                1255                1260

Asp Asp Pro Ser Asp Ile Lys Ser Phe Arg Ile Val Gln Ser Gly
1265                1270                1275

Ala Ala Ser Gly Ala Thr Val Thr Gly Thr Val Tyr Asp Ala Ala
1280                1285                1290

Thr Gly Thr Thr Ala Gly Val Thr Ala Arg Ala Ala Arg Ser
1295                1300                1305

Ala Ser Glu Val Thr Phe Gly Thr Leu Glu Gln Ala Ile Asn Glu
1310                1315                1320

Phe Lys Val Pro Asp Gly Lys Gln Leu Leu Ser Val Lys Ile Ala
1325                1330                1335

Trp Gly Asn Ala Ile Pro Glu Ile Ser Glu Phe Ile Thr Leu Asp
1340                1345                1350

Ser Ala Asp Thr Asp Ala Asp Ile Thr Thr Ala Lys Ala Ala Leu
1355                1360                1365

Lys Glu Lys Ile Asp Ala Thr Val Asp Thr Ser Ala Trp Thr Ala
1370                1375                1380

Asn Ala Lys Thr Ala Tyr Asp Glu Ala Lys Ala Thr Ala Gln Ala
1385                1390                1395

Val Tyr Gly Ser Pro Leu Val Gly Lys Ala Ser Ile Asp Ala Ala
1400                1405                1410

Ala Ser Ala Val Gln Ser Ala Ile Asp Ala Ala Gln Thr Lys Ala
1415                1420                1425

Asp Ala Ala Ala Val Ala Ala Leu Arg Lys Leu Val Asp Ala Ala
1430                1435                1440

Val Thr Asn Asp Gly His Phe Tyr Thr Thr Val Thr Phe Thr Ala
1445                1450                1455

Tyr Thr Asp Ala Leu Asp Glu Val Lys Glu Ala Leu Lys Asp Thr
1460                1465                1470

Asn Asn Leu Ser Thr Ala Asp Ala Ala Ser Leu Lys Lys Ala Val
1475                1480                1485

Asp Asp Ala Leu Ala Ala Leu Lys Asp Ser Thr Tyr Gln Arg Glu
1490                1495                1500

Leu Ala Thr Ile Ala Val Asp Ser Phe Ala Thr Ile Asp Glu Ala
1505                1510                1515

Asp Tyr Thr Thr Asn Ser Tyr Ala Ala Phe Lys Ala Ala Lys Glu
1520                1525                1530

```
Ala Leu Asp Thr Leu Ile Ala Ala Asp Gly Thr Lys Pro Ala Thr
1535                1540                1545

Phe Lys Thr Lys Thr Ala Glu Tyr Thr Thr Ala Lys Thr Ala Leu
1550                1555                1560

Val Asn Val Ala Ala Leu Lys Ala Gln Ile Ala His Glu Ser Asn
1565                1570                1575

Tyr Val Glu Ala Asn Tyr Thr Ala Asp Ser Trp Lys Ala Tyr Ser
1580                1585                1590

Asp Ala Leu Lys Ala Ala Lys Ala Glu Leu Val Asn Gly Thr Thr
1595                1600                1605

Asp Ser Val Ala Ala Ala Leu Thr Ala Leu Thr Thr Ala Glu Asn
1610                1615                1620

Ala Leu Val Arg Thr Thr Thr Pro Pro Asp Thr Thr Val Leu Asp
1625                1630                1635

Glu Thr Ile Ala Asp Met Glu Lys Val Asn Gly Ser Glu Tyr Thr
1640                1645                1650

Thr Asp Ser Tyr Lys Ala Leu Thr Asp Ala Ile Ala Lys Ala Lys
1655                1660                1665

Ser Asp Lys Ala Lys Gly Asp Ala Gly Leu Asn Gln Gln Asn Ile
1670                1675                1680

Asp Ala Met Lys Ala Ala Lys Glu Ala Leu Val Ser Thr Val Glu
1685                1690                1695

Leu Lys Ala Lys Val Ala Glu Ala Gly Lys Val Asp Ser Ser Lys
1700                1705                1710

Tyr Thr Thr Ala Ser Tyr Glu Ala Leu Ser Lys Leu Leu Ala Ala
1715                1720                1725

Lys Asp Asp Thr Thr Ser Asp Pro Val Val Lys Gly Leu Asp Thr
1730                1735                1740

Leu Tyr Lys Ser Gly Thr Val Lys Glu Leu Ala Glu Arg Val Ala
1745                1750                1755

Ala Ile Asp Ala Ala Val Ala Lys Leu Asp Ala Arg Ala Thr Gly
1760                1765                1770

Val Lys Asp Tyr Val Asp Gly Ile Lys Leu Lys Asp Asn Asp Lys
1775                1780                1785

Gly Tyr Tyr Thr Asp Ala Ser Tyr Lys Ala Tyr Ser Asp Ala Tyr
1790                1795                1800

Lys Ala Leu Lys Lys Leu Ala Ala Ala Gly Glu Gly Glu Val Gly
1805                1810                1815

Ile Ala Glu Phe Thr Glu Ala Lys Glu Ala Phe Glu Ala Ala Glu
1820                1825                1830

Ala Lys Leu Ala Tyr Lys Ser Ala Asp Tyr Gly Lys Ile Asp Asp
1835                1840                1845

Leu Leu Ala Lys Val Pro Ser Asp Leu Ser Gly Tyr Thr Ala Asp
1850                1855                1860

Ser Val Ala Lys Phe Glu Ala Ala Lys Lys Ala Val Lys Arg Gly
1865                1870                1875

Leu Thr Ile Asp Gln Gln Ser Lys Val Asp Ala Met Ala Asp Ala
1880                1885                1890

Leu Glu Ala Ala Ile Lys Gly Leu Thr Leu Lys Ser Gln Ala Pro
1895                1900                1905

Gly Gly Asn Lys Gly Asp Gly Thr Gln Ser Gly Thr His Lys Gly
1910                1915                1920
```

```
Asp Asp Ile Ser Lys Thr Gly Ala Asp Val Gln Val Phe Ala Ile
    1925                1930                1935

Ile Ile Ala Leu Ala Thr Cys Ala Gly Leu Gly Ala Val Ala Tyr
    1940                1945                1950

Ala Arg Arg Arg Arg Glu Ala
    1955                1960

<210> SEQ ID NO 114
<211> LENGTH: 1923
<212> TYPE: PRT
<213> ORGANISM: Bifidobacterium bifidum CCOS 571

<400> SEQUENCE: 114

Met Ala Thr Leu Met Cys Gly Leu Ile Thr Ser Gly Arg Leu Ala Arg
1               5                   10                  15

Ala Val Glu Pro Ala Ile Ala Gly Val Thr Ala Ser Gly Ala Ala Ala
            20                  25                  30

Asp Gly His Ala Ala Ala Ala Val Asp Gly Asp Pro Ala Thr Tyr
        35                  40                  45

Trp Gln Ser Pro Ala Asp Ser Ser Met Gln Asp Tyr Arg Arg Phe Leu
    50                  55                  60

Asp Phe Asp Leu His Gly Thr Tyr Ser Ile Ser Gln Ile Asp Ile Thr
65                  70                  75                  80

Asn Leu Ala Gly Ser Tyr Tyr His Tyr Glu Val Tyr Leu Ser Lys Asp
                85                  90                  95

Gly Ala Asp Tyr Gly Lys Val Ala Tyr Lys Ser Asp Ala Pro Ala
            100                 105                 110

Thr Gly Ala Ala Asp Thr His Pro Ile Asp Ala Thr Glu Ala Ala Tyr
        115                 120                 125

Ala Arg Ile Ser Val Ser Tyr Asn Ser Ala Ala Gln Gln Val Asn Leu
    130                 135                 140

Ala Glu Val Ala Phe His Gly Thr Lys Val Ser Asp Glu Gln Ala Ser
145                 150                 155                 160

Pro Lys Ala Ile Ser Val Thr Asp Phe Asp Ser Ser Trp Gly Arg
            165                 170                 175

Glu Trp Ala Arg Val Glu Thr Asp Ala Asp Tyr Ala Ala Glu Lys Thr
            180                 185                 190

Val Thr Glu Val Arg Asn Leu Val Gly Arg Val Ile Gly Glu Arg Trp
        195                 200                 205

Val Asp Lys Phe Asp Phe Gln Leu Arg Gly Lys Ala Asp Gly Lys Asp
    210                 215                 220

Val Phe Glu Ile Ser Asp Ala Gly Asp Asp Arg Ile Ser Ile Arg Gly
225                 230                 235                 240

Asn Asn Gly Val Ser Leu Ala Ser Gly Leu Asn Tyr Tyr Leu Arg His
                245                 250                 255

Trp Cys Lys Val Asp Tyr Asn Pro Leu Phe Gly Ser Gln Leu Ser Met
            260                 265                 270

Pro Glu Ser Leu Pro Ala Val Gly Arg Lys Ile Leu Lys Tyr Thr Asn
        275                 280                 285

Tyr Glu Tyr Arg Tyr Ala Leu Asn Phe Cys Thr Tyr Ser Tyr Thr Met
    290                 295                 300

Ala Phe Trp Asn Trp Asp Asp Tyr Glu Pro Phe Leu Asp Trp Ala Ala
305                 310                 315                 320

Met Asn Gly Val Asn Leu Met Leu Asp Ile Val Gly Gln Glu Glu Val
                325                 330                 335
```

```
Leu Arg Glu Thr Leu Thr Gln Tyr Gly Tyr Ser Asp Asp Glu Val Arg
                340                 345                 350

Glu Tyr Leu Ser Gly Pro Gly Tyr Tyr Ala Trp Phe Tyr Met Gln Asn
            355                 360                 365

Leu Tyr Ser Val Gly Gly Pro Leu Pro Ala Ala Trp Phe Glu Gln Arg
        370                 375                 380

Val Glu Leu Gly Arg Arg Ile His Asp Arg Met Gln Ala Tyr Gly Ile
385                 390                 395                 400

Thr Pro Val Ile Gln Gly Phe Gly Gly Gln Val Pro Val Asp Phe Gln
                405                 410                 415

Glu Lys Asn Pro Thr Ser Val Ala Ala Ser Ser Gly Thr Trp Ser Gly
            420                 425                 430

Phe Asp Arg Pro Tyr Met Ile Lys Thr Tyr Leu Thr Asp Ala Asp Lys
        435                 440                 445

Ala Ala Gly Lys Glu Asp Tyr Phe Gln Lys Val Gly Asp Thr Phe Tyr
    450                 455                 460

Lys Ala Gln Glu Asn Val Phe Gly Lys Val Ser Asn Tyr Tyr Ala Val
465                 470                 475                 480

Asp Pro Phe His Glu Gly Gly Thr Ile Pro Asp Gly Phe Asp Ile Val
                485                 490                 495

Asp Ile Tyr Arg Thr Val Gln Arg Lys Met Leu Asp His Asp Pro Ala
            500                 505                 510

Ala Val Trp Val Met Gln Gln Trp Gln Trp Gly Ile Asp Glu Thr Lys
        515                 520                 525

Leu Ser Gly Leu Ala Asp Lys Gly Gln Ala Leu Val Leu Asp Leu Gln
    530                 535                 540

Ser Asp Leu Arg Ser Gln Ala Ser Pro Met Glu Asn Gln Gly Val Pro
545                 550                 555                 560

Trp Val Trp Asn Met Leu His Asn Phe Gly Gly Arg Met Gly Leu Asp
                565                 570                 575

Gly Val Pro Glu Val Ile Ser Gln Asp Ile Thr Lys Ala Tyr Asn Ser
            580                 585                 590

Ser Gly Tyr Met Arg Gly Ile Gly Ile Thr Pro Glu Ala Ile Asp Asn
        595                 600                 605

Ser Pro Ile Val Tyr Glu Leu Leu Phe Asp Met Thr Trp Glu Gln Asp
    610                 615                 620

Pro Val Asp Tyr Arg Ser Trp Thr Gln Glu Tyr Ala Glu Arg Arg Tyr
625                 630                 635                 640

Gly Gly Thr Asp Gly Thr Ile Glu Lys Ala Trp Asp Ile Leu Leu Asp
                645                 650                 655

Thr Ala Tyr Lys His Thr Asp Gly Glu Tyr Tyr Gln Gly Ala Gly Glu
            660                 665                 670

Ser Ile Ile Asn Ala Arg Pro Ser Asp Asn Thr Ile Gly Ser Ala Ser
        675                 680                 685

Thr Trp Gly His Ser Asp Ile Asp Tyr Asp Lys Arg Gln Phe Glu Lys
    690                 695                 700

Ala Ala Ala Leu Phe Glu Gln Ala Tyr Asp Ser Tyr Lys Asp Ser Ala
705                 710                 715                 720

Gly Phe Arg Tyr Asp Tyr Val Asp Val Met Arg Gln Val Leu Ala Asn
                725                 730                 735

Ser Phe Gln Glu Tyr Gln Pro Leu Ala Gly Gln Ala Tyr Lys Ser Gly
            740                 745                 750
```

```
Asp Leu Glu Thr Phe Arg Thr Leu Ser Ser Arg Met Leu Asp Ile Ile
            755                 760                 765

Lys Ala Gln Asp Lys Leu Leu Ser Ser Ser Asp Phe Leu Val Gly
770                 775                 780

Ala Trp Ile Asp Asp Ala Arg Thr Met Leu Asp Gly Ala Asp Trp
785                 790                 795                 800

Thr Ala Asp Leu Phe Glu Leu Asn Ala Arg Ala Leu Val Thr Thr Trp
                    805                 810                 815

Gly Leu Asn Lys Asn Gly Ser Leu Ile Asp Tyr Ser Asn Arg Gln Trp
            820                 825                 830

Ala Gly Leu Thr Gly Asp Tyr Tyr Arg Arg Trp Lys Thr Tyr Val
            835                 840                 845

Asp Asn Arg Leu Asn Lys Leu Glu His Gly Thr Asp Phe Thr Asp Pro
            850                 855                 860

Asp Trp Phe Asp Tyr Gly Trp Gln Trp Ala Asn Arg Lys Ser Asp Glu
865                 870                 875                 880

Asp Gly Tyr Gly Phe Ala Thr Glu Ala Ala Asp Val Asp Gln Lys
                    885                 890                 895

Ala Leu Gly Lys Ile Ile Leu Asp Gln Tyr Ser Val Thr Ala Met Asp
                    900                 905                 910

Asp Val Thr Asp Gly Gly Thr Ala Val Glu Arg Thr Asn Leu Ala Leu
            915                 920                 925

Gly His Asp Val Thr Asp Glu Asp Thr Gly Thr Val Val Pro Asp Val
            930                 935                 940

Thr Asp Gly Asn Thr Asp Thr Gly Trp Thr Gln Thr Gly Lys Thr Asp
945                 950                 955                 960

Ala Thr Leu Val Val Asp Leu Asp Gly Thr Tyr Ser Ile Thr Gly Ala
                    965                 970                 975

Gly Ile Thr Leu Gln Gln Ile Ala Ala Asp Phe Pro Leu Arg Tyr Glu
            980                 985                 990

Ile Asp Val Trp Asn Gly Ser Gly  Trp Val Glu Ile Gly  Arg Ser Glu
            995                 1000                1005

Ala Asp  Ala Val Ser Ser Lys  Asn Glu Val Ala Ala  Asp Ile Leu
1010                1015                1020

Gly Ser  Lys Val Arg Trp Lys  Leu His Ser Thr Asn  Gly Arg Asp
1025                1030                1035

Leu Thr  Gly Ile Tyr Glu Leu  Ser Val Trp Gly Ala  Ala Gln Pro
1040                1045                1050

Gln Pro  Glu Tyr Thr Asn Leu  Ala Leu Gly Gly Ala  Ala Ser Ala
1055                1060                1065

Gly Pro  Ser Glu Arg Pro Ala  Ser Asn Gly Asn Asp  Gly Asp Asp
1070                1075                1080

Gly Thr  Leu Trp Val Gly Asn  Gly Ser Asp Pro Asn  Trp Tyr Arg
1085                1090                1095

Ile Asp  Leu Ala Ser Ala Gln  Arg Val Asp Arg Val  Arg Leu Val
1100                1105                1110

Phe Glu  Thr Ala Gly Arg Leu  Phe Gln Phe Arg Val  Val Ala Gly
1115                1120                1125

Leu Ala  Asp Gly Thr Glu Arg  Thr Leu Ile Asp Glu  Thr Gln Asn
1130                1135                1140

Gln Gly  Ala Leu Asp Gln Val  Tyr Ala Ala Asn Leu  Gly Glu Glu
1145                1150                1155
```

```
Val Glu His Val Thr Val Glu Phe Thr Gly Ser Val Gly Gly Thr
1160                1165                1170

Ala Trp Pro Ala Leu Ala Glu Leu Glu Leu Leu Gln Glu Ala Gly
1175                1180                1185

Asp Thr Ile Glu Gly Val Asn Ile Ala Thr Ser Ala Ala Ile Thr
1190                1195                1200

Ser Ser Pro Thr Lys Asp Ala Pro Glu Asn Ala Gly Ala Leu Val
1205                1210                1215

Asp Gly Lys Ala Thr Ala Trp Val Ser Arg Asp Gly Ala Thr Pro
1220                1225                1230

Ala Trp Phe Gln Leu Asp Tyr Ala Lys Ala Arg Glu Val Asp Ser
1235                1240                1245

Ile Arg Leu Lys Phe Glu Glu Gly Gln Pro Asp Arg Ser Met Gln
1250                1255                1260

Phe Thr Leu Lys Val Ile Asp Ala Asn Gly Asp Glu His Thr Val
1265                1270                1275

Ala Glu Arg Thr Glu Ala Asp Leu Ser Lys Gln Gln Gly Ile Val
1280                1285                1290

Met Asp Val Pro Val Gly Met Ser Ile Thr Arg Ile Arg Met Asp
1295                1300                1305

Ile Ala Asp Ala Arg Ile Pro Ser Ser Gly Ser Pro Ala Trp Pro
1310                1315                1320

Leu Val Ser Glu Ile Glu Val Tyr Ala Thr Pro Gly Asn Val Ala
1325                1330                1335

Arg Asp Ala Lys Thr Thr Ala Ser Asp Gly Ser Thr Leu Thr Ala
1340                1345                1350

Ala Asp Leu Ala Lys Leu Thr Asp Gly Asp Arg Asp Ser Ala Ala
1355                1360                1365

Thr Leu Thr Ala Thr Ala Asp Lys Thr Leu Thr Phe Thr Leu Ala
1370                1375                1380

Lys Ala Ala Asp Ile Asn Met Leu Gly Leu Leu Ala Ser Gly Asn
1385                1390                1395

Ser Glu Pro Val Arg Phe Lys Ala Glu Tyr Arg Val Val Pro Gln
1400                1405                1410

Asp Gly Gly Gly Ala Gly Asp Gly Ala Ala Asp Gln Trp Lys Thr
1415                1420                1425

Leu Thr Asp Tyr Ser Gly Asn Ala Gln Met Lys Pro Glu Ile Val
1430                1435                1440

Ala Arg Leu Ala Arg Pro Val Tyr Thr Asp Ala Val Arg Ile Thr
1445                1450                1455

Val Leu Asn Glu Asn Pro Val Ala Ile Asn Glu Leu Tyr Leu Tyr
1460                1465                1470

Gln Ala Asp Ala Gly Ala Ser Leu Glu Ser Tyr Leu Ser Ser Val
1475                1480                1485

Glu Thr Val Leu Gly Lys Leu Thr Val Gly Glu Tyr Ala Gly Asn
1490                1495                1500

Val Thr Arg Ala Ala Lys Thr Lys Leu Glu Val Val Leu Glu Arg
1505                1510                1515

Ala Arg Ala Ala Leu Asp Ala Gly Leu Thr Ser Arg Glu Ala Gly
1520                1525                1530

Arg Trp Thr Thr Thr Val Glu Asp Ala Val Ser Glu Phe Tyr Arg
1535                1540                1545
```

-continued

```
Thr Gly Tyr Val Ser Leu Asp Arg Asn Ala Leu Tyr Val Ala Ile
1550                1555                1560

Asp Asp Ala Ala Ala Leu Ile Ala Ser Leu Asp Ala His Gly Leu
1565                1570                1575

Pro Ala Ser Ser Ala Ala Leu Ala Glu Ala Arg Ala Ser Ala Lys
1580                1585                1590

Gln Val Ser Asp Ala Tyr Gly Thr Val Thr Gln Gln Asp Leu Asp
1595                1600                1605

Asp Ala Ala Ala Leu Arg Arg Ser Ala Asp Thr Ala Leu Ala
1610                1615                1620

Gln Leu Asp Ala Gln Glu Arg Tyr Gln Val Val Leu Asp Ala Ala
1625                1630                1635

Val Lys Thr Leu Glu Asp Ala Gln Thr Ala Gly Ser Val Gly Glu
1640                1645                1650

Tyr Glu Gly Gln His Pro Gln Ser Ala Ala Asp Ala Leu Arg Gln
1655                1660                1665

Ala Ile Asp Asp Ala Lys Ala Ala His Gly Ala Ala Ala Gly Asp
1670                1675                1680

Ala Asp Lys Val Asp Ala Ala Ala Asp Ala Leu Arg Gln Ala Thr
1685                1690                1695

Thr Ala Phe Asn Glu Ser Ile Val His Ile Asp Ala Ala Ala Leu
1700                1705                1710

Asp Ala Ala Lys Arg Ala Ala Thr Gly Leu Val Glu Ser Gln Tyr
1715                1720                1725

Asp Arg Ala Ala Trp Ala Thr Met Arg Glu Ala Leu Ala Ala Ala
1730                1735                1740

Gly Asp Thr Asp Met Ala His Ile Ser Gln Ala Asp Val Asp Thr
1745                1750                1755

Leu Ala Ala Arg Leu Asn Asp Ala Ile Ala Ala Leu Ser Asp Ala
1760                1765                1770

Arg Leu Asp Arg Gly Pro Leu Ser Asp Ala Ile Ala Ser Ala Gln
1775                1780                1785

Ala Leu Lys Glu Gly Asp Tyr Thr Ala Glu Ser Trp Lys Ala Phe
1790                1795                1800

Ala Glu Ala Leu Ala Ala Ala Gln Glu Glu Cys Gly Arg Arg Ser
1805                1810                1815

Thr Thr Gln Gly Asp Leu Asp Lys Ala Val Lys Ala Leu Thr Gln
1820                1825                1830

Ala Arg Asp Gly Leu Glu Arg Lys Gln Pro Gly Gly Gly Glu Glu
1835                1840                1845

Pro Gly Gly Gly Glu Asp Pro Glu Gln Pro Gly Ser Gly Gly Gln
1850                1855                1860

Thr Glu Arg Pro Gly Gly Val Lys Pro Gly Ala Gly Gly Asn Ala
1865                1870                1875

Asp Thr Ser Lys Pro Gly Thr Ala Gly Thr Glu Thr Leu Ser Lys
1880                1885                1890

Thr Gly Ala Gln Thr Leu Leu Leu Ala Val Thr Ala Cys Ile Met
1895                1900                1905

Leu Ala Ala Gly Phe Ser Ile Thr Thr Ala Arg Ser Arg Arg Arg
1910                1915                1920
```

```
<210> SEQ ID NO 115
<211> LENGTH: 1112
<212> TYPE: PRT
<213> ORGANISM: Bifidobacterium bifidum CCOS 571

<400> SEQUENCE: 115

Met Glu Lys Ser Ser Asn Arg Arg Phe Gly Val Arg Thr Val Ala Ala
1               5                   10                  15

Ile Val Ala Gly Leu Met Val Gly Gly Met Cys Thr Ala Met Thr Ala
            20                  25                  30

Ser Ala Ala Asp Asp Ser Ala Ala Gly Tyr Ser Ala Thr Ala Pro Val
        35                  40                  45

Asn Leu Thr Arg Pro Ala Thr Val Pro Ser Met Asp Gly Trp Thr Asp
    50                  55                  60

Gly Thr Gly Ala Trp Thr Leu Gly Glu Gly Thr Arg Val Val Ser Ser
65                  70                  75                  80

Asp Ala Leu Ala Ala Arg Ala Gln Ser Leu Ala Ser Glu Leu Thr Lys
                85                  90                  95

Phe Thr Asp Val Asp Ile Lys Ala Ala Thr Gly Ser Ala Thr Gly Lys
            100                 105                 110

Asp Ile Ser Leu Thr Leu Asp Ala Ser Lys Lys Ala Glu Leu Gly Asp
        115                 120                 125

Glu Gly Phe Lys Leu Ser Ile Gly Ser Lys Gly Leu Glu Val Ile Gly
    130                 135                 140

Ala Thr Asp Ile Gly Val Phe Tyr Gly Thr Arg Ser Val Ser Gln Met
145                 150                 155                 160

Leu Arg Gln Gly Gln Leu Thr Leu Pro Ala Gly Thr Val Ala Thr Lys
                165                 170                 175

Pro Lys Tyr Lys Glu Arg Gly Ala Thr Leu Cys Ala Cys Gln Ile Asn
            180                 185                 190

Ile Ser Thr Asp Trp Ile Asp Arg Phe Leu Ser Asp Met Ala Asp Leu
        195                 200                 205

Arg Leu Asn Tyr Val Leu Leu Glu Met Lys Leu Lys Pro Glu Glu Asp
    210                 215                 220

Asn Thr Lys Lys Ala Ala Thr Trp Ser Tyr Tyr Thr Arg Asp Asp Val
225                 230                 235                 240

Lys Lys Phe Val Lys Lys Ala Asn Asn Tyr Gly Ile Asp Val Ile Pro
                245                 250                 255

Glu Ile Asn Ser Pro Gly His Met Asn Val Trp Leu Glu Asn Tyr Pro
            260                 265                 270

Glu Tyr Gln Leu Ala Asp Asn Ser Gly Arg Lys Asp Pro Asn Lys Leu
        275                 280                 285

Asp Ile Ser Asn Pro Glu Ala Val Lys Phe Tyr Lys Thr Leu Ile Asp
    290                 295                 300

Glu Tyr Asp Gly Val Phe Thr Thr Lys Tyr Trp His Met Gly Ala Asp
305                 310                 315                 320

Glu Tyr Met Ile Gly Thr Ser Phe Asp Asn Tyr Ser Lys Leu Lys Thr
                325                 330                 335

Phe Ala Glu Lys Gln Tyr Gly Ala Gly Ala Thr Pro Asn Asp Ala Phe
            340                 345                 350

Thr Gly Phe Ile Asn Asp Ile Asp Lys Tyr Val Lys Ala Lys Gly Lys
        355                 360                 365

Gln Leu Arg Ile Trp Asn Asp Gly Ile Val Asn Thr Lys Asn Val Ser
    370                 375                 380
```

Leu Asn Lys Asp Ile Val Ile Glu Tyr Trp Tyr Gly Ala Gly Arg Lys
385                 390                 395                 400

Pro Gln Glu Leu Val Gln Asp Gly Tyr Thr Leu Met Asn Ala Thr Gln
            405                 410                 415

Ala Leu Tyr Trp Ser Arg Ser Ala Gln Val Tyr Lys Val Asn Ala Ala
            420                 425                 430

Arg Leu Tyr Asn Asn Asn Trp Asn Val Gly Thr Phe Asp Gly Gly Arg
            435                 440                 445

Gln Ile Asp Lys Asn Tyr Asp Lys Leu Thr Gly Ala Lys Val Ser Ile
            450                 455                 460

Trp Pro Asp Ser Ser Ile Tyr Gln Thr Glu Asn Glu Val Glu Lys Glu
465                 470                 475                 480

Ile Phe Asp Gly Met Arg Phe Ile Ser Gln Met Thr Trp Ser Asp Ser
            485                 490                 495

Arg Pro Trp Ala Thr Trp Asn Asp Met Lys Ala Asp Ile Asp Lys Ile
            500                 505                 510

Gly Tyr Pro Leu Asp Ile Arg Glu Tyr Asp Tyr Thr Pro Val Asp Ala
            515                 520                 525

Gly Ile Tyr Asp Ile Pro Gln Leu Lys Ser Ile Ser Lys Gly Pro Trp
            530                 535                 540

Glu Leu Ile Thr Thr Pro Asp Gly Tyr Tyr Gln Met Lys Asp Thr Val
545                 550                 555                 560

Ser Gly Lys Cys Leu Ala Leu Phe Thr Gly Ser Lys His Leu Asp Val
            565                 570                 575

Val Thr Gln Val Gly Ala Thr Pro Glu Leu Arg Asn Cys Ala Asp Val
            580                 585                 590

Ser Val Gly Gln Asp Gln Arg Asp Thr Ala Asn Glu Arg Asn Thr Gln
            595                 600                 605

Lys Trp Gln Ile Arg Ala Asp Lys Asp Gly Lys Tyr Thr Ile Ser Pro
            610                 615                 620

Ala Leu Thr Gln Gln Arg Leu Ala Ile Ala Thr Gly Asn Glu Gln Asn
625                 630                 635                 640

Ile Asp Leu Glu Thr His Arg Pro Ala Gly Thr Val Ala Gln Phe
            645                 650                 655

Pro Ala Asp Leu Val Ser Asp Asn Ala Leu Phe Thr Leu Thr Gly His
            660                 665                 670

Met Gly Met Ser Ala Thr Val Asp Ser Lys Thr Val Asn Pro Ala Ser
            675                 680                 685

Pro Ser Lys Ile Thr Val Lys Val Arg Ala Ala Ser Asn Ala Asn Thr
            690                 695                 700

Gly Asp Val Thr Val Thr Pro Val Val Pro Glu Gly Trp Glu Ile Lys
705                 710                 715                 720

Pro Gly Ser Val Ser Leu Lys Ser Ile Pro Ala Gly Lys Ala Ala Ile
            725                 730                 735

Ala Tyr Phe Asn Val Val Asn Thr Thr Gly Thr Gly Asp Ala Thr Val
            740                 745                 750

Gln Phe Lys Leu Thr Asn Thr Lys Thr Gly Glu Glu Leu Gly Thr Thr
            755                 760                 765

Ser Val Ala Leu Thr Gly Ser Leu Thr Lys Asp Val Glu Ala Ser Asp
            770                 775                 780

Tyr Ala Ala Ser Ser Gln Glu Thr Thr Gly Glu His Ala Pro Val Gly
785                 790                 795                 800

Asn Ala Phe Asp Lys Asn Ala Asn Thr Phe Trp His Ser Lys Tyr Ser
                805                 810                 815

Asn Pro Ser Ala Asn Leu Pro His Trp Leu Ala Phe Lys Ala Ser Pro
            820                 825                 830

Gly Glu Gly Asn Lys Ile Ala Ala Ile Thr His Leu Tyr Arg Gln Asp
        835                 840                 845

Lys Leu Asn Gly Pro Ala Lys Asn Val Ala Val Tyr Val Val Ala Ala
850                 855                 860

Ser Asp Ala Asn Ser Val Ala Asp Val Thr Asn Trp Gly Glu Pro Val
865                 870                 875                 880

Ala Thr Ala Glu Phe Pro Tyr Thr Lys Glu Leu Gln Thr Ile Ala Leu
                885                 890                 895

Pro Asn Thr Ile Pro Ser Gly Asp Val Tyr Val Lys Phe Gln Ile Asn
            900                 905                 910

Asp Ala Trp Gly Leu Thr Glu Thr Ser Ala Gly Val Thr Trp Ala Ala
        915                 920                 925

Val Ala Glu Leu Ala Ala Thr Lys Ala Thr Pro Val Glu Leu Thr
930                 935                 940

Glu Pro Glu Gln Pro Lys Asp Asn Pro Glu Val Thr Glu Thr Pro Glu
945                 950                 955                 960

Ala Thr Gly Val Thr Val Ser Gly Asp Gly Val Ala Asn Gly Ala Leu
                965                 970                 975

Ser Leu Lys Lys Gly Thr Thr Ala Gln Leu Thr Ala Lys Val Ala Pro
            980                 985                 990

Asp Asp Ala Asp Gln Ala Val Thr Trp Ala Ser Ser Asp Asp Lys Val
        995                 1000                1005

Val Thr Val Asp Lys Thr Gly Lys Val Thr Ala Val Ala Lys Gly
    1010                1015                1020

Val Ala Lys Val Thr Ala Thr Thr Ala Asn Gly Lys Ser Ala Ser
    1025                1030                1035

Val Thr Val Thr Val Thr Glu Asp Ser Glu Val Pro Gly Pro Thr
    1040                1045                1050

Gly Pro Thr Glu Pro Thr Lys Pro Gly Thr Glu Lys Pro Thr Thr
    1055                1060                1065

Lys Pro Thr Thr Lys Pro Asn Asp Gly Lys Leu Ser Ala Thr Gly
    1070                1075                1080

Ala Asp Thr Ala Val Leu Ala Thr Ile Ala Ala Leu Phe Ala Leu
    1085                1090                1095

Ala Gly Gly Ala Val Val Ala Val Arg Arg Arg Ser Val Arg
    1100                1105                1110

<210> SEQ ID NO 116
<211> LENGTH: 673
<212> TYPE: PRT
<213> ORGANISM: Bifidobacterium breve CCOS 586

<400> SEQUENCE: 116

Met Asn Gly Gln Thr Ser Leu Gln Gly Trp Thr Ile Ile Pro Met Pro
1               5                   10                  15

Gln Thr Met Gln His Lys Ala Asn Ile Ala Leu Leu Pro Met Cys Gly
            20                  25                  30

Arg Ile Asn Glu Ala Arg Ala Val Gly Asp Asp Arg His Ile Leu Ala
        35                  40                  45

Val Gln Leu Ile Asp Asp Ile Arg Ala Ala Thr Gly Leu Glu Trp Asp
    50                  55                  60

-continued

```
Ile Ala Thr Gly Asp Arg Trp Pro Gly Phe Ile Thr Leu Thr Thr Phe
 65                  70                  75                  80

Asp Asp Pro His Ala His Pro Ser Gly Ala Tyr Thr Leu Asp Val Thr
                 85                  90                  95

Pro Asp Gly Val Thr Val Ala Gly Ala Asp Phe Glu Gly Val Arg Asn
            100                 105                 110

Gly Val Gln Thr Leu Arg Gln Leu Ile Arg Gln Cys Gly Ala Ala Leu
        115                 120                 125

Pro Cys Leu His Ile Glu Asp Arg Pro Ala Phe Thr Arg Gly Tyr
130                 135                 140

Tyr Leu Asp Val Thr Arg Gly Arg Val Pro Thr Leu Asp Trp Leu Lys
145                 150                 155                 160

His Trp Ala Asp Lys Leu Cys Leu Tyr Lys Tyr Asn Gln Leu Gln Leu
                165                 170                 175

Tyr Ile Glu His Thr Phe Ala Phe Asp Ser Met Ser Glu Thr Trp Arg
            180                 185                 190

Gly Ser Ser Pro Leu Thr Pro Arg Asp Ile Leu Glu Phe Asp Asp Tyr
        195                 200                 205

Cys Ala Glu Arg Gly Ile Glu Leu Val Pro Ser Val Ser Thr Phe Gly
210                 215                 220

His Leu Tyr Met Ala Leu Arg Thr Gln Ser Leu Arg Asp Leu Gly Glu
225                 230                 235                 240

Phe Pro Glu Thr Ala Asp Glu Pro Phe Gly Phe Ile Asp Arg Met His
                245                 250                 255

His His Thr Leu Asn Ile Ser Asp Asp Arg Ala Phe Asp Leu Ser Cys
            260                 265                 270

Arg Leu Ile Asp Asp Tyr Leu Gln Leu Phe Arg Ser Asp Lys Phe Asn
        275                 280                 285

Ile Cys Ala Asp Glu Thr Phe Asp Leu Gly Lys Gly Arg Ser Lys Pro
290                 295                 300

Leu Ala Asp Arg Ile Gly Val Ala Ala Met Tyr Ala Asp Tyr Val Thr
305                 310                 315                 320

Arg Leu Cys Arg His Leu Glu Ala Arg Gly Arg Pro Met Met Trp
                325                 330                 335

Gly Asp Ile Ala Leu Glu His Pro Glu Ile Leu Asp Arg Leu Pro Glu
            340                 345                 350

Thr Val Thr Leu Leu Asn Trp Gln Tyr Asp Pro Gln Val Thr Asp Glu
        355                 360                 365

Lys Ile Arg Thr Val Ala Glu Ser Gly Ala Lys Gln Ile Val Cys Pro
370                 375                 380

Ala Val Trp Cys Trp Asn Ala Leu Leu Pro Arg Ile Asp Asp Ala Trp
385                 390                 395                 400

Asn Asn Ile Thr Arg Met Ala Arg Tyr Gly Ala Gln Tyr His Ala Gln
                405                 410                 415

Gly Met Leu Ile Thr Asp Trp Gly Asp Phe Gly His Val Asn Asp Pro
            420                 425                 430

Arg Met Ala Ile Pro Gly Met Ile Ile Gly Ala Gln Glu Ser Trp Asn
        435                 440                 445

Pro Gly Arg Ile Pro Asp Glu Ala Asp Met Leu Arg Arg Ile Ser Arg
450                 455                 460

Leu Glu Tyr His Asp Ala Ser Gly Glu Leu Leu Asp Ile Leu Ala Arg
465                 470                 475                 480
```

```
Ala Ser His Ala Ala Ser Phe Glu Trp Asn His Leu Ile Thr Trp Leu
                485                 490                 495

Glu Leu Asp Asp Gly Gln Gly Gly Val Asn Thr Gly Val Leu Gln Thr
            500                 505                 510

Ile Pro Gly Leu Leu Pro Glu Asn Glu Arg Pro Asp Asp Val Ile Arg
        515                 520                 525

Ser Leu Gln Asn Glu Ser Lys Thr Pro Ser Leu Ala Glu Ser Arg Arg
    530                 535                 540

Met Leu Leu Arg Tyr Leu Lys His Arg Ile Thr Leu Gly Glu Thr Ala
545                 550                 555                 560

Asp His Leu Leu Gln Ala Ser Thr Arg Arg Ile Ser Ala Ile Thr Ala
                565                 570                 575

Thr Ala Gly Pro Arg Asn Ala Gly Asn Ala Ala Ala Phe Arg Ile Ala
            580                 585                 590

Val Glu Gly Gln Arg Leu Leu Asn Arg Val Gly Leu Arg Leu Ala Ser
        595                 600                 605

Glu Thr Gly Ile Thr Asp Thr Leu Gln Pro Asn Thr Thr Ser Gln His
    610                 615                 620

Asp Asp Glu Ala Asn Leu Ala Glu Ala Leu Glu Ile Trp Met Glu Ala
625                 630                 635                 640

Tyr Ala Thr Gln Trp Ser Thr Val Ser Arg Asp Ser Glu Leu Arg Arg
                645                 650                 655

Leu Gln Asp Thr Val Trp Lys Leu Thr Asp His Leu Arg Phe Gln Ser
            660                 665                 670

Val

<210> SEQ ID NO 117
<211> LENGTH: 174
<212> TYPE: PRT
<213> ORGANISM: Bifidobacterium breve CCOS 586

<400> SEQUENCE: 117

Met Lys Tyr Pro Asp Ile Pro Asn Val Thr Lys Glu Tyr Leu Asp Glu
1               5                   10                  15

Val Arg Pro Ala Ile Asn Ala Gly Gly Ser Cys Ser Ala Thr Ala Gly
            20                  25                  30

Ala Thr Ile Gly Ala Leu Ser Pro Leu Val Val Asp Gly Thr Ser
        35                  40                  45

Ile Asp Ile Asp Ala Ser Gly Val Pro Val Ala Ser Ile Asn Ser Tyr
    50                  55                  60

Ser Val Gly Gln Cys Thr Trp Trp Ala Ala Ala Arg Arg Gln Gln Ile
65                  70                  75                  80

Gly Lys Pro Val Asp Pro Tyr Met Gly His Gly Tyr Met Trp Ala Ala
                85                  90                  95

Ser Ala Glu Lys His Gly Tyr Pro Thr Gly Gly Thr Ile Gln Leu Gly
            100                 105                 110

Asp Val Met Ser Phe Glu Arg Gly Val Leu Gly Ala Ser Gly Glu Tyr
        115                 120                 125

Gly His Val Ala Ile Val Glu Glu Ile His Glu Asp Gly Ser Ile Leu
    130                 135                 140

Ile Ser Glu Ser Gly Val Asp Gln Arg Arg Ala Trp Thr Arg Leu Leu
145                 150                 155                 160

Thr Arg Glu Gln Ala Glu Asn Pro Gly Ile Thr Tyr Ile His
                165                 170
```

<210> SEQ ID NO 118
<211> LENGTH: 616
<212> TYPE: PRT
<213> ORGANISM: Bifidobacterium breve CCOS 586

<400> SEQUENCE: 118

```
Met Arg Leu Ser Ser Gly Asp His Ala Gly Arg Ala Ser Ala Arg Thr
1               5                   10                  15

Arg His Arg Lys Trp Leu Arg Ser Gly Leu Ala Ala Val Leu Ser Met
            20                  25                  30

Ala Thr Leu Ala Ala Leu Ala Ala Pro Ala Ser Ala Thr Asp Thr Met
        35                  40                  45

Pro Trp Gly Gly Gln Tyr Ala Asp Thr Ser His Pro Glu Gln Ser Ala
50                  55                  60

Gly Ala Asn Gln Pro Tyr Gln His Gly Tyr Thr Gly Leu Asp Ile Leu
65                  70                  75                  80

Asn Trp Asn Pro Asp Ala Asp Lys Asp Ser Glu Tyr Leu Arg Ser Arg
                85                  90                  95

Val Pro Leu Gln Thr Arg Ile Ala Ala Asn Ala Ala Thr Gln Lys Asp
            100                 105                 110

Pro Asn Leu Pro Ala Asp Thr Glu Met Phe Asn Leu Ala Gly Asp Tyr
        115                 120                 125

Gly Asn Ala Phe Phe Glu Ser Phe His Asp Asn Ser Val Phe Ser Gln
130                 135                 140

Tyr Leu Phe Asn Tyr Trp Gln Tyr Thr Asp Tyr Tyr Gly Thr Trp His
145                 150                 155                 160

Gly Gln Pro Thr Ala Asn Val Pro Lys Ser Leu Tyr Asp Glu Lys Ala
                165                 170                 175

Gln Ser Asp Trp Thr Gln Lys Trp Phe Glu Phe Gly Thr Leu Asn Leu
            180                 185                 190

Pro Asn Ala Ala Tyr Thr Asn Val Ala His Lys Asn Gly Ala Lys Ser
        195                 200                 205

Ile Ala Thr Ile Phe Tyr Ser Gly Asn Asp Arg Gly Glu Gln Thr Tyr
210                 215                 220

Lys Asp Leu Leu Gln Gly Lys Arg Ala Asp Gly Thr Tyr Pro Val Ala
225                 230                 235                 240

Asp Lys Leu Val Glu Ile Ala Lys Tyr Tyr Gly Phe Asp Gly Tyr Phe
                245                 250                 255

Val Asn Gln Glu Ser Ser Val Asn Ser Ala Asp Val Pro Ala Tyr Gln
            260                 265                 270

Asp Phe Met Lys Gln Ile Ile Asp Gln Gly Ile Tyr Ile Gln Trp Tyr
        275                 280                 285

Asp Ser Ala Thr Tyr Pro Asn Gly Gly Val Ser Tyr Gln Asn Met Phe
290                 295                 300

Asn Asp Ala Asn Ser Pro Trp Val Gln Asp Pro Asn Lys Gly Lys Ile
305                 310                 315                 320

Ser Asp Ser Ile Phe Leu Asn Tyr Trp Phe Ser Gly Asn Met Leu Gln
                325                 330                 335

Asp Ser Ala Asp His Ala Lys Ser Leu Gly Ile Asp Pro Lys Tyr Ala
            340                 345                 350

Val Phe Ala Gly Ile Glu Ala Gly Gln Lys Lys Phe Gly Ser Ile Ala
        355                 360                 365

Ser Asn Ala Asn Tyr Met Asn Val Asn Leu Asp Ala Asp Gly Lys Pro
370                 375                 380
```

```
Tyr Val Ser Leu Ala Ala Leu Gly Thr Asp Phe Val Ser His Glu Leu
385                 390                 395                 400

Gly Asp Asp Lys Lys Val Tyr Pro Lys Tyr Gln Asn Gln Val Phe Asp
            405                 410                 415

Arg Glu Arg Arg Leu Trp Thr Gly Ser Ser Thr Gly Glu Lys Gly Thr
            420                 425                 430

Thr Asp Ile Ser Asp Pro Tyr Ile Asp Asp Gly Thr Ser Ser Asp Ser
        435                 440                 445

Trp Lys Gly Phe Ala Ser Gln Ile Ala Glu Arg Ser Val Ile Asp Gly
    450                 455                 460

Pro Val Phe Ser Thr Ser Phe Asn Thr Gly His Gly Leu Glu Trp Arg
465                 470                 475                 480

Asp Asn Gly Glu Gln Thr Ser Asn Gln Gln Trp Gly Asn Ile Asn Leu
                485                 490                 495

Gln Asp Ile Leu Pro Thr Trp Gln Trp Trp Ile Asp Ala Asp Ser Asp
            500                 505                 510

Pro Leu Gln Ala Asp Phe Asp Tyr Gly Lys Lys Tyr Glu Ala Ala Pro
        515                 520                 525

Arg Phe Asn Tyr Thr Lys Val Gly Gly Tyr Glu Gly Gly Asp Ser Leu
    530                 535                 540

Val Leu Ser Gly Lys Leu Ser Ser Asp Asn Thr Val Arg Leu Tyr Lys
545                 550                 555                 560

Thr Asp Leu Ser Val Ala Ala Gly Ser Lys Val Glu Leu Thr Tyr Asn
                565                 570                 575

Lys Leu Asn Ser Asp Asp Ser Lys Leu Gln Leu Gly Leu Ile Phe Ala
            580                 585                 590

Asp Asp Thr Lys Thr Ile Val Pro Val Asp Met Glu Thr Val Gly Gln
        595                 600                 605

Ala Thr Ala Gly Arg Pro Gln Leu
    610                 615

<210> SEQ ID NO 119
<211> LENGTH: 627
<212> TYPE: PRT
<213> ORGANISM: Bifidobacterium breve CCOS 586

<400> SEQUENCE: 119

Met Glu Phe Thr Val Ser Gly Thr Thr Val Arg Phe Asp Glu Arg Thr
1               5                   10                  15

Met Gln Phe Ala Phe Thr Arg Asp Gly Ala Glu Trp Asn Thr Cys Ala
            20                  25                  30

Asp Phe Lys Pro Thr Leu Gln Cys Thr Gln Gly Thr Phe Ala Phe Ala
        35                  40                  45

Asp Ala Thr Ser Ile Thr His Glu Gln Arg Glu Thr Gly Thr Gly Thr
    50                  55                  60

Gly Ile Arg Ser Ile Phe Thr Gly Phe Gly His Ser Ala Tyr Ser Phe
65                  70                  75                  80

Glu Thr Tyr Val Trp Val Glu Arg Ala Ser Gly Asp Val Leu Phe Glu
                85                  90                  95

Trp Ile Pro Leu Asn Glu Gln Gly Leu Thr Val Thr Gly Val Thr Trp
            100                 105                 110

Pro Ala Ala Ile Ala Phe Asp Arg Asp Ser His Asp Val Thr Leu
        115                 120                 125

Ile Thr His Glu Gln Gly Val Met Ile Pro Asn Thr Trp Pro Thr Ala
    130                 135                 140
```

```
Val Ser Thr Lys Asp Ile Thr Phe Asp Gly Arg Phe Glu Thr Ala Gly
145                 150                 155                 160

Gly Tyr Met Pro Trp Phe Ala Gln Leu Arg Ala Asp Gly His Gly Tyr
                165                 170                 175

Ile Ala Ile Cys Glu Thr Pro Trp Asn Ala Gly Tyr Gly Ile Asp His
            180                 185                 190

Pro Ser Asn Gly Pro Tyr Thr His Ile Asn Thr Trp Phe Glu Pro Ser
        195                 200                 205

Leu Gly Thr Met Asn Tyr Arg Val Val Arg Tyr Gln Phe Leu Asp
    210                 215                 220

His Ala Asp His Thr Ala Val Cys Lys Ala Tyr Arg Ser Tyr Val Asn
225                 230                 235                 240

Glu Arg Gly Arg Leu Arg Thr Leu Ala Glu Lys Ala Ala Arg Asn Pro
                245                 250                 255

Ser Val Arg Asp Leu Ile Gly Arg Ser Trp Val His Val Gly Ile Lys
            260                 265                 270

Thr Lys Val Gln Pro Asp Ser Phe Tyr Tyr Asp Lys Asp His Pro Glu
        275                 280                 285

Lys Asn Asp Ser Leu Val Thr Phe Ala Gln Arg Glu Lys Gln Met Arg
290                 295                 300

Thr Leu His Ser Met Gly Ala Gly Arg Leu Tyr Met His Leu Asp Gly
305                 310                 315                 320

Trp Ala Gln Pro Gly Tyr Asp Asn Ala His Pro Asp Tyr Leu Pro Ala
                325                 330                 335

Cys Gln Glu Ala Gly Gly Trp Glu Gly Met Lys Ser Leu Val Asp Ala
            340                 345                 350

Cys His Glu Gln Gly Asp Ile Phe Gly Thr His Asp Gln Tyr Arg Asp
        355                 360                 365

Tyr Tyr Phe Thr Ala Gln Thr Phe Asp Ala Asn Asn Ala Ile Arg Leu
    370                 375                 380

Ala Asp Gly Thr Met Pro Glu His Ala Arg Trp Ala Gly Gly His Gln
385                 390                 395                 400

Thr Tyr Leu Cys Ala Glu Leu Ala Pro Asp Tyr Val Arg Arg Asn Phe
                405                 410                 415

Thr Gln Ile Ala Ala His Gly Ile Lys Leu Asp Cys Ala Tyr Leu Asp
            420                 425                 430

Val Phe Thr Cys Asn Glu Gly Asp Glu Cys Ser Asn Pro Glu His Arg
        435                 440                 445

Met Thr Arg Arg Glu Cys Phe Asp Arg Arg Thr Glu Cys Phe Glu Tyr
450                 455                 460

Leu Leu Ser His Gly Ile Leu Ser Ser Ser Glu Val Ser Asp Trp
465                 470                 475                 480

Ala Val Pro Ser Leu Ile Phe Cys His Tyr Ala Pro Tyr Asp Phe Gln
                485                 490                 495

Met Arg Ser Pro Asn Glu Pro Arg Gln Gly Val Pro Val Pro Leu Tyr
            500                 505                 510

Asn Leu Val Tyr His Asp Cys Val Ile Glu Pro Trp Met Met Glu Arg
        515                 520                 525

Val Val Asn Gly Asp Asp Tyr Met Leu Tyr Ala Leu Leu Asn Gly Gly
530                 535                 540

Ala Pro Tyr Leu Ile Arg Asp Ala Ala Tyr Ile Gly Val Asp Gly Asp
545                 550                 555                 560
```

Met Asp Asp Glu Gln Arg Ala Arg Thr Glu Asn Asp Ile Glu Arg Cys
                565                 570                 575

His Thr Val Ala Ala Phe His Glu Arg Val Gly Met Gln Glu Leu Val
            580                 585                 590

Arg His Glu Phe Val Asp Asp Pro Leu Val Gln Arg Ser Val Phe
        595                 600                 605

Val Asp Gly Thr Ala Val Thr Cys Asp Phe His Thr Gln Thr Tyr Arg
    610                 615                 620

Ile Thr Asp
625

<210> SEQ ID NO 120
<211> LENGTH: 237
<212> TYPE: PRT
<213> ORGANISM: Bifidobacterium breve CCOS 586

<400> SEQUENCE: 120

Met Ser Thr Asp Gln Leu Arg Gln Ser Ala Ser Val Trp Gly Ser Gln
1               5                   10                  15

Leu Ala Ala Ala Gly Ile Asn Val Asp Leu Ala Pro Val Leu Gly Thr
            20                  25                  30

Val Val Ala Asn Arg Ala Ala Asn Ala Pro Ile Gly Ala Leu Tyr Arg
        35                  40                  45

Asp Phe Gly Leu Asp Ala Ala Gly Asn Ala Ala Gln Gly Thr Ala Phe
    50                  55                  60

Val Gln Gly Met Ala Asp Ala Gly Val Gln Ser Ala Ile Lys His Tyr
65                  70                  75                  80

Pro Gly Leu Gly Ala Val Thr Gly Asn Thr Asp Phe Thr Ala Asp Gly
                85                  90                  95

Ile Leu Asp Thr Thr Thr Thr Leu Asp Gly Thr Glu Ile Lys Ala Phe
            100                 105                 110

Asp Thr Thr Ile Asp Gln Ala Asp Pro Ala Met Val Met Met Ala Leu
        115                 120                 125

Ala Thr Tyr Gln Ala Ile Asp Pro Asn Asp Pro Ala Val Phe Ser Ser
    130                 135                 140

Ile Ile Ile Asp Gly His Leu Arg Gly Asp Leu Gly Tyr Asp Gly Val
145                 150                 155                 160

Val Ile Ser Asp Ser Met Ser Ala Ala Ala Val Ser Ala Tyr Asp Thr
                165                 170                 175

Thr Gln Leu Gly Val Lys Leu Val Glu Ala Gly Gly Asp Leu Ala Cys
            180                 185                 190

Ile Gly Tyr Thr Asn Tyr Val Ala Pro Ile Leu Asp Gly Leu Ser Thr
        195                 200                 205

Arg Ala Ala Ser Asp Pro Ala Phe Ala Asn Glu Val Thr Gln Ser Ala
    210                 215                 220

Ile Arg Val Met Thr Leu Lys Ile Lys Met Gly Leu Ala
225                 230                 235

<210> SEQ ID NO 121
<211> LENGTH: 133
<212> TYPE: PRT
<213> ORGANISM: Bifidobacterium breve CCOS 586

<400> SEQUENCE: 121

Met Ser Ile Gly Glu Asp Thr Ala Gly Val Arg Leu Cys Gly Glu Val
1               5                   10                  15

Arg Gly Gly Gly Leu Phe Leu Tyr Pro Leu Gly Glu Gly Gln Ile Arg
            20                  25                  30

Lys Ile Ser Asp Val Pro Pro Thr Thr Asp Thr Ala Leu Phe Asp Lys
        35                  40                  45

Gly Tyr Glu Gly Ser Ala Ser Tyr Arg Ile Pro Ser Leu Val Thr Thr
    50                  55                  60

Pro Ser Gly Val Thr Ile Ala Gly Ala Asp Gln Arg Val Val Ile Ser
65                  70                  75                  80

Asn Asp Ala Pro Met Arg Ser Ile Ser Leu Ser Ala Ala Pro Trp Ile
                85                  90                  95

Ala Asp Arg Arg Gly Cys Arg Cys Lys Pro Ser Ser Pro Phe Pro Val
            100                 105                 110

Met Gly Trp Met Ala Arg Ala Ser Ser Thr His Ala Ser Ser Val Ile
        115                 120                 125

Val Arg Gln Ala Val
    130

<210> SEQ ID NO 122
<211> LENGTH: 433
<212> TYPE: PRT
<213> ORGANISM: Bifidobacterium breve CCOS 586

<400> SEQUENCE: 122

Met Ser Thr Phe Pro Gln Leu Ala Thr His Pro Gly Met Asn Pro Ala
1               5                   10                  15

Ala Val Ile Gln Gly Asp Arg Trp Arg Ile Gly Ile Ile Thr Glu Ser
            20                  25                  30

Leu Val Arg Leu Glu Trp Gln Asp Asn Gly Lys Phe Glu Asp His Ala
        35                  40                  45

Thr Gln Met Ile Val Asn Arg Asp Trp Leu Ser Asp Asp Ala Asn Gly
    50                  55                  60

Ala Asp Gly Ala Asn Arg Ala Asp Gly Thr Ser Asn Pro Pro Lys Phe
65                  70                  75                  80

Thr Lys Thr Glu Arg Asp Gly Leu Leu Ile Ile Asp Thr Pro Ala Leu
                85                  90                  95

Arg Leu Thr Tyr Asp Met Gln Pro Phe Ser Lys Glu Gly Leu Ser Ile
            100                 105                 110

Val Val Lys Gly Val Ala Asn Ser Gln Met Asn Thr Trp His Tyr Gly
        115                 120                 125

Glu Ala Gln Asp Gly Asn Leu Arg Gly Thr Ala Arg Thr Leu Asp Ala
    130                 135                 140

Val Asp Gly Glu Ile Glu Leu Gly Leu Gly Val Ile Ser Arg Asp Gly
145                 150                 155                 160

Trp Ala Val Leu Asp Asp Ser Ala Ser Asn Val Ile Val Glu Gly Ala
                165                 170                 175

Glu Ala Ala Thr Val Lys Gly Glu Ala Asn Pro Phe Gly Met Trp Val
            180                 185                 190

Ile Pro Arg Glu His Pro Gly Lys Asp Leu Tyr Val Phe Gly Tyr Gly
        195                 200                 205

His Arg Tyr Ile Glu Ala Val Gln Asp Phe Tyr Lys Leu Thr Gly Pro
    210                 215                 220

Thr Pro Leu Leu Pro Arg Phe Ala Leu Gly Asn Trp Trp Ser Arg Tyr
225                 230                 235                 240

```
His Arg Tyr Thr Glu Ala Glu Tyr Leu Glu Leu Val Asp Arg Phe Glu
                245                 250                 255

Gln Glu Gly Leu Pro Phe Thr Thr Ala Val Ile Asp Met Asp Trp His
            260                 265                 270

Leu Val Asp Asn Val Asp Pro Lys Tyr Gly Ser Gly Trp Thr Gly Tyr
            275                 280                 285

Thr Trp Asn Arg Glu Phe Phe Pro Asp Pro Glu Arg Phe Gln Arg Ile
            290                 295                 300

Leu His Glu His Gly Leu Arg Thr Thr Leu Asn Val His Pro Arg Asp
305                 310                 315                 320

Gly Val Arg Ala Phe Glu Asp Gly Tyr Ala Lys Val Ala Glu His Met
                325                 330                 335

Gly Ile Asp Pro Ala Gly Gly Glu Pro Val Glu Phe Asp Leu Thr Ser
            340                 345                 350

Pro Arg Phe Met Glu Ala Tyr Phe Asp Leu His His Gly Leu Glu Thr
            355                 360                 365

Leu Gly Thr Asp Phe Trp Trp Leu Asp Trp Gln Gly Gly Val Thr
            370                 375                 380

Arg Gln Lys Gly Leu Asp Pro Leu Trp Met Leu Asn His Met His Tyr
385                 390                 395                 400

Leu Asp Ser Ala Val Thr Gly Ala Gly Arg Ser Arg Ser Arg Asp Met
                405                 410                 415

Pro Ala Arg Ala Arg Thr Val Ile Arg Ser Gly Ser Pro Ala Thr Gln
            420                 425                 430

Ser

<210> SEQ ID NO 123
<211> LENGTH: 338
<212> TYPE: PRT
<213> ORGANISM: Bifidobacterium breve CCOS 586

<400> SEQUENCE: 123

Met Ile Asp Val Ser Ala Trp Gln Gly Asn Ile Asn Trp Gln Ala Val
1               5                   10                  15

Lys Asn Ser Gly Val Glu Gly Ala Ile Ile Arg Ile Gly Tyr Gly Trp
            20                  25                  30

Asp Asn Gly Phe Asp Lys Gln Ala Leu Arg Asn Ile Ser Glu Cys Arg
        35                  40                  45

Arg Leu Gly Ile Pro Phe Gly Ile Tyr Leu Tyr Ser Tyr Ala Tyr Asp
    50                  55                  60

Ala Asn Thr Gly Ala Ala Glu Gly Ser Ser Leu Val Asn Leu Leu Gln
65                  70                  75                  80

Lys Ala Gly Val Ser Ser Ser Asp Leu Gly Tyr Pro Val Tyr Tyr Asp
                85                  90                  95

Leu Glu Arg Trp Thr Trp Thr Gly His Glu Val Pro Asn Asp Pro Gly
            100                 105                 110

Thr Tyr Asp Gly Ile Val Asn Ala Trp Tyr Gly Arg Leu Gln Ser Ala
            115                 120                 125

Gly Tyr Asn Asn Leu Ala Val Tyr Ser Tyr Thr Ser Tyr Leu Asn Thr
        130                 135                 140

Ala Leu Asn Ser Gly Asn Ile His Ser Lys Thr Arg Trp Val Ala Gln
145                 150                 155                 160

Tyr Gly Ser Ser Met Gly Tyr Thr Ala Phe Pro Thr Asn Asp Arg Gly
                165                 170                 175
```

```
Trp Gln Tyr Thr Ser Arg Gly Ser Val Ser Gly Ile Ser Gly Thr Val
            180                 185                 190

Asp Leu Asn Ala Phe Gly Asn Gln Thr Ala Thr Ser Ser Ala Pro Ser
            195                 200                 205

Val Pro Val Tyr Arg Val Tyr Asn Pro Asn Ser Gly Leu His His Tyr
    210                 215                 220

Thr Met Asn Tyr Asn Glu Val Ile Met Leu Val Gly Lys Gly Trp Arg
225                 230                 235                 240

Tyr Glu Lys Thr Ala Phe Arg Ala Gly Gln Ser Gly Ile Pro Val Tyr
                245                 250                 255

Arg Val Tyr Asn Pro Asn Asp Gly Asn His Leu Phe Thr Met Asn Ser
            260                 265                 270

Tyr Glu Arg Asp Asn Leu Ala Arg Leu Gly Trp His Asp Glu Gly Val
            275                 280                 285

Ser Trp Tyr Val Pro Ser Gly Gly Ser Ile Asn Val Tyr Arg Leu Tyr
            290                 295                 300

Asn Pro Asn Asn Gly Glu His Val Phe Thr Thr Glu Tyr Gly Glu Tyr
305                 310                 315                 320

Val Leu Val Gly Arg Ala Gly Trp His Gln Glu Gly Val Ala Trp Thr
                325                 330                 335

Ser Leu

<210> SEQ ID NO 124
<211> LENGTH: 124
<212> TYPE: PRT
<213> ORGANISM: Bifidobacterium longum CCOS 974

<400> SEQUENCE: 124

Met Gly Ile Pro Val Arg Ser Gly Gly Tyr Gln Leu Ile Gly Ala Lys
1               5                   10                  15

Lys Thr Phe Ile Asp Glu Met Asn Gln Trp Met Lys Thr Glu Ser Asn
            20                  25                  30

Lys Pro Phe Leu Phe Thr Glu Tyr Gly Ala Asp Thr Asp Ala Gly Val
        35                  40                  45

His Lys Leu Pro Ser Val Gln Trp Ser Glu Glu Tyr Gln Cys Glu Tyr
    50                  55                  60

Leu Ala Met Gln His Glu Val Phe Asp Met Phe Glu Ala Val Val Gly
65                  70                  75                  80

Glu Gln Val Trp Asn Leu Cys Asp Phe Gln Thr Gly Glu Gly Ile Met
                85                  90                  95

Arg Val Asp Gly Asn Lys Lys Arg Leu His Ser Arg Pro Ser Ala Gln
            100                 105                 110

Ser Arg Arg Leu Cys Thr Gln Gly Ala Leu Gly Asp
        115                 120

<210> SEQ ID NO 125
<211> LENGTH: 400
<212> TYPE: PRT
<213> ORGANISM: Bifidobacterium longum CCOS 974

<400> SEQUENCE: 125

Met Ala Thr Ile Cys Ala Leu Ala Val Val Leu Ala Gly Val Ala Ala
1               5                   10                  15

Tyr Gly Trp His Val Gly Trp Phe Ala Lys Ser Thr Ser Asn Gly Asn
            20                  25                  30
```

```
Thr Thr Thr Pro Gln Thr Ser Gln Thr Ser Ala Leu Pro Arg Ala Asp
        35                  40                  45

Val Pro Ser Pro Lys Lys Asn Glu Pro Ala Ala Gln Ala Gln Arg Ala
 50                  55                  60

Val Ser Ala Met Thr Leu Glu Glu Arg Val Gly Gln Leu Val Met Val
 65                  70                  75                  80

Pro Leu Leu Ala Gly Ser Asp Pro Ser Ser Leu Ala Ser Thr Ile Ala
                 85                  90                  95

Asp Glu His Ile Gly Ser Ala Ile Leu Ile Gly Asn Trp Asn Thr Gly
                100                 105                 110

Val Asp Thr Val Lys Thr Ala Thr Ala Gln Leu Gln Gly Tyr Ala Pro
                115                 120                 125

Ala Gly Asn Arg Leu Ile Ile Ala Thr Asp Gln Glu Gly Gly Gln Val
130                 135                 140

Gln His Leu Thr Gly Thr Gly Phe Asp Thr Met Pro Ser Ala Val Glu
145                 150                 155                 160

Gln Gly Thr Met Ser Ala Asp Ala Leu Arg Gln Ser Ala Gly Thr Trp
                165                 170                 175

Gly Ser Gln Leu Ala Ala Ala Gly Ile Asn Val Asp Leu Ala Pro Val
                180                 185                 190

Leu Gly Thr Val Val Gly Asp Arg Ala Ser Asn Thr Pro Ile Gly Ala
                195                 200                 205

Leu Asp Arg Asp Phe Gly Leu Asp Ala Ala Gly Asn Ala Glu His Gly
                210                 215                 220

Ile Ala Val Ile Glu Gly Leu Arg Asp Ala Gln Val Gly Ala Ala Val
225                 230                 235                 240

Lys His Tyr Pro Gly Leu Gly Ala Val Ser Gly Asn Thr Asp Phe Thr
                245                 250                 255

Thr Glu Gly Ile Leu Asp Thr Thr Thr Leu Asp Gly Ala Glu Ala
                260                 265                 270

Gly Ala Phe Asp Gln Ala Ile Thr Lys Thr Asp Pro Ala Met Ala Met
                275                 280                 285

Met Ser Leu Ala Thr Tyr Gln Ser Ile Asp Pro Asn Asn Pro Ala Val
                290                 295                 300

Phe Ser Thr Ile Ile Asp Gly His Ile Arg Asn Ala Leu Lys Tyr
305                 310                 315                 320

Thr Gly Val Val Ile Ser Asp Ser Met Ser Ala Glu Ala Leu Ser Ser
                325                 330                 335

Tyr Asp Val Ser Gln Leu Gly Val Lys Leu Val Glu Ala Gly Gly Asp
                340                 345                 350

Met Ser Cys Ile Gly Gln Thr Asp Tyr Val Lys Pro Ile Val Asp Gly
                355                 360                 365

Leu Asn Glu Arg Ala Lys Ser Asp Pro Ala Phe Ala Ser Lys Val Thr
                370                 375                 380

Ala Ala Ala Thr Arg Val Met Ala Leu Lys Ile Lys Met Gly Leu Ala
385                 390                 395                 400

<210> SEQ ID NO 126
<211> LENGTH: 631
<212> TYPE: PRT
<213> ORGANISM: Bifidobacterium longum CCOS 974

<400> SEQUENCE: 126

Met Glu Phe Thr Val Ser Gly Thr Val Arg Phe Asp Glu Arg Thr
1               5                   10                  15
```

```
Met Gln Phe Ala Phe Thr Arg Asp Gly Ala Glu Trp Asn Thr Cys Ala
                20                  25                  30
Asp Phe Lys Pro Thr Leu Gln Cys Ala Gln Gly Thr Phe Ala Phe Ala
            35                  40                  45
Asp Ala Thr Ser Ile Thr His Glu Gln Arg Glu Thr Gly Thr Gly Thr
 50                  55                  60
Gly Ile Arg Ser Ile Phe Thr Gly Phe Gly His Ser Ala Tyr Ser Phe
 65                  70                  75                  80
Glu Thr Tyr Val Trp Val Glu Arg Ala Ser Gly Asp Val Leu Phe Glu
                85                  90                  95
Trp Ile Pro Leu Asn Glu Gln Gly Leu Asn Ile Thr Asn Val Thr Trp
            100                 105                 110
Pro Ala Ala Met Asp Phe Asp Cys Ala Asp Asp His Asp Thr Thr Leu
            115                 120                 125
Ile Thr His Glu Gln Gly Val Met Ile Pro Asn Thr Trp Pro Thr Ala
 130                 135                 140
Val Ser Thr Lys Asp Ile Ala Phe Asp Gly Arg Phe Glu Thr Ala Gly
 145                 150                 155                 160
Gly Tyr Met Pro Trp Phe Ala Gln Leu Arg Ala Asp Gly His Gly Tyr
                165                 170                 175
Ile Ala Ile Cys Glu Thr Pro Trp Asn Ala Gly Tyr Gly Ile Asp His
            180                 185                 190
Pro Ser Asn Gly Pro Tyr Thr His Ile Asn Thr Trp Phe Glu Pro Ser
            195                 200                 205
Leu Gly Thr Met Asn Tyr Arg Arg Val Val Arg Tyr Gln Phe Leu Asp
 210                 215                 220
His Ala Asp His Thr Ala Val Cys Lys Ala Tyr Arg Ser Tyr Val Asn
 225                 230                 235                 240
Glu Arg Gly Arg Leu Arg Thr Leu Ala Glu Lys Ala Ala Arg Asn Pro
                245                 250                 255
Ser Val Arg Asp Leu Ile Gly Arg Ser Trp Val His Ile Gly Ile Lys
            260                 265                 270
Thr Lys Val Gln Pro Asp Ser Tyr Tyr Asp Lys Asp His Pro Glu
            275                 280                 285
Lys Asn Glu Ser Leu Val Thr Phe Ala Gln Arg Glu Lys Gln Met Arg
 290                 295                 300
Thr Leu His Gly Met Gly Ala Gly Arg Leu Tyr Met His Leu Asp Gly
 305                 310                 315                 320
Trp Ala Gln Pro Gly Tyr Asp Asn Ala His Pro Asp Tyr Leu Pro Ala
                325                 330                 335
Cys Gln Glu Ala Gly Gly Trp Glu Gly Met Lys Ser Leu Val Asp Ala
            340                 345                 350
Cys His Glu Gln Gly Asp Ile Phe Gly Thr His Asp Gln Tyr Arg Asp
            355                 360                 365
Tyr Tyr Phe Thr Ala Gln Thr Phe Asp Ala Asn Asn Ala Ile Arg Leu
 370                 375                 380
Ala Asp Gly Thr Met Pro Glu His Ala Arg Trp Ala Gly Gly Arg Gln
 385                 390                 395                 400
Thr Tyr Leu Cys Ala Glu Leu Ala Pro Asp Tyr Val Arg Arg Asn Phe
                405                 410                 415
Thr Gln Ile Ala Ala His Gly Ile Lys Leu Asp Cys Ala Tyr Leu Asp
            420                 425                 430
```

-continued

```
Val Phe Thr Cys Asn Glu Gly Asp Glu Cys Ser Asn Pro Glu His Arg
            435                 440                 445

Met Thr Arg Arg Glu Cys Phe Asp Arg Arg Ala Glu Cys Phe Glu Tyr
450                 455                 460

Leu Leu Ser His Gly Ile Leu Ser Ser Glu Glu Val Ser Asp Trp
465                 470                 475                 480

Ala Val Pro Ser Leu Ile Phe Cys His Tyr Ala Pro Tyr Asp Phe Gln
                485                 490                 495

Met Arg Ser Pro Asn Glu Pro Arg Gln Gly Val Pro Val Pro Leu Tyr
            500                 505                 510

Asn Leu Val Tyr His Asp Cys Val Ile Glu Pro Trp Met Met Glu Arg
            515                 520                 525

Val Val Asp Gly Asp Asp Tyr Met Leu Tyr Ala Leu Leu Asn Gly Gly
530                 535                 540

Ala Pro Tyr Leu Ile Arg Asp Ala Ala Tyr Ile Gly Val Asp Gly Asp
545                 550                 555                 560

Met Asp Asp Glu Gln Arg Ala Arg Thr Glu Asn Asp Ile Glu Arg Cys
                565                 570                 575

His Thr Val Ala Ala Phe His Glu Arg Val Gly Met Gln Glu Leu Val
            580                 585                 590

Arg His Glu Phe Val Asp Asp Pro Leu Val Gln Arg Ser Val Phe
595                 600                 605

Ala Asp Gly Thr Ala Val Thr Cys Asp Phe His Thr Gln Thr Tyr Arg
610                 615                 620

Ile Thr Asp Cys Pro His His
625                 630

<210> SEQ ID NO 127
<211> LENGTH: 315
<212> TYPE: PRT
<213> ORGANISM: Bifidobacterium longum CCOS 974

<400> SEQUENCE: 127

Met Gly Ile Leu Asn Lys Gly Lys Pro Lys His Gly His Leu His Arg
1               5                   10                  15

Arg Val Gly Met Thr Leu Thr Ala Leu Ala Val Ala Val Ser Met Ala
                20                  25                  30

Phe Ala Pro Ala Ala Met Ala Asp Met Gln Gly Val Asp Met Ser Asn
            35                  40                  45

Trp Gln Cys Gly Ala Asp Val Tyr Asn Met Gln Ala Asp Phe Ile Val
    50                  55                  60

Val Gly Thr Thr Trp Gly Thr Gly Gln Val Asn Asn Cys Leu Val
65                  70                  75                  80

Ser Gly Val Asn Thr Asp Ala Asn Arg Met Ile Ala Gln Ala Gln Ala
                85                  90                  95

Ser Gly Lys Lys Phe Gly Leu Tyr His Tyr Ala Met Gly Gly Asn Pro
            100                 105                 110

Glu Ala Glu Ala Gln Phe Phe Tyr Arg Asn Thr Ser Asn Tyr Trp Arg
        115                 120                 125

His Gly Ile Val Ala Leu Asp Trp Glu Met Asp Asp Asn Pro Ala Trp
    130                 135                 140

Gly Asp Trp Asp Trp Val Arg Arg Phe Thr Ala Glu Cys Glu Arg Leu
145                 150                 155                 160

Ser Gly Gly Val Lys Pro Leu Leu Tyr Thr Gly Pro Val Ala Gly Thr
                165                 170                 175
```

```
Ile Pro Gly Asp Ile Arg Ala Asn Tyr Gly Leu Trp Ile Ala Gln Tyr
            180                 185                 190

Ala Asn Met Ser Pro Thr Gly Tyr Gln Ala Asn Pro Trp Met Leu Gly
        195                 200                 205

Ala Tyr Gly Glu Ala Met Arg Gln Tyr Ser Gly Thr Gly Val Val Asn
    210                 215                 220

Thr Trp Ser Pro Ile Asp Leu Asn Ile Phe Arg Gly Glu Gly Trp Gln
225                 230                 235                 240

Trp Ile Cys Thr Pro Thr Pro Ala Pro Gln Pro Arg Pro Arg Gln
                245                 250                 255

Arg Pro Arg Pro Cys Ser Arg Ala Leu Pro Arg Pro Thr Pro Thr Arg
            260                 265                 270

Val Ala Ser Ala Thr Ser Cys Asn Gly Glu Lys Pro Ser Gly Asp Ser
        275                 280                 285

Pro Ser Pro Met Met Leu Gly Pro Cys Pro Arg Gly Ile Arg Arg Ala
    290                 295                 300

Val Thr Ser Thr Ala Thr Thr Trp Ala Thr Ser
305                 310                 315

<210> SEQ ID NO 128
<211> LENGTH: 711
<212> TYPE: PRT
<213> ORGANISM: Bifidobacterium longum CCOS 974

<400> SEQUENCE: 128

Met Pro Thr Phe Glu Tyr Lys Ala Asp Ala Ala Thr Pro Cys Leu Thr
1               5                   10                  15

Leu Ile Pro Ala Pro Val Thr Leu Glu Tyr Thr His Gly Thr Ala Met
            20                  25                  30

Ile Gly Ser Leu Val Thr Ile Glu Lys Arg Ile Pro Glu Tyr Ala Val
        35                  40                  45

Thr Glu Asp Ala Asp Glu Thr Trp Glu Thr Leu Pro Ile Glu Gln Leu
    50                  55                  60

Ser Ser Glu Leu Glu Arg Tyr Cys Gly Val Ala Val Arg Thr Arg Arg
65                  70                  75                  80

Val Leu Thr Ala Thr Asp Glu Ala Asp Ala Gly Ala Asn Ala Ala Glu
                85                  90                  95

Lys Ala Arg Asp Ala Gly Val Gly Ala Gly Ala Gly Ala Gly Ala Pro
            100                 105                 110

Ala Ala Met Asn Gly Thr Val Ile Leu Leu Cys Val Asp Ala Arg Leu
        115                 120                 125

Ala His Asp Glu Tyr Thr Leu Asp Val Phe Ala Ser Asp Thr Ile Ala
    130                 135                 140

Val Arg Gly Gly Ser Glu Ser Gly Leu Arg Tyr Gly Met Gln Thr Leu
145                 150                 155                 160

Arg Gln Met Ile Arg Gln Thr Ser Arg Thr Leu Pro Cys Leu His Ile
                165                 170                 175

Gln Asp Lys Pro Ala Phe Ala Val Arg Ala Tyr Ser Leu Asp Val Thr
            180                 185                 190

Arg Gly Arg Val Pro Thr Met Ala Phe Leu Thr Trp Phe Ile Asp Gln
        195                 200                 205

Leu Ala Leu Tyr Lys Tyr Asn Gln Phe Gln Leu Tyr Val Glu His Ala
    210                 215                 220

Phe Ala Phe Gly Glu Leu Ser Glu Ala Trp Arg Gly Thr Asp Pro Leu
225                 230                 235                 240
```

```
Thr Ala Asp Asp Ile Met Phe Leu Asp Glu Tyr Cys Ala His His Gly
                245                 250                 255
Ile Glu Leu Val Pro Ser Leu Ala Thr Phe Gly His Met Tyr Met Asn
            260                 265                 270
Leu Arg Thr Arg Glu His Arg Gly Leu Gly Glu Phe Pro Glu Asp Ala
        275                 280                 285
Asp Arg Pro Phe Ser Phe Ile Glu Arg Met Glu His His Thr Leu Asn
    290                 295                 300
Ala Ala Asn Pro Lys Ser His Asp Phe Ala Ser Arg Leu Ile Glu Glu
305                 310                 315                 320
Tyr Ala Pro Leu Phe Arg Ser Arg Ser Phe Asn Ile Gly Gly Asp Glu
                325                 330                 335
Thr Phe Asp Leu Gly Arg Gly Arg Ser Val Gln Asp Ser Pro Gly Ala
            340                 345                 350
Ser Arg Asp Glu Leu Tyr Ala Asp Phe Val Lys Asp Leu Cys Ser Thr
        355                 360                 365
Leu Ala His Arg Gly Leu Gln Pro Met Leu Trp Ala Asp Ile Ala Leu
    370                 375                 380
Glu Asn Pro His Thr Met Asp Leu Leu Pro Gly Asp Ile Thr Met Leu
385                 390                 395                 400
Asn Trp Met Tyr Glu Pro Asp Ile Asp Glu Ser Lys Ile Gln Thr Ile
                405                 410                 415
Ala Ser Gln Gly Arg Arg Gln Phe Val Cys Pro Ala Val Arg Ala Trp
            420                 425                 430
Ser Arg Phe Phe Pro Asp Tyr Asp Gly Ala Trp Leu Asn Thr Tyr Arg
        435                 440                 445
Met Ala Val Ala Gly Leu Lys Tyr Gly Ala Glu Gly Met Val Val Thr
    450                 455                 460
Asp Trp Gly Asp Tyr Gly His Val Asn Asp Pro Arg Leu Ser Val Pro
465                 470                 475                 480
Gly Leu Cys Tyr Gly Ala Gln Asn Ala Trp Asn Pro Val Ala Ile Asp
                485                 490                 495
Ala Cys Glu Met Asn His Arg Ile Ser Asn Leu Ala Tyr Gly Asp Glu
            500                 505                 510
Ser Gly Trp Leu Met Asp Ser Leu Ala Arg Ile Asp Ser Asp Gly Val
        515                 520                 525
Ser Phe Pro Trp Asp Leu Ala Val Gln Val Leu Glu Leu Glu Tyr Gly
    530                 535                 540
Ser Gly Thr Gly Met Leu Asn Thr Asp Val Ala Ser Tyr Val Glu Arg
545                 550                 555                 560
Ser Cys Gly Gly Glu Leu Met Phe Asp Arg Ala Leu Gly Cys Ala Asp
                565                 570                 575
Ala Arg Arg Arg Leu Leu Leu Arg Asn His Ala Arg Leu Glu Arg Arg
            580                 585                 590
Arg Asp Cys Asp Arg Ala Leu Ile Asp Cys Gly Ser Ala Val Val Ala
        595                 600                 605
Val Leu Asp Gly Leu Ala Arg Gly Gly Leu Asn Pro Glu Leu Leu Trp
    610                 615                 620
Val Met Leu Asp Gly Gln Arg Leu Phe Asn Arg Leu Gly Glu Glu Leu
625                 630                 635                 640
Leu Val Leu Ala Gly Gly Glu Asp Ala Cys Asp Thr Lys Asp Val Thr
                645                 650                 655
```

Gly Arg Ala Leu Asp Ala Ser Arg Ala Arg Leu Ala Ala Asp Leu
            660                 665                 670

Glu Leu Trp Phe Glu Arg Tyr Arg Val Gln Trp Leu Ser Ile Gly Arg
        675                 680                 685

Tyr Ala Glu Leu Ala Arg Ile Ala His Val Val Trp Ser Phe Ala Asp
    690                 695                 700

Ile Leu Arg Arg Gly Ala Leu
705                 710

<210> SEQ ID NO 129
<211> LENGTH: 634
<212> TYPE: PRT
<213> ORGANISM: Bifidobacterium longum CCOS 974

<400> SEQUENCE: 129

Met Val Glu Lys Lys Arg Leu Asp Gly Ser Asp Ala Lys Gly Ala Thr
1               5                   10                  15

Gly Ala Ala Arg Ala Thr Gly Met Leu Arg Ala Leu Arg Ala Arg Ala
            20                  25                  30

Ala Ala Ser Gly Ala Gly Arg Gly Val Thr Ala Ala Val Thr Ser Val
        35                  40                  45

Ala Ala Val Ala Met Leu Gly Ala Val Cys Val Thr Pro Ala Ser Ala
    50                  55                  60

Leu Ala Asp Val Asn Ala Asp Asp Ala Ser Gly Val Arg Ser Ala
65                  70                  75                  80

Ala Ser Ala Thr Ala Ser Asp Gly Thr Ser Ser Asp Ala Arg Ser Gln
            85                  90                  95

Ala Arg Ser Ala Thr Ser Ala Thr Arg Pro Val Ala Asn Gly Val Thr
        100                 105                 110

Val Ala Asp Glu Thr Ala Ala Asp Ala Met Pro Asp Asn Pro Asp Ala
    115                 120                 125

Glu Leu Pro Asp Lys Val Ser Ala Glu Ile Ser Asp Asp Ala Met Val
    130                 135                 140

Val Ser Glu Gln Tyr Ala Ala Thr Pro Glu Gly Glu Leu Lys Asp Ile
145                 150                 155                 160

Glu Thr Gly Glu Thr Val Thr Asp Pro Lys Ile Val Gly Thr Glu Ser
                165                 170                 175

Lys Gln Pro Asp Pro Leu Ala Lys Thr Asp Gly Glu Ser Phe Ile Pro
            180                 185                 190

Val Ser Ala Ala Asp Val Lys Glu Lys Val Ala Ala Asn Gly Gly Asp
        195                 200                 205

Val Asn Ala Val Ser Ser Lys Thr Arg Ala Ala Asn Ala Ser Val Lys
    210                 215                 220

Leu Ala Ala Leu Gln Asn Asn Glu Tyr Gly Ala His Trp Gly Thr Tyr
225                 230                 235                 240

Asn Gly Thr Gln Ala Phe Phe Asp Ala Arg Asn Asn Leu Phe Ala Gln
                245                 250                 255

Gln Ala Lys Gly Val Ile Asp Val Ser Ala Trp Gln Asn Thr Ile Asp
            260                 265                 270

Trp Gln Ala Val Lys Asn Ala Gly Val Glu Gly Ala Ile Ile Arg Leu
        275                 280                 285

Ser Tyr Gly Trp Gly Asn Gly Phe Asp Val Gln Ala Lys Arg Asn Ile
    290                 295                 300

Ser Glu Cys Lys Arg Leu Gly Ile Pro Phe Gly Val Tyr Val Phe Ser
305                 310                 315                 320

Tyr Ala Glu Ser Ala Ala Asp Gly Ala Ser Glu Gly Ala Asp Val Val
            325                 330                 335

Asn Leu Leu Arg Gln Ala Gly Val Asn Pro Gly Asp Leu Ser Tyr Pro
        340                 345                 350

Val Phe Tyr Asp Leu Glu Asn Trp Thr Tyr Thr Gly His Lys Ser Pro
    355                 360                 365

Thr Ser Pro Ser Val Tyr Asp Gly Met Val Asn Ser Trp Tyr Gly Lys
370                 375                 380

Leu Gln Ala Ala Gly Tyr Asn Asn Leu Ser Val Tyr Ser Tyr Thr Ser
385                 390                 395                 400

Tyr Leu Asn Ser Ala Leu Asn Ser Ser Asn Ile His Gly Lys Thr Arg
                405                 410                 415

Trp Val Ala Gln Tyr Gly Ser Thr Met Gln Tyr Thr Ala Phe Pro Thr
            420                 425                 430

Asn Asp Arg Gly Trp Gln Tyr Thr Ser Gly Gly Ser Ile Asn Gly Ile
        435                 440                 445

Ser Gly Arg Val Asp Met Asn Ala Phe Gly Asn Tyr Gln Phe Thr Pro
    450                 455                 460

Ala Val Gln Ile Thr Trp Val Tyr Arg Ser Glu Asp Ile Ala Val Gly
465                 470                 475                 480

Ala Ser Val Asp Tyr Pro Ser Ser Asp Ile Asp Tyr Lys Trp Gln Ser
                485                 490                 495

Tyr Asn Leu Ser Ser Lys Arg Trp Lys Thr Ile Thr Asp Trp Thr Gly
            500                 505                 510

Ala Asn Trp Ala Gly Trp Val Asp Gln Leu Gly Asp Tyr Trp Leu His
        515                 520                 525

Val Glu Ala Arg Asp Ser Arg Thr Arg Lys Ile Ile Gly Ser Gln Thr
    530                 535                 540

Ile Ala Phe Arg Tyr Ala Pro Gly Thr Thr Arg Val Ala Ala Thr Tyr
545                 550                 555                 560

Ala Gly Trp Gln Asn Asn His Val Leu Leu Gly Glu Ser Ser Asn Asn
                565                 570                 575

Ala Ala Ala His Tyr Glu Ile Lys Ile Tyr Asp Val Arg Arg Ser Lys
            580                 585                 590

Trp Val Gln Gly Phe Lys Gly Pro Trp Ala Ile Trp Lys Pro Lys Lys
        595                 600                 605

Gly Ile Tyr Trp Thr His Tyr Glu Val Tyr Thr Ser Asp Gly Arg Leu
    610                 615                 620

Ala Asp Thr Lys Thr Tyr Ala Phe Gly Val
625                 630

<210> SEQ ID NO 130
<211> LENGTH: 439
<212> TYPE: PRT
<213> ORGANISM: Lactococcus lactis CCOS 949

<400> SEQUENCE: 130

Met Pro Val Ser Arg Ile Lys Val Lys Asn Arg His Leu Lys Lys Lys
1               5                   10                  15

Ala Lys Lys Pro Leu Ala Phe Tyr Lys Pro Ala Thr Lys Phe Ala Gly
            20                  25                  30

Ala Val Leu Ile Ala Gly Thr Leu Thr Thr Thr His Glu Leu Leu Leu
        35                  40                  45

Gln Gln Thr Ser Pro Met Val Gln Ala Ala Thr Asn Ser Thr Glu Ala
    50                  55                  60

Phe Ile Glu Ser Ile Ala Ala Ser Ala Lys Pro Val Ala Asp Ser Asn
 65                  70                  75                  80

Gly Leu Tyr Pro Ser Val Met Ile Ala Gln Ala Ile Leu Glu Ser Asn
             85                  90                  95

Trp Gly Ser Ser Gln Leu Ser Arg Ala Pro Tyr Tyr Asn Leu Phe Gly
            100                 105                 110

Ile Gln Gly Thr Tyr Gln Gly Lys Ser Val Val Phe Lys Thr Gln Glu
            115                 120                 125

Tyr Leu Asn Gly Lys Trp Val Thr Lys Asp Met Pro Phe Arg Val Tyr
            130                 135                 140

Pro Ser Phe Asn Gln Ser Phe Gln Asp Asn Ala Tyr Val Leu Lys Thr
145                 150                 155                 160

Thr Asn Phe Gly Asn Gly Pro Tyr Tyr Ala Lys Ala Trp Arg Ala Asn
                165                 170                 175

Ala Ala Thr Tyr Gln Ala Ala Thr Ala Ala Leu Thr Gly Lys Tyr Ala
                180                 185                 190

Thr Asp Pro Asn Tyr Gly Ala Ser Leu Asn Arg Ile Ile Ser Gln Tyr
            195                 200                 205

Asn Leu Thr Arg Phe Asp Gly Ala Ser Ser Ala Gly Thr Ser Asn Ser
210                 215                 220

Gly Gly Ser Thr Ala Thr Asn Thr Asn Asn Ser Asn Thr Ser Ser
225                 230                 235                 240

Thr Thr Tyr Thr Val Lys Ser Gly Asp Thr Leu Trp Gly Ile Ser Gln
                245                 250                 255

Lys Tyr Gly Ile Ser Val Ala Gln Ile Gln Ser Ala Asn Asn Leu Lys
            260                 265                 270

Ser Thr Val Ile Tyr Ile Gly Gln Lys Leu Val Leu Thr Thr Ser Ser
            275                 280                 285

Ser Ser Ser Asn Thr Asn Ser Ser Thr Ser Ser Gly Asn Ser Ala Gly
            290                 295                 300

Thr Thr Thr Pro Thr Thr Ser Val Thr Pro Ala Lys Pro Ala Ser Gln
305                 310                 315                 320

Thr Thr Ile Lys Val Lys Ser Gly Asp Thr Leu Trp Gly Leu Ser Val
                325                 330                 335

Lys Tyr Lys Thr Thr Ile Ala Gln Leu Lys Ser Trp Asn His Leu Asn
            340                 345                 350

Ser Asp Thr Ile Phe Ile Gly Gln Asn Leu Ile Val Ser Gln Ser Ala
            355                 360                 365

Gly Ser Ser Ser Ser Ser Thr Gly Ser Ser Ala Ser Thr Ser Ser
            370                 375                 380

Thr Ser Asn Ser Ser Ala Ala Ser Asn Thr Ser Ile His Lys Val Val
385                 390                 395                 400

Lys Gly Asp Thr Leu Trp Gly Leu Ser Gln Lys Ser Gly Ser Pro Ile
            405                 410                 415

Ala Ser Ile Lys Ala Trp Asn His Leu Ser Ser Asp Thr Ile Leu Ile
            420                 425                 430

Gly Gln Tyr Leu Arg Ile Lys
            435

<210> SEQ ID NO 131
<211> LENGTH: 347
<212> TYPE: PRT
<213> ORGANISM: Lactococcus lactis CCOS 949

<400> SEQUENCE: 131

Met Lys Lys Val Ile Lys Arg Lys Val Ile Leu Phe Ser Leu Pro Phe
1               5                   10                  15

Leu Leu Leu Leu Leu Pro Ile Leu Ala Phe Phe Ala Leu Phe Val Gly
            20                  25                  30

Ser Ser Asp Leu Ser Ser Asp Thr Asp Ile Asn Thr Asn Thr Pro Gln
        35                  40                  45

Gln Gln Thr Ala Lys Val Ile Trp Asp Arg Val Leu Lys Glu Gly Gly
    50                  55                  60

Thr Lys Glu Gly Ala Ala Leu Leu Gly Asn Asn Gln Ala Glu Ser
65                  70                  75                  80

Glu Leu Gln Pro Ser Ile Ile Gln Ser Asn Ala Thr Tyr Asn Glu Ala
                85                  90                  95

Lys Ala Met Asp Thr Thr Leu Gly Gly Tyr Ala Phe Gly Leu Ala Gln
            100                 105                 110

Trp Asp Ser Gly Arg Arg Val Asn Leu Leu Asn Tyr Ala Lys Ser Gln
        115                 120                 125

Lys Lys Ser Trp Thr Asp Thr Asn Leu Gln Val Glu Phe Met Phe Glu
130                 135                 140

Gln Asp Gly Thr Asp Ser Thr Leu Leu Lys Gln Leu Ile Lys Gly Thr
145                 150                 155                 160

Asn Val Lys Gln Thr Thr Glu Asp Ile Met Arg Lys Trp Glu Arg Ala
                165                 170                 175

Gly Ala Val Asp Ser Leu Pro Lys Arg Gln Gly Phe Ala Glu Tyr Trp
            180                 185                 190

Tyr Thr Phe Met Thr Thr Gly Gly Asp Ser Gly Thr Gly Gly Gly Ser
        195                 200                 205

Gly Ile Thr Pro Asp Ile Pro Ser Gly Trp Thr Leu Asp Lys Pro Ile
    210                 215                 220

Asn Thr Ser Gly Tyr Leu Ala Thr Ser Tyr Glu Tyr Lys Gln Cys Thr
225                 230                 235                 240

Trp Phe Thr Trp Asn Arg Ala Gln Asp Phe Gly Ile Thr Phe Gly Met
                245                 250                 255

Tyr Met Gly Asn Gly Ala Asp Trp Gln His Gln Ala Gly Tyr Thr Val
            260                 265                 270

Thr Thr Thr Pro Thr Leu His Ser Ala Val Ser Phe Ser Gly Gly Gln
        275                 280                 285

Thr Val Gly Gly Gln Trp Thr Ala Asp Pro Gln Tyr Gly His Val Ala
    290                 295                 300

Phe Val Glu Gly Ile His Ser Asp Gly Ser Val Leu Ile Ser Gln Ser
305                 310                 315                 320

Gly Thr Gly Phe Ser Thr Val Tyr Thr Phe Gln Val Leu Thr Lys Ala
                325                 330                 335

Gln Ala Ser Gln Leu His Tyr Val Ile Gly Lys
            340                 345

<210> SEQ ID NO 132
<211> LENGTH: 297
<212> TYPE: PRT
<213> ORGANISM: Lactococcus lactis CCOS 949

<400> SEQUENCE: 132

Met Gln Tyr Lys Lys Lys Glu Asn Lys Val Leu Val Ile Phe Val Leu
1               5                   10                  15

Val Val Ile Phe Ile Leu Cys Gly Cys Ile Tyr Val Leu Leu Val Arg
            20                  25                  30

Tyr Thr His Thr Asp Lys Ile Thr Ile Ser Tyr Lys Gln Pro Thr
        35                  40                  45

Lys Thr Ser Ala Ser Asn Gly Tyr Val Glu Lys Gly Glu Glu Ala
 50                  55                  60

Ala Val Gly Ser Ile Thr Leu Val Asp Asp Ala Gly Val Pro Glu Trp
 65                  70                  75                  80

Val Lys Val Pro Ser Lys Val Asn Leu Asp Lys Phe Thr Asp Leu Ser
                85                  90                  95

Thr Asn Asn Ile Thr Ile Tyr Arg Ile Asn Asn Pro Glu Val Leu Lys
            100                 105                 110

Thr Val Thr Asn Arg Thr Asp Gln Arg Met Lys Met Ser Glu Val Ile
        115                 120                 125

Ala Lys Tyr Pro Asn Ala Leu Ile Met Asn Ala Ser Ala Phe Asp Met
130                 135                 140

Gln Thr Gly Gln Val Ala Gly Phe Gln Ile Asn Asn Gly Lys Leu Ile
145                 150                 155                 160

Gln Asp Trp Ser Pro Gly Thr Thr Thr Gln Tyr Ala Phe Val Ile Asn
                165                 170                 175

Lys Asp Gly Ser Cys Lys Ile Tyr Asp Ser Ser Thr Pro Ala Leu Thr
            180                 185                 190

Ile Ile Lys Asn Gly Gly Gln Gln Ala Tyr Asp Phe Gly Thr Ala Ile
        195                 200                 205

Ile Arg Asp Gly Lys Ile Gln Pro Ser Asp Gly Ser Val Asp Trp Lys
210                 215                 220

Ile His Ile Phe Ile Ala Asn Asp Lys Asp Asn Leu Tyr Ala Ile
225                 230                 235                 240

Leu Ser Asp Thr Asn Ala Gly Tyr Asp Asn Ile Met Lys Ser Val Ser
                245                 250                 255

Asn Leu Lys Leu Gln Asn Met Leu Leu Leu Asp Ser Gly Gly Ser Ser
            260                 265                 270

Gln Leu Ser Val Asn Gly Lys Thr Ile Val Ala Ser Gln Asp Asp Arg
        275                 280                 285

Ala Val Pro Asp Tyr Ile Val Met Lys
290                 295

<210> SEQ ID NO 133
<211> LENGTH: 499
<212> TYPE: PRT
<213> ORGANISM: Lactococcus lactis CCOS 949

<400> SEQUENCE: 133

Met Thr Asn Asn Asp Lys Thr Lys Arg Leu Lys Lys Glu Lys Phe Ile
1               5                   10                  15

Ala Gly Thr Ala Leu Ile Leu Gly Met Thr Thr Phe Gly Val Ala Gly
            20                  25                  30

His Ala Asp Gly Val Thr Val Gly Ser Ser Asp Ala Ser Ser Ser
        35                  40                  45

Thr Gly Ser Ser Ser Ser Ser Gly Thr Gly Ser Ser Ser Ser
    50                  55                  60

Ser Ser Thr Gly Ser Ser Ser Ser Ser Asn Ser Asn Ala Ser Ser
65                  70                  75                  80

Ser Ser Ser Ser Thr Gly Asn Ser Ser Ser Ser Lys Pro Ser Thr
                85                  90                  95

-continued

```
Ser Gly Ser Thr Ser Lys Pro Ser Asn Pro Ser Ser Ser Thr Asn Asn
                100                 105                 110

Asn Ser Thr Ser Asn Ser Ser Thr Thr Gln Ala Pro Ser Thr Ser
        115                 120                 125

Val Ser Thr Ile Ala Pro Ser Ala Ser Thr Ser Thr Val Ala Pro Ser
    130                 135                 140

Asn Tyr Ser Gln Asp Asn Ala Tyr Tyr Gln Thr Ser Thr Ala Ala Gln
145                 150                 155                 160

Ile Pro Asn Ser Ser Ala Asp Ser Ala Pro Ser Ile Tyr Ala Gly Pro
                165                 170                 175

Val Leu Lys Thr Ile Glu Ala Ala Lys Ser Ile Asp Lys Ile Asp Thr
            180                 185                 190

Ser Ser Thr Glu Ala Phe Ile Lys Ser Ile Ala Asp Arg Val Arg Ile
        195                 200                 205

Leu Ala Gly Lys Asn Asn Leu Tyr Ala Ser Ile Ile Leu Ala Gln Ala
    210                 215                 220

Ile Leu Glu Ser Gly Ser Gly Gln Ser Asn Met Ser Gln Gln Tyr Phe
225                 230                 235                 240

Asn Ile Phe Asn Ile Thr Gly Ala Tyr Leu Gly Lys Ser Ile Ser Phe
                245                 250                 255

Lys Thr Glu Glu Phe Ser Gly Asn Asn Pro Tyr Tyr Ile Glu Gln Ser
            260                 265                 270

Phe Arg Val Tyr Ser Asn Tyr Asp Gln Ala Leu Asp Asp Tyr Ile Asn
        275                 280                 285

Leu Met Ile Lys Gly Thr Thr Trp Asn Ser Glu Ile Tyr Ala Gly Ala
    290                 295                 300

Trp Lys Ser His Ala Lys Thr Tyr Gln Glu Ala Ala Gln Ala Leu Gln
305                 310                 315                 320

Gly Ile Phe Ala Thr Asp Pro Ala Tyr Ala Gln Lys Leu Ile Glu Ile
                325                 330                 335

Ile Gln Glu Tyr Lys Leu Asp Ala Tyr Asp Asn Val Asp Ser Thr Thr
            340                 345                 350

Gln Val Val Asp Ser Lys Ile Pro Glu Ser Pro Leu Ala Ser Lys
        355                 360                 365

Leu Asp Asn Ser Ala Tyr Pro Glu Tyr Asn Gly Val Glu Tyr Pro Gly
370                 375                 380

Ala Asp Ser Tyr Ala Phe Gly Asn Cys Thr Gln Tyr Val Tyr Asn Arg
385                 390                 395                 400

Ile Ile Gln Leu Gly Gly Leu Val Gly Thr His Met Gly Asn Gly Gly
                405                 410                 415

Glu Trp Gly Ile Asn Ala Gln Ala Gln Gly Tyr Phe Thr Thr Thr Val
            420                 425                 430

Pro Thr Glu Gly Tyr Ala Val Ser Phe Pro Pro Gly Val Ala Gly Ser
        435                 440                 445

Ser Ser Glu Tyr Gly His Val Ala Phe Val Glu Lys Val Tyr Ser Asp
    450                 455                 460

Asn Ser Ile Leu Val Ser Glu Met Asn Val Lys Gly Asn Asn Ile Val
465                 470                 475                 480

Ser Glu Arg His Ile Ser Ala Gly Val Ala Ala Leu Ala Thr Tyr Ile
                485                 490                 495

Gln Pro Lys
```

```
<210> SEQ ID NO 134
<211> LENGTH: 259
<212> TYPE: PRT
<213> ORGANISM: Lactococcus lactis CCOS 949

<400> SEQUENCE: 134
```

| | | | | | | | | | | | | | | |
|---|---|---|---|---|---|---|---|---|---|---|---|---|---|---|
| Met | Ser | Ser | Ile | Glu | Asn | Met | Ile | Ala | Trp | Met | Gln | Ala | Arg | Lys | Gly |
| 1 | | | | 5 | | | | | 10 | | | | | 15 | |
| Lys | Val | Thr | Tyr | Ser | Met | Thr | Leu | Arg | Met | Gly | Pro | Arg | Ser | Tyr | Asp |
| | | | 20 | | | | | 25 | | | | | 30 | | |
| Cys | Ser | Ser | Ser | Val | Phe | Phe | Ala | Met | Ile | Ala | Gly | Gly | Phe | Leu | Ser |
| | | | 35 | | | | | 40 | | | | | 45 | | |
| Glu | Gly | Ser | Met | Gly | Asn | Thr | Glu | Thr | Leu | Phe | Gly | Met | Ser | Gly | Thr |
| | | 50 | | | | | 55 | | | | | 60 | | | |
| Lys | Leu | Lys | Glu | Ile | Ser | Arg | Gly | Glu | Val | His | Arg | Gly | Asp | Ile | Phe |
| 65 | | | | | 70 | | | | | 75 | | | | | 80 |
| Ile | Ser | Gly | Thr | Pro | Gly | Gly | Ser | Ala | Gly | Ser | Asp | Gly | His | Thr | Gly |
| | | | | 85 | | | | | 90 | | | | | 95 | |
| Ile | Phe | Leu | Ser | Asn | Gly | Ser | Phe | Ile | His | Cys | Ser | Tyr | Thr | His | Asn |
| | | | | 100 | | | | | 105 | | | | | 110 | |
| Gly | Ile | Ala | Val | Asp | Thr | Asn | Asp | Ala | Tyr | Met | Ser | Thr | Arg | Leu | Pro |
| | | | 115 | | | | | 120 | | | | | 125 | | |
| His | His | Phe | Tyr | Arg | Ile | Val | Gly | Ser | Gly | Ser | Ala | Asn | Thr | Asp | Ser |
| | | 130 | | | | | 135 | | | | | 140 | | | |
| Lys | Pro | Gln | Met | Val | Thr | Leu | Asn | Val | Asp | Gly | Gln | Phe | Gly | Asn | Ala |
| 145 | | | | | 150 | | | | | 155 | | | | | 160 |
| Thr | Ala | Lys | Arg | Leu | Gln | Glu | Tyr | Phe | Asp | Thr | Ala | Gly | Lys | Asp | Gly |
| | | | | 165 | | | | | 170 | | | | | 175 | |
| Val | Ile | Ser | His | Gln | Tyr | Lys | Gln | Thr | Phe | Asn | Gln | Asn | Ile | Tyr | Ala |
| | | | 180 | | | | | 185 | | | | | 190 | | |
| Ala | Gln | Phe | Asp | Ser | Ser | Leu | Thr | Gly | Ser | Asn | Val | Val | Lys | Ala | Leu |
| | | | 195 | | | | | 200 | | | | | 205 | | |
| Gln | Arg | Phe | Leu | Gly | Ile | Gly | Gln | Asp | Gly | Leu | Phe | Gly | Gln | Gly | Thr |
| | | 210 | | | | | 215 | | | | | 220 | | | |
| Ile | Lys | Ala | Leu | Gln | Lys | His | Leu | Gly | Thr | Thr | Gln | Asp | Gly | Thr | Ile |
| 225 | | | | | 230 | | | | | 235 | | | | | 240 |
| Ser | Pro | Val | Ser | Asp | Ser | Val | Arg | Glu | Leu | Gln | Arg | Arg | Leu | Asn | Ala |
| | | | | 245 | | | | | 250 | | | | | 255 | |
| Asn | Lys | Leu | | | | | | | | | | | | | |

```
<210> SEQ ID NO 135
<211> LENGTH: 271
<212> TYPE: PRT
<213> ORGANISM: Lactococcus lactis CCOS 949

<400> SEQUENCE: 135
```

| | | | | | | | | | | | | | | |
|---|---|---|---|---|---|---|---|---|---|---|---|---|---|---|
| Met | Lys | Pro | Lys | Met | Arg | Arg | Lys | Leu | Lys | Lys | Met | Gly | Ala | Phe | Ile |
| 1 | | | | 5 | | | | | 10 | | | | | 15 | |
| Phe | Thr | Ala | Ser | Met | Ile | Ala | Met | Ile | Ala | Leu | Leu | Gly | Leu | Val | Arg |
| | | | 20 | | | | | 25 | | | | | 30 | | |
| Ile | Arg | Pro | Val | Glu | Pro | Pro | Lys | Lys | Ala | Ala | Thr | Glu | Lys | Ile | Val |
| | | | 35 | | | | | 40 | | | | | 45 | | |
| Val | Asn | His | Ile | Leu | Asp | Glu | Lys | Val | Leu | Asp | Leu | Asn | Lys | Pro | Val |
| | | | 50 | | | | | 55 | | | | | 60 | | |
| Val | Asp | Leu | Ser | Gly | Trp | Gln | Arg | Pro | Glu | Asp | Ile | Asp | Tyr | Asn | Thr |
| 65 | | | | | 70 | | | | | 75 | | | | | 80 |

```
Leu Ser Gln His Val Ile Gly Ala Val Ile Arg Val Asn Gly Ser Tyr
                85                  90                  95

Gly His Ala Asp Asn Ser Ala Ser Lys Asp Gly Glu Asp Thr Ala Tyr
            100                 105                 110

Lys Gln His Ile Lys Ala Phe Gln Glu Arg Gly Ile Pro Thr Ala Val
        115                 120                 125

Tyr Ala Phe Val Thr Gly Glu Asn Thr Ser Glu Met Arg Lys Gln Ala
    130                 135                 140

Arg Asp Phe Tyr Arg Arg Ala Ser Pro Tyr Lys Pro Thr Tyr Tyr Trp
145                 150                 155                 160

Leu Asp Val Glu Val Thr Asn Met Lys Asn Met Asn Gln Gly Ile Glu
                165                 170                 175

Ala Phe Arg Ser Glu Leu Glu Lys Gln Gly Ala Lys Asn Ile Gly Ile
            180                 185                 190

Tyr Ala Gln Asp Trp Phe Leu Arg Asp Asn Gln Ile Lys Val Asp Lys
        195                 200                 205

Phe Lys Ala Ile Trp Ile Ala Ala Tyr Gly Arg Asn Thr Gly Tyr Trp
    210                 215                 220

Asp Ala Ser Pro Glu Thr Thr Leu Ser Tyr Lys Met Gln Gln Phe Thr
225                 230                 235                 240

Asp Gln Gly Thr Leu Pro Gly Tyr Ser Gly Asn Val Asp Leu Asn Met
                245                 250                 255

Val Asn Asn Gln Thr Asn Tyr Asn Glu Leu Phe Lys Asn Gln Lys
            260                 265                 270

<210> SEQ ID NO 136
<211> LENGTH: 870
<212> TYPE: PRT
<213> ORGANISM: Lactococcus lactis CCOS 949

<400> SEQUENCE: 136

Met Asp Lys Arg Ser Lys Glu Asn Phe Lys Ala Ser Leu Asn Val Gln
1               5                   10                  15

Lys Arg Val Ser Asp Gly Ile Asp Ala Asn Ala Phe Arg Lys Pro Arg
            20                  25                  30

Gln Ala Thr Gln Leu Ser Lys Gln Ala Phe Lys Glu Gly Lys Lys Thr
        35                  40                  45

Leu Lys Ile Arg Arg Lys Asn Tyr Arg Lys Leu Lys Ala Gly Ser Gly
    50                  55                  60

Leu Gln Val Val Ala Ala Lys Lys Val Leu Glu Ala Lys Ala Asp
65                  70                  75                  80

Lys Thr Val Ser Lys Ala Val Phe Lys Asn Ala Lys Lys Ser Asp Pro
                85                  90                  95

Thr Arg Ala Ala Asn Gln Ala Lys Gly Tyr Ala Lys Asn Gln Ala Lys
            100                 105                 110

Gln Thr Ala Val Asn His Leu Val Leu Ser Pro Leu Glu Lys Asp Asp
        115                 120                 125

Thr Leu Arg Glu Gly Ser Asp Leu Tyr Arg Lys Thr Gln Arg Thr Lys
    130                 135                 140

Ser Gly Leu Lys Leu Ser Lys Asp Val Val Thr Ser Ser Ala Lys Ala
145                 150                 155                 160

Ser Val Asn Leu Ser Asn His Thr Tyr Gly Leu Ala Asn Arg Ser Val
                165                 170                 175

Asn Ile Val Arg Gly Arg Gly Phe Val Arg Thr Pro Ser Glu Leu Gly
            180                 185                 190
```

```
Phe Arg Arg Gln Ala Ala Lys Arg Met Arg Asn Phe Gln Asn Lys Leu
            195                 200                 205

Ser Ala Ala Arg Lys Ala Lys Lys Ala Glu Gln Gly Phe Ser Leu Ile
210                 215                 220

Arg Ser Ile Leu Lys Gly Gln Gln Thr Leu Ser Arg Ala Phe Thr Leu
225                 230                 235                 240

Ile Val Thr Ser Lys Gly Leu Leu Val Val Leu Ala Val Met Phe Ile
                245                 250                 255

Leu Cys Leu Leu Gly Ile Leu Asn Met Ala Ser Ser Val Pro Thr Lys
            260                 265                 270

Gln Asp Asp Phe Gln Leu Thr Lys Ser Trp Thr Tyr Phe Thr Lys Leu
        275                 280                 285

Asp Ala Asp Asn Ser Glu Asn Gly Asn Ser Phe Tyr Thr Pro Leu Asp
    290                 295                 300

Asp Val Met Phe Tyr Met Asn Asp Gln Phe Glu Asp Tyr Asn Leu Gln
305                 310                 315                 320

Asp Gln Val Pro Val Gly Ser Asn Gly Ala Ala Leu Pro Asn Gln Asn
                325                 330                 335

Tyr Glu Gln Tyr Leu Thr Gly Leu Trp Ser Ala Leu Asn Gly Ser Ser
            340                 345                 350

Pro Asp Tyr Lys Leu Thr Thr Met Glu Ala Leu Glu Thr Asp Lys Arg
        355                 360                 365

Ser Lys Tyr Tyr Leu Ser Pro Asp Asp Tyr Ser Asp Phe Lys Glu Arg
    370                 375                 380

Val Asn Glu Val Gly Tyr Asp Ser Leu Asp Gly Gln Leu Gln Phe Pro
385                 390                 395                 400

Tyr Gln Thr Glu Ser Leu Val Ile Asn Arg Arg Tyr Gly Tyr Glu Arg
                405                 410                 415

Asn Gly Asp Lys Thr Glu Leu His Ala Ser Ile Asp Val Ser Ser Ala
            420                 425                 430

Pro Gly Gln Asp Leu Thr Ser Pro Met His Gly Ile Val Asn Ser Val
        435                 440                 445

Thr Asp Pro Asn Thr Leu Val Ile Ser Glu Ala Glu Asn Ala Arg Leu
    450                 455                 460

Thr Ile Val Gly Ile Asn Ser Gly Arg Phe Ile Gly Gly Glu Thr Val
465                 470                 475                 480

Asp Ala Gly Thr Leu Leu Gly Lys Ala Thr Lys Ser Ser Leu Asn Met
                485                 490                 495

Thr Tyr Glu Lys Tyr Asn Glu Asp Asp Lys Lys Trp Glu Lys Val Asn
            500                 505                 510

Pro Ala Phe Tyr Phe Pro Lys Val Thr Tyr Thr Gln Phe Thr Ser Leu
        515                 520                 525

Ala Ser Asp Ser Phe Asp Pro Gly Lys Ser Val Ser Glu Arg Ala Glu
    530                 535                 540

Ala Val Tyr Asn Phe Leu Thr Lys Leu Gly Tyr Lys Lys Glu Gly Ile
545                 550                 555                 560

Cys Ala Ile Leu Gly Ser Phe Thr Glu Glu Ser Gln Ile Asn Pro Lys
                565                 570                 575

Arg Ala Glu Gly Asp Tyr Leu Ser Pro Val Gly Ala Ser Gly Asn
            580                 585                 590

Ser Trp Asp Asp Pro Ala Trp Leu Ala Met Gly Gly Leu Asp Ile Tyr
        595                 600                 605
```

Gly Lys Tyr Pro Asn Ile Leu His Arg Gly Leu Gly Leu Gly Gln Trp
610                 615                 620

Thr Asp Thr Ser Asp Gly Ser Glu Arg His Thr Leu Leu Leu Asn Tyr
625                 630                 635                 640

Ala Lys Ala Lys Asn Lys Lys Trp Tyr Asp Leu Asp Leu Gln Leu Asp
                645                 650                 655

Phe Met Leu Asn Gly Asp Thr Pro Gly Asn Gln Thr Met Phe Lys Asn
                660                 665                 670

Thr Ala Ser Asn Ala Val Ser Ser Ile Pro Glu Leu Thr Asn Tyr
                675                 680                 685

Phe Leu Thr Tyr Trp Glu Gly Asn Pro Gly Asp Lys Ile Gln Ala Arg
690                 695                 700

Val Gln Ala Ala Gln Asn Trp Phe Thr Tyr Phe Ser Asn Asn Gly Gly
705                 710                 715                 720

Ser Asp Ala Asp Met Ser Ala Ser Ser Lys Glu Leu Phe Glu Lys Tyr
                725                 730                 735

Lys Asp Lys Ile Lys Pro Leu Pro Ser Asn Lys Glu Thr Gln Gln Gly
                740                 745                 750

Gln Gly Trp Pro Gly Asn Gly Tyr Glu Pro Gly Asn Cys Thr Trp Tyr
                755                 760                 765

Val Phe Asn Arg Gln Ala Gln Ile Gly His Asn Ile Asn Gly Tyr Met
770                 775                 780

Gly Asn Gly Gly Gln Trp Gly Tyr Asn Tyr Thr Lys Thr Pro Gly Ala
785                 790                 795                 800

Thr Ile Asp Ser Lys Pro Gln Val Gly Asp Ala Val Ser Phe Ser Pro
                805                 810                 815

Gly Val Ala Gly Ser Ser Glu Tyr Gly His Val Ala Gln Val Glu
                820                 825                 830

Val Val Asn Pro Asp Gly Thr Phe Leu Val Ser Glu Met Asn Thr Leu
                835                 840                 845

Gly Leu Tyr Ser Met Gly Tyr Arg Met Phe Lys Pro Gly Ala Gly Met
                850                 855                 860

Thr Phe Val His Phe Lys
865                 870

<210> SEQ ID NO 137
<211> LENGTH: 325
<212> TYPE: PRT
<213> ORGANISM: Lactococcus lactis CCOS 949

<400> SEQUENCE: 137

Met Glu Lys Gly Leu Leu Val Asp Ile Gly Arg Lys Tyr Trp Ser Ile
1               5                   10                  15

Ala Glu Leu Lys Arg Leu Val Leu Leu Gln Glu His Lys Leu Thr
                20                  25                  30

His Leu Gln Leu His Leu Asn Glu Asn Glu Gly Phe Ala Leu Asn Phe
            35                  40                  45

Thr Asp Ser Pro Val Ser Lys Lys Tyr Ser Glu Asn Met Leu Lys Glu
50                  55                  60

Leu Lys Glu Phe Ala Lys Thr His Glu Ile Thr Leu Ile Pro Asp Phe
65                  70                  75                  80

Asp Ser Pro Gly His Met Gly Ser Leu Leu Glu Gln Asn Pro Glu Phe
                85                  90                  95

Ala Leu Pro Asp Ser Asn Gln Gln Ala Val Asp Val Thr Asn Pro Ala
                100                 105                 110

Val Ile Asp Trp Ile Met Gly Ile Asp Lys Ile Asp Ile Phe
            115                 120                 125

Pro Asp Ser Asp Thr Phe His Ile Gly Ala Asp Glu Phe Ile Asp Phe
    130                 135                 140

Arg Gln Ile Glu Lys Tyr Pro Tyr Leu Val Glu Lys Thr Arg Glu Lys
145                 150                 155                 160

Tyr Gly Asn Lys Ala Ser Gly Leu Glu Phe Tyr Tyr Asp Tyr Val Asn
                165                 170                 175

Gln Leu Thr Glu His Leu Gln Lys Gly Lys Gln Val Arg Ile Trp
            180                 185                 190

Asn Asp Gly Phe Leu Arg Lys Asp Leu Gln Ser Leu Val Pro Leu Asn
    195                 200                 205

Lys Asn Val Glu Val Cys Tyr Trp Thr Asn Trp Asp Lys Gly Met Ala
210                 215                 220

Glu Val Lys Glu Trp Leu Thr Lys Gly Tyr Thr Leu Ile Asn Phe Cys
225                 230                 235                 240

Asp Asn Asp Leu Tyr Tyr Val Leu Gly Glu Glu Ala Gly Tyr Ser Tyr
                245                 250                 255

Pro Thr Ala Glu Lys Leu Glu Arg Glu Gly Lys Ile Gln Lys Phe Ser
            260                 265                 270

Gly Gln Gln Tyr Leu Asn Gln Glu Glu Met Lys Ala Val Arg Gly Thr
    275                 280                 285

Tyr Phe Ser Ile Trp Ala Asp Asn Ala Ala Ala Lys Ser Val Ser Glu
    290                 295                 300

Ile Leu Asp Asp Leu Ser Lys Val Leu Pro Val Phe Met Lys Ile Tyr
305                 310                 315                 320

Gly Gly Asn Asp Glu
            325

<210> SEQ ID NO 138
<211> LENGTH: 546
<212> TYPE: PRT
<213> ORGANISM: Lactococcus lactis CCOS 949

<400> SEQUENCE: 138

Met Lys Lys Ser Lys Phe Phe Ile Arg Ile Cys Leu Ser Thr Gly
1               5                   10                  15

Ile Leu Ala Ser Ala Thr Leu Leu Thr Ala Cys Phe Gly Thr Pro Ala
            20                  25                  30

Lys His Val Lys Ala Asn Tyr Lys Val Thr Ala Glu Ala Ile Pro Asp
        35                  40                  45

Tyr Gln Ser Lys Asn Ala Pro Ile Ser Ser Tyr Trp Met Pro Asp Lys
50                  55                  60

Phe Leu Glu Trp Ser Ala Glu Asn Asp Lys Asp Leu Val Tyr Asn Gln
65                  70                  75                  80

Ser Arg Val Pro Leu Thr Lys Arg Ile Ser Pro Asp Lys Leu Ser Pro
                85                  90                  95

Ser Asn Gln Asn Gln Asn Lys Lys Thr Lys Ile Val Ala Leu Ser Met
            100                 105                 110

Met Asn Ser Gln Thr Ser Gly Asn Pro Ser Arg Gly Thr Thr Lys Phe
        115                 120                 125

Glu Ser Tyr Thr Phe Asp Tyr Trp Gln Tyr Ile Asp Thr Leu Val Tyr
    130                 135                 140

Trp Gly Gly Ser Ser Gly Glu Gly Ile Ile Val Thr Pro Ser Ala Asp
145                 150                 155                 160

```
Val Ile Asp Glu Ala His Ser Asn Gly Val Pro Leu Gly Thr Ile
                165                 170                 175

Phe Leu Pro Pro Lys Glu Tyr Gly Lys Val Asp Trp Val Lys Thr
            180                 185                 190

Met Leu Lys Lys Asp Glu Gln Gly Gln Tyr Pro Phe Ala Ser Gln Met
            195                 200             205

Val Lys Val Ala Lys Thr Tyr Gly Phe Glu Gly Trp Phe Ile Asn Glu
210                 215                 220

Glu Thr Gln Gly Leu Asn Ala Asp Asp Ala Ala Asn Met Lys Ala Leu
225                 230                 235                 240

Ile Gln Gln Val Lys Lys Glu Asp Ser Ser Leu Gln Ile Met Trp Tyr
                245                 250                 255

Asp Ala Met Thr Lys Asp Gly Lys Val Asp Trp Gln Asn Gln Leu Asn
                260                 265                 270

Asp Gln Asn Ala Thr Phe Val Gln Asp Lys Ala Ala Asp Ala Met Phe
                275                 280                 285

Leu Asn Phe Trp Trp Thr Gln Asn Asn Leu Ala Asp Gln Lys Leu Leu
            290                 295                 300

Glu Lys Ser Asn Leu Tyr Ala Lys Asn His Asn Ile Asp Pro Tyr Asn
305                 310                 315                 320

Ile Tyr Ala Gly Ile Asp Val Gln Ala Lys Asp Val Gln Thr Pro Val
                325                 330                 335

Lys Trp Asn Leu Leu Glu Lys Gly Asn Gln Ala Thr Gln Thr Ser Ile
                340                 345                 350

Gly Leu Tyr Ala Ala Ser Ala Thr Tyr Thr Asn Ala Ser Asn Trp Asp
            355                 360                 365

Asp Phe Gln Asn Arg Glu Ser Ala Phe Trp Val Asn Gln Lys Ala Asp
            370                 375                 380

Pro Arg Gln Val Asp His Ser Val Asn Glu Ser Trp Thr Gly Leu Ser
385                 390                 395                 400

Lys Tyr Val Leu Glu Lys Ser Ala Ile Ser Gly Asn Glu Phe Asn Thr
                405                 410                 415

Asn Phe Asn Leu Gly Asn Gly Tyr Asn Tyr Phe Lys Ala Gly Gln Lys
            420                 425                 430

Ile Ser Glu Met Asp Trp Asn Asp Arg Ser Leu Ala Gly Ile Leu Pro
            435                 440                 445

Ser Tyr Arg Trp Ile Ile Asp Asn Glu Gly Lys Asn Lys Ile Ser Pro
            450                 455                 460

Ser Phe Asp Phe Ala Asn Ala Tyr Asn Gly Gly Asn Ser Leu Lys Phe
465                 470                 475                 480

Met Ala Glu His Leu Asp Ala Gly Lys Ser Ser Asn Ile Thr Leu Phe
                485                 490                 495

Ala Ser Asp Leu Lys Ile Ala Met Gly Ala Lys Phe Ser Val Ser Met
            500                 505                 510

Arg Ser Asp Gln Ala Leu Lys Val Ser Ala Ile Leu Glu Leu Ala Asn
            515                 520                 525

Gly Gln Lys Val Ser Ile Ala Gly Asp Lys Ser Leu Thr Glu Asn Trp
530                 535                 540

Ser Lys
545
```

-continued

```
<210> SEQ ID NO 139
<211> LENGTH: 209
<212> TYPE: PRT
<213> ORGANISM: Lactococcus lactis CCOS 949

<400> SEQUENCE: 139

Met Lys Tyr Lys Thr Arg Arg Lys Pro Asn Arg Arg Gln Ser Leu
1               5                   10                  15

Leu Lys Gln Leu Ile Phe Ile Phe Leu Val Ile Leu Gly Ile Leu Val
                20                  25                  30

Tyr Asn Lys Ile Phe Asn Asn Gln Ala Gln Lys Pro Ser Glu Ala Gln
            35                  40                  45

Leu Gln Glu Ile Asn Glu His Lys Phe Ile Lys Glu Ile Ala Pro Leu
    50                  55                  60

Ala Gln Lys Ser Gln Lys Glu Ser Gln Val Leu Ala Ser Ile Thr Ile
65                  70                  75                  80

Ala Gln Ala Cys Leu Glu Ser Asn Phe Gly Lys Ser Glu Leu Ala Ser
                85                  90                  95

Lys Tyr His Asn Leu Phe Gly Val Lys Ala Ser Asp Asp Val Pro Lys
            100                 105                 110

Val Ser Leu Ala Thr Gln Glu Tyr Glu Asn Gly Gln Trp Val Thr Val
    115                 120                 125

Gln Gly Val Phe Arg Val Tyr Pro Asn Phe Ala Asp Ser Val Ser Ala
130                 135                 140

His Thr Gln Leu Phe Leu Tyr Gly Thr Thr Trp Asn Ser Lys Gln Tyr
145                 150                 155                 160

Ala Ser Val Leu Ser Ala Thr Asp Tyr Lys Thr Ala Ala Lys Ala Val
                165                 170                 175

Gln Asn Ser Gly Tyr Ala Thr Asp Pro Thr Tyr Ala Asp Lys Leu Ile
            180                 185                 190

Asn Met Ile Glu Thr Tyr His Leu Asn Gln Tyr Asp Lys Ser Ser Ser
        195                 200                 205

Ile

<210> SEQ ID NO 140
<211> LENGTH: 259
<212> TYPE: PRT
<213> ORGANISM: Lactococcus lactis CCOS 949

<400> SEQUENCE: 140

Met Ser Ser Ile Glu Asn Met Ile Ala Trp Met Gln Ala Arg Lys Gly
1               5                   10                  15

Lys Val Thr Tyr Ser Met Thr Leu Arg Met Gly Pro Arg Ser Tyr Asp
                20                  25                  30

Cys Ser Ser Val Phe Phe Ala Met Ile Ala Gly Gly Phe Leu Ser
            35                  40                  45

Glu Gly Ser Met Gly Asn Thr Glu Thr Leu Phe Gly Met Ser Gly Thr
    50                  55                  60

Lys Leu Lys Glu Ile Ser Arg Gly Glu Val Gln Arg Gly Asp Ile Phe
65                  70                  75                  80

Ile Ser Gly Thr Pro Gly Gly Ser Ala Gly Ser Asp Gly His Thr Gly
                85                  90                  95

Ile Phe Leu Ser Asn Gly Ser Phe Ile His Cys Ser Tyr Thr His Asn
            100                 105                 110

Gly Ile Ala Val Asp Thr Asn Asp Ala Tyr Met Ser Thr Arg Leu Pro
    115                 120                 125
```

```
His His Phe Tyr Arg Ile Val Gly Ser Gly Ser Gly Asn Thr Asp Asn
            130                 135                 140

Lys Pro Gln Met Val Thr Leu Asn Val Asp Gly Gln Phe Gly Asn Ala
145                 150                 155                 160

Thr Ala Lys Arg Leu Gln Glu Tyr Phe Asp Thr Ala Gly Lys Asp Gly
                165                 170                 175

Val Ile Ser His Gln Tyr Lys Gln Thr Phe Asn Gln Asn Ile Tyr Ala
            180                 185                 190

Ala Gln Phe Asp Ser Ser Leu Thr Gly Ser Lys Val Val Lys Ala Leu
            195                 200                 205

Gln Arg Phe Leu Gly Ile Gly Gln Asp Gly Leu Phe Gly Gln Ala Thr
            210                 215                 220

Ile Lys Ala Leu Gln Lys His Leu Gly Thr Thr Gln Asp Gly Thr Ile
225                 230                 235                 240

Ser Pro Val Ser Asp Ser Val Arg Glu Leu Gln Arg Arg Leu Asn Ala
                245                 250                 255

Asn Lys Leu
```

<210> SEQ ID NO 141
<211> LENGTH: 259
<212> TYPE: PRT
<213> ORGANISM: Lactococcus lactis CCOS 949

<400> SEQUENCE: 141

```
Met Ser Ser Ile Glu Asn Met Ile Ala Trp Met Gln Ala Arg Lys Gly
1               5                   10                  15

Lys Val Thr Tyr Ser Met Thr Ser Arg Met Gly Pro Lys Ser Tyr Asp
            20                  25                  30

Cys Ser Ser Ser Val Phe Phe Ala Met Ile Ala Gly Gly Phe Leu Ser
            35                  40                  45

Glu Gly Ser Met Gly Asn Thr Glu Thr Leu Phe Gly Met Ser Gly Thr
50                  55                  60

Lys Leu Lys Glu Ile Ser Arg Gly Glu Val Gln Arg Gly Asp Ile Phe
65                  70                  75                  80

Ile Ser Gly Thr Pro Gly Gly Ser Ala Gly Ser Asp Gly His Thr Gly
                85                  90                  95

Ile Phe Leu Ser Asn Gly Ser Phe Ile His Cys Ser Tyr Thr His Asn
            100                 105                 110

Gly Ile Ala Val Asp Thr Asn Asp Ala Tyr Met Ser Thr Arg Leu Pro
            115                 120                 125

His His Phe Tyr Arg Ile Val Gly Ser Gly Ser Gly Lys Thr Asp Ser
            130                 135                 140

Lys Pro Gln Met Ile Thr Leu Asn Val Asp Gly Gln Phe Gly Asn Ala
145                 150                 155                 160

Thr Ala Lys Arg Leu Gln Glu Tyr Phe Asp Thr Ala Gly Lys Asp Gly
                165                 170                 175

Val Ile Ser His Gln Tyr Lys Gln Thr Phe Asn Gln Asn Ile Tyr Ala
            180                 185                 190

Ala Gln Phe Asp Ser Ser Leu Thr Gly Ser Asn Val Val Lys Ala Leu
            195                 200                 205

Gln Arg Phe Leu Gly Ile Gly Gln Asp Gly Leu Phe Gly Gln Gly Thr
            210                 215                 220

Ile Lys Ala Leu Gln Lys His Leu Gly Thr Thr Gln Asp Gly Thr Ile
225                 230                 235                 240
```

```
Ser Pro Val Ser Asp Ser Val Arg Glu Leu Gln Arg Arg Leu Asn Ala
                245                 250                 255

Asn Lys Leu

<210> SEQ ID NO 142
<211> LENGTH: 403
<212> TYPE: PRT
<213> ORGANISM: Lactococcus lactis CCOS 949

<400> SEQUENCE: 142

Met Thr Lys Arg Leu Lys Lys Ala Lys Pro Val Val Phe Leu Ala
1               5                   10                  15

Leu Val Leu Gly Cys Ala Leu Ile Leu Ser Gly Val Leu Gly Leu Ala
                20                  25                  30

Gly His Leu Asn Glu Gln Glu Ser Ser Lys Thr Lys Lys Lys Ser Gln
            35                  40                  45

Leu Ser Glu Thr Lys Arg Ser Ser Thr Ser Pro Lys Asn Met Asp Lys
50                  55                  60

Asn Ile Glu Gln Met Thr Leu Glu Gln Lys Val Gly Gln Leu Phe Met
65                  70                  75                  80

Thr Gly Met Pro Ala Asn Asn Tyr Asn Gln Ala Thr Phe Asp Ala Ile
                85                  90                  95

Glu Lys Tyr Gln Val Gly Ser Ile Ile Leu Thr Gly Arg Ser Asn Leu
            100                 105                 110

Ser Val Pro Glu Met Lys Asp Ile Thr Asp Lys Leu Gln Gly Leu Glu
        115                 120                 125

Pro Ala Asn Arg Lys Leu Leu Ile Ser Cys Asp Gln Glu Gly Gly Asn
    130                 135                 140

Val Gln Val Leu Gln Gly Gln Gly Phe Ser Gln Ile Pro Asp Gly Leu
145                 150                 155                 160

Thr Gln Gly Ser Trp Thr Ala Asp Lys Leu Gln Lys Glu Ser Gln Thr
                165                 170                 175

Trp Gly Ser Glu Leu Tyr Ala Ala Gly Val Asn Phe Asp Leu Ala Pro
            180                 185                 190

Val Ala Asp Gln Val Leu Ser Ala Asp Phe Ala Pro Gln Asn Ala Pro
        195                 200                 205

Ile Gly Tyr Trp Ser Arg Gln Tyr Ala Tyr Asp Lys Ala Ser Ile Ile
    210                 215                 220

Ser His Ala Gln Ala Phe Thr Glu Gly Met Lys Ala Ala Lys Val Leu
225                 230                 235                 240

Thr Thr Ala Lys His Phe Pro Gly Leu Gly Ala Val Thr Gly Asn Thr
                245                 250                 255

Asp Ile Ser Ala Gly Val Arg Asp Asp Gln Thr Asn Ser Asn Ser Glu
            260                 265                 270

Ser Val Gln Ile Phe Lys Asp Leu Ile Ser Ser Gly Thr Pro Ser Ile
        275                 280                 285

Met Thr Ala Thr Ala Ile Tyr Asp Lys Ile Asp Pro Asn Leu Pro Gly
    290                 295                 300

Ala Phe Ser Ser Lys Met Val Asp Gly Leu Leu Arg Lys Gln Leu Gly
305                 310                 315                 320

Phe Asp Gly Leu Val Ile Thr Asp Asp Leu Ser Asn Ala Val Gln Val
                325                 330                 335

Gln Ser Trp Thr Pro Gly Gln Arg Ala Val Leu Ala Leu Ser Ala Gly
            340                 345                 350
```

Asn Asp Leu Val Leu Ala Asn Glu Pro Thr Gln Ile Pro Glu Met Ile
            355                 360                 365

Ser Glu Val Leu Gln Lys Val Lys Ala Asp Pro Asp Phe Ala Lys Lys
370                 375                 380

Ile Ser Gln Ser Ala Thr Arg Val Ile Lys Val Lys Glu Glu Met Lys
385                 390                 395                 400

Leu Val Glu

<210> SEQ ID NO 143
<211> LENGTH: 312
<212> TYPE: PRT
<213> ORGANISM: Lactococcus lactis CCOS 949

<400> SEQUENCE: 143

Met Ile Ala Gln Gly Ile Leu Glu Ser Ser Gly Gly Gln Ser Ala Leu
1               5                   10                  15

Ala Ser Asn Tyr Asn Asn Ile Phe Gly Val Lys Tyr Thr Ser Gly Thr
            20                  25                  30

Pro Val Tyr Leu Pro Thr Gln Glu Tyr Leu Asn Gly Thr Met Thr Asn
        35                  40                  45

Val Val Glu Pro Phe Gln Ala Tyr Ser Ser Val Tyr Asp Ala Cys Val
50                  55                  60

Ala Gln Ala Lys Met Leu Arg Ala Ser Ser Tyr Tyr Ser Gly Ala Trp
65                  70                  75                  80

Arg Glu Asn Thr Ser Ser Tyr Leu Asp Ala Thr Ala Trp Leu Glu Gly
                85                  90                  95

Arg Tyr Ala Thr Asp Pro Thr Tyr Ala Ser Lys Leu Asn Ser Val Ile
            100                 105                 110

Ser Glu Leu Gly Leu Ser Val Tyr Asp Gln Gly Gly Glu Ile Ser Gly
        115                 120                 125

Gly Thr Ala Val Thr Thr Ser Ser Ala Ser Thr Asn Ser Ala Gly
130                 135                 140

Thr Tyr Lys Val Gln Glu Gly Asp Ser Leu Ser Ala Ile Ala Ala Gln
145                 150                 155                 160

Tyr Gly Thr Thr Val Asp Ala Leu Val Ser Ala Asn Ser Leu Glu Asn
                165                 170                 175

Ala Asn Asp Ile His Val Gly Glu Val Leu Gln Val Ala Gly Ala Ser
            180                 185                 190

Thr Thr Thr Thr Ser Thr Asn Thr Thr Ser Asn Val Ser Ser Ser Ser
        195                 200                 205

Thr Tyr Thr Val Lys Ser Gly Asp Ser Leu Tyr Ser Ile Ala Glu Gln
210                 215                 220

Tyr Gly Met Thr Val Ser Ser Leu Met Ser Ala Asn Gly Ile Tyr Asp
225                 230                 235                 240

Val Asn Ser Met Leu Gln Val Gly Gln Val Leu Gln Val Thr Val Ser
                245                 250                 255

Thr Ser Ala Thr Thr Ser Asn Thr Thr Thr Ser Asn Ser Tyr Thr Ile
            260                 265                 270

Gln Asn Gly Asp Ser Ile Tyr Ser Ile Ala Thr Ala Asn Gly Met Thr
        275                 280                 285

Ala Asp Gln Leu Ala Ala Leu Asn Gly Phe Gly Ile Asn Asp Met Ile
290                 295                 300

His Pro Gly Gln Thr Ile Arg Ile
305                 310

<210> SEQ ID NO 144
<211> LENGTH: 346
<212> TYPE: PRT
<213> ORGANISM: Lactococcus lactis CCOS 949

<400> SEQUENCE: 144

| Met | Glu | Lys | Ala | Ile | Lys | Arg | Lys | Val | Ile | Leu | Val | Ser | Leu | Pro | Phe |
|---|---|---|---|---|---|---|---|---|---|---|---|---|---|---|---|
| 1 | | | | 5 | | | | | 10 | | | | | 15 | |

Leu Leu Leu Leu Leu Pro Ile Leu Ala Phe Phe Ser Leu Phe Val Gly
            20                  25                  30

Ser Asn Ser Ser Ser Asp Thr Asp Ile Asn Thr Asn Thr Pro Gln Gln
            35                  40                  45

Gln Thr Ala Lys Val Ile Trp Asp Arg Val Leu Lys Glu Gly Gly Thr
    50                  55                  60

Lys Glu Gly Ala Ala Leu Leu Gly Asn Asn Gln Ala Glu Ser Glu
65                  70                  75                  80

Leu Gln Pro Ser Ile Ile Gln Ser Asn Ala Thr Tyr Asn Glu Ala Lys
                85                  90                  95

Ala Met Asp Thr Thr Leu Gly Gly Tyr Ala Phe Gly Leu Ala Gln Trp
            100                 105                 110

Asp Ser Gly Arg Arg Val Asn Leu Leu Asn Tyr Ala Lys Ser Gln Lys
        115                 120                 125

Lys Ser Trp Thr Asp Thr Asn Leu Gln Val Glu Phe Met Phe Glu Gln
130                 135                 140

Asp Gly Thr Asp Ser Thr Leu Leu Lys Gln Leu Val Lys Gly Thr Asn
145                 150                 155                 160

Val Lys Gln Thr Thr Glu Asp Ile Met Arg Lys Trp Glu Arg Ala Gly
                165                 170                 175

Ala Val Asp Ser Leu Pro Lys Arg Gln Gly Phe Ala Glu Tyr Trp Tyr
            180                 185                 190

Thr Phe Met Thr Thr Gly Gly Asp Ser Gly Thr Gly Gly Ser Gly
        195                 200                 205

Ile Thr Pro Asp Ile Pro Ser Gly Trp Thr Leu Asp Lys Pro Ile Asn
210                 215                 220

Thr Ser Gly Tyr Leu Ala Thr Ser Tyr Glu Tyr Lys Gln Cys Thr Trp
225                 230                 235                 240

Phe Thr Trp Asn Arg Ala Lys Asp Phe Gly Ile Thr Phe Gly Met Tyr
                245                 250                 255

Met Gly Asn Gly Ala Asp Trp Gln His Gln Ala Gly Tyr Thr Val Thr
            260                 265                 270

Thr Thr Pro Thr Leu His Ser Ala Val Ser Phe Ser Gly Gly Gln Thr
        275                 280                 285

Val Gly Gly Gln Trp Asn Ala Asp Pro Val Tyr Gly His Val Ala Phe
290                 295                 300

Val Glu Gly Ile His Ser Asp Gly Ser Val Leu Ile Ser Gln Ser Gly
305                 310                 315                 320

Thr Gly Phe Ser Ala Val Tyr Thr Phe Gln Val Leu Thr Lys Ala Gln
                325                 330                 335

Ala Ser Gln Leu His Tyr Val Ile Gly Lys
            340                 345

<210> SEQ ID NO 145
<211> LENGTH: 717
<212> TYPE: PRT
<213> ORGANISM: Lactococcus lactis CCOS 949

-continued

```
<400> SEQUENCE: 145

Met Lys Ile Asn Lys Ile Asp Thr Arg His Gly Thr Ala Asn Gln Ser
1               5                   10                  15

Thr Phe Ser His Gly Asn Cys Leu Pro Tyr Thr Gly Phe Pro Trp Gly
            20                  25                  30

Met Asn Tyr Phe Ser Pro Ser Thr Gly Ala Ala Arg Gly Ala Trp Trp
        35                  40                  45

Phe His Pro Glu Asp Arg Thr Phe Glu Gly Tyr Arg Ile Thr His Gln
    50                  55                  60

Pro Ser Pro Trp Met Gly Asp Phe Ser His Leu Thr Met Thr Pro Val
65                  70                  75                  80

Ala Gly Pro Leu Pro Glu Thr Ser Leu Trp His Thr Val Ser Ser Tyr
                85                  90                  95

Arg Pro Glu Glu Ser Thr Phe Asn Pro Thr Gln Leu Lys Ile Thr Gln
            100                 105                 110

Leu Arg Tyr Gln Ile Thr Ser Gln Leu Ile Pro Ser Met Tyr Gly Gly
        115                 120                 125

Ile Leu Ser Met Asn Tyr Gln Asn Leu Ser Leu Lys Asp Asn Gly Leu
    130                 135                 140

Met Leu His Leu Pro Gly Ser Tyr Glu Leu Gln Gln Leu Asp Asp Tyr
145                 150                 155                 160

Ser Leu Glu Leu Ser Ile Ile Asn Phe Ala Gly Cys Glu Asp Glu Asn
                165                 170                 175

Phe Thr Phe Tyr Leu Lys Phe Thr Ala Asp Gln Pro Phe Val Leu Ser
            180                 185                 190

Gly Asn Leu Ser Asp Glu Asp Ser Ser Val Arg Leu Asp Phe Lys Ala
        195                 200                 205

Ala Lys Gln Val Gln Ile His Phe Ala Thr Ser Phe Ile Ser Lys Glu
    210                 215                 220

Gln Ala Ala Leu Asn Leu Glu Arg Glu Gln Asp Asn Ser Ala Glu Thr
225                 230                 235                 240

Tyr Leu Glu Asn Ala Glu Ser Ala Trp Asn Asn Leu Phe Ser Arg Ile
                245                 250                 255

Glu Ile Glu His His Asn Gln Gln Glu Val Ser Thr Phe Tyr His Asn
            260                 265                 270

Leu Tyr Arg Ser Phe Leu Phe Pro Gln Thr Phe Tyr Glu Phe Asp Gln
        275                 280                 285

Glu His Gln Lys Ile His Tyr Asp Thr Ser Ser Lys Thr Val Lys Lys
    290                 295                 300

Gly Pro Leu Tyr Thr Asn Asn Gly Phe Trp Asp Thr Phe Arg Thr Val
305                 310                 315                 320

Tyr Pro Leu Tyr Ser Leu Ile Ala Val Asp Glu Tyr Gly Asp Met Leu
                325                 330                 335

Glu Gly Phe Leu Asn Ser Tyr Arg Ala Thr Gly Phe Leu Pro Lys Trp
            340                 345                 350

Leu Ser Pro Asp Glu Arg Gly Leu Met Pro Gly Thr Leu Ile Asp Ala
        355                 360                 365

Val Ile Ala Asp Ala Ala Ser Lys Asn Ile Arg Pro Asp Leu Met Pro
    370                 375                 380

Glu Phe Leu Glu Ala Met Lys Lys Gly Ala Thr Ser Gln Ser Glu Asn
385                 390                 395                 400

Ser Asn Tyr Gly Arg Arg Gly Thr Lys Asp Tyr Leu Lys Leu Gly Tyr
                405                 410                 415
```

Val Pro Leu Thr His His Glu Ser Val Asn His Thr Leu Asp Tyr Ala
            420                 425                 430

Phe Ser Asp Tyr Cys Ile Ser Gln Val Ala Lys Gln Thr Gly Asp Lys
            435                 440                 445

Glu Ile Ser Asp Phe Tyr Ala His Gln Ala Lys Asp Tyr Gln Asn Ile
450                 455                 460

Phe Asp Ser Glu Thr Gly Phe Met Arg Ala Lys Asp Ala Asp Gly Asn
465                 470                 475                 480

Phe Arg Ala Asp Phe Leu Asp Ile Arg Trp Gly Arg Asp Tyr Ala Glu
            485                 490                 495

Gly Ser Ala Trp Gln Thr Ser Trp Ser Val Leu His Asp Phe Ala Gly
            500                 505                 510

Leu Ile Lys Leu His Gly Ser Arg Glu Asn Phe Glu Asn Lys Leu Ile
            515                 520                 525

Glu Leu Cys Asn Gln Arg Pro Asn Phe Asn Val Glu Gly Tyr Gly Phe
            530                 535                 540

Glu Ile His Glu Met Ser Glu Met Ala Ala Ile Glu Phe Gly Gln Val
545                 550                 555                 560

Ala Ile Ser Asn Gln Pro Ser Phe His Tyr Pro Tyr Leu Phe Ser Tyr
            565                 570                 575

Ile Gly Lys Pro Trp Met Ala Thr Pro Leu Ile Lys Asn Leu Leu Thr
            580                 585                 590

Glu Thr Phe Asn Asp Ser Pro Lys Gly Tyr Pro Gly Asp Glu Asp Asn
            595                 600                 605

Gly Thr Met Ala Ala Trp Tyr Ile Phe Ser Ser Leu Gly Phe Tyr Pro
610                 615                 620

Val Thr Ala Ala Ser Asn Gln Tyr Val Leu Gly Ile Pro Leu Trp Asp
625                 630                 635                 640

Lys Ala Arg Ile Asn Leu Ser Ser Gly Gln Gln Leu Thr Ile Leu Ala
            645                 650                 655

Glu Pro Asn Ala Pro Gln Gln Val Phe Val Asn Gln Ile Thr Phe Thr
            660                 665                 670

Asp Lys Lys Val Asn Asp Thr Phe Ile Lys His Glu Glu Leu Ile Lys
            675                 680                 685

Gly Gly Thr Leu Lys Phe Asp Leu Gly Ile Val Pro Asn Pro Leu Lys
            690                 695                 700

Tyr Thr Asn Glu Gln Leu Pro Tyr Ser Leu Thr Glu Asn
705                 710                 715

<210> SEQ ID NO 146
<211> LENGTH: 384
<212> TYPE: PRT
<213> ORGANISM: Lactococcus lactis CCOS 949

<400> SEQUENCE: 146

Met Val Lys Ile Ser Phe Asp Val Lys Lys Phe Glu Gly Gln Thr Ile
1               5                   10                  15

Lys Lys Ile Gly Leu Ser Ile Lys Ser Asp Gln Ala Met Asp Phe Lys
            20                  25                  30

Ala Ile Asn Leu Gly Glu Met Thr Leu Thr Asn Gly Gln Lys Val Ala
            35                  40                  45

Pro Ile Ala Leu Ser Asp Ala Lys Val Thr Asp Glu Ala Phe Glu Glu
            50                  55                  60

Glu Gly Thr Val Gly Gly Phe Arg Leu Ser Trp Lys Ser Asp Ala Asn
65                  70                  75                  80

```
Lys Asn Asn Phe Ser Thr Tyr Glu Ile Tyr Gln Leu Asn Asp Asp Gly
                85                  90                  95

Ser Lys Glu Phe Leu Gly Ala Ser Asn Ile Asn Ala Phe Phe Val Asn
            100                 105                 110

Ala Leu Lys Arg Gly Lys Asn Ile Asn Ser Thr Lys Phe Glu Ile Val
            115                 120                 125

Pro Ile Asn Lys Ala Gly Glu Ser Gly His Ser Val Thr Thr Ser Val
            130                 135                 140

Lys Trp Pro Asp Asn Ser Leu Ala Lys Ala Ala Phe Val Ala Asp Lys
145                 150                 155                 160

Thr Leu Val Thr Ile Gly Glu Lys Val Thr Leu Met Asn Gln Ser Asn
                165                 170                 175

Leu Ala Ser Val Lys Tyr Lys Trp Asp Ile Asp Gly Ala Ser Pro Ala
            180                 185                 190

Thr Ser Thr Glu Lys Asn Pro Gln Val Ser Phe Asp Lys Ala Gly Ser
            195                 200                 205

Tyr Ser Val Lys Leu Thr Val Ile Asn Glu Lys Gly Gln Glu Asp Ser
            210                 215                 220

Val Thr Gln Thr Glu Leu Ile Thr Val Ile Asp Gln Pro Val Glu Leu
225                 230                 235                 240

Thr Asn Phe Ala Leu Asn Gln Ser Val Gln Val Asp Ser Phe Thr Asn
                245                 250                 255

Glu Ser Glu Ser Gly Pro Lys Ala Val Asp Gly Lys Leu Asn Thr Lys
            260                 265                 270

Trp Cys Ala Val Gly Pro Gly Lys His Asn Ile Thr Ile Asp Ile Gly
            275                 280                 285

Lys Ser Glu Lys Ile Asn Gln Val Leu Ile Asp His Ala Gln Lys Gly
            290                 295                 300

Gly Glu Ser Pro Asp Met Asn Thr Ser Asp Tyr Thr Ile Glu Ile Ser
305                 310                 315                 320

Lys Asp Asn Gln Asn Trp Thr Glu Val Val Asn Val Lys Lys Asn Lys
                325                 330                 335

Leu Gly Glu Thr Lys Asp Ser Phe Lys Gln Thr Glu Ala Arg Tyr Val
            340                 345                 350

Arg Ile Thr Ala Thr Lys Pro Thr Gln Gly Ala Asp Thr Ala Val Arg
            355                 360                 365

Leu Tyr Glu Ile Gln Val Leu Gly Gln Lys Lys Ala Asp Lys Gly Leu
            370                 375                 380

<210> SEQ ID NO 147
<211> LENGTH: 569
<212> TYPE: PRT
<213> ORGANISM: Lactobacillus jensenii CCOS 962

<400> SEQUENCE: 147

Met Thr Lys Gln Thr Leu Gln Ala Glu Ala Asn Gly Arg Asn Gly Lys
1               5                   10                  15

Ile Lys Phe Asp Ile Asn Ile Asp Asn Asn Glu Ile Lys Asp Ile Lys
                20                  25                  30

Val Thr Lys Ser Ser Glu Thr Pro Ala Ile Phe Asn Gln Val Phe Asp
            35                  40                  45

Lys Leu Lys Asn Ser Ile Ile Glu Glu Gln Ser Phe Asp Val Asp Ala
            50                  55                  60

Val Ser Gly Ala Thr Ile Met Thr Ser Ala Leu Leu Asp Ser Gly Lys
65                  70                  75                  80
```

```
Lys Ala Leu Asn Gln Ala Gly Val Thr Pro Val Ala Lys Glu Ser Asp
                 85                  90                  95
Lys Thr His Arg Glu Val Asn Leu Asp Val Asp Val Ala Val Ile Gly
            100                 105                 110
Ser Gly Ala Ala Gly Leu Ile Ala Ala Cys Arg Ala Leu Ser Met Gly
        115                 120                 125
Lys Asn Val Val Val Leu Glu Lys Asn Gly Tyr Leu Gly Gly Ala Thr
    130                 135                 140
Ile Leu Asn Gly Ser Asn Val Val Ala Thr Gly Ser Asn Leu Ala Gln
145                 150                 155                 160
Gln Leu Phe Gly Thr Glu Ala Gln Glu Asp Ser Ser Lys Arg Leu Phe
                165                 170                 175
Ala Asp Ile Thr Arg Glu Cys Arg Gly Thr Asn Tyr Pro Glu Leu Ser
            180                 185                 190
Lys Val Leu Val Glu Asn Ile Gly Lys Ala Val Asp Phe Ile Lys Glu
        195                 200                 205
Phe Ala Gly Leu Thr Tyr Gln Lys Ala Glu Thr Gln Thr Ile Glu His
    210                 215                 220
Ser Val Asn Arg Gln Val Glu Met Pro Ser Glu Ser Ser Tyr Glu Leu
225                 230                 235                 240
Ile Lys Lys Ile Ala Ala Ala Phe Glu Glu Lys Gly Gly Lys Ile Leu
                245                 250                 255
Leu Asp Ala Arg Val Glu Lys Ile Asn Ser Glu Asn Gly Val Pro Ile
            260                 265                 270
Ser Leu Val Ala Glu Gly Lys His Gln Thr Thr Asn Val Lys Phe Lys
        275                 280                 285
Ser Leu Ile Leu Ala Ala Gly Gly Trp Gly Ala Lys Asp Phe Lys Glu
    290                 295                 300
Lys Arg Thr Ser Ile Pro Tyr Tyr Gly Pro Met Thr Ser Thr Gly Asp
305                 310                 315                 320
Tyr Phe Phe Phe Asn Lys Gly Leu Asn Leu Ala Ser Arg Asn Leu Asp
                325                 330                 335
Trp Tyr Lys Val Tyr Pro His Gly Leu Glu Val Glu Pro Gly Ile Ala
            340                 345                 350
Lys Leu Thr Thr Tyr Ser Thr Lys Glu Ala Ser Asp Met Gly Ala Ile
        355                 360                 365
Phe Ile Asn Arg Ala Gly Asn Arg Ile Val Asn Glu Ser Asp Pro Tyr
    370                 375                 380
Thr His Phe Arg Asp Ala Ile Ala Ala Gln Lys Asp Gln Ile Ala Phe
385                 390                 395                 400
Val Leu Met Asp Gln Arg Ile Trp Asn Arg Phe Tyr Glu Leu Met Leu
                405                 410                 415
Lys Tyr Gly Phe Thr Ala Asp Glu Ile Ser His Tyr Phe Ala Leu Asp
            420                 425                 430
Gly Lys Gln Ser Pro Ile Leu Val Lys Gly Thr Leu Glu Thr Val Ala
        435                 440                 445
Asn Lys Ala Gly Ile Asn Phe Glu Asn Leu Gln His Thr Leu Ser Asn
    450                 455                 460
Tyr Gln Asn Tyr Ala Lys Asn Gly Lys Asp Pro Glu Phe Gly Arg Glu
465                 470                 475                 480
Ala Lys Phe Met His Glu Tyr Ser Gly Asp Thr Tyr Tyr Val Ile Glu
                485                 490                 495
```

-continued

```
Gln Lys Leu Arg Phe Cys Thr Thr Leu Gly Gly Tyr Glu Thr Asn Ser
            500                 505                 510

Gln Met Gln Leu Leu Asn Asn Asp Met Lys Pro Val Ala Asn Tyr Tyr
        515                 520                 525

Ala Ala Gly Glu Val Ile Gly Gly Ala Asn Gly His Asp Ser Met Pro
    530                 535                 540

Ser Met Met Asn Ser Trp Ser Tyr Ala Ser Gly Phe Leu Ala Gly Thr
545                 550                 555                 560

Asn Ala Ser Asp Asn Cys Asn Asn Arg
                565

<210> SEQ ID NO 148
<211> LENGTH: 717
<212> TYPE: PRT
<213> ORGANISM: Lactobacillus jensenii CCOS 962

<400> SEQUENCE: 148

Met Lys Thr Lys Lys Ile Thr Gly Val Ala Thr Ala Ala Leu Leu Ala
1               5                   10                  15

Ser Val Ala Val Pro Val Thr Asn Asn Leu Ala Asn Ile Gln Thr Ser
            20                  25                  30

Tyr Thr Ala Lys Ala Val Thr Gly Gln Gln Gln Ala Phe Leu Asn Thr
        35                  40                  45

Ala Ile Pro Asn Ala Glu Ala Ser Ala Arg Tyr Gly Thr Tyr Thr
    50                  55                  60

Ser Val Met Leu Ala Gln Ser Ile Leu Glu Ser Gly Trp Gly Ala Ser
65                  70                  75                  80

Leu Leu Ala Thr Gln Ala Asn Asn Leu Phe Gly Met Lys Gly Ser Tyr
                85                  90                  95

Asn Gly Gln Thr Tyr Tyr Thr Asn Thr Ser Glu Trp Ala Ser Gly Thr
            100                 105                 110

Gly Tyr Tyr Asn Ile Asn Ala Gly Phe Arg Lys Tyr Pro Ser Trp Ala
        115                 120                 125

Ala Ser Phe Glu Asp Asn Gly Tyr Lys Leu Arg Thr Gly Thr Thr Asp
    130                 135                 140

Asn Pro Ser Arg Tyr Arg Met Ala Trp Ile Glu Asn Ala Ala Asn Tyr
145                 150                 155                 160

Gln Val Ala Thr Gln Gly Leu Lys Asp Gly Gly Tyr Ala Thr Ser Pro
                165                 170                 175

Thr Tyr Pro Gln Ser Leu Asn Arg Val Ile Ser Ser Tyr Gly Leu Asn
            180                 185                 190

Gln Tyr Asp Pro Ser Val Asp Thr Thr Thr Lys Thr Met Arg Val Leu
        195                 200                 205

Ser Asn Gly Thr Val Tyr Ser Gly Pro Ala Asp Ser Ser Val Val Ser
    210                 215                 220

Ala Thr Gly Asn Ile Thr Ala Gly Gln Val Val Thr Val Asp Lys Thr
225                 230                 235                 240

Val Thr Tyr Lys Asn Gly Leu Ser Tyr Met His Ile Ser Asn Gly Trp
                245                 250                 255

Ile Asn Gly Ser Leu Leu Thr Gly Ser Ser Thr Gln Ala Thr Thr Thr
            260                 265                 270

Glu Lys Ala Gly Thr Thr Thr Asp Ala Gly Asn Ala Ala Ile Lys Val
        275                 280                 285

Val Tyr Ser Ala Ile Ala Glu Trp Lys Asn Pro Gly Ser Gly Val
    290                 295                 300
```

```
Val Gly Tyr Leu Gln Lys Gly Thr Thr Gln Thr Val Gly Lys Ile
305                 310                 315                 320

Gln Val Asn Gly Ala Trp Trp Tyr Lys Leu Ser Ser Gly Asn Trp Val
                325                 330                 335

Pro Gly Glu Tyr Val Tyr Val Thr Gly Ala Ser Arg Ile Pro Thr Ile
                340                 345                 350

Asp Asn Asn Val Val Asn Gln Asn Thr Lys Val Lys Ile Lys Tyr Ile
                355                 360                 365

Ser Gly Tyr Ser Ile Ala Val Trp Ser Asn Pro Ala Ile Gly Thr Thr
370                 375                 380

Gly Gln Tyr Leu Lys Asp Gly Thr Glu Val Gln Thr Ile Gly Tyr Thr
385                 390                 395                 400

Thr Ala Asn Gly Lys Lys Trp Tyr Lys Leu Ala Asn Asn Thr Trp Ile
                405                 410                 415

Pro Ala Glu Tyr Thr Glu Val Val Ser Ser Thr Val Val Thr Asn
                420                 425                 430

Ile Thr Asn Glu Ser Asn Thr Val Ala Ile Asn Tyr Pro His Tyr Ser
                435                 440                 445

Ile Ala Val Trp Ser Glu Pro Gly Arg Asn Ser Thr Gly Lys Tyr Leu
450                 455                 460

Ser Asp Gly Thr Lys Val Gln Thr Val Gly Tyr Thr Thr Val Asn Gly
465                 470                 475                 480

Lys Lys Trp Tyr Lys Leu Ala Asp Asn Thr Trp Ile Pro Ala Glu Tyr
                485                 490                 495

Thr Lys Val Val Ser Ser Ser Thr Val Val Thr Asn Ile Thr Asn Glu
                500                 505                 510

Ser Asn Thr Val Ala Ile Asn Tyr Pro His Tyr Ser Ile Ala Val Trp
                515                 520                 525

Gly Glu Pro Gly Lys Asn Ser Thr Gly Lys Tyr Leu Ser Asp Gly Thr
530                 535                 540

Lys Val Gln Thr Val Gly Tyr Thr Thr Val Asn Gly Lys Lys Trp Tyr
545                 550                 555                 560

Lys Leu Ala Asp Asn Thr Trp Ile Pro Ala Glu Tyr Thr Lys Ala Val
                565                 570                 575

Ser Ser Thr Asp Thr Thr Ser Gly Asn Asn Thr Val Thr Val Asn Tyr
                580                 585                 590

Pro Gly Tyr Ser Ile Val Val Trp Ser Glu Pro Gly Arg Asn Ser Thr
                595                 600                 605

Gly Lys Tyr Ile Ser Asp Gly Thr Ser Val Lys Tyr Tyr Ala Thr Ala
610                 615                 620

Asn Tyr Asn Gly Gln Thr Trp Tyr Lys Ile Gly Glu Asn Gln Trp Val
625                 630                 635                 640

Pro Gly Gln Tyr Val Lys Val Asn Ala Ser Asn Ser Gly Ser Val
                645                 650                 655

Thr Val Lys Tyr Ile Ser Gly Tyr Gly Ile Ala Ile Trp Ser Asn Pro
                660                 665                 670

Gly Arg Asn Ser Thr Gly Lys Tyr Leu Glu Asn Gly Thr Thr Val Lys
                675                 680                 685

Tyr Phe Glu Thr Gln Asn Tyr Asn Gly Gln Thr Trp Tyr Lys Ile Gly
                690                 695                 700

Glu Asn Gln Trp Val Pro Ala Gln Tyr Val Ser Val Asn
705                 710                 715
```

```
<210> SEQ ID NO 149
<211> LENGTH: 775
<212> TYPE: PRT
<213> ORGANISM: Lactobacillus jensenii CCOS 962

<400> SEQUENCE: 149
```

| | | | | | | | | | | | | | | |
|---|---|---|---|---|---|---|---|---|---|---|---|---|---|---|
| Met | Ala | Glu | Asn | Asn | His | Arg | Ser | Ala | Ser | Asn | Thr | Ala | Pro | Lys | Asn |
| 1 | | | | 5 | | | | | 10 | | | | | 15 | |

Ser Arg Met Ala Asn Leu His His Asp Ser Gly Gln Pro Lys Arg Arg
                20                  25                  30

Leu Trp Leu Gln Ile Leu Lys Trp Phe Ser Ile Gly Ile Leu Leu Ile
            35                  40                  45

Leu Val Ser Gly Val Gly Leu Phe Ala Tyr Tyr Ala Lys Asp Ala Pro
        50                  55                  60

Ser Ile Ser Gln Asp Gln Leu Gln Ser Gly Gly Ser Ser Ser Phe Tyr
65                  70                  75                  80

Thr Ser Asp Gly Lys Phe Leu Leu Ser Leu Gly Ser Glu Lys Arg Thr
                85                  90                  95

Tyr Val Lys Asn Ser Asp Ile Pro Gln Thr Leu Lys Asp Ala Val Val
            100                 105                 110

Ser Val Glu Asp Lys Arg Phe Tyr Gln Glu Asn Leu Gly Ile Asp Pro
        115                 120                 125

Ile Arg Ile Val Gly Ser Ile Val Ser Asn Ala Lys Ser Ser Gly Ile
130                 135                 140

Ala Ala Gly Gly Ser Ser Ile Thr Gln Gln Leu Val Lys Leu Thr Val
                150                 155                 160
145

Phe Ser Thr Ala Ala Ser Gln Arg Thr Leu Lys Arg Lys Ala Gln Glu
            165                 170                 175

Ala Trp Leu Ala Ile Arg Val Glu His Asp Tyr Thr Lys Asn Gln Ile
        180                 185                 190

Leu Glu Tyr Tyr Ile Asn Lys Val Tyr Met Asn Tyr Gly Val Tyr Gly
            195                 200                 205

Met Gly Thr Ala Ala Asp Tyr Tyr Gly Lys Ser Leu Lys Asp Leu
210                 215                 220

Asp Leu Ala Gln Thr Ala Leu Ile Ala Gly Met Pro Asn Ala Pro Val
225                 230                 235                 240

Ala Tyr Asp Pro Tyr Thr Tyr Pro Lys Ala Ala Lys Tyr Arg Arg Asp
            245                 250                 255

Ile Val Leu Asn Ala Met Tyr Ala Asn Gly Lys Ile Ser Lys Ala Gln
        260                 265                 270

Leu Lys Ala Ala Lys Ala Glu Ser Ile Thr Gln Gly Leu Lys Thr Gln
            275                 280                 285

Gln Asn Ser Ser Glu Ser Ser Ile Arg Arg Ile Asp Asp Pro Tyr Ile
290                 295                 300

Lys Glu Ala Ile Ser Glu Val Lys Ser Lys Gly Tyr Asp Pro Tyr Asn
305                 310                 315                 320

Asp Asn Leu Lys Ile Thr Leu Asn Ile Asp Gln Asp Ala Gln Asn Lys
            325                 330                 335

Leu Tyr Glu Leu Ala Asn Gly Ser Ser Ile Pro Phe Ser Ser Ser Lys
        340                 345                 350

Met Gln Val Gly Ala Thr Ile Ile Asn Pro Ser Asn Gly His Val Val
            355                 360                 365

Ala Ile Ile Gly Gly Arg Asn Leu Pro Ser Val Gln Leu Gly Leu Asp
370                 375                 380

```
Arg Ala Val Gln Thr Gly Arg Ser Thr Gly Ser Ser Ile Lys Pro Val
385                 390                 395                 400

Leu Asp Tyr Ala Pro Ala Ile Glu Tyr Leu Asn Trp Ser Thr Ala His
            405                 410                 415

Tyr Leu Glu Asp Thr Lys Tyr Val Tyr Pro Gly Thr Ser Ile Gln Leu
            420                 425                 430

Tyr Asp Trp Asp Asn Lys Tyr Met Gly Lys Met Thr Met Arg Tyr Ala
            435                 440                 445

Leu Glu Gln Ser Arg Asn Val Pro Ala Val Lys Thr Leu Ala Lys Val
450                 455                 460

Gly Met Lys Lys Ala Ser Leu Phe Ala Lys Lys Met Asn Ile Ser Val
465                 470                 475                 480

Gly Ser Asn Gln Gly Leu Ser Val Ala Ile Gly Ala Asn Ala Ser Ser
            485                 490                 495

Leu Gln Met Ala Gly Ala Tyr Ala Ala Phe Ala Asn Glu Gly Val Tyr
            500                 505                 510

Tyr Lys Pro Gln Phe Val Ser Gln Ile Glu Thr Ala Asp Gly Val Val
            515                 520                 525

His Ser Tyr Ser Ala Thr Gly Thr Arg Val Met Lys Lys Ser Thr Ala
            530                 535                 540

Tyr Met Ile Thr Asp Met Leu Lys Gly Val Leu Thr Glu Gly Ser Gly
545                 550                 555                 560

Thr Asn Ala Arg Thr Gly Leu Tyr Glu Ala Gly Lys Thr Gly Thr Val
                565                 570                 575

Lys Tyr Ser Asp Asp Glu Leu Val Lys Tyr Pro Ser Tyr Ala Asn Thr
            580                 585                 590

Pro Lys Asp Ala Trp Phe Val Gly Tyr Thr Lys Lys Tyr Ser Ile Gly
            595                 600                 605

Ile Trp Thr Gly Tyr Asp Asn Leu Ser Asp Gly Thr Ile Ser Gly Gln
610                 615                 620

Gly Gln Tyr Ala Ser Gln Tyr Leu Tyr Lys Tyr Met Met Lys Tyr Leu
625                 630                 635                 640

Met Ser Asp Lys Glu Asn Ser Asn Trp Thr Lys Pro Ser Asn Val Val
            645                 650                 655

Arg Lys Arg Ile Val Lys Gly Ser Asp Pro Leu Glu Val Thr Ser Ser
            660                 665                 670

Lys Lys Asn Ser Thr Ser Glu Leu Phe Leu Arg Gly His Thr Pro Asp
            675                 680                 685

Gly Ser Asn Glu Asp Ser Asp Glu Ser Ser Ser Ser Asn Ser Ser
            690                 695                 700

Ser Ser Ser Lys Asp Asn Glu Val Val Thr Asn Lys Ser Ser Ser Ser
705                 710                 715                 720

Ser Ser Ser Ser Ser Glu Gly His Glu Asp Gly Ser Thr Ser Asn
            725                 730                 735

Ser Ser Ser Ser Gln Ser Ser Ser Gly Gly Ser Pro Asn Asn Asn Gln
            740                 745                 750

Gly Thr Thr Thr Asn Asn Gln Thr Asn Asn Asn Asn Thr Gly Gln
            755                 760                 765

Asn Asn Gly Gly Gly Asn Asn
770                 775
```

<210> SEQ ID NO 150
<211> LENGTH: 2089
<212> TYPE: PRT
<213> ORGANISM: Lactobacillus jensenii CCOS 962

<400> SEQUENCE: 150

```
Met Phe Ser Lys Asn Asn Met Lys Met Arg Met Gln Lys Val Ala Asp
1               5                   10                  15

Lys Glu Gln Gln His Phe Ala Leu Arg Lys Leu Asn Val Gly Leu Val
            20                  25                  30

Ser Val Leu Met Gly Thr Thr Leu Phe Phe Val Gly Gln Thr Ser Ile
        35                  40                  45

Ala Lys Ala Asp Thr Leu Glu Ser Thr Lys Thr Ser Val Thr Glu Ile
    50                  55                  60

Ser Ser Ser Ser Asn Ser Asn Gln Glu Lys Leu Glu Gln Ala Lys Ala
65                  70                  75                  80

Val Ser Ser Gln Glu Gln Thr Thr Ser Thr Glu Glu Asn Val Asp Ser
                85                  90                  95

Ala Ser Ser Ser Gln Ser Lys Ser Glu Asn Asn Ser Ser Ser Ser Ala
            100                 105                 110

Lys Ser Glu Val Ser Thr Gln Asp Arg Thr Asp Ser Asn Asp Asn Ala
        115                 120                 125

Thr Thr Asn Gln Val Asp Thr Thr Gln Val Ser Thr Thr Ser Leu Lys
    130                 135                 140

Ala Val Gln Ser Ser Asn Gln Ala Ala Asn Leu Leu Ala Glu Ser Lys
145                 150                 155                 160

Val Glu Asp Ser Thr Thr Ala Asn Val Ser Asp Phe Asp Ser Phe Asn
                165                 170                 175

Ser Ala Leu Met Asn Gln Asn Ile Thr Thr Ile Asn Ile Asn Ser Asp
            180                 185                 190

Phe Thr Ser Gly Asn Tyr Gly Thr Asn Val Glu His Arg Arg Val Val
        195                 200                 205

Pro Arg Thr Leu Val Ile Asn Gly Asn Gly His Thr Val Asp Leu Gly
    210                 215                 220

Ser Ile Gly Tyr Phe Met Asn Pro Gly Gly Asn Gln Ala Ala Asp Trp
225                 230                 235                 240

Thr Val Glu Asn Gly Thr Phe Tyr Ser Lys Ser Ala Val Gly Pro Phe
                245                 250                 255

Ala Leu Thr Gly Asp His Gly Thr Asp Lys Ala Trp Gln Ala Thr Asn
            260                 265                 270

Gly Ala Val His Arg Met Thr Tyr Lys Asp Met Thr Val Tyr Ala Gly
        275                 280                 285

Gly Gly Ala Tyr Ala Ala Asn Ala Glu Ile Asp Leu Glu Gly Thr Asn
    290                 295                 300

Asn Leu Asn Ala Thr Ala Ser Tyr Gln Ser Lys Phe Ser Asn Gly Thr
305                 310                 315                 320

Val Tyr Thr Glu Thr Gly Gly Asn Arg Ser Gly Val Glu Gly Gln Trp
                325                 330                 335

Ile Ile Ile Lys Asp Asn Ala Asn Val Thr Val Asn Thr Asp His Gly
            340                 345                 350

Gln Ala Ile Ser Thr Glu Tyr Ser Asp Gly Asn His Arg Ile Glu Val
        355                 360                 365

Gly Glu Asn Ala Thr Leu Asn Gly Asn Tyr Leu Tyr Thr Thr Tyr Gly
    370                 375                 380
```

```
Thr Pro Tyr Gly Gly Gly Lys Ile Ala Val Leu Ser Asn Gly Ala Asn
385                 390                 395                 400

Gly Gly Thr Val Ile Phe His Lys Gly Ser Lys Ser His Phe Thr Met
            405                 410                 415

Pro Asn Gln Asn Val Thr Gly Phe Gly Gly Asn Gly Phe Ser Asn Tyr
        420                 425                 430

Gly Thr Gly Ser Val Leu Tyr Leu Gly Ala Ala Asn Thr Thr Ile Glu
            435                 440                 445

Lys Gly Ala Glu Val Thr Ile Asp Asn Pro Lys Glu Ala Asn Asn Asp
450                 455                 460

Asn Ser Ile Phe Ile Arg Ser Asp Gly Thr Gln Leu Asn Ile Phe Gly
465                 470                 475                 480

Asn Leu Ile Ile Asn Asp Gly Ala Arg Asp Tyr Thr Ile Arg Ala Asp
            485                 490                 495

Asn Arg Val Ser Ile Asn Val Gly Gln Ser Ile Ala Asp Asp Asp Tyr
            500                 505                 510

Ser Asn Asp Asn Gly Lys Leu Ile Ile Asn Arg Asn Gly Asp Phe Tyr
            515                 520                 525

Leu Asn Asn Asp Gly Gly Ala Leu Ser Met Trp Gly Pro Ile Thr Ile
530                 535                 540

Asn Val Asn Ser Gly Ala Ala Leu Glu Val Tyr Ser Thr Gly Ile Asn
545                 550                 555                 560

Asn Val Ser Gly Ser Gly Ala Asn Pro Ala Leu Met Arg Val Gly Gly
            565                 570                 575

Ser Ser Lys Leu Asn Val Tyr Lys Arg Gly Thr Phe Ile Leu Ser Asp
            580                 585                 590

Ser Ser Asn Gly Lys Val Ser Leu Val Asp Asp Tyr Asn Ala Asn Gly
            595                 600                 605

Asn Phe Asn Phe Asp Asn Thr Ala Lys Val Ile Phe Asp Ile Ser Asn
        610                 615                 620

Asn Asn Asn Gln Asn Ser Arg Ile Phe Ala Leu Asn Gly Thr Val Tyr
625                 630                 635                 640

Ala Thr His Asp Lys Val Arg Ala Met Leu Thr Pro Ser Ser Asn Ile
            645                 650                 655

Ala Asp Met Gly Thr Phe Lys Thr Val Gln Phe Asn Thr Ser Gly Gln
            660                 665                 670

Gly Gly Val Thr Gly Asp Ala Leu His Ser Glu Tyr Gln Asn Gln Ala
            675                 680                 685

Tyr Asn Asn Ile Val Ala Ile Arg Asp Ala Ile Arg Thr Gly Gln Leu
690                 695                 700

Arg Tyr Leu Glu Phe Ser Thr Arg Ser Val Asn Asn Ala Ser Ile Thr
705                 710                 715                 720

Gly Glu Gly His Gly Phe Thr Asp Asn Gly Ala Gln Ile Lys Gly Ser
            725                 730                 735

Val Val Asp Glu Ser Thr Asn Thr Gly Ala Val Ala Val Ala Tyr Asp
            740                 745                 750

Lys Asp Asn Asn Lys Val Gly Ser Gly Asn Val Asp Asp Gln Gly Asn
            755                 760                 765

Phe Thr Ile Asn Leu Asp Lys Pro Leu Leu Asn Lys Glu Glu Val Lys
        770                 775                 780

Val Arg Ile Glu Thr Pro Arg Gly Ala Ser Gly Phe Val Ser Thr Thr
785                 790                 795                 800
```

```
Ala Pro Leu Gly Pro Thr Ala Lys Ser Pro Ile Thr Val Ala Lys Asp
                805                 810                 815

Asp Asn Leu Ala Gly Gln Asp Ala Ser Gln Tyr Ile Thr Asn Lys Asp
        820                 825                 830

Glu Ile Ala Asn Ile Lys Pro Gly Thr Thr Asp Tyr Glu Pro Thr Phe
            835                 840                 845

Lys Ser Ala Ala Trp Lys Ser Val Asp Thr Asn Thr Lys Lys Gly Ile
        850                 855                 860

Ile Thr Val Thr Tyr Ala Asp Asn Thr Thr Asp Leu Asp Val Asp
865                 870                 875                 880

Leu Asn Val Val Asp Lys Ile Thr Asp Ala Asp Lys Phe Thr Pro Glu
                885                 890                 895

Gly Gly Thr Ile Lys Val Asp Asn Gly His Lys Leu Asp Gly Asn Asp
            900                 905                 910

Ala Tyr Glu Ala Ile Lys Asn His Asp Asp Leu Pro Ala Asp Lys Ala
        915                 920                 925

Gly Tyr Asn Trp Val Val Asp Glu Asn His Pro Ala Val Asp Thr Thr
    930                 935                 940

Lys Pro Gly Asp Gln Thr Gly Tyr Val Gln Val Thr Tyr Asn Asp Gly
945                 950                 955                 960

Ser Lys Ser Asp Leu Val Pro Val Thr Val His Val Ile Ala Asp Asn
                965                 970                 975

Glu Lys Tyr Thr Ala Ile Gly Lys Thr Gln Asn Leu Gln Lys Gly Gln
            980                 985                 990

Ser Ala Asn Pro Gln Asp Phe Ile Ala Asn Lys Asp Gly Glu Val Ser
        995                 1000                1005

Gln Asp Gly Lys Thr Tyr Thr Lys Leu Pro Asp Gly Thr Lys Tyr
    1010                1015                1020

Glu Trp Val Asp Gly Gly Ile Asp Thr Ser Thr Ile Gly Pro Lys
    1025                1030                1035

Gln Ala Gln Val Lys Val Thr Tyr Pro Asp Gly Thr Thr Gln Ile
    1040                1045                1050

Val Pro Val Lys Ala Asn Val Tyr Ser Asp Ala Asn Leu Ser Thr
    1055                1060                1065

Val Val Gly Lys Asp Ile Asn Ala Gly Tyr Lys Glu Asp Leu Thr
    1070                1075                1080

Asn Arg Ala Ile Asp Ala Ile Asp Lys Asp Lys Ser Thr Asn Leu
    1085                1090                1095

Pro Thr Asp Pro Ser Ala Tyr Thr Trp Val Asn Gly Ala Pro Asp
    1100                1105                1110

Thr Ser Lys Thr Gly Asp Ile Pro Ala Thr Val Lys Val Thr Tyr
    1115                1120                1125

Pro Asp Gly Ser Tyr Asn Thr Val Asp Val Thr Val His Val Thr
    1130                1135                1140

Ser Asp Ala Glu Lys Tyr Ser Pro Val Pro Glu Thr Ile Ser Val
    1145                1150                1155

Pro Lys Gly Thr Asp Leu Ser Gly Arg Ala Lys Asp Gly Ile Ala
    1160                1165                1170

Asn Ala Asp Lys Asp Ala Asn Gly Lys Glu Lys Leu Pro Asp Gly
    1175                1180                1185

Thr Lys Tyr Glu Trp Asp Gly Gly Val Pro Asn Thr Ser Val Thr
    1190                1195                1200
```

```
Asn Asn Lys Tyr Gly His Val Lys Val Thr Tyr Pro Asp Gly Ser
    1205                1210                1215

Ser Thr Val Val Glu Val Pro Leu Asn Ile Thr Asp Asn Asn Lys
    1220                1225                1230

Ser Asp Ala Glu Lys His Asn Pro Gln Ala Asn Ile Leu His Ala
    1235                1240                1245

Thr Leu Asn Gln Asp Leu Ser Ser Asn Asp Trp Ala Lys Lys Gly
    1250                1255                1260

Ile Leu Asn Ala Asp Glu Gln Asp Gly Ala Thr Phe Arg Trp Arg
    1265                1270                1275

Lys Gly Tyr Val Pro Asp Thr Ser Lys Glu Gly Gln Val Trp Gly
    1280                1285                1290

Ile Val Val Ser Tyr Pro Asp Ser Ser Ile Asn Glu Val Arg
    1295                1300                1305

Val Pro Val Ile Val Gln Ser Asp Ala Ser Lys Tyr Gly Ile Glu
    1310                1315                1320

Thr Gln Glu Ile Asn Val His Glu Gly Thr Asp Ile Ser Ser Asp
    1325                1330                1335

Glu Trp Ala Arg Lys Gly Ile Leu Asn Ala Asp Gln Ala Gly Lys
    1340                1345                1350

Gln Asn Glu Gln Leu Pro Asp Gly Thr Ser Tyr Thr Trp Ala Asn
    1355                1360                1365

Gly Asn Val Pro Asp Thr Thr Lys Pro Asn Lys Lys Thr Gly Tyr
    1370                1375                1380

Val Thr Val Thr Phe Pro Asp Asn Ser Ser Arg Thr Val Pro Val
    1385                1390                1395

Ile Val Asn Val Ile Gly Asp Gly Arg Ser Asp Ala Glu Lys Tyr
    1400                1405                1410

Gln Leu Lys Ala His Asp Ile Trp Thr Tyr Ile Asn Asp Thr Pro
    1415                1420                1425

Val Ala Glu Lys Ala Val Ser Asn Leu Asp Glu Leu Lys Asp Val
    1430                1435                1440

Ser Ser Ile Thr Trp Ala Thr Thr Pro Asp Val Ser Lys Val Gly
    1445                1450                1455

Asn Val Pro Ala Ile Val Val Thr Tyr Lys Asp Gly Thr Ser
    1460                1465                1470

Asn Ala Ala Pro Ile Asn Ile Glu Val Lys Gly Leu Ala Asn Asp
    1475                1480                1485

Tyr Lys Pro Glu Gly Thr Thr Ile Tyr Ala Gly Leu Asn Glu Asp
    1490                1495                1500

Ile Thr Asn Arg Ala Ala Asp Gly Ile Ala Asn Lys Asp Gln Met
    1505                1510                1515

Pro Val Ala Asn Lys Pro Glu Gly Thr Val His Thr Thr Tyr Ser
    1520                1525                1530

Trp Lys Asp Asn Ile Ile Pro Asp Thr Thr Lys Pro Gly Thr Lys
    1535                1540                1545

Tyr Gly Ile Val Glu Val Asn Phe Pro Asp Gly Ser Thr Lys Asp
    1550                1555                1560

Val Pro Val Glu Val Lys Val Thr Ser Leu Ala Ser Asp Tyr Gln
    1565                1570                1575

Asn Lys Ile Asp Thr Lys Gln Ile Ile Ala Lys Tyr Lys Gly Asn
    1580                1585                1590
```

```
Ile Pro Gln Ala Ser Asp Gly Ile Ala Asn Lys Asp Gln Ala Thr
1595                1600                1605

Lys Glu Gly Asp Lys Asp Phe Pro Ser Leu Ala Asp Val Leu Ala
1610                1615                1620

Pro Asn Gly Ile Gln Trp Lys Lys Asn Phe Glu Pro Asp Leu Ser
1625                1630                1635

Lys Pro Gly Leu Thr Ser Gly Glu Ala Ile Leu Thr Phe Lys Asp
1640                1645                1650

Gly Ser Thr Ala Glu Val Thr Ile Pro Val Leu Val Gln Thr Asp
1655                1660                1665

Ala Asp Arg Asn Thr Pro Glu Thr Gln Thr Ile Lys Thr Leu Pro
1670                1675                1680

Gly Gln Thr Val Asn Pro Glu Asp Gly Val Ile Asn Leu His Lys
1685                1690                1695

Pro Gly Glu Asn Asn Pro Gln Leu Pro Asp Gly Thr Lys Val Thr
1700                1705                1710

Phe Asp Asn Gln Ser Asp Val Asp Asp Phe Thr Lys His Gly Met
1715                1720                1725

Pro Gly Ser Asp Lys Ser Phe Asp Ala Thr Val Thr Tyr Pro Asp
1730                1735                1740

Gly Thr Thr Asp Lys Ile Lys Leu Pro Val His Ile Thr Ala Asp
1745                1750                1755

Asn Glu Val Asn Thr Pro Ile Thr Gln Gly Ile Ile Thr Pro Lys
1760                1765                1770

Asp Ser Val Pro Asp Ala Asn Lys Gly Ile Ala Asn Leu Lys Lys
1775                1780                1785

Ala Thr Thr Lys Glu Gly Lys Thr Tyr Pro Ala Leu Pro Glu Asn
1790                1795                1800

Thr Thr Val Glu Trp Val Asn Pro Gly Gln Met Lys Thr Glu Leu
1805                1810                1815

Glu Asn Ala Lys Gly Gly Thr Thr Lys Asn Tyr Asp Ala Val Val
1820                1825                1830

Ile Tyr Pro Asp Lys Ser Thr Glu Ile Val Ser Ile Pro Val Thr
1835                1840                1845

Val Ala Thr Asp Ala Asp Thr Tyr Lys Val Val Thr Gln Pro Ile
1850                1855                1860

Asp Leu Lys Asp Arg Asn Leu Pro Asp Asn Ala Asp Asp Gly Ile
1865                1870                1875

Thr Asn Leu His Lys Pro Ala Asp Phe Lys Thr Pro Gln Leu Pro
1880                1885                1890

Asp Gly Thr His Ala Glu Trp Gln Asp Lys Asp Ala Ala Gln Glu
1895                1900                1905

Val Val Lys Asn Leu Lys Pro Gly Glu Thr Val Lys Leu Pro Ala
1910                1915                1920

Thr Val Val Phe Pro Asp Gly Ser Lys Lys Gly Glu Gly Ile Asp
1925                1930                1935

Val Ser Val His Leu His Gly Gln Ser Asp Asp Tyr Asn Ile Glu
1940                1945                1950

Thr Gln Pro Val Asn Thr Asp Lys Asp Gly Asn Leu Pro Glu Asn
1955                1960                1965

Ala Asp Ser Gly Ile Lys Asn Leu Gly Lys Leu Pro Glu Gly Thr
1970                1975                1980
```

His Ala Ser Trp Gly Asp Gly Ala Gln Asp Ile Ala Lys Asn Leu
    1985                1990                1995

Lys Leu Gly Glu Thr Lys Asp Val Pro Ala Thr Val Val Phe Pro
    2000                2005                2010

Asp Gly Ser Lys Lys Glu Ile Thr Ile Pro Val His Arg Glu Gly
    2015                2020                2025

Gln Ser Asp Gly Tyr Asp Val Glu Pro Gln Leu Val Asn Thr Asp
    2030                2035                2040

Lys Asn Gly Gln Leu Pro Asn Ala Lys Glu Gly Ile Lys Asn Leu
    2045                2050                2055

Ala Asp Leu Pro Glu Gly Thr Asn Gln Pro Gly Gln Ile Glu Leu
    2060                2065                2070

Lys Ile Lys Leu Ile Arg Leu Ser Leu Val Gln Ile Gln Leu Leu
    2075                2080                2085

Lys

<210> SEQ ID NO 151
<211> LENGTH: 214
<212> TYPE: PRT
<213> ORGANISM: Lactobacillus jensenii CCOS 962

<400> SEQUENCE: 151

Met Ala Arg Ser Gly Ser Arg Val Lys Thr Thr Leu Thr Leu Val
1               5                   10                  15

Lys Val Phe Gly Val Leu Leu Ile Leu Val Ala Phe Val Cys Phe
                20                  25                  30

Arg Tyr Tyr Arg Arg Gln Ala Ile Asn Asn Glu Leu Ile Arg Gln Glu
                35                  40                  45

Gln Leu Ala Arg Glu Gln Ala Ala Lys Glu Leu Lys Ile Lys Thr
    50                  55                  60

Asp Phe Ile Lys Lys Ile Gly Pro Ile Ala Gln Lys Ala Asp Gln Gly
65                  70                  75                  80

Phe Ala Leu Leu Pro Ser Ile Thr Ile Ala Gln Ala Cys Leu Glu Ser
                85                  90                  95

Asn Tyr Gly Gln Ser Glu Leu Ser Gln Lys Tyr Asn Asn Leu Phe Gly
                100                 105                 110

Val Lys Ser Asn Asp Pro Asn Thr Ser Lys Ile Leu Ser Thr Lys Glu
                115                 120                 125

Tyr Val Asn Gly Lys Trp Ile Thr Val Lys Ala Ser Phe Gln Ile Tyr
                130                 135                 140

Asp Ser Tyr Glu Ser Ser Ile Gln Ala His Ala Arg Leu Phe Gln Asn
145                 150                 155                 160

Gly Thr Thr Trp Asn Lys Asp Gln Tyr Gln His Val Leu Ala Ala Lys
                165                 170                 175

Asp Tyr Lys Thr Gln Ala Lys Ala Leu Val Thr Asp Gly Tyr Ala Thr
                180                 185                 190

Asp Pro Asp Tyr Ala Ser Lys Leu Ile Asn Leu Ile Glu Gln Phe Asn
                195                 200                 205

Leu Asn Lys Tyr Asp Asn
    210

<210> SEQ ID NO 152
<211> LENGTH: 1323
<212> TYPE: DNA
<213> ORGANISM: Lactobacillus rhamnosus CCOS 965

<400> SEQUENCE: 152

```
atgaaacata tcggacaact taagaaatgg ccgctggtga tcttattggc gctattgttt      60
ggcgttggtg ccgcaacaac cagtgtgatg ccaacaccc aatacatgac agtcaaagcc     120
gagagcgtca atgtacggct aggtcccggc ttggcatatg gcatcatggg tcaggtaaaa     180
tccggcaatg aattgaccat tatcggttcc aaaaattcct ggtatcaagt gcgccttgcc     240
ggcaataaaa tcggttgggt tgcttcatgg ttagtcgatc aaagcgaagc cgcaaccacg     300
agtgcgaaag ttgccacggt gaatcaaccg gttaacgttc gcgaatatgc cagccaggat     360
gccaagcagt taggaacgct taatgccggc gatagtgtca agttgtgta tcaagaaggc     420
gattggaccc agattgccta taacaatacg gcggcatgga tcactagcag cagtgtccag     480
ctcactggtc agacaactaa tctggcacaa cctgcccaag ccaatctgac gcaagccaaa     540
agcggggccg cattgaaagt caccaccaat accatgacta acctgcgcaa tgcggcgggt     600
atcaatgccc catccgtcga gaaactcgat aaaggcactg aactgaccgt taccaaacaa     660
caagacgatt ggtatcaagt cactgcccct gatggcaaat cgggttatgt tgccagctgg     720
accgtcaccg ccccgaataa tggtcaaacc caaaaagcgg caacgaaact atccgaagcc     780
acgattgttc tggatcccgg acatggtggt acagacacgg tgcgccagc taacaataat     840
catgattacg aaaaaaccta taccttgaaa acggccgaac tcgttgccaa tgctttgcgg     900
gctgctggtg ctaacgttat catgacgcga acgactgaca cctttgtcga cctcgcgcca     960
cgtccgacaa ctgctaacaa cgcccatgcc gatgcattta tctccttcca ttttgactcc    1020
agcccgtcca aaaactctgc ctccgggttc accacctatt actacagcag caaaaaggat    1080
ctcgccttgg ctaaggcagt taacaacgct tttgatgact taccactaga aaatcgtggg    1140
gttgcatttg gtaactatga agttctacgc gataataaac agccggccat cctgaatgaa    1200
atgggttata tcaataacga caaagacttt aagtatatta aaaacccaac gtatcaatct    1260
aaaattgcga ccaatattgt taacggttta aatgcttact ttaaagccgg tcatcatcaa    1320
taa                                                                    1323
```

<210> SEQ ID NO 153
<211> LENGTH: 636
<212> TYPE: DNA
<213> ORGANISM: Lactobacillus rhamnosus CCOS 965

<400> SEQUENCE: 153

```
ttggcgaaaa agcgccgacg tttaccttta agaaggttc cattggcggc ttggctggtc      60
atcgcttttt ttgcggttgg ttcaatgttg gttgtcagct cgtattggtc gcaacggcaa     120
gccgaagttt cacagcgcca agcaattgtc gataagaagg cggctgaaaa agcgaagaaa     180
gaggctttta tcaagcgatt ggtgccgaca gcccaggcca tgcagaaaca gtatggtgtc     240
ttaacgagca ttacgctgtc ccaagcgatt cttgagtctg attggggaac gagcacgtta     300
gccaaggatt accataactt atttggcatt aaagggacgg atcctgccac cacgaaagta     360
ttacggacga aggaatatgt taacgataaa tggattaccg ttaatggtcg gtttcgggtt     420
tatagcgatg atgctgcttc gattcgtgat catgccttgt tattcgttaa cggtaccgac     480
tggaatccgc aacagtatgc aacggtaaga gccgcaaaag attataagac tgctgcctcg     540
gctttgcaga cggacggcta tgccactgat ccggattatc cccagaagct gattcatttg     600
atcgaagcat ggaatctgac ccagtatgac aattga                               636
```

```
<210> SEQ ID NO 154
<211> LENGTH: 765
<212> TYPE: DNA
<213> ORGANISM: Lactobacillus rhamnosus CCOS 965

<400> SEQUENCE: 154
atggcgatgt taatggcaga tgtaagcagt tggcagccgg attcggatag ctggtttcgc      60
aagttggctg atctgggtgt caaggcggtg gtcgtcaaac tgacagaagg aacgacttac     120
cagaatccta aggcggcggc acagttggcg gctgggcgca ggatggggat gcaggtgcac     180
gcttatcact atgcccattt tcataacagt gccgaagccg ttgcagaagg acgtttcttc     240
ggcgtcacgg cccgcgcgct gggcgtgtcg acgcaaagtg tgatggcagc ggatgttgaa     300
gcacctgatt tgaatgggga gctgacgggg ctgacgaatg ttttcattca gacggtcaaa     360
gcgctagggt atccacacac agacctgtat acaatggcga attggatgaa aaccagacgc     420
tttgatcgcg tggcattgat tcctaagaac ctgtggattg cgagttatgg cgttgatcag     480
ccgggcatca ataatgtcgg gacctggcag tttaccaata actttcacgg cttaggggtg     540
gatatgagtt atgactttt cggtcactac accacgcgct tgaccggtaa cctcaatggc     600
ggcgtggcgc gcgttcccac gattcgctat cacacggttt tggcaggcga agctggtgg     660 gcgattgcag atcgatatgg cttgaatatg tacaagctcg cggccctcaa tggtaagacg     720
atctacagtg tgattcatcc gggcgatcag ctgcggttga attaa                    765

<210> SEQ ID NO 155
<211> LENGTH: 1323
<212> TYPE: DNA
<213> ORGANISM: Lactobacillus paracasei CCCOS 1201

<400> SEQUENCE: 155
atgaagaaaa ttggacaatt aaaaaaatgg ccgctggtcg ttctggtggc gctactttc      60 ggcgttggtg ttgcaacaac cagtgtaatg gccaacacac aatacatgac tgtcaaggca    120
gataccgtca acgtgcggtt aggtcctggt ttggcatatt caattatggg acaagtgaaa    180
tccggtaatg aactgtcgat tatcggtgcg aaaaactcct ggtatcaagt ccgactagct    240
ggtaataaaa tcggctgggt tgcctcttgg ttggtggatc aaagtgaagc agcaacttca    300
caggccaaag tggcaacggt taatcaaccg gttaacgtcc gtgaatatgc cagtcaaaat    360
gcaaaacaac taggttcgct aaatgccggc gacagcgtca aggtcgtcta tcaagaaggc    420
gcttggactc agattgcgta caacaccacg gctgcatgga tcaccagcag cagcgttcag    480
ttaaccggcc aaaccaccaa tttagcccag cctgcgcaaa cggcgttggc aaccgagaaa    540
agtgcgccgg cgctgaaggt aacaaccaat acgatgacca accttcgcaa tgccgccggt    600
atcaatgcgc cttcggttga aaagctagac aaaggcaccg aactgacggt ctctaagcaa    660
caagatgatt ggtatgcggt cacggcacca gatggcaaaa ctggctacgt tgcgagctgg    720
accgtcagcg caccaaatga cgggcaaacg caaaaagccg ctacaaaact gtcagaggct    780
acgattgtcc ttgatccagg tcacggcggc tccgacactg gtgcgattgc caatgatggc    840
accgactatg aaaaaacata cacgcttaag acggccaatt tagttgctaa cgttttacgc    900
gcggctggtg ccaatgtcat tatgacccgt acaacggata ctttcgttga tttggcacct    960
cgaccaaata ctgccaacaa tgctcacgcg gatgctttca tctctttcca ttttgactcc   1020
agtccatcca agaattcagc atctgggatc accacctatt actacgacag caaaaaagac   1080
cttgccttgg ccaagtccgt caacagtgct ttcagcggcc ttccgctgga aaccgcggt    1140
```

```
gtcgcctttg gtaatttcga agtcctgcgt gataataaac aacctgctat tctgaacgag    1200
atgggttaca tcaacaacga taaagatttc cgtcaaatca agatccgag  ctatcagtcc    1260 aagattgcta ccgatattgt aaatggccta acgcctact  ttaaggcagg caatcatcag    1320
tga                                                                  1323

<210> SEQ ID NO 156
<211> LENGTH: 765
<212> TYPE: DNA
<213> ORGANISM: Lactobacillus paracasei CCCOS 1201

<400> SEQUENCE: 156
atggtgatat taatggcaga gtgagtagc  tggcagccgg aattggacag ctggtttcgc      60
aagctggcgg atgttggggt gaaggcggtg gtggtaaagc tgacggaagg caccacctac     120
cgcaatccta aggccgcagc gcaattggcg gcaggtcggc gaatggggat gcaggtgcat     180
ggttatcatt acgcgcatta tcacaacagc gctgatgccg tggcggaagg acggttcttc     240
ggaaccacag ccaaggcttt aggtttgtca accgagtcgg taatggcagc agatgtggag     300
gatccgggtt tatctggtga gttgacgggg gtgacgaatg ttttctcca  aactgtcaaa     360 gcgatcggat atcctcacac ggatctatat accatggcca gttggctgac cgcgcggcgc     420
tttgatcggg ttgccttgat tccgaaaaat ctgtggcttg ccagttacgg cgtgaatcaa     480
ccgggcgttg ataatgtcgg cacatggcag ttcacgaata actttcaggg gctaggtgtt     540
gatatgagtt acgactttt  tggtcactat acgacgcgtc tcactggcac actcaacggt     600
ggtgtcgcgc gcgtgccaac gattcggttt cataccgtgc agccagggga gagctggtgg     660
gcgattgcgc accagtacgg acatgacatg gacaagctgg ctgcattgaa tggcaagacg     720
attttgagtg tgattcaccc tggggatcag ctgcgggtgg aataa                    765

<210> SEQ ID NO 157
<211> LENGTH: 738
<212> TYPE: DNA
<213> ORGANISM: Lactobacillus paracasei CCCOS 1201

<400> SEQUENCE: 157
gtgcgcagtc gggtcattta tgctgatacc tatcgcaaac gtcatcaaag acgcttattt      60
ttgctggccg tttaatcat  cgctttgggc gcactgtttg tttggtggca tcagcgcaac     120
ccccgccctg atccgcagac ctatcccgtg ttgggcgtgc gtcttgacca aaccgatggg     180
gtgcaggatt ttgacagttt gcgcagcagc aaagtcagtt ttgtctatct caaagcgact     240
gaaggcagca gctattttga tgataatttt aatacgaatt ttaatcaggc agctggcagt     300
cgactgagca tcggcattta ccatgtgttc agctttgaaa cgacaccca  agcccaagct     360 gaccaattca cgcgccaagt cggccaaaat atcggtgatt taccgattgg catttactta     420
agctattaca ctgaaaagaa gccaagcaca caatggctga caactcattt acaaactttt     480
gtcacattgg tgcagcaaca ttatcatcgc caagtgttgc tgatgggtag cccaagtatt     540
ttaaaagctg tccaaaaagt cgacccgcaa gcaccacgct gggttgtaag cgacaagaag     600
ccgacaacga gcagtggttt ctggcaatat acgtctggcg cccggttgcc gaatgggcca     660
cacgcagatt accgtgctgc cgtatttatg ggggatcggg cggccttttt aaaactgtct     720
cagcagatag tcaattaa                                                  738
```

```
<210> SEQ ID NO 158
<211> LENGTH: 440
<212> TYPE: PRT
<213> ORGANISM: Lactobacillus rhamnosus CCOS 965

<400> SEQUENCE: 158

Met Lys His Ile Gly Gln Leu Lys Lys Trp Pro Leu Val Ile Leu Leu
1               5                   10                  15

Ala Leu Leu Phe Gly Val Gly Ala Ala Thr Thr Ser Val Met Ala Asn
            20                  25                  30

Thr Gln Tyr Met Thr Val Lys Ala Glu Ser Val Asn Val Arg Leu Gly
        35                  40                  45

Pro Gly Leu Ala Tyr Gly Ile Met Gly Gln Val Lys Ser Gly Asn Glu
    50                  55                  60

Leu Thr Ile Ile Gly Ser Lys Asn Ser Trp Tyr Gln Val Arg Leu Ala
65                  70                  75                  80

Gly Asn Lys Ile Gly Trp Val Ala Ser Trp Leu Val Asp Gln Ser Glu
                85                  90                  95

Ala Ala Thr Thr Ser Ala Lys Val Ala Thr Val Asn Gln Pro Val Asn
            100                 105                 110

Val Arg Glu Tyr Ala Ser Gln Asp Ala Lys Gln Leu Gly Thr Leu Asn
        115                 120                 125

Ala Gly Asp Ser Val Lys Val Val Tyr Gln Glu Gly Asp Trp Thr Gln
    130                 135                 140

Ile Ala Tyr Asn Asn Thr Ala Ala Trp Ile Thr Ser Ser Ser Val Gln
145                 150                 155                 160

Leu Thr Gly Gln Thr Thr Asn Leu Ala Gln Pro Ala Gln Ala Asn Leu
                165                 170                 175

Thr Gln Ala Lys Ser Gly Ala Ala Leu Lys Val Thr Thr Asn Thr Met
            180                 185                 190

Thr Asn Leu Arg Asn Ala Ala Gly Ile Asn Ala Pro Ser Val Glu Lys
        195                 200                 205

Leu Asp Lys Gly Thr Glu Leu Thr Val Thr Lys Gln Gln Asp Asp Trp
    210                 215                 220

Tyr Gln Val Thr Ala Pro Asp Gly Lys Ser Gly Tyr Val Ala Ser Trp
225                 230                 235                 240

Thr Val Thr Ala Pro Asn Asn Gly Gln Thr Gln Lys Ala Ala Thr Lys
                245                 250                 255

Leu Ser Glu Ala Thr Ile Val Leu Asp Pro Gly His Gly Gly Thr Asp
            260                 265                 270

Thr Gly Ala Pro Ala Asn Asn His Asp Tyr Glu Lys Thr Tyr Thr
        275                 280                 285

Leu Lys Thr Ala Glu Leu Val Ala Asn Ala Leu Arg Ala Ala Gly Ala
    290                 295                 300

Asn Val Ile Met Thr Arg Thr Thr Asp Thr Phe Val Asp Leu Ala Pro
305                 310                 315                 320

Arg Pro Thr Thr Ala Asn Asn Ala His Ala Asp Ala Phe Ile Ser Phe
                325                 330                 335

His Phe Asp Ser Ser Pro Ser Lys Asn Ser Ala Ser Gly Phe Thr Thr
            340                 345                 350

Tyr Tyr Tyr Ser Ser Lys Lys Asp Leu Ala Leu Ala Lys Ala Val Asn
        355                 360                 365

Asn Ala Phe Asp Asp Leu Pro Leu Glu Asn Arg Gly Val Ala Phe Gly
    370                 375                 380
```

```
Asn Tyr Glu Val Leu Arg Asp Asn Lys Gln Pro Ala Ile Leu Asn Glu
385                 390                 395                 400

Met Gly Tyr Ile Asn Asn Asp Lys Asp Phe Lys Tyr Ile Lys Asn Pro
            405                 410                 415

Thr Tyr Gln Ser Lys Ile Ala Thr Asn Ile Val Asn Gly Leu Asn Ala
            420                 425                 430

Tyr Phe Lys Ala Gly His His Gln
            435                 440

<210> SEQ ID NO 159
<211> LENGTH: 211
<212> TYPE: PRT
<213> ORGANISM: Lactobacillus rhamnosus CCOS 965

<400> SEQUENCE: 159

Met Ala Lys Lys Arg Arg Arg Phe Thr Leu Lys Val Pro Leu Ala
1               5                   10                  15

Ala Trp Leu Val Ile Ala Phe Phe Ala Val Gly Ser Met Leu Val Val
            20                  25                  30

Ser Ser Tyr Trp Ser Gln Arg Gln Ala Glu Val Ser Gln Arg Gln Ala
        35                  40                  45

Ile Val Asp Lys Lys Ala Ala Glu Lys Ala Lys Glu Ala Phe Ile
50                  55                  60

Lys Arg Leu Val Pro Thr Ala Gln Ala Met Gln Lys Gln Tyr Gly Val
65                  70                  75                  80

Leu Thr Ser Ile Thr Leu Ser Gln Ala Ile Leu Glu Ser Asp Trp Gly
                85                  90                  95

Thr Ser Thr Leu Ala Lys Asp Tyr His Asn Leu Phe Gly Ile Lys Gly
            100                 105                 110

Thr Asp Pro Ala Thr Thr Lys Val Leu Arg Thr Lys Glu Tyr Val Asn
            115                 120                 125

Asp Lys Trp Ile Thr Val Asn Gly Arg Phe Arg Val Tyr Ser Asp Asp
130                 135                 140

Ala Ala Ser Ile Arg Asp His Ala Leu Leu Phe Val Asn Gly Thr Asp
145                 150                 155                 160

Trp Asn Pro Gln Gln Tyr Ala Thr Val Arg Ala Ala Lys Asp Tyr Lys
                165                 170                 175

Thr Ala Ala Ser Ala Leu Gln Thr Asp Gly Tyr Ala Thr Asp Pro Asp
            180                 185                 190

Tyr Pro Gln Lys Leu Ile His Leu Ile Glu Ala Trp Asn Leu Thr Gln
            195                 200                 205

Tyr Asp Asn
210

<210> SEQ ID NO 160
<211> LENGTH: 254
<212> TYPE: PRT
<213> ORGANISM: Lactobacillus rhamnosus CCOS 965

<400> SEQUENCE: 160

Met Ala Met Leu Met Ala Asp Val Ser Ser Trp Gln Pro Asp Ser Asp
1               5                   10                  15

Ser Trp Phe Arg Lys Leu Ala Asp Leu Gly Val Lys Ala Val Val Val
            20                  25                  30

Lys Leu Thr Glu Gly Thr Thr Tyr Gln Asn Pro Lys Ala Ala Ala Gln
            35                  40                  45
```

```
Leu Ala Ala Gly Arg Arg Met Gly Met Gln Val His Ala Tyr His Tyr
 50                  55                  60

Ala His Phe His Asn Ser Ala Glu Ala Val Ala Glu Gly Arg Phe Phe
 65                  70                  75                  80

Gly Val Thr Ala Arg Ala Leu Gly Val Ser Thr Gln Ser Val Met Ala
                 85                  90                  95

Ala Asp Val Glu Ala Pro Asp Leu Asn Gly Glu Leu Thr Gly Leu Thr
            100                 105                 110

Asn Val Phe Ile Gln Thr Val Lys Ala Leu Gly Tyr Pro His Thr Asp
            115                 120                 125

Leu Tyr Thr Met Ala Asn Trp Met Lys Thr Arg Arg Phe Asp Arg Val
130                 135                 140

Ala Leu Ile Pro Lys Asn Leu Trp Ile Ala Ser Tyr Gly Val Asp Gln
145                 150                 155                 160

Pro Gly Ile Asn Asn Val Gly Thr Trp Gln Phe Thr Asn Asn Phe His
                165                 170                 175

Gly Leu Gly Val Asp Met Ser Tyr Asp Phe Phe Gly His Tyr Thr Thr
            180                 185                 190

Arg Leu Thr Gly Asn Leu Asn Gly Gly Val Ala Arg Val Pro Thr Ile
            195                 200                 205

Arg Tyr His Thr Val Leu Ala Gly Glu Ser Trp Trp Ala Ile Ala Asp
210                 215                 220

Arg Tyr Gly Leu Asn Met Tyr Lys Leu Ala Ala Leu Asn Gly Lys Thr
225                 230                 235                 240

Ile Tyr Ser Val Ile His Pro Gly Asp Gln Leu Arg Leu Asn
                245                 250

<210> SEQ ID NO 161
<211> LENGTH: 440
<212> TYPE: PRT
<213> ORGANISM: Lactobacillus paracasei CCCOS 1201

<400> SEQUENCE: 161

Met Lys Lys Ile Gly Gln Leu Lys Lys Trp Pro Leu Val Val Leu Val
 1               5                  10                  15

Ala Leu Leu Phe Gly Val Gly Val Ala Thr Thr Ser Val Met Ala Asn
                 20                  25                  30

Thr Gln Tyr Met Thr Val Lys Ala Asp Thr Val Asn Val Arg Leu Gly
             35                  40                  45

Pro Gly Leu Ala Tyr Ser Ile Met Gly Gln Val Lys Ser Gly Asn Glu
 50                  55                  60

Leu Ser Ile Ile Gly Ala Lys Asn Ser Trp Tyr Gln Val Arg Leu Ala
 65                  70                  75                  80

Gly Asn Lys Ile Gly Trp Val Ala Ser Trp Leu Val Asp Gln Ser Glu
                 85                  90                  95

Ala Ala Thr Ser Gln Ala Lys Val Ala Thr Val Asn Gln Pro Val Asn
            100                 105                 110

Val Arg Glu Tyr Ala Ser Gln Asn Ala Lys Gln Leu Gly Ser Leu Asn
            115                 120                 125

Ala Gly Asp Ser Val Lys Val Tyr Gln Glu Gly Ala Trp Thr Gln
130                 135                 140

Ile Ala Tyr Asn Thr Thr Ala Ala Trp Ile Thr Ser Ser Ser Val Gln
145                 150                 155                 160

Leu Thr Gly Gln Thr Thr Asn Leu Ala Gln Pro Ala Gln Thr Ala Leu
                165                 170                 175
```

Ala Thr Glu Lys Ser Ala Pro Ala Leu Lys Val Thr Thr Asn Thr Met
            180                 185                 190

Thr Asn Leu Arg Asn Ala Ala Gly Ile Asn Ala Pro Ser Val Glu Lys
            195                 200                 205

Leu Asp Lys Gly Thr Glu Leu Thr Val Ser Lys Gln Gln Asp Asp Trp
        210                 215                 220

Tyr Ala Val Thr Ala Pro Asp Gly Lys Thr Gly Tyr Val Ala Ser Trp
225                 230                 235                 240

Thr Val Ser Ala Pro Asn Asp Gly Gln Thr Gln Lys Ala Ala Thr Lys
            245                 250                 255

Leu Ser Glu Ala Thr Ile Val Leu Asp Pro Gly His Gly Gly Ser Asp
            260                 265                 270

Thr Gly Ala Ile Ala Asn Asp Gly Thr Asp Tyr Glu Lys Thr Tyr Thr
            275                 280                 285

Leu Lys Thr Ala Asn Leu Val Ala Asn Val Leu Arg Ala Ala Gly Ala
        290                 295                 300

Asn Val Ile Met Thr Arg Thr Thr Asp Thr Phe Val Asp Leu Ala Pro
305                 310                 315                 320

Arg Pro Asn Thr Ala Asn Asn Ala His Ala Asp Ala Phe Ile Ser Phe
            325                 330                 335

His Phe Asp Ser Ser Pro Ser Lys Asn Ser Ala Ser Gly Ile Thr Thr
            340                 345                 350

Tyr Tyr Tyr Asp Ser Lys Lys Asp Leu Ala Leu Ala Lys Ser Val Asn
        355                 360                 365

Ser Ala Phe Ser Gly Leu Pro Leu Glu Asn Arg Gly Val Ala Phe Gly
370                 375                 380

Asn Phe Glu Val Leu Arg Asp Asn Lys Gln Pro Ala Ile Leu Asn Glu
385                 390                 395                 400

Met Gly Tyr Ile Asn Asn Asp Lys Asp Phe Arg Gln Ile Lys Asp Pro
            405                 410                 415

Ser Tyr Gln Ser Lys Ile Ala Thr Asp Ile Val Asn Gly Leu Asn Ala
            420                 425                 430

Tyr Phe Lys Ala Gly Asn His Gln
        435                 440

<210> SEQ ID NO 162
<211> LENGTH: 254
<212> TYPE: PRT
<213> ORGANISM: Lactobacillus paracasei CCCOS 1201

<400> SEQUENCE: 162

Met Val Ile Leu Met Ala Asp Val Ser Ser Trp Gln Pro Glu Leu Asp
1               5                   10                  15

Ser Trp Phe Arg Lys Leu Ala Asp Val Gly Val Lys Ala Val Val Val
            20                  25                  30

Lys Leu Thr Glu Gly Thr Thr Tyr Arg Asn Pro Lys Ala Ala Ala Gln
            35                  40                  45

Leu Ala Ala Gly Arg Arg Met Gly Met Gln Val His Gly Tyr His Tyr
        50                  55                  60

Ala His Tyr His Asn Ser Ala Asp Ala Val Ala Glu Gly Arg Phe Phe
65                  70                  75                  80

Gly Thr Thr Ala Lys Ala Leu Gly Leu Ser Thr Glu Ser Val Met Ala
            85                  90                  95

Ala Asp Val Glu Asp Pro Gly Leu Ser Gly Glu Leu Thr Gly Val Thr
            100                 105                 110

Asn Val Phe Leu Gln Thr Val Lys Ala Ile Gly Tyr Pro His Thr Asp
            115                 120                 125

Leu Tyr Thr Met Ala Ser Trp Leu Thr Ala Arg Arg Phe Asp Arg Val
130                 135                 140

Ala Leu Ile Pro Lys Asn Leu Trp Leu Ala Ser Tyr Gly Val Asn Gln
145                 150                 155                 160

Pro Gly Val Asp Asn Val Gly Thr Trp Gln Phe Thr Asn Asn Phe Gln
            165                 170                 175

Gly Leu Gly Val Asp Met Ser Tyr Asp Phe Phe Gly His Tyr Thr Thr
            180                 185                 190

Arg Leu Thr Gly Thr Leu Asn Gly Gly Val Ala Arg Val Pro Thr Ile
            195                 200                 205

Arg Phe His Thr Val Gln Pro Gly Glu Ser Trp Trp Ala Ile Ala His
            210                 215                 220

Gln Tyr Gly His Asp Met Asp Lys Leu Ala Ala Leu Asn Gly Lys Thr
225                 230                 235                 240

Ile Leu Ser Val Ile His Pro Gly Asp Gln Leu Arg Val Glu
                245                 250

<210> SEQ ID NO 163
<211> LENGTH: 245
<212> TYPE: PRT
<213> ORGANISM: Lactobacillus paracasei CCCOS 1201

<400> SEQUENCE: 163

Met Arg Ser Arg Val Ile Tyr Ala Asp Thr Tyr Arg Lys Arg His Gln
1               5                   10                  15

Arg Arg Leu Phe Leu Leu Ala Val Leu Ile Ala Leu Gly Ala Leu
            20                  25                  30

Phe Val Trp Trp His Gln Arg Asn Pro Arg Pro Asp Pro Gln Thr Tyr
            35                  40                  45

Pro Val Leu Gly Val Arg Leu Asp Gln Thr Asp Gly Val Gln Asp Phe
50                  55                  60

Asp Ser Leu Arg Ser Ser Lys Val Ser Phe Val Tyr Leu Lys Ala Thr
65                  70                  75                  80

Glu Gly Ser Ser Tyr Phe Asp Asp Asn Phe Asn Thr Asn Phe Asn Gln
            85                  90                  95

Ala Ala Gly Ser Arg Leu Ser Ile Gly Ile Tyr His Val Phe Ser Phe
            100                 105                 110

Glu Thr Thr Pro Gln Ala Gln Ala Asp Gln Phe Thr Arg Gln Val Gly
            115                 120                 125

Gln Asn Ile Gly Asp Leu Pro Ile Gly Ile Tyr Leu Ser Tyr Tyr Thr
            130                 135                 140

Glu Lys Lys Pro Ser Thr Gln Trp Leu Thr Thr His Leu Gln Thr Phe
145                 150                 155                 160

Val Thr Leu Val Gln Gln His Tyr His Arg Gln Val Leu Leu Met Gly
            165                 170                 175

Ser Pro Ser Ile Leu Lys Ala Val Gln Lys Val Asp Pro Gln Ala Pro
            180                 185                 190

Arg Trp Val Val Ser Asp Lys Lys Pro Thr Thr Ser Ser Gly Phe Trp
            195                 200                 205

Gln Tyr Thr Ser Gly Ala Arg Leu Pro Asn Gly Pro His Ala Asp Tyr
            210                 215                 220

```
-continued

Arg Ala Ala Val Phe Met Gly Asp Arg Ala Ala Phe Leu Lys Leu Ser
225                 230                 235                 240

Gln Gln Ile Val Asn
                245
```

PROBIOTIC BACTERIAL STRAINS PRODUCING ANTIMICROBIAL PROTEINS AND COMPOSITIONS COMPRISING THESE FOR USE IN THE TREATMENT OF DIARRHEAL AND OTHER MICROBIAL DISEASES

RELATED APPLICATIONS

This application is a National Stage of PCT/EP2019/061259, filed 2 May 2019, titled PROBIOTIC BACTERIAL STRAINS PRODUCING ANTIMICROBIAL PROTEINS AND COMPOSITIONS COMPRISING THESE FOR USE IN THE TREATMENT OF DIARRHEAL AND OTHER MICROBIAL DISEASES, which claims the benefit and priority to European Patent Application No. 18170567.4, filed on 3 May 2018, both of which are incorporated herein by reference in their entirety for all purposes.

The present invention is directed to a bacterial, preferably probiotic bacterial peptidoglycan hydrolase (PGH), a peptidoglycan hydrolase (PGH)-comprising bacterial, preferably probiotic bacterial strain or a peptidoglycan hydrolase (PGH)-comprising composition for use in the therapeutic or prophylactic treatment of a bacterial infection, preferably for the treatment of a bacterial infection resulting in diarrhea. Further aspects of the present invention relate to corresponding methods for preparing a medicament and to a corresponding method of treatment.

Treatment of diarrhea by administering living (e.g. yogurt) or tyndallized (e.g. "Lactéol®") dried bacteria to restore a disturbed intestinal microflora was introduced in the twenties of the last century and is still practiced. Additionally, in recent decades, many strains of probiotics have been used in the attempt to prevent or cure diarrheal diseases. Different types of diarrhea were investigated clinically (Ref. de Vrese, M. et al., J. Nutr. 137, 803S-811S, 2007) including antibiotic-associated diarrhea (AAD), *Clostridium difficile* gastroenteritis, traveler's diarrhea, chemo- or radio-induced diarrhea. Even though many studies yielded inconsistent results it appears ascertained that *L. rhamnosus* LGG may be effective in preventing *C. difficile* infections, whereas *S. boulardii* may be useful in the treatment of *C. difficile*-associated diarrhea in combination with antibiotics.

S. Guandalini (J Clin Gastroeneterol, 2011 November; 45 Suppl: S149-53) concluded the same: "The vast majority of published trials show a statistically significant benefit and moderate clinical benefit of a few, well identified probiotic strains—mostly *Lactobacillus* GG and *S. boulardii*—in the treatment of acute, watery diarrhea . . . ". However, the achieved improvements seem rather modest: "Such a beneficial effect results, on average, in a reduction of diarrhea duration of approximately one day".

The mechanisms of action of the above-mentioned two leading strains used in general practice and in hospital for diarrheal conditions have been studied and published in detail, main findings are reported in De Keersmaecker S C et al. (FEMS Microbiol Lett. 2006 June; 259(1):89-96) who report that "*Lactobacillus rhamnosus* GG produced a low-molecular weight, heat-stable, non-proteinaceous bactericidal substance, active at acidic pH against a wide range of bacterial species. SCS of *L. rhamnosus* GG grown in MRS medium contained five compounds that could meet the above description, if present at the appropriate concentration. Therefore, the antimicrobial activity of *L. rhamnosus* GG against *S. typhimurium* is not due the production of a bacteriocin".

With respect to peptidoglycan hydrolases the enzyme spectrum of LGG was studied and published as early as 1994 (W. H. Ling et al., Microbial Ecology in Health and Disease: Vol. 7:99-104 (1994)). The aforementioned article teaches the enzyme profile of *Lactobacillus* GG, and the value for producing enzyme E18, i.e. glucosaminidase, is zero. In other words, no NAGase or other glycosidase production was detected. Hence, no defined type of antimicrobial low- or high-molecular peptide has been associated with the observed antimicrobial activity of LGG.

For *S. boulardii* many different mechanisms were postulated for its activity alone or as adjuvant for use in *C. difficile* infections (Therap Adv Gastrenterol. 2012 March: 5(2):111-125). For nosocomial infections a special protease is postulated that cleaves the *C. difficile* Toxin A and, thus, inhibits its action. No bacteriocin-like substance produced by *S. boulardii* has been reported so far.

With respect to peptidoglycan hydrolases, the APIZYM profiles of a number of *Saccharomyces cerevisiae* have been studied (C. Pennacchia et al., Journal of Applied Microbiology, 105:1919-1928 (2008)). All studied strains of *S. cerevisae* do not secrete N-acetyl-β-glucosaminidase or equivalent PGH.

In conclusion, none of the two leading probiotic strains used in the treatment or prevention of CDI/CDAD were found to produce bacteriocins or antimicrobial enzymes active against *C. diff*.

The bacterial cell wall consists of glycan strands which are cross-linked by flexible peptide side chains, providing strength and rigidity to the bacterial cell wall. The peptidoglycan of both the Gram-positive and Gram-negative bacteria features repeating units of N-acetylglucosamine (NAG) and β-(1-4)-N-acetylmuramic acid (NAM) cross-linked by peptide stem chains attached to NAM residues. The so-called peptidoglycan hydrolases (PGHs) are the enzymes responsible for cleaving the bonds within the peptidoglycan chains and side-chains branches. PGHs maintain the overall cell wall peptidoglycan turnover. Furthermore, PGH are involved in many essential processes of the bacteria, e.g. the separation of daughter cells during cell division and autolysis (Waldemar Vollmer Bernard Joris Paulette Charlier Simon Foster, *FEMS Microbiology Reviews*, Volume 32, Issue 2, 1 Mar. 2008, Pages 259-286).

Peptidoglycan hydrolases originate from different sources including animals, plants, bacteria and phages. According to their sources PGHs can be classified into lysozymes, bacteriocins, autolysins and endolysins (Current Research, Technology and Education Topics in Applied Microbiology and Microbial Biotechnology, Chapter: Peptidoglycan hydrolases, Editors: Mendez-Vilas, pp. 463-472).

It is noted that there is a substantial difference between the single lysozymes of animal origin (human, chicken, a.s.o.), discovered by Fleming in 1921, and the class of muramidases/PGHs (also sometimes referred to as lysozymes) of bacterial origin, i.e. bacterial PGHs. The lysozymes of animal origin (human, chicken, a.s.o.) are abundant in animal secretions as tears, milk, mucus a.s.o., are part of the innate immune system and exhibit only a weak antimicrobial activity against Gram-positive bacteria. The bacterial muramidases/PGHs possess the properties listed above and differ in size, function and structure from the former of animal origin. Egg-white derived lysozyme has, e.g. a molecular weight of 14.3 kDa, which corresponds to 1'166 bp DNA, whereas the bacterial PGHs found and reported in this patent application are molecular sequences varying from e.g. as little as 201 to 999 and to 1542 bp DNA.

Alternatively, peptidoglycan hydrolases are also classified in 3 groups according to their substrate specificity:
- Glycosidases: N-acetylglucosaminidases (NAGases) and N-acetylmuramidases,
- Amidases: N-acetylmuramoyl-L-alanine amidase, and
- Peptidases: carboxypeptidases and endopeptidases.

Besides NAGases, that cleave NAG units from the peptidoglycan, also more broadly active N-acetylhexosaminidases as well as other specific glycosidases like N-acetylgalactosaminidase and N-acetylmannosidase have been described/published and will be referred to herein. NAGases and muramidases both cleave the same glycosidic bond between the N-acetylglucosamin and N-acetylmuramic acid units of the glycan chains and are functionally and structurally closely related.

Another type of peptides, gene encoded and ribosomally produced by bacteria is categorized as bacteriocins (see: Rodney H Perez, Takeshi Zendo, and Kenji Sonomoto, Microb Cell Fact. 2014; 13(Suppl 1): S3 for a recent review). Mainly, these bacteriocins (polypeptides) can kill or inhibit taxonomically closely related bacteria within their narrow spectrum of activity, but do not have an essential role in bacterial meta- and catabolism as do PGH. Those bacteriocins produced by safe (GRAS/QPS) bacteria like probiotics are mostly used in the food and dairy industry as preservatives (e.g. nisin from *Lactococcus lactis* under E-number E234, a representative of the Class I of bacteriocins, the so-called lantibiotics). It is thus important to clearly separate between bacterial PGHs and bacteriocins, bacterial PGHs being, among other things, much larger in size than bacteriocins. For example, the bacteriocin nisin A has a molecular weight of 3'354.07 Dalton, whereas a typical NAGase, e.g. isolated from *Xanthomonas manihotis* (New England BioLabs, Catalog #P0732) has a MW of 71 kDalton.

In summary, consistent and significant results in diarrhea, in particular in *C. diff.*-associated diarrhea (CDAD) and/or the *C. diff.*-infection (CDI) are reported only for *Lactobacillus rhamnosus* LGG and for *Saccharomyces boulardii*. With regard to the direct antimicrobial activity against gastrointestinal pathogens causing infections and diarrhea, in particular against *C. difficile*, neither of the above-mentioned two probiotics produces peptidoglycan hydrolases, e.g. of the type of N-acetylglucosaminidase or glycosidase. Furthermore, it appears that they do not produce other antimicrobial peptides of the type of bacteriocins.

*Clostridium difficile* (CD or *C. diff.*) is an enterotoxin-producing (enterotoxin A and cytotoxin B), anaerobic, motile, spore-forming Gram-positive bacterium that is ubiquitous in nature, especially prevalent in soil and which is present in 2 to 5% of the adult human population. *C. diff.*-infection (CDI) is one of the most prevalent nosocomial infections with a dramatic increase in incidence and severity in the past decade.

*C. diff.*-associated diarrhea (CDAD) and *C. diff.*-infection (CDI) are a major burden for Western health systems. Next to antibiotic therapy, many attempts for treating CDAD or CDI focus on different probiotics. The efficacy of probiotics in the prevention of CDAD is by the majority positive, as it typically reduces the occurrence of diarrhea by around 50%. Lau and Chamberlain (Intl Gen Med. 2016 Feb. 22; 9:27-37) concluded that *Lactobacillus* GG and *Saccharomyces* probiotics significantly reduce the risk of CDAD in both adults and children, especially among hospitalized patients. However, they also point out that these preliminary results will require additional research for determining the optimum probiotic strain.

The topic of *Clostridium difficile* colitis is regularly updated in Medscape by Faten N Aberra (http://emedicine.medscape.com/article/186458-overview, Update: Apr. 6, 2017) and the author emphasizes that presently "Probiotics are not recommended as a single agent for the treatment of active CDI owing to limited data supporting their benefit and a potential risk for septicemia. Use of *Saccharomyces boulardii* and *Lactobacillus* species have shown mixed results in reducing the risk of CDI relapse. However, *S. boulardii* has generated interest for the treatment of CDI, because it seems to inhibit the effects of toxins A and B on the human colonic mucosa."

Allen et al. (*The Lancet*, Volume 382, No. 9900, p 1249-1257, 12.10.2013) observed that older inpatients suffering from CDI did not benefit from a probiotic combined Lactobacilli and Bifidobacteria supplementation against antibiotic-associated diarrhoea (AAD) and CDAD. The investigators admitted that they " . . . identified no evidence that a multi-strain preparation of lactobacilli and bifidobacteria was effective in prevention of AAD or CDD". So far, neither *bifidobacterium* nor *Lactobacillus* have shown a significant clinical efficacy in CDI.

It is generally assumed that 4 different mechanisms may play a role in the treatment with CDI/CDAD by probiotics (Corr, Hill & Gahan, *Adv Food Nutr Res.* 2009; 56:1-15):
1. direct antimicrobial activity through production of lactic acid, hydrogen peroxide and bacteriocins;
2. competitive exclusion at binding sites or stimulation of the epithelial barrier function;
3. stimulation of immune responses via increase of sIgA and influence on the production of cytokines;
4. and inhibition of virulence genes or protein expression in gastrointestinal pathogens.

Mechanisms 2 and 3 involve functions of the host and/or of the entire gut microbiome, which are extremely complex to investigate. Only mechanism 1, the direct inhibition of the pathogen by metabolites of lactic acid bacteria such as lactic acid, hydrogen peroxide bacteriocins and the like can be verified relatively easily. This approach has been tried before in different clinical studies that mainly failed.

In the search for probiotic strains against *C. difficile* P. Naaber (*Journal of Medical Microbiology* (2004) 53, 551-554) selected strains of different species such as *L. plantarum* and *L. paracasei*, and the observed antimicrobial effects were attributed to lactic acid and $H_2O_2$ production.

More recently, M Ratsep (J. Prob. Health 2014, 2:1) reported in vitro results on the effect of *L. plantarum* on clinical isolates of *C. diff*. Although several *L. plantarum* strains inhibited different clinical isolates of *C. diff.* (supposedly on account of the bacteriocin plantaricin), some *C. diff.* strains were not inhibited by any of the probiotic *L. plantarum* strains. And a clinical study with the commercially successful probiotic *L. plantarum* strain 299v failed to show any significant positive effect on the production of *C. diff.* toxin in AAD patients (Lönnermark et al., *J Clin Gastroenterol.* 2010; 44(2):106-12).

Schoster et al. (Anaerobe, vol. 20, April 2013, Pages 36-41) assessed the inhibitory effects of 16 *Lactobacillus* and one *Bifidobacterium* commercial strains on reference strains of *C. diff.* and *C. perfringens* by an agar well diffusion assay and by a broth culture inhibition assay using cell-free supernatant harvested at different growth phases, with and without pH neutralization. The cell-free supernatant (CFSN) of the probiotics (mainly *L. rhamnosus, L. casei* and *L. plantarum*) inhibited most of the *C. diff.* and *C. perfringens* strains when applied after 6, 12 or 24 h (at a pH of 4 or lower). However, when neutralized (to pH 6.9), no one of the CFSN of the probiotics significantly inhibited *C. difficile*. The effect of other possible agents against *C. difficile* produced by these lactic acid bacteria (LAB) was in the end masked by the dominating antimicrobial effect of lactic acid at low pH.

More sophisticated experiments were performed by Lee et al. (Toxicol Res. 2013 June; 29(2): 99-106) in order to investigate the activity of 4 different lactic acid bacteria and bifidobacteria (*Lacto-bacillus rhamnosus, Lactococcus lactis, Bifidobacterium breve*, and *Bifidobacterium lactis*) against *C. difficile*. These probiotics inhibited *C. diff.* in different experimental set-ups. However, the authors eventually admit that the effect of putative antimicrobial substances against *C. diff.* produced by the lactic acid bacteria is masked by the same effect caused by lactic or acetic acid. The strongest anti-*C. diff.* activity exerted by a *Lactococcus lactis* strain was supposed likely to be mediated through the action of a bacteriocin similar to nisin.

In fact, nisin is presently almost the sole bacteriocin of any probiotic strain that has proven in vitro to inhibit *C. difficile*.

In summary, the present literature indicates that certain species of lactic acid bacteria, in particular Bifidobacteria and Lactococci, might possess the ability to produce substances that inhibit *C. diff.* However, in the experiments this inhibition was masked by lactic and other acids produced by these bacteria which eventually lower the pH of the medium and cause an unspecific antimicrobial activity also towards *C. diff.* And none of these antimicrobial substances were identified, except for *Lactococcus* which is known to produce nisin, an already FDA- and EU-approved substance, widely used in the dairy and food industry against food spoilage.

The therapeutic use of nisin as an antimicrobial against *C. difficile* has 2 main drawbacks because it is rapidly degraded by proteolytic enzymes in the upper part of the intestine (Ahmad et al., *The American Journal of Gastroenterology* 108, 625, April 2013), and because it exhibits inhibitory activity against many strains of protective gut bacteria such as Bifidobacteria and Lactobacilli, which activity could be detrimental upon administration to patients (Le Blay et al., *Letters in Applied Microbiology* 45, 2007, 252-257).

Nisin is bactericidal on the germinated cells of *C. difficile* as well as on its spores (Avila et al., Int. J Food Microbio. 2014 Feb. 17; Z172:70-5), but it cannot be administered as pure substance (see Ahmad et al., above).

Last but not least, nisin activity is pH-dependent. A pH-value around 4 (Schoster et al. (Anaerobe, vol. 20, April 2013, 36-41) is only relevant for a vaginal environment, whereas in the intestine the pH is higher than, or equal to 5, and depends on the position in this organ.

Next to *C. difficile*, the most important causative bacterial pathogens for diarrheas include: entero-pathogenic *Escherichia coli*, diarrhoeagenic *Salmonella typhimurium, Shigella flexneri* or *sonnei, Listeria monocytogenes, Campylobacter jejuni* and *Clostridium perfringens*.

It is the objective of the present invention to provide improved compounds, bacterial strains, compositions and methods for use in the treatment and prophylaxis of bacterial, preferably diarrheal diseases, preferably without the significant drawbacks and side-effects of current antibiotic-based treatments.

Disclosed herein are a bacterial peptidoglycan hydrolase (PGH), preferably a probiotic bacterial PGH, a peptidoglycan hydrolase (PGH)-secreting bacterial strain, preferably a PGH-secreting probiotic bacterial strain and a bacterial peptidoglycan hydrolase (PGH)-comprising composition, preferably a probiotic bacterial PGH-comprising composition for use in the therapeutic or prophylactic treatment of a bacterial infection.

In a first aspect, the present invention is directed to a peptidoglycan hydrolase (PGH)-secreting probiotic bacterial strain selected from the group consisting of

*Lactococcus lactis*, preferably subsp. *lactis* and subsp. *cremoris, Lactobacillus gasseri, Lactobacillus crispatus, Lactobacillus jensenii, Lactobacillus plantarum* CCOS 893 (DSM 32352), *Lactobacillus fermentum, Lactobacillus johnsonii, Lactobacillus rhamnosus, Lactobacillus paracasei, Lactobacillus casei, Bifidobacterium animalis* subsp. *lactis, Bifidobacterium longum, Bifidobacterium breve, Bifidobacterium pseudocatenulatum* and *Bifidobacterium bifidum*, for use in the therapeutic or prophylactic treatment of a bacterial infection.

It was surprisingly found that bacterial and probiotic bacterial strains producing and secreting N-acetylglucosaminidase (NAGase), or more generally, producing and secreting suitable peptidoglycan hydrolases (PGHs) such as glycosidases, have an antimicrobial effect on pathogenic, including enteropathogenic, bacteria and in particular on *Clostridium difficile* strains.

The bacterial, preferably probiotic bacterial peptidoglycan hydrolases (PGH), peptidoglycan hydrolase (PGH)-secreting bacterial strains, preferably probiotic bacterial strains, or bacterial, preferably probiotic bacterial peptidoglycan hydrolase (PGH)-comprising compositions disclosed herein can disrupt any pathogen featuring a cell-wall consisting of a peptidoglycan layer, such as Gram-positives, Gram-negatives and mycobacteria.

The term "PGH-secreting" for a bacterial and/or probiotic bacterial strain means that the strain for use according to the present invention contains the corresponding gene and is capable to secrete the PGH into the extracellular environment.

The term "bacterial, preferably probiotic bacterial PGH-comprising" as used herein, means that a composition contains the bacterial, preferably probiotic bacterial PGH next to at least one further component.

The term "bacterial, preferably probiotic bacterial PGH" refers to any PGH that is preferably produced by bacteria, preferably probiotic bacteria, and therefore preferably is of bacterial origin, more preferably of probiotic bacterial origin. Optionally, the term "bacterial PGH" can exclude PGHs from animals such as humans, chicken or dogs. For example, the term "probiotic bacterial PGH" can exclude PGHs from non-probiotic bacteria, e.g. from pathogenic bacteria. Optionally, the bacterial and probiotic bacterial PGH disclosed herein also exclude any non-bacterial and/or non-probiotic bacterial lysozyme.

It is further preferred that the bacterial PGH is a PGH of probiotic bacteria. It is further preferred that the bacterial and/or probiotic bacterial PGH is a PGH from non-pathogenic bacteria. It is also preferred that the PGH disclosed herein is a PGH that is genotypically encoded and/or expressed and/or secreted by a probiotic strain for use in the present invention, preferably a probiotic strain selected from the group consisting of *Lactococcus lactis* (preferably subsp. *lactis* and subsp. *cremoris*), *Lactobacillus gasseri, Lactobacillus crispatus, Lactobacillus jensenii, Lactobacillus plantarum, Lactobacillus fermentum, Lactobacillus johnsonii, Lactobacillus rhamnosus, Lactobacillus paracasei, Lactobacillus casei, Bifidobacterium animalis* subsp. *lactis, Bifidobacterium longum, Bifidobacterium breve, Bifidobacterium pseudocatenulatum* and *Bifidobacterium bifidum*;

more preferably a probiotic strain selected from the group consisting of *Lactococcus lactis* CCOS 949 (DSM 32294), *Lactobacillus gasseri* CCOS 960 (DSM 32296); *Lactobacillus crispatus* CCOS 961 (CCOS 961); *Lactobacillus plantarum* CCOS 893 (DSM 32352); *Lactobacillus johnsonii* CCOS 824 (CCOS 824); *Lactobacillus paracasei* subsp. *paracasei* CCOS 1205 (CCOS 1205); *Lactobacillus paracasei* subsp. *paracasei* CCOS 1201 (CCOS 1201); *Lactobacillus fermentum* CCOS 1030 (CCOS 1030); *Lactobacillus jensenii* CCOS 962 (CCOS 962); *Lactobacillus rhamnosus* CCOS 965 (CCOS 965); *Bifidobacterium bifidum* CCOS 571 (CCOS 571); *Bifidobacterium longum* CCOS 974 (CCOS 974); *Bifidobacterium breve* CCOS 971 (CCOS 971) and *Bifidobacterium breve* CCOS 586 (CCOS 586), most preferably, the bacterial, preferably probiotic bacterial strain is *Lactococcus lactis* CCOS 949 (DSM 32294).

The term "a bacterial infection", as used herein, is meant to define any bacterial invasion into a host, preferably into an animal host, more preferably into a mammalian host, most preferably into a human host, which invasion is undesired, i.e. results in negative health impact(s) and/or is pathological. More preferably the bacterial infection is by Gram-positives, Gram-negatives and/or mycobacteria.

The terms "probiotics" or "probiotic bacterial strains" are commonly defined as "live microorganisms (here: bacteria) that, when administered in adequate amounts, confer a health benefit on the host" (Hill et al., (2014) "Expert consensus document. The International Scientific Association for Probiotics and Prebiotics consensus statement on the scope and appropriate use of the term probiotic" Nat Rev Gastroenterol Hepatol 11: 506-514).

In the context of the present invention, the terms "probiotic bacteria" or "probiotic bacterial strains" are preferably understood as defined by the European Food Safety Administration (EFSA) which grants the label QPS (Qualified Presumption of Safety) to those bacterial strains that are considered "probiotic" in the present application. The EFSA publishes a list of such probiotic strains or family of strains periodically and reference is made to the EFSA Journal, Volume 14, issue 7, published in July 2016, Appendix B, Table B1. Therefore, in the context of the present invention and in addition to the general understanding in the art, the term "probiotic" or "probiotic strain" refers to all the bacterial microorganisms contained in the mentioned list of approved QPS-labelled phyla, classes, families or specific strains of bacterial microorganisms. More preferably, "probiotic bacteria" in the context of the present invention are those of the families Lactobacillaceae, Bifidobacteriaceae and Lactococcaceae; more preferably of the genus *Lactobacillus*, *Bifidobacterium* and *Lactococcus*; most preferably of the species *Bifidobacterium bifidum*, *Bifidobacterium longum*, *Bifidobacterium breve*, *Lactobacillus crispatus*, *Lactobacillus fermentum*, *Lactobacillus gasseri*, *Lactobacillus rhamnosus*, *Lactobacillus jensenii*, *Lactobacillus johnsonii*, *Lactobacillus paracasei*, *Lactobacillus plantarum* and *Lactococcus lactis*.

Additionally, and in line with the QPS label, the label GRAS (Generally Recognized As Safe) issued in the USA is preferably used to characterize "probiotics" or "probiotic strain" as used herein. Generally and as understood by those skilled in the art, the term "probiotic" excludes pathogenic bacteria, in particular bacteria that are pathogenic to humans.

Disclosed herein are the bacterial, preferably probiotic bacterial PGH, the bacterial, preferably probiotic bacterial strain or the composition for use in the present invention are for use in therapeutic or prophylactic treatment of a bacterial infection, which infection results in diarrhea. In a preferred embodiment, the peptidoglycan hydrolase (PGH)-secreting probiotic bacterial strain is for use in the treatment of a bacterial infection that results in diarrhea or is a bacterial urogenital, preferably vaginal infection. The present disclosure also relates to the bacterial, preferably probiotic bacterial PGH or the composition for use in the present invention are for use in therapeutic or prophylactic treatment of a bacterial urogenital, preferably vaginal infection.

As used herein and with reference to the factsheet "Diarrhoeal disease" issued by the World Health Organization (WHO) in May 2017, the term "diarrhea" is defined as the passage of three or more loose or liquid stools per day (or more frequent passage than is normal for the individual). Frequent passing of formed stools is not diarrhoea, nor is the passing of loose, "pasty" stools by breastfed babies. The three clinical types of diarrhoea are: acute watery diarrhoea—lasts several hours or days and includes cholera; acute bloody diarrhoea—also called dysentery; and persistent diarrhoea—lasts 14 days or longer.

It was surprisingly found that probiotic bacteria strains featuring the production of one or more PGH class enzymes, preferably one or more glycosidases such as N-acetylglucosaminidases (NAGase) or hexosaminidases or galactosaminidase exhibit high activity against pathogenic, preferably enteropathogenic bacteria, in particular against *Clostridium difficile* (*C. diff.*). The data reported in the Examples below demonstrate that the probiotic PGH-secreting strains, in particular the glycosidases- and NAGase-secreting strains, exert a strong inhibitory activity against hospital isolates of *C. diff.* Preferred non-limiting examples of such PGHs-secreting strains are *L. lactis* CCOS 949, *L. plantarum* CCOS 893, *L. gasseri* CCOS 960 and *L. crispatus* CCOS 961 (see below for deposition details). These strains in particular *L. lactis* CCOS 949 are preferably also active against spores of *C. diff.*

It is preferred that probiotic bacteria for use in the present invention are administered in a concentration of between about 1×10^6 and 1×10^11 cfu/dose, preferably between about 1×10^9 and about 1×10^10 cfu/dose. The total bacterial dose can, e.g., vary between about 1×10^9 and about 5×10^11 for a total weight between 0.5 and 20 g per dose, for example 1 g, 5 g, or 10 g.

In a further preferred embodiment, the present invention is directed to a peptidoglycan hydrolase (PGH)-secreting probiotic bacterial strain for use in the therapeutic or prophylactic treatment of a bacterial infection, preferably a bacterial diarrhoe or a bacterial urogenital, preferably vaginal infection, wherein the bacterial infection is caused by a pathogenic microorganism selected from the group consisting of enteroinvasive *Escherichia coli*, enterohaemorragic *Escherichia coli*, diarrheagenic *Escherichia coli*, *Helicobacter pylori*, *Salmonella enterica*, *Shigella flexneri* and *sonnei*, *Campylobacter jejuni*, *Listeria monocytogenes*, *Bacillus cereus*, *Vibrio cholerae*, *Staphylococcus aureus*, *Gardnerella vaginalis*, *Clostridium perfringens* and *Clostridium difficile*, preferably the pathogenic microorganism is *Clostridium difficile*. Also disclosed herein is a bacterial, preferably probiotic bacterial peptidoglycan hydrolase (PGH) for the use described above.

If the diarrhoeal disease of bacterial origin is caused by, or associated with, an infection by *C. difficile*, this disease is termed *C. difficile*-associated diarrhea (CDAD).

The bacterial, preferably probiotic bacterial PGH, PGH-secreting bacterial, preferably probiotic bacterial strain or bacterial, preferably probiotic bacterial PGH-comprising composition is active against the peptidoglycan-comprising cell-wall of a bacterial pathogen. For example, the bacterial, preferably probiotic bacterial PGH as such, produced by the strain or forming part of the composition can be, but is not limited to, a bacterial, preferably probiotic bacterial PGH selected from the group consisting of N-acetylglucosaminidase (NAGase), N-acetylhexosaminidase, N-acetylgalactosaminidase, N-acetylmuramidase, endopeptidase, carboxypeptidase, and N-acetylmuramoyl-L-alanine amidase.

Further disclosed herein is the bacterial, preferably probiotic bacterial PGH, the bacterial, preferably probiotic bacterial strain or the composition for use in the present invention, wherein the bacterial, preferably probiotic bacterial PGH is selected from the group consisting of:
  alpha- and beta-N-acetylglucosaminidase (NAGase), preferably beta-N-acetylglucosaminidase, more preferably exo- or endo-beta-N-acetylglucosaminidase;
  N-acetylmuramidase;
  alpha- and beta-N-acetylhexosaminidase, preferably beta-N-acetylhexosaminidase;
  alpha- and beta-N-acetylgalactosaminidase, preferably beta-N-acetylgalactosaminidase;
  mannosyl-glycoprotein endo-beta-N-acetylglucosaminidase;
  beta-hexosaminidase;
  alpha-mannosidase;
  N-acetylmuramoyl-L-alanine amidase;
  glycoside hydrolase;
  endopeptidase;
  carboxy-petidase;
  bacterial surface protein AcmA; and
  neuraminidase.

In a preferred embodiment, the peptidoglycan hydrolase (PGH)-secreting probiotic bacterial strain for use according to the present invention is one, wherein the peptidoglycan hydrolase (PGH) is selected from the group described above.

The bacterial enzymes listed above with peptidoglycan-hydrolase activity are systematically described and listed in the Brenda-Database of enzyme classification (https://www-.brenda-enzymes.org). This database is referred to for all synonyms of the above-listed PGHs. Preferably, the bacterial, preferably probiotic bacterial PGHs as such, secreted by the bacterial, preferably probiotic bacterial strain or comprised by the composition for use in the present invention are members of the Enzyme Class E.C. 3.2.1., with, e.g., 3.2.1.52 denoting beta-D-acetylglucosaminidase.

It is further preferred that the bacterial, preferably probiotic bacterial peptidoglycan hydrolase (PGH) described herein, preferably a glycosidase, more preferably an N-acetylglucosaminidase (NAGase) or hexosaminidase or muramidase is combined with nisin or another bacteriocin, and/or that the bacterial, preferably probiotic bacterial strains for use according to the present invention also secrete nisin or another bacteriocin, e.g., for enhancing antimicrobial activity. Such other bacteriocins can, e.g., be found in the genomes of the probiotic strains mentioned in this invention and/or are preferably selected from the group consisting of: Pediocin; Gassericin; Enterolysisn; Helveticin; Penocin; Lactoccin; and Colicin.

Optionally, the bacterial, preferably probiotic bacterial peptidoglycan hydrolase (PGH), bacterial, preferably probiotic bacterial strain or composition for use according to the present invention is one, wherein the PGH-secreting bacterial, preferably probiotic bacterial strain is selected from the group consisting of *Lactococcus lactis*, preferably subsp. *lactis* and subsp. *cremoris*, *Lactobacillus gasseri*, *Lactobacillus crispatus*, *Lactobacillus jensenii*, *Lactobacillus plantarum*, *Lactobacillus fermenturn*, *Lactobacillus johnsonii*, *Lactobacillus rhamnosus*, *Lactobacillus paracasei*, *Lactobacillus casei*, *Bifidobacterium animalis* subsp. *lactis*, *Bifidobacterium longum*, *Bifidobacterium breve*, *Bifidobacterium pseudocatenulatum* and *Bifidobacterium bifidum*.

The present disclosure also encompasses a combination of two or more, preferably 3 to 7, bacterial, preferably probiotic bacterial peptidoglycan hydrolases (PGH) or a composition comprising two or more, preferably 3 to 7, bacterial, preferably probiotic bacterial peptidoglycan hydrolases (PGH) for the use described above.

In a preferred embodiment, the present invention is also directed to a combination of two or more, preferably 3 to 7, bacterial, preferably probiotic bacterial strains for use according to the embodiments of the present invention. Preferably, and as an example, a strain for use according to the present invention, preferably *L. lactis*, more preferably *L. lactis* CCOS 949, which produces bacteriocins, preferably nisin and/or lactococcin, is combined with other PGH-producing, preferably glycosidase-producing strains as described herein, preferably *L. gasseri* CCOS 960, *L. plantarum* CCOS 893, *B. breve* CCOS 571 and/or *B. breve* CCOS 971, to potentiate, preferably synergistically potentiate the antipathogen activity against *C. diff.*

Preferably the bacterial, preferably probiotic bacterial PGH as such and when comprised in the composition for use as described herein is a PGH expressed and secreted in one or more of the herein-identified PGH-comprising bacterial, preferably probiotic bacterial strains.

The finding that bacterial, preferably probiotic bacterial strains secreting PGHs have an antimicrobial effect on bacterial pathogens, in particular enteropathogenic species, and in particular on *C. diff.* strains, was verified for the representative organism *Lactococcus* and subsequently for *Lactobacillus* strains, as well as for another large family of (probiotic) bacteria, the Bifidobacteria (see Examples below).

The bacterial, preferably probiotic bacterial strains for use in the present invention demonstrate a significant inhibitory activity against bacterial pathogens including *C. diff.*, and preferably up to an intermediate pH-range of 5-6. Therefore, the bacterial, preferably probiotic bacterial strains for use in the present invention have the advantage that their activity is extended over the entire length of the intestine while damages to the healthy part of the gut microbiota are avoided or at least reduced.

*Lactococcus lactis* is a Gram-positive, aerotolerant, non-motile and non-sporulating bacterial species belonging to the Streptococcaceae family. *L. lactis* includes four subspecies, *cremoris*, *hordniae*, *lactis* and *tructae*, and one biovar, *L. lactis* subsp. *lactis* bv. diacetylactis. In accordance with their traditional use in food, members of the *L. lactis* species has been listed in the "inventory of microbial food cultures" with documented use in food fermentations and are most commonly classed as Generally Recognized as Safe (GRAS) by the Food and Drug Administration (FDA); Salminen et al. (1998) "*Demonstration of safety of probiotics—a review*" *Int J Food Microbiol* 44: 93-106).

Furthermore, *L. lactis* received from the European Food Safety Authority (EFSA) the status of Qualified Presumption of Safety (QPS), which is granted to those taxonomic groups deliberately introduced into the food chain that do not raise safety concerns and are considered "probiotic" herein (doi:10.2903/j.efsa.2007.587).

Although the intestine is not its primary habitat, *L. lactis* can survive the gastrointestinal transit and may remain metabolically active in various compartments of the alimentary canal (Drouault et al., (1999) *Appl Environ Microbiol* 65: 4881-4886; Kimoto et al., (2003) *Can J Microbiol* 49: 707-711), demonstrating that *L. lactis* is a suitable microorganism for probiotic applications.

*L. lactis* is particularly preferred for use in the present invention, e.g. because of its various habitats. It possesses wide genetic variability, has a variety of phenotypes and is potentially beneficial for the host's health.

CDI occurs preferably in the colon, but also in the small intestine. Consequently, a transient probiotic colonization with anti-*C. difficile* probiotic strains should reach both parts of the gut, which can, for example, be implemented by the parallel administration of *Lactobacillus*, more strongly present in the small intestine, and Bifidobacteria, more strongly present in the large intestine.

In a preferred embodiment the peptidoglycan hydrolase (PGH)-secreting, bacterial, preferably probiotic bacterial strain or composition for use according to the present invention is one, wherein the bacterial, preferably probiotic bacterial strain is selected from the group consisting of *Lactococcus lactis* CCOS 949 (DSM 32294), *Lactobacillus gasseri* CCOS 960 (DSM 32296); *Lactobacillus crispatus* CCOS 961 (CCOS 961); *Lactobacillus plantarum* CCOS 893 (DSM 32352); *Lactobacillus johnsonii* CCOS 824 (CCOS 824); *Lactobacillus paracasei* subsp. *paracasei* CCOS 1205 (CCOS 1205); *Lactobacillus paracasei* subsp. *paracasei* CCOS 1201 (CCOS 1201); *Lactobacillus fermentum* CCOS 1030 (CCOS 1030); *Lactobacillus rhamnosus* CCOS 965 (CCOS 965), *Lactobacillus jensenii* CCOS 962 (CCOS 962), *Bifidobacterium bifidum* CCOS 571 (CCOS 571); *Bifidobacterium longum* CCOS 974 (CCOS 974); *Bifidobacterium breve* CCOS 971 (CCOS 971) and *Bifidobacterium breve* CCOS 586 (CCOS 586), preferably, the bacterial strain is *Lactococcus lactis* CCOS 949 (DSM 32294).

Also disclosed herein is a bacterial, preferably probiotic bacterial peptidoglycan hydrolase (PGH) secreted by one or more of the above-listed strains.

It is noted that the strain *Lactobacillus paracasei* subsp. *paracasei* CCOS 1205 (CCOS 1205) is identical to the strain *Lactobacillus paracasei* subsp. *paracasei* CCOS 1201 (CCOS 1201) and this strain was deposited twice.

It is noted that *Lactococcus lactis* CCOS 949 produces the bacteriocin nisin on one hand and, on the other hand, several peptidoglycan hydrolases (PGH) of the glycosidase type. A preferred embodiment of the present invention is directed to the use of a bacterial, preferably probiotic bacterial strain that expresses bacteriocins, preferably nisin, and a PGH, preferably of the glycosidase type. Without wishing to be bound by theory, it is noted that a bacteriocin, preferably nisin, and a PGH, preferably of the glycosidase type act together synergistically, thus exhibiting a potent, unexpected inhibitory activity against *C. diff*.

*Lactococcus lactis* CCOS 949 was deposited under the Budapest Treaty on 21 Apr. 2016 under number accession DSM 32294 by Probioswiss GmbH, Technoparkstrasse 1, Zürich, Switzerland with the DSMZ (Deutsche Sammlung von Mikroorganismen und Zellkulturen, Leibniz-Institut, Inhoffenstraße 7B,38124 Braunschweig, Germany).

*Lactobacillus gasseri* CCOS 960 was deposited under the Budapest Treaty on 21 Apr. 2016 under accession number DSM 32296 by Probioswiss GmbH, Technoparkstrasse 1, Zürich, Switzerland with the DSMZ (Deutsche Sammlung von Mikroorganismen und Zellkulturen, Leibniz-Institut, Inhoffenstraße 7B,38124 Braunschweig, Germany).

*Lactobacillus crispatus* CCOS 961 was deposited under the Budapest Treaty on 10 Dec. 2017 under deposit accession number CCOS 961 by Crigasseni AG, Ledergasse 34, Beckenried, Switzerland with the Culture Collection of Switzerland AG (CCOS, Einsiedlerstr. 34, 8820 Wädenswil, Switzerland).

*Lactobacillus plantarum* CCOS 893 was deposited under the Budapest Treaty on 27 Jul. 2016 under accession number DSM 32352 by Probioswiss GmbH, Technoparkstrasse 1, Zürich, Switzerland with the DSMZ (Deutsche Sammlung von Mikroorganismen und Zellkulturen, Leibniz-Institut, Inhoffenstra261 e 7B, 38124 Braunschweig, Germany).

*Lactobacillus johnsonii* CCOS 824 was deposited under the Budapest Treaty on 16 Apr. 2018 under deposit accession number CCOS 824 by Crigasseni AG, Ledergasse 34, Beckenried, Switzerland with the Culture Collection of Switzerland AG (CCOS, Einsiedlerstre. 34, 8820 Wädenswil, Switzerland).

*Lactobacillus paracasei* subsp. *paracasei* CCOS 1205 was deposited under the Budapest Treaty on 21 Apr. 2018 under deposit accession number CCOS 1205 by the Culture Collection of Switzerland AG (CCOS, Einsiedlerstr. 34, 8820 Wädenswil, Switzerland) at the same institution.

*Lactobacillus paracasei* subsp. *paracasei* CCOS 1201 was deposited under the Budapest Treaty on 17 Apr. 2019 under deposit accession number CCOS 1201 by Crigasseni AG, Ledergasse 34, Beckenried, Switzerland with the Culture Collection of Switzerland AG (CCOS, Einsiedlerstr. 34, 8820 Wädenswil, Switzerland).

*Lactobacillus fermentum* CCOS 1030 was deposited under the Budapest Treaty on 10 Apr. 2018. under deposit accession number CCOS 1030 by Crigasseni AG, Ledergasse 34, Beckenried, Switzerland with the Culture Collection of Switzerland AG (CCOS, Einsiedlerstr. 34, 8820 Wädenswil, Switzerland).

*Lactobacillus jensenii* CCOS 962 was deposited under the Budapest Treaty on 17 Apr. 2019. under deposit accession number CCOS 962 by Crigasseni AG, Ledergasse 34, Beckenried, Switzerland with the Culture Collection of Switzerland AG (CCOS, Einsiedlerstr. 34, 8820 Wädenswil, Switzerland).

*Lactobacillus rhamnosus* CCOS 965 was deposited under the Budapest Treaty on 17 Apr. 2019. under deposit accession number CCOS 965 by Crigasseni AG, Ledergasse 34, Beckenried, Switzerland with the Culture Collection of Switzerland AG (CCOS, Einsiedlerstr. 34, 8820 Wädenswil, Switzerland).

*Bifidobacterium bifidum* CCOS 571 was deposited under the Budapest Treaty on 6 Nov. 2017 under deposit accession number CCOS 571 by Martin Sievers of the Culture Collection of Switzerland AG, Wädenswil, Switzerland, with the Culture Collection of Switzerland AG (CCOS, Einsiedlerstr, 34, 8820 Wädenswil, Switzerland).

*Bifidobacterium longum* CCOS 974 was deposited under the Budapest Treaty on 10 Apr. 2018 under deposit accession number CCOS 974 by Crigasseni AG, Ledergasse 34, Beckenried, Switzerland with the Culture Collection of Switzerland AG (CCOS, Einsiedlerstr. 34, 8820 Wädenswil, Switzerland).

*Bifidobacterium breve* CCOS 971 was deposited under the Budapest Treaty on 20 Apr. 2018 under deposit accession number CCOS 971 by Crigasseni AG, Ledergasse 34, Beckenried, Switzerland with the Culture Collection of Switzerland AG (CCOS, Einsiedlerstr. 34, 8820 Wädenswil, Switzerland).

*Bifidobacterium breve* CCOS 586 was deposited under the Budapest Treaty on 6 Nov. 2017 under deposit accession number CCOS 586 by Martin Sievers of the Culture Collection of Switzerland AG, Wädenswil, Switzerland, with the Culture Collection of Switzerland AG (CCOS, Einsiedlerstr. 34, 8820 Wädenswil, Switzerland).

All depositions were made on the same terms as those laid down in the Budapest Treaty on the International Recognition of the Deposit of Microorganisms for the purpose of Patent Procedure. Probioswiss GmbH, Zürich Switzerland, the Culture Collection of Switzerland AG and Martin Sievers of the Culture Collection of Switzerland AG have assigned the deposited strains to Crigasseni AG, Beckenried, Switzerland and have given their unreserved and irrevocable consent to the deposited material being made available to the public as evidenced by the Statements of Authorization and Consent filed with the European Patent Office (as the Receiving Office).

For some probiotic strains for use in the present invention it can be of advantage for stable growth and maintenance of viability to administer these in combination with strain-specific nutritional compounds, which compounds might not be, e.g. naturally, available in sufficient amounts in the gut.

In a further preferred embodiment, the composition, preferably a composition comprising the bacterial, preferably probiotic bacterial strain, more preferably *Lactococcus lactis*, most preferably subspecies *lactis* or subspecies *cremoris*, for use as described above, further comprises at least one N-acetylated monosaccharide;
at least one prebiotic carbon source;
at least one nitrogen source;
and/or at least a sulfur source.

Lowering the pH in the intestine is a further preferred option when administering the (probiotic) bacteria or (probiotic) bacteria-comprising composition for use in the present invention.

In some instances, bacterial, preferably probiotic bacterial strains capable of inhibiting pathogenic bacteria, e.g. *C. diff.*, can incur a partial loss of inhibition, which is sometimes observed at a pH higher than 5.5. To minimize or avoid such loss, a dose of at least one prebiotic carbon source (e.g. between 2 and 15 g per dosage, preferably between 5 and 10 g, more preferably between 5 and 6 g) can preferably be provided that is sufficient to lower the pH of the intestinal milieu. The lowering of the pH in the intestinal milieu can be achieved by fermentation of the at least one prebiotic carbon source by the bacterial, preferably probiotic bacterial strain, thus leading to the production of lactic acid and/or short chain fatty acids (SCFA) like acetic or butyric acid.

In this context, a prebiotic carbon source is a compound that can be, preferably selectively, fermented by bacterial, preferably probiotic and eubiotic bacterial strains for use in the present invention and preferably leads to fermentation products that lower the pH in the intestinal milieu. Examples of preferred prebiotic carbon sources are provided further below.

In many cases the production of PGHs by (probiotic) bacterial strains for use in the present invention, e.g. of NAGase, is stimulated by the presence of the corresponding simple sugar, e.g. N-acetyl-glucosamine (NAG). In a preferred embodiment, the composition, preferably the bacterial, preferably probiotic bacterial strain-comprising composition, for use in the present invention further comprises an N-acetylated monosaccharide selected from the group consisting of N-acetylglucosamine, N-acetylgalactosamine, N-acetyl-hexosamine, N-acetylmannosamine, and mixtures thereof.

Prebiotic carbon sources for use in combination with the bacterial, preferably probiotic bacterial strains and composition for use in the present invention are preferably selective carbon sources specific for the (probiotic) bacterial strains which sources preferably cannot be utilized by competing pathogens. Kondepudi et al. (Anaerobe 18 (5), 489-497. 2012 Aug. 24) investigated the ability of C. diff strains to ferment a selection of different prebiotic non-digestible oligosaccharides (NDOs). Whereas the tested *Bifidobacterium* (*breve*, *longum*, *lactis*, etc.) fermented all the NDOs to different extents, *C. diff* strains could not. Feeding bacterial, preferably probiotic bacterial strains with such selective prebiotics (e.g. fructooligosaccharides (FOS), galacto-oligosaccharides (GOS), glycooligosaccharides, lactulose, xylooligosaccharides (XOS) and/or isomaltooligosaccharides (IMOS)) can warrant that the benefit is limited to the (probiotic) bacterial strains.

In a further preferred embodiment, the composition for use in the present invention is one, wherein the prebiotic carbon source is selected from the group consisting of a fructooligosaccharide, galactooligosaccharide, glyco-oligosaccharide, lactulose, xylooligosaccharide, isomaltooligosaccharide, and mixtures thereof.

Preferably, a prebiotic carbon source or carbon source mix should weigh in the range of about 0.5 to 10 grams per dosis bacterial, preferably probiotic bacterial formulation(s), or about 2% to 50% by weight of a composition for use in the present invention comprising bacterial, preferably probiotic bacterial strain(s), prebiotic carbon source(s) and other galenical ingredients.

Nitrogen sources for use in combination with the bacterial, preferably probiotic bacterial strains and composition for use in the present invention are, e.g., ammonium salts (e.g. ammonium chloride or citrate), urea, amino acids, preferably nitrogen-rich amino acids such as, e.g., glutamic acid, arginine, aspartic acid and/or alanine, as well as mixtures thereof, preferably capable of supporting the growth of intestinal and vaginal lactobacilli.

Because nisin, as well as further lantibiotic, sulfur-containing bacteriocins, is an effective agent against pathogenic bacteria, in particular against *C. diff.*, it is important to optimize its production in the intestine. Nisin production can be increased by adding physiologically effective sulfur sources (L. de Vuyst, 1995, *Journal of Applied Bacteriology*, 78:28-33) to bacterial, preferably probiotic bacterial strains for use in the present invention. For example, suitable sources may be the amino acids methionine, serine or cysteine, which can be administered to the intestine in amounts of about 0.1 to 5 g of cysteine/cystine, N-acetyl-cysteine, methionine and/or serine), preferably about 0.2 to 2.0 g per dosage form.

In another preferred embodiment, the composition for use in the present invention comprises at least one sulfur source selected from the group consisting of methionine, cysteine, cystine, cystathionine, a sulfur-containing inorganic salt, preferably magnesium sulfate, sodium or potassium thiosulfate, and mixtures thereof.

A preferred proportion of the sulfur source(s) for preparing a composition for use in the present invention may vary between about 1% and 10%, preferably about 3% to 8% by weight of the total weight of the composition.

In another aspect, the present invention is directed to a peptidoglycan hydrolase (PGH) for use in the therapeutic or prophylactic treatment of a bacterial infection, preferably a bacterial infection that results in diarrhea or a bacterial urogenital, preferably vaginal infection, wherein the PGH is a polypeptide selected from the group consisting of:

(a) polypeptides comprising, preferably having an amino acid sequence selected from the group consisting of SEQ ID NOs: 89 to 151 and 158 to 163;
(b) polypeptides comprising an amino acid sequence having an amino acid sequence identity of at least 70 or 80%, preferably at least 90 or 95% with an amino acid sequence selected from the group consisting of SEQ ID NOs: 89 to 151 and 158 to 163, preferably over the whole length of the sequence; and
(c) functional fragments and/or functional derivatives of (a) or (b).

The identity of related amino acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two amino acid sequences comprise, but are not limited to, TBLASTN, BLASTP, BLASTX, TBLASTX (Altschul et al., (1990) J. Mol. Biol., 215, 403-410), ClustalW (Larkin M A et al., Bioinformatics, 23, 2947-2948, 2007) or PHYRE2 (Kelley L A et al., (2015) Nature Protocols 10, 845-858). The BLAST programs can be obtained from the National Center for Biotechnology Information (NCBI) and from other sources (BLAST handbook, Altschul et al., NCB NLM NIH Bethesda, MD 20894). The ClustalW program can be obtained from http://www.clustal.org and the PHYRE2 program from http://www.sbg.bio.ic.ac.uk/phyre2/html/page.cgi?id=index.

The term "functional derivative" of a polypeptide for use in the present invention is meant to include any polypeptide or fragment thereof that has been chemically or genetically modified in its amino acid sequence, e.g. by addition, substitution and/or deletion of amino acid residue(s) and/or has been chemically modified in at least one of its atoms and/or functional chemical groups, e.g. by additions, deletions, rearrangement, oxidation, reduction, etc. as long as the derivative still has at least some PGH activity to a measurable extent, e.g. of at least about 1 to 10% or more than 50% PGH activity of the original unmodified polypeptide for use in the invention, e.g. SEQ ID NOs: 89 to 151 and 158 to 163. Functional derivatives of a polypeptide for use in the present invention include non-natural polypeptides and glycosylated, phosphorylated, PEGylated, etc. derivatives.

In this context a "functional fragment" for use in the invention is one that forms part of a polypeptide or derivative for use in the invention and still has at least some PGH activity to a measurable extent, e.g. of at least about 1 to 10% or more than 50% PGH activity of the original unmodified polypeptide for use in the invention, e.g. SEQ ID NOs: 89 to 151 and 158 to 163.

In another aspect, the present invention is directed to a peptidoglycan hydrolase (PGH) for use in the therapeutic or prophylactic treatment of a bacterial infection, preferably a bacterial infection that results in diarrhea or a bacterial urogenital, preferably vaginal infection, wherein the PGH is encoded by a nucleic acid comprising or consisting of a nucleic acid sequence selected from the group consisting of:
(a) nucleic acid sequences selected from the group consisting of SEQ ID NOs: 1 to 11, 24 to 53, 65 to 81, 84 to 88 and 152 to 157;
(b) nucleic acid sequences having at least 80 or 90% identity, preferably at least 95% identity, more preferred at least 98% identity with a nucleic acid sequence listed in SEQ ID NOs: 1 to 11, 24 to 53, 65 to 81, 84 to 88 and 152 to 157, preferably over the whole sequence;
(c) nucleic acid sequences that hybridize to a nucleic acid sequence of (a) or (b) under stringent conditions;
(d) fragments of any of the nucleic acid sequences (a) to (c), that hybridize to a nucleic acid sequence of (a) or (b) under stringent conditions; and
(e) a nucleic acid sequence, wherein said nucleic acid sequence is derivable by substitution, addition and/or deletion of one of the nucleic acids of (a) to (d) that hybridizes to a nucleic acid sequence of (a) or (b) under stringent conditions.

The term "% (percent) identity" as known to the skilled artisan and used herein in the context of nucleic acids indicates the degree of relatedness among two or more nucleic acid molecules that is determined by agreement among the sequences. The percentage of "identity" is the result of the percentage of identical regions in two or more sequences while taking into consideration the gaps and other sequence peculiarities.

The identity of related nucleic acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two nucleic acid sequences comprise, but are not limited to, BLASTN (Altschul et al., (1990) J. Mol. Biol., 215:403-410) and LALIGN (Huang and Miller, (1991) Adv. Appl. Math., 12:337-357). The BLAST programs can be obtained from the National Center for Biotechnology Information (NCBI) and from other sources (BLAST handbook, Altschul et al., NCB NLM NIH Bethesda, MD 20894).

The nucleic acid molecules encoding the PGH for use according to the invention may be prepared synthetically by methods well-known to the skilled person, but also may be isolated from suitable DNA libraries and other publicly available sources of nucleic acids and subsequently may optionally be mutated. The preparation of such libraries or mutations is well-known to the person skilled in the art.

In some instances, the present invention also provides PGHs for use as described herein which are encoded by novel nucleic acids characterized in that they have the ability to hybridize to a specifically referenced nucleic acid sequence, preferably under stringent conditions. Next to common and/or standard protocols in the prior art for determining the ability to hybridize to a specifically referenced nucleic acid sequence under stringent conditions (e.g. Sambrook and Russell, (2001) Molecular cloning: A laboratory manual (3 volumes)), it is preferred to analyze and determine the ability to hybridize to a specifically referenced nucleic acid sequence under stringent conditions by comparing the nucleotide sequences, which may be found in gene databases (e.g. http://www.ncbi.nlm.nih.gov/entrez/query.fcgi?db=nucleotide and http://genome.jgi.doe.gov/programs/fungi/index.jsf) with alignment tools, such as e.g. the above-mentioned BLASTN (Altschul et al., (1990) J. Mol. Biol., 215:403-410), LALIGN alignment tools and multiple alignment tools such as e.g. CLUSTALW (Sievers F et al., (2011) Mol. Sys. Bio. 7: 539), MUSCLE (Edgar., (2004) Nucl. Acids Res. 32:1792-7) or T-COFFEE (Notre-dame et al., (2000) J of Mol. Bio 302 1: 205-17).

Most preferably, the ability of a nucleic acid of the present invention to hybridize to a nucleic acid, e.g. those listed in any of SEQ ID NOs: 1 to 11, 24 to 53, 65 to 81, 84 to 88 and 152 to 157, is confirmed in a Southern blot assay under the following conditions: 6× sodium chloride/sodium citrate (SSC) at 45° C. followed by a wash in 0.2×SSC, 0.1% SDS at 65° C.

The term "PGH encoded by a nucleic acid" as used in the context of the present invention is meant to include allelic variations and redundancies in the genetic code.

The nucleic acid encoding the PGH for use in the present invention is preferably operably linked to a promoter that governs expression in suitable vectors and/or host cells producing the PGH of the present invention in vitro or in vivo.

Suitable promoters for operable linkage to the isolated and purified nucleic acid are known in the art. In a preferred embodiment the nucleic acid encoding the PGH for use in the present invention is one that is operably linked to a promoter selected from the group consisting of the *Pichia pastoris* GAP promoter, AUG1 promoter, FLD1 promoter and AOX1 promoter (see for example *Pichia* Expression Kit Instruction Manual, Invitrogen Corporation, Carlsbad, Calif.), the *Saccharomyces cerevisiae* GAL1, ADH1, GAP, ADH2, MET25, GPD, CUP1 or TEF promoter (see for example Methods in Enzymology, 350, 248, 2002), the Baculovirus polyhedrin p10 or ie1 promoter (see for example Bac-to-Bac Expression Kit Handbook, Invitrogen Corporation, Carlsbad, Calif., and Novagen Insect Cell Expression Manual, Merck Chemicals Ltd., Nottingham, UK), the Lentivirus CMV, UbC, EF1α, or MSCV promoter (see for example System Biosciences, Mountain View, CA, USA), the Adenovirus CMV promoter (see for example ViraPower Adenoviral Expression System, Life Technologies, Carlsbad, CA, USA), the Simian virus 40 promoter SV40, the *E. coli* T7, araBAD, rhaP BAD, tetA, lac, trc, tac or pL promoter (see Applied Microbiology and Biotechnology, 72, 211, 2006), the *B. subtilis*, vegI, vegII, σA, $P_{grac}$, $P_{glv}$, manP or P43 promoter (see Applied Microbiology and Biotechnology, 72, 211, 2006), the plant CaMV35S, ocs, nos, Adh-1, Tet promoters (see e.g. Lau and Sun, Biotechnol Adv. 2009, 27, 1015-22) or inducible promoters for mammalian cells as described in Sambrook and Russell (2001).

In a further preferred embodiment, the present invention is directed to a recombinant vector for producing a PGH for use as described herein, comprising a nucleic acid as described above, preferably a viral or episomal vector, preferably a baculovirus vector, lentivirus vector, adenovirus vector, vaccinia or retroviral vector, yeast or bacterial episomal vector.

The selection of a suitable vector and expression control sequences as well as vector construction are within the ordinary skill in the art. Preferably, the viral vector is a lentivirus vector (see for example System Biosciences, Mountain View, CA, USA), adenovirus vector (see for example ViraPower Adenoviral Expression System, Life Technologies, Carlsbad, CA, USA), baculovirus vector such as bacmid (or see for example Bac-to-Bac Expression Kit Handbook, Invitrogen Corporation, Carlsbad, Calif.), the pcDNA, pVITRO, pSV and pCMV series of plasmid vectors, vaccinia and retroviral vectors (see for example Hruby, D. E. (1990). Vaccinia virus vectors: new strategies for producing recombinant vaccines. Clinical Microbiology Reviews, 3(2), 153-170), bacterial vector pGEX and pET (or see for example Novagen, Darmstadt, Germany)) or yeast vector pPIC (or see for example ATCC Manassas, Virginia). Vector construction, including the operable linkage of a coding sequence with a promoter and other expression control sequences, is within the ordinary skill in the art.

In another preferred embodiment, the present invention is directed to a host cell producing and/or secreting a PGH for use as described herein, comprising a nucleic acid or a vector as described above.

Preferred host cells for producing the polypeptide of the invention are selected from the group consisting of yeast cells preferably *Saccharomyces cerevisiae* (see for example Methods in Enzmology, 350, 248, 2002), *Pichia pastoris* cells (see for example *Pichia* Expression Kit Instruction Manual, Invitrogen Corporation, Carlsbad, Calif.)], bacterial cells preferably *E. coli* cells (BL21(DE3), K-12 and derivatives) (see for example Applied Microbiology and Biotechnology, 72, 211, 2006) or *B. subtilis* cells (1012 wild type, 168 Marburg or WB800N) (see for example Westers et al., (2004) Mol. Cell. Res. Volume 1694, Issues 1-3 P: 299-310), plant cells, preferably *Nicotiana tabacum* or *Physcomitrella patens* (see e.g. Lau and Sun, Biotechnol Adv. 2009 May 18. [electronic publication ahead of print]), NIH-3T3 mammalian cells (see for example Sambrook and Russell, 2001), Human Embryonic Kidney 293 cells (HEK 293, adherent or in suspension, also large T antigen transformed HEK 293T cells), Chinese hamster ovary (CHO) cells, COS cells, and insect cells, preferably sf9 insect cells (see for example Bac-to-Bac Expression Kit Handbook, Invitrogen Corporation, Carlsbad, Calif.).

More preferably, the host cell for use in the present invention is selected from the group consisting of yeast cells, preferably *Saccharomyces cerevisiae, Pichia pastoris* cells, bacterial *E. coli, Vibrio natriegens* or *B. subtilis* cells, plant cells, preferably *Nicotiana tabacum* or *Physcomirella patens* cells, NIH-3T3, HEK293, HEK293T, CHO and COS mammalian cells, and insect cells, preferably sf9 insect cells In another aspect, the present invention is directed to the use of a a peptidoglycan hydrolase (PGH)-secreting bacterial, preferably probiotic bacterial strain, a composition comprising the PGH-secreting strain, a PGH comprising an amino acid sequence as defined herein and/or encoded by the nucleic acids described herein, a recombinant vector or a host cell as described herein for the manufacture of a medicament for the therapeutic or prophylactic treatment of a bacterial infection, preferably a bacterial infection resulting in diarrhoe or a bacterial urogenital, preferably vaginal infection.

Also disclosed herein is the use of a bacterial, preferably probiotic bacterial peptidoglycan hydrolase (PGH) or a bacterial, preferably probiotic peptidoglycan hydrolase (PGH)-comprising composition for the manufacture of a medicament for the therapeutic or prophylactic application described above.

In another aspect, the present invention is directed to a pharmaceutical composition comprising a peptidoglycan hydrolase (PGH)-secreting bacterial, preferably probiotic bacterial strain or a bacterial, preferably probiotic bacterial peptidoglycan hydrolase (PGH)-secreting strain-comprising composition, as defined herein, a PGH comprising an amino acid sequence as defined herein an/or encoded by the nucleic acids described herein, a recombinant vector or a host cell as described herein and at least one physiologically acceptable excipient.

Also disclosed herein is a pharmaceutical composition comprising a bacterial, preferably probiotic bacterial peptidoglycan hydrolase (PGH) or a bacterial, preferably probiotic peptidoglycan hydrolase (PGH)-comprising composition and at least one physiologically acceptable excipient.

In a further aspect, the present invention encompasses corresponding food- or feed additive-compositions or dietary compositions, which, next to food, feed, and/or other dietary components, comprise a peptidoglycan hydrolase (PGH)-secreting bacterial, preferably probiotic bacterial strain, a PGH that comprises the amino acid sequences defined herein or that is encoded by the nucleic acids, a recombinant vector or a host cell for use in the present invention. Also disclosed are food- or feed additive-compositions or dietary compositions, which, next to food, feed, and/or other dietary components, comprise a bacterial, preferably probiotic bacterial peptidoglycan hydrolase (PGH). These compositions have particular utility for the prophylactic treatment/prevention of bacterial infections, preferably bacterial diarrhoe, preferably in humans and animals, more preferably in humans.

It is preferred that the bacteria, preferably probiotic bacteria as such or, e.g., in the form of their lyophilisates, tyndallisates, sonicates, cell-walls and cell extracts are present in the pharmaceutical, food additive, feed additive or dietary composition for use in the present invention in a quantity of about 0.5% to 50%, preferably about 5% to 20% by weight, relative to the total weight of the composition.

For therapeutic or prophylactic use the pharmaceutical composition of the invention may be administered in any conventional dosage form in any conventional manner. Suitable routes of administration include oral, rectal or intravenous, intramuscular and subcutaneous injections. The preferred modes of administration are oral and rectal for bacterial lyophilisates and derived forms or injectable (intravenous or subcutaneous) for the pure (probiotic) bacterial PGH enzymes and their mixtures. In general, the galenical form of the pharmaceutical composition for use in the present invention can be a tablet, a capsule, a sachet, a vial or a ready-to-use liquid preparation.

The bacterial, preferably probiotic bacterial PGH, the bacterial, preferably probiotic bacterial strain, the composition, the PGH comprising the amino acid sequences or encoded by the nucleic acids, the recombinant vector or the host cell described herein may be administered alone or in combination with adjuvants that enhance stability of the PGH, nucleic acids, vectors, host cell and/or strains, facilitate administration of pharmaceutical compositions containing them in certain embodiments, provide increased dissolution or dispersion, increase activity, provide adjunct therapy (e.g. corticosteroids, beta-adrenoceptor antagonists, anti-inflammatory drugs, immune-suppressants), and the like, including other active ingredients, in particular antibiotics. Advantageously such combination therapies utilize lower dosages of the conventional therapeutics, in particular antibiotics, thus avoiding possible toxicity and adverse side effects incurred when those agents are used as monotherapies. The herein-described (probiotic) bacterial PGH, (probiotic) bacterial strains, PGH comprising the amino acid sequences or encoded by the nucleic acids, recombinant vectors or host cells as described herein may be physically combined with conventional therapeutics or other adjuvants into a single pharmaceutical composition. Reference in this regard may be made to Cappola et al.: U.S. patent application Ser. No. 09/902,822, PCT/US 01/21860 and U.S. provisional application No. 60/313,527, each incorporated by reference herein in their entirety. Advantageously, the bacterial, preferably probiotic bacterial PGH and the bacterial, preferably probiotic bacterial strain may be administered together in a single dosage form, thus forming a composition for use in the present invention. The optimum percentage (w/w) of the (probiotic) bacterial PGH, the (probiotic) bacterial strain, PGH comprising the amino acid sequence or encoded by the nucleic acids, recombinant vector or host cell in a composition for use in the invention may vary and is within the purview of those skilled in the art. Alternatively, the (probiotic) bacterial PGH, the (probiotic) bacterial strain, the composition, the PGH comprising the amino acid sequence or encoded by the nucleic acids, the recombinant vector or host cell for use in the present invention may be administered separately (either serially or in parallel). Separate dosing allows for greater flexibility in the dosing regime.

As mentioned above, dosage forms of the bacterial, preferably probiotic bacterial PGH, the bacterial, preferably probiotic bacterial strain, the composition, the PGH comprising the amino acid sequence or encoded by the nucleic acids, the recombinant vector or host cell for the use described herein optionally include pharmaceutically acceptable carriers and adjuvants known to those of ordinary skill in the art. Methods for preparing such dosage forms are known (see, for example, Ansel and Popovish, Pharmaceutical *Dosage Forms and Drug Delivery Systems*, 5$^{th}$ ed., Lea and Febiger (1990)). Dosage levels and requirements are well-recognized in the art and may be selected by those of ordinary skill in the art from available methods and techniques suitable for a particular patient. Dosages for the bacterial, preferably probiotic bacterial peptidoglycan hydrolase (PGH), the peptidoglycan hydrolase (PGH)-comprising composition, the PGH comprising the amino acid sequence or encoded by the nucleic acids, the recombinant vector or host cell for the use described herein optionally range from 10-200 mg/dose for a 70 kg patient (Masaro KAJI et al., Journal of the Japanese Association for Infectious Diseases, Volume 40 (1966-1967) Issue 8 Pages 295-309).

Although one dose per day may be sufficient, optionally up to 5 doses per day may be given. In total, 1'000 mg/day may be required. In some embodiments, dosages for the peptidoglycan hydrolase (PGH)-comprising (probiotic) bacterial strain for the use described herein may range between $1 \times 10^6$ and $1 \times 10^{11}$ cfu/dose, preferably between about $1 \times 10^9$ and about $1 \times 10^{10}$ cfu/dose. The total bacterial dose can, e.g., vary between about $1 \times 10^9$ and about $5 \times 10^{11}$ for a total weight between 0.5 and 20 g per dose, for example 1 g, 5 g, or 10 g.

Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

In preferred embodiments, the present invention also encompasses bacterial, preferably probiotic bacterial PGH and nisin-secreting strains, preferably *Lactococcus* cells, more preferably live *Lactococcus* cells that may transiently colonize the gut and deliver PGH and nisin in situ. For example, a PGH and nisin-secreting *Lactococcus* strain such as *L. lactis* CCOS 949 is strongly active against C. diff and therefore advantageous for use as effective oral probiotic formulation directed against this pathogen. In another preferred embodiment, the present invention also encompasses bacterial, preferably probiotic bacterial PGH secreting strains such as *L. gasseri* CCOS 960 producing bacteriocins like pediocin, gassericin and helveticin. In another preferred embodiment the invention contains as well bacterial, preferably probiotic bacterial PGH producers and *L. crispatus* CCOS 961 capable of producing enterolysin A and penocin. For more evenly distributing a bacterial, preferably probiotic bacterial strain, more preferably a PGH and nisin-secreting (probiotic) bacterial strain, e.g. a *Lactococcus* strain such as *L. lactis* CCOS 949, along the intestine, it is preferred to prepare retard/slow release formulations, e.g. capsules, so that the slow release-formulated bacteria, preferably probiotic bacteria will also reach the large intestine. Alternatively, lyophilisates of very active, i.e. preferred strains, such as *L. lactis* CCOS 949 or *L. plantarum* CCOS 893 can be microencapsulated to reach the same retard/slow release effect (A. Kumar, Trends in Food Science and Technology, Vol. 18, Issue 5, May 2007, pg. 240-251).

It is further preferred to formulate retard/slow release formulations of Bifidobacteria strains, such as for example *B. longum* CCOS974 and/or *B. breve* CCOS 971, suitable for use in the present invention, e.g. capsules that protect the (probiotic) bacterial strain(s) from acidity and bile salts during the gastric and duodenal passage, e.g. by microencapsulation.

In a further aspect, the present invention is directed to a method for the prophylaxis and/or treatment of a bacterial infection, preferably a bacterial infection resulting in diarrhoe or a bacterial urogenital, preferably vaginal infection, in a patient in need of such treatment or prophylaxis, comprising the steps of:

(i) administering an effective amount of a peptidoglycan hydrolase (PGH)-secreting bacterial, preferably probiotic bacterial strain, a peptidoglycan hydrolase (PGH)-secreting strain-comprising composition, a PGH comprising an amino acid sequence as described herein and/or encoded by the nucleic acids described herein, a recombinant vector or a host cell as defined above, preferably a pharmaceutical composition as described above to the patient, preferably an animal selected from the group consisting of mammalian animals, preferably agricultural farm animals, or humans, and (ii) repeating said administration if needed.

Also disclosed herein is a method as described above, wherein a bacterial, preferably probiotic bacterial peptidoglycan hydrolase (PGH) or a bacterial, preferably probiotic bacterial peptidoglycan hydrolase (PGH)-comprising composition are administered instead of or in addition to the peptidoglycan hydrolase (PGH)-secreting bacterial, preferably probiotic bacterial strain.

In a preferred embodiment, the method according to the present invention is one, wherein the effective amount of the peptidoglycan hydrolase (PGH)-secreting bacterial, preferably probiotic bacterial strain, the PGH comprising an amino acid sequence as described herein and/or encoded by the nucleic acids described herein, the recombinant vector or the host cell is administered orally or rectally.

Also disclosed herein is a method as described above, wherein the effective amount of the bacterial, preferably probiotic bacterial peptidoglycan hydrolase (PGH), the bacterial, preferably probiotic bacterial peptidoglycan hydrolase (PGH)-comprising composition, the PGH comprising an amino acid sequence as described herein and/or encoded by the nucleic acids described herein, the recombinant vector or the host cell is administered orally or by intravenous or subcutaneous injection.

Unless specified otherwise, within the scope of the present invention the percentages and amounts of a component in a mixture are intended to refer to the weight of that component relative to the total weight of the mixture.

Unless specified otherwise, within the scope of the present invention, in relation to ranges of numerical values for a certain feature, the indication "from X to Y" comprises the extremes, i.e. X and Y, as well as all the possible intermediate numerical values.

In the context of the present invention, the term "composition(s)" is meant to include a pharmaceutical composition, a composition for a food or feed supplement, or a composition for a food/dietary product.

The following Figures and Examples serve to illustrate the invention and are not intended to limit the scope of the invention as described in the appended claims.

FIG. 1: shows inhibitory effects of *Lactococcus lactis* on *C. difficile*. The bars represent the ratio between the colony forming units determined at beginning and after 25 hours of incubation in the co-cultivation experiments.

Figure 2:
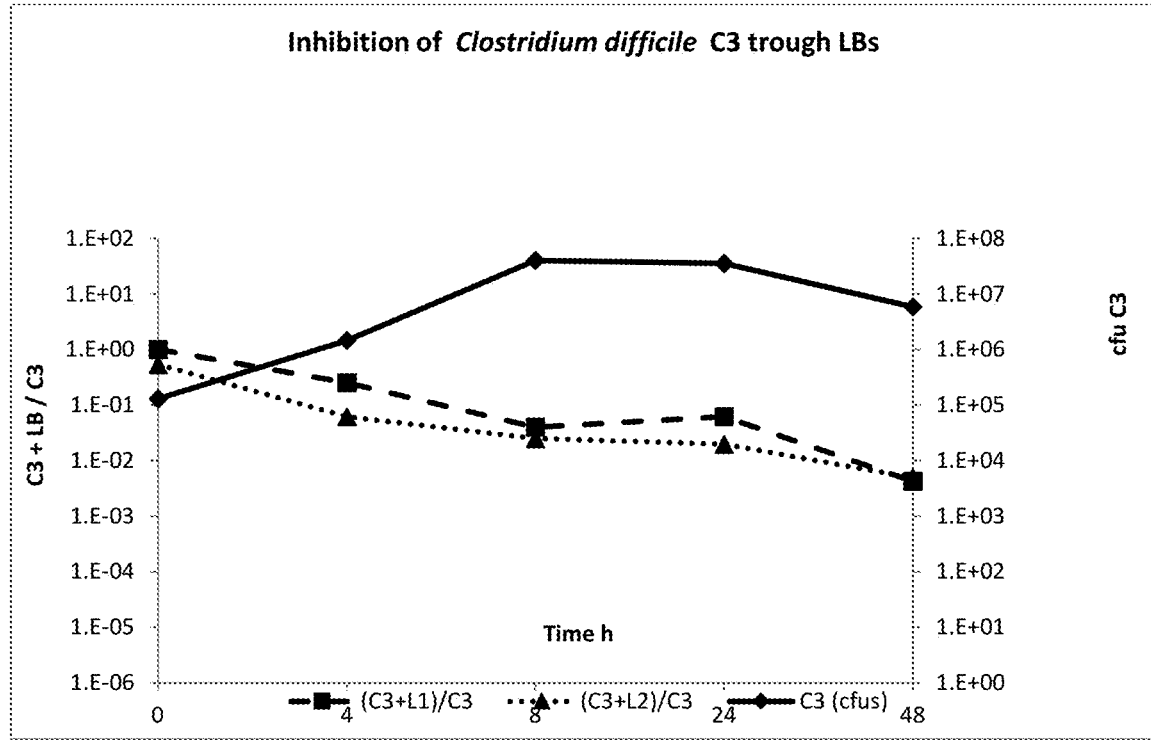

FIG. 2: shows the data of the inhibition of *C. difficile* C3 through L1 and L2 as outlined in Example 7 (Table 8b).

Figure 3:
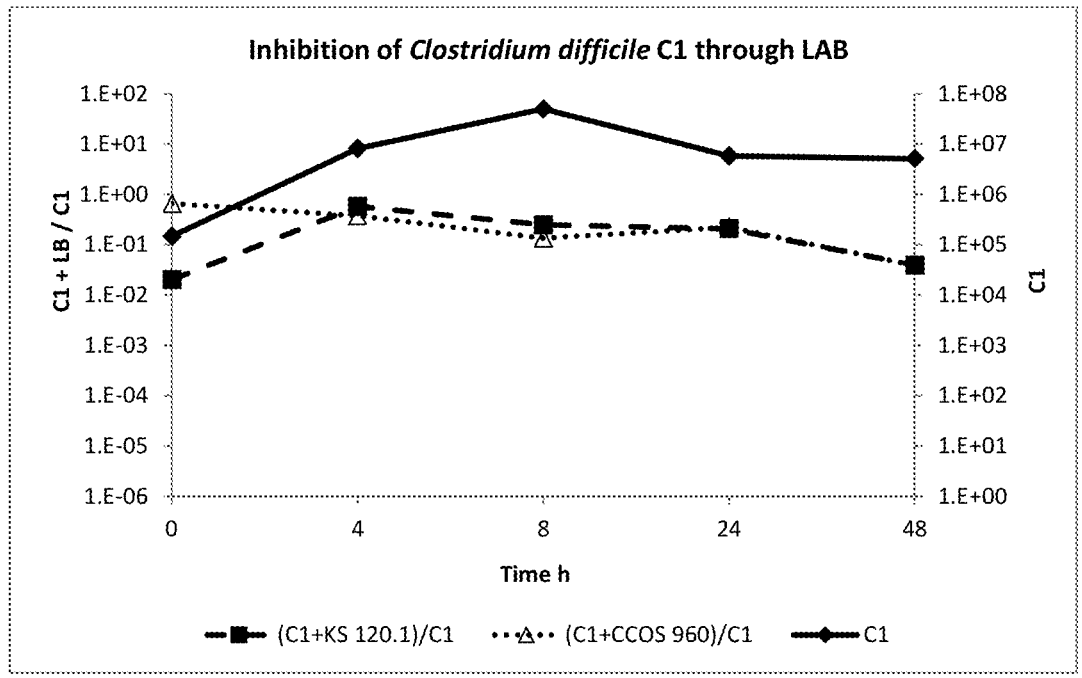

FIG. 3: shows the data of the inhibition of *C. difficile* C1 through L1 and L2 as outlined in Example 7 (Table 8c).

Figure 4:
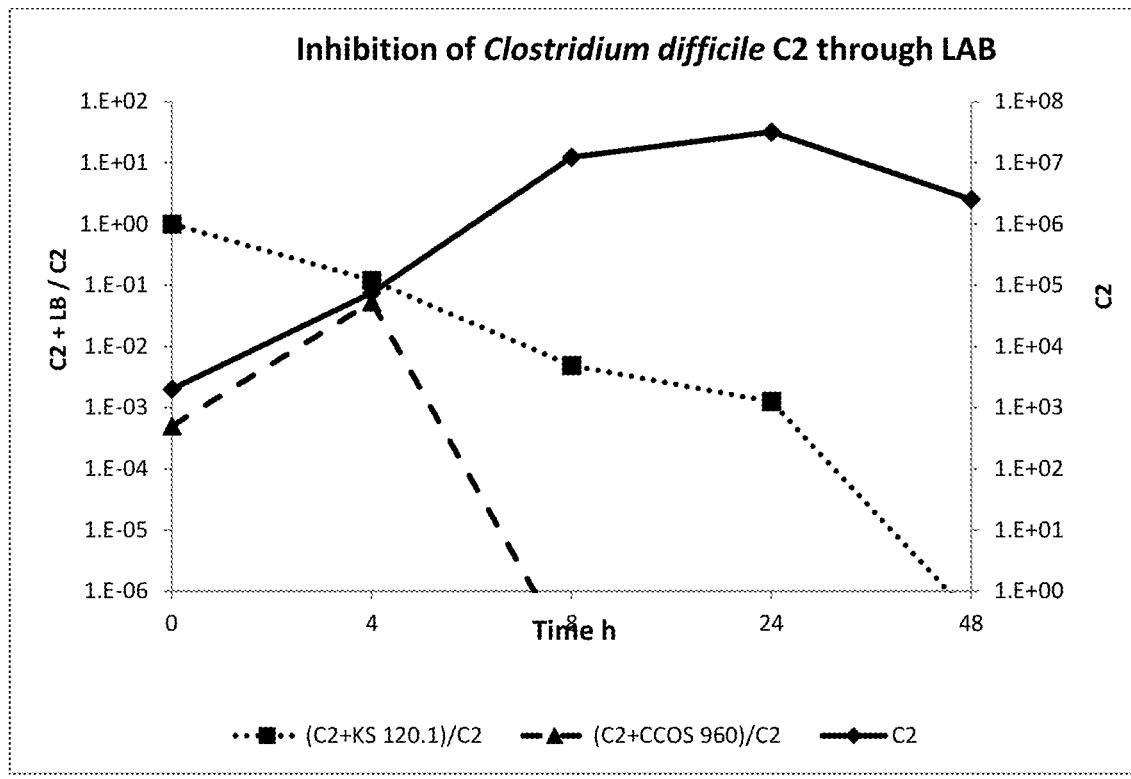

FIG. 4: shows the data of the inhibition of *C. difficile* C2 by Lactobacilli L1 and L2 as outlined in Example 7 (Table 8d).

Figure 5:
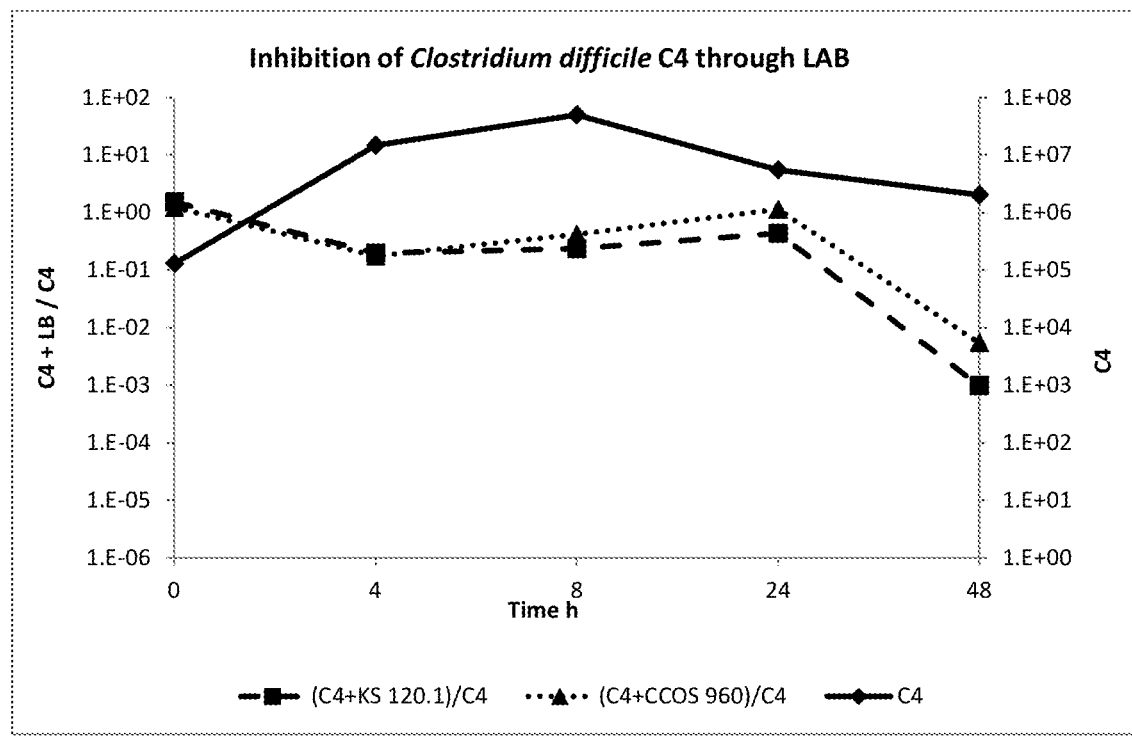

FIG. 5: shows the data of the inhibition of *C. difficile* C4 by *Lactobacillus* L1 and L2 as outlined in Example 7 (Table 8e).

Figure 6:
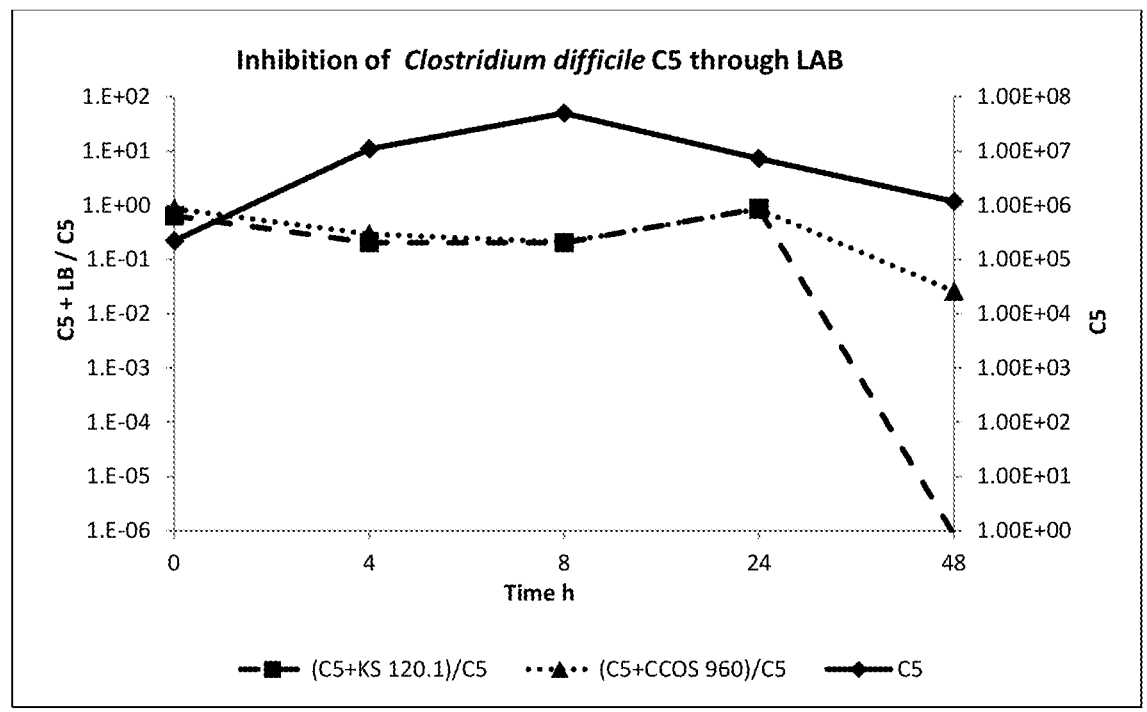
Figure 7A:
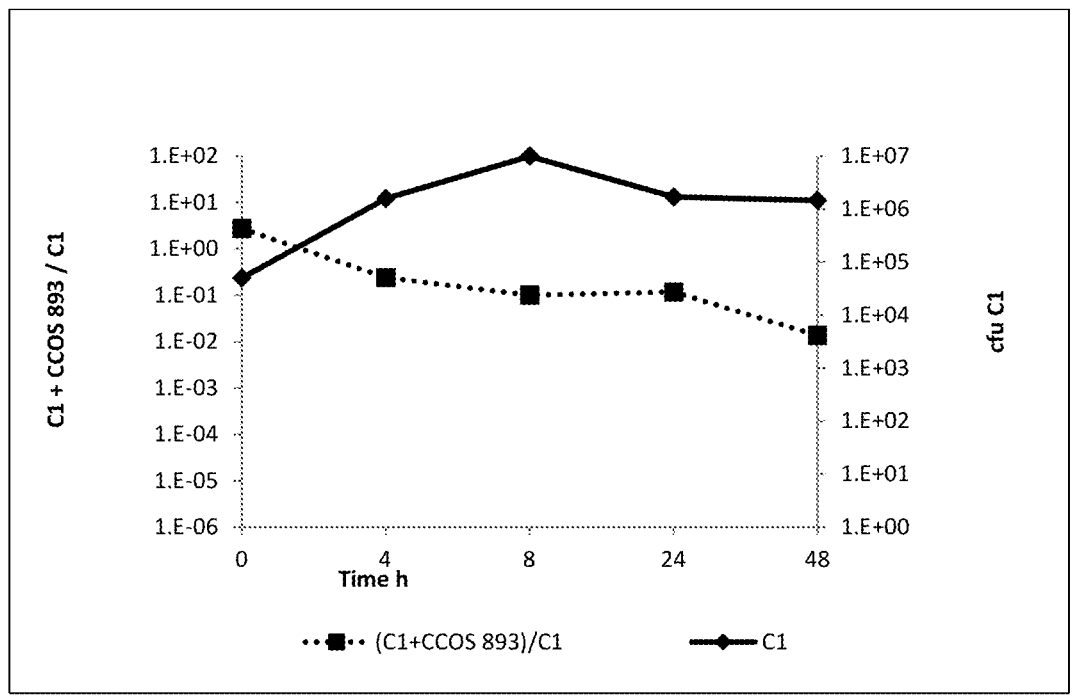
Figure 7B:
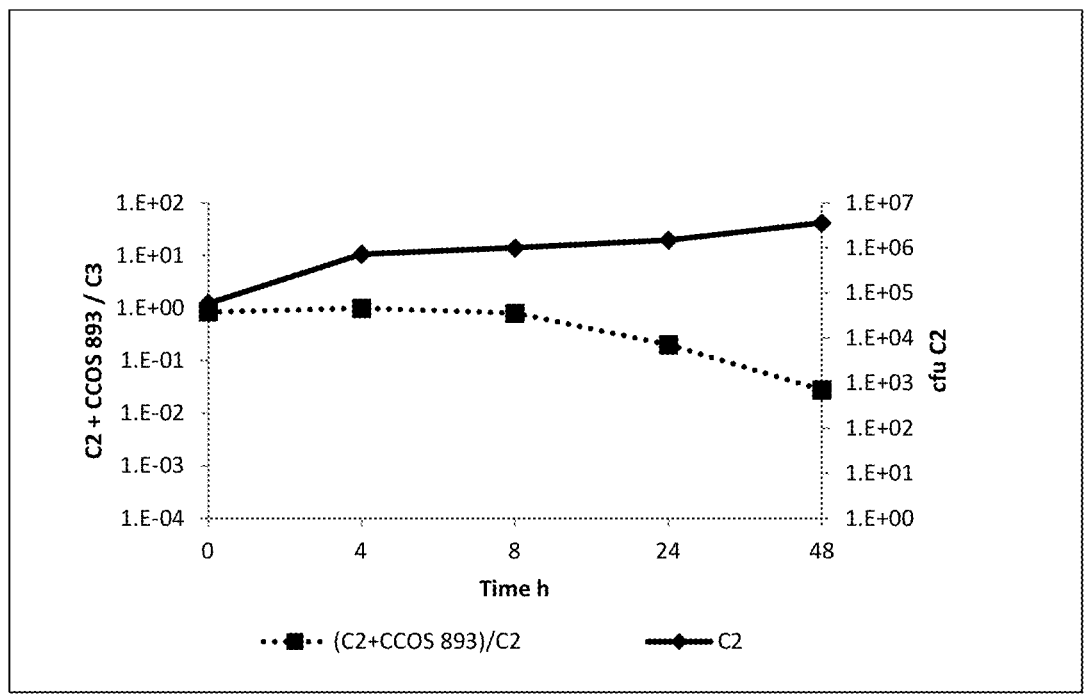
Figure 7C:
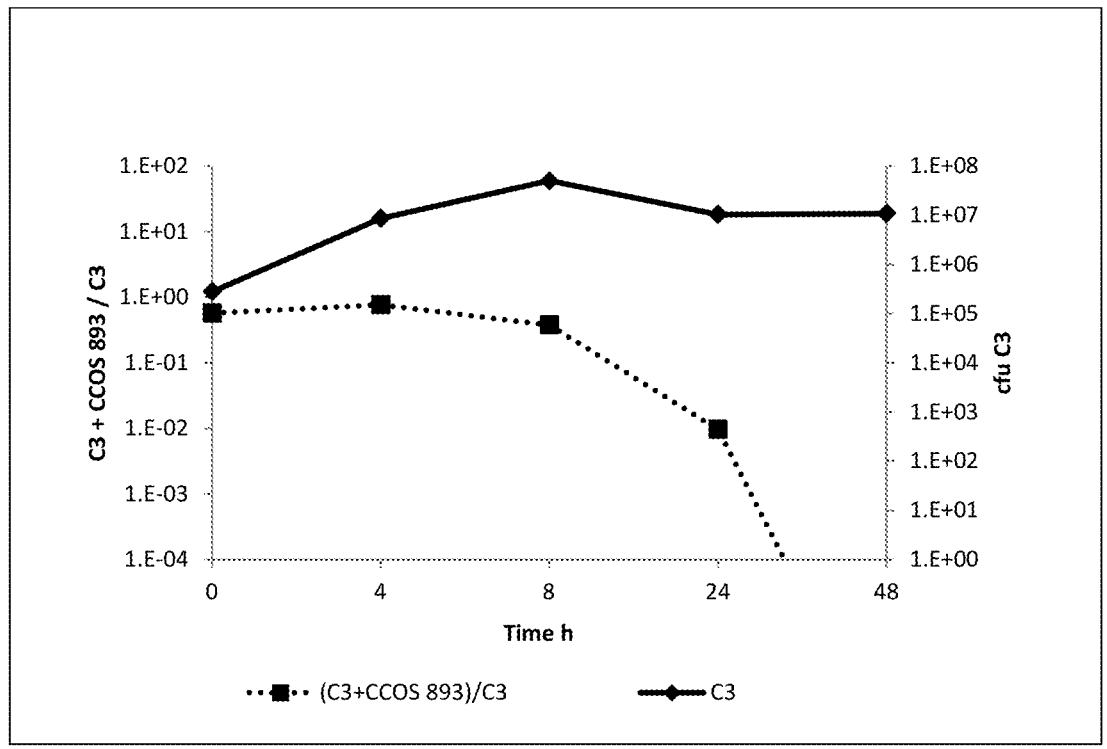
Figure 7D:
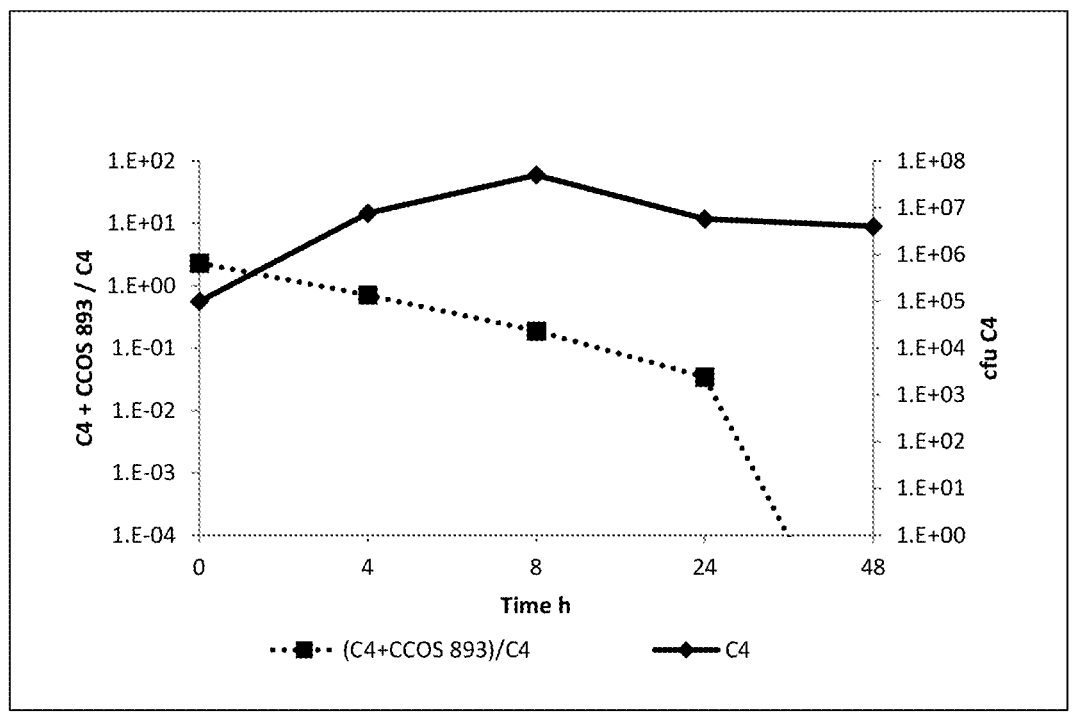
Figure 7E:
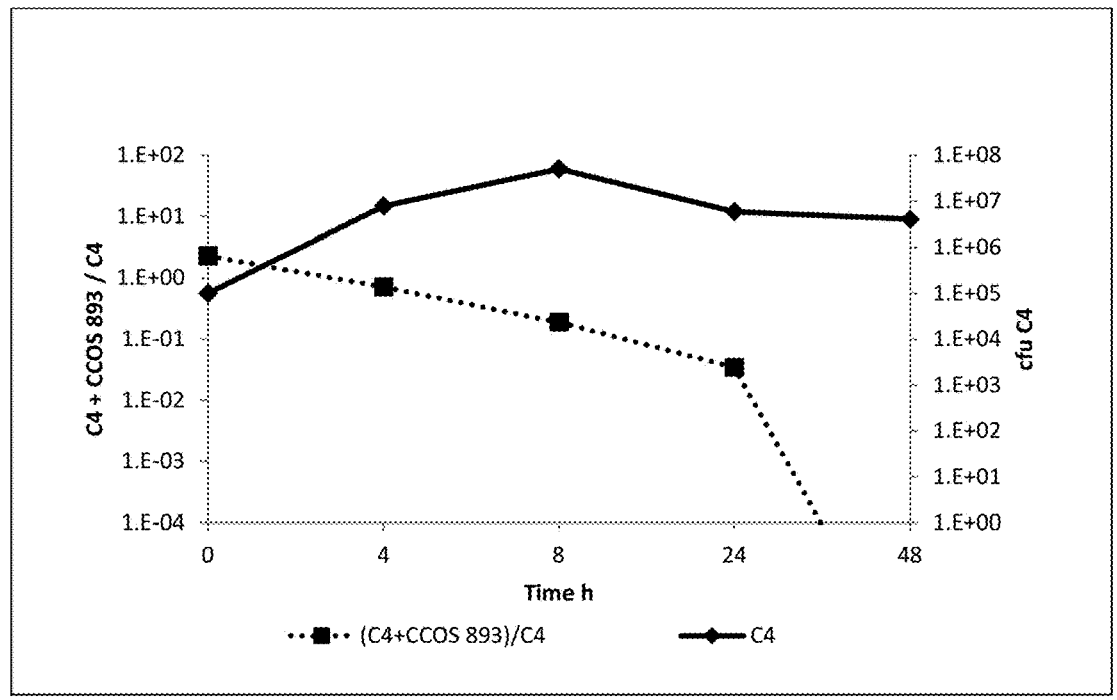

FIG. 6: shows the data of the inhibition of *C. difficile* C5 by *Lactobacillus* L1 and L2 as outlined in Example 7 (Table 8f).

FIG. 7A-E: shows the data of the inhibition of *C. difficile* C1, C2, C3, C4 and C5 by *L. plantarum* CCOS 893, respectively as outlined in Example 8 (Tables 9a-e).

Figure 8:
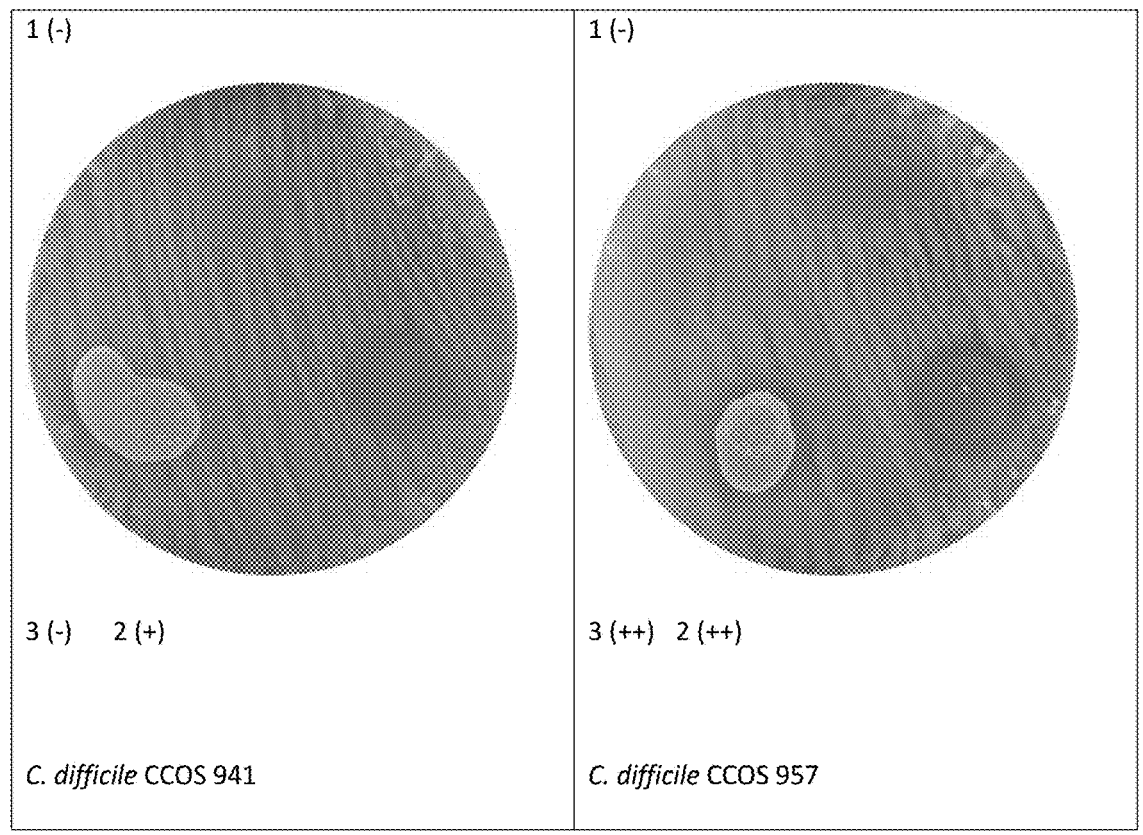

FIG. 8: shows examples of inhibitory effects of 3 Bifidobacteria against 2 different *C. difficile* strains. 1: *B. lactis* BB12, 2: *B. bifidum* CCOS 571, 3: *B. breve* CCOS 586. (−): no zone of inhibition, (+): inhibition detected, (++): strong inhibitory effect.

Figure 9:
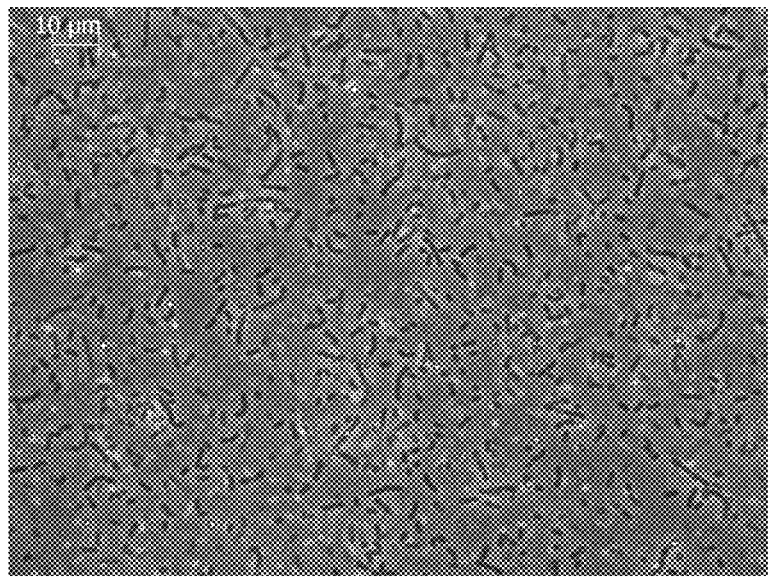

FIG. 9: shows a phase contrast image of *L. lactis* CCOS 949.

Figure 10:
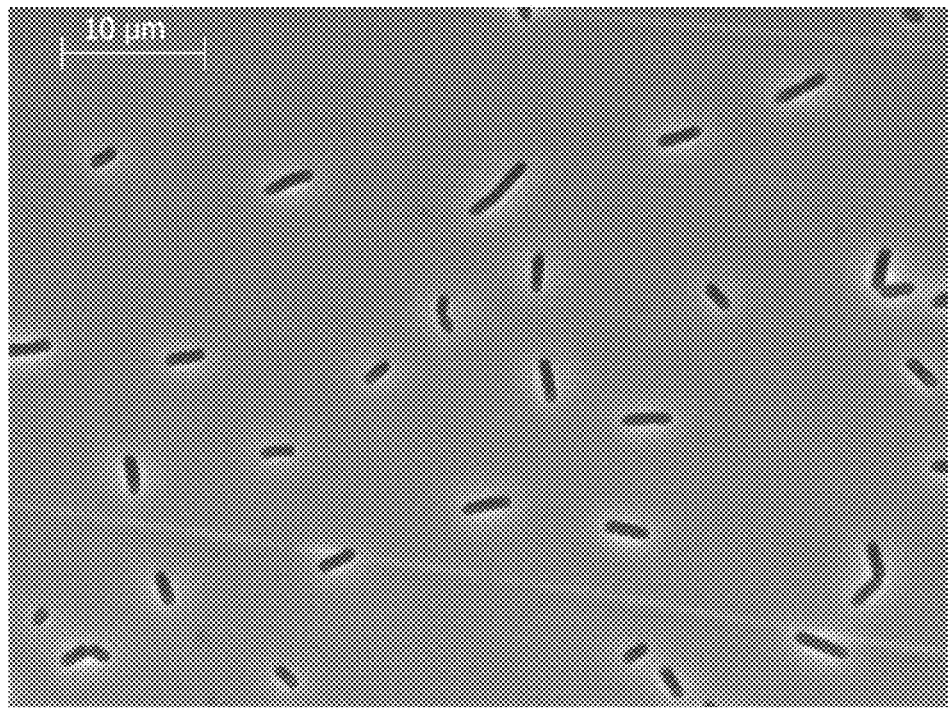

FIG. 10: shows a phase contrast image of *Lactobacillus plantarum* CCOS 893.

Figure 11:
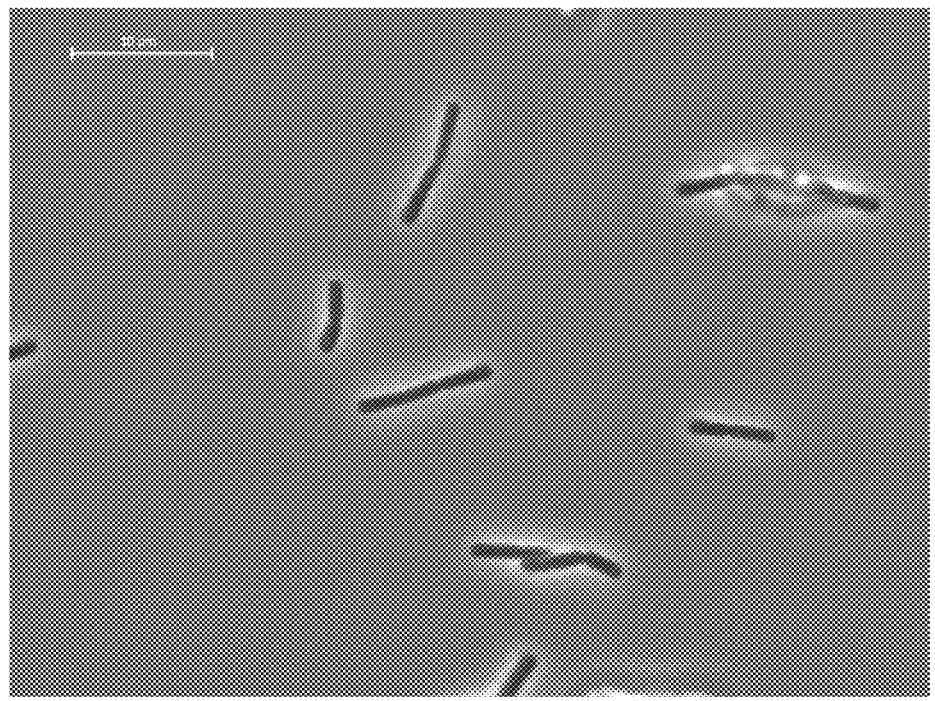

FIG. 11: shows a phase contrast image of *Lactobacillus crispatus* CCOS 961.

Figure 12:
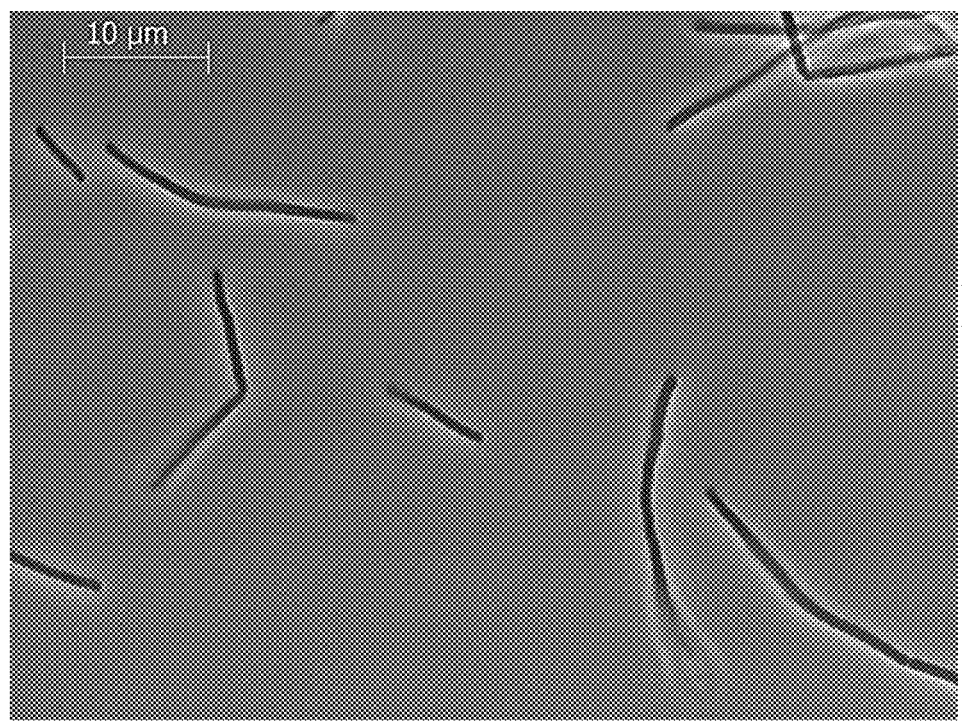

FIG. 12: shows a phase contrast image of *Lactobacillus gasseri* CCOS 960.

Figure 13:
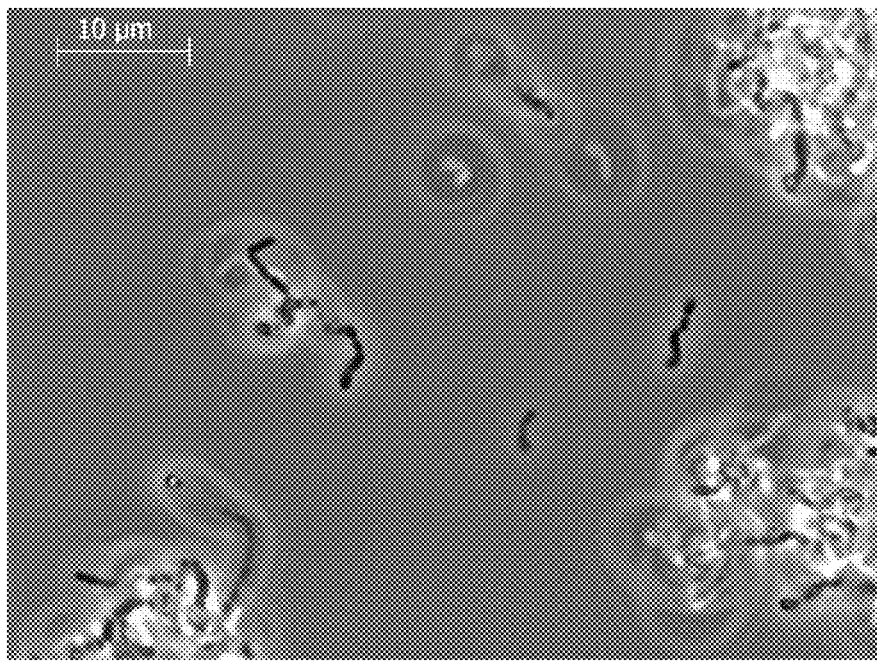

FIG. 13: shows a phase contrast image of *Lactobacillus jensenii* CCOS 962.

Figure 14:
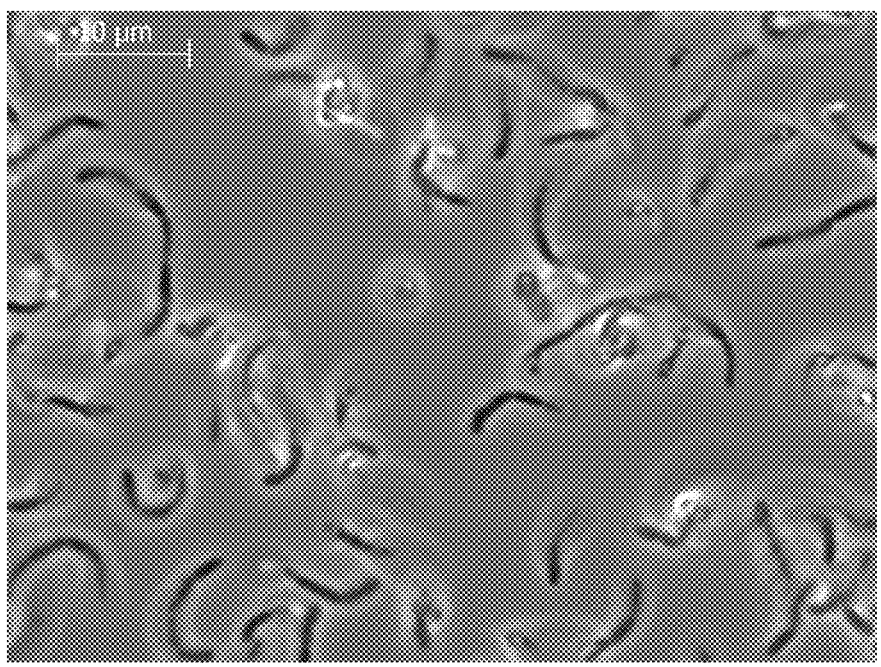

FIG. 14: shows a phase contrast image of *Lactobacillus rhamnosus* CCOS 965.

Figure 15:
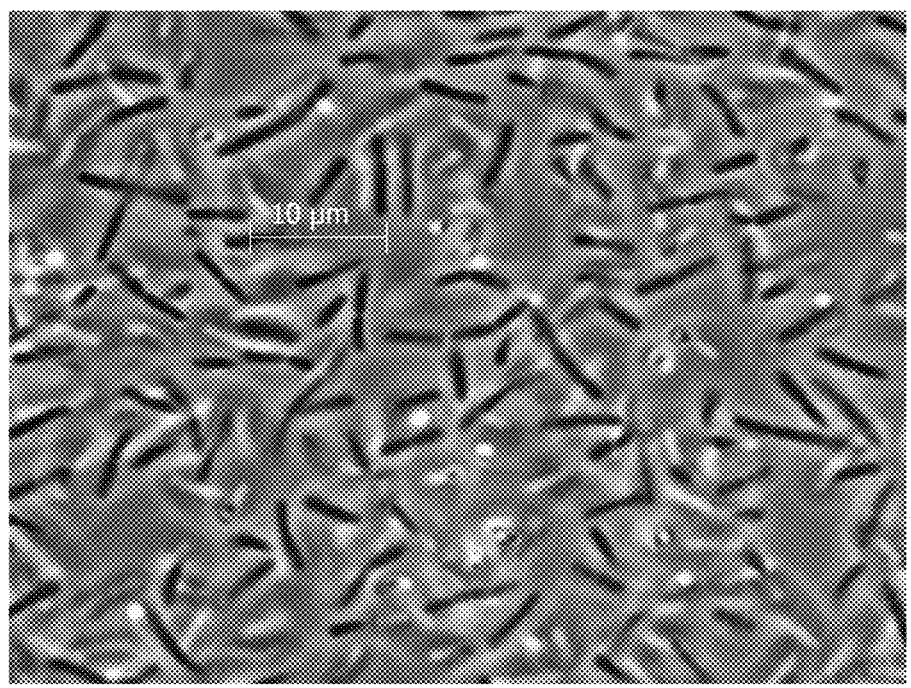

FIG. 15: shows a phase contrast image of *Lactobacillus paracasei* CCOS 1201.

Figure 16:
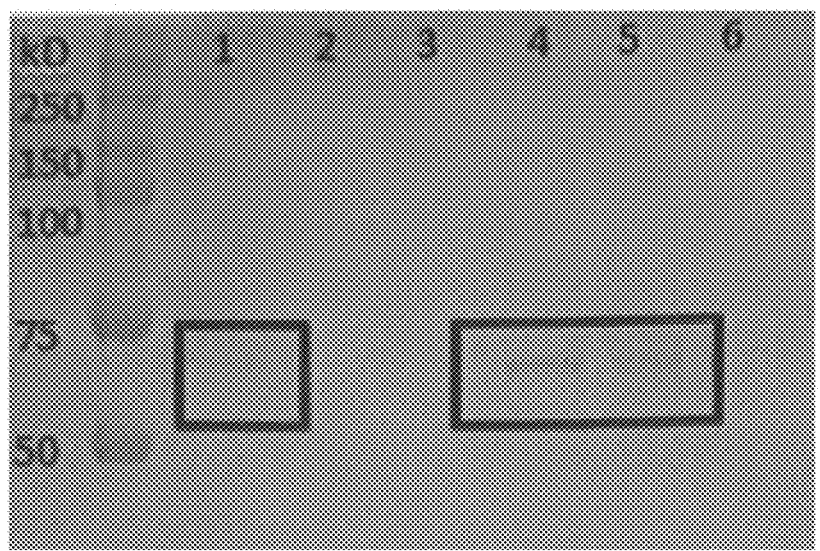

FIG. 16: shows the WesternBlot analysis of purified NAGase. Lanes 1&2: Protein fractions from expression at 37° C., lanes: 3 to 6: expression at 20° C.

EXAMPLE 1: SPOT EXPERIMENTS: COMPARATIVE INHIBITION OF *C. DIFFICILE* BY DIFFERENT STRAINS OF LACTOCOCCI a. Introduction In order to have a more comprehensive basis for a comparison between the killing activities of different probiotic strains against *C. diff.*, 3 different *Lactococcus* strains were tested against 5 hospital isolates of *C. diff.*

TABLE 1

| Nr. | Species | Working Code | Access Code/Provider |
|---|---|---|---|
| L1 | Lactococcus lactis | FG 03 | CCOS 949 |
| L2 | Lactococcus lactis | SP 38 | DSM 26868 |

TABLE 1-continued

| Nr. | Species | Working Code | Access Code/Provider |
|---|---|---|---|
| L3 | *Lactococcus lactis* | SP 47 | Sacco S.r.l., 22071 Cadorago (IT) |
| C1 | *Clostridium difficile* | 2014 11678 | CCOS 937 |
| C2 | *Clostridium difficile* | 2014 11648 | CCOS 938 |
| C3 | *Clostridium difficile* | 2014 11698 | CCOS 939 |
| C4 | *Clostridium difficile* | 2015 11285 | CCOS 940 |
| C5 | *Clostridium difficile* | Test-strain Lab | CCOS 941 |

The *Clostridium difficile* strains are available from the public collection of the Culture Collection of Switzerland CCOS, Einsiedlerstrasse 34, 8820 Wädenswil, Switzerland, www.ccos.ch. Lyophilisates of strains L2 (SP38) and L3 (SP47) were purchased from Sacco S.r.l. 22071 Cadorago (IT).

b. Methods

Media and growth conditions of *Lactococcus* sp.: the preparatory cultures were incubated for 48 h at 37° C. (with $CO_2$ 7.5%) on COS sheep blood plates (aerobically, without $CO_2$). Afterwards fresh cultures were inoculated in MRS broth and incubated over night at 37° C. (aerobically, without $CO_2$).

c. Test Procedure

The overnight cultures of the C. diff. strains were then evenly scratched out on the COS plates (for each one C1-C5 one plate). Then 10 microliters of the suspensions of the overnight cultures of the *Lactococcus lactis* strains were pipetted on the plates that had been before inoculated with *C. difficile*. In order to observe the effect of pH value each suspension was additionally neutralized (with NaOH 4%) at a pH-value of 5-6 and likewise pipetted onto the inoculated plates. Finally, the plates were incubated at 37° C. for 48 hours and the inhibition of *C. difficile* assessed.

d. Results

TABLE 1a

Inhibition of *Clostridium difficile* by *Lactococci* in spot experiments

| Lactococcus | pH-value | C. difficile | | | | |
| | | CCOS 937 (C1) | CCOS 938 (C2) | CCOS 939 (C3) | CCOS 940 (C4) | CCOS 941 (C5) |
|---|---|---|---|---|---|---|
| CCOS 949 | 5 | ++ | ++ | ++ | ++ | ++ |
| CCOS 949 n | 6 | ++ | ++ | ++ | ++ | ++ |
| DSM 26868 | 4.5 | + | + | +/− | +/− | +/− |
| DSM 26868 n | 5-5.5 | + | + | − | − | +/− |
| SP 47 | 4.5 | +/− | +/− | − | − | +/− |
| SP 47 n | 5.5 | +/− | +/− | − | − | +/− |
| MRS (neg. control) | >6 | − | − | − | − | − |

Legend:
++: very good-;
+: good-;
+/−: weak-;
−: no inhibition;
n = neutralized e. Conclusion For the *Lactococcus lactis* DSM 26868 and SP 47, both nisin producers, the usual pattern was observed: The activity is good at pH 4.5, but then clearly diminishes when the pH is raised to pH 5.5.

However, the *Lactococcus lactis* strain CCOS 949 (DSM 32294, also abbreviated as LCL 949) shows a different behavior: Not only it is strongly active against all of the tested *Clostridium difficile* at pH<=5, but this activity remains strong even after raising the pH to 6. From Table 1a, one preliminary conclusion can be drawn: although DSM 26868 and SP 47 are also nisin producer, they are less active against *C. difficile* (C1-C5) than LCL 949. Hence, there must be another anti-microbial factor beside nisin that confers to LCL 949 its particular efficacy (see below).

EXAMPLE 2: DETERMINATION OF THE INHIBITORY PROPERTIES *LACTOCOCCUS LACTIS* CCOS 949 AGAINST *CLOSTRIDIUM DIFFICILE* IN CO-CULTIVATION EXPERIMENTS IN LIQUID MEDIUM

TABLE 2

Tested bacterial cultures and cultivation conditions

| Test strains | Strain code | Pre-cultue medium | Co-culture medium |
|---|---|---|---|
| *Clostridium difficile* | CCOS 941 | Thioglycollate | Thioglycollate-MRS (9:1) broth |
| *Lactococcus lactis* | CCOS 949 | MRS | Thioglycollate-MRS (9:1) broth | a. Methods

All cultures were re-activated from being cryopreserved (−80° C.) working stocks by cultivation on suitable agar medium at 37° C. under anaerobic conditions. For the co-cultivation experiments, 10 mL of the pre-cultivation medium were inoculated with a single colony of each strain and incubated (overnight for *Lactococcus lactis*, 4-5 hours for *C. difficile*). These cultures were used as inocula for the co-cultivation medium (a 9:1 vol/vol mixture of Thioglycollate and MRS broth). The ratio of *Lactococcus lactis* to *C. difficile* was set to approx. 100:1 based on optical density measurements at 590 nm of the inocula. In addition, all strains were inoculated separately and run as controls in parallel. The growth of the cultures was monitored anaerobically for 25 hours at 37° C., with shaking (120 rpm) by measuring pH, OD and colony forming units (cfu) at 3 to 4 time points. Colony numbers for *Lactococcus lactis* were determined by plating on MRS agar with aerobic incubation at 37° C. for 1-2 days, the aerobic incubation inhibited the growth of *C. difficile*. The number of *C. difficile* was determined by plating on Thioglycollate agar and anaerobe incubation at 37° C. for 1 day. Both *C. difficile* and *Lactococcus lactis* were able to grow on this medium, however a discrimination between *Lactococcus lactis* and *C. difficile* was possible by colony morphology. For the quantification of the inhibitory capacity of *Lactococcus lactis* against *C. difficile* the ratio of the number of colony forming units at the beginning and the end of the experiment for both *Lactococcus lactis* and *C. difficile* was calculated. The lower the ratio the stronger the inhibitory effect.

To determine the effect of pH on *C. difficile* survival due to lactic acid formation by *Lactococcus lactis*, additional experiments with buffered co-cultivation medium (0.2 M sodium phosphate, pH 5.5) were performed. All anaerobic work was carried out in an anaerobic chamber (Coy Laboratory Products, USA).

b. Results

Results are illustrated in FIG. 1. Table 3 shows the results of co-cultivation experiments, development of pH and cell numbers (cfu/mL).

TABLE 3

| | | t = 0 h | | | t = 25 h | | |
|---|---|---|---|---|---|---|---|
| Cultures | Code | cfu/mL Lc. lactis | cfu/mL CDI | pH | cfu/mL Lc. lactis | cfu/mL CDI | pH |
| Thioglycollate-MRS (1:9) medium, not buffered | | | | | | | |
| Lc. lactis | 949 | 9.0E+6 | — | 6.98 | 2.6E+5 | — | 4.55 |
| C. difficile | 941 | — | 2.9E+7 | 6.98 | — | 1.2E+9 | 5.74 |
| Lc. lactis × CDI | 949 × 941 | 9.0E+6 | 2.9E+7 | 6.98 | 4.7E+5 | <100 | 4.70 |
| Thioglycollate-MRS (1:9) medium, buffered: 2 m M NaP, pH 5.5 | | | | | | | |
| Lc. lactis | 949 | 1.9E+6 | — | 5.55 | 4.2E+9 | — | 4.90 |
| C. difficile | 941 | — | 6.7E+5 | 5.59 | — | 2.5E+8 | 5.60 |
| Lc. lactis × CDI | 949 × 941 | 2.5E+6 | 2.7E+5 | 5.54 | 9.8E+9 | <1000 | 5.16 |

× = co-cultivation c. Conclusion a) Non-buffered medium, individual strains: this apparently gives a preference to *C. difficile* as compared to *Lactococcus lactis* CCOS 949. The latter decreases after 25 h by one log, the former increases by 3 log. In the co-culture to *Lactococcus lactis* CCOS 949 decreases by 1 log, whereas *C. difficile* decreases by 5-6 logs. Alternatively, the *Lactococcus lactis* culture is already exhausted after 25 h.

b) Buffered medium: surprisingly *Lactococcus lactis* CCOS 949 has a better growth by 3 logs, about the same as for *C. difficile*. In the co-culture *Lactococcus lactis* CCOS 949 increases by 3 logs, whereas *C. difficile* decreases about 3 logs.

c) The inhibitory effect of *Lactococcus lactis* CCOS 949 on *C. difficile* is maintained in the buffered co-culture even at pH over 5 (pH=5.16) as compared to the unbuffered one with pH=4.70.

The co-culture experiments confirm the spot experiments in as much as the *Lactococcus lactis* CCOS 949 has an anti-*C. difficile* activity, which is less dependent on pH as compared with other strain of the species *Lactococcus*.

Screening for enzymes was carried out, with the aim of identifying other, different anti-microbial products contributing besides nisin to the anti-microbial activity of LCL 949. Besides lactic (mainly L-) and acetic acids, and nisin in certain cases, *Lactococcus lactis* is not known to produce other kind of antimicrobial metabolites like e.g. hydrogen peroxide, that only certain *Lactobacillus*, especially those of vaginal origin, produce. The enzyme spectrum of *Lactococcus lactis* CCOS 949 was therefore investigated, looking for proteins which could potentially have anti-microbial activities and contribute to the remarkable antibacterial activity of *Lactococcus lactis* CCOS 949. As potential candidates for such active proteins the different peptidases, esterases, galactosidases a.s.o. were considered, but eventually the peptidoglycan hydrolases were more closely investigated.

The different functions of the peptidoglycan hydrolases in the cell meta- and catabolism were reviewed in detail by W. Vollmer et al. (FEMS Microbiol Rev. 2008 March; 32(2): 259-86. doi: 10.1111/j.1574-6976.2007.00099.x. Epub 2008 Feb. 11. Bacterial peptidoglycan (murein) hydrolases, Vollmer W, Joris B, Charlier P, Foster S.).

However, the prior art does not mention the production of glycosidases (e.g. N-acetyl-glucosaminidase (NAGase) or N-acetylmuramidases or N-acetylhexosaminidases) or more generally a peptidoglycan hydrolase by some lactic acid bacteria, or more specifically some bacteria or probiotic bacteria, for the purpose of inhibiting or killing competing, pathogenic bacteria.

EXAMPLE 3: NAGASE PRODUCTION AMONG LACTIC ACID BACTERIA (LAB)

The screening experiments conducted by the inventors showed that the NAGase activity as revealed by established enzymatic tests kits varies between species and strains of lactic acid bacteria.

TABLE 4

| | Assay with whole cells | | | | | |
|---|---|---|---|---|---|---|
| | Score (0-5) | | | Concentration (nmol) | | |
| Strain | 12 h | 18 h | 24 h | 12 h | 18 h | 24 h |
| Lactobacillus jensenii KS 119.1 | 2 | 1 | 0 | 10 | 5 | 0 |
| Lactococcus lactis CCOS 949 | 4 | 2 | 0 | 30 | 10 | 0 |
| Lactobacillus gasseri KS 120.1 | 5 | 2 | 3 | >40 | 20 | 30 | a. Method

Lactic acid bacteria strains were tested for their enzyme activity using APIzym test from BioMérieux, reference no. 25200. All test cultures were first checked for identity and purity and preserved at −80° C. After reactivation the lactic acid bacteria were grown on MRS agar for 24 to 48 hours under anaerobe conditions. Bacterial cells were then harvested from the agar plates and the enzyme activities were determined according to the manufacturer's instructions. The tests were performed in duplicate and measurements were done at 12, 18 and 24 hours after incubation, interpretation of the results was done according to the guidelines of the manufacturer by attributing values from 0 to 5 to the observed colour reactions.

b. Results

Comparing the detection of NAGase of the 3 strains it was observed observed that *L. jensenii*, used as the negative control, secretes only low levels of this enzyme whereas *L. gasseri* KS 120.1, the positive control, does it at high levels. *Lactococcus lactis* CCOS 949 also significantly produces NAGase.

c. Conclusion

Hence it was concluded that NAGase (and hexosaminidase or muramidase) contributes, besides nisin, to the significant anti-*C. difficile* activity of *Lactococcus lactis* CCOS 949. If NAGase/muramidase/hexosaminidase (that is: glycosidase) is an independent contributor to the activity of *Lactococcus lactis*. CCOS 949 against *C. difficile*, then in bacteria lacking nisin, but producing/expressing NAGase/muramidase, a correlation should be found between the degree of glycosidase production and the antimicrobial activity. Furthermore, the genome analysis of LCL 949 should then reveal, besides genes for nisin-type bacteriocins also genes corresponding to peptidoglycan hydrolases, in particular glycosidases.

EXAMPLE 4: GENOME SEQUENCING AND ANALYSIS OF *LACTOCOCCUS LACTIS* CCOS 949

4.1 Whole Genome Sequencing, Assembly and Annotation.

Whole genomic high molecular weight DNA extraction of *Lactococcus lactis* CCOS 949—*Lactococcus lactis* was grown in 10 ml of liquid MRS (Man, Rogosa and Sharpe medium) at 37° C. without shaking in a 50 ml conical tube for 48 h (cell density $1 \times 10^9$ cells/ml). A 1 ml aliquot was centrifuged for 5 min at 8,000×g. The supernatant was removed and resuspended in 500 µl of 5M LiCl. The cells were placed on ice and vigorously vortexed every 2 minutes for 15 minutes. The cells were then centrifuged at 8,000×g for 5 min. A total of 500 µl of saturated phenol was added to the cell pellet, vortexed and centrifuged at 8,000×g. The cell pellet was washed with PBS and resuspended in 500 µl of PBS. Whole genomic DNA was extracted using Master-Pure™ DNA Purification Kit (Epicentre, Cat. No. MCD85201). A total of 10 µg of DNA was used to construct a large insert (5-20 kb) SMRTbell™ sequencing library that was sequenced on a PacificBiosciences RSII instruments according to the manufacturer recommendations at the Institute for Genome Sciences, University of Maryland School of Medicine, Baltimore, MD USA.

Two SMRT cells were sequenced (P6 polymerase and C4 chemistry) which generated a total of 467,794 sequence reads with a mean read length of 6,038 bp totaling 2.8 billion bp and a maximum read length of 47,345 bp. The genome of *Lactococcus lactis* CCOS 949 was assembled using the MinHash Alignment Process (MHAP) (Berlin K, Koren S, Chin C-S, Drake J P, Landolin J M, Phillippy A M. "*Assembling large genomes with single-molecule sequencing and locality-sensitive hashing*" Nat Biotechnol. 2015; 33:623-30).

4.2 Analysis of N-Acetyl-Glucosaminidase Encoding Genes

The genome of *Lactococcus lactis* CCOS 949 encodes different genes for PGHs and in particular four genes annotated as encoding for N-acetylglucosaminidase.

| Gene ID | SEQ ID NO nucleotide | SEQ ID NO amino acid | Annotation |
|---|---|---|---|
| Llactis_02290 | 65 | 130 | Muramidase-2 precursor |
| Llactis_03700 | 66 | 131 | N-acetylmuramoyl-L-alanine amidase domain containing protein precursor |
| Llactis_04950 | 67 | 132 | Exopolysaccharide biosynthesis protein related to Nacetylglucosamine-1-phosphodiester alpha-N-acetylglucosaminidase |
| Llactis_11300 | 68 | 133 | N-acetylmuramoyl-L-alanine amidase domain containing protein precursor |
| Llactis_14060 | 69 | 134 | Bacteriophage peptidoglycan hydrolase |
| Llactis_14990 | 70 | 135 | Lyzozyme M1 (1,4-beta-N-acetylmuramidase) |
| Llactis_15230 | 71 | 136 | N-acetylmuramoyl-L-alanine amidase domain containing protein precursor |
| Llactis_18610 | 72 | 137 | Beta-N-acetylhexosaminidase precursor |
| Llactis_18640 | 73 | 138 | Endo-beta-N-acetylglucosaminidase D |
| Llactis_19470 | 74 | 139 | Exo-glucosaminidase LytG precursor |
| Llactis_22080 | 75 | 140 | Bacteriophage peptidoglycan hydrolase |
| Llactis_22440 | 76 | 141 | Bacteriophage peptidoglycan hydrolase |
| Llactis_22630 | 77 | 142 | Beta-hexosaminidase |
| Llactis_23080 | 78 | 143 | Muramidase-2 precursor |
| Llactis_25570 | 79 | 144 | N-acetylmuramoyl-L-alanine amidase domain containing protein precursor |
| Llactis_18530 | 80 | 145 | putative alpha-1,2-mannosidase |
| Llactis_18650 | 81 | 146 | Alpha-mannosidase |

Endo-ß-N-acetylglucosaminidase (as well as N-acetylmuramoyl-L-alanine amidase, 1,4-beta-N-acetylmuramidase, Beta-hexosaminidase a.s.o.) are a class of proteins with activity against bacterial peptidoglycan and as such have potential antibacterial activities.

4.3 Bacteriocin Analysis of *L. lactis* CCOS 949

Using the BAGEL3 Algorithm (de Jong A, van Heel A J, Kok J, Kuipers O P. "*BAGEL2: mining for bacteriocins in genomic data*" Nucleic Acids Res. 2010; 38:W647-51) and BLAST, two bacteriocin biosynthetic gene clusters were identified: nisin and lactococcin.

4.4 Nisin A

This biosynthetic gene cluster encodes for the biosynthesis and modification of Nisin A. The gene cluster highly similar to that found in *Lactococcus lactis* M78 [Trmčić A, Samelis J, Monnet C, Rogelj I, Matiješić B B. "*Complete nisin A gene cluster from Lactococcus lactis M78*

(*HM219853*)—*obtaining the nucleic acid sequence and comparing it to other published nisin sequences" Genes Genom.* 2011; 33:217-21]. The 16.3 kb pathway is located on contig tig00000001 and comprises 11 genes and is flanked by insertion sequence IS904.

The gene nisA (SEQ ID NO: 54) encodes for NisA, a 57-amino acid peptide that contains a leader peptide of 23 aa. The sequence of NisA is (^ indicates the activation site):

(SEQ ID NO 82)
MSTKDFNLDLVSVSKKDSGASPR^ITSISLCTPGCKTGALMGCNMKTAT

CHCSIHVSK

The sequence of each the 11 core genes is as follows:

| Gene | Gene length | SEQ ID NO | Annotation |
|------|-------------|-----------|------------|
| nisA | 174 bp | 54 | Nisin A |
| nisB | 2,982 bp | 55 | Dehydratase |
| nisT | 1,803 bp | 56 | Transporter - Translocation protein |
| nisC | 1,113 bp | 57 | Thioether-forming enzyme (Lanthionine formation) |
| nisI | 738 bp | 58 | Lipoprotein - Immunity |
| nisP | 2,049 bp | 59 | Subtilisin-like serine protease |
| nisR | 687 bp | 60 | Regulator |
| nisK | 1344 bp | 61 | Regulator |
| nisF | 678 bp | 62 | Transporter - Immunity |
| nisE | 729 bp | 63 | Transporter - Immunity |
| nisG | 645 bp | 64 | Transporter - Immunity |

4.6 Lactococcin

The gene cluster putatively associated with the biosynthesis of a lactococcin bacteriocin is not encoded on a plasmid. This gene was originally annotated as coding for a hypothetical protein, but BAGEL3 identified it as a Lactococcin. Further, a Conserved Domain search shows similarity to members of PFAM04639, defined as Lactococcin-like family (family of bacteriocins from lactic acid bacteria).

Genomic analysis thus confirmed that *Lactococcus lactis* CCOS 949's exceptional activity against *C. difficile* may be linked to the production of peptogylcan hydrolases (PGHs). The one and same strain carries genes for, on one side, peptogylcan hydrolases (PGHs), specifically N-acetylglucosaminidases (4 in number), muramidases (2 in number) and, on the other side, for 3 bacteriocins, specifically 1 of the Nisin type. This combination is of particular relevance to the present invention as it allows to postulate that it is the presence of peptidoglycan hydrolases such as glycosidases and amidases that contributes in this particular strain to the said unexpected activity.

4.7 Conclusion of Example 4

Both the Nisin genes and the glycosidase-type genes (e.g. Nagase) expected on the basis of the enzyme and the inhibitory activity experiments could be indeed found. These genomic data support the concept that the exceptional activity of this particular strain is also due to the combined action of two types of antimicrobial peptides, bacteriocins (nisin and lactococcin) and PGHs (NAGases and muramidases).

In other words, LAB strains lacking nisin, but expressing PGHs, can be expected to possess an inhibitory activity against *C. difficile*, too. The data hereafter and those relating to further tests with *Lactobacillus* strains reported further below confirm this finding.

EXAMPLE 5: SPOT EXPERIMENTS CORRELATING NAGASE PRODUCTION AND ANTI-*C. DIFFICILE* INHIBITION

Spot-experiment Series 1 was performed in order to qualitatively assess the inhibitory effect of cultures of *Lactobacillus* on *C. difficile*. To this end 2 *Lactobacillus* strains and 5 *C. difficile* hospital isolates were used. In a semi-quantitative set-up, the sediments of the cultured *Lactobacillus* were pipetted on sheep blood agar plates that had been previously inoculated with *C. difficile*. In order to boost the *Lactobacillus* counts the sampled cultures were suspended in MRS broth.

The *Lactobacillus* strains were enriched overnight with MRS broth. From these cultures 1-2 drops of the sediment were retrieved and filled in a tube. Out of this tube one drop was pipetted onto the agar plates previously spread over with *C. difficile* (McF 0.5-1). The plates prepared in the said way were incubated overnight (24 h) and results were read off the next day. Results are shown in Table 5.

TABLE 5

Reference *Lactobacillus* strains tested in spot-experiments against 5 *C. diff* in Series 1

| | *Lactobacillus* | | | *C. difficile* Access number | | | | |
|---|---|---|---|---|---|---|---|---|
| Species | Code | Access number | "NAGase" activity in APIZYM test | CCOS 958 | CCOS 957 | CCOS 938 | CCOS 937 | CCOS 939 |
| *L. gasseri* | KS 120.1 | CNCM I-3218 | high | (+) | ++ | + | + | + |
| *L. jensenii* | KS 119.1 | CNCM I-3217 | Low or absent | − | (+) | (+) | − | + |

Legend to Table 5:
Antimicrobial activity:
++: strong;
+: medium;
(+): weak;
−: no activity
Enzymatic activity for N-acetyl-glucosaminidase (NAGase) as determined by APYzym kit of Biomérieux:
Score range: 0 to 5.
Score >= 3: high activity;
Score = 1-2: low activity;
Score = 0 : absent activity.

The finding that the production of glycosidase is related to an anti-*C. difficile* activity in vitro was thus confirmed at the phenotypic level. Further experiments were conducted on *Lactobacillus* strains belonging to different species to verify the hypothesis that the presence glycosidases (NAGases or muramidases) is related to the anti-*C. difficile* activity.

After having found a remarkably active, nisin-producing *Lactococcus lactis* (CCOS 949) and based on the assumption, in view of experimental evidence, that such activity might be due to the contribution of the activity of Peptoglycan Hydrolases, in particular NAGase, investigation was extended to include a number of probiotic *Lactobacillus* species to see whether this hypothesis can be confirmed.

Like the other members of the *Lactobacillus acidophilus* group A, *Lactobacillus gasseri* is an anaerobic, gram-positive bacterium that falls into the category of lactic acid bacteria. It is also a rod shaped and of the non-spore-forming type. It was first described by Lauer and Kandler as a novel species in 1980 (Ref Lauer, Eckhard, and Otto Kandler. "*Lactobacillus gasseri* sp. nov., a new species of the subgenus *Thermobacterium*." Zentralblatt für Bakteriologie: I. Abt. Originale C: *Allgemeine, angewandte und ökologische Mikrobiologie* 1.1 (1980): 75-78). It is typically found in the gastrointestinal tracts of humans and animals due to its largely fermentative function (Alatossova, T., Munro, K., Ng, J., Tannock, G. W., & Tilsala-Timisjarvi, A. (1999) Identification of *Lactobacillus* Isolates from the Gastrointestinal Tract, Silage, and Yoghurt by 16S-23S rRNA Gene Intergenic Spacer Region Sequence Comparisons. Applied and Enviromental Microbiology. 65(9). 4364-4267; Falsen, E, Pascual, C, Sjoden, B, Ohlen, M, & Collins, MD (1999) Phenotypic and phylogenetic characterization of a novel *Lactobacillus* species from human sources: description of *Lactobacillus iners* sp. Nov. Int J Syst Bacteriol. 49. 217-221; Mitsuoka, T. (1992) "*The human gastrointestinal tract. In, The Lactic Acid Bacteria: Volume* 1, *The Lactic Acid Bacteria in Health and Disease*" B. J. B. Wood (ed), pp 69-114. Elsevier Science Publishers, Ltd. Essex, England).

Although mainly found in the GI tract, it can also be found in many other locations as well, in particular in the lower genital tract of healthy females.

Isolation of this bacterium was achieved by taking a sample from the gastrointestinal tract and was discovered to be part of what is today known as the *Lactobacillus acidophilus* complex (Kullen, M. J., R. B. Sanozky_Dawes, D. C. Crowell and T. R. Klaenhammer. (2000) Use of DNA sequence of variable regions of the 16SrRNA gene for rapid and accurate identification of bacteria in the *Lactobacillus acidophilus* complex. J. Appl. Microbiol. 89:511-518). One of its roles, as described above, is fermentation in the GI tract. Recently, its function as a probiotic has been the area of most interest (Alatossova et al, see above). The complete genome of the type strain, *L. gasseri* ATCC 33323, has been sequenced by a combination of efforts from the Joint Genome Institute, Fidelity Systems Inc., and the North Carolina State University. The final draft was accepted on Oct. 13, 2006. (see DOE Joint Genome Institute http://genome.jgi-psf.org/finished_microbes/lacga/lacga.home.html). *L. gasseri* is an anaerobe so it lives mostly in body sites where no oxygen is present. It also participates in fermentative actions, which produce lactic acid as well as the energy required for growth.

*Lactobacillus plantarum* is a Gram positive, catalase negative bacterium, belonging to the heterogenous *Lactobacillus* genus, which includes more than 200 species. It is a lactic acid bacterium with a facultative heterofermentative metabolism. Unlike other members of the *Lactobacillus* genus, the distribution of *L. plantarum* in nature is rather wide, ranging from dairy products, vegetables, meat, silage, wine, as well as oral, gastrointestinal, vaginal and urogenital tracts (Seddik H A, Bendali F, Gancel F, Fliss I, Spano G, Drider D. "*Lactobacillus plantarum and Its Probiotic and Food Potentialities*" Probiotics Antimicrob Proteins. 2017; 9(2):111-22). The species *L. plantarum* is characterized by genomic and phenotypic variability, as around 120 genes (within more than 2000 constituting the core genome of *L. plantarum*) were found to be unique for this species, and 50 genes to be unique for the reference strain WCFS1 (Siezen, R. J., Bayjanov, J., Renckens, B., Wels, M., van Hijum, S. A., Molenaar, D., and van Hylckama Vlieg, J. E. (2010) "*Complete genome sequence of Lactococcus lactis subsp. lactis KF*147, *a plant-associated lactic acid bacterium*". J Bacteriol 192: 2649-2650). The genus *Lactobacillus* includes Gram positive rods with fastidious growth requirement, most of which are commensals of gut and vaginal ecosystem, where, in particular, their preponderance is a sign of health (Petrova M I, Lievens E, Malik S, Imholz N, Lebeer S. "*Lactobacillus species as biomarkers and agents that can promote various aspects of vaginal health*" Front Physiol. 2015 Mar. 25; 6:81). Inside the genus, *Lactobacillus crispatus* includes strains colonizing the gastro-intestinal tract (Ojala T, Kuparinen V, Koskinen J P, Alatalo E, Holm L, Auvinen P, Edelman S, Westerlund-Wikström B, Korhonen T K, Paulin L, Kankainen M. "*Genome sequence of Lactobacillus crispatus ST*1" J Bacteriol. 2010 July; 192(13):3547-8) and, typically, is one of the dominant species of the human vagina, together with *L. gasseri, L. jensenii* and *L. iners* (Ravel J, Gajer P, Abdo Z, Schneider G M, Koenig S S, McCulle S L, Karlebach S, Gorle R, Russell J, Tacket C O, Brotman R M, Davis C C, Ault K, Peralta L, Forney L J. "*Vaginal microbiome of reproductive-age women*" Proc Natl Acad Sci USA. 2011 Mar. 15; 108 Suppl 1:4680-7).

In the perspective of its use in food, notably, *L. crispatus* received in 2013 the qualified presumption of safety (QPS) status (https://www.efsa.europa.eu/it/efsajournal/pub/4522), which allows its deliberate use in food and feed in Europe. Although *L. crispatus* does not ferment milk efficiently, it can survive in milk up to one month at 4° C., suggesting the use of this bacterium as adjunctive culture in dairy products with probiotic potential (Siroli L, Patrignani F, Serrazanetti D I, Parolin C, Ñahui Palomino R A, Vitali B, Lanciotti R. Determination of Antibacterial and Technological Properties of Vaginal Lactobacilli for Their Potential Application in Dairy Products. Front Microbiol. 2017 Feb. 7; 8:166). The spot-experiment Series 1 described below was performed in order to assess qualitatively the inhibitory effect of cultures of *Lactobacillus* on *C. difficile*. To this end, 12 *Lactobacillus* strains typical of the urogenital or the intestinal tract and 5 *C. difficile* hospital isolates were used. In a semi-quantitative set-up the sediment of the cultured *Lactobacillus* was pipetted on sheep blood agar plates that had been previously inoculated with *C. difficile*. In order to boost the *Lactobacillus* counts the sampled cultures were suspended in MRS broth.

a. Method

*Lactobacillus* strains were enriched over night with MRS broth. From these cultures 1-2 drops of the sediment were retrieved and filled in a tube. Out of this tube 1 drop was pipetted onto the agar plates previously spread over with *C. difficile* (McF 0.5-1). The plates prepared in the said way were incubated overnight (24 h) and results were read off the next day.

b. Results
Results are shown in Table 6.

TABLE 6

Inhibitory activity of reference *Lactobacillus* strains in spot-experiments against 5 *C. difficile* in Series 1

| | *Lactobacillus* | | | *C. difficile* Access number | | | | |
|---|---|---|---|---|---|---|---|---|
| Species | Code | Access number | NAGase activity | CCOS 957 | CCOS 958 | CCOS 938 | CCOS 937 | CCOS 939 |
| *L. gasseri* Type strain | CCOS 696 | LMG 9203T | 1 | ++ | + | − | − | − |
| *L. gasseri* | KS 120.1 | CNCM I-3218 | 3 | ++ | + | ++ | + | + |
| *L. gasseri* | KS 124.3 | CNCM I-3220 | 2 | ++ | (+) | + | (+) | + |
| *L. gasseri* | 123.1 | CNCM I- 3485 | 0 | − | + | − | (+) | − |
| *L. crispatus* | KS 116.1 | CNCM I-3483 | 0 | (+) | − | + | + | (+) |
| *L. jensenii* | KS 119.1 | CNCM I-3217 | 1 | (+) | − | (+) | − | + |
| *L. jensenii* | KS 121.1 | CNCM I-3219 | 0 | + | − | − | − | − |
| *L. helveticus* | KS 300 | CNCM I-3360 | 0 | ++ | (+) | − | (+) | − |
| *L. johnsonii* | 824 | CCOS 824 | 3 | + | ++ | + | + | + |
| *L. reuteri* | RC 14 | ATCC 55845 | 0 | − | − | (+) | (+) | − |
| *L. rhamnosus* | GR-1 | ATCC 55826 | 0 | + | − | − | − | − |
| *L. rhamnosus* | LGG | ATCC 53103 | 0 | + | − | (+) | − | + |
| *L. rhamnosus* type strain | | DSM 20021 | 2 | + | (+) | + | (+) | + |
| *L. acidophilus* type strain | | ATCC 4356 | 0 | (+) | − | − | − | (+) |
| *L. paracasei* subsp. *paracasei* | DG ® | CNCM I - 1572 | 0 | − | + | − | (+) | − |
| *L. paracasei* subsp. *paracasei* | | CCOS 1205/1201 | 4 | + | ++ | + | (+) | + |

Legend to Table 6:
Antimicrobial activity:
++: strong;
+: medium;
(+): weak;
−: no activity
Enzymatic activity for N-acetyl-glucosaminidase (NAGase) as determined by APYZym kit of Biomérieux:
Score range: 0 to 5.
Score >= 3: high activity;
Score = 1-2: medium-low activity;
Score = 0: not detected activity c. Conclusion From Series 1 it can be seen that the stronger and more consistent activity against *C. difficile* is exhibited by those strains with medium to high NAGase activity, e.g. *L. gasseri* KS 120.1, *L. johnsonii* CCOS 824, *L. paracasei* subsp. *paracasei* CCOS 1205 (identical to CCOS 1201). For most species strains can be found with no or low NAGase production, which are in the majority, as well as strains with high activity, actually a minority. It was found that *L. paracasei* subsp. *paracasei* DG has a low NAGase production and a low anti-*Clostridium difficile* activity, whereas the strain of the same species CCOS 824 has a a significant NAGase production and anti-*C. difficile* activity. For the *gasseri* species it was found that examples with high, medium and low/no Nagase activity correlated to the *C. difficile* inhibition. The well-documented *L. rhamnosus* LGG, albeit reported active against numerous pathogens, does not strongly perform against *C. difficile* inhibition and lacks NAGase production.

A consistent inhibitory activity exhibited by *L. johnsonii* CCOS 824 was noted against different biotypes of *C. difficile* and its correlation with a high NAGase production. This combination—high NAGase activity with high inhibition of *C. difficile*—makes it a good probiotic strain for anti-infective applications, in particular for CDAD/CDI. This strain was also tested against different *C. difficile* strains in co-culture experiments yielding positive results above average thus confirming its inhibitory activity against this pathogen (data not shown).

Noticeable is also the good performance of *L. paracasei* strains producing NAGase e.g. CCOS 1205 (identical to CCOS 1201), as generally speaking *L. paracasei* exhibit numerous interesting probiotic properties and are suitable for industrial production.

In this line of reasoning, said correlation was tested with further *Lactobacillus* strains against the same *C. difficile* hospital strains used in the preceding experiment, with the perspective extend the knowledge of new strains with clear anti-*C. difficile* activity. In the same experiment, the pH-dependence of the activity was also evaluated, a point already considered in the co-culture experiment concerning *Lactococcus lactis* CCOS 949.

EXAMPLE 6: SERIES 2 SPOT EXPERIMENTS: COMPARATIVE INHIBITION OF *C. DIFFICILE* STRAINS BY DIFFERENT SPECIES OF *LACTOBACILLUS*

New test strains belonging to the species *L. plantarum, L. gasseri* and *L. reuteri* were investigated. The dependency on the pH value and the correlation with the NAGase production of the strains was measured. As a negative control, *L. reuteri* RC-14 was used, as in the previous Examples.

TABLE 7

*Lactobacillus* strains tested in spot experiments against 5 *C. difficile* in Example 6 (Series 2)

| Species/Strain | Access Code |
| --- | --- |
| Lactobacillus plantarum | CCOS 893 |
| Lactobacillus plantarum BG 112 | LMG P-20353 |
| Lactobacillus gasseri | CCOS 960 |
| Lactobacillus crispatus | CCOS 961 |
| Lactobacillus reuteri RC14 | ATCC 55845 |
| Clostridium difficile | CCOS 937* |
| Clostridium difficile | CCOS 938* |
| Clostridium difficile | CCOS 939* |
| Clostridium difficile | CCOS 940* |
| Clostridium difficile | CCOS 941* |

*Strains available from CCOS, Wädenswil, Switzerland a. Methods

Media and growth conditions *Lactobacillus* spp.: the preparatory cultures were incubated for 48 h at 37° C. (with $CO_2$ 7.5%) on COS sheep blood plates (aerobically, without $CO_2$). Afterwards fresh cultures were inoculated in MRS broth and incubated overnight at 37° C. (aerobically, without $CO_2$). The overnight cultures of the *C. difficile* strains were then evenly scratched out on the COS plates (for each one C1-C5 one plate). Then 10 microliters of the suspensions of the overnight cultures of the Lactobacilli were pipetted on the plates that had been before inoculated with *C. difficile*. In order to observe the effect of pH value each suspension was additionally neutralized (with NaOH 4%) at a pH-value of 5-6 and likewise pipetted onto the inoculated plates. Finally the plates were incubated at 37° C. over the weekend and the inhibition of *C. difficile* assessed.

b. Results

TABLE 7a

Inhibition of *Clostridium difficile* by selected *Lactobacilli* in spot experiment

| | | | C. difficile | | | | |
| --- | --- | --- | --- | --- | --- | --- | --- |
| Lactobacillus | pH - value suspension | NAGase activity | CCOS 937 | CCOS 938 | CCOS 939 | CCOS 940 | CCOS 941 |
| RC 14 | 4.5 | low | +/− | +/− | − | − | − |
| RC 14 n | 5.5 | | +/− | − | − | − | − |
| CCOS 960 | 4 | high | + | ++ | + | + | + |
| CCOS 960 n | 5.5 | | + | +/− | − | − | +/− |
| BG 112 | 4 | medium | + | +/− | + | + | + |
| BG 112 n | 5.5 | | +/− | − | − | − | +/− |
| CCOS 893 | 4 | high | + | +/− | + | + | + |
| CCOS 893 n | 5.5 | | +/− | − | +/− | +/− | +/− |
| CCOS 961 | 4.5 | medium | + | +/− | + | +/− | +/− |
| CCOS 961n | 5.0-5.5 | | +/− | +/− | − | − | − |
| MRS | >6 | — | − | − | − | − | − |

Legend to Table 7a:
n: neutralized;
Antimicrobial activity:
++: strong;
+: medium;
+/−: weak;
−: no activity;
Enzymatic activity for N-acetyl-glucosaminidase (NAGase) as determined by APYZym kit of Biomérieux:
Score range: 0 to 5.
Score >= 3: high activity;
Score = 1-2: medium activity;
Score = 0: low or undetected activity c. Conclusion The strain *L. reuteri* RC 14 shows only a feeble activity at low pH, which disappears completely at higher pH., whereas *L. plantarum* BG 112 is quite active especially at low pH. The 2 strains *L. gasseri* CCOS 960 and *L. plantarum* CCOS 893 exhibit a consistent antimicrobial activity at lower pH that is partially maintained at higher pH. Clearly, *L. plantarum* CCOS 893 shows the best, and *L. gasseri* CCOS 960 the second-best performance. It is also worth noticing that the data Table 7a, showing a positive correlation between NAGase production and anti-*C. difficile* activity, confirm this link already reported for other species/strains in the experiments in Tables 1-6. On this basis, these 2 last strains are thus considered useful for being used in a probiotic anti-*C. difficile* or more generally in an anti-diarrhoeal formulation according to the present invention. Co-culture experiments of *C. difficile* with selected *Lactobacillus* test strains (*L. gasseri* and *L. plantarum*) were then carried out.

EXAMPLE 7: SERIES 3 EXPERIMENTS: TEST TRAINS VERSUS STRAIN ESTABLISHED IN THE GASTRO-INTESTINAL TRACT

In order to confirm the above results on a more quantitative basis the inhibition of *C. difficile* by *Lactobacillus* was studied by means of a co-culture technique. Three *Lactobacillus* strains known for their marked activity were investigated against a selection of *C. difficile* isolates in a similar way as in the previous Examples.

TABLE 8

Test and Reference *Lactobacillus* Strains tested in co-culture experiments against 5 *C. difficile* in Serie 3

| Nr. | Species | Working Code | Access Code |
|---|---|---|---|
| L1 | *Lactobacillus gasseri* | KS 120.1 | CNCM I - 3218 |
| L2 | *Lactobacillus gasseri* | CCOS 960 | DSM 32296 |
| L6 | *Lactobacillus plantarum* | CCOS 893 | DSM 32352 |
| C1 | *Clostridium difficile* | 2014 11678 | CCOS 937 |
| C2 | *Clostridium difficile* | 2014 11648 | CCOS 938 |
| C3 | *Clostridium difficile* | 2014 11698 | CCOS 939 |
| C4 | *Clostridium difficile* | 2015 110285 | CCOS 940 |
| C5 | *Clostridium difficile* | Test-strain Lab | CCOS 941 | a. Method:

Media and growth conditions: *Lactobacillus* sp. pre-cultures were inoculated in MRS-broth and incubated over the weekend at 37° C. (without $CO_2$). Out of this broth fresh cultures were subsequently inoculated in MRS-broth and aerobically incubated overnight at 37° C. (without $CO_2$). *C. difficile* pre-cultures were inoculated in CMC under gas flow and incubated anaerobically over the weekend at 37° C. (without CO2). Out of this broth fresh cultures were subsequently inoculated in CMC-broth under gas-flow and incubated overnight at 37° C. (without $CO_2$).

Experimental procedure: The overnight cultures of the *Lactobacillus* strains were diluted to a McFarland standard 4 with MRS broth. The overnight cultures of the *C. difficile* strains were diluted in a 1:100 ratio in CMC. Co-cultures were made by inoculating 3 ml of the diluted *C. difficile* strains with 600 mcl of the *Lactobacillus* strain suspension diluted to McFarland 4 in small Pyrex-tubes (with air-tight locked screw cap). In that way co-cultures resulted with a CMC-MRS ratio of 5:1. For the growth control of the pathogens 600 µl MRS broth were added to a diluted *C. difficile* culture and carried along in the incubation. At time of mixing, *Lactobacillus* outnumber *C. difficile* by about 2 powers of 10. Shortly after the assemblage the first test-sample was withdrawn (t=0 h) and the co-cultures were incubated for 48 h, whereby at any one time additional samples were withdrawn after 4 h, 8 h, 24 h and 48 h. At each sample taking 100 µl of the co-cultures were pipetted in 900 microliter NaCl-solution and out of it a dilution series of 1:10, 1:100 and 1:1000 was made. Subsequently, out of each dilution 10 microliter were pipetted onto a sheep blood agar plate and evenly smoothed over the same. These plates were finally incubated for 2 d and the respective colonies forming unit (cfu) counted. As the *C. difficile* colonies and those of the *Lactobacillus* are morphologically different it was feasible to distinguish on the same plate. *C. difficile* colonies were assessed quantitatively, those of the *Lactobacillus* semi-quantitatively. The media used as well as the co-culture medium were such as to guarantee the growth of both *Lactobacillus* and *C. difficile*.

The average values measured were as follows:
CMC not inoculated: 7
MRS not inoculated: 6.5
Mixed Growth Medium
Precultures *Lactobacillus*: 4
Precultures *C. difficile*: 6

| pH | Co-culture medium | *C. difficile*-only in medium |
|---|---|---|
| t = 0 h | 6.5 | 7 |
| t = 24 h | 5 | 6 |
| t = 48 h | 5 | 6 | b. Results

TABLE 8a

In a first experiment *Lactobacillus* L1 and L2 were tested against each one of the reference *C. difficile* strains C1 to C5. The raw data are shown in detail for e.g. *C. difficile* C3

| Point in time | Dilution | Control | L1 | | L2 | |
|---|---|---|---|---|---|---|
| t = 0 h | 1:10 | 123 | 91 | +++ | 42 | ++ |
| | 1:100 | 13 | 13 | ++ | 7 | + |
| | 1:1000 | 0 | 0 | + | 0 | +/− |
| t = 4 h | 1:10 | nc | 200* | +++ | 150 | +++ |
| | 1:100 | 145 | 37 | +++ | 9 | ++ |
| | 1:1000 | 18 | 4 | ++ | 0 | + |
| t = 8 h | 1:10 | nc | nc | +++ | nc | +++ |
| | 1:100 | nc | 86 | +++ | 84 | ++ |
| | 1:1000 | 400* | 16 | ++ | 10 | + |
| t = 24 h | 1:10 | nc | nc | +++ | nc | +++ |
| | 1:100 | nc | 148* | ++ | 105 | ++ |
| | 1:1000 | nc | 356* | ++ | 7 | + |
| t = 48 h | 1:10 | nc | 25 | +++ | 29 | +++ |
| | 1:100 | nc | 1 | ++ | 0 | ++ |
| | 1:1000 | 59 | 0 | ++ | 0 | + |

Quantitation *C. difficile*
Number: cfus on plate
*number extrapolated
nc: not countable (>>100 cfus)
Estimation *Lactobacillus*
+++: bacterial lawn on plate
++: bacterial lawn with single colonies delimitable
+: >500 cfu
+/−: 100-500 cfus In order to represent graphically the data *C. difficile* concentrations were processed as follows:
Control concentrations: in rounded-up cfus on a logarithmic scale
Co-cultures: as a rounded-up ratio between the cfus in the presence of *Lactobacillus* and the control cfus at the same point in time The corresponding Table 8b for the same *C. difficile* C3 looks then as follows TABLE 8b Inhibition of *C. difficile* C3 through L1 and L2. This data is shown graphically in FIG. 2.

| Hours | C3 (cfus) | (C3 + L1)/C3 | (C3 + L2)/C3 |
|---|---|---|---|
| 0 | 1.E+05 | 1.E+00 | 5.E−01 |
| 4 | 1.E+06 | 3.E−01 | 6.E−02 |
| 8 | 4.E+07 | 4.E−02 | 3.E−02 |
| 24 | 4.E+07 | 6.E−02 | 2.E−02 |
| 48 | 6.E+06 | 4.E−03 | 5.E−03 |

From the diagram in FIG. 2, it can be concluded that, the concentration of C3 on the average increases over time, indicating that the medium is suitable for the vitality and growth of *C. difficile* and that there is therefore no medium-related bias. In the following, the results for the other 4 *C. difficile* strains are shown in compact form.

Table 8c (left) Inhibition of *C. difficile* C1 through L1 and L2. These data are reported in the graphic of FIG. 3 and Table 8d (right): Inhibition of *C. difficile* C2 by Lactobacilli L1 and L2. These data are reported in the graphic of FIG. 4.

| Hours | C1 | (C1 + L1)/C1 | (C1 + L2)/C1 |
|---|---|---|---|
| 0 | 1.E+05 | 2.E−02 | 7.E−01 |
| 4 | 8.E+06 | 6.E−01 | 4.E−01 |
| 8 | 5.E+07 | 3.E−01 | 1.E−01 |
| 24 | 6.E+06 | 2.E−01 | 2.E−01 |
| 48 | 5.E+06 | 4.E−02 | 4.E−02 |

| Hours | C2 | (C2 + L1)/C2 | (C2 + L2)/C2 |
|---|---|---|---|
| 0 | 2.E+03 | 1.E+00 | 5.E−04 |
| 4 | 8.E+04 | 1.E−01 | 5.E−02 |
| 8 | 1.E+07 | 5.E−03 | 8.E−08 |
| 24 | 3.E+07 | 1.E−03 | 3.E−08 |
| 48 | 3.E+06 | 4.E−07 | 4.E−07 |

The two *L. gasseri* achieve a reduction of almost 2 logs in the viability of *C. difficile* C1 after 48 h. This shows that the NAGase-producing strains L1 (*Lactobacillus gasseri* KS 120.1, CNCM I-3218) and L2 (*Lactobacillus gasseri* CCOS 960, deposit number DSM 32296) are able to efficiently kill *C. difficile* C2.

Table 8e (left): Inhibition of *C. difficile* C4 by *Lactobacillus* L1 and L2. These data are reported in the graphic of FIG. 5. Table 8f (right): Inhibition of *C. difficile* C5 by *Lactobacillus* L1 and L2. These data are reported in the graphic of FIG. 6.

| | C4 | (C4 + L1)/C4 | (C4 + L2)/C4 |
|---|---|---|---|
| 0 | 1.E+05 | 2.E+00 | 1.E+00 |
| 4 | 1.E+07 | 2.E−01 | 2.E−01 |
| 8 | 5.E+07 | 2.E−01 | 4.E−01 |
| 24 | 6.E+06 | 4.E−01 | 1.E+00 |
| 48 | 2.E+06 | 1.E−03 | 5.E−03 |

| Hours | C5 | (C5 + L1)/C5 | (C5 + L2)/C5 |
|---|---|---|---|
| 0 | 2.20E+05 | 6.E−01 | 9.E−01 |
| 4 | 1.09E+07 | 2.E−01 | 3.E−01 |
| 8 | 5.00E+07 | 2.E−01 | 2.E−01 |
| 24 | 7.20E+06 | 9.E−01 | 8.E−01 |
| 48 | 1.17E+06 | 9.E−07 | 3.E−02 |

*L. gasseri* KS 120.1 shows the best activity of the 3 *Lactobacillus* with a reduction of 3 log after 48 h.

c. Conclusion

The *C. difficile* Test-strain Lab CCOS 941 (C5) is a strain sensitive to specific probiotics: after 48 h *L. gasseri* KS 120.1 eliminates the pathogen in the co-culture. L1 (*L. gasseri* KS 120.1, CNCM I-3218) and L2 (*L. gasseri* CCOS 960, deposit number DSM 32296) show activity against *C. difficile*. In order to gather more information, it was then decided to add to the test another relevant species investigated before for its reported consistent activity against *C. difficile*, *L. plantarum*.

EXAMPLE 8: EXPERIMENTS SERIES 4

The same methods and experimental procedures were used as described in Example 7.

TABLE 9 strains involved in Experiments Series 4

| Codes | Species | Working Code | Access Code |
|---|---|---|---|
| L6 | *Lactobacillus plantarum* | CCOS 893 | DSM 32352 |
| C1 | *Clostridium difficile* | 2014 11678 | CCOS 937 |
| C2 | *Clostridium difficile* | 2014 11648 | CCOS 938 |
| C3 | *Clostridium difficile* | 2014 11698 | CCOS 939 |
| C4 | *Clostridium difficile* | 2015 110285 | CCOS 940 |
| C5 | *Clostridium difficile* | Test-strain Lab | CCOS 941 | a. Results Series 4: Tables 9a-e and FIGS. 1-5

Tables 9a-e regarding inhibition of *C. difficile* C1-C5 by *L. plantarum* CCOS 893 are reported hereunder (The same data are reported in the Graphics in FIGS. 7A-7E). The absolute concentration of the *C. difficile* alone (cfu) as well as the relative reduction of the concentration of *C. difficile* in the presence of a *Lactobacillus* are shown as a function of time TABLE 9a Inhibition of *C. difficile* C1 by *L. plantarum* CCOS 893

| time h | C1 | (C1 + CCOS 893)/C1 |
|---|---|---|
| 0 | 5.E+04 | 3.E+00 |
| 4 | 2.E+06 | 2.E−01 |
| 8 | 1.E+07 | 1.E−01 |
| 24 | 2.E+06 | 1.E−01 |
| 48 | 1.E+06 | 1.E−02 |

TABLE 9b

Inhibition of *C. difficile* C2 by *L. plantarum* CCOS 893

| time h | C2 | (C2 + CCOS 893)/C2 |
|---|---|---|
| 0 | 6.E+04 | 8.E−01 |
| 4 | 7.E+05 | 1.E+00 |
| 8 | 1.E+06 | 8.E−01 |
| 24 | 2.E+06 | 2.E−01 |
| 48 | 4.E+06 | 3.E−02 |

TABLE 9c

Inhibition of *C. difficile* C3 by *L. plantarum* CCOS 893

| time h | C3 | (C3 + CCOS 893)/C3 |
|---|---|---|
| 0 | 3.E+05 | 6.E−01 |
| 4 | 9.E+06 | 8.E−01 |
| 8 | 5.E+07 | 4.E−01 |
| 24 | 1.E+07 | 1.E−02 |
| 48 | 1.E+07 | 9.E−08 |

TABLE 9d

Inhibition of *C. difficile* C4 by *L. plantarum* CCOS 893

| time h | C4 | (C4 + CCOS 893)/C4 |
|---|---|---|
| 0 | 1.E+05 | 2.E+00 |
| 4 | 8.E+06 | 7.E−01 |

TABLE 9d-continued

Inhibition of *C. difficile* C4 by *L. plantarum* CCOS 893

| time h | C4     | (C4 + CCOS 893)/C4 |
|--------|--------|--------------------|
| 8      | 5.E+07 | 2.E−01             |
| 24     | 6.E+06 | 3.E−02             |
| 48     | 4.E+06 | 3.E−07             |

TABLE 9e

Inhibition of *C. difficile* C5 by *L. plantarum* CCOS 893

| time h | C5     | (C5 + CCOS 893)/C5 |
|--------|--------|--------------------|
| 0      | 1.E+05 | 9.E−01             |
| 4      | 1.E+07 | 5.E−01             |
| 8      | 5.E+07 | 2.E−01             |
| 24     | 3.E+06 | 1.E−01             |
| 48     | 1.E+06 | 2.E−02             | b. Conclusion

Against all *C. difficile*, the more resistant C1 and C5 as well as the less resistant C2, C3 and C4, *L. plantarum* CCOS 893 achieves to gradually reduce over time the concentration of all the tested *C. difficile* strains between 2 and 6 logs. This is even better than the results of the strains in Series 3. The results of the investigations show that a correlation between the production of NAGase and the antimicrobial activity against *C. difficile* can be assessed for different strains of probiotic species comprising: *L. gasseri*, *L. plantarum* and *L. crispatus*. This could be verified in spot and/or co-culture experiments even at pH= or >5.0.

EXAMPLE 9: GENOME SEQUENCES OF *LACTOBACILLUS GASSERI* CCOS 960, *LACTOBACILLUS PLANTARUM* CCOS 893, *LACTOBACILLUS CRISPATUS* CCOS 961 AND *LACTOBACILLUS JENSENII* CCOS 962

Whole genomic high molecular weight DNA extraction of each strain was grown in 10 ml of liquid MRS (Man, Rogosa and Sharpe medium) at 37° C. without shaking in a 50 ml conical tubes for 48 h (cell density $1\times10^9$ cells/ml). A 1 ml aliquot was centrifuged for 5 min at 8,000×g. The supernatant was removed and resuspended in 500 µl of 5M LiCl. The cells were placed on ice and vigorously vortexed every 2 minutes for 15 minutes. The cells were then centrifuged at 8,000×g for 5 min. A total of 500 µl of saturated phenol was added to the cell pellet, vortexed and centrifuged at 8,000×g. The cell pellet was washed with PBS and resuspended in 500 µl of PBS. Whole genomic DNA was extracted using MasterPure™ DNA Purification Kit (Epicentre, Cat. No. MCD85201). A total of 10 µg of DNA was used to construct a large insert (5-20 kb) SMRTbell™ sequencing library that was sequenced on a PacificBiosciences RSII instruments according to the manufacturer recommendations at the Institute for Genome Sciences, University of Maryland School of Medicine, Baltimore, MD USA. The genomes were assembled using the MinHash Alignment Process (MHAP) (Berlin K, Koren S, Chin C-S, Drake J P, Landolin J M, Phillippy A M. "*Assembling large genomes with single-molecule sequencing and locality-sensitive hashing*" Nat Biotechnol. 2015; 33:623-630 The estimated genome sizes, number of contigs, gene and coding sequence counts are shown in Table 10a. Annotation was generated using the Prodigal annotation pipeline (Hyatt D, Chen G-L, LoCascio P F, Land M L, Larimer F W, Hauser L J. "*Prodigal: prokaryotic gene recognition and translation initiation site identification*" BMC Bioinformatics. 2010; 11:119).

Glucosaminidase in these *Lactobacillus* strains are mostly mannosyl-glycoprotein endo-beta-N-acetylglucosaminidase and muramidase (cell-wall hydrolases). This large family of protein is involved in peptidoglycan catabolic processes. Of note is the identification of homologues to AcmA, a modular autolysin, consisting of a N-terminal Nacetylglucosaminidase and C-terminal LysM domains (peptidoglycan binding domain). The enzyme has a muramidase activity. Other muramidases were identified (Table 10a).

TABLE 10a beta-D-N-acetylglucosaminidase and further PGHs encoded on the genomes of *Lactobacillus gasseri* CCOS 960, *Lactobacillus plantarum* CCOS 893, *Lactobacillus crispatus* CCOS 961.

| Strain | Gene name | SEQ ID NO nucleotide | SEQ ID NO amino acid | Annotation/function |
|---|---|---|---|---|
| *L. gasseri* CCOS 960 | LG_M960_06890 | 2 | 90 | Mannosyl-glycoprotein endo-beta-N-acetylglucosaminidase |
|  | LG_M960_00270 | 1 | 89 | Mannosyl-glycoprotein endo-beta-N-acetylglucosaminidase |
|  | LG_M960_22860 | 3 | 91 | Muramidase-2 |
|  | LG_M960_22870 | 4 | 92 | Muramidase (Glucosaminidase Superfamily) |
| *L. plantarum* CCOS 893 | Lplant_09370 | 5 | 93 | Mannosyl-glycoprotein endo-beta-N-acetylglucosaminidase |
|  | Lplant_29740 | 6 | 94 | Mannosyl-glycoprotein endo-beta-N acetylglucosaminidase |
|  | Lplant_14230 | 7 | 95 | Mannosyl-glycoprotein endo-beta-N acetylglucosaminidase |
|  | Lplant_20460 | 8 | 96 | mannosyl-glycoprotein endo-beta-N acetylglucosaminidase |
|  | Lplant_20470 | 9 | 97 | mannosyl-glycoprotein endo-beta-N acetylglucosaminidase |
| *L. crispatus* CCOS 961 | LC119_17710 | 11 | 99 | Mannosyl-glycoprotein endo-beta-N-acetylglucosaminidase |
|  | LC119_09570 | 10 | 98 | Bacterial surface layer protein acmA |

Using the BAGEL3 Algorithm (de Jong A, van Heel A J, Kok J, Kuipers O P. "*BAGEL2: mining for bacteriocins in genomic data*" Nucleic Acids Res. 2010; 38:W647-51) and BLAST these bacteriocin biosynthetic gene clusters were identified encoded in the genomes of *L. gasseri* CCOS 960 and *L. crispatus* CCOS 961 (Table 10b). No bacteriocins were found encoded in the genome of *L. plantarum* CCOS 893.

TABLE 10b

| Strain | Gene name | SEQ ID NO | Annotation |
|---|---|---|---|
| *L. gasseri* CCOS 960 | LG_M960_18060 | 12 | Pediocin [1e-09] |
|  | LG_M960_18120 | 13 | Acidocin_LF221B(GassericinK7B) [3e-27] |
|  |  |  | Acidocin_LF221B(GassericinK7B) [1e-11] |
|  | LG_M960_18130 | 14 | Gassericin_T [3e-40] |
|  | LG_M960_19200 | 15 | Bacteriocin_helveticin J [5e-60] |
| *L. crispatus* CCOS 961 | LC119_03500 | 16 | enterolysin_A [9e-22] |
|  | LC119_04790 | 17 | Bacteriocin_helveticin_J [3e-171] |
|  | LC119_12230 | 18 | Helveticin-J [3e-124] |
|  | LC119_14630 | 19 | bacteriocin_LS2chaina [1e-09] |
|  | LC119_14940 | 20 | Penocin_A [1e-08] |
|  | LC119_15020 | 21 | Penocin_A [2e-12] |
|  | LC119_27080 | 22 | enterolysin_A [1e-59] |
|  | LC119_27330 | 23 | enterolysin_A [3e-94] |

Table 10c. Peptidoglycan hydrolases (PGH) encoded on the genome of *Lactobacillus jensenii* CCOS 962

| locus tag | SEQ ID NO nucleotide | SEQ ID NO amino acid | Annotation | Site of action |
|---|---|---|---|---|
| CCOS-96249 00293 | 84 | 147 | Urocanate reductase | Glycan-Peptide bond |
| CCOS-96249 01072 | 85 | 148 | Exo-glucosaminidase LytG | Glycan-Peptide bond |
| CCOS-96249 01421 | 86 | 149 | Penicillin-binding protein 1A | Glycan-Peptide bond |
| CCOS-96249 01513 | 87 | 150 | C protein alpha-antigen | Glycan-Peptide bond |
| CCOS-96249 00553 | 88 | 151 | Exo-qlucosaminidase LvtG | Glycan strand |

Genomic analysis thus confirms that all 4 new *Lactobacillus* with clear inhibitory activity against *C. difficile* possess genes for different PGHs (mainly of the type Mannosyl-glycoprotein endo-beta-N-acetylglucosaminidase, but also e.g. muramidases or bacterial surface layer protein AcmA) that enable the carrier bacterium to attack, modify and/or disrupt bacterial cell walls. For instance, *L. plantarum* CCOS 893 is endowed with as much as 5 such genes.

On the side of the bacteriocins mainly such belonging to Class II were found (e.g. Gassericin, Helveticin, Penocin a.s.o.) with *L. crispatus* CCOS 961 having a total of 10 of the corresponding genes.

These data as presented above make it plausible that in these probiotic *Lactobacillus* the presence of PGHs targeted against the typical cell wall of bacterial pathogens, i.e. exhibiting NAGases or Muramidases a.s.o., possibly associated with Class II bacteriocins, enables these probiotic strains to exert an anti-microbial activity against *C. difficile* Of course, the presence of the genes does not per se warrant the production of the PGHs, for our probiotic *Lactobacillus* this was indeed confirmed by in vitro enzyme tests.

Of note, *L. plantarum* CCOS 893 does not possess bacteriocins genes (and therefore no bacteriocin activity) even though such are known for this species and have been described since the 1990's (e.g. plantaricins). Thus, this example proves that PGHs may not only contribute to the anti-microbial activity of *Lactococcus* and *Lactobacillus*, as discussed above, but even, as in this particular case of *L. plantarum* CCOS 893, constitute the main if not only component for the pronounced anti-microbial activity against *C. difficile* (as lactic acid alone or hydrogen peroxide are not sufficient to generally inhibit *C. difficile*). This proves that PGHs are a so far unrecognized, independent class of anti-microbial peptides of probiotic bacteria, a discovery of significant practical value.

EXAMPLE 10: COMPARATIVE ACTIVITY OF SELECTED BIFIDOBACTERIA AGAINST *C. DIFFICILE* IN SPOT EXPERIMENTS AND CORRELATION WITH PGHS

*Bifidobacterium longum* subsp. *longum* strain CCOS 974 is a gram-positive, obligate anaerobic, non-motile and non-spore forming bacterium, belonging to the *Bifidobacterium* genus, phylum Actinobacteria. Bifidobacteria are strict anaerobic microorganisms with a fermentative metabolism, particularly adapted to gut environments (Sun, Z. et al. "Comparative genomic analysis of 45 type strains of the genus *Bifidobacterium*: a snapshot of its genetic diversity and evolution" *PLoS One* 10(2), e0117912, 2015).

In the review by Christine S M Lau and Ronald S Chamberlain ("Probiotics are effective at preventing *Clostridium difficile*-associated diarrhea: a systematic review and meta-analysis" *Int J Gen Med.* 2016; 9: 27-37. doi: 10.2147/IJGM.S98280 26 RCT) involving 7,957 patients were analysed and some effect in CDAD found. None of these studies showed, however any positive clinical effect related to Bifidobacteria on CDAD.

There are only scarce papers in the literature dealing with the antimicrobial activity of Bifidobacteria against *C. difficile*. One of the reasons, is that bifidobacteria do not produce bacteriocins as do *Lactobacillus*. Lacking these substances, which are potent weapons against similar competing species as well as against pathogens, the Bifidobacteria were up to now not deemed as performant as the *Lactobacillus* w.r.t. antimicrobial activity.

Even at the laboratory level no successful results referring to an inhibition of *C. difficile* have been so far reported. For instance, in the systematic investigation reported by P. Hutt et al. (*Journal of Applied Microbiology* 100 (2006) 1324-1332, "Antagonistic activity of probiotic lactobacilli and bifidobacteria against entero- and uropathogens") 5 best-in-class *Lactobacillus* and 2 such Bifidobacteria were systematically tested for their anti-microbial activity against the leading uro- and enteropathogens. With respect to *C. difficile* the result for the best-in-class Bifidobacteria (*Bifidobacterium lactis* Bb12, *Bifidobacterium longum* 46) was clear: "No efficient antagonist against *C. difficile* was found". Nevertheless, the inventors attempted to investigate the possible use of bifidobacteria against enteropathogens in particular *Clostridium difficile*.

a. Method

In a first step, detection of NAGase activity of selected Bifidobacteria was investigated by means of the APIZym test kit of Biomérieux as summarized in Table 11.a. Bifidobacteria were first grown anaerobically in liquid MRS and then incubated under anaerobic conditions for 24 h at 37° C. APIZYM tests were prepared and analysed according the manufacturers instructions. Bifidobacteria were grown on MRS medium supplemented with cystein (0.5 g/l) under anaerobe conditions. For the test, a fresh overnight culture grown was re-suspended in sterile physiological saline solution at an optical density corresponding to a McFarland standard of 5 to 6. This solution was dispensed into the wells of the strips of the test system. The tests strips were incubated at 37° C. for 20 hours. After addition of the test reagents the strips were exposed to light and then read visually and interpreted according to the test instructions resulting as a value from 0 (negative) to 5 (strong positive) for each test. Each test was repeated at least twice.

TABLE 11a

List of test and reference Bifidobacteria and their NAGase score

| Bifidobacterium species | Strain code | Origin | Commercial resp. Deposit code | NAGase score |
|---|---|---|---|---|
| B. breve | CCOS 586 | Infant faeces | CCOS 586 | 4 |
| B. bifidum | CCOS 571 | Infant faeces | CCOS 571 | 5 |
| B. lactis BB12 | CCOS 973 | Probiotic Isolate | DSM 15954 | 1 |
| B. longum | CCOS 974 | Probiotic isolate | CCOS 974 | 4 | b. Conclusion:

From these experiments we infer that Bifidobacteria are able, like *Lactobacillus* spp., to produce, depending on the species and the strain, different amounts of N-acetylglucosaminidase (or glycosidase). For instance *B. breve* CCOS 586 and *B. bifidum* CCOS 571 produce high amounts (>=40 nmol), whereas the *B. longum* CCOS 974 produces about 30 mmol and BB12 only 10 nmol of this particular PGH.

EXAMPLE 11: SERIES 3 EXPERIMENTS: INHIBITION OF *C. DIFFICILE* BY SELECTED BIFIDOBACTERIA

TABLE 11c

List of tested *C. difficile* strains

| Strain code | Origin | Access # |
|---|---|---|
| CCOS 871 | Type strain | LMG 21717 |
| CCOS 876 | Clinical isolate | CCOS 876, public collection |
| CCOS 877 | Clinical isolate | CCOS 877, public collection |
| CCOS 937 | Clinical isolate | CCOS 937, public collection |
| CCOS 938 | Clinical isolate | CCOS 938, public collection |
| CCOS 939 | Clinical isolate | CCOS 939, public collection |
| CCOS 940 | Clinical isolate | CCOS 940, public collection |
| CCOS 941 | Clinical isolate | CCOS 941, public collection |
| CCOS 957 | Clinical isolate | CCOS 957, public collection |
| CCOS 958 | Clinical isolate | CCOS 958, public collection |

TABLE 11.d

Number of times a *Bifidobacterium* strain showed inhibitory activity aganst a *C. difficile* strain. The number in parenthesis refer to the number of experiments. The table is vertically sorted according to the number of *C. difficile* strains inhibited by a certain *Bifidobacterium*

| | | *Clostridium difficile* strains | | | | | | | | | | |
|---|---|---|---|---|---|---|---|---|---|---|---|---|
| Bifido-bacteria | Strain code | CCOS 871 | CCOS 876 | CCOS 877 | CCOS 937 | CCOS 938 | CCOS 939 | CCOS 940 | CCOS 941 | CCOS 957 | CCOS 958 | Number of inhibited *C. difficile* strains |
| *B. bifidum* | CCOS 571 | 0 (2) | 3 (3) | 1 (3) | 1 (7) | 0 (4) | 0 (1) | 1 (2) | 1 (6) | 2 (4) | 1 (4) | 7 |
| *B. longum* | CCOS 974 | 0 (2) | 1 (2) | 0 (2) | 5 (6) | 3 (3) | 1 (1) | 0 (2) | 3 (5) | 1 (3) | 1 (3) | 7 |
| *B. breve* | CCOS 586 | 0 (2) | 0 (3) | 0 (3) | 1 (7) | 0 (4) | 0 (1) | 0 (2) | 0 (6) | 1 (4) | 1 (4) | 3 |
| *B. lactis* | BB12 | 0 (0) | 0 (0) | 0 (0) | 0 (3) | 0 (3) | 0 (1) | 0 (0) | 1 (3) | 0 (0) | 0 (0) | 1 |
| Number of Bifidobacteria inhibiting a strain certain *C. difficile* | | 0 | 2 | 1 | 3 | 1 | 1 | 1 | 3 | 3 | 3 | |

The *Clostridium difficile* strains are available from the public collection of the Culture Collection of Switzerland CCOS, Einsiedlerstrasse 34, 8820 Wädenswil, Switzerland, www.ccos.ch.

Examples of inhibitory effects out of this experimental series of 3 Bifidobacteria against 2 different *C. difficile* strains are shown in FIG. 8. 1: *B. lactis* BB12, 2: *B. bifidum* CCOS 571, 3: *B. breve* CCOS 586. (−): no zone of inhibition, (+): inhibition detected, (++): strong inhibitory effect. The activity against *C. difficile* strains correlates also for Bifidobacteria with the NAGase activity. The strain *B. longum* CCOS 974, which ranks highest together with *B. bifidum* CCOS 571 in the inhibitory activity, produces a medium level of NAGase. It can be anticipated at this point that the genome of *B. longum* CCOS 974 contains indeed also an N-acetyl-galactosaminidase gene (see below) and that *C. diff.* possesses also a glycan layer containing galactosamin In looking for Bifidobacteria to be used against CDI/CDAD by acting as inhibitors of the pathogen *C. difficile*, strains showing a high production of NAGase, or more generally specific PGHs, are preferred. Suitable candidates are e.g. *B. bifidum* CCOS 571, *B. longum* CCOS 974 and *B. breve* CCOS 586. Also another *B. breve*, CCOS 971, which produces high concentrations (>40 nmol) of NAGase according to the APIZYM test showed strong inhibitory activity against the tested *C. difficile* isolates (data not shown).

EXAMPLE 12: GENOME SEQUENCES OF *BIFIDOBACTERIUM BIFIDUM* CCOS 571, *BIFIDOBACTERIUM LONGUM* CCOS 974 AND *BIFIDOBACTERIUM BREVE* CCOS 586

Whole genomic high molecular weight DNA extraction of each strain was grown in 10 ml of liquid MRS (Man, Rogosa and Sharpe medium) at 37° C. without shaking in a 50 ml conical tubes for 48 h (cell density 1×10$^9$ cells/ml). A 1 ml aliquot was centrifuged for 5 min at 8,000×g. The supernatant was removed and resuspended in 500 µl of 5M LiCl. The cells were placed on ice and vigorously vortexed every 2 minutes for 15 minutes. The cells were then centrifuged at 8,000×g for 5 min. A total of 500 µl of saturated phenol was added to the cell pellet, vortexed and centrifuged at 8,000×g. The cell pellet was washed with PBS and resuspended in 500 µl of PBS. Whole genomic DNA was extracted using MasterPure™ DNA Purification Kit (Epicentre, Cat. No. MCD85201). A total of 10 µg of DNA was used to construct a large insert (5-20 kb) SMRTbell™ sequencing library that was sequenced on a Pacific Biosciences RSII instruments according to the manufacturer recommendations at the Institute for Genome Sciences, University of Maryland School of Medicine, Baltimore, MD USA. The genomes were assembled using the MinHash Alignment Process (MHAP) (Berlin K, Koren S, Chin C-S, Drake J P, Landolin J M, Phillippy A M. Assembling large genomes with single-molecule sequencing and locality-sensitive hashing. Nat Biotechnol. 2015; 33:623-630). The estimated genome sizes, number of contigs, gene and coding sequence counts are shown in Table 12.a. Annotation was generated using the Prodigal annotation pipeline (Hyatt D, Chen G-L, LoCascio P F, Land M L, Larimer F W, Hauser L J. "*Prodigal: prokaryotic gene recognition and translation initiation site identification*" BMC Bioinformatics. 2010; 11:119).

*Bifidobacterium* strains sequenced are not so much rich in glucosaminidase, at least in enzymes with similarities to those carried by *Lactobacillus* spp. Interestingly, these strains carry galactosaminidases (Table 12.a). *B. bifidum* CCOS 571 furthermore has a large panoply of glycoside hydrolases compared to the other two species/strains.

TABLE 12a

N-acetylglucosaminidases and N-acetylgalactosaminidases encoded on the genomes of *Bifidobacterium bifidum* CCOS 571, *Bifidobacterium longum* CCOS 974 and *Bifidobacterium bifidum* CCOS 586

| Strain | Gene name | SEQ ID NO nucleotide | SEQ ID NO amino acid | Annotation/function |
|---|---|---|---|---|
| *B. bifidum* CCOS 571 | b_bifidum_ccos_571_07770 | 24 | 100 | beta-N-acetylhexosaminidase |

TABLE 12a-continued

N-acetylglucosaminidases and N-acetylgalactosaminidases encoded on the genomes of *Bifidobacterium bifidum* CCOS 571, *Bifidobacterium longum* CCOS 974 and *Bifidobacterium bifidum* CCOS 586

| Strain | Gene name | | | Annotation/function |
|---|---|---|---|---|
| | b_bifidum_ccos_571_09950 | 25 | 101 | endo-alpha-N acetylgalactosaminidase |
| | b_bifidum_ccos_571_10670 | 26 | 102 | hexosaminidase |
| | b_bifidum_ccos_571_10680 | 27 | 103 | hexosaminidase |
| | b_bifidum_ccos_571_10690 | 28 | 104 | hexosaminidase |
| | b_bifidum_ccos_571_12320 | 29 | 105 | endo-alpha-N acetylgalactosaminidase |
| | b_bifidum_ccos_571_14230 | 30 | 106 | Lysozyme M1 (1,4-beta-N acetylmuramidase) |
| | b_bifidum_ccos_571_14480 | 31 | 107 | beta hexosamidase or lacto-N biosidase or beta N acetylglucosamidase |
| | b_bifidum_ccos_571_14630 | 32 | 108 | glycoside hydrolase |
| | b_bifidum_ccos_571_16210 | 33 | 109 | glycoside hydrolase - Endo-alpha-N acetylgalactosaminidase |
| | b_bifidum_ccos_571_16870 | 34 | 110 | Hyaluronoglucosaminidase |
| | b_bifidum_ccos_571_17230 | 35 | 111 | neuraminidase |
| | b_bifidum_ccos_571_17880 | 36 | 112 | hexosaminidase |
| | b_bifidum_ccos_571_18050 | 37 | 113 | Hyaluronoglucosaminidase |
| | b_bifidum_ccos_571_18170 | 38 | 114 | glycoside hydrolase - alpha_N_acetylglucosaminidase |
| | b_bifidum_ccos_571_18860 | 39 | 115 | hexosaminidase |
| *B. breve* CCOS 586 | | | | |
| | b_breve_ccos_586_09940 | 43 | 119 | Endo-alpha-N acetylgalactosaminidase glycoside hydrolase |
| | b_breve_ccos_586_21940 | 46 | 122 | glycoside hydrolase |
| | b_breve_ccos_586_07460 | 42 | 118 | mannosyl-glycoprotein endo beta-N-acetylglucosaminidase |
| | b_breve_ccos_586_12590 | 44 | 120 | beta-N-acetylhexosaminidase |
| | b_breve_ccos_586_19890 | 45 | 121 | neuraminidase |
| | b_breve_ccos_586_02180 | 40 | 116 | beta hexosamidase or lacto-N biosidase or beta N acetylglucosamidase |
| | b_breve_ccos_586_02560 | 41 | 117 | N-acetylmuramoyl-L-alanine amidase |
| | b_breve_ccos_586_23580 | 47 | 123 | Lyzozyme M1 (1,4-beta-N acetylmuramidase) |
| Strain | Gene name | | | Annotation/function |
| *B. longum* CCOS 974 | | | | |
| | Blong_03460 | 48 | 124 | beta-galactosidase/beta glucuronidase |
| | Blong_06280 | 50 | 126 | Endo-alpha-N acetylgalactosaminidase glycoside hydrolase |
| | Blong_03970 | 49 | 125 | glycoside hydrolase |
| | Blong_09530 | 51 | 127 | glycoside hydrolase |
| | Blong_17510 | 53 | 129 | glycoside hydrolase |
| | Blong_12820 | 52 | 128 | glycoside hydrolase |

In the context of the present invention, it was investigated whether bifidobacteria, which were active against *Clostridium difficile*, would produce PGH or equivalent substances. As described above, it was indeed found that the investigated Bifidobacteria are capable of producing a few N-acetyl-beta-glucosaminidase but more often e.g. endo-alpha-N-acetylgalactosaminidases, beta-hexosaminidases and glycoside hydrolases. *Bifidobacterium bifidum* CCOS 571 and *B. breve* CCOS 586 strains as described herein produce significant signals of amounts of N-acetyl-glucosaminidase in the enzymatic testing, that is they have at the phenotypic level a proven equivalent NAGase activity. In conclusion, a clear correlation was found between the in vitro anti-*C. difficile* activity and the NAGase enzymatic activity in vitro (with the presence of PGH-genes in the genome constituting the final proof).

In conclusion it is the production specific PGHs the main reason for the up-to now unexplained antimicrobial activity of the bifidobacteria and for the differences in anti-microbial activity among *Bifidobacterium* strains themselves.

Considering more generally the structure of cell walls in the Gram-positive bacteria a single lipid membrane is present, surrounded by a cell wall composed of a thick layer of peptidoglycan and lipoteichoic acid, which is anchored to the cell membrane by diacylglycerol. Gram-negative bacteria exhibit additionally an outer membrane carrying lipopolysaccharides. Cell walls of mycobacteria consist of thin layers of peptidoglycan and arabinogalactan, and, as the most outer layer, a thick layer of mycolic acids. In summary, without wishing to be bound by theory, it can be considered that the probiotic strains of the present invention, able to produce the different peptidoglycan hydrolases, possess a weapon with which they can attack and disrupt basically the cell wall of every pathogen as it contains a peptidoglycan layer.

For the therapeutic practice this means that the use of such PGH-producing probiotics as described in this invention is justified whenever the cell wall of a pathogenic microorganism of any of the 3 types: Gram-positives, Gram-negatives and mycobacteria is to be tackled in a probio-therapeutic application. Besides lactic acid (D and L), hydrogen peroxide, bacteriocins and other up to now unknown metabolites, the PGHs are an important, basically novel agent for this use, of selected probiotic bacteria in their fight for nutrition and against pathogens. PGHs of viruses, phages or multicellular organisms have been described including their antimicrobial action, but not of probiotic strains.

The scope of the present invention includes not only nosocomial CDI/CDAD, but also other types of infectious diarrhoeal disorders. Besides *C. difficile*, the most important causative pathogens for such nosocomial diarrhoeas, there are also: entero-pathogenic *E. coli* (EPEC), diarrhoeagenic *Salmonella typhimurium*, *Shigella flexneri* or *sonnei*, *Campylobacter jejuni*, *Listeria monocytogenes* and *Clostridium perfringens*.

EXAMPLE 13: SELECTED REPRESENTATIVES OF PATHOGEN SPECIES TESTED WITHIN SPOT EXPERIMENTS WITH RESPECT TO THEIR INHIBITION BY THE PROBIOTIC STRAINS OF THE PRESENT INVENTION a. Method All cultures were passaged 2 times under respective optimal growth conditions prior to the test. All suspensions were prepared in sterile peptone-salt solution (0.1% peptone, 0.9% NaCl). A suspension of each pathogen, corresponding to a McFarland Standard of 0.5 was spread on the surface of Muller-Hinton agar plates. On these plates, 10 μl (corresponding to a McFarland standard of 4 to 5) of each probiotic strain was spotted. After drying, the agar plates were incubated for 24 hours and the zones of inhibition were valued visually.)

b. Results

TABLE 13

| Species | Strain code | L. jensenii KS 119.1 | L. gasseri CCOS 960 | L. crispatus CCOS 961 | L. lactis CCOS 949 | L. plantar. CCOS 893 | L. paracasei CCOS 1201 | L. fermentum CCOS 1030 | L. rhamnosus CCOS 965 |
|---|---|---|---|---|---|---|---|---|---|
| Campylob. jejuni | CCOS 1192 | (+) | + | (+) | ++ | ++ | + | (+) | + |
| Salmonella enterica | CCOS 505 | ++ | + | ++ | + | (+) | + | − | ++ |
| Shigella flexneri | CCOS 471 | + | − | ++ | + | + | ++ | − | ++ |
| Listeria monocytog. | CCOS 468 | (+) | ++ | + | ++ | (+) | + | ++ | − |
| Escherichia coli | CCOS 492 | + | + | ++ | + | ++ | ++ | (+) | ++ |
| Staph. aureus | CCOS 666 | ++ | ++ | − | ++ | + | + | ++ | − |

Legend:
(−): no inhibition,
(+): slight inhibition,
+: inhibition:
++: strong inhibition c. Conclusion Against the most common pathogens involved in infectious diarrhoea the probiotic strains found active against *C. difficile* show, over a row of the above matrix, a medium to good activity against these pathogens.

Combining a strain of *L. lactis* (e.g. *L. lactis* CCOS 949) which produces the bacteriocins nisin and lactococcin, with other probiotic strains as e.g. *L. gasseri* CCOS 960, *L. plantarum* CCOS 893 or *B. breve* 571 or 971, which are strong producers of glycosidases, would allow to syergistically potentiate the antipathogen activity against *C. diff*.

A multi-strain formulation containing *Lactococcus lactis* 949 and 1 or more of *Lactobacillus plantarum* CCOS 893, *Lactobacillus gasseri* CCOS 960, *Lactobacillus jensenii* KS 119.1, *Lactobacillus crispatus* CCOS 961, *L. paracasei* CCOS 1205 (identical to CCOS 1201) is able to inhibit the most common pathogens causing infectious diarrhoeas comprising, but not limited to those caused by entero-pathogenic *E. coli*, diarrhoeagenic *Salmonella enterica*, *Shigella flexneri*, *Campylobacter jejuni*, and *Clostridium perfringens*. A multi-strain formulation in the above sense is thus suitable for the prevention and treatment of general diarrhoeal diseases of bacterial origin.

EXAMPLE 14: THE *LACTOBACILLUS CASEI* GROUP (LCG)

The *Lactobacillus casei* group (LCG) is composed of the closely related *Lactobacillus casei*, *Lactobacillus paracasei*, and *Lactobacillus rhamnosus*.

The following selected PGHs were identified in *L. paracasei* CCOS 1201 (identical to CCOS 1205) and *L. rhamnosus* CCOS 965.

TABLE 14a

Selected PGHs identified in *L. paracasei* CCOS 1201 (1205) and *L. rhamnosus* (CCOS 965)

| Strain | Gene name | SEQ ID NO nucleotide | SEQ ID NO amino acid | Annotation | Site of action |
|---|---|---|---|---|---|
| *L. paracasei* CCOS 1201 (1205) | CCOS-1201-19_00127 | 155 | 161 | N-acetylmuramoyl-L-alanine amidase LytC | Glycan-Peptide bond |
|  | CCOS1201-19_01355 | 156 | 162 | Autolytic lysozyme | Glycan-Peptide bond |
|  | CCOS1201-19_01655 | 157 | 163 | Lysozyme M1 | Glycan strand |
| *L. rhamnosus* CCOS 965 | CCOS-965-19_00255 | 152 | 158 | Sporulation-specific N-acetylmuramoyl-L-alanine amidase | Glycan-Peptide bond |
|  | CCOS-965-19_00690 | 153 | 159 | Exo-glucosaminidase LytG | Glycan strand |
|  | CCOS-965-19_01009 | 154 | 160 | Autolytic lysozyme | Glycan-Peptide strand |

Of *Lactobacillus rhamnosus* GG we already knew, as disclosed above on page 1, that it does not produce NAGase. Therefore, *Lactobacillus casei* Shirota YIT9029 was used as a reference and was compared with members of the LCG.

The production of NAGase by the strains was correlated with the antimicrobial activity against the representative gastro-intestinal pathogen *Clostridium difficile*.

Investigated strains in the tests below:

TABLE 14b

Investigated strains

| Species | Code | Reference or Test |
|---|---|---|
| *L. paracasei* | CCOS 1201 | Test |
| *L. paracasei* Shirota | CCOS 1226 | Reference |
| *L. rhamnosus* | CCOS 967 | Test |
| *L. rhamnosus* | CCOS 965 | Test |
| *L. plantarum* | CCOS 893 | Reference |
| *L. rhamnosus* LGG | CCOS 832 | Reference |

TABLE 14c

Results of the APIZYM test

| *Lactobacillus* Strain | APIZYM Score | | Corresp. nanomoles | | Calculated Conc, (nmol/ul) | |
|---|---|---|---|---|---|---|
|  | 18 h | 24 h | 18 h | 24 h | 18 h | 24 h |
| *L. paracasei* CCOS 1201 | 3 | 5 | 20 | >40 | 0.31 | 0.62 |
| *L. paracasei* CCOS 1243 | 1 | 3 | 5 | 20 | 0.08 | 0.31 |
| *L. rhamnosus* CCOS 967 | 1 | 1 | 5 | 5 | 0.08 | 0.08 |
| *L. rhamnosus* CCOS 965 | 2 | 5 | 10 | >40 | 0.15 | 0.62 |
| *L. plantarum* CCOS 893 | 1 | 3 | 5 | 20 | 0.08 | 0.31 |

The strain *L. plantarum* CCOS 893 described above (see Example 13) confirmed the significant production of NAGase with 0.31 nmol/ul after 24 hour incubation. The Shirota strains also showed a significant production of NAGase at 24 h.

The results confirm that NAGase production, and more generally PGH production, is an important antimicrobial mechanism of probiotic strains. One *rhamnosus* strain, CCOS 967, showed a detectable, but low production of NAGase, whereas the *rhamnosus* strain 965 had a very high production of this enzyme amounting to calculated 0.62 nmol/ul. The test strain *L. paracasei* CCOS 1201 reaches the same high level of calculated 0.62 nmol/ul after 24 h.

Proof of this correlation was provided by the experimental assessment of antimicrobial activity. To this end, the same strains underwent the same inhibition experiments against *Clostridium difficile* strains as described above.

a. Method

The pH of the growth plate was adjusted to pH 5 with a phosphate buffer to limit the effect of lactic acid on inhibition.

b. Results

TABLE 14d

Inhibition of *C. difficile*

| Genus | Species | | 937 | 940 | 941 | 948 |
|---|---|---|---|---|---|---|
| *Lactobacillus* | *paracasei* | 1201 | +++ | + | ++ | ++ |
| *Lactobacillus* | *paracasei* Shirota | 1243 | ++ | ++ | ++ | ++ |
| *Lactobacillus* | *rhamnosus* | 967 | + | + | ++ | + |
| *Lactobacillus* | *rhamnosus* | 965 | ++ | + | ++ | ++ |
| *Lactobacillus* | *rhamnosus* LGG | 832 | ++ | + | ++ | + |

Legend:
CCOS 937, 940, 941 and 958 are *C. difficile* strains of the CCOS collection.
+++, ++, +, (+), (−) stand for: strong, medium, weak, very weak, missing inhibition.

*L. paracasei* Shirota and CCOS 1201 show about the same pattern of consistent strong to medium inhibition as also *L. rhamnosus* CCOS 965, whereas the CCOS 967 of this species is slightly less active. *L. rhamnosus* LGG exhibits a medium to weak activity depending on the indicator strain.

To more completely reduce the effect of the lactic acid TSB/MRS plates were used with a phosphate buffer at pH=6.2 with the following results.

TABLE 14e

Inhibition of *C. difficile* on TSB/MRS plates

| Genus | Species | CCOS-Nr. | 937 | 941 | 958 |
|---|---|---|---|---|---|
| Lactobacillus | paracasei | 1201 | − | + | + |
| Lactobacillus | paracasei Shirota | 1243 | − | + | (+) |
| Lactobacillus | rhamnosus | 967 | − | + | (+) |
| Lactobacillus | rhamnosus | 965 | + | + | + |
| Lactobacillus | rhamnosus LGG | 832 | − | − | − |

It is concluded that, within the important LCG Group, with respect to the activity against *C. difficile*, *L. paracasei* CCOS 1201 is about equivalent to *L. paracasei* Shirota and the *L. rhamnosus* CCOS 965. *L. rhamnosus* 967 is less active. That the observed activity is not due to undissociated lactic acid is confirmed by the fact that *L. rhamnosus* LGG, which is a huge producer of L-lactic acid (but does not produce NAGase) is about inactive at this pH, where the lactic acid is almost completely dissociated.

EXAMPLE 15: SELECTED REPRESENTATIVES OF PATHOGEN SPECIES IN UROGENITAL INFECTIONS TESTED WITHIN SPOT EXPERIMENTS WITH RESPECT TO THEIR INHIBITION BY THE PROBIOTIC STRAINS OF THE PRESENT INVENTION

The most common vaginal infection among women of childbearing age is bacterial vaginosis (BV). This condition is characterized by replacement of vaginal lactobacilli with predominantly anaerobic microorganisms such as *Gardnerella vaginalis* and *Prevotella, Peptostreptococcus* and *Bacteroides* spp. Historically; *G. vaginalis* is thought to have the leading role in the infection, making the niche suitable for colonization by strict anaerobes that are largely responsible for the clinical symptoms of BV (Swidsinski et al. Am J Obstet Gynecol. 2008 January; 198(1):97.e1-6. Epub 2007 Nov. 19)

Treatment of this condition using recommended antibiotics is often associated with failure and high rates of recurrence. This is due, among other reasons, to the fact that an adherent *Gardnerella vaginalis* biofilm persists on the vaginal epithelium after standard therapy with oral metronidazole.

The present invention shows that the probiotic strains described herein, which produce NAGase or other PGHs, are capable of inhibiting and/or killing *Gardnerella vaginalis*, the leading germ of BV. *Gardnerella* is a genus of Gram-variable-staining (mostly Gram positive) facultative anaerobic bacteria of which *Gardnerella vaginalis* is the only species. The organisms are small non-spore-forming, non-motile coccobacilli.

A number of lactic acid bacteria mostly of vaginal origin or at least of species reported to have been isolated from vagina was selected as test or reference strains. They are summarized in the following table.

TABLE 15a

Strain selection for *Gardnerella vaginalis* inhibition experiments

| Species | Code | Comment |
|---|---|---|
| *L. rhamnosus* | CCOS 965 | Test |
| *L. fermentum* | CCOS 1030 | Test |
| *L. jensenii* | KS 119.1 | Reference |
| *L. jensenii* | CCOS 962 | Test |
| *L. crispatus* | CCOS 961 | Test |
| *L. gasseri* | CCOS 960 | Test |
| *Lactococcus lactis* | CCOS 949 | Test |
| *L. plantarum* | CCOS 893 | Test |
| *Gardnerella vaginalis* Type strain | CCOS 807 | Indicator strain | a. Agar Spot Assay:

20 µl of probiotic culture (McFarland Standard of 6) were spotted onto Muller Hinton Agar, incubated anaerobically at 37° C. for 2 days. 10 ml of liquid soft agar (Tryptic soy broth with 0.7% agar) were inoculated with 200 µL of a suspension of *Gardnerella vaginalis* (McFarland Std. 0.5) and poured on top of the plates with the grown probiotics. After incubation (37° C., anaerob, 2 days) the zones of inhibition (no growth of *G. vaginalis*) around each spot were compared visually.

b. Cross Streaking Assay:

10 µL of probiotic culture were streaked in a horizontal line on BHI agar (supplemented with 10% fetal calf serum, 1% yeast extract, 0.1% maltose, 0.1% glucose), incubated anaerobically at 37° C. for 2 days. 10 µL of a suspension of *Gardnerella vaginalis* (McFarland Std. 0.5) were streaked in a vertical line as close to the probiotic line as possible. After incubation (37° C., anaerob, 2 days) the distances of inhibition (no growth of *G. vaginalis*) between the lines were compared visually.

c. Results:

TABLE 15b inhibition of *C. difficile*

| Species | Code | <<Spot Assay>> | <<Cross-Streaking Assay>> | NAGase activity |
|---|---|---|---|---|
| *L. rhamnosus* | CCOS 965 | + | + | ++ |
| *L. fermentum* | CCOS 1030 | − | + | + |
| *L. jensenii* | KS 119.1 | + | + | + |
| *L. jensenii* | CCOS 962 | − | (+) | + |
| *L. crispatus* | CCOS 961 | − | − | − |
| *L. gasseri* | CCOS 960 | + | + | ++ |
| *Lactococ. lactis* | CCOS 949 | +++ | +++ | ++ |
| *L. plantarum* | CCOS 893 | + | not tested | ++ |

There is a significative correlation between the NAGase activity as measured by APIZYM and the inhibition activity of the strains. Similarly as for *Clostridium difficile* inhibition the strongest activity is exhibited by *Lactococcus lactis* strain CCOS 949.

EXAMPLE 16: STIMULATING PGH PRODUCTION WITH SUGARS

For the probiotic strains showing an inhibitory effect against *C. difficile* and producing NAGase in the enzymatic tests the corresponding genes could be found in their respective genomes. However, the quantity of the produced PGHs and the rate of production can vary according to the environment. In this respect, methods to stimulate the production of the PGHs are helpful in increasing the efficacy of the anti-*C. difficile* formulation. The present inventors found that in most cases the production of NAGase or more generally of the PGHs is stimulated by the presence of the corresponding simple sugar, e.g. N-acetyl-glucosamine (NAG), in the reaction solution.

The following results were obtained with the VITEK 2 System (bioMérieux, France) following the manufacturer's instructions, utilizing cards GP respectively ANC (c.f. Instrument User Manual). Lactic acid bacteria were grown aerobically on MRS medium and Bifidobacteria on MRS medium supplemented with cystein (0.5 g/l) under anaerobic conditions. For the test, a fresh overnight culture grown was resuspended in sterile physiological saline solution at an optical density corresponding to a McFarland standard of 5 to 6. This solution was dispensed into the wells of the strips of the test system. The tests strips were incubated at 37° C. for 20 hours. After addition of the test reagents the strips were exposed to light and then read visually and interpreted according to the test instructions resulting in a value from 0 (negative) to 5 (strong positive) for each test. Each test was repeated at least twice.

TABLE 16

Fermentation of N-acetylglusosamine (NAG) by selected probiotic bacteria suitable for an anti-*C. difficile* multi-strain formulation.

| Strain | Card GP | Card ANC |
|---|---|---|
| *Lactococcus lactis* CCOS 949 | | |
| *L. gasseri* CCOS 960 | neg | pos |
| *L. gasseri* KS 120.1 | neg | n.a. |
| *L. gasseri* 124.3 | pos | pos |
| *L. crispatus* CCOS 961 | pos | pos |
| *L. jensenii* KS 119.1 | pos | pos |
| *L. plantarum* CCOS 893 | pos | pos |
| *B. bifidum* CCOS 571 | n.a. | pos |
| *B. breve* CCOS 586 | n.a. | neg |
| *B. longum* CCOS 974 | n.a | n.a |
| *B. bifidum* CCOS 975 | pos | pos |

Legend: pos: positive, neg: negative, n.a.: not available

Among the candidates for the multi-strain anti-*C. difficile* symbiotic composition there is a majority of probiotic strains fermenting N-acetyl-D-glucosamine. The bacterial PGHs of the probiotic bacteria selectively attack the cell walls of pathogens. The addition of simple N-acetylated sugars like N-acetyl-D-glucosamine, N-acetylgalactosamine, N-acetylhexosamine, and the like was found by the present inventors to boost the production of the corresponding lytic enzymes. Typically, they can be added to the formulation in amounts varying between 0.5 and 5 g per dosage.

EXAMPLE 17: RECOMBONANT PRODUCTION OF β-N-ACETYLGLUCAMINIDASE (NAGASE) IN *E. COLI*

An *E. coli* codon optimised DNA sequence was determined based on the DNA sequence of the β-N-Acetyglucamindase (GenBank Acc. No. AB025100) from *Lactobacillus paracasei* CCOS 1201. This DNA sequence was commercially synthesised and cloned into the *E. coli* expression vector pRSET A (Thermo Fisher) (using the restriction sites BamHI and HindIII and T4-DNA ligase).

This construct (pRsetA_Nagase_lc) was first transformed into *E. coli* TOP10F' (Thermo Fisher), 5 clones were selected and the inserted plasmids were verified by restriction digest and DNA-sequencing and one plasmid was then used to transform the expression strain *E. coli* Lemo21 (DE3) (NEB).

The expression strain was cultivated in LB-broth supplemented with 50 μg/mL ampicillin at 30° C. in an orbital shaker (120 rpm). After an $OD_{600\ nm}$ of 0.6 was reached, protein expression was induced with IPTG (400 μM final conc.).

In a first step, a small scale expression experiment with 10 mL culture volume, different L-Rhamnose concentrations and expression temperatures as shown as in Error! Reference source not found.7 was performed.

TABLE 17

Expression conditions

| Sample | L-rhamnose concentration (μM) | Temperature/Expression time |
|---|---|---|
| 1 | 0 | 18° C., 16 hours |
| 2 | 100 | 18° C., 16 hours |
| 3 | 250 | 18° C., 16 hours |
| 4 | 500 | 18° C., 16 hours |
| 5 | 750 | 18° C., 16 hours |
| 6 | 1000 | 18° C., 16 hours |
| 7 | 2000 | 18° C., 16 hours |
| 8 | 0 | 37° C., 16 hours |
| 9 | 100 | 37° C., 16 hours |
| 10 | 250 | 37° C., 16 hours |
| 11 | 500 | 37° C., 16 hours |
| 12 | 750 | 37° C., 16 hours |
| 13 | 1000 | 37° C., 16 hours |
| 14 | 2000 | 37° C., 16 hours |

After expression, the cells were harvested by centrifugation. The pellets and the supernatants were then analyzed by SDS PAGE and Western Blot (anti-His6, Novagen). On SDS-PAGE gels, no expression was detectable. In the corresponding Western Blot, weak signals could be detected, and no difference in signal intensities was observed.

Two larger scale expression experiment with 100 ml culture volume was performed (no Rhamnose, 20° C. and 37° C. induction temperature, for 16 hours).

After expression the cells were harvested by centrifugation, the cell pellets were resuspended in binding buffer (containing 6 M Urea) and lysed by sonication. After centrifugation the supernatant was purified by FPLC (Äkta FPLC system, with HisTrap FF Crude, GE Lifes Sciences), several fractions were collected for further analysis.

After a buffer exchange by dialysis (Amicon Ultra-4, PLGC Ultracel-PL Membran, 10 kDa) the protein fractions were analysed by SDS PAGE and Western Blot. Signals were detected in the Western Blot in 3 fractions (see FIG. 16).

EXAMPLE 18: CHARACTERIZATION OF OF *LACTOCOCCUS LACTIS* CCOS 949

*Lactococcus lactis* CCOS 949 was deposited on 3 May 2016 under number DSM 32294 with the DSMZ (Deutsche Sammlung von Mikroorganismen und Zellkulturen, Leibniz-Institut, Braunschweig, Germany).

| Specifications | |
|---|---|
| Organism: | *Lactococcus lactis* |
| Strain code: | CCOS 949 |
| | Patent Deposit |
| Deposited at: | Leibniz-Institut, DSMZ-Deutsche Sammlung von Mikroorganismen und Zellkulturen GmbH, Inhoffenstra8e 7 B, 38124 Braunschweig, Germany |

-continued

| | |
|---|---|
| Depositon date: | 21 Apr. 2016 |
| Deposition code: | DSM 32294 |

Taxonomy

| | |
|---|---|
| Kingdom: | Bacteria |
| Phylum: | Firmicutes |
| Class: | *Bacilli* |
| Order: | *Lactobacillales* |
| Family: | *Streptococcaceae* |
| Species reference: | Schleifer et al. 1986 |

Depositor

| | |
|---|---|
| Name | Probioswiss GmbH, Zurich |
| Country: | Switzerland |

Origin

| | |
|---|---|
| Source: | Food |
| Source material: | Cheese |
| Country: | Switzerland |
| Strain history: | <- F. Graf, Crigasseni AG |

Biosafety

| | |
|---|---|
| Biosafety level: | 1 |

Growth conditions

| | |
|---|---|
| Recommended growth medium: | MRS Agar or MRS Broth |
| Alternative growth media: | TSA (Tryptic Soy Agar) |
| | BLA (Tryptic Soy Agar with 5% Sheep blood) |
| Temperature: | 30° C. |
| Oxygen requirements: | facultative aerobe, anaerobic growth conditions recommended |

Rapid tests

| | |
|---|---|
| Gram type: | positive |
| KOH test: | negative |
| Catalase test: | negative |

Preservation

| | |
|---|---|
| Method: | Cryopreservation |
| Temperature: | −80° C. |
| Antifreeze: | 50% Glycerol |

Morphology: cocci, in chains up to 8, non motile (Phase contrast image of *L. lactis* CCOS 949 in FIG. 9). Identification tests: MALDI-TOF, *Lactococcus lactis* subsp. *lactis*, score: 2.37 (+++) (Bruker Biotyper); 16S rDNA sequencing: *Lactococcus lactis*, 99% ID (NCBI Genbank); DNA Sequencing: GenePartial 16S rDNA; Method: Sanger Sequencing; Sequence: SEQ ID NO: 83.

EXAMPLE 19: CHARACTERIZATION OF *LACTOBACILLUS PLANTARUM* CCOS 893

*Lactobacillus plantarum* CCOS 893 was deposited on 27 Jul. 2016 under number DSM 32352 with the DSMZ (Deutsche Sammlung von Mikroorganismen und Zellkulturen, Leibniz-Institut, Braunschweig, Germany).

Specifications

| | |
|---|---|
| Organism: | *Lactobacillus plantarum* |
| Strain code: | CCOS 893 |

Taxonomy

| | |
|---|---|
| Kingdom: | Bacteria |
| Phylum: | Firmicutes |
| Class: | *Bacilli* |
| Order: | *Lactobacillales* |
| Family: | *Lactobacillaceae* |
| Species reference: | (Orla-Jensen 1919) Bergey et al. 1923 |

Depositor

| | |
|---|---|
| Name | Probioswiss GmbH, Zürich, Switzerland on 27 Jul. 2016 |

-continued

| | |
|---|---|
| Country: | Switzerland |

Origin

| | |
|---|---|
| Source: | Plant |
| Source material: | Silage |
| Country: | Switzerland |

Biosafety

| | |
|---|---|
| Biosafety level: | 1 |

Growth conditions

| | |
|---|---|
| Growth medium: | MRS |
| Alternative growth media: | BLA (Tryptic Soy Agar with 5% Sheep blood) |
| Temperature: | 37° C. |
| Oxygen requirements: | facultative aerobe, anaerobic growth conditions recommended |
| Microscopy | Morphology: rods, not motile |
| | (Phase contrast image shown in FIG. 10) |

Rapid tests

| | |
|---|---|
| Gram type: | positive |
| KOH test: | negative |

Identification tests

| | |
|---|---|
| MALDI-TOF | *Lactobacillus plantarum*, score: 2.463 (+++) (Bruker Biotyper) |
| 16S rDNA sequencing | *Lactobacillus plantarum*, 99% ID (NCBI Genbank) |
| VITEK ANC-Card | not determined |

Preservation

| | |
|---|---|
| Method: | Cryopreservation |
| Temperature: | −80° C. |
| Antifreeze: | 50% Glycerol |

EXAMPLE 20: CHARACTERIZATION OF *LACTOBACILLUS CRISPATUS* CCOS 961

*Lactobacillus crispatus* CCOS 961 was deposited on 10.12.2017 under deposit number CCOS 961 with the Culture Collection of Switzerland AG (CCOS, Wädenswil, Switzerland).

Specifications

| | |
|---|---|
| Organism: | *Lactobacillus crispatus* |
| Strain code: | CCOS 961 |

Taxonomy

| | |
|---|---|
| Kingdom: | Bacteria |
| Phylum: | Firmicutes |
| Class: | Bacilli |
| Order: | Lactobacillales |
| Family: | Lactobacillaceae |
| Species reference: | (Brygoo and Aladame 1953) Moore and Holdeman 1970 |

-continued

| Depositor | |
|---|---|
| Name | Crigasseni AG, Beckenried, Switzerland on 10 Dec. 2017 |
| Country: | Switzerland |

| Origin | |
|---|---|
| Source: | Healthy Human |
| Source material: | Vaginal swab |
| Country: | Switzerland |
| Strain history: | <- F. Graf Crigasseni |

| Biosafety | |
|---|---|
| Biosafety level: | 1 |

| Growth conditions | |
|---|---|
| Growth medium: | MRS |
| Alternative growth media: | BLA (Tryptic Soy Agar with 5% Sheep blood) |
| Temperature: | 37° C. |
| Oxygen requirements: | facultative aerobe, anaerobic growth conditions recommended |
| Microscopy: | Morphology: rods, non motile (Phase contrast image shown in FIG. 11). |

| Rapid tests | |
|---|---|
| Gram type: | positive |
| KOH test: | negative |

| Identification tests | |
|---|---|
| MALDI-TOF | *Lactobacillus crispatus*, score: 2.273 (++) (Bruker Biotyper) |
| 16S rDNA sequencing | not determined |
| VITEK ANC-Card | not determined |

| Preservation | |
|---|---|
| Method: | Cryopreservation |
| Temperature: | −80° C. |
| Antifreeze: | 50% Glycerol |

EXAMPLE 21: CHARACTERIZATION OF *LACTOBACILLUS GASSERI* CCOS 960

*Lactobacillus gasseri* identified as *Lactobacillus gasseri* CCOS 960 was deposited on 21 Apr. 2016 under number DSM 32296 with the DSMZ (Deutsche Sammlung von Mikroorganismen und Zellkulturen, Leibniz-Institut, Braunschweig, Germany).

| Specifications | |
|---|---|
| Organism: | *Lactobacillus gasseri* |
| Strain code: | CCOS 960 |

| Taxonomy | |
|---|---|
| Kingdom: | Bacteria |
| Phylum: | Firmicutes |
| Class: | *Bacilli* |
| Order: | *Lactobacillales* |
| Family: | *Lactobacillaceae* |
| Species reference: | Lauer and Kandler 1980 |

| Depositor | |
|---|---|
| Name | Probioswiss GmbH, Zürich, Switzerland on 21 Apr. 2016 |
| Country: | Switzerland |

| Biosafety | |
|---|---|
| Biosafety level: | 1 |

| Growth conditions | |
|---|---|
| Growth medium: | MRS |
| Alternative growth media: | BLA (Tryptic Soy Agar with 5% Sheep blood) TSA (Tryptic Soy Agar) |
| Temperature: | 37° C. |
| Oxygen requirements: | facultative aerobe, anaerobic growth conditions recommended |
| Microscopy | Morphology: Very long rods, non-motile (Phase contrast image in FIG. 12) |

| Rapid tests | |
|---|---|
| Gram type: | positive |
| KOH test: | negative |

| Identification tests | |
|---|---|
| MALDI-TOF | *Lactobacillus gasseri*, score: 2.425 (+++) (Bruker Biotyper) |
| 16S rDNA sequencing | not determined |
| VITEK ANC-Card | no identification, Bionumber 2173100020001 |

| Preservation | |
|---|---|
| Method: | Cryopreservation |
| Temperature: | −80° C. |
| Antifreeze: | 50% Glycerol |

EXAMPLE 22: CHARACTERIZATION OF *LACTOBACILLUS JENSENII* CCOS 962

*Lactobacillus jensenii* identified as *Lactobacillus jensenii* CCOS 962 was deposited on 17 Apr. 2019 under number CCOS 962 with the CCOS (Culture Collection of Switzerland AG, Wädenswil, Switzerland).

| Specifications | |
|---|---|
| Organism: | *Lactobacillus jensenii* |
| Strain code: | CCOS 962 |

| Taxonomy | |
|---|---|
| Kingdom: | Bacteria |
| Phylum: | Firmicutes |
| Class: | *Bacilli* |
| Order: | *Lactobacillales* |
| Family: | *Lactobacillaceae* |
| Species reference: | Gasser et al. 1970 |

| Depositor | |
|---|---|
| Name | Crigasseni AG, Ledergasse 34, 6375 Beckenried, Switzerland, 30 May 2016 |
| Country: | Switzerland |

| Biosafety | |
|---|---|
| Biosafety level: | 1 |

| Growth conditions | |
|---|---|
| Growth medium: | MRS |
| Alternative growth media: | BLA (Tryptic Soy Agar with 5% Sheep blood) TSA (Tryptic Soy Agar) |
| Temperature: | 37° C. |
| Oxygen requirements: | facultative aerobe, anaerobic growth conditions recommended |
| Microscopy | Morphology: short rods, in chains up to 4, non-motile (Phase contrast image in FIG. xx) |

| Rapid tests | |
|---|---|
| Gram type: | positive |
| KOH test: | negative |

| Identification tests | |
|---|---|
| MALDI-TOF | *Lactobacillus jensenii*, score: 2.251 (+++) (Bruker Biotyper) |
| 16S rDNA sequencing | *Lactobacillus jensenii*, 99% ID (16S rRNA, NCBI Genbank) |
| VITEK | ANC-Card not determined |

| Preservation | |
| --- | --- |
| Method: | Cryopreservation |
| Temperature: | −80° C. |
| Antifreeze: | 50% Glycerol |

EXAMPLE 23: CHARACTERIZATION OF *LACTOBACILLUS RHAMNOSUS* CCOS 965

*Lactobacillus rhamnosus* identified as *Lactobacillus rhamnosus* CCOS 965 was deposited on 17 Apr. 2019 under number CCOS 965 with the CCOS (Culture Collection of Switzerland AG, Wädenswil, Switzerland).

| Specifications | |
| --- | --- |
| Organism: | *Lactobacillus rhamnosus* |
| Strain code: | CCOS 965 |
| Taxonomy | |
| Kingdom: | Bacteria |
| Phylum: | Firmicutes |
| Class: | *Bacilli* |
| Order: | *Lactobacillales* |
| Family: | *Lactobacillaceae* |
| Species reference: | (Hansen 1968) Collins et al. 1989 |
| Depositor | |
| Name | Crigasseni AG, Ledergasse 34, 6375 Beckenried, Switzerland, 30 May 2016 |
| Country: | Switzerland |
| Biosafety | |
| Biosafety level: | 1 |
| Growth conditions | |
| Growth medium: | MRS |
| Alternative growth media: | BLA (Tryptic Soy Agar with 5% Sheep blood) TSA (Tryptic Soy Agar) |
| Temperature: | 37° C. |
| Oxygen requirements: | facultative aerobe, anaerobic growth conditions recommended |
| Microscopy | Morphology: Very long rods, non-motile (Phase contrast image in FIG. xx) |
| Rapid tests | |
| Gram type: | positive |
| KOH test: | negative |
| Identification tests | |
| MALDI-TOF | *Lactobacillus rhamnosus*, score: 2.177 (++) (Bruker Biotyper) |
| 16S rDNA sequencing | *Lactobacillus rhamnosus*, 99% ID (16S rRNA, NCBI Genbank) |
| VITEK ANC-Card | not determined |
| Preservation | |
| Method: | Cryopreservation |
| Temperature: | −80° C. |
| Antifreeze: | 50% Glycerol |

EXAMPLE 24: CHARACTERIZATION OF *LACTOBACILLUS PARACASEI* CCOS 1201

*Lactobacillus paracasei* identified as *Lactobacillus paracasei* CCOS 1201 (identical to CCOS 1205) was deposited on 17 Apr. 2019 under number CCOS 1201 with the CCOS (Culture Collection of Switzerland AG, Wädenswil, Switzerland).

| Specifications | |
| --- | --- |
| Organism: | *Lactobacillus paracasei* |
| Strain code: | CCOS 1201 |
| Taxonomy | |
| Kingdom: | Bacteria |
| Phylum: | Firmicutes |
| Class: | *Bacilli* |
| Order: | *Lactobacillales* |
| Family: | *Lactobacillaceae* |
| Species reference: | Collins et al. 1989 |
| Depositor | |
| Name | Crigasseni AG, Ledergasse 34, 6375 Beckenried, Switzerland, 30 May 2016 |
| Country: | Switzerland |
| Biosafety | |
| Biosafety level: | 1 |
| Growth conditions | |
| Growth | medium: MRS |
| Alternative growth media: | BLA (Tryptic Soy Agar with 5% Sheep blood) TSA (Tryptic Soy Agar) |
| Temperature: | 37° C. |
| Oxygen requirements: | facultative aerobe, anaerobic growth conditions recommended |
| Microscopy | Morphology: rods, non-motile (Phase contrast image in FIG. xx) |
| Rapid tests | |
| Gram type: | positive |
| KOH test: | negative |
| Identification tests | |
| MALDI-TOF | *Lactobacillus paracasei*, score: 2.35(+++) (Bruker Biotyper) |
| 16S rDNA sequencing | *Lactobacillus paracasei*, 99% ID (16S rRNA, NCBI Genbank) |
| VITEK ANC-Card | not determined |
| Preservation | |
| Method: | Cryopreservation |
| Temperature: | −80° C. |
| Antifreeze: | 50% Glycerol |

The invention claimed is:

1. A method for the prophylaxis and/or treatment of a *Clostridium difficile* infection in a patient in need of such treatment or prophylaxis, comprising the steps of:
   administering an effective amount of a peptidoglycan hydrolase (PGH)-secreting probiotic bacterial strain that includes *Lactococcus lactis* CCOS 949 (DSM 32294), *Lactobacillus gasseri* CCOS 960 (DSM 32296), *Lactobacillus plantarum* CCOS 893 (DSM 32352), *Lactobacillus johnsonii* CCOS 824 (CCOS 824), *Lactobacillus paracasei* subsp. *Paracasei* CCOS 1205 (CCOS 1205), *Lactobacillus paracasei* subsp. *Paracasei* CCOS 1201 (CCOS 1201), or *Lactobacillus rhamnosus* CCOS 965 (CCOS 965),
   wherein the peptidoglycan hydrolase (PGH) is alpha-N-acetylglucosaminidase, beta-N-acetylglucosaminidase, or a combination thereof, and the method effectuates the prophylaxis and/or treatment of the *Clostridium difficile* infection in the patient.

2. The method according to claim 1, wherein the bacterial infection results in diarrhea.

3. The method according to claim 1, further comprising repeating said administration.

4. The method according to claim 1, wherein the probiotic bacterial strain includes *Lactococcus lactis* CCOS 949 (DSM 32294) or *Lactobacillus rhamnosus* CCOS 965 (CCOS 965).

5. The method according to claim 1, wherein the peptidoglycan hydrolase (PGH)-secreting probiotic bacterial strain is in the form of a pharmaceutical composition further comprising at least one physiologically acceptable excipient.

6. The method according to claim 1, wherein the peptidoglycan hydrolase (PGH)-secreting probiotic bacterial strain is administered orally, rectally, by intravenous injection or by subcutaneous injection.

7. The method according to claim 1, wherein the peptidoglycan hydrolase (PGH)-secreting probiotic bacterial strain is in the form of a composition further comprising
   at least one N-acetylated monosaccharide;
   at least one prebiotic carbon source;
   at least one nitrogen source;
   and/or at least a sulfur source.

8. The method according to claim 1, wherein the N-acetylated monosaccharide is selected from the group consisting of N-acetylglucosamine, N-acetylgalactosamine, N-acetylhexosamine, N-acetylmannosamine, and mixtures thereof.

9. The method according to claim 7, wherein the prebiotic carbon source is selected from the group consisting of a fructooligosaccharide, galactooligosaccharide, glyco-oligosaccharide, lactulose, xylooligosaccharide, isomaltooligosaccharide, and mixtures thereof.

10. The method according to claim 7, wherein the at least one sulfur source is selected from the group consisting of methionine, cysteine, cystine, cystathionine, a sulfur-containing inorganic salt, magnesium sulfate, sodium or potassium thiosulfate, and mixtures thereof.

11. The method according to claim 7, wherein the at least one nitrogen source is selected from the group consisting of ammonium salts, ammonium chloride or citrate, urea, amino acids, nitrogen-rich amino acids, glutamic acid, arginine, aspartic acid, alanine, and mixtures thereof.

12. A method for the prophylaxis and/or treatment of a *Clostridium difficile* infection in a patient in need of such treatment or prophylaxis, comprising the steps of:
   administering an effective amount of a peptidoglycan hydrolase (PGH)-secreting probiotic bacterial strain that includes *Lactobacillus gasseri* CCOS 960 (DSM 32296), *Lactobacillus plantarum* CCOS 893 (DSM 32352), *Lactobacillus johnsonii* CCOS 824 (CCOS 824), *Lactobacillus paracasei* subsp. *Paracasei* CCOS 1205 (CCOS 1205), *Lactobacillus paracasei* subsp. *Paracasei* CCOS 1201 (CCOS 1201), or *Lactobacillus rhamnosus* CCOS 965 (CCOS 965),
   wherein the peptidoglycan hydrolase (PGH) is alpha-N-acetylglucosaminidase, beta-N-acetylglucosaminidase, or a combination thereof, and the method effectuates the prophylaxis and/or treatment of a Clostridium difficile infection in the patient.

13. The method of claim 12, further comprising repeating said administration.

14. The method of claim 12, wherein the bacterial infection results in diarrhea.

15. The method of claim 12, wherein the probiotic bacterial strain includes *Lactobacillus rhamnosus* CCOS 965 (CCOS 965).

16. The method of claim 12, wherein the peptidoglycan hydrolase (PGH)-secreting probiotic bacterial strain is in the form of a pharmaceutical composition further comprising at least one physiologically acceptable excipient.

17. The method of claim 12, wherein the peptidoglycan hydrolase (PGH)-secreting probiotic bacterial strain is administered orally, rectally, by intravenous injection or by subcutaneous injection.

18. The method of claim 12, wherein the peptidoglycan hydrolase (PGH)-secreting probiotic bacterial strain is in the form of a composition further comprising
   at least one N-acetylated monosaccharide;
   at least one prebiotic carbon source;
   at least one nitrogen source;
   and/or at least a sulfur source.

19. The method of claim 18, wherein the N-acetylated monosaccharide is selected from the group consisting of N-acetylglucosamine, N-acetylgalactosamine, N-acetylhexosamine, N-acetylmannosamine, and mixtures thereof.

20. The method of claim 18, wherein the prebiotic carbon source is selected from the group consisting of a fructooligosaccharide, galactooligosaccharide, glyco-oligosaccharide, lactulose, xylooligosaccharide, isomaltooligosaccharide, and mixtures thereof.

21. The method of claim 18, wherein the at least one sulfur source is selected from the group consisting of methionine, cysteine, cystine, cystathionine, a sulfur-containing inorganic salt, magnesium sulfate, sodium or potassium thiosulfate, and mixtures thereof.

22. The method of claim 18, wherein the at least one nitrogen source is selected from the group consisting of ammonium salts, ammonium chloride or citrate, urea, amino acids, nitrogen-rich amino acids, glutamic acid, arginine, aspartic acid, alanine, and mixtures thereof.

\* \* \* \* \*